US007736853B2

(12) United States Patent
Afar et al.

(10) Patent No.: US 7,736,853 B2
(45) Date of Patent: Jun. 15, 2010

(54) METHODS OF DIAGNOSIS OF ANDROGEN-DEPENDENT PROSTATE CANCER, PROSTATE CANCER UNDERGOING ANDROGEN WITHDRAWAL, AND ANDROGEN-INDEPENDENT PROSTATE CANCER

(75) Inventors: Daniel E. H. Afar, Brisbane, CA (US); David Agus, Beverly Hills, CA (US); David H. Mack, Menlo Park, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 11/565,589

(22) Filed: Nov. 30, 2006

(65) Prior Publication Data

US 2007/0161016 A1 Jul. 12, 2007

Related U.S. Application Data

(62) Division of application No. 10/160,233, filed on May 31, 2002, now abandoned.

(60) Provisional application No. 60/295,917, filed on Jun. 4, 2001, provisional application No. 60/368,689, filed on Mar. 29, 2002, provisional application No. 60/350,666, filed on Nov. 13, 2001, provisional application No. 60/372,246, filed on Apr. 12, 2002.

(51) Int. Cl.
*C12Q 1/68* (2006.01)

(52) U.S. Cl. .......................................................... 435/6

(58) Field of Classification Search ...................... 435/6
See application file for complete search history.

(56) References Cited

OTHER PUBLICATIONS

Jain (Scientific American Jul. 1994).*
Dillman (Annals of Internal Medicine, vol. 111, pp. 592-605, 1989).*
Weiner (Seminars Oncology, vol. 26, No. 4, 1999, pp. 41-50).*
Gura (Science, 1997, 278:1041-1042.).*
Siedman et al (The Journal of Urology, 1992, 147:931-934).*
Jain (Scientific American Jul. 1994).*
Dillman (Annals of Internal Medicine, vol. 111, pp. 592-603, 1989).*
Weiner (Seminars Oncology, vol. 26, No. 4, 1999, pp. 41-50).*
Oh et al (The Journal of Urology, 1998, 160:1220-1229).*
Panda et al (Proceedings of the National Academy of Sciences USA, 1997, 94:10560-10564).*
Tockman et al (Cancer Res., 1992, 52:2711s-2718s).*
Albanesi et al (Journal of Investigative Dermatology, Feb. 1998, 110(2): 138-142).*
Albanesi et al (Journal of Investigative Dermatology, Feb. 1998, 110(2): 138-142).*
Tockman et al (Cancer Res., 1992, 52:2711s-2718s).*
Albanesi et al (Journal of Investigative Dermatology, Feb. 1998, 110(2): 138-142).*
Talpin et al (The New England Journal of Medicine, May 1995, 332(21): 1393-1398).*
Talpin et al (The New England Journal of Medicine, May 1995, 332(21): 1393-1398).*
International Search Report dated Jun. 5, 2003.
Ray, et al, "AIM1, a novel non-lens member of the βγ-crystallin superfamily, is associated with the control of tumorigenicity in human malignant melanoma," *Proc. Natl. Acad. Sci USA* 94:3228-3234.

* cited by examiner

*Primary Examiner*—Sean E Aeder
(74) *Attorney, Agent, or Firm*—Seth D. Levy; Davis Wright Tremaine LLP

(57) ABSTRACT

Described herein are genes whose expression are up-regulated or down-regulated in prostate cancer. Also described are such genes whose expression is further up-regulated or down-regulated in drug-resistant prostate cancer cells. Related methods and compositions that can be used for diagnosis and treatment of prostate cancer are disclosed. Also described herein are methods that can be used to identify modulators of prostate cancer.

9 Claims, No Drawings

METHODS OF DIAGNOSIS OF ANDROGEN-DEPENDENT PROSTATE CANCER, PROSTATE CANCER UNDERGOING ANDROGEN WITHDRAWAL, AND ANDROGEN-INDEPENDENT PROSTATE CANCER

CROSS-REFERENCES TO RELATED APPLICATIONS

This application claims the benefit of priority under 35 U.S.C. §121 as a divisional of U.S. patent application Ser. No. 10/160,233, filed May 31, 2002, which claims priority from the following applications: U.S. Ser. No. 60/295,917, filed Jun. 4, 2001, U.S. Ser. No. 60/368,689, filed Mar. 29, 2002; U.S. Ser. No. 60/350,666, filed Nov. 13, 2001; and U.S. Ser. No. 60/372,246, filed Apr. 12, 2002; each of which is incorporated herein by reference in its entirety.

FIELD OF THE INVENTION

The invention relates to the identification of nucleic acid and protein expression profiles and nucleic acids, products, and antibodies thereto that are involved in prostate cancer; and to the use of such expression profiles and compositions in the diagnosis, prognosis, and therapy of prostate cancer. The invention further relates to methods for identifying and using agents and/or targets that inhibit prostate cancer.

BACKGROUND OF THE INVENTION

Prostate cancer is the most frequently diagnosed cancer and the second leading cause of male cancer death in North America and northern Europe. Early detection of prostate cancer using a serum test for prostate-specific antigen (PSA) has dramatically improved the treatment of the disease (Oesterling (1992) *J. Am. Med. Assoc.* 267:2236-2238). Treatment of prostate cancer consists largely of surgical prostatectomy, radiation therapy, androgen ablation therapy and chemotherapy. Although many prostate cancer patients are effectively treated, the current therapies can all induce serious side effects which diminish quality of life. Patients who present with metastatic disease are most often treated with androgen-ablation therapy. Hormone blockade results in significant regression of the tumor. However, this treatment rarely cures the patient and invariably results in progression to androgen-independent disease, which is incurable. Afrin and Stuart (1994) *J.S.C. Med. Assoc.* 90:231-236.

The identification of novel therapeutic targets and diagnostic markers is essential for improving the current treatment of prostate cancer patients. Recent advances in molecular medicine have increased the interest in tumor-specific cell surface antigens that could serve as targets for various immunotherapeutic or small molecule strategies. Antigens suitable for immunotherapeutic strategies should be highly expressed in cancer tissues and ideally not expressed in normal adult tissues. Expression in tissues that are dispensable for life, however, may be tolerated. Examples of such antigens include Her2/neu and the B-cell antigen CD20. Humanized monoclonal antibodies directed to Her2/neu (Herceptin) are currently in use for the treatment of metastatic breast cancer. Ross and Fletcher (1998) *Stem Cells* 16:413-428. Similarly, anti-CD20 monoclonal antibodies (Rituxin) are used to effectively treat non-Hodgkin's lymphoma. Maloney, et al. (1997) *Blood* 90:2188-2195; Leget and Czuczman (1998) *Curr. Opin. Oncol.* 10:548-551.

Several potential immunotherapeutic targets have been identified for prostate cancer. They include prostate-specific membrane antigen (PSMA)(Israeli, et al. (1993) *Cancer Res.* 53:227-230), prostate stem cell antigen (PSCA; Reiter, et al. (1998) *Proc. Natl. Acad. Sci. USA* 95:1735-1740), and serpentine transmembrane epithelial antigen of the prostate (STEAP; Hubert, et al. (1999) *Proc. Natl. Acad. Sci. USA* 96:14529-14534). PSMA is a type II transmembrane hydrolase with significant homology to a rat neuropeptidase (Carter, et al. (1996) *Proc. Natl. Acad. Sci. USA* 93:749-753). Antibodies directed towards PSMA are currently being used to detect metastasized prostate cancer as the Prostascint Scan (Sodee, et al. (1996) *Clin. Nucl. Med.* 21:759-767) and are also being evaluated for treatment of advanced disease (Gregorakis, et al. (1998) *Semin. Urol. Oncol.* 16:2-12; Liu, et al. (1998) *Cancer Res.* 58:4055-4060; Murphy, et al. (1998) *J. Urol.* 160:2396-2401). In a study on bone metastasis of prostate cancer, only 8 out of 18 patient samples expressed PSMA (Silver, et al. (1997) *Clin. Cancer Res.* 3:81-85). Therefore, it is clear that other targets need to be identified to manage metastasized disease. PSCA is a member of the Thy-1/Ly-6 family of glycosylphosphatidylinositol-linked plasma membrane proteins (Reiter, et al. (1998) *Proc. Natl. Acad. Sci. USA* 95:1735-1740). Immunohistochemical data shows that PSCA is up-regulated in the majority of prostate cancer epithelia and is also detected in bone metastasis (Gu, et al. (2000) *Oncogene* 19:1288-1296). Recent work shows that antibodies directed to PSCA can prevent metastatic spread of prostate cancer in a mouse model (Saffran, et al. (2001) *Proc. Natl. Acad. Sci. USA* 98:2658-2663). STEAP is a multi-transmembrane prostate-specific protein that may function as a channel or transporter protein (Hubert, et al. (1999) *Proc. Natl. Acad. Sci. USA* 96:14529-14534). Its protein expression is specific to the basolateral membranes of normal prostate and prostate cancer epithelia. STEAP expression was most highly concentrated at cell-cell boundaries, implying a potential function in intercellular communication. Therapeutic monoclonal antibodies have so far not been reported for STEAP.

SUMMARY OF THE INVENTION

The present invention therefore provides nucleotide sequences of genes that are up- and down-regulated in androgen-independent prostate cancer cells or prostate cells undergoing androgen withdrawal. Such genes are useful for diagnostic purposes, and also as targets for screening for therapeutic compounds that modulate prostate cancer, such as hormones or antibodies. Other aspects of the invention will become apparent to the skilled artisan by the following description of the invention.

In one aspect, the present invention provides a method of detecting an androgen independent prostate cancer-associated transcript in a cell from a patient, the method comprising contacting a biological sample from the patient with a polynucleotide that selectively hybridizes to nucleic acid molecule comprising a sequence at least 80% identical to a sequence as shown in Tables 1A-4.

In one embodiment, the present invention provides a method of determining the level of a prostate cancer associated transcript in a cell from a patient.

In one embodiment, the present invention provides a method of detecting a prostate cancer-associated transcript in a cell from a patient, the method comprising contacting a biological sample from the patient with a polynucleotide that selectively hybridizes to a sequence at least 80% identical to a sequence as shown in Tables 1A-4.

In various embodiments, the polynucleotide selectively hybridizes to a sequence at least 95% identical to a sequence as shown in Tables 1A-4; the polynucleotide comprises a sequence as shown in Tables 1A-4; the biological sample is a tissue sample; the biological sample comprises isolated nucleic acids, e.g., mRNA; the polynucleotide is labeled, e.g., with a fluorescent label; the polynucleotide is immobilized on a solid surface; the patient is undergoing a therapeutic regimen to treat prostate cancer; the patient is suspected of having metastatic prostate cancer; the patient is a human; the patient is suspected of having a taxol-resistant cancer; or the prostate cancer associated transcript is mRNA.

In other embodiments, the method further comprises the step of amplifying nucleic acids before the step of contacting the biological sample with the polynucleotide.

In another aspect, the present invention provides a method of monitoring the efficacy of a therapeutic treatment of prostate cancer, the method comprising the steps of: (i) providing a biological sample from a patient undergoing the therapeutic treatment; and (ii) determining the level of a prostate cancer-associated transcript in the biological sample by contacting the biological sample with a polynucleotide that selectively hybridizes to a sequence at least 80% identical to a sequence as shown in Tables 1A-4, thereby monitoring the efficacy of the therapy. In a further embodiment, the patient has metastatic prostate cancer. In a further embodiment, the patient has a drug resistant (e.g., taxol resistant) form of prostate cancer.

In one embodiment, the method further comprises the step of: (iii) comparing the level of the prostate cancer-associated transcript to a level of the prostate cancer-associated transcript in a biological sample from the patient prior to, or earlier in, the therapeutic treatment.

Additionally, provided herein is a method of evaluating the effect of a candidate prostate cancer drug comprising administering the drug to a patient and removing a cell sample from the patient. The expression profile of the cell is then determined. This method may further comprise comparing the expression profile to an expression profile of a healthy individual. In a preferred embodiment, said expression profile includes a gene of Tables 1A-4.

In one aspect, the present invention provides an isolated nucleic acid molecule consisting of a polynucleotide sequence as shown in Tables 1A-4.

In one embodiment, an expression vector or cell comprises the isolated nucleic acid.

In one aspect, the present invention provides an isolated polypeptide which is encoded by a nucleic acid molecule having polynucleotide sequence as shown in Tables 1A-4.

In another aspect, the present invention provides an antibody that specifically binds to an isolated polypeptide which is encoded by a nucleic acid molecule having polynucleotide sequence as shown in Tables 1A-4.

In certain embodiments, the antibody is conjugated to an effector component, e.g., a fluorescent label, a radioisotope or a cytotoxic chemical; the antibody is an antibody fragment; or the antibody is humanized.

In one aspect, the present invention provides a method of detecting a prostate cancer cell in a biological sample from a patient, the method comprising contacting the biological sample with an antibody as described herein.

In another aspect, the present invention provides a method of detecting antibodies specific to prostate cancer in a patient, the method comprising contacting a biological sample from the patient with a polypeptide encoded by a nucleic acid comprising a sequence from Tables 1A-4.

In another aspect, the present invention provides a method for identifying a compound that modulates a prostate cancer-associated polypeptide, the method comprising the steps of: a) contacting the compound with a prostate cancer-associated polypeptide, the polypeptide encoded by a polynucleotide that selectively hybridizes to a sequence at least 80% identical to a sequence as shown in Tables 1A-4; and b) determining the functional effect of the compound upon the polypeptide.

In one embodiment, the functional effect is a physical effect, an enzymatic effect, or a chemical effect.

In one embodiment, the polypeptide is expressed in a eukaryotic host cell or cell membrane. In another embodiment, the polypeptide is recombinant.

In one embodiment, the functional effect is determined by measuring ligand binding to the polypeptide.

In another aspect, the present invention provides a method of inhibiting proliferation of a prostate cancer-associated cell to treat prostate cancer in a patient, the method comprising the step of administering to the subject a therapeutically effective amount of a compound identified as described herein.

In one embodiment, the compound is an antibody.

In another aspect, the present invention provides a drug screening assay comprising the steps of: a) administering a test compound to a mammal having prostate cancer or to a cell sample isolated therefrom; b) comparing the level of gene expression of a polynucleotide that selectively hybridizes to a sequence at least 80% identical to a sequence as shown in Tables 1A-4 in a treated cell or mammal with the level of gene expression of the polynucleotide in a control cell sample or mammal, wherein a test compound that modulates the level of expression of the polynucleotide is a candidate for the treatment of prostate cancer.

In one embodiment, the control is a mammal with prostate cancer or a cell sample therefrom that has not been treated with the test compound. In another embodiment, the control is a normal cell or mammal.

In one embodiment, the test compound is administered in varying amounts or concentrations. In another embodiment, the test compound is administered for varying time periods. In another embodiment, the comparison can occur after addition or removal of the drug candidate.

In one embodiment, the levels of a plurality of polynucleotides that selectively hybridize to a sequence at least 80% identical to a sequence as shown in Tables 1A-4 are individually compared to their respective levels in a control cell sample or mammal. In a preferred embodiment the plurality of polynucleotides is from three to ten.

In another aspect, the present invention provides a method for treating a mammal having prostate cancer comprising administering a compound identified by the assay described herein.

In another aspect, the present invention provides a pharmaceutical composition for treating a mammal having prostate cancer, the composition comprising a compound identified by the assay described herein and a physiologically acceptable excipient.

In one aspect, the present invention provides a method of screening drug candidates by providing a cell expressing a gene that is up- and down-regulated as in a prostate cancer. In one embodiment, a gene is selected from Tables 1A-4. The method further includes adding a drug candidate to the cell and determining the effect of the drug candidate on the expression of the expression profile gene.

In one embodiment, the method of screening drug candidates includes comparing the level of expression in the absence of the drug candidate to the level of expression in the presence of the drug candidate, wherein the concentration of the drug candidate can vary when present, and wherein the comparison can occur after addition or removal of the drug candidate. In a preferred embodiment, the cell expresses at least two expression profile genes. The profile genes may show an increase or decrease.

Also provided is a method of evaluating the effect of a candidate prostate cancer drug comprising administering the drug to a transgenic animal expressing or over-expressing the prostate cancer modulatory protein, or an animal lacking the prostate cancer modulatory protein, for example as a result of a gene knockout.

Moreover, provided herein is a biochip comprising one or more nucleic acid segments of Tables 1A-4, wherein the biochip comprises fewer than 1000 nucleic acid probes. Preferably, at least two nucleic acid segments are included. More preferably, at least three nucleic acid segments are included.

Furthermore, a method of diagnosing a disorder associated with prostate cancer is provided. The method comprises determining the expression of a gene of Tables 1A-4, in a first tissue type of a first individual, and comparing the distribution to the expression of the gene from a second normal tissue type from the first individual or a second unaffected individual. A difference in the expression indicates that the first individual has a disorder associated with prostate cancer.

In a further embodiment, the biochip also includes a polynucleotide sequence of a gene that is not up- and down-regulated in prostate cancer.

In one embodiment a method for screening for a bioactive agent capable of interfering with the binding of a prostate cancer modulating protein (prostate cancer modulatory protein) or a fragment thereof and an antibody which binds to said prostate cancer modulatory protein or fragment thereof. In a preferred embodiment, the method comprises combining a prostate cancer modulatory protein or fragment thereof, a candidate bioactive agent and an antibody which binds to said prostate cancer modulatory protein or fragment thereof. The method further includes determining the binding of said prostate cancer modulatory protein or fragment thereof and said antibody. Wherein there is a change in binding, an agent is identified as an interfering agent. The interfering agent can be an agonist or an antagonist. Preferably, the agent inhibits prostate cancer.

Also provided herein are methods of eliciting an immune response in an individual. In one embodiment a method provided herein comprises administering to an individual a composition comprising a prostate cancer modulating protein, or a fragment thereof. In another embodiment, the protein is encoded by a nucleic acid selected from those of Tables 1A-4.

Further provided herein are compositions capable of eliciting an immune response in an individual. In one embodiment, a composition provided herein comprises a prostate cancer modulating protein, preferably encoded by a nucleic acid of Tables 1A-4, or a fragment thereof, and a pharmaceutically acceptable carrier. In another embodiment, said composition comprises a nucleic acid comprising a sequence encoding a prostate cancer modulating protein, preferably selected from the nucleic acids of Tables 1A-4 and a pharmaceutically acceptable carrier.

Also provided are methods of neutralizing the effect of a prostate cancer protein, or a fragment thereof, comprising contacting an agent specific for said protein with said protein in an amount sufficient to effect neutralization. In another embodiment, the protein is encoded by a nucleic acid selected from those of Tables 1A-4. In another aspect of the invention, a method of treating an individual for prostate cancer is provided. In one embodiment, the method comprises administering to said individual an inhibitor of a prostate cancer modulating protein. In another embodiment, the method comprises administering to a patient having prostate cancer an antibody to a prostate cancer modulating protein conjugated to a therapeutic moiety. Such a therapeutic moiety can be a cytotoxic agent or a radioisotope.

DETAILED DESCRIPTION OF THE INVENTION

In accordance with the objects outlined above, the present invention provides novel methods for diagnosis and evaluation of androgen-dependent prostate cells (malignant or non-malignant), prostate cells undergoing androgen withdrawal, and androgen-independent prostate cancer, as well as methods for treating androgen-dependent prostate cells (malignant or non-malignant), prostate cancer undergoing androgen withdrawal, and androgen-independent prostate cancer. The current Specification incorporates the text of U.S. Ser. No. 09/976,858, filed Oct. 12, 2001, U.S. Ser. No. 60/295,917, filed Jun. 4, 2001, U.S. Ser. No. 60/368,689, filed Mar. 29, 2002; U.S. Ser. No. 60/350,666, filed Nov. 13, 2001; and U.S. Ser. No. 60/372,246, filed Apr. 12, 2002.

Table 1A provides unigene cluster identification numbers for the nucleotide sequence of genes that exhibit increased or decreased expression in androgen-independent prostate cancer samples. Table 1A also provides an exemplar accession number that provides a nucleotide sequence that is part of the unigene cluster. The expression patterns of the genes of Table 1A can be broadly defined into the following categories:

Genes that are expressed early in the time course, then drop off in expression, and then express again with emergence of androgen-independence (hi-lo-hi pattern in table 1A). Genes that are expressed early in the time course, then drop off in expression, and do not express again with emergence of androgen-independence (hi-lo-lo pattern in 1A). Genes that are not expressed early in the time course, but express only with emergence of androgen-independence (lo-lo-hi pattern in table 1A). Genes that are not expressed early in the time course, but then express as androgen is withdrawn and continue to express with emergence of androgen-independence (lo-hi-hi pattern in table 1A). Genes that are not expressed early in the time course, but then express as androgen is withdrawn and drop, off again with emergence of androgen-independence (lo-hi-lo pattern in table 1A).

Tables 2A-C provide unigene cluster identification numbers for the nucleotide sequence of genes that exhibit increased or decreased expression in androgen-dependent prostate cancer, prostate cancer undergoing androgen withdrawal and androgen-independent prostate cancer. Tables 2A-C also provide an exemplar accession number that provides a nucleotide sequence that is part of the unigene cluster. The expression patterns of the genes of Tables 2A-C can be broadly defined into the following 6 categories:

Genes that are expressed early in the time course of androgen withdrawal, then drop off in expression, and then express again with emergence of androgen-independence (hi-lo-lo-hi pattern in Table 2A). Genes that are expressed early in the time course, then drop off in expression immediately after androgen-withdrawal, and do not express again with emergence of androgen-independence (hi-lo-lo-lo pattern in Table 2A). Genes that are expressed early in the time course, then drop off in expression after several days of androgen withdrawal, and do not express again with emergence of androgen-independence (hi-hi-lo-lo pattern in Table 2A). Genes that are not expressed early in the time course, but express only with emergence of androgen-independence (lo-lo-lo-hi pattern in Table 2A). Genes that are not expressed early in the time course, but then express as androgen is withdrawn and continue to express with emergence of androgen-independence (lo-lo-hi-hi pattern in Table 2A). Genes that are not expressed early in the time course, but then express as androgen is withdrawn and drop off again with emergence of androgen-independence (lo-lo-hi-lo pattern in Table 2A).

Definitions

The term "androgen ablation therapy" refers to techniques for the removal or destruction of sources of male hormones, such as testosterone. These techniques include, for example, 1) surgical removal of the testicles, 2) medications such as gonadatropin releasing hormone analogs that inhibit testosterone production, or 3) anti-androgenic drugs that block androgen receptors.

The term "androgen-independent prostate cancer protein" or "androgen-independent prostate cancer polynucleotide" or "androgen-independent prostate cancer-associated transcript" refers to nucleic acid and polypeptide polymorphic variants, alleles, mutants, and interspecies homologues that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleotides, to a nucleotide sequence of or associated with a unigene cluster of Tables 1A-4; (2) bind to antibodies, e.g., polyclonal antibodies, raised against an immunogen comprising an amino acid sequence encoded by a nucleotide sequence of or associated with a unigene cluster of Tables 1A-4 and conservatively modified variants thereof; (3) specifically hybridize under stringent hybridization conditions to a nucleic acid sequence, or the complement thereof of Tables 1A-4 and conservatively modified variants thereof; or (4) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino sequence identity, preferably over a region of over a region of at least about 25, 50, 100, 200, 500, 1000, or more amino acid, to an amino acid sequence encoded by a nucleotide sequence of or associated with a unigene cluster of Tables 1A-4. These polynucleotides or proteins may also be expressed during a period following androgen withdrawal. A polynucleotide or polypeptide sequence is typically from a mammal including, but not limited to, primate, e.g., human; rodent, e.g., rat, mouse, hamster; cow, pig, horse, sheep, or other mammal. A "prostate cancer polypeptide" and a "prostate cancer polynucleotide," include both naturally occurring or recombinant forms, and may refer to those polypeptides or polynucleotides which are expressed in prostate proliferative cells.

A "full length" prostate cancer protein or nucleic acid refers to a prostate cancer polypeptide or polynucleotide sequence, or a variant thereof, that contains the elements normally contained in one or more naturally occurring, wild type prostate cancer polynucleotide or polypeptide sequences. The "full length" may be prior to, or after, various stages of post-translation processing or splicing, including alternative splicing.

"Biological sample" as used herein is a sample of biological tissue or fluid that contains nucleic acids or polypeptides, e.g., of a prostate cancer protein, polynucleotide or transcript. Such samples include, but are not limited to, tissue isolated from primates, e.g., humans, or rodents, e.g., mice, and rats. Biological samples may also include sections of tissues such as biopsy and autopsy samples, frozen sections taken for histology purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), by collecting a sample which contains a soluble polypeptide or nucleic acid derived from a prostate cell, or by performing the methods of the invention in vivo. Archival tissues, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Watermnan (1981) *Appl. Math.* 2:482, by the homology alignment algorithm of Needleman and Wunsch (1970) *J. Mol. Biol.* 48:443-453, by the search for similarity method of Pearson and Lipman (1988) *Proc. Nat'l. Acad. Sci. USA* 85:2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel, et al. (eds. 1995 and supplements) *Current Protocols in Molecular Biology* Lippincott).

Preferred examples of algorithms that are suitable for determining percent sequence identity and sequence similarity include the BLAST and BLAST 2.0 algorithms, which are a described in Altschul, et al. (1977) *Nuc. Acids Res.* 25:3389-3402 and Altschul, et al. (1990) *J. Mol. Biol.* 215:403-410. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative-score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915-919) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. Certain diagnostic methods may evaluate secreted or breakdown products present only because the producing cell is present, and would otherwise be absent in a normal individual.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitutions providing functionally similar amino acids are well known in the art. Such conservatively modified variants are in addition to and do not exclude polymorphic variants, interspecies homologs, and alleles of the invention, typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M)(see, e.g., Creighton (1984) *Proteins* Freeman).

Macromolecular structures such as polypeptide structures can be described in terms of various levels of organization. For a general discussion of this organization, see, e.g., Alberts, et al. (2001) *Molecular Biology of the Cell* (4th ed.) and Cantor and Schimmel (1980) *Biophysical Chemistry Part I: The Conformation of Biological Macromolecules* Freeman. "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the noncovalent association of independent tertiary units. Anisotropic terms are also known as energy terms.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of virtually any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein (1992) *Oligonucleotides and Analogues: A Practical Approach*, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Sanghvi and Cook (eds. 1994) *Carbohydrate Modifications in Antisense Research* ACS Symposium Series 580. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage, et al. (1993) *Tetrahedron* 49(10):1925-1963 and references therein; Letsinger (1970) *J. Org. Chem.* 35:3800-3803; Sprinzl, et al. (1977) Eur. J. Biochem. 81:579-589; Letsinger, et al. (1986) *Nucl. Acids Res.* 14:3487-499; Sawai, et al (1984) *Chem. Lett.* 805, Letsinger, et al. (1988) *J. Am. Chem. Soc.* 110:4470-4471; and Pauwels, et al. (1986) Chemica Scripta 26:141-149), phosphorothioate (Mag, et al. (1991) *Nucleic Acids Res.* 19:1437-441; and U.S. Pat. No. 5,644, 048), phosphorodithioate (Briu, et al. (1989) *J. Am. Chem. Soc.* 111:2321-xxx, O-methylphosphoroamidite linkages (see Eckstein (1992) *Oligonucleotides and Analogues: A Practical Approach* Oxford University Press), and peptide nucleic acid backbones and linkages (see Egholm (1992) *J. Am. Chem. Soc.* 114:1895-1897; Meier, et al. (1992) *Chem. Int. Ed. Engl.* 31:1008-1010; Nielsen (1993) *Nature* 365:566-568; Carlsson, et al. (1996) *Nature* 380:207, each of which is incorporated by reference). Other analog nucleic acids include those with positive backbones (Denpcy, et al. (1995) *Proc. Natl. Acad. Sci. USA* 92:6097-101; non-ionic backbones (U.S. Pat. Nos. 5,386,023, 5,637,684, 5,602,240, 5,216,141 and 4,469,863; Kiedrowshi, et al. (1991) *Angew. Chem. Intl. Ed. English* 30:423-426; Letsinger, et al. (1988) *J. Am. Chem. Soc.* 110:4470; Letsinger, et al. (1994) *Nucleoside and Nucleotide* 13:1597-xxx; Chapters 2 and 3 in Sanghvi and Cook (eds. 1994) *Carbohydrate Modifications in Antisense Research* ACS Symposium Series 580; Mesmaeker, et al. (1994) *Bioorganic and Medicinal Chem. Lett.* 4:395-xxx; Jeffs, et al. (1994) *J. Biomolecular NMR* 34:17; Horn (1996) *Tetrahedron Lett.* 37:743-xxx) and non-ribose backbones, including those described in U.S. Pat. Nos. 5,235,033 and 5,034,506, and Chapters 6 and 7 in Sanghvi and Cook (eds. 1994) *Carbohydrate Modifications in Antisense Research* ACS Symposium Series 580. Nucleic acids containing one or more carbocyclic sugars are also included within one definition of nucleic acids (see Jenkins, et al. (1995) *Chem. Soc. Rev.* xx:169-176). Several nucleic acid analogs are described in Rawls (p. 35, Jun. 2, 1997) *C&E News*. Each of these references is hereby expressly incorporated by reference.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched base pairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the prostate cancer nucleic acids, proteins, and antibodies at virtually any position. Many methods for conjugating the antibody to the label may be employed, including those methods described by Hunter, et al. (1962) *Nature,* 144:945; David, et al. (1974) *Biochemistry* 13:1014-1021; Pain, et al. (1981) *J. Immunol. Meth.* 40:219-230; and Nygren (1982) *J. Histochem. and Cytochem.* 30:407-412.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found "Overview of principles of hybridization and the strategy of nucleic acid assays" in Tijssen (1993) *Hybridization with Nucleic Probes* (*Techniques in Biochemistry and Molecular Biology vol.* 24) Elsevier. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50-65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are provided, e.g., in Innis, et al. (1990) *PCR Protocols: A Guide to Methods and Applications* Academic Press, N.Y.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Ausubel, et al. (eds. 1991 and supplements) *Current Protocols in Molecular Biology*

The phrase "functional effects" in the context of assays for testing compounds that modulate activity of a prostate cancer protein includes the determination of a parameter that is indirectly or directly under the influence of the prostate cancer protein or nucleic acid, e.g., a functional, physical, or chemical effect, such as the ability to decrease prostate proliferation (malignant or non-malignant). It includes ligand binding activity; cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of prostate cancer cells. "Functional effects" include in vitro, in vivo, and ex vivo activities.

By "determining the functional effect" is meant assaying for a compound that increases or decreases a parameter that is indirectly or directly under the influence of a prostate cancer protein sequence, e.g., functional, enzymatic, physical and chemical effects. Such functional effects can be measured by means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the prostate cancer protein; measuring binding activity or binding assays, e.g., binding to antibodies or other ligands, and measuring cellular proliferation. Determination of the functional effect of a compound on prostate cancer can also be performed using prostate cancer assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of prostate cancer cells. The functional effects can be evaluated by many means known to those skilled in the art, e.g., microscopy for quantitative or qualitative measures of alterations in morphological features, measurement of changes in RNA or protein levels for prostate cancer-associated sequences, measurement of RNA stability, identification of downstream or reporter gene expression (CAT, luciferase, β-gal, GFP, and the like), e.g., via chemiluminescence, fluorescence, colorimetric reactions, antibody binding, inducible markers, and ligand binding assays.

"Inhibitors", "activators", and "modulators" of prostate cancer polynucleotide and polypeptide sequences are used to refer to activating, inhibitory, or modulating molecules or compounds identified using in vitro and in vivo assays of prostate cancer polynucleotide and polypeptide sequences. Inhibitors are compounds that, e.g., bind to, partially or totally block activity, decrease, prevent, delay activation, inactivate, desensitize, or down regulate the activity or expression of prostate cancer proteins, e.g., antagonists. Antisense nucleic acids may seem to inhibit expression and subsequent function of the protein. "Activators" are compounds that increase, open, activate, facilitate, enhance activation, sensitize, agonize, or up regulate prostate cancer protein activity. Inhibitors, activators, or modulators also include genetically modified versions of prostate cancer proteins, e.g., versions with altered activity, as well as naturally occurring and synthetic ligands, antagonists, agonists, antibodies, small chemical molecules and the like. Such assays for inhibitors and activators include, e.g., expressing the prostate cancer protein in vitro, in cells, or cell membranes, applying putative modulator compounds, and then determining the functional effects on activity, as described above. Activators and inhibitors of prostate cancer can also be identified by incubating prostate cancer cells with the test compound and determining increases or decreases in the expression of 1 or more prostate cancer proteins, e.g., 1, 2, 3, 4, 5, 10, 15, 20, 25, 30, 40, 50 or more prostate cancer proteins, such as prostate cancer proteins encoded by the sequences set out in Tables 1A-4.

Samples or assays comprising prostate cancer proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of a polypeptide is achieved when the activity value relative to the control is about 80%, preferably 50%, more preferably 25-0%. Activation of a prostate cancer polypeptide is achieved when the activity value relative to the control (untreated with activators) is 110%, more preferably 150%, more preferably 200-500% (i.e., two to five fold higher relative to the control), more preferably 1000-3000% higher.

The phrase "changes in cell growth" refers to a change in cell growth and proliferation characteristics in vitro or in vivo, such as cell viability, formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., pp. 231-241 in Freshney (1994) *Culture of Animal Cells: A Manual of Basic Technique* (3d ed.) Wiley-Liss.

"Tumor cell" refers to precancerous, cancerous, and/or normal cells in a tumor.

"Cancer cells," "transformed" cells, or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy. See, Freshney (2001) *Culture of Animal Cells: A Manual of Basic Technique* (4th ed.) Wiley-Liss.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, the antigen-binding region of an antibody or its functional equivalent will be most critical in specificity and affinity of binding. See Paul (ed. 1999) *Fundamental Immunology* (4th ed.) Raven.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce $F(ab)'_2$, a dimer of Fab which itself is a light chain joined to $V_H$—$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Paul (ed. 1993) *Fundamental Immunology* (3d ed.) Raven. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al. (1990) *Nature* 348:552-554.

For preparation of antibodies, e.g., recombinant, monoclonal, or polyclonal antibodies, many technique known in the art can be used (see, e.g., Kohler and Milstein (1975) *Nature* 256:495-497; Kozbor, et al. (1983) *Immunology Today* 4:72; pp. 77-96 in Cole, et al. (1985) *Monoclonal Antibodies and Cancer Therapy* Liss; Coligan (1991) *Current Protocols in Immunology* Lippincott; Harlow and Lane (1988) *Antibodies: A Laboratory Manual* CSH Press; and Goding (1986) *Monoclonal Antibodies: Principles and Practice* (2d ed.) Academic Press. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty, et al. (1990) *Nature* 348:552-554; Marks, et al. (1992) *Biotechnology* 10:779-783).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Identification of Prostate Cancer-associated Sequences

In one aspect, the expression levels of genes are determined in different patient samples for which diagnosis information is desired, to provide expression profiles. An expression profile of a particular sample is essentially a "fingerprint" of the state of the sample; while two states may have a particular gene similarly expressed, the evaluation of a number of genes simultaneously allows the generation of a gene expression profile that is characteristic of the state of the cell. That is, normal tissue (e.g., normal prostate or other tissue) may be distinguished from pathological prostate cells, e.g., cancerous or metastatic cancerous tissue of the prostate, or prostate cancer tissue or metastatic prostate cancerous tissue can be compared with tissue samples of prostate and other tissues from surviving cancer patients. By comparing expression profiles of tissue in known different prostate cancer states, information regarding which genes are important (including both up- and down-regulation of genes) in each of these states is obtained.

The identification of sequences that are differentially expressed in prostate cancer versus non-prostate cancer tissue allows the use of this information in a number of ways. For example, a particular treatment regime may be evaluated: does a chemotherapeutic drug act to down-regulate prostate cancer or other proliferative disorders, and thus tumor growth or recurrence, in a particular patient. Alternatively, a treatment step may induce other markers which may be used as targets to destroy tumor cells. Similarly, diagnosis and treatment outcomes may be done or confirmed by comparing patient samples with the known expression profiles. Maliganant disease may be compared to non-malignant conditions. Metastatic tissue can also be analyzed to determine the stage of prostate cancer in the tissue, or origin of primary tumor, e.g., metastasis from a remote primary site. Furthermore, these gene expression profiles (or individual genes) allow screening of drug candidates with an eye to mimicking or altering a particular expression profile; e.g., screening can be done for drugs that suppress the prostate cancer expression profile. This may be done by making biochips comprising sets of the important prostate cancer genes, which can then be used in these screens. These methods can also be done on the protein basis; that is, protein expression levels of the prostate cancer proteins can be evaluated for diagnostic purposes or to screen candidate agents. In addition, the prostate cancer nucleic acid sequences can be administered for gene therapy purposes, including the administration of antisense nucleic acids, or the prostate cancer proteins (including antibodies and other modulators thereof) administered as therapeutic drugs.

Thus the present invention provides nucleic acid and protein sequences that are differentially expressed in prostate cancer relative to normal tissues and/or non-malignant disease, or in different types of related diseases, herein termed "prostate cancer sequences." As outlined below, prostate cancer sequences include those that are up-regulated (i.e., expressed at a higher level) in prostate cancer, as well as those that are down-regulated (i.e., expressed at a lower level). In a preferred embodiment, the prostate cancer sequences are from humans; however, as will be appreciated by those in the art, prostate cancer sequences from other organisms may be useful in animal models of disease and drug evaluation; thus, other prostate cancer sequences are provided, from vertebrates, including mammals, including rodents (rats, mice, hamsters, guinea pigs, etc.), primates, farm animals (including sheep, goats, pigs, cows, horses, etc.) and pets, e.g., (dogs, cats, etc.). Prostate cancer sequences from other organisms may be obtained using the techniques outlined below.

Prostate cancer sequences can include both nucleic acid and amino acid sequences. As will be appreciated by those in the art and is more fully outlined below, prostate cancer nucleic acid sequences are useful in a variety of applications, including diagnostic applications, which will detect naturally occurring nucleic acids, as well as screening applications; e.g., biochips comprising nucleic acid probes or PCR microtiter plates with selected probes to the prostate cancer sequences can be generated.

A prostate cancer sequence can be initially identified by substantial nucleic acid and/or amino acid sequence homology to the prostate cancer sequences outlined herein. Such homology can be based upon the overall nucleic acid or amino acid sequence, and is generally determined as outlined below, using either homology programs or hybridization conditions.

For identifying prostate cancer-associated sequences, the prostate cancer screen typically includes comparing genes identified in different tissues, e.g., normal and cancerous tissues, or tumor tissue samples from patients who have metastatic disease vs. non metastatic tissue. Other suitable tissue comparisons include comparing prostate cancer samples with metastatic cancer samples from other cancers, such as lung, breast, gastrointestinal cancers, ovarian, etc. Samples of different stages of prostate cancer, e.g., survivor tissue, drug resistant states, and tissue undergoing metastasis, are applied to biochips comprising nucleic acid probes. The samples are first microdissected, if applicable, and treated as is known in the art for the preparation of mRNA. Suitable biochips are commercially available, e.g., from Affymetrix. Gene expression profiles are generated and the data analyzed.

In one embodiment, the genes showing changes in expression as between normal and disease states are compared to genes expressed in other normal tissues, preferably normal prostate, but also including, and not limited to lung, heart, brain, liver, breast, kidney, muscle, colon, small intestine, large intestine, spleen, bone, and placenta. In a preferred embodiment, those genes identified during the prostate cancer screen that are expressed in a significant amount in other tissues are removed from the profile, although in some embodiments, this is not necessary. That is, when screening for drugs, it is usually preferable that the target be disease specific, to minimize possible side effects on other organs were there expression.

In a preferred embodiment, prostate cancer sequences are those that are up-regulated in prostate cancer or related conditions; that is, the expression of these genes is higher in the prostate cancer tissue as compared to non-cancerous tissue. "Up-regulation" as used herein often means at least about a two-fold change, preferably at least about a three fold change, with at least about five-fold or higher being preferred. Another embodiment is directed to sequences up-regulated in non-malignant conditions relative to normal.

Unigene cluster identification numbers and accession numbers herein are for the GenBank sequence database and the sequences of the accession numbers are hereby expressly incorporated by reference. GenBank is known in the art, see, e.g., Benson, et al. (1998) *Nucleic Acids Research* 26:1-7 and http://www.ncbi.nlm.nih.gov/. Sequences are also available in other databases, e.g., European Molecular Biology Laboratory (EMBL) and DNA Database of Japan (DDBJ). U.S. patent application Ser. Nos. 09/687,576 and 09/976,858 (-001-3) further disclose related sequences, compositions, and methods of diagnosis and treatment of prostate cancer and related conditions and are hereby expressly incorporated by reference.

In another preferred embodiment, prostate cancer sequences are those that are down-regulated in the prostate cancer; that is, the expression of these genes is lower in prostate cancer tissue as compared to non-cancerous tissue. "Down-regulation" as used herein often means at least about a two-fold change, preferably at least about a three fold change, with at least about five-fold or higher being preferred.

Informatics

The ability to identify genes that are over or under expressed in prostate cancer can additionally provide high-resolution, high-sensitivity datasets which can be used in the areas of diagnostics, therapeutics, drug development, pharmacogenetics, protein structure, biosensor development, and other related areas. For example, the expression profiles can be used in diagnostic or prognostic evaluation of patients with prostate cancer. Or as another example, subcellular toxicological information can be generated to better direct drug structure and activity correlation (see Anderson, *Pharmaceutical Proteomics: Targets Mechanism, and Function*, paper presented at the IBC Proteomics conference, Coronado, Calif. (Jun. 11-12, 1998)). Subcellular toxicological information can also be utilized in a biological sensor device to predict the likely toxicological effect of chemical exposures and likely tolerable exposure thresholds (see U.S. Pat. No. 5,811,231). Similar advantages accrue from datasets relevant to other biomolecules and bioactive agents (e.g., nucleic acids, saccharides, lipids, drugs, and the like).

Thus, in another embodiment, the present invention provides a database that includes at least one set of assay data. The data contained in the database is acquired, e.g., using array analysis either singly or in a library format. The database can be in a form in which data can be maintained and transmitted, but is preferably an electronic database. The electronic database of the invention can be maintained on an electronic device allowing for the storage of and access to the database, such as a personal computer, but is preferably distributed on a wide area network, such as the World Wide Web.

The focus of the present section on databases that include peptide sequence data is for clarity of illustration only. It will be apparent to those of skill in the art that similar databases can be assembled for assay data acquired using an assay of the invention.

The compositions and methods for identifying and/or quantitating the relative and/or absolute abundance of a variety of molecular and macromolecular species from a biological sample undergoing prostate cancer, i.e., the identification of prostate cancer-associated sequences described herein, provide an abundance of information, which can be correlated with pathological conditions, predisposition to disease, drug testing, therapeutic monitoring, gene-disease causal linkages, identification of correlates of immunity and physiological status, among others. Although the data generated from the assays of the invention is suited for manual review and analysis, in a preferred embodiment, prior data processing using high-speed computers is utilized.

An array of methods for indexing and retrieving biomolecular information is known in the art. For example, U.S. Pat. Nos. 6,023,659 and 5,966,712 disclose a relational database system for storing biomolecular sequence information in a manner that allows sequences to be catalogued and searched according to one or more protein function hierarchies. U.S. Pat. No. 5,953,727 discloses a relational database having sequence records containing information in a format that allows a collection of partial-length DNA sequences to be catalogued and searched according to association with one or more sequencing projects for obtaining full-length sequences from the collection of partial length sequences. U.S. Pat. No. 5,706,498 discloses a gene database retrieval system for making a retrieval of a gene sequence similar to a sequence data item in a gene database based on the degree of similarity between a key sequence and a target sequence. U.S. Pat. No. 5,538,897 discloses a method using mass spectroscopy fragmentation patterns of peptides to identify amino acid sequences in computer databases by comparison of predicted mass spectra with experimentally-derived mass spectra using a closeness-of-fit measure. U.S. Pat. No. 5,926,818 discloses a multi-dimensional database comprising a functionality for multi-dimensional data analysis described as on-line analytical processing (OLAP), which entails the consolidation of projected and actual data according to more than one consolidation path or dimension. U.S. Pat. No. 5,295,261 reports a hybrid database structure in which the fields of each database record are divided into two classes, navigational and informational data, with navigational fields stored in a hierarchical topological map which can be viewed as a tree structure or as the merger of two or more such tree structures.

See also Mount, et al. (2001) *Bioinformatics* CSH Press; Durbin, et al. (eds. 1999) *Biological Sequence Analysis: Probabilistic Models of Proteins and Nucleic Acids* Cambridge Univ. Press; Baxevanis and Oeullette (eds., 1998) *Bioinformatics: A Practical Guide to the Analysis of Genes and Proteins* Wiley-Liss; Rashidi and Buehler (1999) *Bioinformatics: Basic Applications in Biological Science and Medicine* CRC Press; Setubal, et al. (eds. 1997) *Introduction to Computational Molecular Biology* Brooks/Cole; Misener and Krawetz (eds. 2000) *Bioinformatics: Methods and Protocols* Human Press; Higgins and Taylor (eds. 2000) *Bioinformatics: Sequence, Structure, and Databanks: A Practical Approach* Oxford Univ. Press; Brown (2001) *Bioinformatics: A Biologist's Guide to Biocomputing and the Internet* Eaton Pub; Han and Kamber (2000) *Data Mining: Concepts and Techniques* Kaufmann Pub.; and Waterman (1995) *Introduction to Computational Biology: Maps, Sequences, and Genomes* Chap and Hall.

The present invention provides a computer database comprising a computer and software for storing in computer-retrievable form assay data records cross-tabulated, e.g., with data specifying the source of the target-containing sample from which each sequence specificity record was obtained.

In an exemplary embodiment, at least one of the sources of target-containing sample is from a control tissue sample known to be free of pathological disorders. In a variation, at least one of the sources is a known pathological tissue specimen, e.g., a neoplastic lesion or another tissue specimen to be analyzed for prostate cancer. In another variation, the assay records cross-tabulate one or more of the following parameters for each target species in a sample: (1) a unique identification code, which can include, e.g., a target molecular structure and/or characteristic separation coordinate (e.g., electrophoretic coordinates); (2) sample source; and (3) absolute and/or relative quantity of the target species present in the sample.

The invention also provides for the storage and retrieval of a collection of target data in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the target data records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor). In one embodiment, the invention provides such storage devices, and computer systems built therewith, comprising a bit pattern encoding a protein expression fingerprint record comprising unique identifiers for at least 10 target data records cross-tabulated with target source.

When the target is a peptide or nucleic acid, the invention preferably provides a method for identifying related peptide or nucleic acid sequences, comprising performing a computerized comparison between a peptide or nucleic acid sequence assay record stored in or retrieved from a computer storage device or database and at least one other sequence. The comparison can include a sequence analysis or comparison algorithm or computer program embodiment thereof (e.g., FASTA, TFASTA, GAP, BESTFIT) and/or the comparison may be of the relative amount of a peptide or nucleic acid sequence in a pool of sequences determined from a polypeptide or nucleic acid sample of a specimen.

The invention also preferably provides a magnetic disk, such as an IBM-compatible (DOS, Windows, Windows95/98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding data from an assay of the invention in a file format suitable for retrieval and processing in a computerized sequence analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The invention also provides a method for transmitting assay data that includes generating an electronic signal on an electronic communications device, such as a modem, ISDN terminal adapter, DSL, cable modem, ATM switch, or the like, wherein the signal includes (in native or encrypted format) a bit pattern encoding data from an assay or a database comprising a plurality of assay results obtained by the method of the invention.

In a preferred embodiment, the invention provides a computer system for comparing a query target to a database containing an array of data structures, such as an assay result obtained by the method of the invention, and ranking database targets based on the degree of identity and gap weight to the target data. A central processor is preferably initialized to load and execute the computer program for alignment and/or comparison of the assay results. Data for a query target is entered into the central processor via an I/O device. Execution of the computer program results in the central processor retrieving the assay data from the data file, which comprises a binary description of an assay result.

The target data or record and the computer program can be transferred to secondary memory, which is typically random access memory (e.g., DRAM, SRAM, SGRAM, or SDRAM). Targets are ranked according to the degree of correspondence between a selected assay characteristic (e.g., binding to a selected affinity moiety) and the same characteristic of the query target and results are output via an I/O device. For example, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

The invention also preferably provides the use of a computer system, such as that described above, which comprises: (1) a computer; (2) a stored bit pattern encoding a collection of peptide sequence specificity records obtained by the methods of the invention, which may be stored in the computer; (3) a comparison target, such as a query target; and (4) a program for alignment and comparison, typically with rank-ordering of comparison results on the basis of computed similarity values.

Characteristics of Prostate Cancer-associated Proteins

Prostate cancer proteins of the present invention may be classified as secreted proteins, transmembrane proteins, or intracellular proteins. In one embodiment, the prostate cancer protein is an intracellular protein. Intracellular proteins may be found in the cytoplasm and/or in the nucleus. Intracellular proteins are involved in all aspects of cellular function and replication (including, e.g., signaling pathways); aberrant expression of such proteins often results in unregulated or disregulated cellular processes (see, e.g., Alberts (ed. 1994) *Molecular Biology of the Cell* (3d ed.) Garland. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

An increasingly appreciated concept in characterizing proteins is the presence in the proteins of one or more structural motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of amino acid sequence; thus, an analysis of the sequence of proteins may provide insight into both the enzymatic potential of the molecule and/or molecules with which the protein may associate. One useful database is Pfam (protein families), which is a large collection of multiple sequence alignments and hidden Markov models covering many common protein domains. Versions are available via the internet from Washington University in St. Louis, the Sanger Center in England, and the Karolinska Institute in Sweden (see, e.g., Bateman, et al. (2000) *Nuc. Acids Res.* 28:263-266; Sonnhammer, et al. (1997) *Proteins* 28:405-420; Bateman, et al. (1999) *Nuc. Acids Res.* 27:260-262; and Sonnhammer, et al. (1998) *Nuc. Acids Res.* 26:320-322.

In another embodiment, the prostate cancer sequences are transmembrane proteins. Transmembrane proteins are molecules that span a phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors such as G protein coupled receptors (GPCRs) are classified as "seven transmembrane domain" proteins, as they contain 7 membrane spanning regions. Characteristics of transmembrane domains include approximately 17 consecutive hydrophobic amino acids that may be followed by charged amino acids. Therefore, upon analysis of the amino acid sequence of a particular protein, the localization and number of transmembrane domains within the protein may be predicted (see, e.g., PSORT web site http://psort.nibb.ac.jp/). Important transmembrane-protein receptors include, but are not limited to the insulin receptor, insulin-like growth factor receptor, human growth hormone receptor, glucose transporters, transferrin receptor, epidermal growth factor receptor, low density lipoprotein receptor, epidermal growth factor receptor, leptin receptor, and interleukin receptors, e.g., IL-1 receptor, IL-2 receptor, etc.

The extracellular domains of transmembrane proteins are diverse; however, conserved motifs are found repeatedly among various extracellular domains. Conserved structure and/or functions have been ascribed to different extracellular motifs. Many extracellular domains are involved in binding to other molecules. In one aspect, extracellular domains are found on receptors. Factors that bind the receptor domain include circulating ligands, which may be peptides, proteins, or small molecules such as adenosine and the like. For example, growth factors such as EGF, FGF, and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell-cell interactions. Cell-associated ligands can be tethered to the cell, e.g., via a glycosylphosphatidylinositol (GPI) anchor, or may themselves be transmembrane proteins. Extracellular domains also associate with the extracellular matrix and contribute to the maintenance of the cell structure.

Prostate cancer proteins that are transmembrane are particularly preferred in the present invention as they are readily accessible targets for immunotherapeutics, as are described herein. In addition, as outlined below, transmembrane proteins can be also useful in imaging modalities. Antibodies may be used to label such readily accessible proteins in situ. Alternatively, antibodies can also label intracellular proteins, in which case samples are typically permeabilized to provide access to intracellular proteins. In addition, some membrane proteins can be processed to release a soluble protein, or to expose a residual fragment. Released soluble proteins may be useful diagnostic markers, processed residual protein fragments may be useful prostate markers of disease.

It will also be appreciated by those in the art that a transmembrane protein can be made soluble by removing transmembrane sequences, e.g., through recombinant methods. Furthermore, transmembrane proteins that have been made soluble can be made to be secreted through recombinant means by adding an appropriate signal sequence.

In another embodiment, the prostate cancer proteins are secreted proteins; the secretion of which can be either constitutive or regulated. These proteins may have a signal peptide or signal sequence that targets the molecule to the secretory pathway. Secreted proteins are involved in numerous physiological events; by virtue of their circulating nature, they often serve to transmit signals to various other cell types. The secreted protein may function in an autocrine manner (acting on the cell that secreted the factor), a paracrine manner (acting on cells in close proximity to the cell that secreted the factor), an endocrine manner (acting on cells at a distance, e.g, secretion into the blood stream), or an exocrine manner (secretion, e.g., through a duct or to adjacent epithelial surface as sweat glands, sebaceous glands, pancreatic ducts, lacrimal glands, mammary glands, sax producing glands of the ear, etc.). Thus secreted molecules find use in modulating or altering numerous aspects of physiology. Prostate cancer proteins that are secreted proteins are particularly preferred in the present invention as they serve as good targets for diagnostic markers, e.g., for blood, plasma, serum, or stool tests. Those which are enzymes may be antibody or small molecule targets. Others may be useful as vaccine targets, e.g., via CTL mechanisms.

Use of Prostate Cancer Nucleic Acids

As described above, prostate cancer sequence is initially identified by substantial nucleic acid and/or amino acid sequence homology or linkage to the prostate cancer sequences outlined herein. Such homology can be based upon the overall nucleic acid or amino acid sequence, and is generally determined as outlined below, using either homology programs or hybridization conditions. Typically, linked sequences on a mRNA are found on the same molecule.

The prostate cancer nucleic acid sequences of the invention, e.g., the sequences in Tables 1A-4, can be fragments of larger genes, i.e., they are nucleic acid segments. "Genes" in this context includes coding regions, non-coding regions, and mixtures of coding and non-coding regions. Accordingly, as will be appreciated by those in the art, using the sequences provided herein, extended sequences, in either direction, of the prostate cancer genes can be obtained, using techniques well known in the art for cloning either longer sequences or the full length sequences; see Ausubel, et al., supra. Much can be done by informatics and many sequences can be clustered to include multiple sequences corresponding to a single gene, e.g., systems such as UniGene (see, http://www.ncbi.nlm.nih.gov/UniGene/).

Once the prostate cancer nucleic acid is identified, it can be cloned and, if necessary, its constituent parts recombined to form the entire prostate cancer nucleic acid coding regions or the entire mRNA sequence. Once isolated from its natural source, e.g., contained within a plasmid or other vector or excised therefrom as a linear nucleic acid segment, the recombinant prostate cancer nucleic acid can be further-used as a probe to identify and isolate other prostate cancer nucleic acids, e.g., extended coding regions. It can also be used as a "precursor" nucleic acid to make modified or variant prostate cancer nucleic acids and proteins.

The prostate cancer nucleic acids of the present invention are used in several ways. In a first embodiment, nucleic acid probes to the prostate cancer nucleic acids are made and attached to biochips to be used in screening and diagnostic methods, as outlined below, or for administration, e.g., for gene therapy, vaccine, and/or antisense applications. Alternatively, the prostate cancer nucleic acids that include coding regions of prostate cancer proteins can be put into expression vectors for the expression of prostate cancer proteins, again for screening purposes or for administration to a patient.

In a preferred embodiment, nucleic acid probes to prostate cancer nucleic acids (both the nucleic acid sequences outlined in the figures and/or the complements thereof) are made. The nucleic acid probes attached to the biochip are designed to be substantially complementary to the prostate cancer nucleic acids, i.e., the target sequence (either the target sequence of the sample or to other probe sequences, e.g., in sandwich assays), such that hybridization of the target sequence and the probes of the present invention occurs. As outlined below, this complementarity need not be perfect; there may be base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e., have some sequence in common), or separate. In some cases, PCR primers may be used to amplify signal for higher sensitivity.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can typically be covalent or non-covalent. By "non-covalent binding" and grammatical equivalents herein is meant one or more of electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant a material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluoresce. A preferred substrate is described in WO0055627, herein incorporated by reference in its entirety.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, e.g., the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, e.g., using linkers as are known in the art; e.g., homo- or hetero-bifunctional linkers as are well known (see 1994 Pierce Chemical Company catalog, technical section on cross-linkers, pages 155-200). In addition, in some cases, additional linkers, such as alkyl groups (including substituted and heteroalkyl groups) may be used.

In this embodiment, oligonucleotides are synthesized as is known in the art, and then attached to the surface of the solid support. As will be appreciated by those skilled in the art, either the 5' or 3' terminus may be attached to the solid support, or attachment may be via an internal nucleoside.

In another embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affymetrix GeneChip™ technology.

Often, amplification-based assays are performed to measure the expression level of prostate cancer-associated sequences. These assays are typically performed in conjunction with reverse transcription. In such assays, a prostate cancer-associated nucleic acid sequence acts as a template in an amplification reaction (e.g., Polymerase Chain Reaction, or PCR). In a quantitative amplification, the amount of amplification product will be proportional to the amount of template in the original sample. Comparison to appropriate controls provides a measure of the amount of prostate cancer-associated RNA. Methods of quantitative amplification are well known to those of skill in the art. Detailed protocols for quantitative PCR are provided, e.g., in Innis, et al. (1990) *PCR Protocols: A Guide to Methods and Applications* Academic Press.

In some embodiments, a TaqMan based assay is used to measure expression. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, e.g., literature provided by Perkin-Elmer, e.g., www2.perkin-elmer.com).

Other suitable amplification methods include, but are not limited to, ligase chain reaction (LCR)(see Wu and Wallace (1989) *Genomics* 4:560-569, Landegren, et al. (1988) *Science* 241:1077-1080, and Barringer, et al. (1990) *Gene* 89:117-122), transcription amplification (Kwoh, et al. (1989) *Proc. Natl. Acad. Sci. USA* 86:1173-1177), self-sustained sequence replication (Guatelli, et al. (1990) *Proc. Nat. Acad. Sci. USA* 87:1874-1878), dot PCR, and linker adapter PCR, etc.

Expression of Prostate Cancer Proteins from Nucleic Acids

In a preferred embodiment, prostate cancer nucleic acids, e.g., encoding prostate cancer proteins are used to make a variety of expression vectors to express prostate cancer proteins which can then be used in screening assays, as described below. Expression vectors and recombinant DNA technology are well known to those of skill in the art (see, e.g., Ausubel, supra, and Fernandez and Hoeffler (eds. 1999) *Gene Expression Systems* Academic Press) and are used to express proteins. The expression vectors may be either self-replicating extrachromosomal vectors or vectors which integrate into a host genome. Generally, these expression vectors include transcriptional and translational regulatory nucleic acid operably linked to the nucleic acid encoding the prostate cancer protein. The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation, and sequences may be operably linked when they are physically linked on the same molecule. Generally, "operably linked" means that the DNA sequences being linked are contiguous, and, in the case of a secretory leader, contiguous and in reading phase. However, enhancers do not have to be contiguous. Linking is typically accomplished by ligation at convenient restriction sites. If such sites do not exist, synthetic oligonucleotide adaptors or linkers are used in accordance with conventional practice. Transcriptional and translational regulatory nucleic acid will generally be appropriate to the host cell used to express the prostate cancer protein. Numerous types of appropriate expression vectors, and suitable regulatory sequences are known in the art for a variety of host cells.

In general, transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, an expression vector may comprise additional elements. For example, the expression vector may have two replication systems, thus allowing it to be maintained in two organisms, e.g., in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art (e.g., Fernandez and Hoeffler, supra).

In addition, in a preferred embodiment, the expression vector contains a selectable marker gene to allow the selection of transformed host cells. Selection genes are well known in the art and will vary with the host cell used.

The prostate cancer proteins of the present invention are produced by culturing a host cell transformed with an expression vector containing nucleic acid encoding a prostate cancer protein, under the appropriate conditions to induce or cause expression of the prostate cancer protein. Conditions appropriate for prostate cancer protein expression will vary with the choice of the expression vector and the host cell, and will be easily ascertained by one skilled in the art through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Saccharomyces cerevisiae* and other yeasts, *E. coli, Bacillus subtilis*, Sf9 cells, C129 cells, 293 cells, *Neurospora*, BHK, CHO, COS, HeLa cells, HUVEC (human umbilical vein endothelial cells), THP1 cells (a macrophage cell line) and various other human cells and cell lines.

In a preferred embodiment, the prostate cancer proteins are expressed in mammalian cells. Mammalian expression systems are also known in the art, and include retroviral and adenoviral systems. One expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter (see, e.g., Fernandez and Hoeffler, supra). Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, prostate cancer proteins are expressed in bacterial systems. Bacterial expression systems are well known in the art. Promoters from bacteriophage may also be used and are known in the art. In addition, synthetic promoters and hybrid promoters are also useful; e.g., the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the prostate cancer protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others (e.g., Fernandez and Hoeffler, supra). The bacterial expression vectors are transformed into bacterial host cells using techniques well known in the art, such as calcium chloride treatment, electroporation, and others.

In one embodiment, prostate cancer proteins are produced in insect cells. Expression vectors for the transformation of insect cells, and in particular, baculovirus-based expression vectors, are well known in the art.

In a preferred embodiment, prostate cancer protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica.*

The prostate cancer protein may also be made as a fusion protein, using techniques well known in the art. Thus, e.g., for the creation of monoclonal antibodies, if the desired epitope is small, the prostate cancer protein may be fused to a carrier protein to form an immunogen. Alternatively, the prostate cancer protein may be made as a fusion protein to increase expression, or for other reasons. For example, when the prostate cancer protein is a prostate cancer peptide, the nucleic acid encoding the peptide may be linked to other nucleic acid for expression purposes.

In a preferred embodiment, the prostate cancer protein is purified or isolated after expression. Prostate cancer proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the prostate cancer protein may be purified using a standard anti-prostate cancer protein antibody column. Ultrafiltration and diafiltration techniques, in conjunction with protein concentration, are also useful. For general guidance in suitable purification techniques, see Scopes (1982) *Protein Purification* Springer-Verlag. The degree of purification necessary will vary depending on the use of the prostate cancer protein. In some instances no purification will be necessary.

Once expressed and purified if necessary, the prostate cancer proteins and nucleic acids are useful in a number of applications. They may be used as immunoselection reagents, as vaccine reagents, as screening agents, etc.

Variants of Prostate Cancer Proteins

In one embodiment, the prostate cancer proteins are derivative or variant prostate cancer proteins as compared to the wild-type sequence. That is, as outlined more fully below, the derivative prostate cancer peptide will often contain at least one amino acid substitution, deletion or insertion, with amino acid substitutions being particularly preferred. The amino acid substitution, insertion, or deletion may occur at most any residue within the prostate cancer peptide.

Also included within one embodiment of prostate cancer proteins of the present invention are amino acid sequence variants. These variants typically fall into one or more of three classes: substitutional, insertional, or deletional variants. These variants ordinarily are prepared by site specific mutagenesis of nucleotides in the DNA encoding the prostate cancer protein, using cassette or PCR mutagenesis or other techniques well known in the art, to produce DNA encoding the variant, and thereafter expressing the DNA in recombinant cell culture as outlined above. However, variant prostate cancer protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the prostate cancer protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed prostate cancer variants screened for the optimal combination of desired activity. Techniques for making substitution mutations at predetermined sites in DNA having a known sequence are well known, e.g., M13 primer mutagenesis and PCR mutagenesis. Screening of the mutants is done using assays of prostate cancer protein activities.

Amino acid substitutions are typically of single residues, insertions usually will be on the order of from about 1 to 20 amino acids, although considerably larger insertions may be tolerated. Deletions range from about 1 to about 20 residues, although in some cases deletions may be much larger.

Substitutions, deletions, insertions or a combination thereof may be used to arrive at a final derivative. Generally these changes are done on a few amino acids to minimize the alteration of the molecule. However, larger changes may be tolerated in certain circumstances. When small alterations in the characteristics of the prostate cancer protein are desired, substitutions are generally made in accordance with the amino acid substitution relationships provided in the definition section.

The variants typically exhibit the same qualitative biological activity and will elicit the same immune response as the naturally-occurring analog, although variants also are selected to modify the characteristics of the prostate cancer proteins as needed. Alternatively, the variant may be designed such that the biological activity of the prostate cancer protein is altered. For example, glycosylation sites may be altered or removed.

Substantial changes in function or immunological identity are made by selecting substitutions that are less conservative than those described above. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., serinyl or threonyl is substituted for (or by) a hydrophobic residue, e.g., leucyl, isoleucyl, phenylalanyl, valyl or alanyl; (b) a cysteine or proline is substituted for (or by) another residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Covalent modifications of prostate cancer polypeptides are included within the scope of this invention. One type of covalent modification includes reacting targeted amino acid residues of a prostate cancer polypeptide with an organic derivatizing agent that is capable of reacting with selected side chains or the N- or C-terminal residues of a prostate cancer polypeptide. Derivatization with bifunctional agents is useful, for instance, for crosslinking prostate cancer polypeptides to a water-insoluble support matrix or surface for use in the method for purifying anti-prostate cancer polypeptide antibodies or screening assays, as is more fully described below. Commonly used crosslinking agents include, e.g., 1,1-bis(diazoacetyl)-2-phenylethane, glutaraldehyde, N-hydroxysuccinimide esters, e.g., esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-((p-azidophenyl)dithio) propioimidate.

Other modifications include deamidation of glutaminyl and asparaginyl residues to the corresponding glutamyl and aspartyl residues, respectively, hydroxylation of proline and lysine, phosphorylation of hydroxyl groups of serinyl, threonyl or tyrosyl residues, methylation of the amino groups of the lysine, arginine, and histidine side chains (e.g., pp. 79-86, Creighton (1983) *Proteins: Structure and Molecular Properties* Freeman), acetylation of the N-terminal amine, and amidation of a C-terminal carboxyl group.

Another type of covalent modification of the prostate cancer polypeptide included within the scope of this invention comprises altering the native glycosylation pattern of the polypeptide. "Altering the native glycosylation pattern" is intended for purposes herein to mean deleting one or more carbohydrate moieties found in native sequence prostate cancer polypeptide, and/or adding one or more glycosylation sites that are not present in the native sequence prostate cancer polypeptide. Glycosylation patterns can be altered in many ways. For example the use of different cell types to express prostate cancer-associated sequences can result in different glycosylation patterns.

Addition of glycosylation sites to prostate cancer polypeptides may also be accomplished by altering the amino acid sequence thereof. The alteration may be made, e.g., by the addition of, or substitution by, one or more serine or threonine residues to the native sequence prostate cancer polypeptide (for O-linked glycosylation sites). The prostate cancer amino acid sequence may optionally be altered through changes at the DNA level, particularly by mutating the DNA encoding the prostate cancer polypeptide at preselected bases such that codons are generated that will translate into the desired amino acids.

Another means of increasing the number of carbohydrate moieties on the prostate cancer polypeptide is by chemical or enzymatic coupling of glycosides to the polypeptide. Such methods are described in the art, e.g., in WO 87/05330, and pp. 259-306 in Aplin and Wriston (1981) *CRC Crit. Rev. Biochem.*

Removal of carbohydrate moieties present on the prostate cancer polypeptide may be accomplished chemically or enzymatically or by mutational substitution of codons encoding for amino acid residues that serve as targets for glycosylation. Chemical deglycosylation techniques are known in the art and described, e.g., by Hakimuddin, et al. (1987) *Arch. Biochem. Biophys.* 259:52-57; and Edge, et al. (1981) *Anal. Biochem.* 118:131-137. Enzymatic cleavage of carbohydrate moieties on polypeptides can be achieved by the use of a variety of endo- and exo-glycosidases as described by Thotakura, et al. (1987) *Meth. Enzymol.* 138:350-359.

Another type of covalent modification of prostate cancer comprises linking the prostate cancer polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337.

Prostate cancer polypeptides of the present invention may also be modified in a way to form chimeric molecules comprising a prostate cancer polypeptide fused to another, heterologous polypeptide or amino acid sequence. In one embodiment, such a chimeric molecule comprises a fusion of a prostate cancer polypeptide with a tag polypeptide which provides an epitope to which an anti-tag antibody can selectively bind. The epitope tag is generally placed at the amino- or carboxyl-terminus of the prostate cancer polypeptide. The presence of such epitope-tagged forms of a prostate cancer polypeptide can be detected using an antibody against the tag polypeptide. Also, provision of the epitope tag enables the prostate cancer polypeptide to be readily purified by affinity purification using an anti-tag antibody or another type of affinity matrix that binds to the epitope tag. In an alternative embodiment, the chimeric molecule may comprise a fusion of a prostate cancer polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; HIS6 and metal chelation tags, the flu HA tag polypeptide and its antibody 12CA5 (Field, et al. (1988) *Mol. Cell. Biol.* 8:2159-2165; the c-myc tag and the 8F9, 3C7, 6E10, G4, B7, and 9E10 antibodies thereto (Evan, et al. (1985) *Molecular and Cellular Biology* 5:3610-3616); and the Herpes Simplex virus glycoprotein D (gD) tag and its antibody (Paborsky, et al. (1990) *Protein Engineering* 3:547-553). Other tag polypeptides include the Flag-peptide (Hopp, et al. (1988) *BioTechnology* 6:1204-1210); the KT3 epitope peptide (Martin, et al. (1992) *Science* 255:192-194); tubulin epitope peptide (Skinner, et al. (1991) *J. Biol. Chem.* 266:15163-15166); and the T7 gene 10 protein peptide tag (Lutz-Freyermuth, et al. (1990) *Proc. Natl. Acad. Sci. USA* 87:6393-6397).

Also included are other prostate cancer proteins of the prostate cancer family, and prostate cancer proteins from other organisms, which are cloned and expressed as outlined below. Thus, probe or degenerate polymerase chain reaction (PCR) primer sequences may be used to find other related prostate cancer proteins from humans or other organisms. As will be appreciated by those in the art, particularly useful probe and/or PCR primer sequences include the unique areas of the prostate cancer nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art (e.g., Innis, *PCR Protocols*, supra).

Antibodies to Prostate Cancer Proteins

In a preferred embodiment, when the prostate cancer protein is to be used to generate antibodies, e.g., for immunotherapy or immunodiagnosis, the prostate cancer protein should share at least one epitope or determinant with the full length protein. By "epitope" or "determinant" herein is typically meant a portion of a protein which will generate and/or bind an antibody or T-cell receptor in the context of MHC. Thus, in most instances, antibodies made to a smaller prostate cancer protein will be able to bind to the full-length protein, particularly linear epitopes. In a preferred embodiment, the epitope is unique; that is, antibodies generated to a unique epitope show little or no cross-reactivity.

Methods of preparing polyclonal antibodies are known to the skilled artisan (e.g., Coligan, supra; and Harlow and Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine-thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein (1975) *Nature* 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Tables 1A-4 or fragment thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) *Monoclonal Antibodies: Principles and Practice* Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for a protein encoded by a nucleic acid of Tables 1A-4 or a fragment thereof, the other one is for another antigen, and preferably for a cell-surface protein or receptor or receptor subunit, preferably one that is tumor specific. Alternatively, tetramer-type technology may create multivalent reagents.

In a preferred embodiment, the antibodies to prostate cancer protein are capable of reducing or eliminating a biological function of a prostate cancer protein, as is described below. That is, the addition of anti-prostate cancer protein antibodies (either polyclonal or preferably monoclonal) to prostate cancer tissue (or cells containing prostate cancer) may reduce or eliminate the prostate cancer. Generally, at least a 25% decrease in activity, growth, size or the like is preferred, with at least about 50% being particularly preferred and about a 95-100% decrease being especially preferred.

In a preferred embodiment the antibodies to the prostate cancer proteins are humanized antibodies (e.g., Xenerex Biosciences; Medarex, Inc.; Abgenix, Inc.; Protein Design Labs, Inc.). Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones, et al. (1986) *Nature* 321:522-525; Riechmann, et al. (1988) *Nature* 332:323-329; and Presta (1992) *Curr. Op. Struct. Biol.* 2:593-596). Humanization can be essentially performed following methods of Winter and co-workers (see, e.g., Jones, et al. (1986) *Nature* 321:522-525; Riechmann, et al. (1988) *Nature* 332:323-327; and Verhoeyen, et al. (1988) *Science* 239:1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom and Winter (1991) *J. Mol. Biol.* 227:381-388; Marks, et al. (1991) *J. Mol. Biol.* 222:581-597) or the preparation of human monoclonal antibodies (e.g., p 77 in Cole, et al. (1985) *Monoclonal Antibodies and Cancer Therapy* Liss; and Boerner, et al. (1991) *J. Immunol.* 147(1):86-95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks, et al. (1992) *Bio/Technology* 10:779-783; Lonberg, et al. (1994) *Nature* 368:856-859; Morrison (1994) *Nature* 368:812-13; Fishwild, et al. (1996) *Nature Biotechnology* 14:845-51; Neuberger (1996) *Nature Biotechnology* 14:826; Lonberg and Huszar (1995) *Intern. Rev. Immunol.* 13:65-93.

By immunotherapy is meant treatment of prostate cancer with an antibody raised against prostate cancer proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen, leading to an immune response.

In a preferred embodiment the prostate cancer proteins against which antibodies are raised are secreted proteins as described above. Without being bound by theory, antibodies used for treatment, bind and prevent the secreted protein from binding to its receptor, thereby inactivating the secreted prostate cancer protein.

In another preferred embodiment, the prostate cancer protein to which antibodies are raised is a transmembrane protein. Without being bound by theory, antibodies used for treatment bind the extracellular domain of the prostate cancer protein and prevent it from binding to other proteins, such as circulating ligands or cell-associated molecules. The antibody may cause down-regulation of the transmembrane prostate cancer protein. As will be appreciated by one of ordinary skill in the art, the antibody may be a competitive, non-competitive or uncompetitive inhibitor of protein binding to the extracellular domain of the prostate cancer protein. The antibody is also often an antagonist of the prostate cancer protein. Further, the antibody may prevent activation of the transmembrane prostate cancer protein. In one aspect, when the antibody prevents the binding of other molecules to the prostate cancer protein, the antibody prevents growth of the cell. The antibody may also be used to target or sensitize the cell to cytotoxic agents, including, but not limited to TNF-$\alpha$, TNF-$\beta$, IL-1, INF-$\gamma$, and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity or antigen-dependent cytotoxicity (ADCC). Thus, prostate cancer is treated by administering to a patient antibodies directed against the transmembrane prostate cancer protein. Antibody-labeling may activate a co-toxin, localized toxin payload, or otherwise provide means to locally ablate cells.

In another preferred embodiment, the antibody is conjugated to an effector moiety. The effector moiety can be a labeling moiety such as a radioactive label or fluorescent label, or can be a therapeutic moiety. In one aspect the therapeutic moiety is a small molecule that modulates the activity of the prostate cancer protein. In another aspect the therapeutic moiety modulates the activity of molecules associated with or in close proximity to the prostate cancer protein. The therapeutic moiety may inhibit enzymatic activity such as protease or collagenase or protein kinase activity associated with prostate cancer.

In a preferred embodiment, the therapeutic moiety can also be a cytotoxic agent. In this method, targeting the cytotoxic agent to prostate cancer tissue or cells, results in a reduction in the number of afflicted cells, thereby reducing symptoms associated with prostate cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, saporin, auristatin, and the like. Cytotoxic agents also include radiochemicals made by conjugating radioisotopes to antibodies raised against prostate cancer proteins, or binding of a radionuclide to a chelating agent that has been covalently attached to the antibody. Targeting the therapeutic moiety to transmembrane prostate cancer proteins not only serves to increase the local concentration of therapeutic moiety in the prostate cancer afflicted area, but also serves to reduce deleterious side effects, e.g., by binding to normal tissues, that may be associated with the therapeutic moiety.

In another preferred embodiment, the prostate cancer protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the prostate cancer protein can be targeted within a cell, i.e., the nucleus, an antibody thereto contains a signal for that target localization, i.e., a nuclear localization signal.

The prostate cancer antibodies of the invention specifically bind to prostate cancer proteins. By "specifically bind" herein is meant that the antibodies bind to the protein with a $K_d$ of at least about 0.1 mM, more usually at least about 1 μM, preferably at least about 0.1 μM or better, and most preferably, 0.01 μM or better. Selectivity of binding is also important.

Detection of Prostate Cancer Sequence for Diagnostic and Therapeutic Applications In one aspect, the RNA expression levels of genes are determined for different cellular states in the prostate cancer phenotype. After androgen ablation therapy, cells that survive the therapy undergo a period of quiescence followed at sometime later by active cell division. As explained above, there are a variety of expression patterns characteristic of the prostate cancer genes involved in androgen-independent prostate cancer. Some genes are expressed early in the time course following ablation therapy, then drop off in expression, and then express again with emergence of androgen-independence (hi-lo-hi pattern in 1A). Other genes are expressed early in the time course following ablation therapy, then drop off in expression, and do not express again with emergence of androgen-independence (hi-lo-lo pattern in Table 1A). Still other genes are not expressed early in the time course, but express only with emergence of androgen-independence (lo-lo-hi pattern in Table 1A). Other genes are not expressed early in the time course, but then express as androgen is withdrawn and continue to express with emergence of androgen-independence (lo-hi-hi pattern in Table 1A). Finally, some genes are not expressed early in the time course, but then express as androgen is withdrawn and drop off again with emergence of androgen-independence (lo-hi-lo pattern in Table 1A). Thus, the data suggest that different antigens are expressed in quiescent cells and actively dividing androgen-independent prostate cancer cells.

In another aspect, the RNA expression levels of genes are determined for different cellular states in the prostate cancer phenotype. After androgen ablation therapy, cells that survive the therapy undergo a period of quiescence followed at sometime later by active cell division. As explained above, there are a variety of expression patterns characteristic of the prostate cancer genes involved in androgen-independent prostate cancer. Some genes are expressed early in the time course following ablation therapy, then drop off in expression, and then express again with emergence of androgen-independence (hi-lo-lo-hi pattern in Table 2A). Other genes are expressed early in the time course following ablation therapy, then drop off in expression, and do not express again with emergence of androgen-independence (hi-lo-lo-lo and hi-hi-lo-lo pattern in Table 2A). Still other genes are not expressed early in the time course, but express only with emergence of androgen-independence (lo-lo-lo-hi pattern in Table 2A). Other genes are not expressed early in the time course, but then express as androgen is withdrawn and continue to express with emergence of androgen-independence (lo-lo-hi-hi pattern in Table 2A). Finally, some genes are not expressed early in the time course, but then express as androgen is withdrawn and drop off again with emergence of androgen-independence (lo-lo-hi-lo pattern in Table 2A). Thus, the data suggest that different antigens are expressed in quiescent cells (during androgen withdrawal) and actively dividing androgen-independent prostate cancer cells.

Effective therapy to combat androgen-independent prostate cancer requires that the timing of therapy coincide with expression of the target genes. Patients can be monitored for the expression of certain diagnostic antigens that indicate the presence of quiescent cells or which indicate the transition to actively dividing androgen-independent prostate cancer cells. Thus, therapy to combat androgen-independent prostate cancer should begin at some time following androgen ablation therapy, depending on the particular target. Typically the transition from quiescence to actively dividing androgen-independent prostate cancer occurs between 6-24 months following androgen ablation therapy. Thus, preferred time periods for the therapies of the invention are as follows:

Expression levels of genes in normal tissue (i.e., not undergoing prostate cancer) and in prostate cancer tissue (and in some cases, for varying severities of prostate cancer that relate to prognosis, as outlined below) or in non-malignant disease are evaluated to provide expression profiles. An expression profile of a particular cell state or point of development is essentially a "fingerprint" of the state. While two states may have a particular gene similarly expressed, the evaluation of a number of genes simultaneously allows the generation of a gene expression profile that is reflective of the state of the cell. By comparing expression profiles of cells in different states, information regarding which genes are important (including both up- and down-regulation of genes) in each of these states is obtained. Then, diagnosis may be performed or confirmed to determine whether a tissue sample has the gene expression profile of normal or cancerous tissue. This will provide for molecular diagnosis of related conditions.

"Differential expression," or grammatical equivalents as used herein, refers to qualitative or quantitative differences in the temporal and/or cellular gene expression patterns within and among cells and tissue. Thus, a differentially expressed gene can qualitatively have its expression altered, including an activation or inactivation, in, e.g., normal versus prostate cancer tissue. Genes may be turned on or turned off in a particular state, relative to another state thus permitting comparison of two or more states. A qualitatively regulated gene will exhibit an expression pattern within a state or cell type which is detectable by standard techniques. Some genes will be expressed in one state or cell type, but not in both. Alternatively, the difference in expression may be quantitative, e.g., in that expression is increased or decreased; i.e., gene expression is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart (1996) *Nature Biotechnology* 14:1675-1680, hereby expressly incorporated by reference. Other techniques include, but are not limited to, quantitative reverse transcriptase PCR, northern analysis and RNase protection. As outlined above, preferably the change in expression (i.e., upregulation or downregulation) is at least about 50%, more preferably at least about 100%, more preferably at least about 150%, more preferably at least about 200%, with from 300 to at least 1000% being especially preferred.

Evaluation may be at the gene transcript, or the protein level. The amount of gene expression may be monitored using nucleic acid probes to the DNA or RNA equivalent of the gene transcript, and the quantification of gene expression levels, or, alternatively, the final gene product itself (protein) can be monitored, e.g., with antibodies to the prostate cancer protein and standard immunoassays (ELISAs, etc.) or other techniques, including mass spectroscopy assays, 2D gel electrophoresis assays, etc. Proteins corresponding to prostate cancer genes, i.e., those identified as being important in a prostate cancer or disease phenotype, can be evaluated in a prostate cancer diagnostic test.

In a preferred embodiment, gene expression monitoring is performed simultaneously on a number of genes. Multiple protein expression monitoring can be performed as well. Similarly, these assays may be performed on an individual basis as well.

In this embodiment, the prostate cancer nucleic acid probes are attached to biochips as outlined herein for the detection and quantification of prostate cancer sequences in a particular cell. The assays are further described below in the example. PCR techniques can be used to provide greater sensitivity.

In a preferred embodiment nucleic acids encoding the prostate cancer protein are detected. Although DNA or RNA encoding the prostate cancer protein may be detected, of particular interest are methods wherein an mRNA encoding a prostate cancer protein is detected. Probes to detect mRNA can be a nucleotide/deoxynucleotide probe that is complementary to and hybridizes with the mRNA and includes, but is not limited to, oligonucleotides, cDNA, or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ (in situ hybridization or ISH). In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a prostate cancer protein is detected by binding the digoxygenin with an anti-digoxygenin secondary antibody and developed with nitro blue tetrazolium and 5-bromo-4-chloro-3-indoyl phosphate.

In a preferred embodiment, various proteins from the three classes of proteins as described herein (secreted, transmembrane, or intracellular proteins) are used in diagnostic assays. The prostate cancer proteins, antibodies, nucleic acids, modified proteins and cells containing prostate cancer sequences are used in diagnostic assays. Such may evaluate tissues, e.g., immunohistochemistry, or evaluate body fluids, e.g., blood. The detection may be direct of cells, or indirect, e.g., of products from cells. This can be performed on an individual gene or corresponding polypeptide level. In a preferred embodiment, the expression profiles are used, preferably in conjunction with high throughput screening techniques to allow monitoring for expression profile genes and/or corresponding polypeptides.

As described and defined herein, prostate cancer proteins, including intracellular, transmembrane, or secreted proteins, find use as prognostic or diagnostic markers of prostate cancer or other prostate conditions. Detection of these proteins in putative prostate cancer tissue allows for detection, diagnosis, or prognosis of prostate proliferative disorders (malignant and non-malignant) including benign prostate hyperplasia (BPH) and cancer, and prostatitis. Diagnosis may also assist in selecting a therapeutic strategy, e.g., based on expression profiles and/or comparison to archival samples. In one embodiment, antibodies are used to detect prostate cancer proteins, directly or indirectly. A preferred method separates proteins from a sample by electrophoresis on a gel (typically a denaturing and reducing protein gel, but may be another type of gel, including isoelectric focusing gels and the like). Following separation of proteins, the prostate cancer protein is detected, e.g., by immunoblotting with antibodies raised against the prostate cancer protein. Methods of immunoblotting are well known to those of ordinary skill in the art.

In another preferred method, antibodies to the prostate cancer protein find use in in situ imaging techniques, e.g., in histology and/or in immunohistochemistry (e.g., Asai (ed. 1993) *Methods in Cell Biology: Antibodies in Cell Biology* (vol. 37) Academic Press. In this method cells are contacted with from one to many antibodies to the prostate cancer protein(s). Following washing to remove non-specific antibody binding, the presence of the antibody or antibodies is detected. In one embodiment the antibody is detected by incubating with a secondary antibody that contains a detectable label. In another method the primary antibody to the prostate cancer protein(s) contains a detectable label, e.g., an enzyme marker that can act on a substrate. In another preferred embodiment each one of multiple primary antibodies contains a distinct and detectable label. This method finds particular use in simultaneous screening for a plurality of prostate cancer proteins. As will be appreciated by one of ordinary skill in the art, many other histological imaging techniques are also provided by the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing prostate cancer from blood, serum, plasma, stool, and other samples. Such samples, therefore, are useful as samples to be probed or tested for the presence of prostate cancer proteins, which may be diagnostic of prostate conditions beyond cancer, e.g., BPH. Antibodies can be used to detect a prostate cancer protein by previously described immunoassay techniques including ELISA, immunoblotting (western blotting), immunoprecipitation, BIACORE technology, and the like. Conversely, the presence of antibodies may indicate an immune response against an endogenous prostate cancer protein.

In a preferred embodiment, in situ hybridization of labeled prostate cancer nucleic acid probes to tissue arrays is done. For example, arrays of tissue samples, including prostate cancer tissue and/or normal tissue, are made. In situ hybridization (see, e.g., Ausubel, supra) is then performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

In a preferred embodiment, the prostate cancer proteins, antibodies, nucleic acids, modified proteins, and cells containing prostate cancer sequences are used in prognosis assays. As above, gene expression profiles can be generated that correlate to prostate cancer or other prostate disorders, in terms of useful aspects of clinical condition, pathology, or other information which may be relevant to long term prognosis. Again, this may be done on either a protein or gene level, with the use of genes being preferred. Single or multiple genes may be useful in various combinations. As above, prostate cancer probes may be attached to biochips for the detection and quantification of prostate cancer sequences in a tissue or patient. The assays proceed as outlined above for diagnosis. PCR method may provide more sensitive and accurate quantification.

Assays for Therapeutic Compounds

In a preferred embodiment members of the proteins, nucleic acids, and antibodies as described herein are used in drug screening assays. The prostate cancer proteins, antibodies, nucleic acids, modified proteins, and cells containing prostate cancer sequences are used in drug screening assays or by evaluating the effect of drug candidates on a "gene expression profile" or expression profile of polypeptides. In a preferred embodiment, the expression profiles are used, preferably in conjunction with high throughput screening techniques to allow monitoring for expression profile genes after treatment with a candidate agent (e.g., Zlokarnik, et al. (1998) *Science* 279:84-88; Heid (1996) *Genome Res.* 6:986-94).

In a preferred embodiment, the prostate cancer proteins, antibodies, nucleic acids, modified proteins, and cells containing the native or modified prostate cancer proteins are used in screening assays. That is, the present invention provides novel methods for screening for compositions which modulate the prostate cancer phenotype or an identified physiological function of a prostate cancer protein. As above, this can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Having identified the differentially expressed genes herein, a variety of assays may be executed. In a preferred embodiment, assays may be run on an individual gene or protein level. That is, having identified a particular gene as up regulated in prostate cancer, test compounds can be screened for the ability to modulate gene expression or for binding to the prostate cancer protein. "Modulation" thus includes both an increase and a decrease in gene expression. The preferred amount of modulation will depend on the original change of the gene expression in normal versus tissue undergoing prostate cancer, with changes of at least 10%, preferably 50%, more preferably 100-300%, and in some embodiments 300-1000% or greater. Thus, if a gene exhibits a 4-fold increase in prostate cancer tissue compared to normal tissue, a decrease of about four-fold is often desired; similarly, a 10-fold decrease in prostate cancer tissue compared to normal tissue often provides a target value of a 10-fold increase in expression to be induced by the test compound.

The amount of gene expression may be monitored using nucleic acid probes and the quantification of gene expression levels, or, alternatively, the gene product itself can be monitored, e.g., through the use of antibodies to the prostate cancer protein and standard immunoassays. Proteomics and separation techniques may also allow quantification of expression.

In a preferred embodiment, gene expression or protein monitoring of a number of entities, i.e., an expression profile, is monitored simultaneously. Such profiles will typically involve a plurality of those entities described herein.

In this embodiment, the prostate cancer nucleic acid probes are attached to biochips as outlined herein for the detection and quantification of prostate cancer sequences in a particular cell. Alternatively, PCR may be used. Thus, a series, e.g., of microtiter plate, may be used with dispensed primers in desired wells. A PCR reaction can then be performed and analyzed for each well.

Expression monitoring can be performed to identify compounds that modify the expression of one or more prostate cancer-associated sequences, e.g., a polynucleotide sequence set out in Tables 1A-4. Generally, in a preferred embodiment, a test modulator is added to the cells prior to analysis. Moreover, screens are also provided to identify agents that modulate prostate cancer, modulate prostate cancer proteins, bind to a prostate cancer protein, or interfere with the binding of a prostate cancer protein and an antibody or other binding partner.

The term "test compound" or "drug candidate" or "modulator" or grammatical equivalents as used herein describes a molecule, e.g., protein, oligopeptide, small organic molecule, polysaccharide, polynucleotide, etc., to be tested for the capacity to directly or indirectly alter the prostate cancer phenotype or the expression of a prostate cancer sequence, e.g., a nucleic acid or protein sequence. In preferred embodiments, modulators alter expression profiles, or expression profile nucleic acids or proteins provided herein. In one embodiment, the modulator suppresses a prostate cancer phenotype, e.g., to a normal or non-malignant tissue fingerprint. In another embodiment, a modulator induced a prostate cancer phenotype. Generally, a plurality of assay mixtures are run in parallel with different agent concentrations to obtain a differential response to the various concentrations. Typically, one of these concentrations serves as a negative control, i.e., at zero concentration or below the level of detection.

Drug candidates encompass numerous chemical classes, though typically they are organic molecules, preferably small organic compounds having a molecular weight of more than 100 and less than about 2,500 daltons. Preferred small molecules are less than 2000, or less than 1500, or less than 1000, or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof. Particularly preferred are peptides.

In one aspect, a modulator will neutralize the effect of a prostate cancer protein. By "neutralize" is meant that activity of a protein is inhibited or blocked and the consequent effect on the cell.

In certain embodiments, combinatorial libraries of potential modulators will be screened for an ability to bind to a prostate cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in most every possible way for a given compound length (i.e., the number of amino acids in a polypeptide compound). Millions of chemical compounds can be synthesized through such combinatorial mixing of chemical building blocks. Gallop, et al. (1994) *J. Med. Chem.* 37:1233-1251.

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Pept. Prot. Res.* 37:487-493, Houghton, et al. (1991) *Nature,* 354:84-88), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs, et al. (1993) *Proc. Nat. Acad. Sci. USA* 90:6909-6913), vinylogous polypeptides (Hagihara, et al. (1992) *J. Amer. Chem. Soc.* 114:6568-xxx), nonpeptidal peptidomimetics with a Beta-D-Glucose scaffolding (Hirschmann, et al. (1992) *J. Amer. Chem. Soc.* 114:9217-9218), analogous organic syntheses of small compound libraries (Chen, et al. (1994) *J. Amer. Chem. Soc.* 116:2661-xxx), oligocarbamates (Cho, et al. (1993) *Science* 261:1303-1305), and/or peptidyl phosphonates (Campbell, et al. (1994) *J. Org. Chem.* 59:658-xxx). See, generally, Gordon, et al. (1994) *J. Med. Chem.* 37:1385-1401), nucleic acid libraries (see, e.g., Stratagene, Corp.), peptide nucleic acid libraries (see, e.g., U.S. Pat. No. 5,539,083), antibody libraries (see, e.g., Vaughn, et al. (1996) *Nature Biotechnology* 14:309-314, and PCT/US96/10287), carbohydrate libraries (see, e.g., Liang, et al. (1996) *Science* 274:1520-1522, and U.S. Pat. No. 5,593,853), and small organic molecule libraries (see, e.g., benzodiazepines, Baum (1993) *C&EN*, January 18, page 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. Many of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The assays to identify modulators are amenable to high throughput screening. Preferred assays thus detect enhancement or inhibition of prostate cancer gene transcription, inhibition or enhancement of polypeptide expression, and inhibition or enhancement of polypeptide activity.

High throughput assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures, including sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

In one embodiment, modulators are proteins, often naturally occurring proteins or fragments of naturally occurring proteins. Thus, e.g., cellular extracts containing proteins, or random or directed digests of proteinaceous cellular extracts, may be used. In this way libraries of proteins may be made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes or ligands and receptors.

In a preferred embodiment, modulators are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may typically incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines, or histidines for phosphorylation sites, etc., or to purines, etc.

Modulators of prostate cancer can also be nucleic acids, as defined above.

As described above generally for proteins, nucleic acid modulating agents may be naturally occurring nucleic acids, random nucleic acids, or "biased" random nucleic acids. For example, digests of prokaryotic or eukaryotic genomes may be used as is outlined above for proteins.

In a preferred embodiment, the candidate compounds are organic chemical moieties, a wide variety of which are available in the literature.

After the candidate agent has been added and the cells allowed to incubate for some period of time, the sample containing a target sequence to be analyzed is added to the biochip. If required, the target sequence is prepared using known techniques. For example, the sample may be treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

In a preferred embodiment, the target sequence is labeled with, e.g., a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246, and 5,681,697, each of which is hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate, and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways. Components of the reaction may be added simultaneously, or sequentially, in different orders, with preferred embodiments outlined below. In addition, the reaction may include a variety of other reagents. These include salts, buffers, neutral proteins, e.g., albumin, detergents, etc., which may be used to facilitate optimal hybridization and detection, and/or reduce non-specific or background interactions. Reagents that otherwise improve the efficiency of the assay, such as protease inhibitors, nuclease inhibitors, anti-microbial agents, etc., may also be used as appropriate, depending on the sample preparation methods and purity of the target.

The assay data are analyzed to determine the expression levels, and changes in expression levels as between states, of individual genes, forming a gene expression profile.

Screens are performed to identify modulators of the prostate cancer or related phenotype. In one embodiment, screening is performed to identify modulators that can induce or suppress a particular expression profile, thus preferably generating the associated phenotype. In another embodiment, e.g., for diagnostic applications, having identified differentially expressed genes important in a particular state, screens can be performed to identify modulators that alter expression of individual genes. In an another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition screens can be done for genes that are induced in response to a candidate agent. After identifying a modulator based upon its ability to suppress a prostate cancer expression pattern leading to a normal expression pattern, or to modulate a single prostate cancer gene expression profile so as to mimic the expression of the gene from normal tissue, a screen as described above can be performed to identify genes that are specifically modulated in response to the agent. Comparing expression profiles between normal tissue and agent treated prostate cancer tissue reveals genes that are not expressed in normal tissue or prostate cancer tissue, but are expressed in agent treated tissue. These agent-specific sequences can be identified and used by methods described herein for prostate cancer genes or proteins. In particular these sequences and the proteins they encode find use in marking or identifying agent treated cells. In addition, antibodies can be raised against the agent induced proteins and used to target novel therapeutics to the treated prostate cancer tissue sample.

Thus, in one embodiment, a test compound is administered to a population of prostate cancer cells, that have an associated prostate cancer expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (e.g., a peptide) may be put into a viral construct such as an adenoviral or retroviral construct, and added to the cell, such that expression of the peptide agent is accomplished, e.g., PCT US97/01019. Regulatable gene therapy systems can also be used.

Once the test compound has been administered to the cells, the cells can be washed if desired and are allowed to incubate under preferably physiological conditions for some period of time. The cells are then harvested and a new gene expression profile is generated, as outlined herein.

Thus, e.g., prostate cancer or non-malignant tissue may be screened for agents that modulate, e.g., induce or suppress the prostate cancer or related phenotype. A change in at least one gene, preferably many, of the expression profile indicates that the agent has an effect on prostate cancer activity. By defining such a signature for the prostate cancer phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular differentially expressed gene as important in a particular state, screening of modulators of either the expression of the gene or the gene product itself can be done. The gene products of differentially expressed genes are sometimes referred to herein as "prostate cancer proteins" or a "prostate cancer modulatory protein". The prostate cancer modulatory protein may be a fragment, or alternatively, be the full length protein to the fragment encoded by the nucleic acids of the Tables 1A-4. Preferably, the prostate cancer modulatory protein is a fragment. In a preferred embodiment, the prostate cancer amino acid sequence which is used to determine sequence identity or similarity is encoded by a nucleic acid of Tables 1A-4. In another embodiment, the sequences are naturally occurring allelic variants of a protein encoded by a nucleic acid of Tables 1A-4. In another embodiment, the sequences are sequence variants as further described herein.

Preferably, the prostate cancer modulatory protein is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the C-terminus of the fragment is kept as a free acid and the N-terminus is a free amine to aid in coupling, i.e., to cysteine.

In one embodiment the prostate cancer proteins are conjugated to an immunogenic agent as discussed herein. In one embodiment the prostate cancer protein is conjugated to BSA.

Measurements of prostate cancer polypeptide activity, or of prostate cancer or the prostate cancer phenotype can be performed using a variety of assays. For example, the effects of the test compounds upon the function of the prostate cancer polypeptides can be measured by examining parameters described above. A suitable physiological change that affects activity can be used to assess the influence of a test compound on the polypeptides of this invention. When the functional consequences are determined using intact cells or animals, one can also measure a variety of effects such as, in the case of prostate cancer associated with tumors, tumor growth, tumor metastasis, neovascularization, hormone release, transcriptional changes to both known and uncharacterized genetic markers (e.g., northern blots), changes in cell metabolism such as cell growth or pH changes, and changes in intracellular second messengers such as cGMP. In the assays of the invention, a mammalian prostate cancer polypeptide is typically used, e.g., mouse, preferably human.

Assays to identify compounds with modulating activity can be performed in vitro. For example, a prostate cancer polypeptide is first contacted with a potential modulator and incubated for a suitable amount of time, e.g., from 0.5 to 48 hours. In one embodiment, the prostate cancer polypeptide levels are determined in vitro by measuring the level of protein or mRNA. The level of protein is measured using immunoassays such as western blotting, ELISA, and the like with an antibody that selectively binds to the prostate cancer polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the prostate cancer protein promoter operably linked to a reporter gene such as luciferase, green fluorescent protein, CAT, or β-gal. The reporter construct is typically transfected into a cell. After treatment with a potential modulator, the amount of reporter gene transcription, translation, or activity is measured according to standard techniques known to those of skill in the art.

In a preferred embodiment, as outlined above, screens may be done on individual genes and gene products (proteins). That is, having identified a particular differentially expressed gene as important in a particular state, screening of modulators of the expression of the gene or the gene product itself can be done. The gene products of differentially expressed genes are sometimes referred to herein as "prostate cancer proteins." The prostate cancer protein may be a fragment, or alternatively, be the full length protein corresponding to a fragment shown herein.

In one embodiment, screening for modulators of expression of specific genes is performed. Typically, the expression of only one or a few genes are evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

In a preferred embodiment, binding assays are done. In general, purified or isolated gene product is used; that is, the gene products of one or more differentially expressed nucleic acids are made. For example, antibodies are generated to the protein gene products, and standard immunoassays are run to determine the amount of protein present. Alternatively, cells comprising the prostate cancer proteins can be used in the assays.

Thus, in a preferred embodiment, the methods comprise combining a prostate cancer protein and a candidate compound, and determining the binding of the compound to the prostate cancer protein. Preferred embodiments utilize the human prostate cancer protein, although other mammalian proteins may also be used, e.g., for the development of animal models of human disease. In some embodiments, as outlined herein, variant or derivative prostate cancer proteins may be used.

Generally, in a preferred embodiment of the methods herein, the prostate cancer protein or the candidate agent is non-diffusably bound to an insoluble support having isolated sample receiving areas (e.g., a microtiter plate, an array, etc.). The insoluble supports may be made of a composition to which the compositions can be bound, is readily separated from soluble material, and is otherwise compatible with the overall method of screening. The surface of such supports may be solid or porous and of a convenient shape. Examples of suitable insoluble supports include microtiter plates, arrays, membranes, and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition should be compatible with the reagents and overall methods of the invention, maintain the activity of the composition, and be nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein, or other innocuous protein or other moiety.

In a preferred embodiment, the prostate cancer protein is bound to the support, and a test compound is added to the assay. Alternatively, the candidate agent is bound to the support and the prostate cancer protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the test modulating compound to the prostate cancer protein may be done in a number of ways. In a preferred embodiment, the compound is labeled, and binding determined directly, e.g., by attaching all or a portion of the prostate cancer protein to a solid support, adding a labeled candidate agent (e.g., a fluorescent label), washing off excess reagent, and determining whether the label is present on the solid support. Various blocking and washing steps may be utilized as appropriate.

In some embodiments, only one of the components is labeled, e.g., the proteins (or proteinaceous candidate compounds) can be labeled. Alternatively, more than one component can be labeled with different labels, e.g., $^{125}I$ for the proteins and a fluorophor for the compound. Proximity reagents, e.g., quenching or energy transfer reagents are also useful.

In one embodiment, the binding of the test compound is determined by competitive binding assay. The competitor is a binding moiety known to bind to the target molecule (i.e., a prostate cancer protein), such as an antibody, peptide, binding partner, ligand, etc. Under certain circumstances, there may be competitive binding between the compound and the binding moiety, with the binding moiety displacing the compound. In one embodiment, the test compound is labeled. Either the compound, or the competitor, or both, is added first to the protein for a time sufficient to allow binding, if present. Incubations may be performed at a temperature which facilitates optimal activity, typically between 4 and 40° C. Incubation periods are typically optimized, e.g., to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the test compound. Displacement of the competitor is an indication that the test compound is binding to the prostate cancer protein and thus is capable of binding to, and potentially modulating, the activity of the prostate cancer protein. In this embodiment, either component can be labeled. Thus, e.g., if the competitor is labeled, the presence of label in the wash solution indicates displacement by the agent. Alternatively, if the test compound is labeled, the presence of the label on the support indicates displacement.

In an alternative embodiment, the test compound is added first, with incubation and washing, followed by the competitor. The absence of binding by the competitor may indicate that the test compound is bound to the prostate cancer protein with a higher affinity. Thus, if the test compound is labeled, the presence of the label on the support, coupled with a lack of competitor binding, may indicate that the test compound is capable of binding to the prostate cancer protein.

In a preferred embodiment, the methods comprise differential screening to identity agents that are capable of modulating the activity of the prostate cancer proteins. In this embodiment, the methods comprise combining a prostate cancer protein and a competitor in a first sample. A second sample comprises a test compound, a prostate cancer protein, and a competitor. The binding of the competitor is determined for both samples, and a change, or difference in binding between the two samples indicates the presence of an agent capable of binding to the prostate cancer protein and potentially modulating its activity. That is, if the binding of the competitor is different in the second sample relative to the first sample, the agent is capable of binding to the prostate cancer protein.

Alternatively, differential screening is used to identify drug candidates that bind to the native prostate cancer protein, but cannot bind to modified prostate cancer proteins. The structure of the prostate cancer protein may be modeled, and used in rational drug design to synthesize agents that interact with that site. Drug candidates that affect the activity of a prostate cancer protein are also identified by screening drugs for the ability to either enhance or reduce the activity of the protein.

Positive controls and negative controls may be used in the assays. Preferably control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc., which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in an order that provides for the requisite binding.

In a preferred embodiment, the invention provides methods for screening for a compound capable of modulating the activity of a prostate cancer protein. The methods comprise adding a test compound, as defined above, to a cell comprising prostate cancer proteins. Preferred cell types include almost any cell. The cells contain a recombinant nucleic acid that encodes a prostate cancer protein. In a preferred embodiment, a library of candidate agents are tested on a plurality of cells.

In one aspect, the assays are evaluated in the presence or absence or previous or subsequent exposure of physiological signals, e.g., hormones, antibodies, peptides, antigens, cytokines, growth factors, action potentials, pharmacological agents including chemotherapeutics, radiation, carcinogenics, or other cells (e.g., cell-cell contacts). In another example, the determinations are determined at different stages of the cell cycle process.

In this way, compounds that modulate prostate cancer agents are identified. Compounds with pharmacological activity are able to enhance or interfere with the activity of the prostate cancer protein. Once identified, similar structures are evaluated to identify critical structural feature of the compound.

In one embodiment, a method of inhibiting prostate cancer cell division is provided. The method comprises administration of a prostate cancer inhibitor. In another embodiment, a method of inhibiting prostate cancer or other prostate proliferative condition is provided. The method comprises administration of a prostate cancer inhibitor. In a further embodiment, methods of treating cells or individuals with prostate cancer are provided. The method comprises administration of a prostate cancer inhibitor.

In one embodiment, a prostate cancer inhibitor is an antibody as discussed above. In another embodiment, the prostate cancer inhibitor is an antisense molecule.

A variety of cell growth, proliferation, and metastasis assays are known to those of skill in the art, as described below.

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow. Soft agar growth or colony formation in suspension assays can be used to identify modulators of prostate cancer sequences, which when expressed in host cells, inhibit abnormal cellular proliferation and transformation. A therapeutic compound would reduce or eliminate the host cells' ability to grow in stirred suspension culture or suspended in semi-solid media, such as semi-solid or soft.

Techniques for soft agar growth or colony formation in suspension assays are described in Freshney (1994) *Culture of Animal Cells a Manual of Basic Technique* 3d ed. Wiley-Liss, herein incorporated by reference. See also, the methods section of Garkavtsev, et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with ($^3$H)-thymidine at saturation density can be used to measure density limitation of growth. See Freshney (1994), supra. The transformed cells, when transfected with tumor suppressor genes, regenerate a normal phenotype and become contact inhibited and would grow to a lower density.

In this assay, labeling index with ($^3$H)-thymidine at saturation density is a preferred method of measuring density limitation of growth. Transformed host cells are transfected with a prostate cancer-associated sequence and are grown for 24 hours at saturation density in non-limiting medium conditions. The percentage of cells labeling with ($^3$H)-thymidine is determined autoradiographically. See, Freshney (1994), supra.

Growth Factor or Serum Dependence

Transformed cells have a lower serum dependence than their normal counterparts (see, e.g., Temin (1966) *J. Natl. Cancer Insti.* 37:167-175; Eagle, et al. (1970) *J. Exp. Med.* 131:836-879); Freshney, supra. This is in part due to release of various growth factors by the transformed cells. Growth factor or serum dependence of transformed host cells can be compared with that of control.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, "Angiogenesis, tumor vascularization, and potential interference with tumor growth" pp. 178-184 in Mihich (ed. 1985) *Biological Responses in Cancer* Plenum. Similarly, Tumor angiogenesis factor (TAF) is released at a higher level in tumor cells than their normal counterparts. See, e.g., Folkman (1992) *Angiogenesis and Cancer, Sem. Cancer Biol.*

Various techniques which measure the release of these factors are described in Freshney (1994), supra. Also, see, Unkless, et al. (1974) *J. Biol. Chem.* 249:4295-4305; Strickland and Beers (1976) *J. Biol. Chem.* 251:5694-5702; Whur, et al. (1980) *Br. J. Cancer* 42:305-312; Gullino, "Angiogenesis, tumor vascularization, and potential interference with tumor growth" pp. 178-184 in Mihich (ed. 1985) *Biological Responses in Cancer* Plenum; and Freshney (1985) *Anticancer Res.* 5:111-130.

Invasiveness into Matrigel

The degree of invasiveness into Matrigel or some other extracellular matrix constituent can be used as an assay to identify compounds that modulate prostate cancer-associated sequences. Tumor cells exhibit a good correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Tumor Growth In Vivo

Effects of prostate cancer-associated sequences on cell growth can be tested in transgenic or immune-suppressed mice. Knock-out transgenic mice can be made, in which the prostate cancer gene is disrupted or in which a prostate cancer gene is inserted. Knock-out transgenic mice can be made by insertion of a marker gene or other heterologous gene into the endogenous prostate cancer gene site in the mouse genome via homologous recombination. Such mice can also be made by substituting the endogenous prostate cancer gene with a mutated version of the prostate cancer gene, or by mutating the endogenous prostate cancer gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi, et al. (1989) *Science* 244:1288-1292). Chimeric targeted mice can be derived according to Hogan, et al. (1988) *Manipulating the Mouse Embryo: A Laboratory Manual* CSH Press; and Robertson (ed. 1987) *Teratocarcinomas and Embryonic Stem Cells: A Practical Approach* IRL Press, Washington, D.C.

Alternatively, various immune-suppressed or immune-deficient host animals can be used. For example, genetically athymic "nude" mouse (see, e.g., Giovanella, et al. (1974) *J. Natl. Cancer Inst.* 52:921-930), a SCID mouse, a thymectomized mouse, or an irradiated mouse (see, e.g., Bradley, et al. (1978) *Br. J. Cancer* 38:263-272; Selby, et al. (1980) *Br. J. Cancer* 41:52-61) can be used as a host. Transplantable tumor cells (typically about $10^6$ cells) injected into isogenic hosts will produce invasive tumors in a high proportions of cases, while normal cells of similar origin will not. In hosts which developed invasive tumors, cells expressing a prostate cancer-associated sequences are injected subcutaneously. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth.

Polynucleotide Modulators of Prostate Cancer

Antisense and RNAi Polynucleotides

In certain embodiments, the activity of a prostate cancer-associated protein is down-regulated, or entirely inhibited, by the use of antisense polynucleotide, i.e., a nucleic acid complementary to, and which can preferably hybridize specifically to, a coding mRNA nucleic acid sequence, e.g., a prostate cancer protein mRNA, or a subsequence thereof. Binding of the antisense polynucleotide to the mRNA reduces the translation and/or stability of the mRNA.

In the context of this invention, antisense polynucleotides can comprise naturally-occurring nucleotides, or synthetic species formed from naturally-occurring subunits or their close homologs. Antisense polynucleotides may also have altered sugar moieties or inter-sugar linkages. Exemplary among these are the phosphorothioate and other sulfur containing species which are known for use in the art. Analogs are comprehended by this invention so long as they function effectively to hybridize with the prostate cancer protein mRNA. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single-stranded nucleic acid sequence (either RNA or DNA) capable of binding to target mRNA (sense) or DNA (antisense) sequences for prostate cancer molecules. A preferred antisense molecule is for a prostate cancer sequences in Tables 1A-4, or for a ligand or activator thereof. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, e.g., Stein and Cohen (1988) *Cancer Res.* 48:2659-2668; and van der Krol, et al. (1988) *BioTechniques* 6:958-976.

RNA interference is a mechanism to suppress gene expression in a sequence specific manner. See, e.g., Brumelkamp, et al. (2002) *Sciencexpress* (21 Mar. 2002); Sharp (1999) *Genes Dev.* 13:139-141; and Cathew (2001) *Curr. Op. Cell Biol.* 13:244-248. In mammalian cells, short, e.g., 21 nt, double stranded small interfering RNAs (siRNA) have been shown to be effective at inducing an RNAi response. See, e.g., Elbashir, et al. (2001) *Nature* 411:494-498. The mechanism may be used to downregulate expression levels of identified genes, e.g., treatment of or validation of relevance to disease.

Ribozymes

In addition to antisense polynucleotides, ribozymes can be used to target and inhibit transcription of prostate cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto, et al. (1994) *Adv. in Pharmacology* 25: 289-317 for a general review of the properties of different ribozymes).

The general features of hairpin ribozymes are described, e.g., in Hampel, et al. (1990) *Nucl. Acids Res.* 18:299-304; European Patent Publication No. 0 360 257; U.S. Pat. No. 5,254,678. Methods of preparing are well known to those of skill in the art. See, e.g., WO 94/26877; Ojwang, et al. (1993) *Proc. Natl. Acad. Sci. USA* 90:6340-6344; Yamada, et al. (1994) *Human Gene Therapy* 1:39-45; Leavitt, et al. (1995) *Proc. Natl. Acad. Sci. USA* 92:699-703; Leavitt, et al. (1994) *Human Gene Therapy* 5:1151-120; and Yamada, et al. (1994) *Virology* 205:121-126.

Polynucleotide modulators of prostate cancer may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of prostate cancer may be introduced into a cell containing the target nucleic acid sequence, e.g., by formation of an polynucleotide-lipid complex, as described in WO 90/10448. It is understood that the use of antisense molecules or knock out and knock in models may also be used in screening assays as discussed above, in addition to methods of treatment.

Thus, in one embodiment, methods of modulating prostate disorders, e.g., cancer in cells or organisms, are provided. In one embodiment, the methods comprise administering to a patient, e.g., to a cell within the patient, an anti-prostate cancer antibody that reduces or eliminates the biological activity of an endogenous prostate cancer protein. Alternatively, the methods comprise administering to a cell or organism a recombinant nucleic acid encoding a prostate cancer protein. This may be accomplished in many ways. In a preferred embodiment, e.g., when the prostate cancer sequence is down-regulated in prostate cancer, such state may be reversed by increasing the amount of prostate cancer gene product in the cell. This can be accomplished, e.g., by overexpressing the endogenous prostate cancer gene or administering a gene encoding the prostate cancer sequence, using known gene-therapy techniques, e.g. In a preferred embodiment, the gene therapy techniques include the incorporation of the exogenous gene using enhanced homologous recombination (EHR), e.g., as described in PCT/US93/03868, hereby incorporated by reference in its entirety. Alternatively, e.g., when the prostate cancer sequence is up-regulated in prostate cancer, the activity of the endogenous prostate cancer gene is decreased, e.g., by the administration of a prostate cancer antisense nucleic acid.

In one embodiment, the prostate cancer proteins of the present invention may be used to generate polyclonal and monoclonal antibodies to prostate cancer proteins. Similarly, the prostate cancer proteins can be coupled, using standard technology, to affinity chromatography columns. These columns may then be used to purify prostate cancer antibodies useful for production, diagnostic, or therapeutic purposes. In a preferred embodiment, the antibodies are generated to epitopes unique to a prostate cancer protein; that is, the antibodies show little or no cross-reactivity to other proteins. The prostate cancer antibodies may be coupled to standard affinity chromatography columns and used to purify prostate cancer proteins. The antibodies may also be used as blocking polypeptides, as outlined above, since they will specifically bind to the prostate cancer protein.

Methods of Identifying Variant Prostate Cancer-associated Sequences

Without being bound by theory, expression of various prostate cancer sequences is correlated with prostate cancer or other prostate disorders. Accordingly, disorders based on mutant or variant prostate cancer genes may be determined. In one embodiment, the invention provides methods for identifying cells containing variant prostate cancer genes, e.g., determining all or part of the sequence of at least one endogenous prostate cancer genes in a cell. This may be accomplished using many sequencing techniques. In a preferred embodiment, the invention provides methods of identifying the prostate cancer genotype of an individual, e.g., determining all or part of the sequence of at least one prostate cancer gene of the individual. This is generally done in at least one tissue of the individual, and may include the evaluation of a number of tissues or different samples of the same tissue. The method may include comparing the sequence of the sequenced prostate cancer gene to a known prostate cancer gene, e.g., a wild-type gene.

The sequence of all or part of the prostate cancer gene can then be compared to the sequence of a known prostate cancer gene to determine if differences exist. This can be done using many known homology programs, such as Bestfit, etc. In a preferred embodiment, the presence of a difference in the sequence between the prostate cancer gene of the patient and the known prostate cancer gene correlates with a disease state or a propensity for a disease state, as outlined herein.

In a preferred embodiment, the prostate cancer genes are used as probes to determine the number of copies of the prostate cancer gene in the genome.

In another preferred embodiment, the prostate cancer genes are used as probes to determine the chromosomal localization of the prostate cancer genes. Information such as chromosomal localization finds use in providing a diagnosis or prognosis in particular when chromosomal abnormalities such as translocations, and the like are identified in the prostate cancer gene locus.

Administration of Pharmaceutical and Vaccine Compositions

In one embodiment, a therapeutically effective dose of a prostate cancer protein or modulator thereof, is administered to a patient. By "therapeutically effective dose" herein is meant a dose that produces effects for which it is administered. The exact dose will depend on the purpose of the treatment, and will be ascertainable by one skilled in the art using known techniques (e.g., Ansel, et al. (1992) *Pharmaceutical Dosage Forms and Drug Delivery*; Lieberman (1993) *Pharmaceutical Dosage Forms* (vols. 1-3, Dekker, ISBN 0824770846, 082476918X, 0824712692, 0824716981; Lloyd (1999) *The Art, Science and Technology of Pharmaceutical Compounding* Amer. Pharma. Assn.; and Pickar (1999) *Dosage Calculations* Thomson). Adjustments for prostate cancer degradation, systemic versus localized delivery, and rate of new protease synthesis, as well as the age, body weight, general health, sex, diet, time of administration, drug interaction, and the severity of the condition may be necessary, and will be ascertainable with routine experimentation by those skilled in the art. U.S. patent application Ser. No. 09/687,576 further discloses the use of compositions and methods of diagnosis and treatment in prostate cancer is hereby expressly incorporated by reference.

A "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. The patient typically will suffer from a prostate proliferative disorder, e.g., malignant or non-malignant, and may include cancer of other related conditions or disorders.

The administration of the prostate cancer proteins and modulators thereof of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, e.g., in the treatment of wounds and inflammation, the prostate cancer proteins and modulators may be directly applied as a solution or spray, or via catheter.

The pharmaceutical compositions of the present invention comprise a prostate cancer protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. "Pharmaceutically acceptable base addition salts" include those derived from inorganic bases such as sodium, potassium, lithium, ammonium, calcium, magnesium, iron, zinc, copper, manganese, aluminum salts, and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that prostate cancer protein modulators (e.g., antibodies, antisense constructs, ribozymes, small organic molecules, etc.) when administered orally, should be protected from digestion. This is typically accomplished either by complexing the molecule(s) with a composition to render it resistant to acidic and enzymatic hydrolysis, or by packaging the molecule(s) in an appropriately resistant carrier, such as a liposome or a protection barrier. Means of protecting agents from digestion are well known in the art.

The compositions for administration will commonly comprise a prostate cancer protein modulator dissolved in a pharmaceutically acceptable carrier, preferably an aqueous carrier. A variety of aqueous carriers can be used, e.g., buffered saline and the like. These solutions are typically sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like in accordance with the particular mode of administration selected and the patient's needs (e.g., (1980) *Remington's Pharmaceutical Science* (15th ed.); and Hardman, et al. (eds. 2001) *Goodman & Gilman: The Pharmacological Basis of Therapeutics* McGraw-Hill.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art, e.g., *Remington's Pharmaceutical Science* and *Goodman and Gilman: The Pharmacological Basis of Therapeutics*, supra.

The compositions containing modulators of prostate cancer proteins can be administered for therapeutic or prophylactic treatments. In therapeutic applications, compositions are administered to a patient suffering from a disease (e.g., a cancer) in an amount sufficient to cure or at least partially retard or arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. The composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal who is suspected of having a significant likelihood of developing cancer, e.g., based partly on gene expression profiles.

It will be appreciated that the present prostate cancer protein-modulating compounds can be administered alone or in combination with additional prostate cancer modulating compounds or with other therapeutic agent, e.g., other anticancer agents or treatments.

In numerous embodiments, one or more nucleic acids, e.g., polynucleotides comprising nucleic acid sequences set forth in Tables 1A-4 such as antisense polynucleotides, silencing RNA, or ribozymes, will be introduced into cells, in vitro or in vivo. The present invention provides methods, reagents, vectors, and cells useful for expression of prostate cancer-associated polypeptides and nucleic acids using in vitro (cell-free), ex vivo or in vivo (cell or organism-based) recombinant expression systems.

The particular procedure used to introduce the nucleic acids into a host cell for expression of a protein or nucleic acid is application specific. Many procedures for introducing foreign nucleotide sequences into host cells may be used. These include the use of calcium phosphate transfection, spheroplasts, electroporation, liposomes, microinjection, plasma vectors, viral vectors, and many other well known methods for introducing cloned genomic DNA, cDNA, synthetic DNA, or other foreign genetic material into a host cell (see, e.g., Berger and Kimmel (1987) *Guide to Molecular Cloning Techniques* from *Methods in Enzymology* (vol. 152) Academic Press; Ausubel, et al., (eds. supplemented through 1999) *Current Protocols* Lippincott; and Sambrook, et al. (1989) *Molecular Cloning: A Laboratory Manual* (2d ed., Vol. 1-3) CSH Press.

In a preferred embodiment, prostate cancer proteins and modulators are administered as therapeutic agents, and can be formulated as outlined above. Similarly, prostate cancer genes (including both the full-length sequence, partial sequences, or regulatory sequences of the prostate cancer coding regions) can be administered in a gene therapy application. These prostate cancer genes can include antisense applications, either as gene therapy (i.e., for incorporation into the genome) or as antisense compositions, as will be appreciated by those in the art.

Prostate cancer polypeptides and polynucleotides can also be administered as vaccine compositions to stimulate HTL, CTL, and antibody responses. Such vaccine compositions can include, e.g., lipidated peptides (see, e.g., Vitiello, et al. (1995) *J. Clin. Invest.* 95:341-349), peptide compositions encapsulated in poly(DL-lactide-co-glycolide)("PLG") microspheres (see, e.g., Eldridge, et al. (1991) *Molec. Immunol.* 28:287-294; Alonso, et al. (1994) *Vaccine* 12:299-306; Jones, et al. (1995) *Vaccine* 13:675-681), peptide compositions contained in immune stimulating complexes (ISCOMS) (see, e.g., Takahashi, et al. (1990) *Nature* 344:873-875; Hu, et al. (1998) *Clin Exp Immunol.* 113:235-243), multiple antigen peptide systems (MAPs)(see, e.g., Tam (1988) *Proc. Natl. Acad. Sci. USA* 85:5409-5413; Tam (1996) *J. Immunol. Methods* 196:17-32), peptides formulated as multivalent peptides; peptides for use in ballistic delivery systems, typically crystallized peptides, viral delivery vectors (Perkus, et al., p. 379, in Kaufmann (ed. 1996) *Concepts in vaccine development de* Gruyter; Chakrabarti, et al. (1986) *Nature* 320:535-537; Hu, et al. (1986) *Nature* 320:537-540; Kieny, et al. (1986) *AIDS Bio/Technology* 4:790-xxx; Top, et al. (1971) *J. Infect. Dis.* 124:148-154; Chanda, et al. (1990) *Virology* 175:535-547), particles of viral or synthetic origin (see, e.g., Kofler, et al. (1996) *J. Immunol. Methods* 192:25-35; Eldridge, et al. (1993) *Sem. Hematol.* 30:16-24; Falo, et al. (1995) *Nature Med.* 7:649-653), adjuvants (Warren, et al. (1986) *Annu. Rev. Immunol.* 4:369-388; Gupta, et al. (1993) *Vaccine* 11:293-306), liposomes (Reddy, et al. (1992) *J. Immunol.* 148:1585-1589; Rock (1996) *Immunol. Today* 17:131-137), or, naked or particle absorbed cDNA (Ulmer, et al. (1993) *Science* 259:1745-1749; Robinson, et al. (1993) *Vaccine* 11:957-960; Shiver, et al., p. 423, in Kaufmann (ed. 1996) *Concepts in Vaccine Development* de Gruyter; Cease and Berzofsky (1994) *Annu. Rev. Immunol.* 12:923-989; and Eldridge, et al. (1993) *Sem. Hematol.* 30:16-24). Toxin-targeted delivery technologies, also known as receptor mediated targeting, such as those of Avant Immunotherapeutics, Inc. (Needham, Mass.) may also be used.

Vaccine compositions often include adjuvants. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, e.g., Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A, and quil A. Cytokines, such as GM-CSF, interleukin-2, -7, -12, and other like growth factors, may also be used as adjuvants.

Vaccines can be administered as nucleic acid compositions wherein DNA or RNA encoding one or more of the polypeptides, or a fragment thereof, is administered to a patient. This approach is described, for instance, in Wolff, et al. (1990) *Science* 247:1465-1468 as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, e.g., as a vector to express nucleotide sequences that encode prostate cancer polypeptides or polypeptide fragments. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover, et al. (1991) *Nature* 351:456-460. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent to those skilled in the art from the description herein (see, e.g., Shata, et al. (2000) *Mol. Med. Today* 6:66-71; Shedlock, et al. (2000) *J. Leuk. Biol.* 68:793-806; Hipp, et al. (2000) *In Vivo* 14:571-85).

Methods for the use of genes as DNA vaccines are well known, and include placing a prostate cancer gene or portion of a prostate cancer gene under the control of a regulatable promoter or a tissue-specific promoter for expression in a prostate cancer patient. The prostate cancer gene used for DNA vaccines can encode full-length prostate cancer proteins, but more preferably encodes portions of the prostate cancer proteins including peptides derived from the prostate cancer protein. In one embodiment, a patient is immunized with a DNA vaccine comprising a plurality of nucleotide sequences derived from a prostate cancer gene. For example, prostate cancer-associated genes or sequence encoding subfragments of a prostate cancer protein are introduced into expression vectors and tested for their immunogenicity in the context of Class I MHC and an ability to generate cytotoxic T cell responses. This procedure may provide for production of cytotoxic T lymphocyte responses against cells which present antigen, including intracellular epitopes.

In a preferred embodiment, the DNA vaccines include a gene encoding an adjuvant molecule with the DNA vaccine. Such adjuvant molecules include cytokines that increase the immunogenic response to the prostate cancer polypeptide encoded by the DNA vaccine. Additional or alternative adjuvants are available.

In another preferred embodiment prostate cancer genes find use in generating animal models of prostate cancer. When the prostate cancer gene identified is repressed or diminished in cancer tissue, gene therapy technology, e.g., wherein antisense RNA directed to the prostate cancer gene will also diminish or repress expression of the gene. Animal models of prostate cancer find use in screening for modulators of a prostate cancer-associated sequence or modulators of prostate cancer. Similarly, transgenic animal technology including gene knockout technology, e.g., as a result of homologous recombination with an appropriate gene targeting vector, will result in the absence or increased expression of the prostate cancer protein. When desired, tissue-specific expression or knockout of the prostate cancer protein may be necessary.

It is also possible that the prostate cancer protein is overexpressed in prostate cancer. As such, transgenic animals can be generated that overexpress the prostate cancer protein. Depending on the desired expression level, promoters of various strengths can be employed to express the transgene. Also, the number of copies of the integrated transgene can be determined and compared for a determination of the expression level of the transgene. Animals generated by such methods find use as animal models of prostate cancer and are additionally useful in screening for modulators to treat prostate cancer.

Kits for Use in Diagnostic and/or Prognostic Applications

For use in diagnostic, research, and therapeutic applications suggested above, kits are also provided by the invention. In the diagnostic and research applications such kits may include one of the following: assay reagents, buffers, prostate cancer-specific nucleic acids or antibodies, hybridization probes and/or primers, antisense polynucleotides, silencing RNA, ribozymes, dominant negative prostate cancer polypeptides or polynucleotides, small molecules inhibitors of prostate cancer-associated sequences, etc. A therapeutic product may include sterile saline or another pharmaceutically acceptable emulsion and suspension base.

In addition, the kits may include instructional materials containing instructions (i.e., protocols) for the practice of the methods of this invention. While the instructional materials typically comprise written or printed materials they are not limited to such. A medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of prostate cancer-associated sequences. Such kits can be prepared from readily available materials and reagents. For example, such kits can comprise one or more of the following materials: a prostate cancer-associated polypeptide or polynucleotide, reaction tubes, and instructions for testing prostate cancer-associated activity. Optionally, the kit contains biologically active prostate cancer protein. A wide variety of kits and components can be prepared according to the present invention, depending upon the intended user of the kit and the particular needs of the user. Diagnosis would typically involve evaluation of a plurality of genes or products. The genes will be selected based on correlations with important parameters in disease which may be identified in historical or outcome data.

EXAMPLES

Example 1

Gene Chip Analyses of Expression Profiles

Molecular profiles of various normal and cancerous tissues were determined and analyzed using gene chips. RNA was isolated and gene chip analysis was performed as described (Glynne, et al. (2000) Nature 403:672-676; Zhao, et al. (2000) Genes Dev. 14:981-993).

Example 2

Identification of Androgen Dependent/independent Genes

To identify gene expression changes during the transition from androgen-dependent to androgen-independent prostate cancer, oligonucleotide microarrays ("K" chips or Affymetrix Eos Hu03) were interrogated with cRNAs derived from the human CWR22 prostate cancer xenograft model propagated in nude mice (Pretlow, et al. (1993) *J. Natl. Cancer Inst.* 85:394-398). The CWR22 xenograft is androgen-dependent when grown in male Nude mice. Androgen-independent sublines can be derived by first establishing androgen-dependent tumors in male mice. The mice are then castrated to remove the primary source of growth stimulus (androgen), resulting in tumor regression. Within 3-10 months molecular events prompt the tumors to relapse and start growing as androgen-independent tumors. See, e.g., Nagabhushan, et al. (1996) *Cancer Res.* 56:3042-3046; Amler, et al. (2000) *Cancer Res.* 60:6134-6141; and Bubendorf, et al. (1999) *J. Natl. Cancer Inst.* 91:1758-1764.

Using the CWR22 xenograft model, tumors were grown subcutaneously in male nude mice. Tumors were harvested at different times after castration. The time points post-castration included (in days): 0, 1, 3, 4, 5, 10, 30, 40, 50, 51, 52, 59, 60, 61, 70, 79, 80, 82, 120, and 125. Analyses also included established androgen-independent xenografts. Castration resulted in tumor regression. At day 120 and thereafter, the tumors relapsed and started growing in the absence of androgen.

cRNAs were generated by in vitro transcription assays (IVTs) from the different samples and were hybridized to the oligonucleotide microarrays (Affymetrix Eos Hu03). Hybridization was measured by the average fluorescence intensity (AI), which is directly proportional to the expression level of the gene.

Two types of analyses were applied to the results:

Analysis A:

The samples were divided into different time groups which included the following time points post castration (in days): 1-5, 10, 30-40, 50-82, 120-125. To identify changes in gene expression, the following calculations were made:

1. The median (or mean, in case there were only 2 samples in a group) was calculated for each group.
2. The medians (or means) for each group was compared to one-another.
3. Genes were selected that exhibited a minimum 2 fold difference in the median (or mean) between any of the groups.
4. The change in gene expression over time was analyzed for each selected gene to look for specific pattern changes.

Only genes with an interesting expression pattern during the androgen-ablation time course were selected as potential new therapeutic targets and/or diagnostic markers. Among the 70,000 gene clusters present on Hu01 and Hu02, we identified 820 gene clusters with the desired expression patterns. These expression patterns can be broadly defined into the following categories:

1. Genes that are expressed early in the time course, then drop off in expression, and then express again with emergence of androgen-independence (hi-lo-hi pattern in Table 1A).
2. Genes that are expressed early in the time course, then drop off in expression, and do not express again with emergence of androgen-independence (hi-lo-lo pattern in Table 1A).
3. Genes that are not expressed early in the time course, but express only with emergence of androgen-independence (lo-lo-hi pattern in Table 1A).
4. Genes that are not expressed early in the time course, but then express as androgen is withdrawn and continue to express with emergence of androgen-independence (lo-hi-hi pattern in Table 1A).
5. Genes that are not expressed early in the time course, but then express as androgen is withdrawn and drop off again with emergence of androgen-independence (lo-hi-lo pattern in Table 1A).

Group 1 is characterized by cell-cycle regulating genes, such as those encoding cyclin B1, p21/WAF1, CDC18-homolog, cyclin A2, cyclin D1, and possible growth factors such as hAG2 (anterior gradient 2 homolog) among others. This indicates that interruption of growth factor and/or cell cycle pathways prevents the emergence of androgen-independent disease, making group 1 genes good targets for treating advanced prostate cancer.

Group 2 represents genes that are androgen-dependent, and do not re-express due to the lack of androgen signal in the androgen-independent phenotype. This group includes genes encoding proteins such as Fibronectin 1, which has been previously shown to be down-regulated with androgen-withdrawal (Amler, et al. (2000) *Cancer Res.* 60:6134-6141).

Group 3 represents genes that are up-regulated by signals that induce the androgen-independent phenotype. This group includes genes encoding stanniocalcin 2, c-fos proto-oncogene product, vascular endothelial growth factor, the cell surface protein transmembrane 4 superfamily member 1 and adrenomedullin among others. Adrenomedullin has recently been shown to act as an autocrine growth factor for the androgen-independent prostate cancer cell line DU145 (Rocchi, et al. (2001) *Cancer Res.* 61:1196-1206), indicating that its up-regulation is critical for supporting an androgen-independent phenotype. Blocking adrenomedullin function, and/or other genes in this group, prevents the growth of androgen-independent tumor cells.

Group 4 represents genes that are androgen-repressed and are only expressed in the absence of androgen. This group includes genes encoding the protein tyrosine phosphatase interacting protein liprin-alpha 2, the CD24 antigen, and the catalytic subunit for phosphatidylinositol 4-kinase amongst others. Patients that are treated for advanced prostate cancer by hormone-ablation may have in their bodies cells that have survived hormone-ablation and are likely to up-regulate genes that belong to Group 4. Therefore, Group 4 gene products are particularly good therapeutic targets for treating patients undergoing hormone-ablation therapy.

Group 5 represents genes that are involved in regulating signals that induce an androgen-independent phenotype. This group includes genes encoding Rab2 (a Ras-like G protein), the Son of Sevenless homolog (a GTP/GDP exchange factor involved in activating Ras-like proteins), and the p85 regulatory subunit for phosphoinositide-3-kinase (PI3-kinase). The PI3-kinase pathway has been implicated in providing a survival signal to the prostate cancer cell line LNCaP (Lin, et al. (1999) *Cancer Res.* 59:2891-2897). This indicates that ras-like signals and signals dependent on PI3-kinase are involved in inducing the androgen-independent phenotype. For that reason, Group 5 gene products are particularly good therapeutic targets for treating patients undergoing hormone-ablation therapy.

Analysis B:

For the second analysis, the samples were divided into 4 time groups which included the following time points post castration (in days): 0-1,3-5, 10-82, >120. To identify changes in gene expression, the following analysis was performed:

1. Genes were selected that exhibited a minimum of 100 A1 units at the 90$^{th}$ percentile expression level of samples.
2. The group mean expression levels for each gene were calculated. The genes were further sub-selected to exhibit a minimum 3 fold difference between the group means.
3. An analysis of variance was then performed on selected genes. From the original 59,680 gene clusters present on the Hu03 gene chip, only about 1165 genes with a P value of <0.01 were identified that also exhibited the above mentioned parameters.
4. A method was then employed for calculating the positive false discovery rate (pFDR), i.e., an estimate of the proportion of false-positives present in a set of findings (Storey and Tibshirani (2001) Technical Report, Department of Statistics, Stanford University, CA). This technique was developed explicitly for use with microarray data. The procedure involves randomly assigning the membership status of each sample to a group and re-performing the analysis of variance. In each simulation, the number of group members (6 for Group 1, 9 for group 2, 15 for group 3, and 4 for group 4) remained constant, but these designations were shuffled and assigned to each sample at random. The permutation was performed 1000 times, and for each simulation, the number of findings at P<0.01 was noted. The number of false positives under null conditions, was then divided by the number of actual findings (n=1165 genes) to obtain an estimate of the proportion of false positive findings. After the application of a correction factor, the final estimate for the pFDR was about 1%. Thus, one can expect that approximately 12 of the 1165 findings are false positives.
5. The approximately 1165 genes were clustered by expression pattern to identify specific pattern changes. Only genes with an interesting expression pattern during the androgen-ablation time course were selected as potential new therapeutic targets and/or diagnostic markers. These expression patterns can be broadly defined into the following categories:

1. Genes that are expressed early in the time course of androgen withdrawal, then drop off in expression, and then express again with emergence of androgen-independence (hi-lo-lo-hi pattern in Table 2A).
2. Genes that are expressed early in the time course, then drop off in expression immediately after androgen-withdrawal, and do not express again with emergence of androgen-independence (hi-lo-lo-lo pattern in Table 2A).
3. Genes that are expressed early in the time course, then drop off in expression after several days of androgen withdrawal, and do not express again with emergence of androgen-independence (hi-hi-lo-lo pattern in Table 2A).
4. Genes that are not expressed early in the time course, but express only with emergence of androgen-independence (lo-lo-lo-hi pattern in Table 2A).
5. Genes that are not expressed early in the time course, but then express as androgen is withdrawn and continue to express with emergence of androgen-independence (lo-lo-hi-hi pattern in Table 2A).
6. Genes that are not expressed early in the time course, but then express as androgen is withdrawn and drop off again with emergence of androgen-independence (lo-lo-hi-lo pattern in Table 2A).

Group 1 is characterized by cell-cycle regulating genes and cell growth promoting genes, such as those encoding cyclin B1 and CDC45 among others, growth factors/hormones such as hAG2 (anterior gradient 2 homolog), adrenomedullin, and stanniocalcin 2 among others, and growth factor receptors, such as the bone morphogenic protein receptor type 1B (BMP-R1B) and the endothelial differentiation lysophosphatidic acid G-protein-coupled receptor 7 among others. Adrenomedullin has recently been shown to act as an autocrine growth factor for the androgen-independent prostate cancer cell line DU145 (Rocchi, et al. (2001) *Cancer Res.* 61:1196-1206), indicating that its up-regulation is critical for supporting an androgen-independent phenotype. This indicates that interruption of growth factor and/or cell cycle pathways prevents the emergence of androgen-independent disease, making group 1 genes good targets for treating both localized and advanced prostate cancer and related conditions.

Group 2 represents genes that are androgen-dependent, and do not re-express due to the lack of androgen signal in the androgen-independent phenotype. This group includes genes encoding proteins such as the endothelial protein C receptor (EPCR) and the potassium intermediate/small conductance calcium-activated channel (subfamily N, member 2). These genes represent targets for treating androgen-dependent prostate cancer and related conditions.

Group 3 also represents genes that are androgen-dependent, and do not re-express due to the lack of androgen signal in the androgen-independent phenotype. This group includes genes encoding proteins such as Fibronectin 1, which has been previously shown to be down-regulated with androgen-withdrawal (Amler, et al. (2000) *Cancer Res.* 60:6134-6141), and genes encoding signaling proteins such as Rho GTPase activating protein 1. These genes represent targets for treating androgen-dependent prostate cancer and related conditions.

Group 4 represents genes that are up-regulated by signals that induce and maintain the androgen-independent phenotype. This group includes genes encoding potential growth promoting proteins such as chemokine-like factor (Unigene ID Hs. 15159), colon cancer-associated protein Mic1, and the mitogen-activated protein kinase-activated protein kinase 2. Blocking function of these proteins, and/or other genes in this group, prevents the growth of androgen-independent tumor cells and related conditions.

Group 5 represents genes that are androgen-repressed and are only expressed in the absence of androgen or that are induced by the absence of androgen. This group includes genes encoding transcriptional regulators such as the androgen receptor, the DNA activated protein kinase (catalytic subunit), and nuclear factor related to kappa B binding protein (NFRKB), among others. Patients that are treated for advanced prostate cancer by hormone-ablation may have in their bodies cells that have survived hormone-ablation and are likely to up-regulate genes that belong to Group 5. Therefore, Group 5 gene products are particularly good therapeutic targets for treating patients undergoing hormone-ablation therapy.

Group 6 represents genes that are involved in regulating signals that are induced during androgen withdrawal and that induce an androgen-independent phenotype. This group includes genes encoding signaling molecules such as phosphoinositide-3-kinase (class 2, alpha polypeptide), signal transducer and activator of transcription 2 (STAT2), phospholipase A2 (group IIA) and the protein tyrosine phosphatase interacting protein liprin-alpha 2, cell surface receptors such as gamma-aminobutyric acid (GABA) A receptor epsilon subunit, G-protein-coupled receptor 48, and immune function proteins such as the major histocompatibility complex class II DR alpha. The PI3-kinase pathway has been implicated in providing a survival signal to the prostate cancer cell line LNCaP (Lin, et al. (1999) *Cancer Res.* 59:2891-2897). This indicates that ras-like signals and signals dependent on PI3-kinase are involved in inducing the androgen-independent phenotype. For that reason, Group 6 gene products are particularly good therapeutic targets for treating patients undergoing hormone-ablation therapy.

TABLE 1A provides Accession numbers for genes, including expressed sequence lags, (incorporated in their entirety here and throughout the application where Accession numbers are provided). Genes with an interesting expression pattern during the androgen-ablation time course were selected as potential new therapeutic targets and/or diagnostic markers. 820 gene clusters were identified with desired expression patterns. These expression patterns can be broadly defined into the following categories:

1. Genes that are expressed early in the time course, then drop off in expression, and then express again with emergence of androgen-independence (hi-lo-hi pattern).
2. Genes that are expressed early in the time course, then drop off in expression, and do not express again with emergence of androgen-independence (hi-lo-lo pattern).
3. Genes that are not expressed early in the time course, but express only with emergence of androgen-independence (lo-lo-hi pattern).
4. Genes that are not expressed early in the time course, but then express as androgen is withdrawn and continue to express with emergence of androgen-independence (lo-hi-hi pattern).
5. Genes that are not expressed early in the time course, but then express as androgen is withdrawn and drop off again with emergence of androgen-independence (lo-hi-lo pattern).

Table 1B lists accession numbers for primekeys lacking a unigeneID in table 1A. For each probeset is listed a gene cluster number from which oligonucleotides were designed. Gene clusters were compiled using sequences derived from Genbank ESTs and mRNAs. These sequences were clustered based on sequence similarity using Clustering and Alignment Tools (Double Twist, Oakland Calif.). Genbank accession numbers for sequences comprising each cluster are listed in the "Accession" column.

Table 1C lists genomic positioning for primekeys lacking unigene ID's and accession numbers in tables 1A. For each predicted exon is listed genomic sequence source used for prediction. Nucleotide locations of each predicted exon are also listed.

TABLE 1A

| Pkey | ExAccn | UnigeneID | Unigene Title | pattern |
|---|---|---|---|---|
| 102772 | U83115 | Hs.161002 | absent in melanoma 1 | hi-lo-hi |
| 128610 | N48373 | Hs.10247 | activated leucocyte cell adhesion molecu | hi-lo-hi |
| 102276 | N48373 | Hs.10247 | activated leucocyte cell adhesion molecu | hi-lo-hi |
| 100654 | A03758 | | | hi-lo-hi |
| 100655 | A03758 | | | hi-lo-hi |
| 135400 | X78592 | Hs.99915 | androgen receptor (dihydrotestosterone r | hi-lo-hi |
| 331363 | AW582256 | *Hs.91011 | anteriror gradient 2 (*Xenepus laevis*) hom | hi-lo-hi |
| 115764 | AW582256 | *Hs.91011 | anteriror gradient 2 (*Xenepus laevis*) hom | hi-lo-hi |
| 120483 | BE251623 | Hs.1578 | baculoviral IAP repeat-containing 5 (sur | hi-lo-hi |
| 101505 | AA307680 | Hs.75692 | asparagine synthetase | hi-lo-hi |
| 127236 | AW661857 | Hs.98658 | budding uninhibited by benzimidazoles 1 | hi-lo-hi |
| 128472 | BE241880 | *Hs.10029 | cathepsin C | hi-lo-hi |

TABLE 1A-continued

| Pkey | ExAccn | UnigeneID | Unigene Title | pattern |
|---|---|---|---|---|
| 102712 | U77949 | Hs.69563 | CDC6 (cell division cycle 6, *S. cerevisi* | hi-lo-hi |
| 314943 | Y00272 | Hs.184572 | cell division cycle 2, G1 to S and G2 to | hi-lo-hi |
| 102123 | NM_001809 | *Hs.1594 | centromere protein A (17 kD) | hi-lo-hi |
| 326213 | | | CH.17_hs gi\|5867224 | hi-lo-hi |
| 327110 | | | CH.21_hs gi\|6117842 | hi-lo-hi |
| 339186 | | | CH22_DA59H18.GENSCAN.72-13 | hi-lo-hi |
| 337755 | | | CH22_EM: AC000097.GENSCAN.109-2 | hi-lo-hi |
| 337674 | | | CH22_EM: AC000097.GENSCAN.67-4 | hi-lo-hi |
| 337675 | | | CH22_EM: AC000097.GENSCAN.67-6 | hi-lo-hi |
| 333516 | | | CH22_FGENES.173_1 | hi-lo-hi |
| 333517 | | | CH22_FGENES.173_2 | hi-lo-hi |
| 333795 | | | CH22_FGENES.275_1 | hi-lo-hi |
| 333796 | | | CH22_FGENES.275_3 | hi-lo-hi |
| 333808 | | | CH22_FGENES.279_2 | hi-lo-hi |
| 333809 | | | CH22_FGENES.280_2 | hi-lo-hi |
| 332792 | | | CH22_FGENES.3_2 | hi-lo-hi |
| 334101 | | | CH22_FGENES.327_59 | hi-lo-hi |
| 334502 | | | CH22_FGENES.397_18 | hi-lo-hi |
| 334616 | | | CH22_FGENES.411_15 | hi-lo-hi |
| 334899 | | | CH22_FGENES.452_13 | hi-lo-hi |
| 334900 | | | CH22_FGENES.452_14 | hi-lo-hi |
| 334902 | | | CH22_FGENES.452_16 | hi-lo-hi |
| 334905 | | | CH22_FGENES.452_20 | hi-lo-hi |
| 334906 | | | CH22_FGENES.452_21 | hi-lo-hi |
| 334951 | | | CH22_FGENES.465_20 | hi-lo-hi |
| 335044 | | | CH22_FGENES.480_1 | hi-lo-hi |
| 335753 | | | CH22_FGENES.604_2 | hi-lo-hi |
| 335755 | | | CH22_FGENES.604_4 | hi-lo-hi |
| 333135 | | | CH22_FGENES.83_11 | hi-lo-hi |
| 333137 | | | CH22_FGENES.83_13 | hi-lo-hi |
| 333138 | | | CH22_FGENES.83_15 | hi-lo-hi |
| 333139 | | | CH22_FGENES.83_16 | hi-lo-hi |
| 336721 | | | CH22_FGENES.83-17 | hi-lo-hi |
| 105012 | AF098158 | Hs.9329 | chromosome 20 open reading frame 1 | hi-lo-hi |
| 134470 | X54942 | Hs.83758 | CDC28 protein kinase 2 | hi-lo-hi |
| 134750 | L29073 | Hs.1139 | cold shock domain protein A | hi-lo-hi |
| 125819 | AA044840 | *Hs.251871 | CTP synthase | hi-lo-hi |
| 102993 | BE262998 | Hs.85137 | cyclin A2 | hi-lo-hi |
| 131185 | BE280074 | Hs.23960 | cyclin B1 | hi-lo-hi |
| 106350 | AK001404 | *Hs.194698 | cyclin B2 | hi-lo-hi |
| 103080 | AU077231 | *Hs.82932 | cyclin D1 (PRAD1: peathyroid adenomatos | hi-lo-hi |
| 101216 | AA284166 | Hs.84113 | cyclin-dependent kinase inhibitor 3 (CDK | hi-lo-hi |
| 100589 | AW247430 | Hs.84152 | cystathionine-beta-synthase | hi-lo-hi |
| 130655 | AI831962 | Hs.17409 | cysteine-rich protein 1 (intestinal) | hi-lo-hi |
| 101473 | M22976 | Hs.83834 | cytochrome b-5 | hi-lo-hi |
| 101468 | BE538296 | *Hs.181028 | cytochrome c oxidase subunit Va | hi-lo-hi |
| 103546 | Z14244 | *Hs.75752 | cytochrome c oxidase subunit VIIb | hi-lo-hi |
| 100829 | AA471098 | Hs.278544 | acetyl-Coenzyme A acetyltransferase 2 (a | hi-lo-hi |
| 102469 | AF058293 | Hs.180015 | D-dopachrome tautomerase | hi-lo-hi |
| 114292 | AI815395 | Hs.184641 | fatty acid desaturase 2 | hi-lo-hi |
| 100656 | BE250162 | *Hs.83765 | dihydrofolate reductase | hi-lo-hi |
| 133799 | W24087 | Hs.76285 | DKFZP5648167 protein | hi-lo-hi |
| 129113 | BE543205 | *Hs.288771 | DKFZP586A0522 protein | hi-lo-hi |
| 332732 | AF191019 | Hs.8361 | hypothetical protein, estradiol-induced | hi-lo-hi |
| 108846 | AL117452 | *Hs.44155 | DKFZP586G1517 protein | hi-lo-hi |
| 133903 | X63692 | *Hs.77462 | DNA (cytosine-5-)-methyltransferase 1 | hi-lo-hi |
| 320099 | AW411307 | Hs.114311 | CDC45 (cell division cycle 45, *S. cerevis* | hi-lo-hi |
| 321960 | AA723883 | Hs.302446 | hypothetical protein MGC10334 | hi-lo-hi |
| 324988 | AK001379 | *Hs.121028 | hypothetical protein FLJ10549 | hi-lo-hi |
| 303274 | AK001468 | Hs.62180 | anillin (*Drosophila* Scraps homolog), act | hi-lo-hi |
| 301804 | AK001468 | Hs.62180 | anillin (*Drosophila* Scraps homolog), act | hi-lo-hi |
| 300551 | AW408800 | Hs.104859 | hypothetical protein DKFZp762E1312 | hi-lo-hi |
| 304541 | AA482561 | Hs.169476 | glyceraldehyde-3-phosphate dehydrogenase | hi-lo-hi |
| 304521 | AA464716 | | gb: zx82c11.s1 Soares ovary tumor NbHOT H | hi-lo-hi |
| 129075 | BE250162 | *Hs.83765 | dihydrofolate reductase | hi-lo-hi |
| 111003 | N52980 | Hs.83765 | dihydrofolate reductase | hi-lo-hi |
| 115536 | AK001468 | Hs.62180 | anillin (*Drosophila* Scraps homolog), act | hi-lo-hi |
| 108857 | AK001468 | Hs.62180 | anillin (*Drosophila* Scraps homolog). act | hi-lo-hi |
| 332397 | AB027249 | Hs.104741 | PDZ-binding kinase; T-cell originated pr | hi-lo-hi |
| 330714 | AA263143 | Hs.24596 | RAD51-interacting protein | hi-lo-hi |
| 104636 | R82252 | Hs.106106 | *Homo sapiens* cAMP-dependent protein kina | hi-lo-hi |
| 104986 | AW088826 | Hs.22971 | ESTs | hi-lo-hi |
| 105076 | AI598252 | Hs.37810 | ESTs | hi-lo-hi |
| 105312 | BE613348 | *Hs.23348 | S-phase kinase-associated protein 2 (p45 | hi-lo-hi |
| 105388 | AW575008 | Hs.11355 | thymopoietin | hi-lo-hi |
| 105953 | BE410556 | Hs.236556 | hypothetical protein STRAIT11499 | hi-lo-hi |
| 106286 | AI765107 | *Hs.274422 | hypothetical protein FLJ20550 | hi-lo-hi |

TABLE 1A-continued

| Pkey | ExAccn | UnigeneID | Unigene Title | pattern |
|---|---|---|---|---|
| 106889 | U46258 | Hs.18349 | HSPC145 protein | hi-lo-hi |
| 109220 | AW958181 | Hs.189998 | ESTs | hi-lo-hi |
| 113158 | AA328102 | Hs.24641 | cytoskeleton associated protein 2 | hi-lo-hi |
| 114542 | AW970128 | *Hs.293380 | ESTs | hi-lo-hi |
| 114986 | AK000361 | Hs.133260 | hypothetical protein FLJ20354 | hi-lo-hi |
| 115291 | BE545072 | *Hs.122579 | hypothetical protein FLJ10461 | hi-lo-hi |
| 115414 | AA662240 | Hs.283099 | AF15q14 protein | hi-lo-hi |
| 115471 | AK001376 | Hs.59346 | hypothetical protein FLJ10514 | hi-lo-hi |
| 115522 | BE614387 | Hs.47378 | ESTs, Moderately similar to T50635 hypot | hi-lo-hi |
| 115652 | BE093589 | Hs.38178 | hypothetical protein FLJ23468 | hi-lo-hi |
| 116121 | AK001330 | Hs.48855 | hypothetical protein FLJ10468 | hi-lo-hi |
| 116130 | AW183533 | Hs.38178 | hypothetical protein FLJ23468 | hi-lo-hi |
| 116448 | BE268321 | Hs.208912 | hypothetical protein MGC861 | hi-lo-hi |
| 116787 | AW362955 | Hs.15641 | ESTs | hi-lo-hi |
| 118336 | BE327311 | Hs.47166 | HT021 | hi-lo-hi |
| 120649 | AA687322 | Hs.192843 | leucine zipper protein FKSG14 | hi-lo-hi |
| 121503 | AA412049 | Hs.290347 | ESTs | hi-lo-hi |
| 121748 | BE536911 | Hs.234545 | *Homo sapiens* NUF2R mRNA, complete cds | hi-lo-hi |
| 122860 | AA464414 | | gb: zx78g01.s1 Soares ovary tumor NbHOT H | hi-lo-hi |
| 123477 | AF217515 | Hs.283532 | uncharacterized bone marrow protein BM03 | hi-lo-hi |
| 130338 | AI375726 | *Hs.279918 | hypothetical protein | hi-lo-hi |
| 130680 | BE567313 | Hs.183109 | monoamine oxidase A | hi-lo-hi |
| 131148 | AW953575 | *Hs.303125 | p53-induced protein PIGPC1 | hi-lo-hi |
| 131626 | BE514805 | *Hs.289092 | *Homo sapiens* cDNA: FLJ22380 fis, clone H | hi-lo-hi |
| 131937 | AI907735 | Hs.21446 | *Homo sapiens* mRNA for KIAA1716 protein, | hi-lo-hi |
| 131965 | W79283 | Hs.35962 | ESTs | hi-lo-hi |
| 132371 | AA235448 | Hs.46677 | PRO2000 protein | hi-lo-hi |
| 133626 | AW836130 | Hs.75277 | hypothetical protein FLJ13910 | hi-lo-hi |
| 300942 | AW301344 | Hs.122908 | *Homo sapiens*, clone IMAGE: 3048353, mRNA, | hi-lo-hi |
| 300953 | AA542845 | Hs.294088 | ESTs | hi-lo-hi |
| 302656 | BE090580 | Hs.70704 | *Homo sapiens*, clone IMAGE: 2823731, mRNA, | hi-lo-hi |
| 311928 | T62216 | Hs.270840 | ESTs | hi-lo-hi |
| 313637 | AK000742 | Hs.126774 | L2DTL protein | hi-lo-hi |
| 313832 | AW271106 | Hs.133294 | ESTs | hi-lo-hi |
| 316465 | AW574774 | Hs.121692 | ESTs | hi-lo-hi |
| 317202 | AA894880 | Hs.181181 | ESTs | hi-lo-hi |
| 320771 | R74441 | Hs.117176 | poly(A)-binding protein, nuclear 1 | hi-lo-hi |
| 321636 | AI820961 | Hs.193465 | ESTs | hi-lo-hi |
| 330867 | AW978991 | Hs.221197 | ESTs | hi-lo-hi |
| 331442 | H77381 | Hs.159420 | ESTs | hi-lo-hi |
| 106654 | AW075485 | Hs.286049 | phosphoserine aminotransferase | hi-lo-hi |
| 106590 | AI350260 | Hs.301539 | hypothetical protein MGC2633 | hi-lo-hi |
| 128460 | T16206 | Hs.237164 | ESTs, highly similar to LDHH__HUMAN L-LA | hi-lo-hi |
| 114394 | T34462 | Hs.103291 | neuritin | hi-lo-hi |
| 315936 | AW069807 | Hs.271252 | ESTs | hi-lo-hi |
| 108886 | AW248434 | Hs.91521 | hypothetical protein | hi-lo-hi |
| 129241 | AI878857 | Hs.109706 | hematological and neurological expressed | hi-lo-hi |
| 104978 | AI199268 | Hs.19322 | ESTs, Weakly similar to CGHU7L collagen | hi-lo-hi |
| 129626 | F13272 | Hs.111334 | ferritin, light polypeptide | hi-lo-hi |
| 118895 | BE304917 | Hs.31097 | hypothetical protein FLJ21478 | hi-lo-hi |
| 332577 | AI826268 | Hs.27769 | ESTs, Weakly similar to MCAT__HUMAN MITOC | hi-lo-hi |
| 116732 | AW152225 | Hs.165909 | ESTs | hi-lo-hi |
| 106774 | AI216748 | Hs.14587 | ESTs, Weakly similar AF151859 1 CGI-1 | hi-lo-hi |
| 108818 | BE612676 | Hs.303116 | stromal cell-derived factor 2-like 1 | hi-lo-hi |
| 315618 | AI287341 | *Hs.154029 | bHLH factor Hes4 | hi-lo-hi |
| 110561 | AA379597 | Hs.5199 | HSPC150 protein similar to ubiquitin-con | hi-lo-hi |
| 132959 | AW014195 | Hs.61472 | ESTs, Weakly similar to unknown [*S. cerev* | hi-lo-hi |
| 103195 | AA351647 | Hs.2642 | eukaryotic translation elongation factor | hi-lo-hi |
| 100368 | D79987 | Hs.153479 | extra spindle poles, *S. cerevisiae*, homo | hi-lo-hi |
| 103177 | BE244377 | *Hs.48876 | farnesyl-diphosphate farnesyltransferase | hi-lo-hi |
| 109141 | AF174600 | Hs.193380 | F-box protein Fbx20 | hi-lo-hi |
| 100676 | X02761 | *Hs.287820 | fibronectin 1 | hi-lo-hi |
| 100254 | AA452181 | Hs.77643 | FK506-binding protein 1B (12.6 kD) | hi-lo-hi |
| 133688 | U71321 | Hs.7557 | FK506-binding protein 5 | hi-lo-hi |
| 107129 | AC004770 | *Hs.4756 | flap structure-specific endonuclease 1 | hi-lo-hi |
| 102696 | BE540274 | Hs.239 | forkhead box M1 | hi-lo-hi |
| 101753 | L11144 | Hs.1907 | galanin | hi-lo-hi |
| 101597 | AA317089 | *Hs.597 | glutamic-oxaloacetic transaminase 1, sol | hi-lo-hi |
| 133512 | L18861 | | gb: Human Golli-mbp gene, exon 1 | hi-lo-hi |
| 130080 | X14850 | Hs.147097 | H2A histone family, member X | hi-lo-hi |
| 101600 | BE561617 | *Hs.119192 | H2A histone family, member Z | hi-lo-hi |
| 101332 | J04088 | *Hs.156346 | topoisomerase (DNA) II alpha (170 kD) | hi-lo-hi |
| 132967 | AA316181 | Hs.61635 | six transmembrane epithelial antigen of | hi-lo-hi |
| 129726 | H15474 | Hs.132898 | fatty acid desaturase 1 | hi-lo-hi |
| 106925 | AK002011 | Hs.37558 | hypothetical protein FLJ11149 | hi-lo-hi |
| 105643 | BE621719 | Hs.173802 | KIAA0603 gene product | hi-lo-hi |
| 116028 | H59799 | Hs.42644 | thioredoxin-like | hi-lo-hi |

TABLE 1A-continued

| Pkey | ExAccn | UnigeneID | Unigene Title | pattern |
|---|---|---|---|---|
| 105437 | AF151076 | Hs.25199 | hypothetical protein | hi-lo-hi |
| 122512 | AF053305 | Hs.98658 | budding uninhibited by benzimidazoles 1 | hi-lo-hi |
| 131991 | AF053306 | Hs.36708 | budding uninhibited by beuzimidazoles 1 | hi-lo-hi |
| 135015 | AW361638 | Hs.278338 | LGN protein | hi-lo-hi |
| 102208 | U22961 | | gb: Human mRNA clone with similarity to L | hi-lo-hi |
| 100144 | AL119964 | Hs.75616 | seladin-1 | hi-lo-hi |
| 100447 | NM_014767 | Hs.74583 | KIAA0275 gene product | hi-lo-hi |
| 116578 | D21262 | Hs.75337 | nucleolar phosphoprotein p130 | hi-lo-hi |
| 130350 | AA369601 | Hs.239138 | pre-B-cell colony-enhancing factor | hi-lo-hi |
| 101045 | J05614 | | gb: Human proliferating cell nuclear anti | hi-lo-hi |
| 101544 | M31169 | | gb: Human propionyl-CoA carboxylase beta- | hi-lo-hi |
| 113674 | NM_014214 | Hs.5753 | inositol(myo)-1(or 4)-monophosphatase 2 | hi-lo-hi |
| 102260 | AL039104 | Hs.159557 | karyopherin alpha 2 (RAG cohort 1, impor | hi-lo-hi |
| 100154 | H60720 | Hs.81892 | KIAA0101 gene product | hi-lo-hi |
| 100199 | BE562298 | Hs.71827 | KIAA0112 protein; homolog of yeast ribos | hi-lo-hi |
| 100372 | NM_014791 | Hs.184339 | KIAA0175 gene product | hi-lo-hi |
| 100387 | D83777 | *Hs.75137 | K1AA0193 gene product | hi-lo-hi |
| 131514 | BE270734 | *Hs.2795 | lactate dehydrogenase A | hi-lo-hi |
| 102938 | W27518 | Hs.234489 | lactate dehydrogenase B | hi-lo-hi |
| 105811 | BE617695 | Hs.286192 | protein phosphatase 1, regulatory (inhib | hi-lo-hi |
| 101013 | BE300094 | *Hs.227751 | lectin, galactoside-binding, soluble, 1 | hi-lo-hi |
| 124148 | BE300094 | *Hs.227751 | lectin, galactoside-binding, soluble, 1 | hi-lo-hi |
| 102968 | AU076611 | Hs.154672 | methylene tetrahydrofolate dehydrogenase | hi-lo-hi |
| 130149 | AW067805 | Hs.172665 | methylenetetrahydrofolate dehydrogenase | hi-lo-hi |
| 114767 | AI859865 | Hs.154443 | minichromosome maintenance deficient (S. | hi-lo-hi |
| 129168 | AI132988 | Hs.109052 | chromosome 14 open reading frame 2 | hi-lo-hi |
| 105011 | BE091926 | Hs.16244 | mitotic spindle coiled-coil related prot | hi-lo-hi |
| 103023 | AW500470 | Hs.117950 | multifunctional polypeptide similar to S | hi-lo-hi |
| 102808 | BE242818 | *Hs.179606 | nuclear RNA helicase, DECD variant of DE | hi-lo-hi |
| 318617 | AW247252 | Hs.75514 | nucleoside phosphorylase | hi-lo-hi |
| 101568 | M81740 | Hs.75212 | ornithine decarboxylase 1 | hi-lo-hi |
| 102076 | BE299197 | Hs.179665 | cyclin-dependent kinase inhibitor 1A (p2 | hi-lo-hi |
| 100202 | BE294407 | *Hs.99910 | phosphofructokinase, platelet | hi-lo-hi |
| 101032 | BE206854 | Hs.46039 | phosphoglycerate mutase 2 (muscle) | hi-lo-hi |
| 130553 | AF062649 | *Hs.252587 | pituitary tumor-transforming 1 | hi-lo-hi |
| 101626 | M57399 | Hs.44 | pleiotrophin (heparin binding growth fac | hi-lo-hi |
| 101992 | X90725 | Hs.77597 | polo (*Drosophia*)-like kinase | hi-lo-hi |
| 132164 | AI752235 | Hs.41270 | procollagen-lysine, 2-oxoglutarate 5-dio | hi-lo-hi |
| 101396 | BE267931 | *Hs.78996 | proliferating cell nuclear antigen | hi-lo-hi |
| 119018 | AA631143 | Hs.179809 | ESTs | hi-lo-hi |
| 101840 | AA236291 | Hs.183583 | sense (or cysteine) proteinase inhibito | hi-lo-hi |
| 332640 | BE568452 | Hs.5101 | protein regulator of cytokinesis 1 | hi-lo-hi |
| 132543 | BE568452 | Hs.5101 | protein regulator of cytokinesis 1 | hi-lo-hi |
| 101118 | AA371931 | *Hs.77422 | proteolipid protein 2 (colonic epitheliu | hi-lo-hi |
| 109166 | AA219691 | Hs.73625 | RAB6 interacting, kinesis-like (rabkines | hi-lo-hi |
| 100830 | AC004770 | *Hs.4756 | flap structure-specific endonuclease 1 | hi-lo-hi |
| 107059 | BE614410 | Hs.23044 | RAD51 (*S. cerevisiae*) homolog (*E coli* Re | hi-lo-hi |
| 321693 | AA227069 | Hs.173737 | ras-related C3 botulinum toxin substrate | hi-lo-hi |
| 101148 | NM_002923 | Hs.78944 | regulator of G-protein signaling 2, 24 k | hi-lo-hi |
| 130567 | AA383092 | Hs.1608 | replication protein A3 (14 kD) | hi-lo-hi |
| 103076 | NM_001034 | Hs.75319 | ribonucleotide reductase M2 polypeptide | hi-lo-hi |
| 103131 | BE536069 | Hs.2962 | S100 calcium-binding protein P | hi-lo-hi |
| 102212 | AW411491 | Hs.75069 | serine hydroxymethyltransferase 2 (mitoc | hi-lo-hi |
| 104254 | AW411425 | Hs.180655 | serine/threonine kinase 12 | hi-lo-hi |
| 102748 | BE018138 | Hs.24447 | sigma receptor (SR31747 binding protein | hi-lo-hi |
| 102012 | BE259035 | Hs.118400 | singed (*Drosophila*)-like (sea urchin fas | hi-lo-hi |
| 102522 | BE250944 | Hs.183556 | solute carrier family 1 (neutral amino a | hi-lo-hi |
| 132994 | AA112748 | Hs.279905 | clone HQ0310 PRO0310p1 | hi-lo-hi |
| 101971 | Z49105 | *Hs.289105 | synovial sarcoma, X breakpoint 2 | hi-lo-hi |
| 126645 | AA316181 | Hs.61635 | six transmembrane epithelial antigen of | hi-lo-hi |
| 103058 | X57348 | Hs.184510 | stratifin | hi-lo-hi |
| 102632 | U66618 | Hs.250581 | SWI/SNF related, matrix associated, acti | hi-lo-hi |
| 103269 | AF230662 | *Hs.289105 | synovial sarcoma, X breakpoint 2 | hi-lo-hi |
| 128920 | AA622037 | Hs.166468 | programmed cell death 5 | hi-lo-hi |
| 100114 | X02308 | Hs.82962 | thymidylate synthetase | hi-lo-hi |
| 102846 | BE264974 | Hs.6566 | thyroid hormone receptor interector 13 | hi-lo-hi |
| 131877 | J04088 | *Hs.156346 | topoisomerase (DNA) II alpha (170 kD) | hi-lo-hi |
| 100866 | U14134 | Hs.75113 | general transcription factor IIIA | hi-lo-hi |
| 133893 | AI434699 | Hs.77356 | transferrin receptor (p90, CD71) | hi-lo-hi |
| 130135 | AA311426 | *Hs.21635 | tubulin, gamma 1 | hi-lo-hi |
| 130287 | AA479005 | Hs.154036 | tumor suppressing subtransferable candid | hi-lo-hi |
| 126180 | L32977 | Hs.3712 | ubiquinol-cytochrome c reductase, Rieske | hi-lo-hi |
| 101536 | NM_006002 | Hs.77917 | ubiquitin carboxyl-terminal esterase L3 | hi-lo-hi |
| 102687 | NM_007019 | *Hs.93002 | ubiquitin carrier protein E2-C | hi-lo-hi |
| 103556 | Z19002 | Hs.37096 | zinc finger protein 145 (Kruppel-liKe, e | hi-lo-hi |
| 300022 | | | | hi-lo-hi-lo |
| 133015 | AJ002744 | Hs.246315 | UDP-N-acetyl-alpha-D-galactosamine:polyp | hi-lo-hi-lo |

TABLE 1A-continued

| Pkey | ExAccn | UnigeneID | Unigene Title | pattern |
|---|---|---|---|---|
| 129642 | NM_001360 | Hs.11806 | 7-dehydrocholesterol reductase | hi-lo-hi-lo |
| 134369 | AF207664 | Hs.8230 | a disintegrin-like and metatlloprotease ( | hi-lo-lo |
| 300023 | | | | hi-lo-lo |
| 125183 | AV660804 | Hs.301417 | AHNAK nucleoprotein (desmoyokin) | hi-lo-lo |
| 101766 | M80899 | *Hs.301417 | AHNAK nucleoprotein (desmoyokin) | hi-lo-lo |
| 133516 | BE265133 | *Hs.217493 | annexin A2 | hi-lo-lo |
| 102146 | AW162057 | Hs.78629 | ATPase, Na+/K+ transporting, beta 1 poly | hi-lo-lo |
| 318538 | AI750979 | Hs.74034 | *Homo sapiens* clone 24651 mRNA sequence | hi-lo-lo |
| 103554 | AI878826 | Hs.323469 | caveolin 1, caveolae protein, 22 KD | hi-lo-lo |
| 329365 | | | CH.X_hs gi\|5868838 | hi-lo-lo |
| 334282 | | | CH22_FGENES.369_12 | hi-lo-lo |
| 334891 | | | CH22_FGENES.452_5 | hi-lo-lo |
| 335149 | | | CH22_FGENES.499_5 | hi-lo-lo |
| 335682 | | | CH22_FGENES.595_2 | hi-lo-lo |
| 335756 | | | CH22_FGENES.604_5 | hi-lo-lo |
| 303951 | AW475081 | Hs.172928 | collagen, type I, alpha 1 | hi-lo-lo |
| 134421 | AU077196 | Hs.82985 | collagen, type V, alpha 2 | hi-lo-lo |
| 131101 | BE387561 | Hs.22981 | DKFZP586M1523 protein | hi-lo-lo |
| 124153 | AU077333 | *Hs.160483 | erythrocyte membrane protein band 7.2 (s | hi-lo-lo |
| 103328 | AU077333 | *Hs.160483 | erythrocyte membrane protein band 7.2 (s | hi-lo-lo |
| 322035 | AL137517 | *Hs.306201 | hypothetical protein DKFZp564O1278 | hi-lo-lo |
| 301872 | H84730 | Hs.326391 | ESTs, Highly similar to KIAA1437 protein | hi-lo-lo |
| 303820 | AB037858 | Hs.173484 | hypothetical protein FLJ10337 | hi-lo-lo |
| 304049 | T58155 | | gb: yb98h03.s1 Stratagene lung (937210) H | hi-lo-lo |
| 304735 | AA576453 | | gb: nm75h11.s1 NCI_CGAP_Co9 *Homo sapiens* | hi-lo-lo |
| 306999 | AI138628 | Hs.308058 | EST, Weakly similar to zinc finger prot | hi-lo-lo |
| 128789 | AW368576 | Hs.139851 | caveolin 2 | hi-lo-lo |
| 132057 | AB037858 | Hs.173484 | hypothetical protein FLJ10337 | hi-lo-lo |
| 114795 | AB037858 | Hs.173484 | hypothetical protein FLJ10337 | hi-lo-lo |
| 104204 | AK001691 | Hs.57655 | hypothetical protein FLJ10829 | hi-lo-lo |
| 105200 | AA328102 | Hs.24641 | cytoskeleton associated protein 2 | hi-lo-lo |
| 105493 | AL047586 | Hs.10283 | RNA binding motif protein 8B | hi-lo-lo |
| 107977 | AI188161 | Hs.144627 | ESTs | hi-lo-hi |
| 108880 | AA766606 | *Hs.47099 | hypothetical protein FLJ21212 | hi-lo-lo |
| 111157 | AL109729 | Hs.18948 | ESTs, Highly similar to A31026 probable | hi-lo-lo |
| 116202 | BE159395 | Hs.87089 | ESTs | hi-lo-lo |
| 120689 | AW134519 | Hs.96125 | ESTs | hi-lo-lo |
| 121847 | AA446628 | Hs.2799 | cartilage linking protein 1 | hi-lo-lo |
| 124182 | AI637471 | Hs.107801 | ESTs | hi-lo-lo |
| 128515 | BE395085 | Hs.10086 | type I transmembrane protein Fn14 | hi-lo-lo |
| 130466 | W19744 | Hs.180059 | *Homo sapiens* cDNA FLJ20653 fis, clone KA | hi-lo-lo |
| 131076 | AA749230 | Hs.22666 | ESTs | hi-lo-lo |
| 131084 | NM_017413 | Hs.303084 | apelin; peptide ligand for APJ receptor | hi-lo-lo |
| 134109 | AA348031 | Hs.7913 | ESTs | hi-lo-lo |
| 300258 | AI478933 | Hs.188260 | ESTs | hi-lo-lo |
| 302767 | H94900 | Hs.17882 | ESTs | hi-lo-lo |
| 312391 | R43707 | Hs.133159 | ESTs, Weakly similar to PIHUSD salivary | hi-lo-lo |
| 312689 | AW450461 | Hs.203965 | ESTs | hi-lo-lo |
| 315715 | AI284219 | Hs.130749 | ESTs | hi-lo-lo |
| 315843 | AA679430 | Hs.191897 | ESTs | hi-lo-lo |
| 322447 | AI735759 | Hs.52620 | integrin, beta 8 | hi-lo-lo |
| 322826 | AI807883 | Hs.201771 | ESTs | hi-lo-lo |
| 324867 | AI624707 | *Hs.5921 | *Homo sapiens* cDNA: FLJ21592 fis, clone C | hi-lo-lo |
| 331336 | AA287450 | Hs.93842 | *Homo sapiens* cDNA: FLJ22554 fis, clone | hi-lo-lo |
| 331353 | AA953006 | Hs.88143 | ESTs | hi-lo-lo |
| 133063 | AI654133 | Hs.30212 | thyroid receptor interacting protein 15 | hi-lo-lo |
| 311034 | BE567130 | Hs.311389 | ESTs, Moderately similar to PT0375 natur | hi-lo-lo |
| 108647 | BE546947 | Hs.44276 | hameo box C10 | hi-lo-lo |
| 124955 | AA376768 | *Hs.324841 | hypothetical protein FLJ22622 | hi-lo-lo |
| 113923 | AW953484 | Hs.3849 | hypothetical protein FLJ22041 similar to | hi-lo-lo |
| 310557 | AI431798 | Hs.164192 | ESTs, Weakly similar to Y161_HUMAN HYPOT | hi-lo-lo |
| 302943 | AI581344 | Hs.127812 | ESTs, Weakly similar to T17330 hypotheti | hi-lo-lo |
| 128453 | X02761 | *Hs.287820 | fibronectin 1 | hi-lo-lo |
| 305232 | AA670052 | Hs.169476 | glyceraldehyde-3-phosphate dehydrogenase | hi-lo-lo |
| 117642 | U55184 | *Hs.154145 | hypothetical protein FLJ11585 | hi-lo-lo |
| 115881 | NM_005756 | Hs.184942 | G protein-coupled receptor 64 | hi-lo-lo |
| 133666 | U56725 | Hs.75452 | heat shock 70 kD protein 2 | hi-lo-lo |
| 103262 | X78565 | Hs.289114 | hexabrachion (tenascin C, cytotactin) | hi-lo-lo |
| 100793 | S69027 | | gb: HOX C6 = class I homeodomain (fragment | hi-lo-lo |
| 102289 | U32114 | | | hi-lo-lo |
| 319109 | Z45662 | Hs.90797 | *Homo sapiens* clone 23620 mRNA sequence | hi-lo-lo |
| 116357 | AF052107 | Hs.90797 | *Homo sapiens* clone 23620 mRNA sequence | hi-lo-lo |
| 101497 | W05150 | *Hs.37034 | homeo box A5 | hi-lo-lo |
| 105508 | AA173942 | Hs.326416 | *Homo sapiens* mRNA; cDNA DKFZp564H1916 (f | hi-lo-lo |
| 302290 | AA179949 | Hs.175563 | *Homo sapiens* mRNA: cDNA DKFZp564N0763 (f | hi-lo-lo |
| 102838 | R34657 | Hs.80658 | uncoupling protein 2 (mitochondrial, pro | hi-lo-lo |
| 100235 | D29954 | Hs.13421 | KIAA0056 protein | hi-lo-lo |

TABLE 1A-continued

| Pkey | ExAccn | UnigeneID | Unigene Title | pattern |
|---|---|---|---|---|
| 133507 | NM_002206 | Hs.74369 | integrin, alpha 7 | hi-lo-lo |
| 125573 | AI351642 | Hs.182241 | interferon induced transmembrane protein | hi-lo-lo |
| 103059 | X57351 | Hs.174195 | interferon induced transmembrane protein | hi-lo-lo |
| 330415 | D83777 | *Hs.75137 | KIAA0193 gene product | hi-lo-lo |
| 303054 | BE265848 | Hs.289080 | colon cancer-associated protein Mic1 | hi-lo-lo |
| 133579 | X75346 | Hs.75074 | mitogen-activated protein kinase-activat | hi-lo-lo |
| 100528 | BE386801 | Hs.21858 | trinucleotide repeat containing 3 | hi-lo-lo |
| 107480 | AF001691 | Hs.74304 | periplakin | hi-lo-lo |
| 133050 | X73424 | Hs.63788 | propionyl Coenzyme A carboxylase, beta p | hi-lo-lo |
| 133061 | AI186431 | Hs.296638 | prostate differentiation factor | hi-lo-lo |
| 106390 | AJ297436 | Hs.20166 | prostate stem cell antigen | hi-lo-lo |
| 302124 | AA676403 | Hs.145078 | regulator of differentiation (in *S. pomb* | hi-lo-lo |
| 129823 | X00949 | *Hs.105314 | relaxin 1 (H1) | hi-lo-lo |
| 134444 | BE184455 | *Hs.251754 | secretory leukocyte protease inhibitor ( | hi-lo-lo |
| 103240 | U81961 | Hs.2794 | sodium channel, nonvoltage-gated 1 alpha | hi-lo-lo |
| 115761 | AA366037 | Hs.90911 | solute carrier family 16 (monocarboxylic | hi-lo-lo |
| 321412 | AI674383 | Hs.22891 | solute carrier family 7 (cationic amino | hi-lo-lo |
| 126487 | AA283809 | Hs.184601 | solute carrier family 7 (cationic amino | hi-lo-lo |
| 101759 | M80244 | Hs.184601 | solute carrier family 7 (cationic amino | hi-lo-lo |
| 112941 | AW163034 | Hs.6467 | synaptogyrin 3 | hi-lo-lo |
| 134351 | BE272506 | *Hs.82109 | syndecan 1 | hi-lo-lo |
| 125924 | BE272506 | *Hs.82109 | syndecan 1 | hi-lo-lo |
| 130982 | AA033627 | Hs.21858 | trinucleotide repeat containing 3 | hi-lo-lo |
| 133473 | AW301993 | Hs.73980 | troponin T1, skeletal, slow | hi-lo-lo |
| 101042 | T46839 | *Hs.10319 | UDP glycosyltransferase 2 family, polype | hi-lo-lo |
| 129565 | X77777 | Hs.198726 | vasoactive intestinal peptide receptor 1 | hi-lo-lo |
| 102992 | M85430 | *Hs.155191 | villin 2 (ezrin) | hi-lo-lo |
| 106868 | BE185536 | Hs.300816 | *Homo sapiens* mRNA; cDNA DKFZp564I172 (fr | lo-hi-lo |
| 132618 | AL050025 | *Hs.279916 | hypothetical protein FLJ20151 | lo-hi-hi |
| 100187 | D17793 | *Hs.78183 | aldo-keto reductase family 1, member C3 | lo-hi-hi |
| 116334 | AL038450 | Hs.48948 | ATP2C1 calcium transport ATPase, same as | lo-hi-hi |
| 134454 | NM_013230 | Hs.286124 | CD24 antigen (small cell lung carcinoma | lo-hi-hi |
| 302067 | BE542706 | Hs.222399 | CEGP1 protein | lo-hi-hi |
| 105500 | AW602166 | Hs.222399 | CEGP1 protein | lo-hi-hi |
| 100732 | AA557660 | *Hs.76152 | decorin | lo-hi-hi |
| 129265 | AA530892 | Hs.171695 | dual specificity phosphatase 1 | lo-hi-hi |
| 117789 | N48294 | Hs.46850 | EST | lo-hi-hi |
| 330786 | BE379594 | *Hs.49136 | ESTs, Moderately similar to ALU7_HUMAN A | lo-hi-hi |
| 319808 | T58960 | Hs.17283 | hypothetical protein FLJ10890 | lo-hi-hi |
| 303502 | BE174240 | | gb: QV1-HT0573-290200-092-106 HT0573 *Homo* | lo-hi-hi |
| 116780 | H22566 | *Hs.30098 | ESTs | lo-hi-hi |
| 104189 | AB040927 | Hs.301804 | KIAA1494 protein | lo-hi-hi |
| 105588 | L43821 | Hs.80261 | enhancer of filamentation 1, (cas-like do | lo-hi-hi |
| 105731 | AA834664 | Hs.29131 | nuclear receptor coactivator 2 | lo-hi-hi |
| 105772 | H57111 | Hs.221132 | ESTs | lo-hi-hi |
| 105794 | H24530 | Hs.273294 | hypothetical protein FLJ20069 | lo-hi-hi |
| 113098 | N77737 | Hs.8349 | Apobec-1 complementation factor; APOBEC- | lo-hi-hi |
| 113803 | AW880709 | *Hs.283683 | chromosome 8 open reading frame 4 | lo-hi-hi |
| 114530 | AA601038 | Hs.191797 | ESTs | lo-hi-hi |
| 116188 | AA468183 | Hs.184598 | *Homo sapiens* cDNA; FLJ23241 fis, clone C | lo-hi-hi |
| 117330 | AI904095 | Hs.43423 | ESTs | lo-hi-hi |
| 117701 | BE063921 | Hs.295971 | ESTs | lo-hi-hi |
| 120911 | AI189754 | Hs.144330 | ESTs | lo-hi-hi |
| 124083 | AW195237 | Hs.7734 | hypothetical protein FLJ22174 | lo-hi-hi |
| 124690 | AW883529 | Hs.173830 | ESTs | lo-hi-hi |
| 130796 | AA088809 | Hs.19525 | hypothetical protein FLJ22794 | lo-hi-hi |
| 131524 | AB040927 | Hs.301804 | KIAA1494 protein | lo-hi-hi |
| 132116 | AW960474 | Hs.40289 | ESTs | lo-hi-hi |
| 132442 | AW970859 | Hs.313503 | ESTs | lo-hi-hi |
| 310219 | AI221087 | Hs.147761 | ESTs | lo-hi-hi |
| 310598 | AI439136 | Hs.140546 | ESTs | lo-hi-hi |
| 310884 | AW014684 | Hs.232189 | ESTs | lo-hi-hi |
| 311587 | AI828254 | Hs.271019 | ESTs, Weakly similar to SMN1_HUMAN SURVI | lo-hi-hi |
| 312240 | R36475 | Hs.24321 | *Homo sapiens* cDNA FLJ12028 fis, clone HE | lo-hi-hi |
| 312803 | AA677934 | Hs.117864 | ESTs | lo-hi-hi |
| 314219 | AA262331 | Hs.48376 | *Homo sapiens* clone HB-2 mRNA sequence | lo-hi-hi |
| 315052 | AA876910 | Hs.134427 | ESTs | lo-hi-hi |
| 331919 | AA446869 | Hs.119316 | ESTs | lo-hi-hi |
| 133240 | AK001489 | Hs.242894 | ADP-ribosylation factor-like 1 | lo-hi-hi |
| 134006 | Z45957 | Hs.7837 | G-protein-coupled receptor induced prote | lo-hi-hi |
| 124847 | W07701 | *Hs.304177 | *Homo sapiens* clone FLB8503 PRO2286 mRNA, | lo-hi-hi |
| 129087 | AI348027 | Hs.108557 | *Homo sapiens* clone PP1057 unknown mRNA | lo-hi-hi |
| 131762 | AA744902 | *Hs.107767 | hypothetical protein PRO1489 | lo-hi-hi |
| 129000 | AA744902 | *Hs.107767 | hypothetical protein PRO1489 | lo-hi-hi |
| 105713 | AI122843 | *Hs.184319 | ESTs, Weakly similar to KIAA1006 protein | lo-hi-hi |
| 118475 | N66845 | | gb: za46c11.s1 Soares fetal liver spleen | lo-hi-hi |
| 118381 | N64513 | Hs.48994 | ESTs, Weakly similar to AF151800 1 CGI-4 | lo-hi-hi |

TABLE 1A-continued

| Pkey | ExAccn | UnigeneID | Unigene Title | pattern |
|---|---|---|---|---|
| 105057 | AA134233 | | gb: zo20f10.s1 Stratagene colon (937204) | lo-hi-hi |
| 131507 | AI826268 | Hs.27769 | ESTs, Weakly similar to MCAT_HUMAN MITOC | lo-hi-hi |
| 124970 | BE272862 | Hs.106534 | hypothetical protein FLJ22625 | lo-hi-hi |
| 130094 | NM_001471 | *Hs.167017 | gamma-aminobutyric acid (GABA) B recepto | lo-hi-hi |
| 302357 | X03178 | Hs.198246 | group-specific component (vitamin D bind | lo-hi-hi |
| 113231 | AA278583 | Hs.180737 | *Homo sapiens* clone 23664 and 23905 mRNA | lo-hi-hi |
| 111923 | BE383234 | Hs.25925 | *Homo sapiens* clone 23860 mRNA sequence | lo-hi-hi |
| 128530 | AI932995 | Hs.183475 | *Homo sapiens* clone 25061 mRNA sequence | lo-hi-hi |
| 128987 | AI339046 | Hs.107637 | hypothetical protein FLJ12806 | lo-hi-hi |
| 315368 | AB037745 | Hs.104696 | KIAA1324 protein | lo-hi-hi |
| 133944 | AW068579 | Hs.7780 | *Homo sapiens* mRNA; cDNA DKFZp564A072 (fr | lo-hi-hi |
| 115084 | BE383668 | *Hs.42484 | hypothetical protein FLJ10618 | lo-hi-hi |
| 132883 | AA373314 | Hs.5897 | *Homo sapiens* mRNA; cDNA DKFZp586P1622 (f | lo-hi-hi |
| 109623 | AW207385 | Hs.295901 | KIAA0493 protein | lo-hi-hi |
| 130577 | M69241 | *Hs.162 | insulin-like growth factor binding prote | lo-hi-hi |
| 101889 | AF188747 | *Hs.181350 | kallikrein 2, prostatic | lo-hi-hi |
| 130336 | AA535210 | *Hs.171995 | kallikrein 3, (prostate specific antigen | lo-hi-hi |
| 128180 | AW949068 | Hs.171995 | kallikrein 3, (prostate specific antigen | lo-hi-hi |
| 134921 | AL137491 | Hs.125511 | *Homo sapiens* mRNA; cDNA DKFZp434P1530 (f | lo-hi-hi |
| 302385 | AJ224172 | Hs.204096 | lipophilin B (uteroglobin family member) | lo-hi-hi |
| 117921 | AA021459 | Hs.306480 | *Homo sapiens* mRNA; cDNA DKFZp761E2112 (f | lo-hi-hi |
| 101701 | NM_002436 | Hs.1861 | membrane protein, palmitoylated 1 (55 kD) | lo-hi-hi |
| 130356 | AF127577 | Hs.155017 | nuclear receptor interacting protein 1 | lo-hi-hi |
| 101763 | AB001914 | Hs.170414 | paired basic amino acid cleaving system | lo-hi-hi |
| 130342 | U81802 | Hs.154846 | phosphatidylinositol 4-kinase, catalytic | lo-hi-hi |
| 130760 | AW379130 | Hs.18953 | phosphodiesterase 9A | lo-hi-hi |
| 101461 | N98569 | Hs.76422 | phospholipase A2, group IIA (platelets, | lo-hi-hi |
| 134032 | NM_005025 | Hs.78589 | serine (or cysteine) proteinase inhibito | lo-hi-hi |
| 303762 | AF034799 | Hs.30881 | protein tyrosine phosphatase, receptor t | lo-hi-hi |
| 110932 | AA021459 | Hs.306480 | *Homo sapiens* mRNA; cDNA DKFZp761E2112 (f | lo-hi-hi |
| 135192 | U83993 | Hs.321709 | purinergic receptor P2X, ligand-gated io | lo-hi-hi |
| 133886 | U97276 | Hs.77266 | quiescin Q6 | lo-hi-hi |
| 134142 | BE244053 | Hs.79362 | retinoblastoma-like 2 (p130) | lo-hi-hi |
| 100877 | X80821 | Hs.302177 | *H. sapiens* mRNA for ribosomal protein L18 | lo-hi-hi |
| 133534 | AU077115 | Hs.201675 | RNA binding motif protein 5 | lo-hi-hi |
| 133011 | NM_006379 | Hs.171921 | sema domain, immunoglobulin domain (Ig), | lo-hi-hi |
| 132160 | W26406 | Hs.295923 | seven in absentia (*Drosophila*) homolog 1 | lo-hi-hi |
| 103110 | X62822 | Hs.2554 | sialyltransferase 1 (beta-galactoside al | lo-hi-hi |
| 130173 | U38847 | Hs.151518 | TAR (HIV) RNA-binding protein 1 | lo-hi-hi |
| 127435 | X69086 | *Hs.286161 | *Homo sapiens* cDNA FLJ3613 fis, clone PL | lo-hi-hi |
| 110520 | N54069 | Hs.4082 | lectin, galactoside-binding, soluble, 8 | lo-hi-hi |
| 114660 | AA071383 | | gb: zm61d05.r1 Stratagene fibroblast (937 | lo-hi-hi |
| 330541 | NM_002038 | Hs.265827 | interferon, alpha-inducible protein (clo | lo-hi-lo |
| 101486 | AA506324 | Hs.1852 | acid phosphatase, prostate | lo-hi-lo |
| 332386 | NM_000481 | Hs.102 | aminomethyltransferase (glycine cleavage | lo-hi-lo |
| 100569 | AA535210 | *Hs.171995 | kallikrein 3, (prostate specific antigen | lo-hi-lo |
| 134738 | AU076801 | Hs.89436 | cadherin 17, LI cadherin (liver-intestin | lo-hi-lo |
| 103119 | X63629 | Hs.2877 | cadherin 3, type 1, P-cadherin (placenta | lo-hi-lo |
| 302892 | AW176909 | Hs.42346 | calcineurin-binding protein calsarcin-1 | lo-hi-lo |
| 105402 | AB014680 | Hs.8786 | carbohydrate (chondroitin 6/keratan) su$$ | lo-hi-lo |
| 102976 | AU077174 | *Hs.288181 | cathepsin H | lo-hi-lo |
| 101793 | W01076 | *Hs.119663 | CD59 antigen p18-20 (antigen identified | lo-hi-lo |
| 129890 | AI868872 | *Hs.282804 | *Homo sapiens* cDNA; FLJ22704 fis, clone H | lo-hi-lo |
| 328164 | | | CH.06_hs gi\|5868068 | lo-hi-lo |
| 328648 | | | CH.07_hs gi\|6004473 | lo-hi-lo |
| 330032 | | | CH.16_p2 gi\|6682596 | lo-hi-lo |
| 330033 | | | CH.16_ps gi\|6682596 | lo-hi-lo |
| 326816 | | | CH.20_hs gi\|6552458 | lo-hi-lo |
| 337603 | | | CH22_C20H12.GENSCAN.16-2 | lo-hi-lo |
| 338561 | | | CH22_EM: AC005500.GENSCAN.421-5 | lo-hi-lo |
| 338562 | | | CH22_EM: AC005500.GENSCAN.421-6 | lo-hi-lo |
| 333743 | | | CH22_FGENES.264_1 | lo-hi-lo |
| 333845 | | | CH22_FGENES.290_3 | lo-hi-lo |
| 333849 | | | CH22_FGENES.290_8 | lo-hi-lo |
| 334221 | | | CH22_FGENES.360_1 | lo-hi-lo |
| 334222 | | | CH22_FGENES.360_3 | lo-hi-lo |
| 334578 | | | CH22_FGENES.406_1 | lo-hi-lo |
| 336662 | | | CH22_FGENES.41-1 | lo-hi-lo |
| 336684 | | | CH22_FGENES.46-1 | lo-hi-lo |
| 335289 | | | CH22_FGENES.527_2 | lo-hi-lo |
| 335290 | | | CH22_FGENES.527_3 | lo-hi-lo |
| 335293 | | | CH22_FGENES.527_6 | lo-hi-lo |
| 337182 | | | CH22_FGENES.570-2 | lo-hi-lo |
| 335809 | | | CH22_FGENES.617_6 (same as BFH4) | lo-hi-lo |
| 335810 | | | CH22_FGENES.617_7 | lo-hi-lo |
| 335824 | | | CH22_FGENES.619_11 (same as BFH5) | lo-hi-lo |
| 336054 | | | CH22_FGENES.683_3 | lo-hi-lo |

TABLE 1A-continued

| Pkey | ExAccn | UnigeneID | Unigene Title | pattern |
|---|---|---|---|---|
| 333124 | | | CH22_FGENES.81_8 | lo-hi-lo |
| 332340 | AP000692 | Hs.129781 | chromosome 21 open reading frame 5 | lo-hi-lo |
| 130380 | AI949359 | Hs.143600 | type II Golgi membrane protein | lo-hi-lo |
| 102962 | R50032 | Hs.159263 | collagen, type VI, alpha 2 | lo-hi-lo |
| 331306 | AF102546 | Hs.63931 | dachshund (*Drosophila*) homolog | lo-hi-lo |
| 319408 | AA448090 | Hs.87359 | ESTs, Highly similar to RB18 MOUSE RAS-R | lo-hi-lo |
| 312197 | T96203 | | gb: ye48b07.r1 Soares fetal liver spleen | lo-hi-lo |
| 312405 | AI523875 | | gb: tg97d04.x1 NCI_CGAP_CLL1 *Homo sapiens* | lo-hi-lo |
| 312939 | AA495930 | Hs.24444 | *Homo sapiens* cDNA: FLJ22165 fis, clone H | lo-hi-lo |
| 313475 | AA010200 | Hs.175551 | ESTs | lo-hi-lo |
| 313624 | AA525775 | Hs.292523 | ESTs | lo-hi-lo |
| 316897 | AA838114 | Hs.221612 | ESTs | lo-hi-lo |
| 317850 | AI681545 | Hs.152982 | hypothetical protein FLJ13117 | lo-hi-lo |
| 318541 | T30290 | Hs.107515 | ESTs | lo-hi-lo |
| 321325 | AB033100 | Hs.300646 | KIAA protein (similar to mouse paladin) | lo-hi-lo |
| 321696 | AA628791 | Hs.76228 | amplified in osteosarcoma | lo-hi-lo |
| 322189 | H65014 | | gb: yu66f10.r1 Weizmann Olfactory Epithel | lo-hi-lo |
| 322463 | AI242754 | Hs.137306 | ESTs | lo-hi-lo |
| 322540 | R76593 | | gb: yi60c11.r1 Soares placenta Nb2HP Homo | lo-hi-lo |
| 323131 | AK002088 | Hs.270124 | *Homo sapiens* cDNA FLJ11226 fis, clone PL | lo-hi-lo |
| 323243 | W47525 | Hs.110771 | *Homo sapiens* cDNA: FLJ21904 fis, clone H | lo-hi-lo |
| 323591 | AA301270 | | gb: EST14192 Testis tumor *Homo sapiens* cD | lo-hi-lo |
| 323753 | AK002161 | Hs.70266 | yeast Sec31p homolog | lo-hi-lo |
| 323835 | AL042005 | Hs.1117 | tripeptidyl peptidase II | lo-hi-lo |
| 323926 | AA354572 | | gb: EST62857 Jurkat T-cells V *Homo sapien* | lo-hi-lo |
| 324047 | AI433357 | *Hs.271340 | ESTs | lo-hi-lo |
| 324330 | AA884766 | | gb: am20a10.s1 Soares_NFL_T_GBC_S1 *Homo s* | lo-hi-lo |
| 324753 | AA612626 | Hs.144871 | *Homo sapiens* cDNA FLJ13752 fis, clone PL | lo-hi-lo |
| 300702 | AA075481 | Hs.111334 | ferritin, light polypeptide | lo-hi-lo |
| 301712 | BE083080 | Hs.274323 | *Homo sapiens*, Similar to sialyltransfera | lo-hi-lo |
| 302380 | AA325633 | Hs.136102 | KIAA0853 protein | lo-hi-lo |
| 302970 | W05608 | Hs.312679 | EST | lo-hi-lo |
| 303187 | AA115962 | Hs.323423 | ESTs, Moderately similar to B Chain B, | lo-hi-lo |
| 303194 | AA082000 | | gb: zn26f07.r1 Stratagene neuroepithelium | lo-hi-lo |
| 305612 | AA782347 | Hs.272572 | hemoglobin, alpha 2 | lo-hi-lo |
| 304263 | AA062837 | | gb: zm05b11.s1 Stratagene corneal stroma | lo-hi-lo |
| 304275 | AA070605 | | gb: zm53h09.s1 Stratagene fibroblast (937 | lo-hi-lo |
| 304309 | AA112147 | | gb: zm64c06.s1 Stratagene fibroblast (937 | lo-hi-lo |
| 305503 | AA759177 | Hs.298148 | ESTs, Weakly similar to KIAA0565 protei | lo-hi-lo |
| 308615 | AK000142 | Hs.101774 | hypothetical protein FLJ23045 | lo-hi-lo |
| 309390 | AW080585 | | gb: xc33f09.x1 NCI_CGAP_Co18 *Homo sapiens* | lo-hi-lo |
| 104667 | AI239923 | Hs.30098 | ESTs | lo-hi-lo |
| 310014 | D60745 | Hs.25925 | *Homo sapiens* clone 23860 mRNA sequence | lo-hi-lo |
| 318814 | W07361 | Hs.22545 | *Homo sapiens* cDNA FLJ12935 fis, clone NT | lo-hi-lo |
| 321896 | C04863 | Hs.47191 | ESTs | lo-hi-lo |
| 331661 | W52448 | Hs.56147 | ESTs | lo-hi-lo |
| 332120 | AA609684 | Hs.112748 | *Homo sapiens* cDNA; FLJ21543 fis, clone C | lo-hi-lo |
| 332256 | AW975028 | Hs.102754 | ESTs | lo-hi-lo |
| 107252 | D60745 | Hs.25925 | *Homo sapiens* clone 23860 mRNA sequence | lo-hi-lo |
| 112068 | AI264847 | Hs.22545 | *Homo sapiens* cDNA FLJ129356 fis, clone NT | lo-hi-lo |
| 117929 | N51075 | Hs.47191 | ESTs | lo-hi-lo |
| 119637 | W52448 | Hs.56147 | ESTs | lo-hi-lo |
| 123712 | AA609684 | Hs.112748 | *Homo sapiens* cDNA; FLJ21543 fis, clone C | lo-hi-lo |
| 124560 | AW975028 | Hs.102754 | ESTs | lo-hi-lo |
| 105039 | AA907305 | Hs.36475 | ESTs | lo-hi-lo |
| 105271 | AA807881 | Hs.25329 | ESTs | lo-hi-lo |
| 106689 | AW296584 | Hs.293782 | ESTs | lo-hi-lo |
| 106849 | AL137281 | Hs.17110 | *Homo sapiens* mRNA; cDNA DKFZp434C2016 (f | lo-hi-lo |
| 107071 | AW385224 | Hs.35198 | ectonucleotide pyrophosphatase/phosphodi | lo-hi-lo |
| 108218 | W57550 | Hs.301526 | hypothetical protein FLJ13181 | lo-hi-lo |
| 110930 | BE242691 | Hs.14947 | ESTs, Weakly similar to ALU1_HUMAN ALU S | lo-hi-lo |
| 112098 | R44714 | Hs.106795 | *Homo sapiens* cDNA FLJ13136 fis, clone NT | lo-hi-lo |
| 112170 | BE246743 | Hs.288529 | hypothetical protein FLJ22635 | lo-hi-lo |
| 112902 | AL035633 | Hs.129190 | Human DNA sequence from clone RP5-1046G1 | lo-hi-lo |
| 114877 | AW024162 | Hs.205125 | ESTs | lo-hi-lo |
| 116312 | BE379794 | Hs.65403 | hypothetical protein | lo-hi-lo |
| 116739 | H01463 | Hs.93534 | ESTs | lo-hi-lo |
| 119267 | AA064970 | Hs.118145 | ESTs | lo-hi-lo |
| 120570 | AA280679 | Hs.271445 | ESTs, Weakly similar to ALU1_HUMAN ALU | lo-hi-lo |
| 121176 | AL121523 | Hs.97774 | ESTs | lo-hi-lo |
| 123360 | AA532718 | Hs.178604 | ESTs | lo-hi-lo |
| 123974 | NM_015678 | Hs.3821 | neurobeachin | lo-hi-lo |
| 124777 | R41933 | | gb: yg04f09.s1 Soares infant brain 1NIB H | lo-hi-lo |
| 128046 | AA873285 | | gb: oh68h05.s1 NCI_CGAP_Kid5 *Homo sapiens* | lo-hi-lo |
| 128666 | AA808466 | Hs.103395 | hypothetical protein FLJ14146 | lo-hi-lo |
| 130639 | AI557212 | *Hs.17132 | ESTs | lo-hi-lo |
| 130693 | R68537 | Hs.17962 | ESTs | lo-hi-lo |

TABLE 1A-continued

| Pkey | ExAccn | UnigeneID | Unigene Title | pattern |
|---|---|---|---|---|
| 131756 | AA443966 | Hs.31595 | ESTs | lo-hi-lo |
| 131985 | AA503020 | Hs.36563 | hypothetical protein FLJ22418 | lo-hi-lo |
| 132932 | AW118826 | Hs.6093 | *Homo sapiens* cDNA: FLJ22783 fis, clone K | lo-hi-lo |
| 134696 | BE326276 | *Hs.8861 | ESTs | lo-hi-lo |
| 300967 | AA565209 | Hs.269439 | ESTs | lo-hi-lo |
| 301182 | AW291411 | Hs.192531 | ESTs, Weakly similar to S00754 zinc fing | lo-hi-lo |
| 302595 | AI699372 | Hs.193247 | *Homo sapiens* mRNA; cDNA DKFZp434A171 (fr | lo-hi-lo |
| 303132 | AI929819 | Hs.4055 | chromosome 21 open reading frame 50 | lo-hi-lo |
| 303506 | AA340605 | Hs.105887 | ESTs, Weakly similar to Homolog of rat Z | lo-hi-lo |
| 303654 | BE246743 | Hs.288529 | hypothetical protein FLJ22635 | lo-hi-lo |
| 310026 | AA278233 | Hs.100691 | ESTs | lo-hi-lo |
| 310056 | AI253072 | Hs.145383 | ESTs | lo-hi-lo |
| 310353 | AI261700 | Hs.145544 | ESTs | lo-hi-lo |
| 310371 | AI262584 | Hs.145575 | ESTs | lo-hi-lo |
| 310430 | AI670843 | Hs.200257 | ESTs | lo-hi-lo |
| 310438 | AW022192 | Hs.200197 | ESTs | lo-hi-lo |
| 310455 | AI277603 | Hs.145990 | ESTs | lo-hi-lo |
| 310787 | AW262580 | Hs.147674 | KIAA1621 protein | lo-hi-lo |
| 311067 | AI587332 | Hs.209115 | ESTs | lo-hi-lo |
| 311422 | F00677 | Hs.101316 | ESTs | lo-hi-lo |
| 311465 | AI758660 | Hs.206132 | ESTs | lo-hi-lo |
| 312073 | AA682393 | *Hs.119237 | ESTs | lo-hi-lo |
| 312105 | T81819 | Hs.302251 | ESTs | lo-hi-lo |
| 312108 | T82331 | *Hs.127453 | ESTs | lo-hi-lo |
| 312292 | AW450103 | Hs.151124 | ESTs | lo-hi-lo |
| 312313 | AW293341 | Hs.122505 | ESTs, Weakly similar to I38022 hypotheti | lo-hi-lo |
| 312600 | AW970985 | Hs.290853 | ESTs | lo-hi-lo |
| 312800 | AI248774 | Hs.126707 | hypothetical protein FLJ11457 | lo-hi-lo |
| 312821 | AA699325 | Hs.269880 | ESTs | lo-hi-lo |
| 313097 | AI676164 | Hs.204339 | ESTs | lo-hi-lo |
| 313166 | AI801098 | Hs.151500 | ESTs | lo-hi-lo |
| 313179 | AA927670 | Hs.131704 | ESTs | lo-hi-lo |
| 313280 | AW960454 | Hs.222830 | ESTs | lo-hi-lo |
| 313689 | AI608810 | Hs.193288 | ESTs | lo-hi-lo |
| 314146 | AI827237 | Hs.282884 | ESTs | lo-hi-lo |
| 314305 | AI280112 | Hs.125232 | *Homo sapiens* cDNA FLJ13266 fis, clone OV | lo-hi-lo |
| 314456 | AI867931 | Hs.164595 | ESTs | lo-hi-lo |
| 314465 | AA602917 | Hs.156974 | ESTs | lo-hi-lo |
| 314881 | AI095087 | Hs.152299 | ESTs, Moderately similar to ALU5_HUMAN A | lo-hi-lo |
| 314916 | AA548906 | Hs.122244 | ESTs | lo-hi-lo |
| 315043 | AA806538 | Hs.130732 | KIAA1575 protein | lo-hi-lo |
| 315074 | AA828284 | Hs.136729 | *Home sapiens* cDNA: FLJ21348 fis, clone C | lo-hi-lo |
| 315214 | AI915927 | Hs.34771 | ESTs | lo-hi-lo |
| 315344 | AW292176 | Hs.245834 | ESTs | lo-hi-lo |
| 315353 | AI373949 | Hs.279610 | hypothetical protein FLJ10493 | lo-hi-lo |
| 315439 | T78413 | Hs.293696 | ESTs | lo-hi-lo |
| 315528 | R37257 | Hs.184780 | ESTs | lo-hi-lo |
| 315720 | AA292998 | Hs.163900 | ESTs | lo-hi-lo |
| 315772 | AW515373 | Hs.271249 | *Homo sapiens* cDNA: FLJ13580 fis, clone PL | lo-hi-lo |
| 315841 | AW136397 | Hs.247572 | ESTs | lo-hi-lo |
| 316042 | AI469960 | Hs.170698 | ESTs | lo-hi-lo |
| 316244 | AI640761 | Hs.224988 | ESTs | lo-hi-lo |
| 316345 | AW139408 | Hs.152940 | ESTs | lo-hi-lo |
| 316625 | BE540690 | Hs.122156 | ESTs | lo-hi-lo |
| 316738 | AA889055 | Hs.123468 | ESTs | lo-hi-lo |
| 316868 | AI660896 | Hs.195602 | ESTs | lo-hi-lo |
| 316905 | AW138241 | Hs.210846 | ESTs | lo-hi-lo |
| 317224 | X73608 | *Hs.93029 | sparc/osteonectin, cwcv and kazal-like d | lo-hi-lo |
| 317275 | AI860444 | Hs.202108 | ESTs | lo-hi-lo |
| 317404 | AI806867 | Hs.126594 | ESTs | lo-hi-lo |
| 317488 | AW071851 | Hs.130628 | ESTs | lo-hi-lo |
| 317916 | AI565071 | Hs.159983 | ESTs | lo-hi-lo |
| 317939 | AI986208 | Hs.244760 | ESTs | lo-hi-lo |
| 318486 | T23514 | | gb: seq3329 1-NIB *Homo sapiens* cDNA clone | lo-hi-lo |
| 319897 | N46574 | Hs.43838 | ESTs | lo-hi-lo |
| 320654 | AI160015 | Hs.118112 | ESTs | lo-hi-lo |
| 320697 | N62937 | Hs.269109 | ESTs | lo-hi-lo |
| 320787 | AW088363 | Hs.24240 | ESTs | lo-hi-lo |
| 321023 | AW294316 | Hs.125608 | ESTs | lo-hi-lo |
| 321899 | AW972832 | Hs.29468 | ESTs | lo-hi-lo |
| 322939 | AA101697 | Hs.211270 | ESTs | lo-hi-lo |
| 323045 | AA148950 | Hs.188836 | ESTs | lo-hi-lo |
| 323091 | AI902456 | Hs.210761 | ESTs | lo-hi-lo |
| 323262 | AL133990 | Hs.190642 | ESTs | lo-hi-lo |
| 323410 | AW118683 | Hs.154150 | ESTs | lo-hi-lo |
| 323645 | AW445014 | Hs.197746 | ESTs | lo-hi-lo |
| 324598 | AW972227 | Hs.163986 | *Homo sapiens* cDNA: FLJ22765 fis, clone K | lo-hi-lo |

TABLE 1A-continued

| Pkey | ExAccn | UnigeneID | Unigene Title | pattern |
|---|---|---|---|---|
| 324666 | T78413 | Hs.293696 | ESTs | lo-hi-lo |
| 324674 | AA541323 | Hs.15831 | ESTs | lo-hi-lo |
| 324713 | AI093930 | *Hs.313466 | ESTs | lo-hi-lo |
| 324790 | AI334367 | Hs.159337 | ESTs | lo-hi-lo |
| 324804 | AI692552 | | gb: wd73f12x1 NCI_CGAP_Lu24 *Home sapiens* | lo-hi-lo |
| 330728 | AI905520 | Hs.29672 | ESTs | lo-hi-lo |
| 330760 | H04588 | Hs.30469 | ESTs | lo-hi-lo |
| 330776 | AW953805 | Hs.21887 | ESTs | lo-hi-lo |
| 330824 | AB037732 | Hs.61441 | KIAA1311 protein | lo-hi-lo |
| 331028 | AI539652 | Hs.28338 | KIAA1546 protein | lo-hi-lo |
| 331046 | N66563 | Hs.191358 | ESTs | lo-hi-lo |
| 331050 | BE007967 | Hs.155795 | ESTs | lo-hi-lo |
| 331053 | AI949841 | Hs.183146 | ESTs, Moderately similar to ALU1_HUMAN A | lo-hi-lo |
| 331180 | R44692 | Hs.6640 | Human DNA sequence from PAC 75N13 on chr | lo-hi-lo |
| 331313 | AA761094 | *Hs.80618 | hypothetical protein | lo-hi-lo |
| 331337 | N74392 | Hs.50495 | ESTs | lo-hi-lo |
| 331393 | AW976438 | *Hs.17428 | RBP1-like protein | lo-hi-lo |
| 331432 | AA262451 | Hs.38485 | ESTs | lo-hi-lo |
| 331517 | AA765603 | Hs.180877 | H3 histone, family 3B (H3.3B) | lo-hi-lo |
| 331686 | AW474960 | Hs.182258 | ESTs | lo-hi-lo |
| 332002 | AI579909 | Hs.105104 | ESTs | lo-hi-lo |
| 332043 | AA371307 | Hs.125056 | ESTs | lo-hi-lo |
| 332265 | AW770320 | Hs.222413 | ESTs | lo-hi-lo |
| 332314 | R41396 | Hs.101774 | hypothetical protein FLJ23045 | lo-hi-lo |
| 131517 | AB037789 | Hs.263395 | sema domain, transmembrane domain (TM), | lo-hi-lo |
| 315352 | AA604799 | Hs.136528 | ESTs, Moderately similar to ALU1_HUMAN A | lo-hi-lo |
| 315498 | AA628539 | Hs.116252 | ESTs, Moderately similar to ALU1_HUMAN A | lo-hi-lo |
| 321489 | AI459177 | Hs.172759 | ESts, Moderately similar to ALU7_HUMAN A | lo-hi-lo |
| 106099 | NM_012068 | Hs.9754 | activating transcription factor 5 | lo-hi-lo |
| 105726 | NM_012068 | Hs.9754 | activating transcription factor 5 | lo-hi-lo |
| 319926 | AI820719 | Hs.154662 | DnaJ (Hsp40) homolog, subfamily A, membe | lo-hi-lo |
| 314915 | AI673735 | Hs.187748 | ESTs, Weakly similar to ALU1_HUMAN ALU S | lo-hi-lo |
| 315198 | AI741506 | Hs.186753 | ESTs, Weakly similar to ALU1_HUMAN ALU S | lo-hi-lo |
| 324302 | AW972771 | Hs.292471 | ESTs, Weakly similar to ALU1_HUMAN ALU S | lo-hi-lo |
| 331341 | BE541042 | *Hs.23240 | *Homo sapiens* cDNA FLJ13496 fis, clone PL | lo-hi-lo |
| 113783 | AL359588 | Hs.7041 | hypothetical protein DKFZp762B226 | lo-hi-lo |
| 313552 | AI889208 | Hs.17283 | hypothetical protein FLJ10890 | lo-hi-lo |
| 103989 | AA315993 | Hs.105484 | *Homo sapiens* regenerating gene type IV m | lo-hi-lo |
| 331492 | AK001114 | Hs.53913 | hypothetical protein FLJ10252 | lo-hi-lo |
| 110837 | H03109 | Hs.108920 | HT018 protein | lo-hi-lo |
| 330814 | AI955040 | Hs.265398 | ESTs, Weakly similar to transformation-r | lo-hi-lo |
| 312226 | AA315703 | Hs.199993 | ESTs | lo-hi-lo |
| 102034 | AI903474 | Hs.230 | fibromodulin | lo-hi-lo |
| 134671 | BE263255 | Hs.302749 | FK506-binding protein 9 (63 kD) | lo-hi-lo |
| 131083 | Y09763 | Hs.22785 | gamma-aminobutyric acid (GABA) A recepto | lo-hi-lo |
| 309575 | AW168096 | Hs.169476 | glyceraldehyde-3-phosphate dehydrogenase | lo-hi-lo |
| 134332 | D86962 | Hs.81875 | growth factor receptor-bound protein 10 | lo-hi-lo |
| 132904 | NM_005518 | Hs.59889 | 3-hydroxy-3-methylglutaryl-Coenzyme A sy | lo-hi-lo |
| 302910 | N77976 | Hs.251577 | hemoglobin, alpha 1 | lo-hi-lo |
| 133731 | N71725 | *Hs.272572 | hemoglobin, alpha 2 | lo-hi-lo |
| 303297 | AF070623 | Hs.13423 | *Homo sapiens* clone 24468 mRNA sequence | lo-hi-lo |
| 108732 | AA258888 | Hs.107476 | ATP synthase, H+ transporting, mitochond | lo-hi-lo |
| 108731 | AA258888 | Hs.107476 | ATP synthase, H+ transporting, mitochond | lo-hi-lo |
| 302123 | AB013452 | Hs.144931 | ATPase, aminophospholipid transporter (A | lo-hi-lo |
| 131614 | AB002438 | Hs.29596 | *Homo sapiens* mRNA from chromosome 5q21-2 | lo-hi-lo |
| 104933 | N94126 | Hs.12969 | hypothetical protein | lo-hi-lo |
| 302235 | AL049987 | Hs.166361 | *Homo sapiens* mRNA; cDNA DKFZp564F112 (ft | lo-hi-lo |
| 320574 | AL049443 | Hs.161283 | *Homo sapiens* mRNA; cDNA DKFZp586N2020 (f | lo-hi-lo |
| 324678 | AI990739 | Hs.77868 | ORF | lo-hi-lo |
| 331022 | H03109 | Hs.108920 | HT018 protein | lo-hi-lo |
| 332430 | H25350 | Hs.21145 | hypothetical protein FLJ22489 | lo-hi-lo |
| 330601 | U90916 | Hs.82845 | *Homo sapiens* cDNA; FLJ21930 fis, clone H | lo-hi-lo |
| 101988 | AF221521 | Hs.8068 | hematopoietic PBX-interacting protein | lo-hi-lo |
| 102859 | AL036058 | *Hs.76807 | major histocompatibility complex, class | lo-hi-lo |
| 101363 | M11321 | | | lo-hi-lo |
| 133968 | AA355986 | Hs.232068 | transcription factor 8 (represses interl | lo-hi-lo |
| 332530 | M31669 | Hs.1735 | inhibin, beta B (activin AB beta polypep | lo-hi-lo |
| 317777 | NM_014785 | Hs.47313 | KIAA0258 gene product | lo-hi-lo |
| 100452 | D87742 | Hs.241552 | KIAA0268 protein | lo-hi-lo |
| 112988 | NM_014867 | Hs.5333 | KIAA0711 gene product | lo-hi-lo |
| 320848 | AB020691 | Hs.198232 | KIAA0884 protein | lo-hi-lo |
| 105162 | AL133033 | *Hs.4084 | KIAA1025 protein | lo-hi-lo |
| 133905 | AB028974 | Hs.137476 | KIAA1051 protein | lo-hi-lo |
| 331406 | BE176893 | Hs.23440 | KIAA1105 protein | lo-hi-lo |
| 321441 | AF107493 | Hs.118498 | *Homo sapiens* LUCA-15 protein mRNA, splic | lo-hi-lo |
| 131913 | AW207440 | Hs.185973 | degenerative spermatocyte (homolog *Droso* | lo-hi-lo |
| 135424 | U67611 | | transaldolase 1 | lo-hi-lo |

TABLE 1A-continued

| Pkey | ExAccn | UnigeneID | Unigene Title | pattern |
|---|---|---|---|---|
| 128506 | L40904 | Hs.100724 | peroxisome proliferative activated recep | lo-hi-lo |
| 330506 | AI130740 | Hs.6241 | phosphoinositide-3-kinase, regulatory su | lo-hi-lo |
| 311251 | AI655662 | Hs.197698 | ESTs | lo-hi-lo |
| 314171 | AI821895 | Hs.193481 | ESTs | lo-hi-lo |
| 106096 | AW379378 | Hs.170121 | protein tyrosine phosphatase, receptor t | lo-hi-lo |
| 133740 | AW162919 | *Hs.170160 | RAB2, member RAS oncogene family-like | lo-hi-lo |
| 119521 | W38038 | | | lo-hi-lo |
| 119546 | W38169 | | | lo-hi-lo |
| 119559 | W38197 | | | lo-hi-lo |
| 133797 | AL133921 | Hs.76272 | retinoblastoma-binding protein 2 | lo-hi-lo |
| 305097 | AA642964 | Hs.163593 | ribosomal protein L18a | lo-hi-lo |
| 120256 | AA169801 | Hs.98710 | hypothetical protein | lo-hi-lo |
| 322919 | AA178955 | Hs.271439 | ESTs | lo-hi-lo |
| 300566 | R34926 | Hs.326392 | son of sevenless (*Drosophila*) homolog 1 | lo-hi-lo |
| 330694 | AI741617 | Hs.108447 | spinocerebellar ataxia 7 (olivopontocere | lo-hi-lo |
| 302416 | AL120259 | Hs.76691 | stannin | lo-hi-lo |
| 319289 | AA037534 | Hs.79059 | transforming growth factor, beta recepto | lo-hi-lo |
| 134656 | AI750878 | Hs.87409 | thrombospondin 1 | lo-hi-lo |
| 130117 | U06641 | Hs.150207 | UDP glycosyltransferase 2 family, polype | lo-hi-lo |
| 124357 | N22401 | | gb: yw37g07.s1 Morton Fetal Cochlea Home | lo-hi-lo |
| 108293 | AA069155 | | gb: zm10f11.s1 Stratagene pancreas (93720 | lo-hi-lo |
| 108657 | BE567753 | Hs.132955 | BCL2/adenovirus E1B 19 kD-interacting pro | lo-hi-lo |
| 108658 | AA641695 | | gb: nr62h10.s1 NCI_CGAP_Lym3 *Homo sapiens* | lo-hi-lo |
| 331278 | AA071383 | | gb: zm61d05.r1 Stratagene fibroblast (937 | lo-hi-lo |
| 108340 | AA069820 | Hs.180909 | peroxiredoxin 1 | lo-hi-lo |
| 108679 | AA115963 | Hs.323423 | ESTs, Moderately similar to B Chain B, | lo-hi-lo |
| 108406 | AA075424 | Hs.325505 | ESTs, Moderately similar to HBA_HUMAN HE | lo-hi-lo |
| 114598 | AA075601 | | gb: zm88c05.r1 Stratagene ovarian cancer | lo-hi-lo |
| 108462 | AA079347 | | gb: zm96c06.s1 Stratagene colon HT29 (937 | lo-hi-lo |
| 108466 | AA079409 | | gb: zm96h02.s1 Stratagene colon HT29 (937 | lo-hi-lo |
| 108489 | AA082977 | | gb: zn07h10.r1 Stratagene hNT neuron (937 | lo-hi-lo |
| 330859 | AA082977 | | gb: zn07h10.r1 Stratagene hNT neuron (937 | lo-hi-lo |
| 108505 | AA083376 | | gb: zn09g08.s1 Stratagene hNT neuron (937 | lo-hi-lo |
| 331283 | AA467736 | Hs.275437 | ESTs | lo-hi-lo |
| 100641 | AW068302 | *Hs.182183 | *Homo sapiens* mRNA for caldesmon, 3' UTR | lo-hi-lo-hi |
| 100642 | AW068302 | *Hs.182183 | *Homo sapiens* mRNA for caldesmon, 3' UTR | lo-hi-lo-hi |
| 325889 | | | CH.16_hs gi\|5867087 | lo-hi-lo-hi |
| 338038 | | | CH22_EM: AC005500.GENSCAN.149-9 | lo-hi-lo-hi |
| 338316 | | | CH22_EM: AC005500.GENSCAN.304-2 | lo-hi-lo-hi |
| 100999 | H38765 | Hs.80706 | diaphorase (NADH/NADPH) (cytochrome b-5 | lo-hi-lo-hi |
| 331131 | R54797 | | gb: yg87b07.s1 Soares infant brain 1NIB H | lo-hi-lo-hi |
| 310955 | AI476732 | Hs.263912 | ESTs | lo-hi-lo-hi |
| 311137 | AW207582 | Hs.196042 | ESTs | lo-hi-lo-hi |
| 311598 | AW023595 | Hs.232048 | ESTs | lo-hi-lo-hi |
| 313070 | AI422023 | Hs.161338 | ESTs | lo-hi-lo-hi |
| 110844 | AI740792 | Hs.167531 | methylcrotonoyl-Coenzyme A carboxylase 2 | lo-hi-lo-hi |
| 120328 | AA923278 | Hs.290905 | ESTs, Weakly similar to protease [*H. sapi* | lo-hi-lo-hi |
| 105914 | AW245680 | Hs.9701 | growth arrest and DNA-damage-inducible, | lo-hi-lo-hi |
| 129389 | NM_012445 | *Hs.288126 | spondin 2, extracellular matrix protein | lo-hi-lo-hi |
| 102759 | NM_005100 | Hs.788 | A kinase (PRKA) anchor protein (gravin) | lo-lo-hi |
| 100168 | H73444 | Hs.394 | adrenomedullin | lo-lo-hi |
| 102348 | U37519 | Hs.87539 | aldehyde dehydrogenase 8 | lo-lo-hi |
| 134158 | U15174 | Hs.79428 | BCL2/adenovirus E1B 19 kD-interacting pro | lo-lo-hi |
| 133908 | AU076820 | Hs.325474 | caldesmon 1 | lo-lo-hi |
| 101883 | AU076743 | Hs.75613 | CD36 antigen (collagen type I receptor, | lo-lo-hi |
| 327821 | | | CH.05_hs gi\|5867968 | lo-lo-hi |
| 134133 | AA262294 | Hs.180383 | dual spacificity phosphatase 6 | lo-lo-hi |
| 103000 | NM_001975 | *Hs.146580 | enolase 2, (gamma, neuronal) | lo-lo-hi |
| 109251 | AA194776 | Hs.85935 | EST | lo-lo-hi |
| 315566 | AB037810 | Hs.18760 | KIAA1389 protein | lo-lo-hi |
| 324697 | AK000742 | Hs.126774 | L2DTL protein | lo-lo-hi |
| 306011 | AA896986 | | gb: at06a08.s1 Barstead spleen HPLRB2 Hom | lo-lo-hi |
| 307111 | AI174528 | | gb: an45g10.s1 Gessler Wilms tumor *Homo s* | lo-lo-hi |
| 106639 | AV655272 | Hs.20252 | novel Ras family protein | lo-lo-hi |
| 106753 | AI656166 | Hs.7331 | hypothetical protein FLJ22316 | lo-lo-hi |
| 107974 | AW956103 | Hs.61712 | pyruvate dehydrogenase kinase, isoenzyme | lo-lo-hi |
| 112033 | R49031 | Hs.22627 | ESTs | lo-lo-hi |
| 113816 | H46008 | Hs.31518 | ESTs | lo-lo-hi |
| 116024 | AA088767 | *Hs.83883 | transmembrane, prostate androgen induced | lo-lo-hi |
| 116158 | AA381807 | Hs.61762 | hypoxia-inducible protein 2 | lo-lo-hi |
| 119071 | R31180 | | gb: yh62b02.s1 Soares placenta Nb2HP *Homo* | lo-lo-hi |
| 120132 | W57554 | Hs.125019 | ESTs | lo-lo-hi |
| 120655 | AA305599 | Hs.238205 | hypothetical protein PRO2013 | lo-lo-hi |
| 122411 | AW172356 | Hs.99083 | ESTs | lo-lo-hi |
| 320779 | AA815354 | Hs.169898 | ESTs | lo-lo-hi |
| 321024 | AW246216 | Hs.32058 | *Homo sapiens* C1orf19 mRNA, partial cds | lo-lo-hi |
| 321408 | AW081530 | Hs.137088 | ESTs, Weakly similar to ALU1_HUMAN ALU S | lo-lo-hi |

TABLE 1A-continued

| Pkey | ExAccn | UnigeneID | Unigene Title | pattern |
|---|---|---|---|---|
| 323620 | AA306997 | Hs.268362 | ESTs, Weakly similar to hypothetical pro | lo-lo-hi |
| 314946 | AI097229 | Hs.217484 | ESTs | lo-lo-hi |
| 320683 | AA334511 | Hs.26638 | ESTs, Weakly similar to unnamed protein | lo-lo-hi |
| 128959 | AI580127 | Hs.107381 | hypothetical protein FLJ11200 | lo-lo-hi |
| 128896 | T53925 | Hs.107 | fibrinogen-like 1 | lo-lo-hi |
| 133592 | AV652066 | Hs.75113 | general transcription factor IIIA | lo-lo-hi |
| 103245 | BE566343 | *Hs.28988 | glutaredoxin (thioltransferase) | lo-lo-hi |
| 314785 | AI538226 | Hs.32976 | guanine nucleotide binding protein 4 | lo-lo-hi |
| 103677 | Z83806 | | gb: *H. sapiens* mRNA for axonemal dynein he | lo-lo-hi |
| 131170 | NM_014253 | *Hs.23796 | odz (odd Oz/ten-m, *Drosophila*) homolog 1 | lo-lo-hi |
| 131164 | AW013807 | Hs.182265 | keratin 19 | lo-lo-hi |
| 100409 | D86957 | Hs.80712 | KIAA0202 protein | lo-lo-hi |
| 133167 | AW162840 | Hs.6641 | kinesin family member 5C | lo-lo-hi |
| 319080 | AW967646 | Hs.23023 | ESTs | lo-lo-hi |
| 330706 | AF097994 | Hs.301528 | L-kynurenine/alpha-aminoadipate aminotra | lo-lo-hi |
| 104052 | NM_002407 | Hs.97644 | mammaglobin 2 | lo-lo-hi |
| 100547 | M57417 | | gb: *Homo sapiens* mucin (mucin) mRNA, part | lo-lo-hi |
| 103145 | X66276 | Hs.169849 | myosin-binding protein C, slow-type | lo-lo-hi |
| 301015 | AV655272 | Hs.20252 | novel Ras family protein | lo-lo-hi |
| 311013 | AA224760 | *Hs.153 | ribosomal protein L7 | lo-lo-hi |
| 132050 | AI267615 | Hs.38022 | ESTs | lo-lo-hi |
| 132349 | AW975654 | *Hs.181286 | serine protease inhibitor, Kazal type 1 | lo-lo-hi |
| 130889 | AW972512 | Hs.20985 | sin3-associated polypeptide, 30 kD | lo-lo-hi |
| 130791 | AF030403 | Hs.199263 | Ste-20 related kinase | lo-lo-hi |
| 130385 | AW067800 | Hs.155223 | stanniocalcin 2 | lo-lo-hi |
| 127229 | AA316181 | Hs.61635 | six transmembrane epithelial antigen of | lo-lo-hi |
| 133820 | S69681 | *Hs.177582 | surfactant, pulmonary-associated protein | lo-lo-hi |
| 129523 | M13231 | Hs.274509 | T cell receptor gamma constant 2 | lo-lo-hi |
| 321415 | BE621807 | Hs.3337 | transmembrane 4 superfamily member 1 | lo-lo-hi |
| 131859 | AW960564 | *Hs.3337 | transmembrane 4 superfamily member 1 | lo-lo-hi |
| 133444 | M63978 | Hs.73793 | vascular endothelial growth factor | lo-lo-hi |
| 332567 | AW939251 | *Hs.25647 | v-fos FBJ murine osteosarcoma viral onco | lo-lo-hi |
| 131328 | AW939251 | *Hs.25647 | v-fos FBJ murine osteosarcoma viral onco | lo-lo-hi |
| 315901 | AI521558 | Hs.7331 | hypothetical protein FLJ22316 | lo-lo-hi |
| 104394 | AA129551 | Hs.172129 | *Homo sapiens* cDNA: FLJ21409 fis, clone C | lo-lo-hi |
| 103739 | AA115173 | | gb: zn30d02.s1 Stratagene neuroepithelium | lo-lo-hi |
| 103797 | AA080912 | | gb: zn04d03.r1 Stratgene hNT neuron (937 | lo-lo-hi |
| 103804 | AA129196 | | gb: zn29d08.r1 Stratgene neuroepithelium | lo-lo-hi |

TABLE 1B

| Pkey | CAT Number | Accessions |
|---|---|---|
| 108462 | 116651_1 | AA079347 AA079506 AA079538 AA079442 |
| 108489 | 118662_1 | AA082977 AA082955 AA082956 |
| 101216 | 17379_1 | AA284166 AA314707 L25876 L27711 AA092745 N92087 U02681 AA315766 BE385121 AA352693 NM_005192 AI739135 AI066521 AW173105 AA257103 AA450169 AW261971 AA305065 AI954494 AW950384 AW732122 AA830348 AA789097 AA777794 AA284072 BE564465 AI005313 AA804528 AI041134 AI700317 AI352491 AA856987 AA769007 AA494334 AA769862 AA831168 AI143496 BE090796 AA831166 AI141222 AI372907 N64843 AI075136 AI076701 AA464156 AI076409 AI273523 AA627383 BE043332 T96666 AA158102 AA158059 AW340182 AA257019 AI206700 AI678081 AA757304 AA055005 AW059834 AL039012 |
| 131328 | 8509_1 | AW939251 NM_005252 AU076596 V01512 V01512 AW579056 AA249247 AI590359 AW510478 AW518282 BE046054 AW874080 AI268596 AA996237 AI695592 AI244117 AA290764 AA401957 AA505878 AA428304 W74018 W74016 AA040944 AI272071 AA745909 AA620979 AA019816 AI245094 AW009706 AA662536 AW024264 AI268601 AA932024 AW513222 AW024169 AI659705 AA932526 AA975329 AI567603 AI889320 AA514238 AA020837 AI623966 AA843677 AA477453 AA496353 AW372625 AV656426 K00650 W96348 N62388 R95977 AA434270 AI093633 T27639 AW960245 AW881177 R15253 N36936 F07701 AA319315 AA337290 AA284642 AA344052 F05184 AA351062 AA378451 AW794233 AW884380 N36951 R49879 AB022276 AA300350 AW839435 AW191708 BE220350 AA280404 AA485546 AW794235 AV654223 AW838891 AA295986 N72823 AA335648 AA371089 AW845414 H63166 R12840 AA379680 AA477579 R13148 H71003 H71015 AA362156 AW750674 AW845415 AA366924 AW608044 AI570388 R31511 R33906 R33921 AW663022 AW360985 AI207838 AW607239 AI672451 AI573282 AW794752 AA370328 AW998896 AW797239 AW998912 AW794742 AI954543 AI810067 AW073373 AA370325 AW195330 C18106 AW998736 R79476 AA429721 AI891081 AI381534 AW022137 AW020000 AI630329 N99428 AI870222 AI971257 AI922196 AI857753 AW579397 D56749 AI925005 AI685727 AW805573 AI982678 AI784604 AI005625 AW877772 AI634947 AI950829 AA493243 BE166086 AI801820 AI925643 AI627992 AW316704 AI261318 D57757 AA887178 AW770406 AI972075 AI222254 AI675794 D58060 AI701954 D58166 AI799500 AW805669 AW276098 AW874253 AI962991 AI248184 AW996924 AI017462 AW022260 AI885957 BE176841 AA878863 AI697419 AW662094 AI479529 BE177025 D57403 AA507952 AW664593 AW800998 AI985773 AA566089 AA442759 AI624670 AI460284 AI800205 AI537788 AI537593 AI244382 AA583463 AA922678 AA864382 AI610837 D58070 AA844283 AA947992 N73801 AI453821 D58184 AI678887 AW243755 AA746085 D57742 AA757380 R44148 AA496403 BE180303 AW363528 BE006616 D57395 AW805507 AW805511 AA617991 AI373585 H30122 D57744 AW805501 D57691 D58148 AW873164 AW768483 D57601 AA777812 AA837997 BE180123 D57599 AA485387 AW022208 D58096 N67917 W95944 AW805506 D57518 D57990 AI074096 D56521 D58151 AA428720 D56648 D57778 AW805504 D57750 D58108 AW021706 D57449 D57041 D58277 D56935 AI356974 D57023 AA018712 H27631 D57851 D57514 D57268 D57468 AW805646 AI278945 D57323 D56986 D57539 D57829 D58078 AW805515 AI348684 D57772 R74449 BE041558 D56746 AW798485 D56640 AA985597 D56702 D56849 D56874 AW581419 AA470397 D57591 AW798984 T27640 N66497 D56803 AA618186 AW805647 D57945 N23726 D56637 N23730 D56992 BE176882 BE176839 BE176909 D56757 N68137 D56987 AI559806 AA631437 D57464 D56718 C17030 T29278 D57377 AW021936 AW118330 AA515358 D56610 AA494092 D56934 T97774 AI473546 R74350 R84834 AA579200 D56616 C03207 D57391 N52416 D56928 R79209 D56925 AA020879 D45546 AI858769 R20750 T09381 F01435 AW627906 D58202 AI933993 F01912 H27552 AA174191 T16515 AW023216 AA434146 H83387 AI346751 V01512 V01512 AA576407 AW365140 AA937471 BE174681 AI568829 AI274663 R85530 AL048225 H83388 AW798734 |
| 124148 | 31218_1 | BE300094 BE384439 AW794648 NM_002305 M57678 AI929016 AU076727 Z83844 Z83844 AI906100 W44519 H98497 AA188069 AA572687 AA035793 W93978 BE409220 AA359751 AA502475 H28319 AA527889 AA432335 AA864762 AA340061 C05180 W68192 AA327811 AA345871 AI750205 N34093 N86639 AA085753 AA603415 AI355561 AA442262 N42135 C04367 N57266 AI038364 AI184846 AI928853 X15256 J04456 AA603552 AA317300 AA588615 AA813495 N40276 AA400624 AW264898 H21418 AA643822 AA603569 AA507955 N44497 AI000869 AW079049 AA614629 AA303987 AA362817 H54502 N85495 W52256 F30575 AA568129 H26935 W93977 AA373651 AA872398 AI332540 AW572787 F20782 AA442263 AW301076 AA558556 AA825366 W23842 AI038829 AA302408 AA374629 AA614477 AA341686 AA374846 AA187091 F24764 AA157099 AA374853 AA991592 F26839 AA744090 AA936881 AA374627 AA329755 AA854398 AA618108 AA973600 AA757956 W44520 AA379779 AA373698 AA369135 AA380039 BE408327 AA375117 AA375744 AA380014 AA373556 AI335987 AA903267 AA828223 F25088 AI246573 AA299386 BE275844 BE275666 BE384214 BE620707 AA975886 AA858048 BE548468 AA193055 BE274324 AI870164 AA129614 AA922761 AA935745 AA374567 AI580916 AA374661 AW239224 AA374466 N52172 F24306 AA300453 AA363443 AA588627 F19159 AA580021 N90877 AA654335 AA679168 AA573071 AW238834 AA988739 AW239423 AA976330 AI074239 AA999911 AI200930 AI971173 AI187321 AA937760 AI016242 AA373684 AI094874 AI302174 AA641237 AI370974 AI971010 AA400379 AA679137 AI096579 AI001918 AA524101 X14829 AA081302 N30374 AI338782 W74444 AA528232 AI734954 AW188024 AA433857 W92348 W94431 AI708356 AI753458 AA494460 AA825257 AA614246 AA039477 AI350213 AI309110 AA745965 AA291936 AW001376 AI066764 W74407 F30627 AA291937 AA480615 AA931667 AA331315 AI936154 AA824332 AA181109 AI017291 AA934736 AA062637 AA599977 H54814 AA635624 AI802655 AA564078 R69997 AA716551 F30469 AA961030 AI126757 AI183943 AI066798 AI419436 AA302095 AA157768 |

TABLE 1B-continued

| Pkey | CAT Number | Accessions |
|---|---|---|
| | | AA953030 AA588476 AA131216 T79619 AI752885 AA614820 AA988962 AI143561 AA493182 AI302481 AA301613 R73520 AA069898 AA374944 AW364221 AA342013 AI244949 F36390 AW050980 N79486 AA101160 T68112 AI750204 AA328787 H02617 AA314734 AA527923 AA307835 AI885112 AI872905 AA534666 AA188363 AI192490 H45772 AI824700 AI184276 AW079473 N29847 AA720843 AA720914 AA573391 H54416 T59424 AI824457 AA304220 AA482553 W72882 AA627932 H27514 H28400 W68050 H20953 AA635786 H21376 AA514046 AI342823 F29905 H25999 AA757144 H21636 F22104 AA428650 F27143 F28346 AA535690 H45771 AA548851 AW170154 H45646 W92274 AI921614 AA176461 AW170153 AI927284 AI161206 AA594439 T28595 H41129 AI497579 AA978015 AA328875 AA373653 AA090973 AA328623 AA328759 AA366468 AA375406 H46976 R86050 H02722 AA328321 AA328205 R62358 AA373717 AA304138 AA304224 AA301603 H54867 AA374783 AA376232 AA373239 AA374917 AA375673 AA303857 AA376466 AA376461 AA302613 AA304082 AA301731 AA357988 AA303328 R25744 AA301587 N78746 H20508 AA659423 R47960 AA825456 AI001806 AI245114 AA729223 AA860271 AI913845 H26296 AA733035 AA340965 AA304291 H27356 H20598 AA129613 R69996 AA157689 H20992 W16630 W16561 H25964 H21754 W01159 W42885 AA176730 H39504 N39788 AA182956 H27585 AA082164 AA328927 AA339934 H61805 H61804 H45580 AA476229 AA714104 AA507471 AI262184 AI139474 AI139476 AI001045 AA614374 AA593153 F33347 F34679 T68225 N25703 AA186999 AI623318 F18313 N72069 AA903161 H38546 H28672 AI880529 AI128960 AA299183 AW768886 F17445 F30433 AA303984 AA303687 AA309366 H28320 AI659479 AA627222 AA064882 AA507447 R53171 AA039476 T79704 R36589 T83222 H26453 AA298798 R53415 N84918 F37846 R94423 AA352679 AA308615 AA375442 BE173864 AA353674 R73519 R62478 T59480 AA089852 AI265789 AI077675 T90770 R54006 H46977 AA187168 AA157123 H21637 R48072 AA814207 R53082 AA305829 R62359 AI818429 AA887755 AA534238 AI813821 AW023928 AA062712 AI698995 F19074 AA345870 AI658776 AA903325 S44881 AA379844 N86780 AW089895 F29687 W52257 AA131229 AA978007 AW953024 R94945 H28332 |
| 124153 | 25750_1 | AU077333 M81635 NM_004099 X60067 AI686183 AW401439 T39535 AA302410 AV645727 AV653397 AA317395 AA218582 AA219682 AA227317 AI750900 BE440055 H77491 F12371 AA314714 T74055 AI655647 AA489421 AA346569 AI129523 AA094975 AW793582 R97358 H67966 N72440 H79590 H81459 H60508 R39623 H60900 H40547 AA377244 AA318430 H71201 R64651 R65629 H72546 AW798947 N76974 H03029 N77701 AW151751 H60925 AA455839 H72947 N58334 N55487 AI299891 AA581634 AV651323 AV651728 AV650086 AV651295 AV648042 AW020600 AI537887 AA429713 AW080244 N73463 AA471335 AW150316 AA360851 W01407 BE074301 W21371 T87221 AA190691 D16906 AW862400 AV661466 AI357816 AA442743 AI189966 AW887793 BE005206 AI926016 AA317024 AA976151 AA247314 AI767184 R64644 R62817 D57965 N74437 N74385 H60409 N66059 H91165 R79462 F09991 R26175 H77853 N32590 D56667 AA461122 D56666 D56903 AW021856 AA374084 R69734 H66894 T81638 T63958 W23935 R67668 AW021682 H81249 H61959 H89852 R79306 W25710 W42964 AA384428 AW994316 H95163 H95158 R33688 W46557 AW748451 AA029916 AA463826 AA314287 R23084 AA368891 H02926 AA310456 H03632 C02397 R63745 H94539 R32226 R24648 H44502 AA039671 AA345336 W42846 R48024 R79724 R63143 AA379513 R21780 R80704 T70422 H21580 H46388 R62779 AA579734 N64111 AA344527 AI865473 R66666 Z20058 T52284 H95103 R36513 R21874 R31363 AA220939 BE439695 AI189683 AA164901 AI539383 AA768249 AA442361 W02867 AA303315 AW952009 AA314544 AI076799 AA216780 T70338 AA039672 AW629489 AL044620 AA533203 AA043082 AI668619 AW298204 AW195268 AI391606 AA437282 AW304801 AW085720 W02586 AA863279 T82339 AI356879 BE464557 AI038992 AI190018 BE146083 AI860399 AI039572 AI129687 AW468134 AI436074 AI963509 AI682239 AW663467 AW129557 AA680298 AA460262 H91217 N57879 R66069 N95684 AA040855 AA227116 N94486 H04229 H97877 AI161080 AI074367 AI025767 AI754185 AA888150 AI356979 R79463 AA029917 R69637 AI810134 AA460820 AI377990 AI743170 AA854637 AA628548 AA664223 AI362196 AA489363 AI361404 AI363155 AA300504 AI678269 AA633851 H61743 AI161012 AW339721 W42847 W46558 AA143120 AI042475 AA479365 AA219592 AW468142 H67690 AI186516 AA531387 AA835378 H03030 T68119 H95133 AL040491 AI289149 R63701 R32177 R32865 AI811374 AI613274 AA775300 AW192882 R37509 W42965 R47918 AI949525 AI129450 H49378 AI435907 AI832271 AA479271 R21849 H03633 AI888539 C75673 AI261394 AA614478 AW469307 AI261429 W03148 AW026141 AW236371 R79725 AA346568 C06197 T27764 H59538 AI749196 AA485299 AA719227 AI698762 N70790 AI925028 R21734 AA977432 H77905 AI625648 AA918868 AI220069 AI352568 AA668729 AA195395 T63334 AI932783 N32271 R26048 H90697 R24539 AI970287 T55374 N93019 T11162 AA377400 AW882126 AA602293 F35923 AI424237 AI826517 H27442 AA039729 AA382630 AI567304 AA045112 T57779 AI474576 AI352569 R63095 H44456 X85116 AI521609 AA164352 BE146079 H60082 AI334776 AA700506 AA782742 R67386 R22978 R33584 R67011 R80705 AI245311 H81590 AI360786 AI219244 R39564 H66850 AI184385 AA687691 H68013 AA092081 AI445480 AW005734 |
| 100641 | 28620_1 | AW068302 AI754558 AI750727 AI752631 AA302174 AA327522 M64110 AW859944 AW859989 AI751995 AA769620 AI858829 AI924875 AI888836 AA864291 AI685060 AW088029 AI924908 AW466328 AI093800 AA991651 AI254501 BE004703 AA334442 AW938852 AA194330 AL046953 AA852866 AW391995 W30846 AW662928 W25261 AA042863 R99045 H97060 W03910 H94687 T88984 AL048165 T29632 N31556 N36484 AI798679 AA989355 W23832 AA873789 AI743646 AA363587 AI814748 AW338990 N73740 N83666 AL047816 R24137 R63433 AA524984 AA234043 AA195131 N99903 AA453669 AI240302 AA370271 AI950026 AW771049 AA121476 AA569557 AI752632 AI355594 AI471993 AI159941 N94555 AI753138 N21537 H97881 N25769 AW068044 AA808425 R63380 AA384736 AA384738 AA852352 AI073645 AA527960 AA525036 AA044414 AI752460 AA703064 R01216 AA897183 AI751996 T81078 H95047 AA573642 D58348 N20953 AA437143 |

TABLE 1B-continued

| Pkey | CAT Number | Accessions |
|---|---|---|
| | | N95439 AA579540 AW867056 AA770090 AI085180 AI806799 AA426421 AI572513 R24081 AA853189 AA295620 AA234044 AA371020 AW994984 H20896 AW964438 AA318516 AA318499 AA318727 AA318211 AA318478 AA318444 AA318307 AA318497 AA318448 AA318309 AA318496 AA318213 AA318435 AA318424 AA318217 AA318523 AA318438 AA318487 AA318724 AA593185 AW994985 T69842 AI251813 AA478174 AA447737 T68350 F07712 AA121145 H08973 AA345212 BE000667 AW068210 AW608407 R05674 H16712 N85426 N42354 H85516 BE147991 T28113 R32662 AA384678 AW239275 H82382 AW840700 D58229 C04082 W45394 AW795667 R73973 BE002409 AA042828 AA363555 AJ223812 AA344709 BE149590 R70995 W46881 W90778 N71242 AA534826 AL040676 R23797 H96450 AA062957 D79947 W46960 AW959278 AA295997 AA026215 AW579469 AW365135 AW365134 AW994353 AW972886 AW069166 AA343690 AW888731 AI751527 AA937490 AA937506 AI826715 BE465604 AI925532 AI858109 AW339097 AI858524 AI720571 BE046506 AW384981 AA043908 AA375983 AA525181 AW068366 AW070577 AW891837 N83985 AW182753 AI422979 AI679733 BE006555 AL048166 AI081401 AI888821 AI626043 N37087 AI624140 AI801298 AA600048 AI753947 H89615 N66424 AW069756 AI814880 AI982806 AI754287 AI971816 AW069022 AW069069 AW069454 AA342989 AI077712 AI311467 AI087361 AI801015 W46993 AI281324 AW191963 AI421675 AI300881 AI356670 AA873156 AI004219 AI189685 AA478018 AA076063 AI445222 AI753124 AI521569 AI925026 AI022368 AI475993 H20846 AI223234 AI635123 AA579170 N30442 AW117889 AA807935 AA558975 AI306636 AA888963 AI952591 AI935835 AI445293 H16713 AW139833 AA622122 AA972051 AI280828 H09543 AI453725 AW069613 AI865615 AI753921 AI368782 AI633208 AI446651 W46961 N22201 H82276 C16555 AA291477 AW440535 AW517755 AA669921 AI926777 AW662118 AA553369 N67873 AW023948 C15861 C16601 AI251465 AW079187 BE045090 AI273006 C16390 C16503 AI620823 F13661 N66864 Z21311 C16108 C16089 C16400 AA758273 AI287781 AA864676 AW608074 AW385583 AI589944 AA665817 AW192979 AW469065 AA564048 H84715 C16417 AA731072 AA661674 C16487 N29477 AW189997 AI370492 C16471 AA652809 AA936687 AA506512 C16306 AW028413 AI537935 AA528347 C16255 AW029046 C16202 AI868152 AI524662 T94414 AI567041 AI619654 AW008486 AI075624 AA577434 AA345104 T30105 AA932002 C16585 AI750390 AW294265 AI619552 AA669781 AA026678 AW132002 AW263919 C16562 AA759137 AA693351 Z40779 C16577 AA885045 AW073763 R45484 AI520895 U54708 T49285 AI568126 AW006569 AI093317 AL119781 T61046 AI053563 H51958 AF114144 AA305739 AW950394 AW793928 AW793910 AL047737 AV659047 AV659632 AI750389 AA092053 AA092798 H85367 T61597 R23745 Z20418 T78485 AI751528 AW068121 AA853188 AI752459 AA853711 AW950663 R78964 R36359 R21626 R21522 |
| 100642 | 28620_1 | AW068302 AI754558 AI750727 AI752631 AA302174 AA327522 M64110 AW859944 AW859989 AI751995 AA769620 AI858829 AI924875 AI888836 AA864291 AI685060 AW088029 AI924908 AW466328 AI093800 AA991651 AI254501 BE004703 AA334442 AW938852 AA194330 AL046953 AA852866 AW391995 W30846 AW662928 W25261 AA042863 R99045 H97060 W03910 H94687 T88984 AL048165 T29632 N31556 N36484 AI798679 AA989355 W23832 AA873789 AI743646 AA363587 AI814748 AW338990 N73740 N83666 AL047816 R24137 R63433 AA524984 AA234043 AA195131 N99903 AA453669 AI240302 AA370271 AI950026 AW771049 AA121476 AA569557 AI752632 AI355594 AI471993 AI159941 N94555 AI753138 N21537 H97881 N25769 AW068044 AA808425 R63380 AA384736 AA384738 AA852352 AI073645 AA527960 AA525036 AA044414 AI752460 AA703064 R01216 AA897183 AI751996 T81078 H95047 AA573642 D58348 N20953 AA437143 N95439 AA579540 AW867056 AA770090 AI085180 AI806799 AA426421 AI572513 R24081 AA853189 AA295620 AA234044 AA371020 AW994984 H20896 AW964438 AA318516 AA318499 AA318727 AA318211 AA318478 AA318444 AA318307 AA318497 AA318448 AA318309 AA318496 AA318213 AA318435 AA318424 AA318217 AA318523 AA318438 AA318487 AA318724 AA593185 AW994985 T69842 AI251813 AA478174 AA447737 T68350 F07712 AA121145 H08973 AA345212 BE000667 AW068210 AW608407 R05674 H16712 N85426 N42354 H85516 BE147991 T28113 R32662 AA384678 AW239275 H82382 AW840700 D58229 C04082 W45394 AW795667 R73973 BE002409 AA042828 AA363555 AJ223812 AA344709 BE149590 R70995 W46881 W90778 N71242 AA534826 AL040676 R23797 H96450 AA062957 D79947 W46960 AW959278 AA295997 AA026215 AW579469 AW365135 AW365134 AW994353 AW972886 AW069166 AA343690 AW888731 AI751527 AA937490 AA937506 AI826715 BE465604 AI925532 AI858109 AW339097 AI858524 AI720571 BE046506 AW384981 AA043908 AA375983 AA525181 AW068366 AW070577 AW891837 N83985 AW182753 AI422979 AI679733 BE006555 AL048166 AI081401 AI888821 AI626043 N37087 AI624140 AI801298 AA600048 AI753947 H89615 N66424 AW069756 AI814880 AI982806 AI754287 AI971816 AW069022 AW069069 AW069454 AA342989 AI077712 AI311467 AI087361 AI801015 W46993 AI281324 AW191963 AI421675 AI300881 AI356670 AA873156 AI004219 AI189685 AA478018 AA076063 AI445222 AI753124 AI521569 AI925026 AI022368 AI475993 H20846 AI223234 AI635123 AA579170 N30442 AW117889 AA807935 AA558975 AI306636 AA888963 AI952591 AI935835 AI445293 H16713 AW139833 AA622122 AA972051 AI280828 H09543 AI453725 AW069613 AI865615 AI753921 AI368782 AI633208 AI446651 W46961 N22201 H82276 C16555 AA291477 AW440535 AW517755 AA669921 AI926777 AW662118 AA553369 N67873 AW023948 C15861 C16601 AI251465 AW079187 BE045090 AI273006 C16390 C16503 AI620823 F13661 N66864 Z21311 C16108 C16089 C16400 AA758273 AI287781 AA864676 AW608074 AW385583 AI589944 AA665817 AW192979 AW469065 AA564048 H84715 C16417 AA731072 AA661674 C16487 N29477 AW189997 AI370492 C16471 AA652809 AA936687 AA506512 C16306 AW028413 AI537935 AA528347 C16255 AW029046 C16202 AI868152 AI524662 T94414 AI567041 AI619654 AW008486 AI075624 AA577434 AA345104 T30105 AA932002 C16585 AI750390 AW294265 AI619552 AA669781 AA026678 AW132002 AW263919 C16562 AA759137 AA693351 Z40779 C16577 AA885045 AW073763 R45484 AI520895 U54708 T49285 |

TABLE 1B-continued

| Pkey | CAT Number | Accessions |
| --- | --- | --- |
| | | AI568126 AW006569 AI093317 AL119781 T61046 AI053563 H51958 AF114144 AA305739 AW950394 AW793928 AW793910 AL047737 AV659047 AV659632 AI750389 AA092053 AA092798 H85367 T61597 R23745 Z20418 T78485 AI751528 AW068121 AA853188 AI752459 AA853711 AW950663 R78964 R36359 R21626 R21522 |
| 100656 | 10385_1 | BE250162 BE296056 NM_002439 U61981 AA421716 AA723916 N32298 H99382 AI817671 AW364509 AW364468 BE250719 AW364498 AW993728 AA382889 AW473270 N44579 BE514508 BE514324 AW069265 AA969963 J00140 AW575796 AA314334 AL040147 R01547 T91432 T29009 W47530 AI242555 AI379077 AI272820 AI467802 AI827163 AI221263 AW592425 AI472183 AI740752 AW044683 BE467755 AA427637 J00146 AA252992 AI784131 AA694127 AI352150 AA290600 AI040148 AI090860 AA215695 AA227746 AI040147 AA401306 AI332971 AI187739 AW013865 AA010576 AA699792 AI131225 AA700469 R91775 AA778381 AA455309 R00884 T91344 AA682438 AW821327 AA290577 AW864100 BE397831 H25209 BE397236 AW821317 BE253372 J00139 X00855 V00507 BE252613 BE250809 BE256056 BE391734 BE295309 AA031848 J04810 AA749344 AA489055 AA129465 AA280816 AA280833 AI803332 AW572941 AW572255 AA725857 AI184392 AI635482 AI186480 AA463881 NM_000791 AA447680 AI830697 H94631 AA129464 BE071304 W23580 AA742541 AA651836 AW885001 AW026548 AI361777 AA665122 AI359154 AI039319 AA423962 AI469383 AI262751 AA134941 AI138260 AI003995 AI096798 N80705 AA292482 AI436158 AI695673 AI141920 AA932994 AI880434 AI131169 AA424790 AW024376 AA707045 AA557160 N73567 AW051136 AI419234 AI423410 AI919237 AI626046 AI359605 AI421996 AI375347 AI394460 AA426588 H79646 AA423961 W07757 AA447831 AA348708 BE566659 AA463389 AW951651 T28939 AA488803 AA307107 AA281033 AA280993 AW408089 F06483 BE541506 W03282 AA454921 N90189 AA701106 AA516401 AA578546 AI093830 AA481792 AW176093 AW845531 AA639142 AI271794 AW104373 AA834961 AA927195 AI274416 AA664231 |
| 124182 | 437383_1 | AI637471 AW511357 AI375047 AA868500 AI125413 AA913457 H48062 AI218202 H80118 W58272 AI243058 AI086307 AW470886 AA757972 AW594655 AI652038 AI652469 H58711 W58271 H78877 H47710 H58321 |
| 116312 | 12146_1 | BE379794 NM_016629 AF208860 AA156356 AI807277 H41872 BE155971 AW380559 AW026522 AW337168 AW338644 AA181032 AW571620 AI160161 AA555059 AI469445 AI304501 AA621819 AI218750 AA993112 AA989022 AI913199 AI863142 AA554244 AA885980 AW004750 AA662654 AI866881 AA665097 AI277973 AA490494 AA962739 T17352 AA970757 AI886406 AI926602 AI056153 AW090653 AW975142 |
| 100676 | 21764_1 | X02761 AL134153 U60067 M27589 H12552 AI750806 AW069698 H00678 T92951 AA156457 T53448 R77777 T47375 AV653325 T60421 W61256 T47700 AI752874 AA116119 AW150500 R46471 R42093 R44355 R62662 R44189 AW813264 T63601 R32764 AW069338 AW023601 AW020233 AA946739 AI752245 AW191877 D58570 AI754285 AI886146 AA342911 AI139349 AW994835 AW263386 AW994830 T65787 C18724 U42404 AW378684 AW580570 BE174525 AA600101 AW750611 AI356556 AI750644 T47699 R81772 T49245 T93048 R36450 T49421 AW390369 AA082805 BE142984 AA129277 N83780 AI370335 H43251 AA330915 R23404 AA367947 AW608529 W25319 AA935923 AA092761 H75833 R15348 AI750474 T78889 R62612 T53447 U41850 U42455 AW947480 W25621 R21374 |
| 130760 | 7278_1 | AW379130 BE465904 AA502909 AA558701 AI140490 AA551857 AI814897 AA954355 AA535891 AW131779 AA157947 AA128997 AA160913 AA764907 R45187 AW341841 AF048837 NM_002606 AF067223 AB017602 R19767 AI243073 R00719 |
| 116334 | 158046_1 | AL038450 N66939 AA805447 AA935480 AW472717 AA176686 AA176900 AA491457 AI005269 AI377928 AI684566 N64278 AW978200 AI969917 AW937573 |
| 130791 | 30310_1 | AF030403 AF099989 NM_013233 AW104402 AA251775 AA251558 AI582744 AI222132 AI351849 AA150838 AA905073 AA278308 AI830043 AI803232 AI813651 AI858774 AI266366 AA286879 AA587082 AI351439 AI080241 AI873470 AI276052 AI392761 AI018158 AW195899 AW274293 AW592760 AA913004 AI936691 AA766905 AA648820 AA824515 AI016857 AA815184 AA642482 AA150717 AA332969 AA286878 AA252004 AU076675 AW385077 AA278967 N85454 AW962882 AA370646 AA371056 AF017635 AA456870 AW362582 AA252778 AA166734 AA251679 R05575 AA393093 N55715 H44200 AA262918 AA411926 H85277 N36353 AA354228 AW957757 AA259102 AA094456 AW804671 AW804977 AA403132 AI983218 AA352380 AA167014 AA367293 AW966089 H87960 AI760615 AI769538 AW020706 AI688310 AW880661 BE465009 AW589896 AW665595 AI421959 N30009 AW500278 AI919235 AA769807 AA628477 AI380646 AW182590 AW152645 BE221635 AI286193 AI819216 H99684 H40111 AI364374 AW148894 AI859448 AI823672 AI797861 N55753 AW962710 AA369410 AI453773 BE464221 AA017250 AA403159 AI359893 AI214320 AI420787 H88348 AI669286 AI272326 AW591912 AW513903 AW085975 AI363885 Z40728 AA977370 H84871 R05469 AA525482 H44199 |
| 116357 | 18555_1 | AF052107 Z44765 F12122 H24165 H11814 R12194 T77282 T64835 AA089708 AA580725 R21570 BE184797 BE184810 D45293 AI697485 AI692614 N47708 AI948516 N45613 AI761250 AI312310 AW301248 AW511017 N47709 AI692277 AI610899 AI201738 AW300013 BE549720 AI373609 AW971740 AW172386 AW300024 AW183736 N39430 AI359607 AA039868 AI348511 AA580605 AA504806 AA917610 T72580 AW444559 N48822 AW341837 N64080 R40970 AW340777 F09760 R42944 AI621350 R38764 Z40580 F04552 H10150 N64071 H24057 T80071 N48545 H11738 |
| 130796 | 49038_3 | AA088809 AA281196 AW383617 W31510 AW383538 R39372 R39390 AA215876 AA372416 AA948676 AW968406 AI031966 AI916558 AW338928 AW473646 N20955 AA433947 AA281071 AW939005 AI810867 BE348759 AI870252 R05526 AA815306 H98625 AA088670 R56113 |

TABLE 1B-continued

| Pkey | CAT Number | Accessions |
|---|---|---|
| | | AW571767 AI244696 AA534742 AI148682 AA635997 BE092847 AI191230 AI934930 AI700266 BE221218 AI219015 R38299 AI039972 W04611 AI192409 AW024404 AA860574 AI681244 AI268589 C16581 BE092623 AI623642 BE011217 AA470441 BE011218 BE011190 BE011222 AW135098 AA907768 AI201833 R38314 AA465584 N62420 AA904266 BE092859 AI762009 AA827837 AA465228 AA430754 AW390464 |
| 109141 | 40042_1 | AF174600 AA176679 AA176413 AA176428 |
| 109166 | 12792_1 | AA219691 AF153329 AA179617 AF070672 NM_005733 AA157866 AA157567 AW672662 AW383906 AW975835 AI655312 AI653243 AA731744 AI889336 AA704870 AW590208 AI671173 AA781842 BE090424 AI669341 AI203090 AW103151 AI654412 AI168283 AI014854 AW075406 AA600977 AA736497 AA179845 AW074368 AA630744 AA789069 AW770138 AW074752 |
| 115761 | 18573_1 | AA366037 AA380228 AW956485 BE382385 R53711 AA244040 AA340660 AA705628 W32795 AI917370 AA421612 AW341435 AW074334 AW631200 W84481 AA421374 W84326 AI358486 R52931 AI003131 AW856014 AW856057 AW856070 AW964801 AW855994 BE563579 |
| 115764 | 18581_1 | AW582256 AW956284 AF038451 NM_006408 AA316115 AA315629 AW369360 AA314225 AF007791 AA421527 BE072059 AI817063 AW194118 AW192785 AI075324 AA298537 AI634717 AI380637 AW151674 AI888294 AW190856 AW364247 AI080640 AW152548 AW002338 AW614754 AI445913 AI828325 AA573742 AI436796 AA909945 AI735767 AW304001 AI475938 AW303846 AA582017 BE076995 BE049240 AI678847 AW471069 AI720013 AW951790 AI888914 AW272720 AI801054 AA582851 AW073291 AA583091 AA315049 AI828251 AI801784 AI805627 AI025266 AA776960 AI559391 AI800431 AI800451 AA838499 AI378681 AA884931 AI242802 AW769127 AI184843 AA316874 AA565996 AA442829 AA593818 AW027843 AI249798 AI378390 AI277266 AA552670 AA970336 AI473626 AI275085 AA622524 AI610106 AI291994 AI476691 AA838482 AI925030 AI146786 AI582452 AI537173 AI040152 AI678427 AI469656 AI445130 AI916480 AI285429 AW602019 AI358508 AA687567 AA421562 AA425142 AW190915 AA570785 AI888732 AA632103 AI924494 AW152169 AI891014 AA565444 AW191880 AW591300 AA581848 AI473553 AI675714 AA501945 AI685830 AI469613 AI933636 AI972701 AI972499 AI581525 AA526975 AI623264 AA639696 AA513297 AI400863 AW080588 AA558986 AI926128 AI537212 AI695291 AA327356 AA625485 AF088867 AA298527 T24475 AA476675 AA055880 AA314206 AA315408 AA316508 AA307697 AW844413 AA314052 AW370274 AW582421 AW364225 AI815198 AW166169 BE072073 AI675865 AA315613 AA426228 AA314146 AA437001 AA307795 AA316233 AA314372 AA316967 AA315724 AA313235 AW369331 AA244356 T86663 AW868072 |
| 107974 | 86033_2 | AW956103 AA034069 AI949847 AW614382 AI755010 AI276949 AA703075 AI378511 AI611646 M85811 AW614309 AA641881 AW956104 AI559931 AI652385 Z28840 BE350594 |
| 107977 | 959661_1 | AI188161 AI190162 AI400979 AA034366 AW194387 W69697 |
| 132050 | 9000_1 | AI267615 AI470943 AI630796 AW612696 N68463 AW615280 BE503091 AA022945 AI693149 AA987332 H62171 H85713 AA088575 N94777 N62260 AA136353 AI677863 AI806221 AI472240 AA028020 AI313182 AI183984 AI337961 AI377319 AI263122 AW264637 AI342300 AA723124 AI286102 AL045995 AA028033 H62172 AI914056 AA581587 AA328012 AW952409 AA598939 AI261715 AI805052 H85206 AA907798 AA977544 AI096679 AW291348 AA136265 |
| 132057 | 27494_1 | AB037858 AW888417 BE168022 BE297137 AI205125 BE003963 AW965680 AA349466 AA351821 AI492558 BE146202 D31580 AK001199 R45887 AI372674 AI755276 BE168407 AW840238 AA160849 AA027021 T18598 AA161281 AA143489 AI372673 D80601 AI870013 AI460100 AA158252 AI971206 AW071873 AI431911 AI493768 AI439206 AI376927 AI038534 AA678831 AI418906 AI356122 AA789304 AW150270 AI499098 T98883 AA349465 AA330631 D80800 AA158399 AA350488 AI334361 AW338483 AA351820 AA301787 AW753882 AI926390 AA702382 AA376185 AI084962 AA355373 AA102488 AA100840 AA325211 AA425180 BE392668 H50462 AA367255 N94717 AA037160 W89039 AI096627 AI750041 AA102418 AI589918 AA313505 AW951928 AW082735 AW189862 AI567485 AI590590 AI494149 AI422826 AW082999 AA043408 AA043409 AI363488 AW104306 AA877117 AA476207 AI811883 AW026405 H63354 AI992015 W88956 AI190217 AI738539 AI361483 N77542 N62261 AI359937 H41345 AA156068 AA102489 AW339965 AW083453 BE139062 AI937868 AW075493 AA654017 AI094530 AA548969 AI686221 AI961671 AI570099 AA904590 AA631107 AW770217 AW471322 W88756 AW134571 AL042199 |
| 101332 | 25130_1 | J04088 NM_001067 AF071747 AJ011741 N85424 AL042407 AA218572 BE296748 BE083981 AL040877 AW499918 AW675045 H17813 BE081283 AA670403 AW504327 BE094229 AA104024 AI471482 AI970337 AA737616 AI827444 AW003286 AI742333 AI344044 AI765634 AI948838 AW235336 AW172827 AA095289 BE046383 AI734240 W16699 AI660329 AI289433 AA933778 AW469242 AA468838 AA806983 AA625873 W78031 BE206307 AA550803 AI743147 AI990075 AA948274 AA129533 AI635399 AA605313 AI624669 AW594319 AI221834 AI337434 AA307706 BE550282 AI760467 AI630636 AI221521 AW674314 AW078889 AI933732 AI686969 AI186928 AW074595 AI127486 AL079644 AI910815 H17814 AA310903 AW137854 T19279 AA026682 AA306035 AW383390 AW383389 AW383422 AW383427 AW383395 H09977 AA306247 AA352501 AW403639 F05421 AA224473 AA305321 H93904 AA089612 AW391543 AW402915 AW173382 AW402701 AW403113 R94438 N73126 H93466 AA090928 AA095051 T29025 AW951071 L47277 L47276 AI375913 BE384156 W24652 AA746288 AA568223 BE090591 H93033 N57027 AA504348 AA327653 AW959913 N53767 AA843715 AI453437 AW263710 AI076594 AA583483 AW873194 AW575166 AI128799 AI803319 AL042776 AW074313 AI887722 AI032284 AA447521 AI123885 N29334 AI354911 AW090687 AA236763 AA435535 AA236910 AA047124 AA236734 AW514610 H93467 AA962007 AI446783 AA127259 AI613495 AI686720 AI587374 AA936731 AA702453 AI859757 AA216786 AI251819 AI469227 AA806022 AI092324 N71868 AA968782 AA236919 AA809450 AA227220 |

TABLE 1B-continued

| Pkey | CAT Number | Accessions |
|---|---|---|
| | | AA765284 AI192007 AA768810 AA805794 AA729280 AA806238 AW768817 N71879 AI050686 AA505822 AA668974 AI688160 BE045915 AW466315 AA731314 AA649568 AA834316 AW591901 AW063876 AW294770 AI300266 AI336094 AI560380 AA721755 H09978 D20305 D29155 AW821790 BE150864 F01675 AI457474 AW466316 AA550969 AA630788 |
| 100732 | 14471_11 | AA557660 N72931 N58682 AK000553 BE616891 BE019441 BE386392 BE617032 AW955142 BE393778 BE614877 AA312756 AF110136 AA308526 AW954708 BE206037 AA862635 AA877204 W93172 AF086486 W93044 AI696392 AI572790 AW296863 AK000953 BE018623 BE617555 W44531 W44532 AW080328 AV658478 F07038 R13156 N94232 AA497078 AW612145 AI095558 AA347381 R92530 AI686040 AI658722 AW068202 H25028 AI953342 AI868754 AI801162 AI140936 W01221 R11347 R21880 H49230 W03324 H11866 AL355731 AV647641 AL042027 AW949467 AA545748 AV647629 AA332120 AA663188 H64362 H58063 D55343 N85086 T81202 AA092966 D55265 AA344264 D53343 R05625 AA852293 AA347291 AA130059 AL044351 AA375416 C04566 AW239018 AI751674 AA346638 AA346997 AA332827 AA346694 AA361969 AA332692 AA332580 AA333328 AA489969 AA344148 AA347995 AA331488 AA330021 AA330267 AA341439 AA347374 AW662969 AA334856 R57854 AI873152 M14219 NM_001920 R17522 W76610 W03199 L01131 AF138300 R87181 AW242264 W30712 H43945 AW747972 AA564201 R83636 AI569141 AA225474 AA455154 AA100348 T54141 AA329561 AA452455 H12824 T68312 AW512798 AI446779 AW152579 F00576 AA598475 AW337220 AI863890 AI216596 R41889 AI141927 AW382271 H28491 N78364 AA634355 AI754556 R25631 H51724 AA598793 H03280 AW382277 AA485695 AA045260 R74254 AI696875 AI962914 AW950369 N70110 AA779030 N95789 AI679464 AI371134 AW862855 AI371125 AI282869 N99052 AW969704 AA916595 AA026628 AA086334 AI339836 AI051715 AA703328 AI808534 AW244107 BE439440 AI354525 AW193117 AI087238 AI589285 AA778065 AA778055 T50574 N62598 R11200 AA620910 AI453739 AI922832 AI083988 R27013 W68196 R01129 AI627480 AW068113 AI754627 AI147036 R05517 AI360559 AI817283 AW007286 AV658015 N69307 F27591 F27593 AI337979 AI582893 AW072368 AA483079 AW130479 C21314 D45487 AW152570 AI860188 W79127 AI866692 R22174 AW072402 AI589431 AI829367 T41249 AW518805 AW169487 AI624605 AI702017 AA327896 AI963416 AI890113 R77374 N78783 AI936044 AI815020 AW242018 AW192368 AI935852 AI571587 AI420021 AW471274 H66838 F17559 AW196100 H60836 R41667 AW150321 W72648 AW471369 AW262984 AI446080 AI920900 AI801261 AI636202 AW272222 AA937821 W44950 AA722200 AI690574 AW514960 AW382654 AW519092 AA573520 AI684168 AA364847 AW262921 AI921640 AW470209 AW474239 AW190673 AW872977 AA582570 BE222328 AI446657 AW572556 N67217 AW613423 AW471053 AA604746 AI246144 AW966754 AW874250 AW069248 AA364096 BE222810 BE350484 AI598283 AI751863 AI017236 AI886478 AW069250 W68075 AI720991 AI015943 AI754467 AI783824 AI571040 D56926 AI961551 D57123 AW028912 AI581082 AI282168 AW342006 F03390 AI423346 AW073389 AI014855 AW024024 AI222770 AA668236 AA428544 AA604221 AW191942 AI969400 AI079642 AA972764 AI143319 W15228 AI970742 AA031278 AW192098 AA318759 AW341999 AA718967 D57111 AW193306 AA598827 AI632396 AI860086 D56506 AI754168 AI682578 AW628379 AI753721 AA564187 D58203 D57443 D57435 D57135 D57411 N34461 AI754630 AW193407 R45190 AW028006 AI313439 AW193071 D53342 T80798 AA968520 AA954159 AA931107 AI539001 D57804 AI491816 D58192 N70195 AI753783 N57952 D57854 AI309918 T93955 AA327690 AA334434 N74205 N62463 N64571 AI304450 N55278 AA496915 N65969 AA056033 AW148825 R77375 AA338658 W94304 AA719311 N26763 AI358580 AI376810 AI278832 W02137 H80122 AI750472 D57929 H94334 D56712 H11506 AI368225 D56651 D56812 N67498 H83245 H03281 AW518735 AL048586 D58033 AI924572 H70601 D56857 D58301 D57914 D58289 D56882 D56564 AA505619 D56932 D57874 AW193948 D57950 AI247213 F02678 AW264711 AW002353 AI888915 D57194 D56604 D56940 D57465 D57971 AA852884 AW964074 R22175 R71187 R87182 R52933 H63525 AA346326 D57252 D57276 D57045 AI750455 AA853331 AI752372 N70924 R44777 AA977380 D56981 R92439 R83282 AI281593 AA299180 R16692 AW022381 H39815 Z18795 AW519084 F04893 AI583937 AI680378 AI709116 N74220 AI571697 AI446098 AI209065 AA599264 AI889395 AI953531 AI624798 AI570991 T29265 AW960203 F13791 AA599365 H64138 AA853492 |
| 101396 | 15685_1 | BE267931 AU077164 D28458 H13004 AW247636 N39666 AA035712 R91038 N94156 H78774 AA305808 R96677 W91932 T52041 AA321569 AA393736 AA332390 N31157 AA143387 T82974 AA189019 AA147291 C17291 AA361459 AA223815 W96541 AA313952 AA361890 AA355945 AW949324 BE513302 AA307417 BE394075 AW967159 R57554 AA352839 AA353199 AA312077 AA393864 NM_002592 M15796 H79840 BE380061 N49784 AA305477 AA450264 N28023 AA082120 BE386156 BE384681 N57269 AA361675 H10500 AA149841 AA352976 J04718 W17271 AA186566 AI750318 AW673623 H72663 W39039 W39006 BE090996 AA305857 AV649575 AA843679 H62619 AW382069 AI348072 D17061 W06825 AW380029 AW800889 AW380015 AI125272 BE350333 AI042167 AA845606 AA191268 BE379634 AA029676 W35262 AA868244 W79062 AA024948 AI927609 AW129714 AA459794 AA459783 AA933747 AA719242 AW063597 W56704 AW063688 AW130928 AW970494 AI978910 AW878857 AW063712 AI203443 AA779705 AI378985 AA843914 N50485 AI831445 AI359205 AI473972 AI285022 AW606502 AW731754 AA987916 AA703995 AI160604 AA627355 BE158282 BE158272 AA622766 AI186133 AI688759 AA523378 AI301839 AA191541 AW272617 AI041480 AI207388 AI186143 AA928300 C17191 T90302 AI246201 AA934733 AW082787 AI829846 AA151916 N26594 AA890438 AA720662 AI002050 AW362863 AA393794 AW370958 AW370975 AA181832 AA353584 AI798191 AA878593 AI184656 AI186650 AA961262 AA916632 AI339961 AA890475 AI811357 AI631255 AI624204 AI371055 AI075444 AI345998 AA687834 W73785 AI343759 AW073775 AI142485 AA829718 BE083991 AA706402 H96572 AA987453 AI075412 AI304681 AA988926 AI242708 N21361 AI253584 W96444 R92698 H05891 AI095790 N33299 N70868 W56739 AA223727 T51961 H72664 AW002227 AA666025 W74474 AA189020 AI344381 BE084076 |

TABLE 1B-continued

| Pkey | CAT Number | Accessions |
|---|---|---|
| | | AI243742 AI750319 AA063528 AA868435 AI708661 AI718683 T28956 AA450265 AI924457 N63798 AA024991 W23447 AA541387 BE538877 H79641 BE538029 AW440710 AA953221 AA156119 AW263927 W94895 AA352730 AW950874 AW007959 N92539 N78866 AI932893 AW337859 AA459672 AA729743 F02479 AW455759 AA729543 T25454 H62547 N50430 T63976 N70049 N54292 T63965 R85599 N49681 D17232 AA910951 W24824 BE386617 AI525551 BE567611 AL034410 AI198816 W73728 AA534300 W61040 AA102496 AA771826 N92556 H50961 N44829 AA628033 AA642158 AA628038 AI613134 AI468860 N87245 R91859 AA091252 |
| 109220 | 139161_1 | AW958181 AA196018 AA706922 AA775199 AI798729 AA192334 AA132242 AA132243 AA973154 AA376742 |
| 116448 | 30623_1 | BE268321 BE270484 BE268500 BE410641 AW247710 AL160131 BE304734 BE559730 BE385420 BE296695 BE270916 BE560389 BE513878 BE269394 BE270031 BE396749 AA307170 BE293090 AW404259 AA356863 AW964092 BE547499 AW390856 BE466126 AI961206 AI740613 AW328206 AA702520 N69694 AI609359 AI431457 AI652656 AA694069 AA700681 AA620615 AI953286 AA719272 AW070980 AI867347 AW248040 AA868106 AW235330 BE349862 AA810299 AW008754 AW083321 AW410286 AW291321 AW014377 AI381686 AI080031 AI571761 AI652312 AI652328 AI621043 AW594175 AI828831 AI363912 AA151932 AA721489 BE271102 BE560816 |
| 130889 | 7593_1 | AW972512 AW236579 NM_003864 AF055993 AW628758 AI372048 AI962241 AI138822 AW340532 AW576942 AI332505 AI765148 AA505291 BE044507 AI936899 AA746205 AW005627 AI245057 AI651847 AW197857 AI420928 AI381889 AI283588 AI219782 AI355977 AW166497 AI090179 AI219676 AI681608 AI830080 AI418165 AW044649 AW294136 AW298132 AW292753 AI186178 BE326292 AI927366 AW589975 AI698895 BE041614 AW008628 AI634520 AI420668 AI272881 AI300751 AI914076 AW149564 AW663108 AW080009 AI336521 AI494509 AW117602 AI651038 AI770019 AI417431 BE222987 AI083931 AI672740 AW055034 AI826705 AW468862 AI873323 AA128147 AA128116 D57622 AI307385 AI559899 AI537834 AA126888 F09994 AA026940 N56214 AA564903 D20488 H87549 AA868491 |
| 108647 | 10525_1 | BE546947 NM_017409 AF255675 AA299577 AA314165 AW961165 AA307551 AW961168 AA659084 AI673757 AI796361 AI670876 AA190344 N42572 BE076253 AA910251 BE621922 AI796528 AI458102 AA502954 AW024150 AI653810 AA411006 AI743397 AA190345 AA888101 AI174335 AA916542 AA112396 AI307395 N31842 AW205660 AI269376 AI129087 AW080195 AW024474 AI369480 AW769611 AI382520 AI942373 AW469953 AI949161 AA865803 AW994250 |
| 108657 | 23226_7 | BE567753 AA084916 AA113136 |
| 108658 | 112832_1 | AA641695 AA113139 AA074156 AA083045 AA074392 AA083158 AA113057 AA084807 |
| 115881 | 29310_1 | NM_005756 X81892 AA397668 W32664 AA436725 AI452634 AI003488 AI521155 AW274256 AA634329 W32478 AA435577 AI908762 AI289997 AA782155 AA730762 AA730771 AL045809 |
| 102012 | 21793_1 | BE259035 AU077338 U03057 NM_003088 AW732635 AL134784 AL120159 BE409858 T09062 BE297271 BE294908 BE273148 BE259718 BE261678 BE260498 BE408153 BE259762 BE261974 BE260884 U09873 AW410121 BE019189 BE278692 BE252072 BE383265 BE263157 BE262507 AA774906 BE296630 AW379502 BE538093 AA040533 BE297056 BE293964 BE297011 AA428510 T27582 BE262958 BE382541 AA077541 R87539 AW905865 AW905869 T49230 BE272643 BE256870 BE279828 AI940330 AI940368 BE019144 BE298451 W47256 BE272651 BE018948 BE256797 BE393014 AA852153 BE312227 BE262096 W07585 AA043912 AA403111 AL134704 AA459745 AA027019 M78875 BE265292 AW168964 AA451618 AA186594 AI187107 AI885355 AI339462 AI090054 AA040756 AI937569 AW055162 AI336276 BE205855 AI857647 W30953 AI375605 W95365 BE207928 W32489 AI857443 AA040292 AI093103 AI924761 AA437003 AI564843 AI369291 BE300843 AI566221 AI500381 BE312463 AI453117 AI885669 W78133 AA677779 AI141855 BE208344 AI627739 AA450215 AI150235 BE206671 AI475936 AI493672 AI031615 AW467734 AA908886 AW297260 AW300302 AW515364 BE207810 AA461327 W68528 AI401541 AW298376 AI223266 AA157956 AA728777 AW268529 W81199 W70220 AI359697 AW360928 AI362260 AI961854 AI453087 AI922508 AI749454 AW771707 AW452557 W70219 R62745 AA041210 W68814 AA627393 AI218944 AI887035 AI088922 AI560788 T48210 AA564373 AI208904 AI950808 AW467727 AI081938 AI743346 AI016931 AA502297 AI924504 AI568845 AI671213 AA554629 AI650618 AW015272 AI283991 AI568493 AI968376 AW594745 AI341863 AW196605 AI656603 AW006227 AI087087 AW439650 AI085505 AI656126 AI001102 AW410122 AA927034 AI814950 AW470573 AI568575 AW073874 AW196325 AA665476 AI654701 AI364353 AI458249 AW150618 AI864978 AW103699 AI500694 T06432 AW304384 AW025677 AI682728 AI928669 AW072118 W95376 AA931596 T49231 W47384 M62123 AI880115 AI695915 BE551908 AA599588 AA587443 AA627613 AI825423 AI434053 AI961070 AI341081 BE019156 AI928667 AA923443 AI950232 AI633812 AI990944 AW337670 AI933222 AI985976 AA903555 AI719748 AI621100 W02798 W02155 AA078409 AA922965 AI146961 AA838643 AW044594 BE241997 BE258694 BE311788 BE259835 BE313211 |
| 132116 | 96515_1 | AW960474 AA328243 AA704789 AI088169 N20591 AI823476 H81760 AA406184 W44795 AI040999 AA035348 AA632324 BE295273 AA815436 AA406294 AW394165 AA094618 BE296595 AI659092 AW297091 AA401881 AI435984 R80433 AI948677 W05276 AA234767 H87282 AA253183 |
| 102034 | 598_1 | AI903474 AI903475 X72913 AL036029 AI903264 AI903383 AI903473 AI903426 AI903263 AI903331 AI903348 AA348154 AA558044 X75546 NM_002023 AA018495 AA568437 AA336463 AA336865 U05291 AA338073 AA360007 H26478 AA151040 R54231 H06222 AA411610 BE184970 R08802 H14537 BE184886 BE184857 BE184972 BE184861 BE184884 BE184890 AA283616 AA486471 H14444 H45124 H42970 H28253 H25914 AA009480 BE184935 AA305772 BE184889 BE184894 BE184931 H28266 T27990 BE184880 AW950249 BE184965 BE395547 |

TABLE 1B-continued

| Pkey | CAT Number | Accessions |
| --- | --- | --- |
| | | W65326 T49139 AA194473 AA194461 AA129907 AI680740 AW513000 AI346045 AA581716 AI674688 AI923173 AA587387 AA411190 AW474604 H06223 AW339985 AA908830 AI143335 AI806156 AW073728 AI570719 AI806149 AI653183 AI138299 AI807167 AI826341 H42900 AI925436 AW190948 AA150949 AI342245 AI991294 AI961468 AI360927 AI264267 AI015857 AI493989 AA527366 AI127268 AI304378 AI911417 AA682520 AI340130 AI346002 AI446304 AA916776 AA621369 AA129908 AI693879 AW836294 H26317 AA469443 H28206 AI609744 AI347112 BE218476 H45427 AA971098 H24697 AA861539 AA947902 AI339991 AI015777 AI828473 AI298202 W51828 AI298200 AW148725 H28218 AI440179 AA018496 AI249821 AI801917 AA663157 AW513059 AI827878 W61309 W48716 AA485748 T49140 AI168001 R08803 AI061052 AI804537 R51837 AI127238 AA284975 AA722722 AI520874 AA993797 AI039374 AA776215 AI084307 AW276143 H44534 AI214418 AW002315 AI422575 AI393603 AW449955 AA029408 AI582937 AI457747 AA194376 AI217628 AI432125 AI474369 AA911062 AI022596 AW276107 AI708968 AA628771 AW263915 AW150018 AA723100 H22132 AW051115 AI424515 AA526379 AI581791 AI933696 AI916839 AW003461 BE502206 AW593940 N67534 AI473431 AA501983 |
| 102076 | 28044_1 | BE299197 Z85996 AW247234 AW249122 U09579 AW245698 AW250360 AW250483 BE241887 BE244900 AW247093 AW247357 AA380910 BE208575 AW583068 BE018355 AI751660 AA853842 BE206983 BE207145 L26165 L25610 U03106 S67388 BE257775 AA456445 W01311 BE263645 BE279085 AW732606 BE263622 BE265001 BE297240 BE263520 BE279288 BE256088 BE255900 BE252329 AW239199 L47232 L47233 BE207178 T08389 BE252557 H24262 BE258576 BE251231 AA381909 AW836368 BE206752 AA029109 AW820448 AW820447 AW843746 AA376396 AA321901 AA310434 AW249019 R46847 AW843743 AA375906 D31116 AA376199 AA065009 AW842884 AW842793 AI752795 W02824 H83378 M79002 R74301 BE545783 BE266009 R87600 BE180828 AA375519 AA376322 T53381 W39472 W44813 AA902104 R79427 AW246239 N44912 AA376207 R27374 BE253553 BE207052 AA376096 AW674390 AA187864 AA382005 N42395 N43766 AA373406 AW167163 AA320920 AA187865 BE245429 AA725216 T73450 AW248657 AW248580 AA614342 AW248690 AA134592 N95402 C06087 AW890404 AW890491 W74355 AW890497 AA481474 BE183394 AA854012 AA574254 AA845586 AW795988 AA029195 AA618214 W24029 N23941 AI753303 N35012 AI094940 W76550 N35823 R27375 AI123889 N33064 AI590965 AI146429 AI818625 N33420 D25587 AA716735 N34995 N35249 C21315 AW996039 AA302439 AA134593 AI494143 BE504194 AI191867 AI018663 AA554359 AI041908 AI369918 AA320526 AI041930 AA631887 AA629728 AI752794 AA857879 AI090388 AI751659 AA932518 AA705773 R46753 W45365 AW192512 AA603001 AA069286 AI355869 AI986250 AI813372 W45293 BE301229 AW511449 AW338097 AW247845 AA454553 AW246700 AA621693 AW780118 BE301970 AW129949 AW001364 AW732086 R79428 AI640886 AI814746 AI671072 AW338463 AI457583 AI955722 AW250453 BE046057 BE301255 AI623838 AI066427 AA069702 AI754612 AI274183 AI818343 AA838666 AI087209 AI859858 AI590130 W46516 AI565171 AI862747 AI453163 AI815083 AI628269 AI073360 AI572101 C05955 BE501618 AI677993 AI354988 AW337646 AI623382 AI890317 AI678661 AI979004 AI634583 AI867024 AI961540 AI973138 AI215141 AI866715 AA962447 AW073998 AI365137 AW798270 AI813378 H22870 AI500446 W46448 AW591391 AA083831 T29792 AI952615 AI086902 T53382 R87514 AI147453 AA972341 AW839649 AI971521 BE257943 AI921309 AI079598 AI808947 AI872642 AI270535 AI826937 AI460140 AW615599 AA725669 AW250749 AA324110 AA310402 AA070728 W80687 AI283834 AW674560 AW572555 AI590414 AA534613 AW615591 AI274741 AA576395 AI148273 AI473483 AA644199 AA069979 AW250955 F32303 AA903331 AI866694 AW513154 AI688374 AI688433 AI270034 AA592895 W45388 AA853841 AI561234 AI572977 AI479694 AI760933 AI197843 AA911744 AI468987 AW615457 AI359185 AA977002 AW247999 AA503804 N73486 AA894383 AW020369 BE267310 AA374780 W80866 AA112103 BE267320 AA522678 N42177 W24033 N35290 BE241689 BE265689 AW952075 R32687 AW246894 W40328 T25822 AA029873 BE266934 |
| 132160 | 128565_1 | W26406 AW136872 BE349103 AA935418 R54810 AI804000 AA879147 AI912294 AI339626 N40443 AA807907 AA446520 AA418512 AA101321 AA281770 AA227954 AI435989 AW975199 AA253044 R42784 R44804 AA227789 AA253099 AA280126 AI383274 |
| 131507 | 89088_2 | AI826268 AW248872 H69511 AI748806 AW779557 AI992254 AI890377 AW151271 AI356374 AI634503 AA777065 AI590131 H37767 AI889058 H69512 AA046480 N27343 AI573008 AW130925 AI635838 AW594603 AW000790 AI208239 AI275835 AW090294 AA021587 AW273456 AA505726 AW469424 AI400222 AI025723 BE046148 AI128668 BE350462 AW302601 AI299977 AA284809 AI640358 AW470364 AI241794 AA650048 AW090027 H15377 AW615318 D60021 AI934336 AW118536 AI041281 AA614238 R85918 AW571741 AW516692 AW572232 AW515188 AI798585 AI392825 Z40518 AI869580 AA469975 AI537819 AI810684 AI701744 AI370410 BE383083 Z44676 BE002481 BE002532 AA456765 N44196 D60022 C14604 AA021099 AA284872 BE266647 AW249292 |
| 132164 | 10250_1 | AI752235 NM_000935 U84573 AA376864 AI752236 H99903 AW958071 AA306948 AA164966 AA091705 AW800587 AW800586 BE179465 AW859424 W00413 H97211 BE177724 AI934537 BE177812 AA047529 AA047470 BE177792 H61340 AI700185 AI754404 AA502791 AW104174 N72144 AI499102 AA600050 AA468755 AI302561 AI300888 AA047409 AW873407 AA047431 H97212 N29559 C75482 AI095284 AW630441 AA115019 C75681 AI754224 AA164967 AI439457 H89682 AA983296 AW662585 AA853277 AA333773 AI754603 W30982 AA853377 BE169188 BE169223 AA115490 AW385682 AA993543 C02404 BE169185 BE169226 AW023640 R64182 AW993827 AI376301 AA043545 H62370 AW069486 D16887 AA343887 AA343832 AW956555 BE175910 N47487 R69794 AW592387 T40161 AA884315 N98463 |

TABLE 1B-continued

| Pkey | CAT Number | Accessions |
|---|---|---|
| | | AI051407 AI678677 AI927978 AW664579 AI590727 AI090077 AI061451 AI147531 AI620584 AA617746 H99816 N47488 AI823867 AA605292 N64131 AI948780 AI767933 AI559698 AI564677 AI269461 AI420317 AI831711 AI146359 AW168879 AI689354 AI346276 AI818252 AW627427 AI564693 AI921964 AI371427 AA853695 AW448942 AI361529 AA136707 AI309578 |
| 131514 | 3341_6 | BE270734 N84664 AW391922 BE562375 AV656944 AU076480 AV657989 AA263039 AI689817 AL035898 BE439785 AW248984 BE439680 NM_005566 BE440087 X02152 BE247355 AA295004 AA352895 N85654 W39536 AA127165 AV661179 AW068778 U46319 AW408320 AW068761 AL046907 N86790 AA324068 AA100170 AA313489 AA337052 AA381153 T18854 AW672854 AA366281 AA356618 BE219350 BE122814 AW630254 AW403442 R29627 AA375795 AW401663 AA683275 AA356222 BE410618 AA303830 AW498613 AW402378 BE258279 BE440060 BE539170 BE547722 BE620522 AW239013 BE618205 BE622304 AA381037 BE537289 BE538975 AW238805 BE546710 AA330972 AA376336 BE513559 BE295994 BE544569 BE543720 AA317908 N88057 BE545225 BE293935 AA360992 BE408886 AA206192 BE206839 BE398082 N84521 BE547881 AW651808 BE315212 BE545550 BE277333 BE274843 AW239248 AA176376 BE542891 AA348058 BE544201 BE548621 BE304755 BE269329 BE548052 BE269921 AL048472 BE560089 BE315560 BE613006 AW401848 BE293081 AA223405 AA356051 AA315114 BE267163 AW610536 BE409389 BE513915 BE270766 BE561005 BE560641 BE548838 BE546443 AA383753 M78064 AA376402 AW958176 AI133342 BE614058 X03077 AA885733 BE548461 AW663131 AA853435 AA324697 AW405517 AW374649 BE019816 AW403098 BE539709 AW673496 AA373182 AA376953 AA090902 AW818624 AW393154 AW363737 AA143265 AA522902 AA375189 AW631262 N85647 BE256998 AL047055 AA489611 AA325311 AA374272 AA191652 AW068352 AA192283 BE265168 AW875505 AW401551 H64734 BE082132 N28721 BE270502 BE542010 AA095724 AA343838 AW862085 BE018237 N87961 AW402423 AW751453 AV648593 AA181533 W22134 AI814282 W27728 AA093676 BE620919 AA190693 BE618676 AW381000 AI675188 AA641654 AV648830 AV649121 W28254 AA133363 BE270651 BE314938 AA305540 W45064 BE613301 BE612706 AA774700 AW384452 AI129236 AA057759 AI904807 W26745 AW084436 AA092287 AA001711 AA148070 AA178879 BE614378 AA179254 AW673499 AW579754 W28174 AA083731 AA329644 AA491628 AA112012 AW673497 R57285 AW890681 BE614541 BE613168 BE184013 AI564430 T20087 AA357545 AA370341 AW020002 BE145977 AW386319 AI133645 AA928522 AA320082 AI564564 BE146370 BE535886 AI689539 AW364263 AW024767 BE181237 AI567727 AW386202 AI571579 AW007432 AW384430 AW751655 AW062554 AW190747 W25883 AW935205 BE409825 AI814738 AI609535 AA091211 AA847334 W25852 AI676217 AI917915 AA133283 AW385898 AW363381 AA676500 AI609403 AI922710 AW364148 AI819125 AI813788 BE439591 AW440632 AI669641 AW607753 AI961251 AW170466 AI813789 AW152388 AA733181 AW881158 AI829362 AI954017 AW089722 AI922140 BE613363 AW168114 AW471245 AI244988 BE612632 BE270925 W23836 AW753365 AI560061 AW607746 AA577685 AA856957 AL035899 N95408 BE546918 AW248541 AI889518 W24244 BE439756 AI493263 AA522799 T12329 AA211606 AW994980 BE140459 AA088784 AW948548 AW473607 AA191367 AW518727 AW882031 AW995169 AW995230 BE350742 AW265117 AW068516 AI590933 AW675814 W44616 AW675815 AW069302 AA088433 AA563768 AW805583 N30472 AW770831 AA055432 AI185055 AA121701 AW361826 N69778 AA192372 H05914 AI719090 R93535 AA129531 AW675529 AA595638 AI922588 AI422336 AI272104 AW151094 AW770435 AA618622 AA258849 AW069346 W94137 AA120950 AW117291 W45032 AI660716 AI075409 W94042 W95255 AW368447 T92573 AI753582 W61154 AA351993 T92645 AW151115 AA022712 W61202 BE547553 R93536 AA988264 AA384897 AI094678 AA022677 AA092958 AA356987 BE301717 W44597 BE539272 AI298981 W28476 AA857019 AA176406 AA126956 AW305382 AI376216 AI697013 AA176377 AA047415 AI368827 AI149318 T29905 AA223193 AW516507 AI952675 AA179002 AI523190 AI783877 AW473510 AW591026 AI689234 AI344434 AI299568 W45074 AW591339 BE042704 AI625502 AI523214 AI130808 AI719319 AA577323 AW473063 AW078789 AW068499 AA143226 AA527432 AW275892 AA100109 AA508682 AA586859 W95157 AI300997 AA534023 AI128750 AW386900 AA614319 AA962754 AA856565 AI000278 AA653314 AA779547 AA206056 AW750900 D52315 AW474584 N28645 AW276688 AA838489 AI282260 BE139186 AI619548 AW779619 AI476382 AI037996 AW263016 AI250703 N23056 AI285729 AW578650 AI289903 AA969812 AA486870 AA320509 AI560614 AI864164 AA353053 AW243842 AI358342 AI797438 AI752952 N94562 AI752940 AI700314 AA057760 AI535686 AI535709 AI535748 AA599435 AA676481 AA528726 AW272953 AA482791 AI077656 AW939918 AA577529 AA506613 H65225 AI700337 AA381152 AI719010 BE073480 BE073615 AW673514 AI289146 AW938944 AW939006 AW938996 AA586484 AW602284 AW938978 AW938935 BE073538 BE162787 BE073576 BE073462 AI459815 AA953334 AA716636 AI950483 AW779608 AW938951 AI889673 BE073553 BE162774 BE185856 AW602273 BE073474 BE073483 BE073618 AW602281 BE073542 BE073475 AW939008 BE073556 AW840704 BE073489 BE073463 BE162767 BE073562 BE073470 BE073496 AW602274 AW939015 BE073512 AW602307 AW602314 AW602294 BE073568 BE073557 AA497029 BE073548 BE073511 BE073573 BE073536 AW939039 AW939026 BE073513 BE073466 BE073484 BE073493 AW603154 BE073625 BE073464 AA826629 AI721117 AA350594 T18953 BE007495 AW386898 AW793511 BE049519 AA565171 AW615051 AI347369 F01518 AI453289 AW071021 AW903128 AI718581 AI865531 AI753430 AW195177 AI753768 AI073727 AA599422 AW581743 AA657963 F01838 AW873884 AW613604 AW118006 AI521539 AW189876 AA853434 AW078573 AW027822 AI949090 AI753184 AI350844 BE162788 AW579284 F21714 BE156356 AI933613 AA953358 BE162875 BE070057 AI890891 AI688843 AW410101 AW276840 AA587013 BE070108 |

TABLE 1B-continued

| Pkey | CAT Number | Accessions |
|---|---|---|
| | | F29773 AI282914 BE070061 AW386904 AW386916 AW194231 AI446479 AA953634 BE161417 AW581762 AW581777 AW581774 BE161422 AW050520 BE543373 AI355481 AW386910 BE547892 BE544480 AW079762 AA528582 AA665889 AA148030 AI253726 AI253505 AW366859 AW873692 AA135307 AA648595 AW386833 |
| 131517 | 33543_2 | AB037789 AI384100 BE385519 BE260428 BE384511 BE275843 BE408781 BE277845 W21965 W16748 BE265242 BE265000 N25829 N31401 AA625166 AA369179 AW957071 AA909230 W92748 N22686 W92871 R11325 R72437 N40002 N24106 AA693637 R11326 R50995 N77818 AI039300 R97694 R43655 T88940 F10026 D56301 N20947 F10378 AI870678 AL120199 N27270 AI699902 AW182302 BE500982 AI422172 T33581 AI982515 Z40886 AI202949 AW572248 AA461382 AI337215 AA461202 AI695957 H23850 BE297221 AL120198 N27816 N46020 R96766 AI907845 BE142664 |
| 131524 | 36097_1 | AB040927 AW503387 AA044786 AI686957 AW157364 AW976667 AI752687 AA191323 AA568170 AI161414 R17699 AI140787 AI140789 AI140788 AA742642 AA044809 AA485805 AA847859 AA480178 Z45709 AW974554 BE043079 AA809758 AA648838 N46563 AA485676 AW304745 AV657192 AI553650 AW118847 AI871278 BE075093 AI243817 BE046860 AI560949 AI669278 AA860508 N39152 AW131465 AA767854 AI457964 AA906227 AA719622 Z41372 T93491 AA954262 BE537985 T96329 |
| 101461 | 14616_1 | N98569 AA029143 W15554 NM_000300 M22430 T39452 T47319 AA371017 N57336 D58694 AA320723 AA296089 R50467 AI346657 BE071861 AA319881 AW843848 AA320114 AW820896 AW610375 AW393463 AW179006 AW610166 M22431 T46945 R70570 H02725 AW055209 R63131 AW392662 R80611 R53758 AA885780 AI749547 AW391366 AI970800 AW610360 AW821761 AI830923 AW000798 AA320004 AI249110 AI720962 AA682561 AA586608 AA643641 H00742 AA582755 AA609109 AA370548 R53759 AI672244 AI832430 AA683552 AA838623 R64075 AA936945 AI445267 AA534281 AI149280 AI274363 AI698468 AI128751 AA707159 AI150776 AA131825 AI991026 AI248667 R77118 AI168206 R50468 AW051904 N80785 R77117 AA037587 R63969 N32242 AW470160 R80612 R22811 AA320457 AI734854 AA534110 AA770261 N69947 R63087 H02619 AW768748 AA507524 T53621 AA535170 AI201371 BE439722 T61271 AA554850 N69967 AI805226 AA320357 H00653 AA229266 AA029021 R25199 AI659785 AI784636 AI186301 AI916742 AI581906 AI924395 AI569357 AI582097 AA534166 AA533431 AA758464 AA642546 AA593596 R70480 AA327298 R21194 R24705 N98328 AA131992 AW150658 AA533307 T29484 AI198476 AI581608 |
| 101468 | 28418_2 | BE538296 AU076471 AW630536 BE256222 BE253314 BE252970 AI879112 W06884 NM_004255 M22760 AA314236 H04946 AW960372 AA037034 AA453915 AI479669 AI570425 AI816357 AI857430 AA707310 AI815828 AA902460 AI138594 BE537040 AA811407 AA886314 AW088314 AI475663 AA742451 BE252179 AA130242 AA251213 AA769095 AW005577 AA928675 AA609855 AA026652 AA576492 AA490735 D53489 AA873557 D52955 N21666 N31071 AA043112 AI459859 AA610021 AI672792 AW874375 AA476653 AI761299 AI198512 AI144552 N32608 AA897060 AI340317 AA506519 AI954210 AA491224 AI572937 AA609533 AA810176 AA609123 AA279511 AA279701 AI185172 AA469914 AI186196 AI186198 AA446610 AA614675 AA931802 AI184480 AA878691 BE169495 BE169554 BE169391 AA279512 AA922867 AI078865 AA455798 AI089454 AI937930 F29215 AI208941 AA040864 AA028138 AI051835 AA811372 AA827855 F28644 AI222577 AA088625 AI215690 AA746208 AA028174 AA028891 F28711 AI310742 AI356711 AW071860 AI184908 AI364522 AI346164 AA453943 AA704200 AW007839 AA724397 AI347685 AA872318 F15198 N70881 AA416857 AI720855 AI343566 AI075332 AI266393 AA456619 AI828157 AW054846 AA972671 AA635482 AA894587 T29696 AI268753 AW050824 AA028892 F31947 AA889496 AA453409 AA453438 F29366 AA279784 AA180970 AA541681 AW016609 AA091866 AA094995 T19137 AA911320 AA133213 F26357 AA501516 AA180885 AA749403 AI821212 AI418748 AI708943 F25360 N93192 AI038196 AA524983 AI363878 F34294 AA916286 AA649613 F30281 AA523148 AI720959 AA873165 AA996284 AA027811 F15187 AA293654 AI277060 AW672721 AF067635 AI749244 F26098 AI804296 AI424121 R28369 AA877457 AW964026 AA122176 AA654077 AF042162 AA807805 |
| 101473 | 17314_8 | M22976 AA345036 AW965168 AA400330 |
| 100829 | 35156_1 | AA471098 AA172156 BE206918 AA312757 AA333112 S70154 NM_005891 BE616558 AW249190 AW245878 AW249313 AW248125 AW247768 BE394856 F06359 R25823 AA232077 BE539645 BE208572 BE208578 BE266662 BE266445 BE280650 BE259594 AW733042 AW328148 AA309505 AA353144 AA341050 T60904 T28076 T47718 AA129946 AA262195 AI193574 T93111 H55877 N91324 AA002113 BE274441 BE568128 |
| 101486 | 2464_1 | AA506324 AA244003 NM_001099 M97589 X53605 T29524 M24902 X52174 M34840 U07097 AA244034 AA370422 AA371462 AI557152 AA371312 AA559165 AA370116 AA370907 AA370806 AA559352 AA642055 AA508355 AA492280 AA659719 AA527805 AA533057 AA369877 AA224876 AA228288 AI611683 AI417485 AA370186 AA602957 AA564484 AA527737 AA502979 AA507777 AA687674 AI821627 AA420721 AA568138 AA226366 AA613900 AA225411 AI547266 AA550913 AA573645 AA603487 AA603374 AA579543 AA603504 AA531198 AA504027 AA654378 AA524778 AA654286 AA532701 AA304845 AA654793 AA541709 AA536037 AA492388 AA658213 AA613916 AA532485 AA507735 AA658552 AA661553 AI826518 AA503930 AA659546 AW974889 AA653856 AA635363 AA492232 AA595853 AI097515 AI810547 AW970997 AA533398 AA579285 AA614165 AA574271 AA224879 AA602106 AI680583 AA513560 AA635456 AA641194 AA574278 AI359820 AA216360 AA507606 AA533172 AA640672 AA525029 AA225232 AA531057 AA507770 AA524780 AA640508 AA226453 AA228672 AA503139 AA650355 AA622824 AW137215 AA480545 AA569791 AA573630 AA507710 AA661901 AA640749 AA665287 AA569735 AA225383 AA603907 AA225146 |

TABLE 1B-continued

| Pkey | CAT Number | Accessions |
|---|---|---|
| | | AA225386 AA640832 AI928272 AA639911 AI826687 AA640364 AA514799 AA531382 AA657931 AI670092 AA614077 AA225527 AA654031 AA643799 AA978215 AA603863 AA548498 W57824 AA468243 AA603506 AA225469 AA657510 AA469463 AA507690 AA468274 AA572717 AA492165 AA630918 AA602090 AA224845 AA809521 AA579441 AA468201 AA513568 AA230147 AA650340 AA468315 AI621137 AA467755 AA492279 AA467793 AI732062 AA493280 AI685444 AA226678 AA565429 AA574197 AA658851 AA225793 AA533879 AA226541 AA531364 AA226206 AA658390 AA229980 AA527610 AA226698 AI401663 AA502080 AA508392 AA564283 AA468972 AA225786 AA635299 AA229727 AA226365 AA507972 AA507213 AA559173 AA526555 AI810857 AI826536 AI926993 AI971003 AI597835 AA532598 AA225414 AA502179 AA653047 AA658361 AA467937 AA527905 AA228275 AA225135 AA230012 AA507232 AA573601 AA579479 AA492263 AA468504 AA494247 AA652678 AA492335 AA658231 AA569773 AA508004 AA658008 AA613784 W57562 AA469306 AI685773 AA531127 |
| 100830 | 4002_1 | AC004770 W05005 AA356068 AA094281 H29358 T56781 AW875313 L37374 BE312466 BE311755 BE207106 BE293320 BE018115 AW239090 BE548830 AW247547 AA776062 BE397382 AA486713 T10111 T09340 AW498981 BE547280 AA356003 AW581520 AW875331 AA580720 AW875336 BE276873 BE408229 AW188148 BE255166 BE253761 AW793727 AW373141 AW581548 AA471223 AA305950 BE263976 AA626820 BE257409 AW360962 AA090655 C00312 BE312741 BE407213 AA209352 AW298199 AW248553 AW297794 AW731722 BE300586 AW731972 AW615446 BE301599 AW615520 AA486714 AW440257 AA196516 AA564630 AA618079 AW192592 AW474985 AA604580 AI627461 AA765440 AI680394 AL135548 AI683224 AI581126 AW245096 AW194154 H29274 N70363 AA629758 AA580602 AA862006 AI863841 AI097667 AI928583 AI358774 BE243487 AA620553 AA653297 AA292690 T10110 Z38906 AA908544 AA340930 AI185438 T03328 T28844 AI687010 AI864965 AI872575 BE388740 T56780 AW373138 BE258717 AA699671 |
| 101497 | 9956_1 | W05150 W17241 W05093 W07524 M26679 AC004080 AW451295 AW663882 AA224113 AA648822 AA811807 AW082129 AW340605 AI223317 AW072578 AW665164 AA907030 AA910417 AW418785 AA612758 AA788595 AI218905 AI370899 AA909614 AA278576 AI370985 AI184862 AI204564 AA706301 N89758 N74705 N75430 AW628799 N80726 AI081840 T29089 AW951105 AW802886 |
| 123712 | 374423_1 | AA609684 AA758732 |
| 100866 | 13430_5 | U14134 AA083438 AA865328 R74488 AI613178 AA258556 AI587586 AW853534 AW753253 AI023878 AA281589 |
| 100877 | 21813_3 | X80821 |
| 130982 | 7771_1 | AA033627 AA650628 AA852154 AA749506 R14835 AI754402 AI986441 AA305911 AA769992 AI969556 AI753575 AW295909 AI753977 AW026089 AI440433 BE465241 T51261 BE501688 AI536600 AA151548 AA157003 AI750203 AA156991 AI638488 AA143718 AI400880 BE465500 AI800299 N33271 AI189809 AI917085 BE503243 BE550457 AI917824 AI335026 AI990577 N40505 BE349570 AA757059 AI038582 N33731 AI376046 AI743134 AA778383 R62502 AA179921 AA188864 BE049597 AI801180 BE350898 AI418495 AI540729 R68585 H02846 N67083 AA188534 N57754 AW269361 AA347405 AA114154 AA991256 AA151883 AW197543 AA121334 BE221052 AA347211 BE350900 AI913571 BE221332 BE465667 AA620881 AI418140 BE220769 AA213468 AA041526 AI942400 AI650440 AW272639 AI590815 AA376044 AW590826 AA351009 AI800711 AW589786 R95691 AA852667 AI752234 AI750723 H38306 AI765216 AI750183 AA852160 AI521999 AI750861 T53495 AW068539 AA853149 T50031 AW021969 AI750937 AI350689 T53494 AI753507 AW971936 AW612632 AI769628 AA853376 AI079435 H87656 AW269198 AW023168 R80032 AI342334 AA749505 N93983 AA341338 AI039889 |
| 116578 | 13667_1 | D21262 AA191530 AA190834 M85417 AW379190 AA332366 AA315951 AI355279 AA361073 AA039243 AA354828 AA158293 AA037752 AI913175 AI886058 AW149765 AA285228 BE259115 AW581581 AW799319 AA854695 BE167356 AA306910 AA380711 AA065300 AA065299 AL042662 AW001637 AI540378 AI834341 AW845164 AW845148 N41585 AW800478 AI834348 BE018761 AW606705 AA984206 AA037820 AI823555 BE621602 AA317943 AI867463 AI834314 AW169072 AA301112 AI393269 AI765681 AA085577 BE206473 BE504372 AA037821 AW904317 AW816615 AA191216 AI419971 AW896673 AI347506 AW474810 H73662 AI719116 AI112312 AA804343 F08714 AI739077 AW293811 AA243182 AA307171 N30810 AW951659 H07013 AI871859 AW137084 R14083 AW604603 F08531 H17699 BE467896 H53670 AA721269 AI347405 AA716645 AI471940 AA586782 AW805850 AA312144 W20312 R10258 AA830285 BE069171 AW820001 AW819991 AW819996 AW820000 AW749364 AA488526 T97118 AA370129 AA128268 AW404500 AW404495 AA251278 R09997 R07421 AA135889 H30073 AI290885 AA465246 H87665 H58579 AA237043 AW582709 W75966 H20420 D19586 W95624 BE613121 W79195 AW051506 AI096635 BE502347 W01058 BE090549 AA740769 Z24773 H22678 H44226 H46705 W74378 AA740861 AA807204 AA126700 H53630 W93517 AW025405 AW237649 AW271261 AI669834 BE463909 T64902 AI949804 AI681513 AI656494 BE502392 AI262290 H30074 AA188798 H46706 AI423181 AA488393 AA196450 BE467847 AI650852 AI768392 AW302213 BE047333 AI936134 H46726 AI887878 AI865821 AI969789 AW576386 AW206228 AI950503 H20421 H73355 AA827834 H05462 H46184 AI690176 AW024743 N70206 AA098927 AA079325 AI279466 AW302583 AW614861 AW002582 BE302327 W60927 BE048732 AA995149 AI144395 BE326903 AA854192 AI130791 AI341272 AA354666 AA767715 AA569154 AW139816 AI123439 AA526024 AA135890 AA593870 AA581556 AI623728 W95625 AA828018 W60796 AA910657 AA829472 H46032 AI091166 AI161324 AI636814 AI825415 AI522055 AI439510 AI093498 R16744 AW675537 H17083 N90709 H62578 AA661505 W70262 D29057 AI077619 AI418692 AI142728 AA659087 AA826189 AA465139 AI122598 T29720 AA732157 AA829358 Z24774 |

TABLE 1B-continued

| Pkey | CAT Number | Accessions |
|---|---|---|
| | | AA516265 AW044679 AA983639 AI708668 F04740 AW248000 AI744014 AI864236 AI927536 AI537721 D51272 F04643 AA854371 AA365196 AI864161 AI632868 AI284585 AI219419 AI693767 T16740 AI219627 T17450 AI204120 AW503744 AA196693 AL040034 AA113068 AW503365 AA356890 AA243243 AA219341 AA773923 R01675 AA034227 H46105 H46183 H46799 H46694 H62511 T97003 AI564807 AW606635 AW606750 AW606755 AW606640 BE301924 BE294562 AI124093 AA206535 |
| 108731 | 20618_1 | AA258888 AA320012 AW976088 AW971357 AW175623 AW175760 AW175769 AW578267 AW162589 N27262 AW160986 AI138629 AA035553 W94453 W94335 AA326606 AF070655 AA040163 AW939331 AA307814 F26425 AW992386 N90194 AA040625 AA150547 W69159 BE138584 AA341766 AI148036 BE566222 W38579 N77160 AI298471 AI343730 AA345321 W39695 W69285 AA010132 W92598 AA046361 W05009 AA318988 F25225 AA150856 N70368 AA044697 AA046123 N80350 AA035042 AA385776 AA188329 H75363 AW966638 AW577569 W79260 F25637 AW406233 H23856 D52811 AA352610 AI143578 BE379846 AW793049 AI343875 AW610545 AA359285 W94758 W47488 H12428 AA358855 AI369400 BE395297 AA525068 AA302040 AI242419 AA149321 AA424437 AA524660 BE253984 AI905952 AA007429 N39993 F31088 BE394339 W45050 AA149322 AA513324 AA314633 AA824412 W51797 AA341568 AA010131 AA694376 AW102890 F34059 W19392 AA812656 AI869736 F27755 AA576131 AI143774 AA716385 AA703096 AA919120 F25391 AA230068 AI356218 AW071769 AA278832 F35953 AI888651 AI493729 AI708640 AI193656 AA687825 AI199196 AI749445 AA699849 AA716240 AW167928 AA862560 AA748006 AI707874 AA644456 AA514577 AA229712 AA702859 AI079192 AI735121 AA860999 AI298063 W73957 AI249062 AA877339 AI344393 AW081418 AI125659 AI253692 AI342137 AA938586 AA996273 AI354251 AI027525 AI000888 AI571807 R98880 AA046297 F30432 AI431253 AA989596 F32819 AA890187 AA723172 BE222820 AW026363 AI358909 AI368760 AI373198 AA424340 AI096897 AA044635 AA992388 F24564 W47548 AA134704 AI001866 AI078849 AW136163 F33003 AW243990 F29682 AA863194 W76357 AI096896 AI833043 AW401684 AA877917 H68905 AI242903 AA936162 AI879810 AA641218 F33251 F21727 AI749228 AA565968 AW328278 T39147 AA723149 AI709266 AI215053 AA953153 AW328279 F36005 F20893 AI126684 AI129650 AI266132 AA369791 BE292945 AA865249 AW204654 AI126335 AA961439 AI144014 AI266463 AA722464 AA007430 AI339922 AI302037 AA126313 AI582281 H68804 AA278267 AI253670 AA046032 AI707513 F20312 AW263859 AA029374 AA742842 W72388 F20313 AI707661 AI581659 AI582684 AA626130 AA648242 AA648339 AA648336 AA725774 AI718756 AA534435 AW841857 F34887 F32906 AA353786 AI719543 AI886600 AI648456 AW887101 BE172996 F24926 N62575 AA283350 NM__006476 AF092124 BE086662 F18594 AW816300 N84990 N85147 AA558336 AA303561 AA380197 AA369267 H42116 R53377 T68016 AA354932 AA036980 F33850 AW374019 AI263680 AA029373 Z21418 Z21417 BE567973 |
| 108732 | 20618_1 | AA258888 AA320012 AW976088 AW971357 AW175623 AW175760 AW175769 AW578267 AW162589 N27262 AW160986 AI138629 AA035553 W94453 W94335 AA326606 AF070655 AA040163 AW939331 AA307814 F26425 AW992386 N90194 AA040625 AA150547 W69159 BE138584 AA341766 AI148038 BE566222 W38579 N77160 AI298471 AI343730 AA345321 W39695 W69285 AA010132 W92598 AA046361 W05009 AA318988 F25225 AA150856 N70368 AA044697 AA046123 N80350 AA035042 AA385776 AA188329 H75363 AW966638 AW577569 W79260 F25637 AW406233 H23856 D52811 AA352610 AI143578 BE379846 AW793049 AI343875 AW610545 AA359285 W94758 W47488 H12428 AA358855 AI369400 BE395297 AA525068 AA302040 AI242419 AA149321 AA424437 AA524660 BE253984 AI905952 AA007429 N39993 F31088 BE394339 W45050 AA149322 AA513324 AA314633 AA824412 W51797 AA341568 AA010131 AA694376 AW102890 F34059 W19392 AA812656 AI869736 F27755 AA576131 AI143774 AA716385 AA703096 AA919120 F25391 AA230068 AI356218 AW071769 AA278832 F35953 AI888651 AI493729 AI708640 AI193656 AA687825 AI199196 AI749445 AA699849 AA716240 AW167928 AA862560 AA748006 AI707874 AA644456 AA514577 AA229712 AA702859 AI079192 AI735121 AA860999 AI298063 W73957 AI249062 AA877339 AI344393 AW081418 AI125659 AI253692 AI342137 AA938586 AA996273 AI354251 AI027525 AI000888 AI571807 R98880 AA046297 F30432 AI431253 AA989596 F32819 AA890187 AA723172 BE222820 AW026363 AI358909 AI368760 AI373198 AA424340 AI096897 AA044635 AA992388 F24564 W47548 AA134704 AI001866 AI078849 AW136163 F33003 AW243990 F29682 AA863194 W76357 AI096896 AI833043 AW401684 AA877917 H68905 AI242903 AA936162 AI879810 AA641218 F33251 F21727 AI749228 AA565968 AW328278 T39147 AA723149 AI709266 AI215053 AA953153 AW328279 F36005 F20893 AI126684 AI129650 AI266132 AA369791 BE292945 AA865249 AW204654 AI126335 AA961439 AI144014 AI266463 AA722464 AA007430 AI339922 AI302037 AA126313 AI582281 H68804 AA278267 AI253670 AA046032 AI707513 F20312 AW263859 AA029374 AA742842 W72388 F20313 AI707661 AI581659 AI582684 AA626130 AA648242 AA648339 AA648336 AA725774 AI718756 AA534435 AW841852 F34887 F32906 AA353786 AI719543 AI886600 AI648456 AW887101 BE172996 F24926 N62575 AA283350 NM__006476 AF092124 BE086662 F18594 AW816300 N84990 N85147 AA558336 AA303561 AA380197 AA369267 H42116 R53377 T68016 AA354932 AA036980 F33850 AW374019 AI263680 AA029373 Z21418 Z21417 BE567973 |
| 102123 | 2230_1 | NM__001809 U82609 U14518 AA400455 AA400481 AI078130 AW973342 AW973351 AI291498 AW973353 AW450679 AI347158 AA527676 AI742233 AW475007 AI221904 AA744802 AA742587 AA605065 AA743630 AA749306 AW305274 AA732441 AW291486 AA743685 AI369629 AW235457 AW594214 AW235145 AW665731 AI911470 AW087730 AA811305 AA768622 AA765731 Z21539 AL042012 |
| 102146 | 15479_2 | AW162057 AW161389 AW973293 AA984706 AA573763 AA774763 U16799 |
| 101505 | 14092_1 | AA307680 AA308686 BE252938 BE162177 AA252561 AW577933 AW750513 AA326527 BE281625 R15975 BE562378 AA315193 R14052 AW875781 AA180011 AW875831 AL134981 AA446427 AA652124 AA662020 AA649534 AA649822 AA652118 AA307419 AW377280 |

TABLE 1B-continued

| Pkey | CAT Number | Accessions |
|---|---|---|
| | | AW377293 AA773574 AW377338 AA362376 AA195483 AI870173 AI090858 W05296 AW383640 AA024647 AA599163 AA630601 AA205487 AA164747 AA164748 AA181056 AI828823 AW574914 AA599212 AI499069 AA581816 AI435156 AI568188 AW673033 AI004571 AI263712 AA894927 BE087002 AA948141 AA446119 AA812415 AA514946 AA456625 AA205318 AA442877 AA435521 AA426166 AI911813 AA243054 BE208046 AA830424 AI090292 AI240388 AA626750 AA424926 AA768432 AI935046 AI433060 AA158206 AI342258 AA989506 AI082283 AI865398 AA024693 AI445024 AA527990 AI363735 BE328333 N75485 AA626448 AA947203 AI028221 AI934643 AW392206 AW392054 AI042562 AI341665 AA159366 AA134971 AI270387 AA315014 AA223574 AA157555 AI085919 T28878 AW518353 AI672839 AA053461 AA654257 AA921347 AA152329 AA362375 AA219493 AI510831 AW470571 AA350306 R15974 AA608732 AI569355 AI719108 AI630717 AA040890 AI932667 W95113 AA954366 C21408 AI632334 AK000379 L35946 AC005326 AW377352 M15798 BE294141 BE271424 R05864 AW383658 AI025236 AA190772 AA300684 R37150 AW951773 BE270119 NM__001673 M27396 L35946 AW247784 AA315660 AA776680 AA314621 AA053213 AA206750 AA205575 AA333552 AA313490 AA243053 AA207213 AU076641 BE019563 AA307677 BE295104 BE295904 AW392327 AA347324 AA152328 AW675263 AA316929 AA307925 AA186979 AA223615 AA307366 AA362586 AA325720 AA219455 AA308175 AA312108 AA376260 AA307046 AI305172 H55311 BE396595 AW950145 BE257066 |
| 131614 | 9180__1 | AB002438 W00433 H12256 R98158 R77102 AA701334 AA701322 R77103 H12257 N72166 R96852 |
| 101536 | 15222__2 | NM__006002 M30496 T29834 N39937 AA316513 AW950176 |
| 131626 | 45414__1 | BE514605 L08436 AI590478 AI312161 AA654215 R55780 BE281613 AI685185 AI027150 AA829230 AI114556 AA872520 AA927788 H02295 R72038 AI311545 AI924584 BE047433 H55754 AW003389 AI922762 AW002156 AA130191 AI128123 AI042068 AI338776 BE394356 AA846236 R42169 AI816544 AA994590 AI023058 AI075372 AW087739 R78530 AW102969 AA872289 AI087159 BE301809 AI587297 AA492554 AW166031 AI283667 AI609795 AI910418 AI367128 AA659148 AA846550 AA146654 AI005022 AI022490 AI085748 BE041311 AA583055 W32214 R05414 AI274348 AI804560 AW024171 AI954076 AI609308 AI038717 AI520768 AW086501 AW024951 AA740507 AI308766 AI333344 AI991833 BE349343 AI804381 AA835043 AI474317 AI310152 AI089576 D19773 AA875857 AI273726 AI274371 AW044248 AI346191 AI016732 AW515815 AW073229 BE301483 AI273293 AI806960 AI382928 BE349588 AW009515 AI476401 AI749191 AI433760 AI718031 AI383416 AA457101 AA680157 AI350706 AI041590 AA952924 AA352572 AI936952 AA862850 AW075244 AI885062 AI301054 W52208 AW236307 AW468453 AI498863 AA927789 N25992 AA947953 AI870803 AW337742 AI264659 L54057 AI597636 N67507 AA353706 AA847447 AW467332 AA918829 AA885137 AI052365 AW950885 AI740846 AA876094 AA194848 AI339043 AA587105 AA894456 BE280647 N51772 AI928529 AI369654 BE243797 AA236259 AI367832 D54289 AI351035 W60955 AA677365 D54292 AW102698 X84716 BE378438 AI349252 AA377496 AA687983 AA236325 AA130282 AA644610 R05413 R72037 AA773844 AA384690 BE279234 AI376139 AA320222 H26943 AA310001 N72735 H02401 H04612 W03480 N36624 T99870 AA424379 R63136 R78490 AW953414 AA376297 AA193310 AW162855 R18233 R55860 T06599 AI003388 AA352503 W32178 AW406614 BE390385 H55845 AW402323 H05360 BE017962 AW291479 AW402622 BE222252 AA353015 AA613135 BE272625 AI816581 AW177750 AW610181 BE410975 BE273573 AA310442 AA143648 R36838 BE336641 AW403965 BE273136 BE390037 AW844934 AI815590 AW405666 AW239114 AW403311 AW402504 BE140599 |
| 101568 | 13504__1 | M81740 NM__002539 X16277 AW328091 AW410397 AV661376 X55362 BE280466 AU076625 BE294443 BE275912 BE263069 BE298146 D28365 AA083969 D56186 AW409782 AW411215 AA329920 AA263021 BE545044 AW948849 AA134430 AA344435 BE407381 BE408932 BE275325 BE409376 BE276228 AI630109 AA352473 D16972 BE266384 BE546467 BE265953 AL041032 AW674950 BE535919 W40557 AA100024 M20372 W40555 AA227011 AA069681 BE559766 BE172822 BE513306 AA085082 AA112665 BE312878 W38689 W07253 AA055687 N85193 BE386316 BE385366 BE384800 AA054667 BE174466 AA182548 BE265553 BE536375 AA329653 AA306812 AA358220 AA338825 AA632690 T90242 AA263176 AI940109 AA299212 AI940112 AA384761 AW405415 AA079789 AI800720 AA136478 AI870516 T79067 AA670138 AI554441 AI559974 AI609383 AW374308 AI354984 AW081618 AA378252 AI200963 AI355847 BE619751 AI884700 AI860536 AI690567 AI924507 AW193963 AW190138 AW999868 AW080817 AW173652 AW439627 AI671643 AI815168 AW468211 AW194664 AI523666 AA306634 AW474229 AA626604 AA630695 AA628750 AW411216 AA729034 AW081271 N93223 BE302222 AW273126 AI762486 AA666010 AI590145 AA588505 AW337835 AW674238 AA461467 AI457245 AA583096 AW675526 BE301409 AA973275 AA516446 AI476314 AI186122 AA612645 BE393260 AI128342 AW675583 AI367650 AA887837 AW009877 AW469012 AA629564 D19880 AI582401 AW575382 AW473901 AW474902 AW089774 AA758334 AI150181 AA768796 AW328092 AW304994 AI201801 AA418796 AI160818 AI147630 AA808372 AW008046 W96304 AI364925 AA665857 AW651624 AW410398 AI168015 AA190876 AA226901 AI217443 AW845131 T90687 AA418741 W42773 AI097159 AI084902 AA235099 W42771 AI277727 D53990 D53195 AA134431 AA112666 AA055467 AI049585 AA099209 AI341729 AI492613 AI061312 AI275005 AW263957 AW006655 AA182616 AA079676 AI183509 W96211 AA086389 AI492863 AW439176 AW173464 AI866892 AA088904 AI368922 N78824 AW193163 T78592 AA055555 AA056273 AA083863 AW410391 AA748823 AI472504 AA412729 AA199595 AW078992 AI866784 AA761535 AW089525 BE140308 AI871389 AI591373 AI718948 AI678334 BE140333 AW806704 BW140339 AA308250 AW950168 AW951719 AI926362 AI885977 T16465 AA740422 AA190845 M16650 BE537237 AA361589 AA315239 BE280907 |

TABLE 1B-continued

| Pkey | CAT Number | Accessions |
|---|---|---|
| | | M33764 M31061 M34158 AW402669 AA460115 AA393056 AA099223 BE173285 AW672851 BE619200 BE382867 AW090831 BE018648 AA533486 AA234818 BE514966 T28236 BE265879 AI273645 BE538586 AI214413 BE542051 AA112869 AA947504 AI276424 AI224401 AW088139 BE262559 BE260861 AA622899 N99955 AW088872 AA307760 |
| 101597 | 1021_1 | AA317089 AA442916 BE018728 R17428 R19922 AA160553 AA164830 H25179 N27678 AA351858 T81276 BE384178 F07423 H85309 AA323562 AA180532 AA180375 H28912 BE254427 R18376 T39966 N31431 F12315 N42439 R13760 AA322782 T17003 AU077087 AW249111 R20863 BE560331 BE280947 T80253 AF052153 F06191 R22683 W86744 NM_002079 M37400 W19305 F12496 AA013284 H22855 T74293 AA223443 W00525 R37531 R25024 AF080467 T19744 R58244 AW409579 AA316170 W44675 H80995 AA316031 W87620 H69824 R18966 R60283 N25020 BE541059 AA307315 R70424 BE206512 R52217 AA339023 R10469 R21094 W31877 W49532 AL134314 AA216031 AA376793 F07621 AW206876 AA135283 F06385 N35354 R16629 AI183934 AA903488 AA284445 N99020 AW410742 AI051965 AA525446 AI056291 AA093408 AW055354 BE541793 AA354750 AA852327 AI040660 BE465585 AA576665 AI248233 AW409837 AW248679 N43896 AI038470 AI004439 AI032035 T15765 BE207923 N91602 AA977665 AI524378 AI143696 AI188531 W87691 N25319 AI243901 AI128726 AI040603 AI040576 AI017003 AA976343 AA587603 AA847257 W87835 AA384689 AA877691 R69443 R60789 AA694380 AI057253 AA255671 AA708176 AA203326 AA203175 AA894963 AI934171 AI052604 H28913 AA453394 T39932 AI026794 AI026795 AA602988 AA704689 R10146 N72237 R38887 AA860444 R09569 N26262 R42579 R16570 AA197075 AA502302 W16861 AA677782 AA196998 W87538 AA341005 W44676 F19219 AA194447 R00509 BE159108 W87692 AA954367 R38605 AI336258 R38726 BE179060 AA729458 AA281308 F03654 F02469 R43389 R10371 N35140 AW135113 AW024385 AA857158 F09940 AI553889 AA311889 AI301685 AW051541 AA135146 AI978868 AW410743 AI811331 AA580894 AI857472 AA449100 AI675166 M78228 F36094 AA873314 F31295 AA203470 BE302295 BE328314 AW512864 AI021916 AA916405 AA223949 AI267965 AA807520 AI222735 F03867 N20841 AI094050 AA872351 AI094049 W87756 AA626786 AI365638 AI280192 AI149419 AA890014 W49533 H82126 H82138 H85381 AW978689 R42042 AA825540 AA808185 AA621319 AI276814 AW675475 N33466 AA844406 AI338233 AA804279 AI140172 R08039 AI371372 AW779420 AA973959 AI350202 AI311858 AA844068 AW051465 R58917 AA262562 AA255513 AA179827 R43808 R43783 AA179748 AA160554 T85488 AA223203 N70089 R52121 R43981 AI350079 H24363 AA844320 H80996 H72681 AA281259 AA863323 AA746986 R42662 T85278 AA194301 AI770137 F10117 T89022 F02675 AA194370 AA287013 N69852 T40917 N48265 R36686 H06305 T29294 R46268 H69825 R45142 AA166673 AA910318 R06282 AA203747 AA194455 R08090 R09678 F01096 R00610 R06340 AV651346 AV651308 AA089496 R57012 BE276300 H22856 AW751492 AW751491 T66408 |
| 100999 | 16380_1 | H38765 AA020909 AU076761 AA055872 M81600 D17043 AA070398 N34699 N40348 N31183 AA353394 AA308285 BE293092 AA295231 AA295488 AA314063 BE018838 AA306417 BE385738 AW239325 W52613 BE276244 AA315325 AA316906 BE277221 AA149601 BE276572 AW067924 NM_000903 J03934 AA302015 N35427 AA036745 AA340817 H84385 N47385 BE074524 H96427 AI952067 AW080961 AW362914 AA132625 AW753879 AW362910 AI084728 AA062713 AW373980 AI806855 AA983938 BE220697 AI620265 BE222822 AW087852 AA534386 AW814921 AA577494 BE293548 BE249850 AI346644 AA635970 AI382151 AI073632 AA857008 AA577392 AI539673 AA581987 AI566246 AA683214 BE081776 AI000994 BE081784 AI074406 N24033 AA588838 AI948709 AA053732 AW068386 AI167981 AA132315 AA365371 N27417 AA774708 N27531 AI346769 AI347233 AI380032 N46995 AI356134 AA057318 AA032219 AA302117 AA301949 W58021 W58020 AA032277 AA582804 AI922277 AW797527 AA456436 N47386 AA134055 AW605681 AW613060 AW610575 AA055612 AW605682 AW605678 AW605679 AW605677 N22709 AA494458 AA631158 AI914846 H84386 BE302400 AW579311 AW579376 AI864110 AW377480 AA516430 AW364730 AW176734 D11877 D11593 D11902 D17214 D11882 H39746 BE568335 H26468 AA314338 BE616916 AA037141 BE620011 AI354561 AA921756 AI814684 AA455538 AA020839 AI471351 AA599499 C05934 AW088447 AW769030 AI659018 AW275300 AW769082 AA458634 AI139093 AW069583 W30763 AI768524 AI083754 W47665 T29569 AW951450 H26309 AI753000 AA070399 AI589457 AW002739 AW769553 AA053548 H46590 AW449900 N99238 AI359496 AW073823 H38680 H53637 AI470579 AW084444 AW449866 AI963530 AA852313 AI039874 BE275283 BE293743 BE564450 AA894813 H25860 AA581530 H96428 AI359031 BE180716 D11495 D12071 BE566000 AW578811 AA857177 AW605673 H95750 R84795 AA295677 AW651685 AA295266 H95751 AA890528 |
| 108818 | 12535_4 | BE612676 BE388276 AI208592 AI927836 AI434086 BE326593 AI597850 AI631538 AI909963 AW609934 AW818899 AI401754 AI739099 AW800995 F31428 BE613282 BE620259 BE139475 BE620798 BE276918 BE276248 AW081215 AA578055 AI685446 BE390326 AI492209 AI499296 AI696727 AA130984 AW136812 AW117918 AI830323 AA983429 AW170783 AA383935 AW206593 AI468402 AW609931 AW818896 AW393030 AI869005 AI766518 F22059 D80091 AW379617 AI638546 AW474465 AA876495 F35620 AW369856 AI337412 BE503448 AI909962 |
| 108846 | 10505_1 | AL117452 AW408005 BE299916 AA135286 BE547298 BE279301 W52878 AA302211 AW957996 AW514270 AI685200 AA928779 AA576884 AA576883 AI218215 AW263592 AA424504 AW082223 AI809292 AI355487 AI265774 AW152614 AA707564 AA933972 N30148 AA927905 AW070728 AI431416 AW606716 AA132983 AA135149 W60086 AA127446 AA247723 AI225124 AI085684 AI630792 BE326510 W40249 W53030 H69149 H80062 AW058274 AI240522 AA595935 AA973544 AA969535 AW298530 AW135145 AI860607 AI334249 AI498814 AI202133 AI346697 AI831564 AA479938 AA992515 AI691071 H80663 N34165 AA455332 N39978 T52099 N88572 AA127445 H68849 AA533580 AW572308 |

TABLE 1B-continued

| Pkey | CAT Number | Accessions |
|---|---|---|
| 108857 | 61_1 | AK001468 AA190315 AA374980 AW961179 AA307782 AA315295 AA347194 AW953073 AW368190 AW368192 AA280772 AA251247 N85676 AI215522 AI216389 N87835 R12261 R57094 AI660045 AA347193 R16712 AW119006 N55905 N87786 AW900167 AI341261 AI818674 D20285 AI475165 AA300756 R40626 AI122827 AA133250 AI952488 AA970372 AA889845 AW069517 AI524385 AA190314 AI673359 AA971105 AI351088 AI872789 AI919056 AI611216 AK001472 BE568761 AA581004 |
| 108880 | 140977_1 | AA766605 AW294190 AA830866 AI954864 AI222410 AI630798 AI633475 AI566491 AA904966 AI223049 AI287382 N50693 BE502927 AW612896 AI252790 AA983811 AI142885 AI268570 AI690020 BE218607 AI870455 AI357770 AA664843 AI185726 AA134576 AW969574 AI301714 AW176717 AW605243 N50776 AA347749 |
| 108886 | 18639_1 | AW248434 AI129487 AW377155 H24275 Z42507 R19016 T08307 T08036 AW953119 AA349548 AA393404 AA236624 AL137347 BE274435 AI702126 AI692761 AA360502 R35012 AA478914 AA358981 AA358985 BE080561 AA055316 AA135291 AA195427 H71951 W03891 AA195210 AW021065 D78699 W95359 AW182965 H22883 AI870307 AI091427 AA478795 AI802072 AA595319 AA947028 AW090367 AA553712 AI336846 AI431686 AA055317 AA135153 AW090348 AI128708 AA237000 AI082120 AW084091 AI339737 AI355101 AI207962 AA708821 AA770603 AA400872 R49399 AI468537 AI735393 AW075343 R44087 AI805398 AI805582 W95360 AW138641 R40312 AA349547 AA788856 AW151109 AI950158 AI694090 N73720 AW995868 AW995801 BE062153 AL041833 AW862418 AW860294 AW860326 AI276718 AW860253 |
| 102212 | 13378_1 | AW411491 BE299348 AW410636 AW411154 AU076490 AW250287 AW411276 AW250611 AW410456 F12758 AW410459 AW410935 BE622198 BE296223 BE266577 BE297764 AA348084 BE296893 BE270394 BE295191 AW411540 T74720 BE297059 AW411486 BE313720 BE263585 BE266491 BE266415 AA356005 AW246316 BE261174 BE296531 AW248301 BE276614 BE295617 BE392105 AA323383 BE296852 BE267620 BE250281 BE296845 BE262427 AA328132 AW410323 BE298824 AW410237 BE297295 BE294633 BE270112 BE279883 BE019252 BE259626 BE299152 BE255582 BE297961 BE296383 BE293980 AW410723 BE019150 BE019068 BE545633 BE019208 BE019193 NM_005412 U23143 BE019174 H96758 L11932 BE294128 H39749 AW411386 H96748 AA131652 BE398084 W19483 AA747352 AA377688 BE560803 AA410805 R34798 AA323741 AA316917 BE396043 AA131143 AW410724 AL135023 BE294085 BE018423 AA361530 BE250748 BE299994 AA313516 AI653986 AA321590 AI591086 BE299410 T77128 AI951452 AI638143 AI609108 AA369495 AW411251 AW386906 AW082929 R95063 BE297935 BE019318 AW411277 AI691054 AI700140 AW474021 AI887587 BE439939 AI950991 AI625764 AW410822 AA911634 AW411541 AW411176 AW410899 AW411490 AW249463 AI817987 AI597735 AW273145 AI632983 AW249523 AA131090 BE302032 AI569538 AA576614 AA633317 AA165578 AA743215 AI560282 AA586625 AW411487 AW411013 AA328880 W44660 T29731 AI285121 AA640605 AW304985 AI566847 AI247281 AI338283 AA643283 BE208030 AI653600 AI554740 AA564212 BE205955 BE206135 AI090753 AW069245 N70336 AA636134 AW410238 AA100409 AI340965 AW410324 BE205997 AA742919 AI341964 N25590 BE206292 AI313459 AA629927 AI014771 AW411387 W73771 AA989313 AA252291 AA812321 W73762 AI126885 AI308864 AW410389 AI350355 AW410460 AA728778 AI318431 AA179613 AA219137 AA643582 AW246735 N90299 AW411162 AW411155 AW410517 AW410637 AI268503 AW411492 T76964 AA086186 AA836520 AA912198 AI302489 AW473107 AI865572 BE244857 AA948010 AA888873 AI564941 AW264652 H22828 AA620477 BE205995 BE267512 AI583139 F10366 W44661 AA888553 AI915153 AW075505 AA810043 AA864537 T15483 AA693453 AI313297 AA131470 AA716519 AA630033 AW296682 AA235484 D11830 BE300090 BE299540 AI421521 BE544882 BE297760 BE250390 BE265381 BE300122 AW250477 BE297420 BE264012 AW410898 BE296797 BE300201 BE297914 BE297671 AA243309 AA171436 AA233215 BE294777 BE294766 BE294251 BE300300 BE252525 BE293999 BE296989 BE297380 BE269794 BE269795 BE298565 AA911054 AW950430 AI557895 T82107 N34189 BE251249 BE294902 AA219520 N87314 BE560258 AA102177 BE561197 AW410725 BE295263 BE295043 BE543993 BE297237 BE294403 BE296639 BE297441 AW410516 AW247727 BE300725 AA179614 BE264672 BE297253 BE390715 BE299154 BE297349 BE295105 BE297999 BE298714 BE296553 AW904545 |
| 132349 | 28499_1 | AW975654 AA652500 AW973307 AI990990 AA918966 AA918970 AA612829 AW582941 AW584007 NM_003122 Y00705 AA983320 AI660251 AW471481 AA845156 AW005713 AA551894 AA844948 AA586834 AA835291 AA627501 AI302919 AA845077 AA921372 AA569123 AA974970 M20530 AI362622 AI310323 AI459618 AA919095 AA844953 AI362470 AA835382 AA740207 |
| 101600 | 21981_2 | BE561617 W27399 AA405963 AA436100 BE393718 AA317393 C19033 C17096 AA365285 AA308297 AW410777 L10138 AA523678 AW328205 AA865267 R55897 W45653 N36027 AI065053 W44608 W44342 W91902 AA136178 AA379874 H38877 AA374479 AA151469 AA305168 C17593 AA305120 D55441 C17625 AA314253 AA211199 AA314589 AA310648 AW328687 AA021359 AA182541 BE565927 BE268825 AA706725 AA158325 AA187406 AI309641 AW006665 AI041213 AW327826 BE073571 AI610917 AW406432 AW600318 AI668800 AI721195 AI440063 BE001611 AI336194 AI089764 AI085958 AA131285 AA164402 AW390484 AI300922 AI031950 AW195168 AA770689 AA300595 AW381349 AW371114 AW381018 AW371113 AW381317 AI857890 AA416820 AL047728 BE620627 AA040552 BE092079 AW474092 BE091920 W73650 BE270992 BE091972 F00585 AL047691 AI038820 AI589872 AW575423 AA416821 AW305222 AA338205 AW575434 AW575384 AA337984 AA337985 AI860434 AW574672 AW410778 AA375029 W45695 BE122782 AI630207 AI630558 AI630580 AA706031 R34806 AA771891 AA771792 AW088662 AA356678 AA379466 AA860623 AI784534 AA356692 AA040298 AA131195 W44569 W37400 AA933570 W58189 AI285471 AA771813 AA774514 AA716769 AI708762 W92042 AA417367 AW371361 AI128895 H02931 AA908594 |

TABLE 1B-continued

| Pkey | CAT Number | Accessions |
| --- | --- | --- |
| | | AA187289 AA643781 AI640830 AW473936 AA436001 AI475021 AI970665 AI057237 AA012954 AI150835 W52421 W57603 AA676596 AI139232 AA579097 AI432689 AA843759 AA573999 AI128740 AA570257 AI131072 AI148346 AA164422 C06015 AI074131 AI032583 AI336298 AA605270 AA782769 W47631 AA021226 AI281342 H04234 AI298277 AW615022 W46975 AI000575 AA040580 AI869185 AW250999 AI174223 AI124799 W60614 AI085737 W45512 N94519 W15579 AA013460 AI300867 W90451 AA021556 AW103801 AW328713 AI168071 AW008381 AI042239 AA158033 AA055893 AA156144 AA182609 AA844304 AA327236 AA676346 AA047883 AI672112 AA383408 AA988468 AI050059 AA939196 AI026759 AI752597 F24182 AA574305 W52183 AA151470 N22910 AI000226 AI926339 H38841 AI289780 BE618650 AI810980 AW801870 AI864364 BE618390 D58020 AW769502 AI272962 AW072096 W15234 AA599174 AA923648 AW842580 AW518382 AA082252 AW074744 BE221061 AW089096 R34699 AA099128 AA033803 AI357526 AI630140 AI123231 AA709402 AA353679 AI864972 AA736798 AW575868 AA661683 F00085 AW023644 AA331174 AA664665 AA369337 AA312279 AA136296 N80820 AL036660 T28180 D56720 AI866433 AA353580 N70710 AW474141 N64463 W58466 M37583 NM__002106 X52317 W23968 R84345 BE296086 BE294435 BE268132 BE391173 BE268771 BE513509 BE263242 BE276783 D19628 AW965243 W90258 AW962703 BE407481 AW406844 BE253043 BE073635 W15620 W47076 W78044 BE259558 BE565194 R00158 AI434559 BE567338 N31298 BE409711 AI752598 AA100988 AA582094 AA902336 BE568220 AA167302 AA018050 AA915972 AA609370 AI184035 AA405697 AI208311 AI536822 AI583135 AI025630 R55812 R85507 AA987581 AA405807 AA082502 T40385 N88454 AA643754 AA093458 R85775 C14737 N24736 W31655 W47630 AA927763 BE268452 W73715 AI984453 H51401 BE537021 |
| 102260 | 25666__1 | AL039104 U28386 NM__002266 U09559 AW402355 AA101448 AW673645 AA333467 AA313053 AA361874 AA313055 AA190353 BE266583 AA315284 AA353614 BE384490 BE386729 AA308968 BE003166 AA090577 N87880 AA301121 BE266042 BE408627 AI142361 BE314868 BE385848 BE273720 BE256168 BE386632 BE410675 BE263522 BE294938 BE267422 AW401794 BE548850 BE565744 AA621902 BE260946 BE251616 AA382536 BE311520 AA314057 AW951825 AA306201 BE254429 BE272238 W56840 BE274165 AW813940 AW378582 AW579664 BE274592 BE409321 AA356118 BE275450 AL044404 AA304717 BE312106 BE019375 AW672848 AA329890 AW579677 AW391679 BE084545 AW403233 AA258536 BE167601 AA361542 R15797 R57897 AI110703 AF063578 AW366787 BE395500 AW327848 AA165009 BE085762 BE336673 BE252444 N47847 W25263 R13400 AL121272 AA095442 AW389843 W60329 N84275 BE082474 T67170 BE392974 AA179780 AA209417 BE281033 AW577789 AA489151 AA091107 AA180441 AA367320 BE407196 AA303762 U46229 AW366470 AW391006 AW391047 AW814482 AW391203 AW582144 AW391056 AW391057 AW379254 AW391139 AW391061 AW379196 AW391066 AW379259 AW390978 AW379268 AW379245 AW379178 AW379198 BE148520 AW390942 AW609241 AW390964 AW390948 AW379243 AW609411 AW379142 AW582168 AW391226 AW379162 AW390949 AW390935 AW379155 AW379236 AW379267 AW379186 AW379277 AW379272 AW379184 AW390924 AW582175 AW391223 AW814488 AW609523 AW379199 AW390914 AW379238 AW379203 AW609716 AW391036 AW582165 AW609473 AW379242 AW609492 AW379228 AW391138 AW605882 AW391103 AW609393 AW391037 AW379271 AW379264 AW379143 AW609410 AW379225 AW609378 AW391122 AW391117 AW391054 AW379273 AW609498 AW390967 AW609380 AW390550 AW609452 AW379276 AW609418 AW379266 AW391143 AW390972 AW609482 AW391012 BE080881 AW391136 AW390984 AW582194 AW609703 AW390959 AW582204 AW390961 AW379232 AW379280 AW379163 AW390987 AW391086 AW582201 AW391035 AW390973 AW609715 AW609713 AI205023 AI804287 AA082457 AW391104 AA353581 AI750699 AI862061 AW391083 AA156974 AI026810 AW380019 AW995531 AI200392 AL044405 AW380010 AW602187 AI287654 BE618491 BE464616 AI440158 AI590856 AA779171 AI089353 AW575085 AA707112 AA847455 AW374009 AI276964 AI147354 AW995425 AI718273 AI951157 BE250641 AI023440 AI417555 AW131393 AI280696 AW391183 AA219739 AW391031 W86618 BE081171 AW007734 AA827997 AW176999 AW058184 AA150508 AI590988 AW615610 AA599903 BE301202 AA588337 AI922935 AW731637 BE622785 AI805733 AW675524 AA913189 AW889950 AA641297 AA993290 AI768929 AW379177 AA621830 AI039755 AA489087 AA744568 AA262632 AI873618 BE302060 AA974509 AA568289 AA062970 AW466367 AA913652 BE464656 AA677610 AA180187 AA582440 AA773895 AW795558 AW795767 AW795582 AW795758 AW795632 AI082013 AW249635 AW795753 AI369704 AI826323 AW795689 AA725266 BE080398 AI873994 AA773175 AW993051 AA258327 AA676460 BE080389 AA157068 AI637594 T67169 AA171491 N99904 AW270777 AA757097 AW768764 AA678785 AA126274 AA761881 AA100373 BE207796 AA196448 AA879043 AI754935 D61373 AW072016 AI934178 AW795572 BE439707 AA852239 AW071728 BE205906 AA503664 AA809927 AA180497 AW151358 C21410 R40914 AI940044 AI940046 BE301963 AA640554 AA179767 N32627 AI933456 BE618891 AW390999 BE281046 AW080974 BE622561 AW390970 AW747913 AA365925 BE386502 BE280446 AA187010 AW245180 AU076841 AA379115 AA311979 AA312425 BE018449 AA227391 AA354713 AA134708 AA310314 AA312764 AW402502 AA171862 AW370218 AW378568 AW579674 BE147599 AW391678 N85488 AW403419 AW370229 BE147600 AW579675 BE560488 BE410797 BE263374 AW750357 BE259476 AA156712 R81373 N46428 AW272974 BE279068 AA448770 AA448674 AW513191 BE254526 W86691 N83371 AA304369 R25161 AA207259 AW391008 AW391096 AW512043 AA779610 BE009692 AW609486 AW609711 AW582164 AW391222 |
| 102276 | 5905__1 | N48373 NM__001627 L38608 Y10183 AA262217 AW753075 N38736 AA262218 AA464900 AA464626 AI692580 R13558 AA214664 AW601683 H09189 AI752497 AA160065 AV653517 AW968888 AV660191 AA482188 T68513 R30733 N46489 W33058 AA336413 AW961079 N26375 AW993589 AA280339 F06946 R20701 R25706 BE067521 AI239631 AA837433 AI220324 AI473782 AA127889 AW968882 AI445486 AI754377 |

TABLE 1B-continued

| Pkey | CAT Number | Accessions |
|---|---|---|
| | | BE465326 BE503131 AI670792 AI685623 R41236 BE348349 AI439167 AW469600 AW172580 R39662 AW130015 AI040222 AA609793 AI753801 R88603 AI288562 BE043005 AI693132 AA160883 H09133 AI684835 N57440 W51882 AA482283 AW505289 AI800765 H97982 AI807890 AA156810 AA156842 AA085507 AA085490 BE348821 AI932782 AI093768 AA280417 AA214471 T23573 AI857238 AW612154 AI351946 N35165 T32021 T31992 T32027 T32022 AA894475 AA877033 AA937480 AW952613 AI285827 AA810590 AW513250 W39699 AA304516 T60647 H19723 D58092 AA160066 AA173200 AA029282 D57784 D57901 T68448 AA481804 AL041869 W55951 H16026 N47520 AA256441 N42928 R62450 AA770631 W76153 AI027075 AA855080 AA782515 AA156721 AA825251 W72486 AW189607 T31384 AA156604 AI752498 T57750 AW119056 AI431803 AW172541 Z40035 AI378630 N94406 AA523778 W73809 AI332387 H05980 N72898 AW172777 AI823902 AI753586 AA687259 AA101774 W45054 AA526261 AA719932 AI492249 N29499 AI914417 AI078799 N29839 H99250 AA025656 AW512390 AI357817 AI435550 AW270260 AA912141 AA101149 N29787 U30999 AI167331 AA814355 AA745134 AI288890 AI376398 AI075396 R38497 N38915 AI082099 AI278455 AA837745 AA256316 H20060 AA917752 AA777157 AI042419 AW117209 AA029426 T31882 AA491892 AI050952 AI184339 AI291162 AI218908 AI147696 AW439899 AI628615 AI417598 AA526236 AI186395 AA954458 AW009491 AI038346 AW172807 AW022922 AA641089 AI358995 AA703922 AA887149 AW339840 AA678724 AW001023 AI141359 AI381394 AW242676 AI424129 AW089435 D30976 AI027975 AI623932 AA888478 AI382482 AA722150 W35209 AA211084 H06029 W02984 AA523581 R46168 R14919 |
| 101626 | 327_1 | M57399 S60110 H84344 AA001485 AW160314 AA090747 AI879135 AW163070 X52946 T85031 AI816405 AI990351 AA090718 AA215860 AA318827 N85463 AI970310 D90226 AI611319 R51511 AW239042 AA460816 AA045054 AI797499 AW590267 AA045053 T29639 H14962 H08105 AI338085 AI636574 AW157101 AI934600 S50409 AI870411 AI199056 AW001766 AI870995 AI200327 AI815462 AA548181 AI005058 AI364123 AA919072 AW162280 N67113 AI051749 AA627119 AI335096 AA889349 AA205839 AA033681 AI767032 AI937847 AI078004 AI825162 H95886 AI028531 AA602217 AL047791 AI419608 AI051018 T91979 AW888449 AA460378 AW379087 AW378780 AI498169 AI805998 AI088088 AI816421 AI815480 AI635541 AW890848 AW160689 AW160462 AI309840 AW378784 AW131706 N75113 AW022822 AW023528 AA001449 AI004224 AW172325 AI160842 AI380075 AI421383 H88713 AW020400 AI422571 AI091966 AW162473 AA846221 AI419278 AI023131 N52342 AA865171 AW072281 AA928643 AI089899 AI123052 AI796292 AW594607 AI741286 N22581 H88665 H08106 AA843274 AI095059 AI919377 R38701 R51512 H14963 AA890721 AA694145 N89430 |
| 132371 | 183136_1 | AA235448 AI458836 |
| 125183 | 14653_3 | AV660804 AA443450 BE394892 AA429418 AI627767 BE394466 AA478501 AL040757 AA034998 AW473341 AW513694 AW103084 AI951172 AL047961 AA088693 H45774 AW827402 AA428362 H01264 AI954170 AI952796 AA225832 H54842 AI017845 AI679536 H54790 AI952110 AI811040 AA352888 AA121506 AA775058 AA908290 W79565 W58332 AA369170 AI744346 AI801419 AI679974 C16833 AA302085 F34028 AI581028 AI798480 C17403 AA127731 F30969 W92452 AA524369 AW073505 AA468039 AA029663 N98810 W58653 C17090 AI223420 AA091620 AA281837 AA335382 AA335380 AA468320 AI640803 F27986 F29052 AA358537 AI950504 AI190136 AI299829 D45468 AA652563 W74582 AA352830 AI193967 AA527869 F20639 AI800624 W79320 AA627717 AA780314 N89058 F31541 AA652505 AW007147 F25197 H64484 AA708812 AI190119 T60664 F36608 AI091953 AI873928 AI587546 AW273407 AI298716 T57765 AI873937 AI610470 AI097163 AI758504 AI244943 AI797420 AW080719 AI351837 W79420 AA889163 AI580703 AI734888 AA467981 AA770510 AI767263 AA350264 AA225831 AA027210 AW516219 AA494321 H64485 AI046025 AW021887 AW269490 AI698517 AI446341 BE169898 AI720010 AW015332 AA369169 AI804880 AW810887 AW388603 AW388292 AI915660 AA587843 AA029725 AA482854 AW264537 AW198020 AW189713 AA468785 AI351203 AA513558 AI689574 AA507450 AA443315 T10884 R33194 BE007983 BE393087 AW810727 |
| 131756 | 41960_1 | AA443966 AJ245902 AL040912 AA364287 H22493 AW264204 AA444148 H46442 D45304 H49447 H18781 AF085871 H42458 AW182961 AI141554 AI740681 AW665439 AA095418 AW316877 H18687 H42979 AI209122 H49448 H22458 N22392 N75630 AW103286 H96116 AA909731 AW629469 AI004384 H46985 AI423900 AW020930 D45262 AW023489 |
| 131762 | 37953_1 | AA744902 AI571767 AI097387 AI357779 AW583460 W39645 AW014996 R85139 H39057 AI675368 AI159850 H96718 W05585 N98881 AI038335 AA206790 AA918345 AI536671 H46750 BE350087 AW197014 Z43666 AI080414 AA886382 H98215 AI202597 C15906 C15872 D80812 D60117 D53401 D81322 D52755 H19694 AA688395 C15801 C15411 AA683218 AA991302 AI263272 AW469791 AI570417 AI114878 AF116637 D61286 R84467 H49688 BE077114 H19693 C15829 H23775 AA339499 W31186 H23900 H97800 AI267364 H46831 AW959927 AA206963 H43859 N80428 H45366 H39083 AA425373 AA425465 AA846590 AA046580 D55145 AA621706 T07073 D54657 T08681 M78869 T31825 N75559 W15471 H39034 AW969557 AA844311 N68003 D11866 AA046666 AW028626 AI692215 AA854854 R85088 H89957 AA131299 AA492538 AA989250 F02980 AW162736 AA158136 AI401506 AA890420 AA917393 AI571336 AI869323 AI827967 AI167686 AI198259 AA158135 AA907273 AA775294 AW162846 AW771452 AI697437 AW134528 AW293478 AI636044 AI339786 AW058021 AW241507 AI633980 AW103281 AI972028 AW058445 AI927316 AI656586 AW590352 AI671179 AI814588 AW241452 AW024820 AW090161 AW273560 AW237544 AI678195 |
| 117330 | 631979_1 | AI904095 AI215045 AI381455 N23719 N23687 N23710 |
| 124560 | 349165_1 | AW975028 AA551969 AA644028 AA689303 AI220334 AI220090 AI925486 N66393 |

TABLE 1B-continued

| Pkey | CAT Number | Accessions |
|---|---|---|
| 116732 | 248581_1 | AW152225 AA353067 AW079016 AW957315 AA424160 N67560 AA781689 AA629538 AA993019 AI766528 F13779 AW166069 |
| 116739 | 1555255_1 | H01463 H95156 R27734 |
| 123974 | 3842_1 | NM_015678 AL137748 N50360 AA365753 AW954010 AI004739 AI052524 C14642 D52944 C14716 AA775279 H15123 C14834 H22898 R44646 AW296616 T03409 R60879 AA310824 F05576 AA668246 AI246710 AA460540 AI763071 R23514 AI168314 BE328200 AI611086 AA460541 T16448 T08984 AI016123 AW451887 R60880 AA971942 R43444 AI223180 Z38546 H24284 |
| 116780 | 82675_2 | H22566 R42536 |
| 116787 | 187589_1 | AW362955 H59488 AI040666 W60959 W94209 H27231 T84625 H75715 W04957 W63676 AA659693 AA514302 W63789 BE046412 T91396 AI951970 AW044233 N20018 AW663548 T90114 AI139947 AA809643 AA846232 AA581966 AA789002 AA295134 AW188870 H75644 AA526037 AA347970 AW961788 H61476 AL133779 AA449282 H28581 AA249370 |
| 133011 | 27092_1 | NM_006379 AB000220 AW275325 AA853649 AW370858 AW576685 AW370845 AW370862 AW370871 AW748615 AW370847 AA342516 BE081445 AA160999 AL119033 BE078994 AI677829 AL135601 AI962897 W95581 AF086506 AI090512 N38844 AW665569 W95474 AI261434 AI241943 AI536930 D29236 U46406 AA853650 AW370398 D32000 AA042990 AW779930 AA161000 AW516300 AL049019 AA779575 AW338339 AI376746 AW338302 AA977698 AW439148 AI619675 AI814082 AW338965 AI581420 AI866867 AI491966 AI275950 AI540535 AA043044 |
| 133015 | 32025_1 | AJ002744 NM_017423 AA322639 AW673417 AW892861 AA310529 AI572711 AA234316 AA112368 BE080374 AW390198 AW377342 AW377386 AW377356 AA059259 AW377302 AA354213 AW377234 AW583071 AI274788 AA376671 BE551018 AA742189 AI992302 AW054764 AW958190 AI355592 AI561117 AA112369 AA234559 AI923292 AW166727 N46618 BE551952 AI587445 AI678832 AI219803 AW377357 BE075761 AI954806 AW129606 AW084750 BE350945 AW020868 BE043949 AA047036 AI290095 AI394310 BE222094 AA346068 AW675817 AI610299 AI766343 AI206131 AA583509 BE049548 AI681849 AA082380 AA301870 AW957983 AA729175 AI824563 AW008429 AL043048 AW966718 AA332444 AW955820 BE151834 |
| 133050 | 12035_1 | X73424 S67325 AJ006487 NM_000532 R15273 AA312224 BE409331 AW630604 H15303 AA371184 R25544 AA093267 W69943 M13573 C75158 R09794 AA902221 AA639000 T27895 AW016032 AA553631 AW950067 AA459122 AA687219 AA506483 AI475344 AA507321 BE043326 AI680312 N47467 H93980 AI680311 AA419435 AA680161 W69833 AI758259 R12384 AW079484 AA223335 AI933243 H15697 F02620 AI873805 F02623 AI191766 AI383543 AI371311 BE564628 AI581822 BE544030 BE408707 H93979 |
| 133061 | 21643_1 | AI186431 AF003934 AF008303 AB000584 U88323 NM_004864 AF019770 U51731 AW589216 R69081 R26165 R77742 R22028 R82310 H03389 R70732 H87477 R38210 AA155580 H69893 AA136010 R21843 H97833 N69922 AI219091 H95143 R33078 H04381 R77138 R71115 H01266 AW970396 H95179 R82332 H86990 R67865 H94993 R66880 R65691 H85270 H94785 H04406 R24897 R66222 H01626 R23984 H93657 R63618 H86996 AF173860 R25620 R39649 R32213 R26948 H94511 R32710 BE256717 BE295046 N30261 R68040 R81913 R26208 R26828 R26198 R73833 H03861 R33205 R66917 H01839 H02963 R69181 R66754 R76067 BE048601 R74293 R70088 H86988 R80794 R34594 R82309 H87589 R78765 R28088 H02432 R38209 R70731 R28299 R23459 AA132076 R33339 R22081 H04437 R34593 R66141 R63170 R22591 R39617 R82861 T53513 R32071 R35747 R24624 R33338 R76595 R33166 |
| 133063 | 198877_1 | AI654133 AI761596 AI681308 AW022404 BE348846 D62530 AI472301 AW629492 AI290922 AI341768 AW118080 AI221713 AI367429 AA886741 AA807330 AW517831 AA746008 AA831276 AA283085 AA648947 H43330 AA721403 R36006 AA503266 AW511687 AI382427 AW971014 |
| 102348 | 17139_1 | U37519 NM_000695 AA773379 AA071510 AA482041 AW170354 AA569888 AA513785 AI188718 AA579992 AA513758 AA481860 AA291699 AA292447 AA443630 AA236671 AA782119 AI352065 AI143450 AI905356 AI909809 AI909789 AW749116 W79586 AW602089 AW602100 W76133 U56857 R25587 AA485853 AW363810 R63387 W79785 W72907 R62853 BE181493 AW371642 R26983 AI252548 AI252283 BE183075 BE410093 BE410638 BE383666 BE407478 BE383743 AA625421 |
| 132442 | 328002_1 | AW970859 R63877 R62589 AA492124 |
| 101701 | 2479_1 | NM_002436 BE246620 M64925 AW247421 R53297 R60247 R70726 R71415 AA323460 F05723 AW250262 F07846 H60485 T71695 AA431041 R08255 AA356584 AA356583 AA216070 AW805293 AV649006 AV648937 H78275 H94710 H95309 BE311770 R62567 W01175 W01240 AW902073 H53235 AI183983 R31484 R94394 H63921 N47172 AA707326 AA133183 AI823796 H80573 AI681183 R83081 AW901933 H64892 BE550314 AW901928 AW195830 H79162 N91640 AI492321 N76884 AA579860 AW839893 AA883505 AW580256 H95259 AI261944 W57593 H38156 AI076352 AW130730 AW606824 H46854 AW236778 AI417727 AA947115 BE207902 AI089192 AW249497 N49873 AA701445 AA993839 BE160869 AI311068 AI433427 AW196387 AA676932 N64845 AA918059 AI640269 AW753776 AW243437 AI654157 AI077368 AA863220 AW248512 R50842 R62568 AA704682 R60059 AI383167 AI140552 R60780 AI150683 N74193 R31485 AA129339 T71768 H95076 BE501016 AI266193 AA129298 R52642 H71929 AA342729 AA338561 AI433899 R08204 H63520 N74236 AI910728 H60439 H53129 F02885 C01264 H55275 F02030 H77840 F04101 R83028 T17236 BE465821 AA368927 F01971 BE281487 AA630220 AA133370 AW615218 AI572093 AI095159 AI193682 BE464731 H65484 |
| 101753 | 2533_2 | L11144 BE503279 AI340259 M77140 AA760994 AA702835 AW971036 AA492353 AI337122 AW593515 |

TABLE 1B-continued

| Pkey | CAT Number | Accessions |
|---|---|---|
| 101759 | 29209_2 | M80244 |
| 101763 | 26912_1 | AB001914 NM_002570 M80482 R17185 AA383835 AW373682 AW373655 BE079853 R84474 W03207 AA359657 R11146 H69430 W85806 AI478762 AW007086 AI025051 AA904501 AI432144 AA634457 AA934693 AI823882 H69843 AI084020 AA969521 AI351998 AI306614 W85807 R01224 AW135609 H48238 AA868372 T28225 AV649213 AV647998 AW950431 H69047 T87338 T91020 R11147 N67035 C00583 AA535598 AA553683 AW016396 BE076633 AA339389 AW373697 AW373678 AW373633 AV661368 H48329 AW373726 AA359198 AA359027 AA359821 AI133136 AW845566 AW859122 AW859237 AW859238 AW859108 AA934701 W03352 R01337 H61633 AI342754 AI698097 AI458905 T87439 H57262 AW877269 H55804 BE536899 |
| 101766 | 14653_1 | M80899 AA368768 AA578114 BE182030 AI902286 AI902284 BE281154 AI906505 AW750499 AW604662 AW373288 AW842405 AW842436 AW579777 AL044828 BE272553 AW379988 AL047960 AA088830 AW950909 T28840 R54641 AW382220 BE003314 F00245 BE273339 AL047393 BE158329 T39134 BE007982 BE158322 AA044249 AW748179 BE158266 AW890855 AW630228 BE007980 AI459550 BE392111 AW603898 AI046762 AA665527 BE389329 AW842437 T10885 BE081680 BE007985 AW835201 AA774783 AW993365 AW946377 BE004719 |
| 131859 | 3672_1 | AW960564 AA092457 T55890 D56120 T92525 AI815987 BE182608 BE182595 AW080238 M90657 AA347236 AW961686 AW176446 AA304671 AW583735 T61714 AA316968 AI446615 AA343532 AA083489 AA488005 W52095 W39480 N57402 D82638 W25540 W52847 D82729 D58990 BE619182 AA315188 AA308636 AA112474 W76162 AA088544 H52265 AA301631 H80982 AA113786 BE620997 AW651691 AA343799 BE613669 BE547180 BE546656 F11933 AA376800 AW239185 AA376086 BE544387 BE619041 AA452515 AA001806 AA190873 AA180483 AA159546 F00242 AI940609 AI940602 AI189753 T97663 T66110 AW062896 AW062910 AW062902 AI051622 AI828930 AA102452 AI685095 AI819390 AA557597 AA383220 AI804422 AI633575 AW338147 AW603423 AW606800 AW750567 AW510672 AI250777 AA083510 AW629109 AW513200 AA921353 AI677934 AI148698 AI955858 AA173825 AA453027 AI027865 AW375542 AA454099 AA733014 AI591384 R79300 R80023 AA843108 AA626058 AA844898 AW375550 AA889018 AI474275 AW205937 AI052270 AW388117 AW388111 AA699452 AI242230 N47476 H38178 AA366621 AA113196 AA130023 H39740 T61629 AI885973 AW083671 AA179730 AA305757 AI285455 N83956 AA216013 AA336155 AW999959 T97525 AA345349 T91762 AA771981 AI285092 AI591386 BE392486 BE385852 AA682601 AI682884 AA345840 T85477 AA292949 AA932079 AA098791 D82607 T48574 AW752038 C06300 |
| 131877 | 25130_1 | J04088 NM_001067 AF071747 AJ011741 N85424 AL042407 AA218572 BE296748 BE083981 AL040877 AW499918 AW675045 H17813 BE081283 AA670403 AW504327 BE094229 AA104024 AI471482 AI970337 AA737616 AI827444 AW003286 AI742333 AI344044 AI765634 AI948838 AW235336 AW172827 AA095289 BE046383 AI734240 W16699 AI660329 AI289433 AA933778 AW469242 AA468838 AA806983 AA625873 W78031 BE206307 AA550803 AI743147 AI990075 AA948274 AA129533 AI635399 AA605313 AI624089 AW594319 AI221834 AI337434 AA307706 BE550282 AI760467 AI630636 AI221521 AW674314 AW078889 AI933732 AI686969 AI186928 AW074595 AI127486 AL079644 AI910815 H17814 AA310903 AW137854 T19279 AA026682 AA306035 AW383390 AW383389 AW383422 AW383427 AW383395 H09977 AA306247 AA352501 AW403639 F05421 AA224473 AA305321 H93904 AA089612 AW391543 AW402915 AW173382 AW402701 AW403113 R94438 N73126 H93466 AA090928 AA095051 T29025 AW951071 L47277 L47276 AI375913 BE384156 W24652 AA746288 AA568223 BE090591 H93033 N57027 AA504348 AA327653 AW959913 N53767 AA843715 AI453437 AW263710 AI076594 AA583483 AW873194 AW575166 AI128799 AI803319 AL042776 AW074313 AI887722 AI032284 AA447521 AI123885 N29334 AI354911 AW090687 AA236763 AA435535 AA236910 AA047124 AA236734 AW514610 H93467 AA962007 AI446783 AA127259 AI613495 AI686720 AI587374 AA936731 AA702453 AI859757 AA216786 AI251819 AI469227 AA806022 AI092324 N71868 AA968782 AA236919 AA809450 AA227220 AA765284 AI192007 AA768810 AA805794 AA729280 AA806238 AW768817 N71879 AI050686 AA505822 AA668974 AI688160 BE045915 AW466315 AA731314 AA649568 AA834316 AW591901 AW063876 AW294770 AI300266 AI336094 AI560380 AA721755 H09978 D20305 D29155 AW821790 BE150864 F01675 AI457474 AW466316 AA550969 AA630788 |
| 101793 | 22080_3 | W01076 R26440 AA368372 N47843 R01320 BE005063 N32862 W67442 AW248115 AA186499 W76617 W47571 AL037045 W23808 W32746 AA419065 R81064 H02504 R06492 R63269 N27697 R08672 AA304278 F12437 H68061 AL049058 T73992 W68065 AA374449 W21155 W19598 AA320041 BE005017 T66993 BE620965 AU076485 BE304581 F05525 D58452 X17198 W93173 BE084847 W40177 W19760 AA399092 R64272 D58690 AW996221 AA312068 H08330 M95708 X16447 T83428 R10003 R08968 T79342 R08967 T79029 AA135367 AA373696 W31973 AA313297 R22120 AW951921 W19465 N56627 AI799711 N40576 AW068402 AA095480 AA398202 AW996208 N31962 AA127153 AI174829 W31739 AA375232 AA055145 W48704 M27909 AA046584 N40754 AW993226 AA369056 AA293552 AA402344 AW382179 AA300060 AW612974 W19817 BE302618 AA314768 W93045 AW239503 W61090 AW999043 AA256093 AW996142 AA115108 AA309885 AI185763 N32387 N25809 M34671 AI420645 BE386553 AW238887 AW239180 W63674 BE548657 AW071670 D58480 AW797405 BE385217 AI364331 M84349 AI139787 AW024513 AA568912 AI139779 AI038908 AI148669 AW996134 R69757 AI208594 AA830271 AI207381 AW996121 AA771863 AI582737 AI032005 BE549231 BE563708 AA772626 BE180449 AA478419 AW805577 AA419093 BE545114 AI198458 AI190821 N41625 W17102 Z14113 AA508606 AA362765 AA373248 AA293553 AW405465 N31225 N41424 N41637 AA493320 N20855 AA937576 D59121 AI219373 AI219369 H96383 W72655 AI126266 AW360865 N28679 AW369020 AW996592 AI138204 N90944 N29632 N90945 AI038241 AW339866 AW374179 AI139040 AA772029 R08861 T79770 AA643867 AW374178 N98229 AA115109 AA806282 |

TABLE 1B-continued

| Pkey | CAT Number | Accessions |
|---|---|---|
| | | AA291973 AI311653 AI718795 AA513330 N25868 W31381 AA182822 AA931679 AI095320 R26192 AI359945 X15861 AW996193 AW374176 R62157 AA187355 N34559 AI084000 AW934902 AA725412 N94600 H02505 AI720858 AA641883 AA641929 N94744 W32747 W47405 AA126943 AA255895 AI351787 AW630699 AW364131 BE439522 N95002 H60548 R64159 AA868813 R22063 AA046717 AA136956 AA158339 AA629233 AA304105 T84075 AW385670 AA812268 R16751 R08862 BE085521 AW382178 W04644 T94008 BE002001 AA974884 AW068220 N21290 H96384 AW800331 AA365897 AA890613 N91280 AW800325 F06415 BE166431 AW884534 AA548032 R06439 W47456 AW797813 T93330 AW993666 N98451 AA320303 BE001813 BE085981 N32624 AI206660 BE002637 AA503223 AI797518 AW881523 N90017 BE173234 AA148026 F25032 AW939327 F08000 AA843961 AA781612 F36942 N30048 AI983462 AI829016 AI433050 BE003093 W48705 BE018011 AW131095 W52359 AI951787 AW007755 N63925 AI538776 BE003013 AA593764 AW381247 AI942470 H97117 W47351 AW182890 AI003551 AW371384 AW802655 AW382188 AW024252 AA629009 AA910868 BE168332 AW998776 AW103467 R08578 T66992 AI095458 AW886999 AW080231 AW516979 AA614751 BE002551 AA853472 AA984190 R32050 AI537347 AI141112 AI139141 H08233 AI025834 AA303846 AI375734 AI051006 AI147858 AA977367 AW628158 H60549 AI074055 AI500604 AA973635 AA634239 T82464 N23014 AA132975 AI000277 AI041951 N70220 AI079383 AA136863 W52320 AI086768 AW993659 R96481 R32011 AA828169 AW067934 AI955379 R32003 AI074036 R01207 AA158340 AW804450 AW578099 AA644310 R80956 AA968816 BE218044 AI085088 AI872179 AA216189 AA865163 H97118 AI582803 AA612993 F10059 AA886257 AA058547 AA128374 AA100313 F01797 F02706 AA364790 AA054935 H99289 AA946573 BE621261 AW081853 C01727 AI684016 AW151033 AW516620 AA428471 AA036832 AI623767 AA747910 BE171975 AI696869 AW994421 AW994366 AA384789 AI985986 AA845776 AW087930 AA523314 AI984555 BE005225 AI904908 AW169269 AI904873 AI904877 AW172963 AW371388 AA630182 AA551835 AW008160 AA738219 AI570065 AI570047 W46411 AI272112 AA587684 AA812331 X84805 AI828196 AI215631 AI537453 AI860680 AA614394 AI627925 AW198219 AI961378 AI244401 AA045686 AW304980 AI224995 AA627603 AI986075 AI924326 AI955752 AW087558 AI432057 AI634283 AI609515 AI146681 AI344543 AW304211 AW205578 AW169004 AA937050 AW193044 AW51929 AI431704 AA872165 AW339126 N22956 BE465565 AW472807 AA865296 AI923130 AI827345 AW276416 AA085767 AA302276 AW263977 BE167417 AA148005 AA526475 BE093121 AW192995 AA622459 AA659824 AI276378 AA831376 AI421270 BE301517 AI907305 AI697299 AA906818 AW514010 AI499412 AA135218 AI914839 AI038155 AA463556 AA010944 AA425683 AA853471 AA514760 AA746481 AI284324 F34374 AI572786 AI127733 AW058539 AI074939 AI081411 W25539 AW075640 AA463507 AI264781 AA011329 AI311659 AI074637 AI991415 AI167852 AI167850 T53244 AA053299 T53243 W19297 AA045687 AI954391 AI739254 AI086380 AA614378 AA564541 AA507879 N33392 AI753208 AW062355 T29153 AW589375 AA385209 AW945139 AA564405 F04248 AI424610 D12053 AW571444 AI261355 AW299788 N93550 AI589366 AW611676 |
| 124690 | 109499_1 | AW883529 AA062566 R05818 AA365680 |
| 109623 | 493131_1 | AW207385 R45035 AI015414 AW027301 AI243732 AI034401 AW593338 AI949909 AA909080 AI827456 AA970506 AA884308 AW469937 AI829671 BE504206 AA991232 AI684476 AA987805 H44342 AW510966 BE047339 F03838 N20155 N33106 N23196 H25554 R69473 T48448 BE326522 N31698 N44929 BE502706 |
| 103000 | 23910_1 | NM_001975 X51956 AL120569 BE439816 M22349 AA171840 AW498683 AA101552 X13120 X14327 M36768 W28995 AA101258 AL134109 AA350962 AW163415 AW163031 AA337943 AA319319 AA337294 AA317603 H17983 H09409 AA321839 M86071 AA323310 AA323820 AA081450 AA322007 AW961616 H29112 AA349600 R88470 AA364106 R59230 H46681 R20685 AA325655 AA323983 D55069 AA353305 AW901191 AI268182 H19403 AA121223 D52401 D52407 D54786 D55281 W29029 Y00691 AA663488 M85440 AW246120 AW166102 AA325339 AA365967 AA422074 AI089418 AI858993 AI934500 AA808119 AW498597 W21815 AW157538 AI498264 AW157962 AA312480 AA450189 Z20539 W23223 AA707786 AI290619 AL133823 AI819350 N45630 AA323692 H44142 AA324278 AI829283 AW615583 AA131334 AA192364 AA129662 AA318854 AA319480 AI767204 AA233642 AW516760 H25864 AI961923 AA928093 AI923661 N50040 AW090665 BE300899 AW471178 AA722936 AW970337 AA339963 AA969003 AA703706 AA678754 AI885747 AW003621 AA988680 AA708466 AA709132 AW872840 AA664299 AA505601 AW249587 BE504375 AI955868 AA811574 AA702297 N26094 AI361920 AA723293 AA019718 H46682 AA971391 AA709459 AI002552 AA302335 H20496 AA987656 AA668640 N92267 AA010292 AI052757 AI536598 AW150310 AA064742 AA665844 AA017375 H17984 AI359833 AA101553 AI267996 AW516383 H29010 H38415 AI636972 AW103310 AA974167 AI216753 AI271426 AA946897 AI969131 AA738339 AI278148 AI859007 AI689251 AI445706 AW193637 AA101259 AI383343 H20501 H09349 R45346 R56255 W47553 T28830 AA450123 AA017516 H61759 AI968954 AA860665 AA233652 AA084731 H38118 W95928 R59174 AA573240 AA047180 AA129686 N48876 H18958 AW118487 AW798948 H87277 H30748 H86314 AA987275 AI868593 AA321899 AA350120 W95927 AA363843 AA363888 AW103324 H38997 H86253 D52358 AA364938 AW250044 AI005189 AW248555 H09050 AW879910 AA013084 AA047056 AA595172 AA084444 AA321838 H86034 AW022121 AW970256 AI343811 C02013 AA013083 AA701077 AA719717 AA365175 H30833 AI861921 AA013170 AA121224 AW014331 W21833 W21831 W21829 AA534823 BE257018 AW245380 W24445 C14610 |
| 103023 | 21730_1 | AW500470 H06789 BE265693 BE267238 F00022 AA227297 AW444618 AA233520 BE245778 N84850 AL121262 AA332218 AA206656 AA134655 AA353793 AA223357 NM_006452 X53793 AA355690 BE254225 AA113953 BE567105 AA373150 BE265222 BE263481 W00332 W20277 N50288 AA356027 AA356432 AA460418 N44764 AA247578 AW603811 AW504855 BE076335 BE535963 BE269055 BE397245 |

TABLE 1B-continued

| Pkey | CAT Number | Accessions |
|---|---|---|
| | | BE207045 R09643 AI524157 N84718 AW750310 AI831649 AW405272 AI608776 D17057 N39761 AI888656 AI630141 AA580499 N26422 AI190574 C19003 D59142 AI934377 AW197655 AW615490 AW770227 AI824301 AI826408 BE613833 AA704469 AA775648 AI871083 AI139200 AI343919 AI364058 AA961406 AI279685 AA169611 N47076 AI589192 H06740 R09530 AI289838 N33274 AI796372 AA773848 AA773403 AI915935 AA564395 AA740676 AI678147 BE176079 AA211898 AW386211 AW604702 AW604700 AW386212 AW386355 AW386354 AA343674 T29717 AW608858 AW754321 AW604707 AW604706 AW604704 AW608862 AW884475 AI470768 N92698 F00491 AA115600 AA210804 AA488215 BE546534 AA090884 N77356 |
| 103058 | 29185_1 | X57348 NM_006142 AW582031 AF029082 AF029081 AW246932 AA191264 BE122860 BE207235 BE563646 AA315939 BE264906 W79136 BE542511 BE615170 BE539669 BE616059 BE279710 BE512901 BE512933 M93010 AW366988 AA315717 AA158555 AW050862 T28709 AW605359 BE293089 AW366532 AW382384 AA064692 AW579542 W81148 AI834243 AA191692 AA641135 AA584037 AI283995 AA593934 AA586733 AA553800 AA838220 AA158556 AA837904 AA552598 AI608618 AW874282 AW081937 AA513205 AI672841 AI356363 AA554950 AW950173 AA308350 AA079732 AA826814 W81149 AW085653 AW269520 AW117948 AW268370 AI969260 AA858392 AW273771 AI354364 AA064650 AW250794 W74461 AI864911 AW087957 AW191846 AW050960 AI802687 AW780270 AI474308 AW516830 AA639425 AW117923 AI857652 AW615768 AW170288 AI354963 AW050763 AW004962 AW079623 AA662510 AI611709 AW117738 AA642581 AW272971 AW801049 AW383834 AW265603 AI832277 AA595966 AI541056 AW246006 |
| 103059 | 23881_3 | X57351 AA654929 X02490 BE395406 BE563953 T58724 T73065 AW950205 AW994424 BE157475 AW362565 R28460 |
| 103076 | 13655_1 | NM_001034 X59618 BE397747 AW503980 AA354118 AA053592 BE514224 BE299426 BE513582 BE297738 BE397292 R95694 BE278429 BE257685 BE613857 BE294663 BE297225 BE292916 BE541841 BE295916 AW239036 AW749733 AW578617 AA187351 AA355709 AW859845 BE297013 AA353332 AA204976 AL120944 AW602526 AW602512 AW750201 AW382889 BE297806 BE293922 AA127256 BE088525 W88898 BE314935 AA188218 H89781 AA403012 AA994536 AI890682 AA304649 AI417572 AW960352 AA702000 AW794142 AI436182 AW473401 AA602545 AA703261 AI831084 AI240268 H89828 H67307 H61911 AI864599 AI032997 AA676787 AW104792 BE208774 AA742288 AI038609 AI365040 N76870 AA703221 AI754744 AA720701 AA127257 AI336455 AA053076 AW378124 H68517 AA702787 AI139965 AW378095 R95695 H89719 H49073 H90680 T17364 AI444936 AI273823 AW673307 H61707 AW778803 T29749 N87596 AA094084 W88654 AI124036 AA046748 AA779414 AI088527 AI074626 BE537223 BE387242 BE396359 BE295232 BE407493 BE298019 BE299374 BE269901 AA186365 BE298410 |
| 133167 | 4750_1 | AW162840 AB011103 NM_004522 AA082585 BE093611 AI651976 AI990737 AW274812 AA325221 T82293 AW614011 AI673309 AI825446 AI699538 BE378544 AF010146 AL046486 AL119071 AI360266 AA580023 AL117393 AW298309 AA332807 AL050070 F11613 M79073 AA081545 T31178 T08358 AA204758 R12072 R15408 AA525065 AA226736 AW995415 AI698127 M62096 H14852 AA541529 AI301724 AI206957 T31267 F09268 AA082009 AW901553 AW901551 AW161605 AA625394 AW901566 AW163345 AW952148 AA319264 AW901574 AI369327 AI366377 AW901577 AW901576 AW901564 AW901578 AI268343 AA878238 AW901575 AW901554 AI810179 AW157290 AA769070 AI302273 AA219660 AI911086 R16149 BE326393 AI078091 N66104 N98707 AA992327 AI290174 AW161945 AW089620 AI216528 AI222342 H92203 AW148612 AA206916 AI032253 AW089301 AI215708 AI214776 F26734 AI802009 AW901573 T16535 AA227443 AI424347 AA602178 AI418719 T16606 H14818 R37133 T06093 |
| 103080 | 17092_1 | AU077231 AA852219 M74092 X59798 M64349 NM_001758 AA226806 M73554 BE409154 AA160096 BE384352 AA160820 BE382880 BE261734 AA113821 BE407745 AA156380 BE390287 BE390020 AA100854 AA127152 AW794066 AW367101 AW367093 U47703 AI347077 W05266 AI824103 AI499061 AA642944 AI042556 AA906539 W60380 AI571777 AL135581 AA112340 N75459 AA592929 AI085348 AI278890 AA126942 AI023701 AI873252 AA156319 AI190622 W60289 AI274886 R81309 AA100801 AA227161 AI568929 AA160603 AI074344 AI344561 AI150778 AA852218 AA158286 N20142 AA622148 AA864225 AA576367 AW182124 T89175 AI758455 AA780573 N71757 R81200 AI659596 AI674613 AA642544 AW503909 AA128851 W39350 N40420 AA113072 BE168116 AI620604 AI298125 BE075272 N40078 BE075109 BE080779 AI918938 BE168117 BE087369 AW995539 BE080949 BE080727 BE075271 BE075108 BE080955 BE089655 BE061115 AW750304 H66084 AI146884 BE075154 AW992247 AI186525 AI752230 AW263140 W03329 N26056 AA948080 AA113073 H99284 AA227101 AA631077 AA148042 AI740837 BE082728 AA149570 W44495 BE089351 AA375044 N26775 H27771 AA064705 BE091204 R89337 N32676 N27141 BE164704 H98049 W67603 AA425549 W31090 AA807411 BE173280 BE000178 T09020 W23852 AA062709 BE167894 AA076515 R97329 BE541980 N42086 AA102307 AA113772 BE276181 H20622 W44436 W67604 W46412 AW771113 AI700678 AA502628 AA133137 BE274186 BE396090 BE613371 BE612645 W46650 W95203 W92651 AI087288 R76299 AW604781 N55320 AI912334 AA403248 AW169156 H24970 AW298822 AW080962 AI073747 W24123 AA577596 H21715 H27925 H26436 AI288304 AA148043 AA204678 BE047090 W48631 AA908347 AA599485 AI276505 AI953979 AA563710 H25674 H51747 AA425389 AA516104 AI095335 T77237 AA151696 T92084 AI689037 AI624162 W49709 AW514883 AA100676 AI366087 AA069474 AA525859 AW771076 AA029402 AA994114 AI351505 AW770816 AI333594 AI289794 AI346589 AA487700 AI081104 AA613344 AI377520 AI284911 AI311390 AA622062 AI055890 AI660881 AI366117 AA403090 AI272818 AI073353 W46300 AA062689 AI755078 AI753397 AI633564 AI273471 AI339890 AA699584 AA983722 AI079968 AI752231 AA076431 AA113245 AI168564 AA918965 AI066484 AI123599 AI921518 W94586 AA535600 AA064665 AA705388 AA064623 AA962503 AI924926 |

TABLE 1B-continued

| Pkey | CAT Number | Accessions |
|---|---|---|
| | | AW131206 AW275281 AI280632 T29597 W48728 AW954336 W38317 W94768 AI084717 W46567 AI245645 AW302501 N72201 AW510563 AW079132 AA207064 AI143740 AW440672 AA632154 AI290286 AI350704 AI271377 AA025369 AI864756 T77451 H97348 AA852165 AI932951 N98526 AA487486 R92970 AA934071 AI080448 AA063257 C05786 N99099 R42969 AA887065 AA662686 AA533833 AA662304 H51748 BE539444 AI382164 AI814595 BE537043 AI168307 BE408935 AA453606 R89428 AA936527 AA936890 AW369618 AW264602 R18074 AI474189 AW372354 AI094358 R37210 AA948510 AA226909 BE172527 AI086652 BE408324 AW292848 AI768962 BE540703 BE409478 AA931692 |
| 132543 | 4172_1 | BE568452 BE297396 AA449593 AW732490 AW069736 BE548667 AA207229 AF044588 NM_003981 BE268994 AW444578 AA471151 BE250747 AW732555 AA074582 BE336856 AW408764 AA191159 BE092129 AA310614 AW958677 AA312276 AW750027 AW750046 AW750032 AW750024 AA188893 AW750054 AW408409 AW750030 BE151875 AA478509 N58721 AA195614 H70079 H75580 BE250401 AA454518 AA007263 AA626405 AA417152 AA004230 AA557354 AW863151 AW863181 AA702179 AI924143 AI671185 BE006198 AA190630 AI638795 AI609113 AI056239 BE537023 BE464668 AA634413 BE208066 BE208833 AW250803 AI337375 AA478510 BE501624 AI814763 AW594726 AI091408 AA827285 AA189108 AW594169 BE618589 BE618040 AL135398 AA632206 AI080126 AI638180 AA725439 AI379107 AI288872 H14801 AI679151 AI263619 AI559213 AI679722 W93249 AA552345 AA417030 AI969543 AA534494 AI038181 AA766364 AA573241 AI754325 AW043937 BE207865 AI291838 N73585 N73539 AW805051 AA808510 AI699813 AW166044 AW104716 H05808 AA248270 BE538022 N56013 AA621586 AA149737 D19671 AW192890 N54283 H73339 AA910989 BE273424 BE560082 AW959012 AA313552 AW750034 BE072537 BE297947 AW732361 AA449336 D29574 |
| 102469 | 28114_1 | AF058293 NM_001355 U49785 AW972510 AF012434 AW162262 AW160759 BE467297 Y11151 AV660796 N36451 AA031856 AA042840 U84143 AA298360 AW245227 AA029537 BE503111 H40824 AA314623 AW967178 AW249699 AV654359 AI816320 AI816115 BE383088 AI816155 AI816242 AA904633 AI857562 AI674662 AA641797 AV661233 AW591120 AA135692 R73165 H22050 AA292995 R74444 AI090155 AI280954 AA995535 AW664217 AA702434 AA897591 AI936198 AA897622 H67967 AI524130 AW593345 AI245949 N94421 AA778106 AI500225 AA315056 AA505428 AA641740 AA916226 AI475784 AI806488 AI674765 N25737 AA946564 AA973960 AI738576 AA741247 AI141160 AI221510 AI743909 AI394171 AI857553 AW005215 R22955 AA766589 AI884977 AA397824 AA913449 AI343606 AI365262 AI739170 H67915 AI304569 AA926749 AA031857 AI266691 AA938649 AA618497 AA723513 AA596001 AA470895 R73113 AA135724 AA703615 AI282652 AA865014 AA554895 AI076871 AA029470 AI791608 AA953956 AA523248 AW797855 AI567853 AA723757 AA228918 AA229626 AI688392 AI868189 AI202062 W42762 AA876330 R26067 AA548143 AA044388 AW272276 N56172 R54763 R70265 R23061 R23472 AV646146 R62911 T56208 T52223 AV661866 AA247611 |
| 131913 | 29330_1 | AW207440 BE550098 BE222538 BE467911 BE502972 AW770991 BE348491 BE464713 BE464895 NM_003676 AF002668 BE382402 AW239002 AA352894 AA188319 AI929163 AW239144 AA308032 AA545785 AW383672 AA486501 AI905278 AA360802 AA427347 BE162891 AA339634 AA504320 T47547 AW608185 AI928909 AI826360 AA039957 C16051 AA186666 N26205 AI802485 AI929789 AW264512 AI766895 AI581200 AW881675 AW881634 BE170014 AA039929 R91936 N22526 AA809857 |
| 101840 | 28941_1 | AA236291 BE293174 AF053630 BE246925 AU076563 AW192831 M93056 AA317328 AA285297 BE549077 AA459452 AA828086 AW867040 AW367439 AW579513 AA381538 AW373811 AW238408 BE181033 BE177198 T64083 AA223079 T29877 AW951546 W52888 BE158927 BE164641 AI819486 AW861145 BE617585 BE080588 AW604529 AI686584 AW853099 AI927997 AW076085 AI609287 AA554776 AW272186 AI697982 AW168740 AW407049 AI651260 AW276041 AW361042 AI749476 AI597941 AA563899 AA596013 AA236225 BE551322 AA996154 AI914153 AI701599 AA747840 AW795777 AA627978 AI697344 BE219518 AI768049 AI379098 AA489298 AA465675 AI755246 AI498642 AA583755 AW753489 AI478385 AA486275 AA009870 AA837593 AI921918 AW342106 AI344412 W60096 AI749707 AW058301 AI640325 AI074661 W60162 AI274417 AW014165 AI908601 R54664 AI762419 AW874141 BE539228 C01662 AW615332 AA640019 AW515606 AW853015 AW467918 AI932439 BE241436 |
| 131937 | 83422_1 | AI907735 AI056357 H51345 AI432456 AI140962 AI524059 AI421702 AI082401 AW291316 AA009744 AI361578 D60684 AI361496 H50507 AI278076 AI572596 AI247598 AA678199 AI750926 AI584110 D60243 AI431834 |
| 131965 | 50779_1 | W79283 AA355584 W55924 AW295902 AA303712 AI762203 AI933087 W86119 AI344052 AI394685 AI380136 AA906535 AI831090 AA587379 AI082049 AI392742 AI024509 AI341096 R98391 AI277506 AI401129 W90323 AA976794 AI493269 H75427 W90146 AA682644 AI002148 AA625829 AA927077 W86120 AW965770 |
| 101883 | 13982_1 | AU076743 C03916 C03241 C17133 AA213939 BE080490 BE080506 L06849 Z32770 AA040112 AV653149 AA034144 AI207499 C03888 AA040113 AI079565 AI079561 C05003 C05006 AI133623 AW629601 C04222 AI040781 AA442031 T58253 C04562 AI630563 AI630360 AA360674 AA923252 N45238 M98399 BE568579 R67556 R09416 N78180 W86398 S60720 W52503 R36333 AA603206 AW613186 AA779254 AI818595 AI807199 W52687 AW081753 AA700589 AI023824 AA873267 AW044569 AA846141 AA916502 AI805330 AI539625 AI242149 F33247 AI140485 N39161 R93521 AW450111 N99618 R30819 R33521 T28585 R35967 AA708427 AA417874 R26399 T93071 R09417 AA342353 N59627 AA446923 AA482528 AI253633 R33425 C17897 AA461273 AA302823 R83148 AW954323 L06849 AW662129 AI418452 |

TABLE 1B-continued

| Pkey | CAT Number | Accessions |
|---|---|---|
| 101889 | 27120_13 | AF188747 S39329 AF188745 AF188746 AC037199 AI557458 AI547068 AA622331 AI547256 AA524779 AI557107 AW973994 AA558557 AW973949 AA523677 AA229207 AI734061 AA614244 AA688115 AA658025 AA532387 AW973151 AA534173 AI669704 AA659396 AA652812 |
| 131985 | 113870_1 | AA503020 AI858190 AI686571 AW615203 AW073686 AW172459 AI828762 AW150534 AI859795 AA411046 AI539195 AA404609 AI638559 AA434329 AA171844 AI684143 AA953518 AW470108 AI870700 AA706376 AI539668 AI683712 AA075579 AI682137 AA291512 AA554431 H51315 AA404225 AA075632 AA172293 H51911 |
| 131991 | 9877_1 | AF053306 AU076682 AL134922 AF107297 AA332513 AF046918 AF035933 AA333217 AA334907 AW502700 AF068760 AW960388 AW175635 AA314793 AF046079 NM_001211 AA134622 AW674724 AA237061 AW967437 AA488324 AA310114 AW965733 AA057453 BE005410 AA436067 W85770 AI949025 R83561 H71285 AA358471 AA447460 AA194971 AA024423 AA431252 AI655861 AA195039 AW339247 AW339252 AA491096 AI742609 AI801073 AA379706 AW958400 AI742619 AI142090 AW027512 AI655899 AI954788 AA252443 BE538707 AA527377 AA625902 AA236861 AA694249 AI086191 W85771 AI378561 AI073565 AA024424 AI056214 AW452190 AI183487 AA490909 AI248560 AA812042 AA251909 H53027 AA715728 N76108 AW449857 AA488460 AI472342 W05597 T70279 |
| 103110 | 3165_1 | X62822 NM_003032 AW503875 AW503871 X54363 AW500693 T87101 AA362158 W86368 T87100 AW500756 AA650479 AW505326 BE174653 AW408118 W86304 AW502416 AW502929 AW503986 AW386276 AW849346 AW849661 AW386237 AW408111 AW408065 AW503146 AW505584 AW501997 T40033 BE513321 T28127 AW950356 AW408733 AW888934 AW888935 AW408672 AW408139 AW408632 AA053191 AF007133 AW402986 T77105 AW607384 AW607226 AW389924 AW390030 AW390003 AW389914 AW389867 AW389905 H50737 AA173350 T85522 T84687 H61889 AA973060 AI827819 AA918297 T78696 R92173 T93773 R00114 AA765771 AW401612 BE092769 BE092751 AW405380 AA101896 AA150821 R10651 AV659513 AA132785 AV659504 AV659244 AV659402 H26119 AV649190 AV649382 R47460 H71379 AV650337 AV650310 AA291331 AW604183 W05049 AA526109 AA525891 AV658596 AW841979 AW841958 N78404 AA081318 AI743792 N39564 AI423316 AW574865 N50105 AW505324 AA176779 AI871039 R91746 AI832017 AI760310 AW575698 AI418288 AI146395 AW474464 AW518261 AW575766 AI831651 N70182 AA740174 AI383512 AI146405 AA327270 AW575779 AA804742 AI694007 AI086143 AA017439 AA725101 AW026365 AI638127 N62633 AI422886 AI094994 BE047172 AI432658 AI347718 N92153 AA886337 AI084853 AI864682 AI888006 AI400481 AA805585 AA714723 AW575739 C06044 AI242399 AA099435 N92154 AA598652 AI340010 AW305208 AI687213 BE221126 AI357202 AI367737 AI222491 AI422563 AI671750 AI865161 AI282392 AA053105 AW977848 AI678203 H26384 AI888547 AW236757 AA969788 AA931708 AW189296 AW104122 AW576574 AA508883 AA886334 AI091462 AW194366 AA983578 AA081319 AA659236 AA507105 AA706401 AA262158 T40957 AW576519 R38174 AI420189 AA740663 AI362399 AA493825 AW243101 AI682049 AA983307 AW591806 AI474216 AI276413 AI243962 AW771756 AI469023 AA677442 AI865219 AA736532 N74338 AI914927 AA491775 AA665867 AI684948 AA577242 AI928042 W72106 AI243044 AW503191 AV647329 AA004332 AW389897 AW389912 AW389887 AW389902 AA004331 AA642384 |
| 103119 | 3394_1 | X63629 NM_001793 BE175433 BE153414 BE153425 AW364593 BE315317 AW950190 AA314252 BE142943 AW365220 AW368405 BE004269 AW366568 AL040609 AI829273 AI591168 BE146183 AI631060 AI830793 W78081 W92295 AI927422 BE009313 AI371793 AW993031 AI204659 AA535113 AW993030 AI190281 AA555159 AW269637 AW993146 AI149268 AA425217 AW473194 AI890930 AA551993 AI952106 W92308 AI827275 W45400 AI952328 AW609233 AA774611 AA551779 AI913967 AI798658 AI537658 AW517535 AA632236 AW339148 AW589522 AA836945 AA961263 AW015821 AW272946 C00249 W40333 BE143121 |
| 103131 | 3455_1 | BE536069 AW393633 AA136789 AW821689 AI834350 AA506274 BE070170 AW821678 AA308168 AA488630 AA131149 AA131160 AI151190 AA308062 AA308355 AA369141 AA534869 AA187915 BE565360 AI148603 AA369104 R76868 AW610308 AA131104 AA130897 AI014579 AI023329 AA314934 X65614 AA622025 NM_005980 AI803595 N41659 AA486010 AI814221 AA552131 AA630697 AA040009 H95165 AI928285 T47376 AI219000 R32242 AW951766 AA780629 AI096571 AI096563 T47401 AA308192 AA126381 AA136673 T47377 AI202505 AA594486 AI815174 R32189 AI200563 AI219279 AA587763 AA128186 AA187916 AI318167 R82349 AI318308 AW393634 W02707 AA484318 AW796740 AW881434 AW881366 AI126103 AA039888 BE067072 AI433932 R82833 AI142659 AW392947 AW392945 R82404 AA053504 R82832 R77101 W25661 T47400 AA622076 |
| 103145 | 26690_2 | X66276 T75146 |
| 133240 | 31972_1 | AK001489 AW860676 AW821784 AW975085 AW821786 AA658188 AW468490 AA410271 AA152126 AA452028 AW473972 W16475 AI475944 AI360390 AI357567 AA226320 AW874359 AI122554 AI091013 AA406478 F37355 F27660 AW439053 F36093 D31309 D31031 AI686163 D31161 D31474 D31095 AI291610 AI866679 AA662158 AA911580 AI302576 AW169600 AA905362 BE327258 C21179 AW969418 T81369 AI076608 AI313185 AI590307 AI017439 AI985266 AI092621 AA393816 AA609830 AW086045 N98729 AI739354 AA455083 AA493714 N36233 AI870707 AA235859 AI082534 AI569628 R42309 AI569818 R79440 AA480260 AA622011 AA858240 AI473130 T10194 C21521 AI245327 BE168785 AW379568 |
| 103177 | 10888_1 | BE244377 AA338310 X69141 AI929380 AW410661 AA351268 AI929004 AA132850 AI816348 AI815503 AW403408 AA312277 AA311923 AL036928 AW163229 AW161244 D52720 F07128 AA223128 BE392377 AA305886 AW247747 AA332907 AW950937 AW160538 AA311963 AA356171 NM_004462 L06105 U47709 R11849 AA232463 AV645555 AV645525 AA053619 BE408788 L06070 T72123 AW601882 T86062 |

TABLE 1B-continued

| Pkey | CAT Number | Accessions |
|---|---|---|
| | | AW374302 H23317 AW176438 R07232 AW849553 AA352210 AW849234 H44685 W94208 AV653813 AA332023 AW250706 AA102094 AA321563 H29164 AW277021 R55980 AA355314 AA360928 N76776 W48614 AA026281 N23771 AW377275 D53282 N28452 H75676 D54754 D55368 D55402 BE181975 F07893 AA355322 BE566904 AA148259 T19343 AA193069 AA083979 AW404668 AA131541 R02406 R08392 AI669055 BE174166 T99624 AA985358 AA985342 AA131697 AW246850 W63788 AW601918 AW074311 AI951130 AI991110 BE070315 AA151763 AI032815 AA613379 AW182204 AW265712 AA747801 AI190719 AA430164 AI494088 AW131526 AW072023 AI004081 AI144397 AI301484 AI590672 AA970146 H99689 AI928778 AA928418 AI815800 AI816268 AW574757 AA102095 AI890190 AW340641 H62539 AI417393 AI608972 AL041908 AI872231 AI984699 AA317075 T99625 F24396 AI161392 AW162148 AW518979 R08341 H48776 F36841 W92663 AW161779 R83726 AW885483 AW440322 AA541604 AI908605 R59607 AW270365 R07180 AW273047 AW162487 AI052719 AW007925 AA366437 AW515604 AA206134 AA322919 AA838608 AW571844 AW023321 AW732262 AA220926 AA405177 AA564787 AA364610 BE220511 T71979 AW157224 H12389 AI990979 T72210 AA857354 AA292662 AA625743 T87002 AW058112 AI312077 AW969444 AI218167 AA534735 AI908780 AA401454 AA947906 AW406988 AA864810 AA483282 AW170751 AW080972 AA830202 AI151023 AA181703 AI914655 AA889601 AI905706 AI201824 AI141932 AI680401 AI283019 AI365250 AI276334 AW410862 AI056909 AW102782 AA807321 AI185943 AI920812 AI140684 AI378069 AW000855 N57455 N27435 AI741814 AA192920 AA026282 H43629 AI183784 AA563831 AW377321 AI084030 AA074123 AI318047 AA053173 AA872727 AA133110 AI929302 AA132757 AA232267 AA129857 AI033785 AI346414 AA148621 AI925122 AA932952 R51330 H08557 AA083810 AA129337 R55981 AW002267 H99629 AA625742 N53963 AA772739 T29282 AI859385 AA223244 AA523979 F28431 W48847 R36966 AA657829 N27973 AA916090 H62606 AI952754 AI564458 T26604 AI468917 AW269805 BE221068 AA569016 H23205 W92664 N20092 AW248053 BE041312 N34384 BE042592 F03417 AA129296 AW298264 AA579647 AA628870 AA173312 N35395 AI815203 AA148258 AW976758 AA927356 AI915614 AA351267 AA534648 AI625062 AI587520 AI582856 AI954097 AI609091 AA766770 AA741469 AI685416 AI719555 AW510313 Z20271 AI251431 AA338309 AW513955 AI804795 AA550813 AA846149 AI453329 AA194782 AW592900 AI140151 N29512 AI742951 AA566029 AA679352 AI336457 H69031 H29061 H12335 AA018590 H48777 C21353 AI698328 AW473013 AI860131 AI679762 T92179 H27238 BE265616 D52299 BE615720 BE614759 BE545737 AA074684 AA089952 D53006 AA232397 AA148760 AA182533 AA232066 AA243199 AA017339 AA018779 N94178 AA071301 T72989 R11772 BE387096 AA773305 BE379275 AW512721 BE256922 AW849540 AA861806 BE250923 AA149746 AI672946 BE565676 AI249672 AW377375 AA380648 AI475401 R11842 AW160619 R02307 AA017065 T85654 D56357 AW367156 R36960 D54522 AA211025 N59047 AA095616 BE268345 AI950148 BE148896 |
| 102522 | 28935_1 | BE250944 BE616901 BE253022 U53347 BE383374 BE313477 AF105423 NM_005628 BE257654 BE336665 AF105230 BE539413 BE273212 BE617083 AF102826 BE274027 BE560310 BE614911 BE273445 BE513318 AW411160 BE278757 BE277970 BE019285 BE531331 BE336692 BE397340 BE296944 AW602538 AW602540 AA099481 BE336620 BE074605 AA306259 BE535395 BE207595 BE207598 AW410410 AW841604 BE305060 BE311530 BE292788 AA306349 BE514955 BE313327 W90214 AL121171 BE539828 T11057 H30086 AA297427 BE514907 AW580873 BE262194 AW580793 AA852674 AA321171 BE074021 AA346337 AA308071 AA309759 AW410411 AW967163 AW411161 AA228909 AA308363 W05341 AI660835 AW999568 AA564660 AI684985 AI660215 AA503541 BE504576 AI633136 BE208096 AA845686 AI288924 AW778797 AI184170 AA977438 AI955727 AI674510 BE208366 AW054876 AI469116 BE300996 AI095478 BE465612 AI860201 AA989620 AW467514 AA098963 AI673787 AI357188 AI446031 AI268863 AW270531 W90118 BE042532 AI932802 AW674178 AI498985 AI698310 AI973241 AA565892 AA618535 T70098 AA701617 N75549 AI801071 AI915998 AI824519 AI453680 T70031 BE043320 AI248317 AA852675 BE208054 AI129615 AI672245 AW517529 AI934217 AI916491 AI932648 AA580366 AA229618 AI003710 AA362311 AL121564 AA605241 T10696 AA612586 AI669543 AW205845 AA862570 AA468628 AI685640 D20937 BE562427 BE616976 BE541016 BE548292 BE617036 BE251847 BE292877 BE386108 BE539045 BE262916 BE544850 BE261696 BE314491 AW168666 |
| 132618 | 4291_2 | AL050025 AK000158 AI908611 AA252048 AW608281 AI908261 AI908258 AI908239 AI160656 AA536091 AI040024 AA026961 AI817577 AW167656 AW805905 AI972086 AW275904 AA633511 AA253330 AI459474 AI991230 AI344436 AI566311 AI200550 AI572667 AI306458 AA938254 AI572658 AI301480 AI986336 AI300709 AI832269 H05110 AA643555 AI050855 AA505873 AA588885 AA253331 AI421242 AA970741 AA740337 AA953925 AA918856 D25681 AA600883 AI306664 AI271982 AA853781 AA975599 AI908238 AA670219 AI799962 AW170074 AI355477 AA962472 AA853646 AI918513 AW051036 AA873683 AI672142 |
| 103195 | 3223_1 | AA351647 NM_001958 X70940 AA351455 AA325548 AW248144 AA351834 AA349397 AA326028 AA338341 BE208623 AA323302 AA339035 AA338365 T08068 AW966573 AW966578 AA351470 L10340 AA188990 T28797 F00492 AI929597 AA158068 AA984807 F00611 AA776020 AI816044 AW732219 AI192682 AI937488 AI368766 AI498010 AW292877 AI381320 AI468632 AI674175 AI955204 AI693207 AI805987 AI926581 D53815 AI803715 AI814727 AI335757 AI480079 AW207047 AI879505 AA553537 F24119 AI017726 AA604272 AI479397 F30442 D51525 AA706359 AI271525 AA232098 AA973543 AI379683 F27731 AA191040 |
| 101971 | 24390_2 | Z49105 X86175 AL040237 Z49106 S79894 U90840 S82471 U90842 AA609599 AA312651 NM_005636 U90841 |
| 124847 | 26986_4 | W07701 AI133664 AI290816 R60044 AA693963 AA493715 AI336061 AI610656 AA693599 N80579 R83001 AI473847 AA633037 AA618329 R82959 |

TABLE 1B-continued

| Pkey | CAT Number | Accessions |
|---|---|---|
| 101988 | 143_1 | AF221521 BE336893 U00952 AI750689 AA326310 AW380330 BE549651 C03372 AA306286 AW958721 AW815548 AW135111 F06006 AA378641 AW953320 AI784570 AA770479 AA351054 BE244284 BE260937 BE246902 BE247701 BE247607 BE246905 AW068681 AW068669 AA985132 AW753657 BE148802 BE148801 BE148803 AW753658 BE148805 AW407779 |
| 101992 | 15051_1 | X90725 U78073 X73458 L19559 AW250659 NM_005030 X75932 U01038 BE301830 BE297455 BE297942 AL040830 BE264516 BE206963 BE545110 BE296425 BE385706 BE273449 BE559796 BE253122 BE254860 BE257891 BE263475 BE273841 BE273308 AA306560 AA331492 BE087719 AW250291 BE087061 BE270383 BE295183 AA380290 AA088731 AW401457 AA043829 AW367195 AA456458 BE260078 AA353672 AA553803 R99809 AA352574 BE614593 H52663 AA327248 R01014 AA193662 T28955 AW950886 AI916283 AI916294 AA206364 N58651 AI949492 AA846584 R68910 AI765140 AW590607 AI949066 AW249935 AA580473 BE140376 BE300829 AA193513 AW615819 AW249527 AW732067 AI936720 AA454565 AI218478 AL040831 BE502128 AW246796 AW251086 AI275562 AA808283 AI923618 R99810 H52664 AI370033 AW574528 AA629262 AI905018 AA088730 AI798262 AA694425 AA852582 R01015 BE504899 R17934 AW207180 R68806 AA205518 D29396 AI867265 BE463980 AW079339 AI497713 AI590016 AI221870 AA991721 BE560361 BE259912 BE563868 BE538225 AI652630 AA088732 AA806326 BE535599 BE277725 BE542387 |
| 117642 | 24585_1 | U55184 C16033 N46366 AA478853 AW162080 AW450573 AA235429 AL120649 AI082827 BE504287 AW156895 N37055 AI452450 AI827985 AA973921 AI078763 AA479952 AW263536 AA234773 N37076 L10665 NM_002071 H49600 H41799 H49592 H43011 H41837 H49694 H49683 H42188 AI277641 H42191 AW960075 D54398 D52975 AI024119 H17636 C00861 R20102 AW138751 AW237500 AI743654 AA642492 AW044105 AA876365 BE242003 AI693444 BE218931 AI693433 AA492549 AI687074 AI241026 N20828 H77392 AI582745 AI362752 AI989343 BE169365 R52708 AA946636 W40411 H77393 AA488909 AI864923 BE169804 AA487362 AW841219 H05313 AI382931 AI623550 R39198 AI625086 AA728766 AA206921 T15418 F10584 D53449 AL047642 T28449 AA418957 H43008 AW389735 AW389737 AI242468 AA418749 AL134374 AA827103 |
| 111003 | 1470402_2 | N52980 |
| 103240 | 3332_1 | U81961 NM_001038 X76180 Z92978 L29007 BE563144 AW752323 AW605213 AW379740 AL036530 AA393950 AA035472 AW249071 BE264628 BE293100 AW974278 BE315490 T28389 AA402773 AW796814 BE001985 AW366994 AA482625 BE093028 R48145 H39921 AA459197 AW363013 AA516464 AA535868 AA402792 AW249694 AW024917 AW178791 AA477362 AI453273 AI885511 AA573425 AW080449 AW190184 AI588881 AI673588 AI804876 AA551653 AW070576 AI261669 AA861895 R48146 AA641560 AA931735 AA812330 AI289786 AA435775 AI017803 AI699795 AA630143 AA834340 AW152290 AI445126 AI337246 AI263551 AI860441 H28438 AA477114 AA885926 AA480364 AA573919 AW247908 AW005377 AA565785 AW007565 D45514 AW578023 |
| 103245 | 9107_1 | BE566343 W25304 N40150 AA033594 W47498 AI346655 N99949 AA011573 N99929 N27026 AA129941 AA766447 AI005601 AI244046 R92122 AI288824 AW074285 AW803318 R81375 AA037205 R32183 AA485073 AA032078 AI022356 AA614770 N47980 AI245088 R92198 F33995 AA665163 D11582 H90397 R69363 R39568 AA129940 AI431751 R26829 AA279280 AW995850 AW995819 AA999877 AA639489 R24153 AA916818 AF115106 X76648 H54165 W52609 W79548 AA279279 AA321573 BE379914 AA037204 AA011591 AA319951 AA312373 AW404037 AA308644 AA343991 T12247 AI188699 T28674 AI417967 AA313657 AW950049 AA485178 R67530 D21238 AF162769 AA131943 AW009604 H53565 W47497 AI884791 AI569215 AA845422 AA133992 AI743284 AA130209 AA779484 AW803387 AW803251 AA576037 N40812 AI580888 AI242038 AA830604 AI000536 AI921820 AI688612 BE439978 R24017 W31100 R69362 R20935 R81374 T79523 T79522 T87471 AW571801 AI244756 AW978497 AA954264 H90449 H54008 AA291163 W74537 AA033593 N51182 R93917 AI127891 T79435 T79434 AW803388 AA933060 AI141910 AI025368 AI095562 AA682885 AI151130 AI537290 AA779362 AI339261 AI242537 AA703360 AA131944 AW390025 AW389998 R67531 AA996112 AA931084 AA676656 AI373155 N94318 AW803369 AI041788 T79958 AA594671 |
| 103262 | 30537_1 | X78565 NM_002160 AW849271 AW849284 BE070169 M55618 X56160 AI752274 X80280 AI752783 BE085280 AI752359 AI752537 BE085357 AW368385 M24630 AA121587 AL135594 AA376236 AA852426 AI752223 AW993043 AA386040 AI752360 AI752581 AW362299 AA219366 AI751903 AI929763 AA852556 AW381589 AW360945 AA375942 AA331744 F13432 AW068004 AW838635 AA223678 AW608183 F13016 AL121433 AI751856 AA344557 AW602147 AW602064 AA037441 AA130202 F13253 T77030 AI751122 AA037359 BE185561 AA134100 AW378339 F08068 AA324181 AW378350 AW378348 AA343458 BE166503 BE175117 AW378344 W47114 AW367718 AA461289 AA293732 AA373768 AA374344 AW749923 AW749934 AW602133 AW835290 AW937984 AA331126 AW937992 AW385977 AA448991 AW378075 AI084804 AW581359 AI312592 AW839221 AA328705 AW176725 AA046543 AW840706 AA070776 AI560816 AW889297 AA693461 AI016493 AA373039 BE162918 AI554313 AW004826 AI569405 AI419439 AA665773 AI828468 AI956098 BE504589 AI767273 AI684182 AA293733 AI473804 AA483299 AA340821 AA873749 AI869519 AA045473 C06097 AA505504 AW104511 AI281389 AA678558 BE551784 AW183737 AA725001 AI222869 AI751121 AI498613 AA598955 AW511819 AA746094 AI783501 AA857548 AA460980 AI183689 AA223510 AA993812 AW608353 AI751857 AI272689 AI090084 AI291427 AI185072 AI341799 AI150420 AI624079 AW075585 AA223394 AW511803 AA665468 AA903413 AI752782 AA679727 AI752273 AI061274 AI049690 BE464029 AI369788 AW628681 AW889130 W52099 AA968750 AA121393 |

TABLE 1B-continued

| Pkey | CAT Number | Accessions |
|---|---|---|
| | | AW189404 AW067838 BE219870 AI424654 AI754980 R39239 AW183352 AA852425 AA488262 AI273011 AA488244 AA340752 AA449457 AA852555 F10855 W47214 R93301 F09300 AA853808 T28785 R38104 AI866639 F04302 AI872543 X56160 AL135631 W40199 T77595 AA219270 AA386039 AW608171 BE174080 |
| 103269 | 24390_3 | AF230662 S79332 AB012575 X79200 N24445 N72228 H99655 AW291679 AA730715 AW975672 AI699644 |
| 102632 | 32834_1 | U66618 NM_003077 BE244439 BE244967 BE242731 AW403224 BE273228 AL079523 AA580844 AI910318 AA121441 AW853822 AA355815 BE257890 BE254018 R54755 H72035 AA378378 AW846512 AW375588 AA402352 AW404560 AI133585 AF113019 AI174740 BE383453 AW375602 W69245 AA323991 AW369719 AI392720 BE076070 BE076246 AA252195 H54149 AW351946 AW371236 BE093129 AW317069 AI816724 BE463581 AI076940 AI123801 BE328399 AI870273 AA603776 AI039302 L31997 W69140 AI040190 BE301142 AI392962 AW189391 AW473894 AW082757 AA605026 AW168194 BE466942 AI222903 AA122012 AW275193 AA654229 AA847182 AI688771 F27116 AI871518 BE221378 AW439462 AW189556 AW193491 AI471650 AI799779 AW242172 AI580420 BE502872 AW452211 AA639503 AI368655 AW192152 AI651528 AI749109 AA761143 AA478436 AW452291 AA853485 AA810038 AI500025 AI363801 AI673822 AA252347 AI089964 BE241994 AA587708 H22237 H53989 |
| 126180 | 3791_1 | L32977 NM_006003 AA158808 AA625124 BE268625 AA401287 AA411487 H93686 BE536275 AA232779 AA406405 BE265593 AA429929 BE293575 H95308 Z82206 BE388670 BE272057 AA216717 BE394775 T70795 AA304678 H78320 AA371448 AI684596 N89414 AI806645 AW883131 AI983340 AW855827 BE154049 AA094511 AA304354 AI806153 AI708422 AW604518 AI765617 AI735380 AW075958 AI963624 AI740521 AA096216 AI459163 AW339112 R00712 AI589173 AA602549 AI879981 AA887659 AI762362 AI937378 AA341466 AW517324 AW157415 AW675434 AA613727 AA576788 AI186410 AA837040 AA165456 AI460082 AA404279 AW004639 AI240300 AW183961 AA243348 AA906904 AA243703 AI275411 AI283440 AA406265 AW661954 AA947892 AI015132 AA977942 AA557310 AI206823 AI339554 AI241703 AI221435 AI199546 AI682610 AA325404 AI139132 AA831282 AI379291 H95258 AW628401 AW628396 AA917089 AA166949 AI635864 AI097345 AI356442 AI339672 AA713531 AI708674 AI460047 AI040539 AI537314 AA936513 AW162216 R58299 AI275038 AA788878 AA828417 AA594488 AA161091 AA772693 AA829967 AI302663 AA861569 AW731618 AW663554 W93673 AI800799 AI140258 AA035338 AW731639 N70360 AA805692 F28732 AI343921 AI289047 AA535684 AA410426 AA436339 AA253373 AA769244 AI122989 N77880 AA809270 AI289953 AI679447 AA426301 AW270437 AA909132 AI741407 T69809 AA884037 W79292 AI474297 N36119 AI832850 R50825 AA076134 AA503751 AA348907 AA709352 AI086497 AI338555 AA883067 AA922475 AA327126 F36722 AW302275 F26852 AI202816 AI363391 H79107 AA605247 AI183576 AI374603 AA862585 AW044276 AA844456 AI858659 AI168636 AI366750 AA135461 AI187796 AI521758 AI752729 AA448184 AW025454 AA622180 BE041579 AA128126 AW081491 AW662005 BE044407 AA835867 AW381493 F24322 F35020 AA922270 AA233263 F22315 AA829016 AA476810 AA171970 AA171733 T29549 D11847 AA348906 H78319 AA876617 AI572829 AW271537 AI284780 AW875817 R00713 BE156643 R00305 AI422469 AI473291 AA157975 AA094326 BE387637 BE541153 BE388199 BE387712 AA233272 AW051428 BE390716 BE378350 BE567621 BE385400 BE514640 AA411294 AA426300 AA524811 AA125817 AA847641 AA135167 AA581376 AA883191 AI277130 AA905986 BE410969 H79106 AI891117 AI690358 BE383378 AV655976 T99958 AW149479 AA165643 AI285299 AI933251 D51255 AA721196 AW604505 AA834904 BE394936 AA166936 |
| 102687 | 18766_1 | NM_007019 U73379 AA403208 AA315182 BE295294 AL050348 W04406 BE618643 BE268039 AA401609 BE618097 BE559663 BE538158 R80990 AI554680 AI650374 AA305922 R95056 AW966695 AI417343 AI935139 AW005769 AI831252 AA554943 AI246563 AW274491 AW020646 AW080931 BE552307 AW472855 AI660049 AI380738 BE504728 AI808876 T86566 AA777748 AI270758 AI281284 BE550389 N88948 AI637467 AA564413 AI264541 AA705085 AI368831 AA403150 AA401483 AA700029 AA913021 AA705555 AI264545 AI097153 AA430504 AA913020 T86744 BE205766 N75989 AI308917 AW590111 AI799019 AA149943 AA629934 AW027600 AI867762 AI909396 AI909403 AA936828 R80790 AA136118 AI909375 AA977854 AA834364 AA974269 AW263663 AA596035 R94970 AW025749 AW188591 AA382274 AI565861 AW016092 AI590646 N89562 AI695116 AW807662 AA160710 AW079637 |
| 118336 | 179356_1 | BE327311 AI808202 AA860831 AW150145 AI948907 AA987955 AI768241 AW340343 AI348657 BE501343 AW299642 AI093850 N63604 AI424600 AI142481 N50995 AI127277 AI383067 AA228931 AW205034 AI041317 AI801898 AA319620 R61165 N44200 AA405345 |
| 102696 | 602_1 | BE540274 AA355711 AW958581 T90364 BE384320 BE389956 AA223822 AA356494 L16783 AW794597 BE255394 BE537206 N41904 AW378227 BE250637 BE540759 R08302 AW878897 AA129552 H79413 BE618724 BE618142 AW629083 AW249531 AA897527 AA857906 T29884 AW103917 AI159918 AW008104 AI358250 AA115314 AW007932 AW575043 AA136566 R08303 AA868003 T06221 AA832447 AI283368 AI612862 AA582882 AA705768 AA922918 AA873051 BE086670 BE086703 BE544606 BE251508 BE258319 BE207699 AW780338 BE208744 AA603671 AI638699 AI150022 AA743293 BE301101 AW468950 AA091000 AW295103 BE265255 AW378192 AW178792 BE535606 AW250295 AW239326 U74612 AA336682 AW630364 BE086826 AA219301 AW403014 AW378147 N32560 AI692175 AI991216 AA991252 AI906098 |
| 125573 | 23881_16 | AI351642 AI341707 |
| 117701 | 387299_1 | BE063921 BE063942 AW601259 BE063918 BE063941 BE063926 AW601254 BE064015 BE063995 BE064010 BE064000 BE064004 BE064005 BE064012 BE063988 BE063994 BE063999 AW601276 BE063937 BE064006 AW601262 BE064018 AW601271 AW601265 |

TABLE 1B-continued

| Pkey | CAT Number | Accessions |
| --- | --- | --- |
| | | AW601263 BE063914 BE063933 BE063922 BE063936 AW601261 AW601260 AW601269 BE063908 BE063931 AW601275 BE063919 BE063909 BE063913 AW601280 AW601257 AW104751 AA909650 AI636164 AI963605 AA634583 AI476578 N41029 AI970121 AI963918 |
| 118381 | 153985_2 | N64513 |
| 124955 | 128540_1 | AA376768 AA121086 AA102312 AW958182 N44159 BE544375 AA102335 AI858272 AA587215 AW603852 AA135360 N36169 AI290208 AA122310 BE243078 AA216644 AW294925 AI279131 AA523335 AI718039 AI298302 AW675772 AW504461 AA573431 AA157727 AI719848 AA101293 AI420820 T08661 AI742968 W40578 W40576 T10598 |
| 124970 | 53587_1 | BE272862 AA451722 AA342154 AW956503 BE001601 W46270 R20126 R18733 R20225 BE068802 R02658 AA093367 N84342 Z45122 AW404957 AA737370 AI268181 D62753 AA436923 BE612675 AW665329 AW276651 AI436023 AA421942 BE082522 AW513555 AA552450 AA902111 AI130683 AA677531 W46271 AI922610 R43184 AI379157 AA436254 R43056 R43316 AA928072 AW135588 AI277543 AA757018 AI290563 R01715 AI286006 AI817546 AI580766 AI809448 AI243390 AA737338 AA878528 BE549899 AA490379 AA677439 AI269156 AI625174 T23799 T32371 AI423766 AI202584 AI867625 AI568784 AA878057 AW801964 BE503376 |
| 134006 | 5164_1 | Z45957 AA977019 AK001319 AW884800 T24618 AW935096 BE077052 BE077059 H30430 AA096374 AA974807 AA991272 AA478898 AA625224 AA487854 BE168198 BE173737 AA336798 AW966519 AW939272 BE168437 BE166482 AA234073 N42386 AI905477 AW062573 BE168373 AW243296 AW082309 BE550935 AA128024 AA659473 AW510824 AA931858 AA128067 AA126620 AI681167 AI829020 AW341066 BE222447 AA126493 AI814350 AW629523 AI340243 AW514576 AI765186 AI332628 AI275546 AI805954 BE467620 BE502644 AA573225 AW271279 AA825364 AA478779 AI982592 AA573330 AI703177 AI738630 AI362767 AI272834 AW514575 AW440959 AI989599 AI769123 AI027197 AW051644 BE465249 AI298527 AI890976 AI299686 AA968889 AI266281 AA935053 AA635761 AA824445 AI400172 AW770719 AA969094 AA975535 AW440812 AA236455 AI653261 AI636923 AA807615 AA971410 AI498399 AI373497 AA973830 AW235436 AI766962 AI253126 AI399784 H30380 AW469278 AW193471 AI493399 AI093994 AI926918 AI468555 AI300692 R60701 AI027391 AI636958 AW263066 T58718 AI521175 AI094088 T32368 AA470382 AW802933 AW802931 AI392989 AA777751 AI926386 AW779202 AI612991 Z41574 AI868604 AI825569 AW590300 AI825092 AA845416 |
| 111157 | 47672_1 | AL109729 AI021970 AI033783 AW292816 AA976653 AI343404 AI829307 AI248462 N68085 AI682705 AA844911 AI014335 AA393642 AA676225 N66613 AA370952 W90703 AA435680 AA985678 AW450047 AW956138 AI692658 AW473059 AA348132 N80524 W90702 R00700 |
| 134032 | 15436_1 | NM_005025 Z81326 R12152 AI133613 AA164563 AA115876 F07041 AA136450 R14666 AI817265 AW903276 AI805394 AA365392 AW959995 AA364817 AA364755 AI742453 AA873052 AI207467 AA165401 AI469988 AA588349 AI797921 AA912147 AA933058 N47859 AI498633 AA773462 AA115877 H09572 AI084579 N59863 AI868483 AW149021 N53887 AW275941 AW275927 R42394 R15085 BE086602 H09005 |
| 110520 | 3910_3 | N54069 AI079533 R97640 H83148 AW517093 AW978663 AI880842 AI659005 H83330 AI684258 AI927403 N35798 AI018674 AA427541 AA938757 AI190040 AI253077 AI744649 AA649064 AW337235 AI308803 AI742133 AW571802 H80392 AA598685 AI263770 AI583731 AI869001 AA609265 AI003434 AA868157 AA936793 AA993053 AW269187 AI290424 AI560859 AI865732 H89866 AI918981 AA609549 AW470626 H67986 F10742 R93584 AI474468 H52072 H86482 R97641 R39279 R96336 AI865468 AI984938 AA640457 H44970 AA029701 R62598 H81129 AA889367 H68025 R96337 H52073 H93374 AI278166 R44303 R37360 H83689 AI290552 BE082698 AW378331 AW378276 AW378300 R92197 AA427540 AA352703 AW953604 H56965 H45023 AA280523 AA029747 R62646 H82927 R23552 R13447 H91145 H68691 R93585 H81033 H80296 H67665 AA516480 H91195 |
| 103328 | 25750_1 | AU077333 M81635 NM_004099 X60067 AI686183 AW401439 T39535 AA302410 AV645727 AV653397 AA317395 AA218862 AA219682 AA227317 AI750900 BE440055 H77491 F12371 AA314714 T74055 AI655647 AA489421 AA346569 AI129523 AA094975 AW793582 R97358 H67966 N72440 H79590 H81459 H60508 R39623 H60900 H40547 AA377244 AA318430 H71201 R64651 R65629 H72546 AW798947 N76974 H03029 N77701 AW151751 H60925 AA455839 H72947 N58334 N55487 AI299891 AA581634 AV651323 AV651728 AV650086 AV651295 AV648042 AW020600 AI537887 AA429713 AW080244 N73463 AA471335 AW150316 AA360851 W01407 BE074301 W21371 T87221 AA190691 D16906 AW862400 AV661466 AI357816 AA442743 AI189966 AW887793 BE005206 AI926016 AA317024 AA976151 AA247314 AI767184 R64644 R62817 D57965 N74437 N74385 H60409 N66059 H91165 R79462 F09991 R26175 H77853 N32590 D56667 AA461122 D56666 D56903 AW021856 AA374084 R69734 H66894 T81638 T63958 W23935 R67668 AW021682 H81249 H61959 H89852 R79306 W25710 W42964 AA384428 AW994316 H95163 H95158 R33688 W46557 AW748451 AA029916 AA463826 AA314287 R23084 AA368891 H02926 AA310456 H03632 C02397 R63745 H94539 R32226 R24648 H44502 AA039671 AA345336 W42846 R48024 R79724 R63143 AA379513 R21780 R80704 T70422 H21580 H46388 R62779 AA579734 N64111 AA344527 AI865473 R66666 Z20058 T52284 H95103 R36513 R21874 R31363 AA220939 BE439695 AI189683 AA164901 AI539383 AA768249 AA442361 W02867 AA303315 AW952009 AA314544 AI076799 AA216780 T70338 AA039672 AW629489 AL044620 AA533203 AA043082 AI668619 AW298204 AW195268 AI1391606 AA437282 AW304801 AW085720 W02586 AA863279 T82339 AI356879 BE464557 AI038992 AI190018 BE146083 AI860399 AI039572 AI129687 AW468134 AI436074 AI963509 AI682239 AW663467 AW129557 AA680298 AA460262 H91217 N57879 R66069 N95684 AA040855 AA227116 N94486 H04229 H97877 AI161080 AI074367 AI025767 AI754185 AA888150 AI356979 R79463 AA029917 R69637 AI810134 AA460820 AI377990 AI743170 AA854637 AA628548 AA664223 AI362196 AA489363 AI361404 AI363155 AA300504 AI678269 AA633851 H61743 AI161012 |

TABLE 1B-continued

| Pkey | CAT Number | Accessions |
|---|---|---|
| | | AW339721 W42847 W46558 AA143120 AI042475 AA479365 AA219592 AW468142 H67696 AI186516 AA531387 AA835378 H03030 T68119 H95133 AL040491 AI289149 R63701 R32177 R32865 AI811374 AI613274 AA775300 AW192882 R37509 W42965 R47918 AI949525 AI129450 H49378 AI435907 AI832271 AA479271 R21849 H03633 AI888539 C75673 AI261394 AA614478 AW469307 AI261429 W03146 AW026141 AW236371 R79725 AA346568 C06197 T27764 H59538 AI749196 AA485299 AA719227 AI698762 N70790 AI925028 R21734 AA977432 H77905 AI625648 AA918868 AI220069 AI352568 AA668729 AA195395 T63334 AI932783 N32271 R26048 H90697 R24539 AI970287 T55374 N93019 T11162 AA377400 AW882126 AA602293 F35923 AI424237 AI826517 H27442 AA039729 AA382630 AI567304 AA045112 T57779 AI474576 AI352569 R63095 H44456 X85116 AI521609 AA164352 BE146079 H60082 AI334776 AA700506 AA782742 R67386 R22978 R33584 R67011 R80705 AI245311 H81590 AI360786 AI219244 R39564 H66850 AI184385 AA687691 H68013 AA092081 AI445480 AW005734 |
| 110561 | 4210_1 | AA379597 NM_014176 AF161499 D60596 AW250547 AA263084 AF160215 AK000504 AI791736 BE619589 AA004600 AA046871 N56803 BE56575 AB032931 AW953735 N56775 AI056896 AI990409 AW376655 AA005074 AW376078 AI337884 AI200949 AI807795 AI023297 AA932357 AI733426 AW512478 N58077 AA910576 AW572795 N27384 AW055339 AW104443 AA904609 N30911 AA911567 AI146665 H13147 AI125234 H67713 AA046828 AA993476 AI377004 AI090522 AA922842 AA505790 AI140513 AI032574 AI355194 AA643701 AA004517 AW249886 AA938964 H59617 H75736 AA985450 N55023 N57685 N32135 AA972188 AI808881 AI672631 AI079135 AA807988 AA705231 N30598 H90512 AA368114 AA622435 AW067367 AW795927 AA864550 AA091926 BE075971 N41842 H13146 H58325 N77541 N64292 H90608 N77212 H64100 H59658 T96922 T97029 H58714 H75871 |
| 133444 | 12849_2 | M63978 M27281 AI811107 W28050 AV649639 |
| 119018 | 176852_1 | AA631143 AI703348 AA225106 AA579486 N95796 AI969820 AA640153 AI587483 AA631024 AA652452 AA652651 AI468280 AI696721 AA579320 AA579735 AA570251 AA492342 AI472447 AA552457 AI984307 |
| 102712 | 12396_1 | U77949 AA232383 NM_001254 AF022109 H59203 W03300 T83032 BE085836 AA113790 BE086769 AI433558 BE565947 AW518847 AA502608 T90351 AA045217 AA830372 AA907374 AA836395 AA813386 AA723372 AI808683 H59204 N69246 AI424746 AI766778 AI341585 BE550416 AI052065 AI699473 AI953729 AI699980 AA099980 AI567411 T85849 AA113200 AW875834 AW608800 AA099840 AI590598 AA233951 T90853 AA788792 AA356355 AW409702 D29175 BE548194 AA210818 AW497626 |
| 133473 | 13028_3 | AW301993 AI305600 AW050452 AI306767 AI289689 AW301832 AW272053 F37364 M19309 AJ011712 F21408 AA620505 |
| 102748 | 8256_1 | BE018138 AW401820 U79528 NM_005866 BE261984 BE407845 BE277280 BE276415 BE275851 BE255885 BE389124 BE312265 BE019581 AA113935 AW368879 C03833 AA279740 BE156147 BE386063 BE386600 AA325860 AW751249 AA296282 AA309501 AL157561 BE258376 BE543357 R48762 R82601 AA135448 AW362528 H81355 AW610370 AW610351 AW957954 AA316259 AW821752 AW821763 AW610377 H58573 BE090207 BE090194 AW606620 AW369343 AW606618 AW363461 R98293 AW374376 AI127995 AI963393 N64225 AA814893 AA156740 AW572566 AW875498 AW608771 AA483617 AA468678 AA845936 AF001977 U75283 AA778401 R94700 AI148384 AI420667 AI808225 AW081100 R67369 AW886677 AW575026 AI591069 AI085323 W47485 R48763 AI936775 AI130869 AW298687 R32351 AA279822 AA767925 BE617533 AW610380 BE261711 AI073481 N58028 AI951949 H58236 AI801362 N31589 AW872950 AA770251 R98053 AA702945 AI803313 W60341 AW473964 H41154 AI927157 AA477980 AI956026 AW771816 AA902628 AA400729 AI686538 BE384763 AA113934 AA987872 AW516129 AA890660 BE548441 AA513291 BE388837 BE386319 W47484 N42600 BE408636 AW196854 AA709430 H81301 R31621 AI718978 AI244069 AW083904 AW615581 BE620020 BE388637 AA636067 AA477979 AW732407 |
| 102759 | 1288_1 | NM_005100 U81607 AF001504 AI796191 AL045541 AA970478 BE350908 AW594487 BE618075 AL041664 AL041405 AW769728 AL040086 AL041983 AL119021 AA296232 AW959775 AA545733 AA344492 M96322 AL041175 AI673283 F11659 F07257 AI281679 AW451038 AA100411 F06749 AL040822 H26057 AA478542 W65406 AA470106 H02800 R62526 R27380 AA159505 AL041580 AL041657 BE378422 N31391 AA010248 AA146779 AA024796 AA032141 T29514 R81732 AA129643 AW900491 AI208015 AA993091 AL040823 AF086250 W68000 H86281 AI803948 H86276 AA907457 AA826591 AI419284 AA888860 AI922283 AA148133 AA047390 AA621006 AW628570 AA729825 AA478543 AI265983 AI186313 AA777453 AL041658 AI039153 AL041406 AA101138 AA094088 AA609075 AA609039 AI446570 AA602322 AA699718 AI160040 AA993512 W67988 AI355176 H95377 AI761641 AA024444 F25831 AI123283 AA191581 AI078016 W61321 N24096 AA581608 AI520962 AA581606 R27381 AA092037 AI242806 AI206886 AA129644 H26013 AI141946 AA047391 AA642821 AA032142 AI655556 H02801 F09320 F03015 R62527 F03530 AA010249 N22255 AA570647 N75280 AA542843 AA835099 AA845150 AL046133 AA082574 AI085443 H95406 |
| 102772 | 25764_1 | U83115 AI065678 AI064965 R78834 AA251227 N98971 AW960425 AI765826 AW272757 AI522011 AA577197 N69832 AI796512 H78699 AA694054 AA251228 AA558167 AI337422 R79329 AI660519 AI800499 AW015732 AA593383 H89714 H12321 H40510 R83261 T53644 AA282101 R97638 AA574200 AW016171 AA847143 AA863087 R67843 AI475399 AA765622 AI282404 R88722 AI810240 AI572819 AA513006 AA931049 AI973063 N58070 AW403490 BE503311 AI189198 AI968748 AI240643 BE551949 H89776 N43164 U52051 AW842100 AW377587 AW388430 AW388316 AW375686 BE242659 R90978 AW747959 AW175677 AW747948 AW500555 BE002933 AW500553 H51690 H78781 AA971992 R67842 H52190 T53643 |

TABLE 1B-continued

| Pkey | CAT Number | Accessions |
|---|---|---|
| 132883 | 4446_1 | AA373314 BE042692 AW135187 AW751673 T30808 T17147 F07527 Z43038 AL110207 N56008 AA295809 AA303946 AA187908 H02145 R82250 R21174 T05429 AA149312 H91287 H47312 T59791 AA327743 AW959920 AA047151 AA042929 W79323 N28243 AW361453 T59658 AI633886 AI825845 AI672514 AI669657 AI917587 AI761837 BE466305 AA042976 AA149242 AW002943 AW662406 AI434624 W79423 AI025949 AI202452 AI635059 H90378 AI373910 AI860143 AI242990 AA972170 H02146 AW237289 AA702239 AA047290 T17146 AI433847 AI086755 AI074424 AI638095 AW303858 AA703636 H62439 AA971818 AA639538 H62425 AI244773 AW104880 AW016719 N23623 R06163 AA961232 AA974465 AI335830 AI991454 AW592598 AW242938 AI611017 AI810716 AW869345 H67615 AI025948 AI420535 AI799741 F34993 AI499542 BE504082 H47393 AI873145 AA918462 R45954 H67078 R06063 H61439 H58198 H61425 R26497 R33068 |
| 134109 | 58458_1 | AA348031 N36289 AA029108 N44785 W32887 AA085513 H99671 N35592 AW025225 N34379 AA908705 H13386 R13339 W02669 W03164 AA938405 D81339 AA197086 AA348647 W03410 AV647005 AA757887 W73230 W73285 AI809089 AA527333 AI096643 AA861288 AA993061 AL119078 N74451 N74398 AA736438 N35475 AW271207 AA782011 AA630851 AI359176 AA911761 N67481 AA470841 W81567 N24828 AA776157 AI220315 AA719560 W35156 AI911196 AA693790 AI023064 AA700944 AA029998 T32810 AA903660 AA991934 AA197014 AI313007 AI244576 AA701095 T32824 N28424 AI620318 AA610082 AI245085 H06050 N42841 Z19860 Z21076 F16768 |
| 134133 | 28210_1 | AA262294 AU076991 D31396 AI750772 AA159676 BE274766 F12663 R59864 R14494 AA393859 BE242904 AB013382 AB013601 X93920 NM_001946 BE302698 BE277522 AA376048 R56303 AW963843 BE303045 AV647942 AA313210 AV645708 AV658608 AV657088 AV656645 AV658779 AA314475 Z44559 R59865 AA304855 AW991466 F10276 R06817 R10611 W03980 T80992 R10613 BE163098 F05427 F05303 T91929 W72835 AA298800 AW389635 AA308036 AA127907 AW389663 AW894164 F12020 T65624 BE175780 H16652 H24811 T59778 BE166275 AA132053 AW290904 AW467431 AI949528 AA120788 AI185315 AI707683 AW020919 AI192556 BE220784 AI342571 BE221591 AW572844 R56221 AA828935 N73917 AW339578 AW613310 T16061 T17184 AW470946 T80993 BE350535 AW088518 BE250462 AA971609 AI085452 D30852 AI418975 AI092872 AI750773 AA779887 AI472189 AI590360 AI913771 AI418318 AA677348 AA857239 AW820356 AA630374 AI570772 AA148198 AA405450 H24635 R06765 AA699326 D45590 AA159077 AW467788 AA776489 T58899 AA639297 AA618367 BE242383 AI814368 Z38329 AW078669 AI925363 AA535062 AA811335 AI361925 AW276471 AI573117 T91845 AW166964 AW665754 AI860504 AI619683 AI491918 BE349335 AI914906 W72836 BE003237 AA610305 AA768101 H16509 AA973395 AA132157 AW304113 AA976980 AA565289 BE207526 AA455254 AA902518 AA856930 AA344776 AI433775 AA446563 AI245402 AI470568 AI167965 AA367742 F09667 AI251112 AA919150 AA302216 AA535575 AI470424 F01686 AI282775 BE349349 AW293481 R62605 T65557 F03626 T25166 AA446688 |
| 104052 | 19362_1 | NM_002407 AF071219 AA297452 AA297456 AJ224173 AA297402 AA297405 AW966513 AW966509 AW510561 AA297482 AW451131 AA393164 AI800231 BE044895 BE044893 AI936084 AI491987 AI659370 AW779377 AA398560 AA493295 AW243774 AA298750 AI937042 AA525178 AW207696 |
| 134142 | 15992_1 | BE244053 AL040314 BE241629 X76061 AL041167 S67171 X74594 NM_005611 AW505566 BE177705 N48402 AW501958 AA095064 N88851 AA093523 AA311592 T16946 R21714 AA181463 H20728 AI240076 AA885217 AA179202 R12761 T29803 N38772 AV661617 AV661687 AI656871 AI680908 AW272833 AA744758 AI807601 AI620692 AI459215 AI333590 AI288993 AI337125 H20729 AA992582 AW241773 R46603 AW772098 AA480678 T16945 AI248936 AI298980 R39808 BE046413 AW502872 AA179192 AA663452 AI753480 AA187067 AA181635 AI754024 AI908250 AI908248 AA460533 AA447057 BE327763 BE327762 AA169617 W24290 BE242332 AW393483 AI910552 BE241508 N42562 AW385629 AW369787 N88431 T75197 AA531494 BE067591 C75198 BE002796 AA160257 AA159758 AL121384 N42147 T07364 AW604888 BE222226 AW610203 BE467093 AI971222 Z24868 W58597 AA034331 AA436730 W58596 N48125 AI201018 N33141 AW516655 Z28612 AA194620 AW303366 AL040073 AW090583 AI651085 AI963161 N31833 AI950136 AI829403 AI638618 BE221314 AA829754 AI040434 AI025340 N38978 AW235932 AA883913 AI418390 AW264746 D57931 AW512616 AI784550 AI559210 AI354322 BE244924 AW518374 AI193259 AW510412 AA460534 AI005669 R43670 AA927423 AA443670 BE245929 AA181203 AA159757 AI624870 AI918422 D58085 AI690361 AI422510 D58004 N50554 D58363 D57416 D56555 AW118278 AA160256 AA678664 F10323 BE067727 |
| 134158 | 16068_3 | U15174 |
| 133507 | 13177_1 | NM_002206 AF032108 AF072132 AF052050 AJ228836 H29373 AL080020 AL047853 AL046489 Z18969 AW950805 T08220 AW498658 BE390321 BE386509 BE390885 AW068588 N84578 AL048523 AL048524 AI142299 X74295 AA194440 AA056036 AA479446 Z98462 AW572932 AW069255 AW068589 H29284 AI148011 AW026097 Z98463 N34517 AA055979 AI128175 AI244981 AI685266 AA194278 AI744738 AI539325 AI888350 F24862 BE208266 AI279218 AW664084 F35707 F24942 F33843 AI300303 AA758310 AI675652 F34015 AA662267 T08219 BE222656 AW168350 F17019 C00848 AI269268 |
| 133516 | 25965_8 | BE265133 D82119 D82548 D82108 BE564452 BE271655 AA159250 AA307115 AW957778 AW957855 BE384770 BE564845 BE613759 BE616283 AA094977 AA090726 BE566205 AI541458 AI905511 BE564334 BE383761 BE543830 BE273482 BE615743 BE277277 BE563390 BE616415 M62898 NM_004039 BE566729 D00017 AW605881 BE262465 Z36789 BE568740 AI541156 BE568537 BE386719 BE621386 M62895 BE569171 BE620550 BE568625 BE564775 AW951474 BE567052 BE564585 BE564336 AA158887 M62896 AA186653 BE569005 BE566752 BE564436 BE568344 AA173037 AA186910 BE615393 BE541140 BE548907 BE385094 BE514560 BE315185 BE615967 BE278660 |

TABLE 1B-continued

| Pkey | CAT Number | Accessions |
|---|---|---|
| | | BE383700 BE386439 BE250047 BE539994 BE249987 BE384668 BE277814 BE541353 BE385626 BE617290 BE265643 BE548769 BE311739 BE408847 BE396400 BE312222 BE540873 BE295024 AA375199 H95312 BE390537 BE315471 AW816692 AA314335 AA370376 BE298921 AW993089 AA304141 AA304371 BE180854 BE379733 AW753635 R79521 BE617783 AA366447 BE569009 AI540902 BE548060 AW838418 BE537832 AI540892 BE621077 BE621678 BE615346 AA652355 BE541787 AA095619 R93371 BE566399 BE293391 AA186441 AA156222 AA155921 AA082679 AA155886 AW383882 BE548278 AI583383 AA176317 BE621909 BE175024 BE379669 T63382 AW838243 T62504 R57147 AW373022 BE180961 AA522706 H58991 BE614628 H41944 T65688 AA075544 AW376033 AW998934 AA071421 AI560134 AA165688 BE393276 H21652 R53923 AA069900 AW391356 H42698 AA186424 AW970677 AW606532 AA890059 AW970552 AI559253 AI984166 H41905 T47539 AI571618 AI540879 AI569320 AI979120 T94131 R69596 AA983300 AW974825 R76210 AA989667 H03427 AA975584 AA151828 H21653 AI582510 AA181033 AA865378 W68332 AW803324 H54786 AI469278 BE149517 AA524331 R35867 AA857151 AI589316 R31675 AW839933 AI284470 AA641473 R37520 AI282236 H58944 AI934113 AA191242 T65704 AA861193 AW196128 AA191415 AI698976 AW087150 AW391335 AI491997 AI654288 AA654567 W46513 AA160136 AA570680 AA187787 AA301838 AA128660 H72633 R33225 N59561 AW373026 AA157247 AI472515 AI554440 AI754953 AW373014 AA160337 AW362293 W46445 AA725273 AA302349 AI583039 AA661718 BE150340 AA243223 AI916458 AA312977 |
| 133534 | 10_1 | AU077115 NM_005778 AF091263 AA558755 AF103802 BE264911 U23946 AA300552 AA300658 AW366740 U73168 BE168234 AA701451 F12188 AI082769 BE304364 Z44416 T64836 AI360219 T99027 AA053236 AA287188 AA705726 AA677451 R21564 W76177 T10051 W73892 AW805335 AW803972 AW935657 AW818294 AW582571 AW858746 AW862020 R37062 AW818366 AW935675 AW949579 AA349791 AA337186 AA369780 AI424264 R45829 Z19624 BE386598 BE391503 AW370456 AI907719 AA593262 AA165466 BE184217 AW884123 AA437179 AA249486 AA367141 AA150882 AI719148 AW662385 AI678082 AI338755 AL044121 AI984749 AI378242 AW080371 AI783726 AW087565 AI351171 AA746150 AI016061 AW862035 AW858817 AI140331 AI831099 AI147008 AI049957 AW182561 AW131871 AA421795 AW103460 AI160679 AA192645 AA773506 AI760715 AA382385 AA889659 AI184597 AI352518 AA570533 AI688574 AW023887 AW473505 N23866 AI689425 AA194028 AW001960 N41616 AI377087 AA699426 AA782487 AI192743 AI140138 AW469862 N29616 AW572110 AA767408 AA192891 AI378243 AI969394 AI923316 AI248994 BE221340 AI076411 AW004939 AA907700 AI247959 AI367846 AW769860 T03540 D19618 AW193738 AI274002 AA724105 AA907774 AA648939 AA904276 AI225052 R45218 AW614769 AI086090 AI417666 AA677951 AA456007 F09819 AA961715 AW149264 AW078952 AI750024 AA659891 AA150773 T31362 AW510627 Z40342 T10050 AA670261 AA563802 T33106 R42942 AA994080 AW512057 AA877988 AI198734 AI653943 AI217242 AI127650 R60960 AI539540 AA782825 AA953465 AW074329 AI701674 AW874346 AA917711 T32698 BE221007 AI125018 AA194215 AW378414 AW378418 |
| 102808 | 28015_1 | BE242818 U90426 NM_005804 BE536818 BE244194 BE264529 BE246230 BE264674 BE266815 AA171779 AW248283 T58690 T34341 AW249231 AA101544 AA315491 BE549048 T34339 AW410813 BE266543 H10115 AW248304 AW248140 BE312083 T35401 BE273547 T34515 AA173847 BE560244 AL079696 T34244 BE389128 T34110 AW249130 BE266743 T04892 BE264706 BE264738 AW403234 AW401535 AA456984 BE207185 AW247060 AW998463 AA121373 AW994780 AA126661 AW407083 AW379415 AW578239 BE018419 AA366688 AA608513 BE378292 BE378337 AW103935 BE397789 AA302580 AI690498 AI697283 AA403211 N85842 AA463406 AW006584 AI589068 AA780276 AI871938 AA626835 AW439624 AW272829 AW512621 AI183842 AI591229 AW337254 AW410814 AA608753 AW009146 AA303726 AA456910 AI627190 AA877724 AW337702 BE302029 AI265957 AA775202 AW248698 AW245062 AW250412 AA173796 AI554428 AI244134 AA976264 AW086156 AA587634 AA425288 AA121363 AI377104 T58642 AA812669 AA812844 AI142489 AW074600 AI149028 AI588887 AW249803 AA425377 AA548184 AI919273 AI363195 AI344708 W76340 AI818834 AA622965 AI568201 AA101545 N52934 AI049533 AA609990 H10061 AI866342 AW182709 AA864718 AW248899 AA805143 AI289603 AW103872 AA171533 BE246291 AA460465 AA772204 BE243011 AA961876 AI382421 AI374630 AA604245 AI927540 AW136766 AA857850 BE327421 AW248810 AI869885 BE075382 AW408520 AA126563 AI471177 AW873754 AI280817 AI810212 AL039534 AL043443 AL046346 BE311964 BE408579 BE264809 BE266189 AA878026 AW965697 BE300560 BE294790 |
| 132904 | 11829_1 | NM_005518 X83618 H67752 AL048890 H83167 U12788 T48046 H53231 AV651015 U12789 H58906 H69259 AW950626 R99877 H56562 T83307 T72708 H78447 R98317 R07226 H80163 H57249 W16627 BE165655 BE085686 AI131009 AV661764 AW364610 AI131228 H53907 H52949 H53464 H95832 AI572027 AI814698 AW862318 AI198645 AA527187 AW009039 N58299 AW361996 H67753 AI720565 AI271867 H53586 AA632458 AA496148 N78771 R98318 N74572 N57819 H66061 R99878 H69260 AW579063 AA496149 T72639 AW579084 AW579090 AI720178 H53125 AA398049 H48552 AA902856 R07174 AA995967 AA399107 BE045173 H78246 H58907 AI025465 AI223006 H94247 AA701417 AI081316 AA687814 T48013 AA661737 AW193061 AA342948 H95833 U81860 AV649759 AV660900 AA659470 AV661937 AV661790 W92241 H66108 AW845212 R91694 R91952 N77665 AW860037 H67807 |
| 133579 | 13380_2 | X75346 AW651720 AW389703 AI015618 BE280175 AA918165 W58725 BE294557 AI024833 BE176376 AI248432 AA171560 W69432 AA400549 AA355384 AW579403 AA815466 AI025585 |
| 102838 | 16362_1 | R34657 AW500183 AJ223477 AF019409 U82819 U76367 NM_003355 BE159769 AW328072 BE514976 BE168044 AW402918 AA331988 AW375453 BE168395 T81698 H27213 AW842834 AA411271 AA298140 BE547677 BE393335 BE162651 AW382467 BE085672 BE166619 |

TABLE 1B-continued

| Pkey | CAT Number | Accessions |
|---|---|---|
| | | BE162581 R11086 BE091612 AW805420 AW947339 BE091755 H61242 H27399 AI630458 AW351489 AW366837 AI560571 F17808 AW188957 AI523437 U94592 BE174858 BE246787 AW403977 AW403235 BE383579 BE560842 AW402066 BE264709 N58719 AI524553 H80695 BE019834 AI133329 AW793563 AW402721 AW406910 AW675332 AW945204 H43787 AA299669 AI862992 AI885914 AI358861 AI951018 AW328073 |
| 102846 | 4725_1 | BE264974 AW245788 BE313711 BE336907 AA972912 U96131 AI358369 AI813492 AW292892 AW341586 AA806168 AA521372 BE315517 BE268193 AA630784 T74142 AA292903 AI141851 AI122551 AA114129 AI183966 AA461026 R94450 AI183968 AA668813 AA401737 BE090548 AA504581 AA134541 AA251208 AW967466 AW161726 AI890569 AI018417 AW162098 AA114284 AW245430 AA716100 BE349100 AW007741 AI885478 AA035686 AA456703 AI590851 AI126434 AI745513 AI572647 R84564 AW161707 W87693 AA456305 AI274246 AA251127 AA063557 AA129647 AA504500 AA524578 AI473676 AI222896 AI222899 T16428 R12705 AA005213 AW591056 F10153 AI383949 AA460677 R94449 |
| 132932 | 60605_1 | AW118826 AA151563 AI867993 AI831098 AW072445 W79392 AA937448 AI804017 AI803482 AW512279 AA862490 AI377076 AW150792 AI707481 AA482606 AA157343 AA357829 AA961039 AA195364 H07932 T59940 AI336627 AI332879 R44897 AA834366 AI753503 AI565390 F08889 AA872967 T15482 AW079827 AA149653 |
| 133592 | 62567_1 | AV652066 AA459880 T58512 T58561 AI651255 N49838 H87921 AW264447 AA428067 AA364094 AW955685 D62894 AW341452 AA243652 AI984618 AI816803 AI871252 AI376942 AI740496 AA452836 AI277917 AI149141 AA456147 AI784566 AI003975 AI245674 AI433703 AI200208 AI268985 AI382921 AI201946 AW304852 AW262780 AI168633 AI468793 AI659125 AA813519 H88317 AI474943 AI382763 AI758206 AI932757 AW955686 |
| 102859 | 14722_11 | AL036058 AL037821 BE244754 AA633954 AW874156 J00204 X00274 AU076840 AI911758 AA486674 BE243874 BE244440 H80088 AI672278 AW404700 AA075663 AA340244 AI301059 AI279790 AI279121 AA341678 AA337350 AA377117 AA436303 AA318490 AA318518 AA318216 AA318721 AA164191 AA318521 AA340447 AA318692 AA318214 AA318475 AW961124 BE396704 AA361838 AA370148 AA376997 AA361329 AA158653 AA352110 AA336391 AA381483 AA075540 AA360644 AW608508 AA361406 AA360490 AW404260 R48091 AI922305 AW402867 AI492745 F05172 R56328 AA337028 AA345741 AA025072 W31336 N94117 W17387 H05357 J00197 M60334 J00194 AA361435 AA761383 BE560529 AA351514 T59813 AW751976 BE514145 AA811273 BE560289 BE561458 BE561470 BE561464 AA352431 AA360193 J00195 AA360735 AW801456 C03921 K01171 AW794714 M35979 AW405331 AA361961 AW630491 AA075553 AW405388 H51680 AW406319 AA381957 AW800697 AV654447 AW407714 AA360590 AA046360 AW404389 AA464089 AW404727 AW392841 AW606266 AW392862 T98228 N76250 J00201 J00196 V00523 AW392850 AW392895 AI439867 AW392851 AW392907 AW392868 AW392870 AW392877 AW377720 AW392869 AW797456 AA486999 AW797463 AW797491 AW939881 AW373825 AA995583 AW938637 AI904703 N41665 T94141 AA634845 AW406658 AW407964 AW404554 AW797413 AW407119 T85518 AW404585 AW385331 AW802223 AA225099 R73988 T89830 AW797521 AW351452 AW351451 AW797414 AW404847 AW407472 AI188765 BE007158 BE169067 AW798425 T93218 BE168398 AW405498 T89816 AW797412 BE620544 AA075781 AW797416 AW878958 AI904300 AA384579 AI887700 BE620111 AW608478 AA991488 AW797537 AW797528 AI439254 AW803869 AA634086 AI439244 AI819573 AI523528 AW803896 AI291284 AI708917 AI357084 AI683367 T92638 AW610199 AW804946 AW392647 AW404194 AW971991 AI937346 AI829988 AI076332 AA360880 AW798412 AW089496 AW404361 AW405148 AI559563 AW007406 AI446040 AI817534 AI434538 AW805246 AW405196 AW194248 AI830979 AI887234 AW887286 AI971647 AW794709 AI758709 AI819619 BE177342 AW027056 AI829829 AI572905 AI818621 AA487097 AA846539 AI439772 AI927714 AI566480 BE164752 AA360901 AW473808 AA902751 H51999 AW798510 AW516038 AI734903 AW385341 AW794589 AA295123 AI956032 AW172887 AW512502 AW072051 AA075664 AI862788 AI963694 AW467426 AI572920 AI819420 AW440267 AI634295 AW515930 AI246033 H47714 H47709 H82665 AW080422 AA295963 AI472760 AV649679 AI445260 AI569116 AI242861 AA860506 AI434332 AW515934 AI719176 AA075729 AA627386 AW519007 AW806335 AW804315 AI573087 AW474057 AI913450 AA514999 AI819471 AI351777 AW794585 BE465694 AI687236 BE042574 AI223118 AW073985 AI692801 AW518189 AI862861 AI831317 AI687668 AI246466 AI671685 AA287225 AI735479 AA654585 AI627720 AW385375 AW518150 AI572865 AI632415 BE220947 AW385377 AW385364 AW385358 AW196648 AW383929 AI817364 AW934780 AW935166 AA166997 AW935226 AI034011 AA662669 AI285689 AW385368 AW513697 BE221244 AW474768 AW273352 AW518869 AI865411 AI240252 AA729055 AW664326 AW169175 AW130819 AI440131 AW572839 AI912407 AW945256 AI242849 AA436176 AA595635 AI204660 AI912483 AA775218 AA668966 AI023617 AI687808 AI582977 AI634920 AI694075 AW518127 AI434958 AI572605 AI817520 AW130831 BE047396 AI627994 AA595639 AI250418 AW088270 AI950857 AI826898 AA614624 AI434297 AA677055 AI285681 AA362302 AI281621 AI865434 AI247986 AI285474 AI061391 AW575830 AA662665 AW515379 AW512025 AW575951 AW797261 AA782227 AI814962 N90939 AI289051 AI687936 AI476180 AA318379 AI434022 AI249911 AA579750 AA486576 AI925838 AI619636 AW474017 AI446079 AI127996 AI864769 AW518165 AI225137 AI471804 AI431517 AW337504 AI434300 AI250354 AI097357 N98394 AI289996 AA975244 AI312644 AI273628 AI433488 AA167336 AI188818 AI439523 AA580264 AW797217 BE501592 AI203650 AI160510 V00528 T59677 J00200 AI439813 AW798943 AW383701 AW383725 BE045310 AA708106 AA293558 AA854679 AA806098 AW130065 AI370164 AI864770 BE501599 AA729896 AA857636 BE138744 AI077331 AA806099 BE143093 AI926401 AA225098 AI250439 AI275981 AI190280 AI250421 AI628049 |

TABLE 1B-continued

| Pkey | CAT Number | Accessions |
|---|---|---|
| | | AA166826 AW798868 AI313364 N54547 AI439271 AA860728 AI168825 AW337794 H48066 H48061 AI804055 AW796048 N98344 AW376713 AW849094 AI708812 AA974257 AW190807 AW769809 AW382573 AW385330 AW578339 AW578340 AW849128 AW392368 AI623811 AA024976 AA903302 AI168497 H24508 AI311134 AI141980 AA680240 AA643036 AI354511 AI758759 AI807641 AI432737 AI382961 AA405841 AI276301 AA719753 AA970345 AA169607 AW382577 AI440321 R56246 AI432911 AA588731 AA879138 H51095 AI275795 AW797274 N80222 AA236638 AA405759 AI864777 AW391618 AW797231 AW805252 AI277575 AW945195 AI250366 AW945196 H05307 BE171370 AI280820 AA886135 AI358036 T92944 AI242424 AA689250 AA705721 AI922249 AA654400 AI802706 AA828751 AI434222 AA975543 AI783920 AA541291 AI357293 AI865283 AW118463 BE244535 AW088998 AI358323 AA992332 AI220691 AA411058 AI274607 AI708927 AW474369 AW515828 AI873552 AA046296 AA836958 AW794708 AW794595 AW338835 AI250682 AW603808 AI468837 N92452 AW385909 AI571563 T73846 AI624371 AW608209 AI290064 AW105658 BE043329 AW581135 AA996306 AW579285 BE049404 AW581148 AW608250 AA159063 AA633965 AW608220 AI633060 AI952191 T89719 AW802096 AW581231 AW608243 T74248 AI433381 T28468 AA804318 AW518376 AW385913 AW083674 AI434034 AA938397 AI568283 AI249444 AA429884 AI719349 AW242259 AA429853 AW083900 AI738855 AI918581 H52597 R96654 AA341390 AA293559 AI680255 AI356472 AI472682 AA676709 AI718177 AA164192 AI339296 AW797221 AW511915 AI589416 AA953338 AI500000 AA876313 AI620034 AI865454 AA659294 AW474126 AW518454 AI719715 AW591921 AW379873 AI224057 AW302596 AI540725 AI499983 AI865593 AA728993 AI982586 AI865084 AA635760 AA946758 AW103642 AA742526 AA343052 AW474659 AI468868 H82407 AA485278 AW518420 AI468940 AW801881 AI497706 AW798431 AW802047 AI865054 AW806331 AI865359 AI468879 AW575637 AA463953 AA974229 AA634007 AI500079 AW132051 AI566981 AW518558 AI344428 AI865335 AA341031 AI864785 AA340691 AW377744 AA888268 AW084380 AW798443 AI250368 AI311592 AA884560 AA876296 BE043978 R47979 AW132040 AW194504 AW131929 AW868536 AA659167 H78841 AW868510 AW868566 AW795288 AI500092 AW868513 AW795236 AI702370 AA931740 AW150418 D57484 AW571419 AA340651 N69295 BE041339 AI699286 AW338685 AA283456 H52117 AA746160 F01419 AI865055 AI660260 AI920895 AI718157 T63514 AW627467 AA865201 AW190214 AI735415 AW768581 BE241961 AI758965 AW264843 AI828746 AI478245 |
| 132959 | 93073_1 | AW014195 AW236028 AI652095 AI927228 AI380704 AI824939 AI949156 AI916799 AI823483 AA977296 AI478932 AI767924 AI878836 AW001812 AI335537 AA028103 BE466764 AA501553 AW611647 AI470601 AI760094 AA636041 AI436769 AI359669 AI279500 AA625548 AI879396 F35913 AA307748 AA028124 AI419586 |
| 132967 | 11897_1 | AA316181 BE439545 AC005053 AF186249 AW386101 AC004969 AA730199 AA032221 AI686139 AI167942 AA809228 AI184070 AI394674 AW969977 AA032279 AW079284 AA513174 AA888312 AI453179 AA483363 AA528432 AA579511 |
| 117921 | 9346_1 | AA021459 AL157453 N48694 AW898879 H08850 N46609 AW014561 N51002 AA482856 AA482842 AA482868 AA885753 AI628670 |
| 117929 | 354923_1 | N51075 AA570794 AA568306 N51516 N51117 AA708939 |
| 104189 | 36097_1 | AB040927 AW503387 AA044786 AI686957 AW157364 AW976667 AI752687 AA191323 AA568170 AI161414 R17699 AI140787 AI140789 AI140788 AA742642 AA044809 AA485805 AA847859 AA480178 Z45709 AW974554 BE043079 AA809758 AA648838 N46563 AA485676 AW304745 AV657192 AI553650 AW118847 AI871278 BE075093 AI243817 BE046860 AI560949 AI669278 AA860508 N39152 AW131465 AA767854 AI457964 AA906227 AA719622 Z41372 T93491 AA954262 BE537985 T96329 |
| 133626 | 13594_1 | AW836130 AW835974 AL050139 N55404 N50647 H65865 AI144372 AI017049 AA705406 AI307184 AI022705 AI968431 AI085083 AA626205 AA425498 AI742520 AA741124 AI142763 AA907209 AW172328 AA287645 N49379 AA953874 W16717 AA301311 AW954269 AA197034 N55846 BE090804 R53137 Z44364 F13150 R20711 T75455 R14200 H20627 R25071 N49469 AA286797 AW008192 AA703511 H70281 Z45243 AA773797 AA773413 BE003771 AA194861 R08091 T82191 AW992244 R36356 AA214332 H70005 R99487 R30887 AA281025 AI608650 AW272887 AA196596 R91025 AI951974 AI832818 BE539680 W37344 H26029 AW609768 AW372093 H88114 W20231 AA022846 AA699455 AA732984 R35984 R45410 F19000 AA425222 AW502919 AI805635 AW150239 N52927 AA196999 R53051 C16460 W37345 AA196597 H20534 AA214291 N33356 AA922316 BE302395 N79536 AA211465 T17038 R37483 AA704178 AA280828 AA680417 AI022452 R30818 AA927124 H69548 H75939 Z40299 F04137 AW089314 BE538997 N90592 R99488 AA501818 AA501883 R98376 H88115 R39229 AA022735 R88766 F10753 |
| 103546 | 14163_1 | Z14244 NM_001866 AW293449 AA373029 AI209213 AW023613 AA629999 C05067 BE185552 AI633443 F31015 D54638 AA362610 W93971 AI057576 AI435557 AA328050 AW327525 AA380084 F26749 AI269382 D55420 C05612 AA729559 AA854074 AW327577 AA362524 AA501364 F25447 F30058 F30458 F32332 AW950628 AV656809 AA374630 F30443 F30670 AI750060 AI041671 F19421 N55333 F35876 AW005526 AI189185 F36277 AI250898 AI031955 AI278272 AI417083 F22157 AI027095 AI806069 AA351962 AI246785 F22562 AI721231 AA354796 AI832784 AI080588 AI139984 AW391514 AA938681 F34040 AI799736 F20642 AA450071 AI041395 F25781 F31026 F26799 F29253 AF042164 AA770218 AA704607 AA447584 BE466635 AI708614 C17594 AA365685 F27273 AI880366 AI832710 T29546 AA715342 F33426 AA664822 F35584 AI097193 F16349 AI688436 AA725197 AA335860 F17677 AA336167 AA974878 F34245 F35499 AA363970 AW779910 AW265335 N29683 AA482887 N86053 AW449724 AA448083 N40786 N56699 AA136905 AA559990 AA086263 H62149 AA004253 N77338 AA452719 AA256349 W56125 H49485 AA658922 N56693 AA132296 AI832633 AA128449 AI749836 AA564094 F33633 AI719308 BE047545 AA004674 C17693 N87723 T54528 T54567 N86261 AI129001 AA654738 AA916211 AA908340 AA876815 AA132212 AA855135 |

TABLE 1B-continued

| Pkey | CAT Number | Accessions |
|---|---|---|
| | | AA737883 W93972 AA506139 AA846271 AA702006 AA715260 AA908337 N40794 R28778 AA096165 AA355108 AW844162 AA880091 AA993050 AA733059 AA136876 C04413 C05425 AA091340 |
| 103554 | 13065_1 | AI878826 AI929158 N31103 AA347183 AA248217 AW961707 N87005 C17652 AA369211 Z18951 H68602 NM_001753 AA328468 AA088613 R68436 N39694 H01840 AA032028 AA047106 AA093459 N83187 C18904 AA159249 AA055368 AA373326 R30895 R28121 N48403 C04762 C16932 C03435 AI335280 C05249 AA188337 BE502929 BE504257 AW612216 AI214662 AW103859 H02347 R83227 BE348483 AI609212 AA715541 AA082794 AI879387 AA031927 AI130038 AI352534 AW242202 R57424 BE220867 AI336460 AI936424 AW096694 AI278810 T29057 AW972291 BE440165 AA810380 AI986274 AA935254 AA568957 AI359149 AA919163 N26590 H39849 AI372934 AI093262 AI075302 AI288547 H97367 AI193751 AI304816 N38775 N33790 AA159152 N66822 N26607 N21174 AA972833 AI268920 AA483005 AA047243 AI752222 AA639275 N34192 AW972286 R83228 AA513168 AA736916 AA484741 N86668 AA516059 AA736624 AW573564 AW573565 R30850 H24902 AI124038 AA487841 H02249 H21816 N72018 D58100 AA055835 W95609 N21091 W80871 BE173251 R60642 AA076608 D59158 C18549 H25070 AA502449 AA502557 W95608 AI561190 AA648092 AA516043 AA648083 R28011 AA483471 |
| 103556 | 10005_1 | Z19002 NM_006006 F00118 AA428940 AA296151 AW960240 AW954317 AI937150 AA845269 F35964 AI198303 F36156 AI832425 AA296152 Z19413 AA614232 AA642184 AA468119 |
| 133666 | 3657_4 | U56725 AL044372 BE259102 R30669 AA470119 L26336 AL046354 F07578 AL044984 AL039371 AL041486 R16445 AA348532 AW949548 AA495899 AL044373 AW243287 AI937198 AI796545 AI927985 AL041487 AI138624 AI923726 AI424368 AI720471 AI422082 AW890976 AW795342 BE349077 AA186792 AI205684 AW452365 AA626358 AA593734 AA128358 AA425007 AI631354 AI580818 AA426338 R12701 T24102 AW195491 AA469947 AW195225 AI081532 AI862189 F03817 AI478136 T28755 AA644433 AL040890 AL040891 AI567406 AA455102 |
| 102938 | 31360_4 | W27518 W28655 W28159 BE396144 BE314414 BE563881 AU077239 BE387326 AW246409 NM_002300 X13794 N87540 BE409589 AA094603 BE561785 BE379931 BE379847 BE560681 BE279936 BE539753 BE612385 AA075862 BE540692 BE540512 BE407898 BE314552 BE563751 BE385102 BE384918 BE388054 BE543067 BE271640 BE409074 BE278029 AA079712 BE515315 BE614966 AA167755 BE278078 BE390807 BE256727 BE278776 BE255634 BE384282 BE540166 BE382485 BE313298 BE395565 BE539775 BE383247 BE394835 BE394810 BE256034 W25756 BE613058 BE379778 AI907279 R09283 AA148289 BE255657 BE379045 AI540576 AI214096 W26070 AA047609 AA746661 F00798 AI275737 |
| 133688 | 5059_1 | U71321 NM_004117 AW500704 AA382675 U42031 N89070 AW590202 AA096449 AW852097 AW501471 AL039381 X97300 F00724 AA345703 AW963258 AL046274 AL045832 AA343895 AI088938 AW963084 AI631283 AA215901 D31377 D30980 D31048 Z28555 AL122066 AL042080 T32481 AI858005 AA294869 AA331701 AI366055 AA360668 AA055614 AA366258 AA366751 R01287 W87312 AA337314 AA385665 AW965077 R72262 D80933 AA370514 AW953859 AW957227 AW957225 AW954027 AA361257 AA343512 R45763 AA449044 AL046951 R45888 H53905 AI791369 AW889729 AA682530 AA345306 AA460554 W86302 W86653 AA705036 AI248463 AA694353 AA678103 AA932445 R01175 R72263 AI033456 AA976417 AA678744 N98804 AA872768 AL039382 AI700793 AI700784 AI220884 AL042081 T93673 BE218475 T25877 AA149239 AA814647 AA492261 AA058961 AA058962 AI679222 AL046952 AI140732 N59657 AI090508 AI096484 AA653318 AA769298 AA833776 AA789188 H53584 AW182642 AW771369 AI914759 AI283811 AA393250 AW337761 AA180323 N57686 AW264434 AI982716 AA873458 AW338312 AW518896 AI023192 AA804811 AI749139 AI130821 AW241260 AA612811 AI250235 AI168023 D60564 AA604012 AA868902 AI367342 N63715 AI055853 AA460555 AA631804 AA435612 AA767954 AA449758 AI351788 AI473448 AA596073 AA854081 AW079219 AA876551 AA617927 AI352199 AW976940 AW105227 AA989268 AA813062 AA370513 AI620591 |
| 125819 | 33253_15 | AA044840 AA044815 |
| 119267 | 110609_1 | AA064970 BE503073 N67391 AW590678 AA985587 T16327 T31477 |
| 126487 | 29209_25 | AA283809 AA482656 AA482505 |
| 102962 | 3947_2 | R50032 BE272542 BE273850 AI207796 AA449892 T52072 H80951 AA478186 AI752477 AI002190 AI678075 W32734 AI084634 AW340003 AL048379 BE049470 AA055941 AI097665 AW190504 AI220113 AI925471 AI921276 AI954135 AI889263 AI422681 AW338076 AA460424 AI262481 AW471355 AI888330 AI955667 AI192464 AW173487 AL041495 AA037436 AA085884 AW081135 AW083505 AW338916 AI628329 AW173532 AI865753 BE068259 AW058253 AW337211 AI925277 AW069174 AA777033 AI983508 AA522923 AW007447 AA928714 AI955927 AI912869 AI752381 AW069151 AW262741 AI419543 AI262262 AA905138 AA617845 AA603114 AA603119 AI982865 AW950575 AI985905 AI217509 W58186 AI935894 AA024736 AI261241 AI034277 W58463 AI222809 AI143266 AI340360 AA516134 AI445983 AI147573 AW589490 AI452671 AI245974 AW068643 AI568995 AA531262 AI800195 AW614789 AI683399 AI094326 AA010450 AL043271 AW104651 AI090519 BE047659 AW582669 AI811424 AI042459 AI376251 AW068644 W93689 AI368075 AI150830 AI500678 AI203947 W74334 AI347032 AI926836 AA024701 AI078415 AA134139 AI752654 AI373142 AI274356 W69433 AA788926 AA600021 AI368734 AA776378 AW572571 AI274128 AI751692 AA974251 AI339891 W84338 AI339892 AI683553 AI438929 AI148296 AI276799 AI358398 AA432017 AI160879 AA709032 AI274927 AI660462 AI074426 AA922713 AA837826 AL046012 AI127095 AA570023 AL044156 AA622932 AI459385 AA722671 AI304662 AI285361 AA705536 AA600036 W60748 W81037 AA668638 AI569547 AI624609 N78758 AA009718 AA515646 AI500679 AI191385 AI077918 AI679977 AI434187 AI499365 AI753338 AI950993 AI203412 AA460425 AI124084 AI095241 AI191662 AI304793 AI963540 AA913941 AA885312 |

TABLE 1B-continued

| Pkey | CAT Number | Accessions |
|---|---|---|
| | | AI139300 AI262525 AI445862 AA055830 AI123114 AI285401 AA588776 AA704872 AI350824 AA486479 AA477436 W68183 W67724 AA009828 AA431767 AA059311 W60858 AI859196 AI358197 AI825980 AW205848 AI282910 AA179654 AW005965 AW014178 AL047327 AW139796 AI873755 AW192856 AA039362 AI087231 AI141935 AA936234 AI338218 AA464748 AA063267 AI092481 AW085685 AA039575 AI982866 AW173430 AI282727 AI754334 AW272157 AI826188 AA195202 AI752541 H80856 AW665920 AW169562 AI863317 AA954341 W58005 AA411120 AA022695 AW069323 AL047329 AA195231 AW134860 AI750968 AI741849 AI751231 W58259 AW089674 AI186339 AA853566 AI590633 W58088 AW014564 AI880250 AA344158 AI131070 W81074 AI049815 AI073348 W58435 AA227175 AA496550 AW168598 AA872429 AI190794 AA478028 AI193735 AA055562 AI537541 AI018639 AW135662 AA853014 AI565886 AI915736 N36240 BE350339 AI750746 AI090756 AI753814 AA853251 AI753168 AI150013 AI249338 AW779255 AW027669 AA852109 AA291980 H72094 AI473398 AA455219 AW196020 AA293319 AA411063 AI682585 AI916014 AA732770 AW083712 AA372104 AI952485 AA250766 T47329 AA454876 AA055831 AA853849 AW241683 AW516455 AI553637 AA151152 AA917756 AW166676 R38279 AW068143 AI186543 AI568846 AA523307 AI377115 AI278710 AI438937 AW168364 AI339639 AW610027 AW581390 AA151151 BE160808 AW580749 AL041494 X15882 AI752382 BE070683 BE070760 BE070596 BE070533 BE070563 AA330678 AA852978 AW067943 AI750456 AW965539 R74150 W81216 W84399 AL360197 AA479598 W44622 AW068813 T53493 AI750988 AA464042 AL042608 AA041497 W93741 T48390 AA027307 AW608273 AA026716 AW836401 AW610000 AW610072 AW610039 AW610063 AW610065 AW819387 AW610067 R71719 H72195 AW610055 AW610003 AW582668 AA045209 |
| 102968 | 24693_1 | AU076611 BE243124 AA343955 AA102186 AA307928 AA227387 AA314740 N86980 X16396 NM_006636 BE544371 AA361582 AA353457 AA172125 AA362045 BE545634 AW935573 AW368435 BE569039 N83453 AA354875 AW504993 W31001 AA281820 AW365599 AW365610 AW365606 BE542972 AI871407 AA480994 AA406118 AW387154 AI638274 C16082 AA210794 AW073141 AW365614 AI393287 AA282659 AI423141 AW365598 AW241512 BE466661 AI037877 AW591887 AW188655 AI683945 AA480995 AW365577 BE090663 AA171977 AI762124 AW875574 AI423138 AW951169 AW134804 AI263972 N98720 AA137110 AI439485 AW608789 AA551270 AA362384 AI739051 AA362456 AI917450 AI990317 AW205913 AA136984 BE503354 AI497794 AI003085 AI421923 AI458196 AI623243 AI672568 AI885912 AI351770 AW105422 AI588936 AW074512 BE467565 H99810 AI361330 AI127546 AA744500 N33204 AI268109 BE466041 AI568274 AA604783 AA865276 AW264668 AW473635 AA555020 AA410386 AA827245 AI337076 AA831189 AW272618 AI027573 AA312452 N35312 AW132154 AA404966 AA743094 AA759005 AA962299 AW769670 AI633795 AI867952 AA868173 T29190 AA814513 AW795635 BE243300 H60660 AA336544 BE537606 N44740 N44684 AA307129 AA312596 |
| 102976 | 14633_1 | AU077174 BE616323 W25010 AL110099 NM_004390 X16832 AA305392 AW391441 R35036 AA309061 AA360805 AW815440 AW815685 BE171565 F06637 R18814 R64213 R68725 X07549 W78193 AA336414 Y18461 AW581172 AA054490 W95582 AA487325 AA487346 AA279600 H96491 AW969271 AA345648 W68555 AA992941 BE563114 AW976109 AI096690 AI122617 AI749481 AW026323 H69902 AI886820 T62554 AA283118 AI198774 N95617 W00965 AA593005 BE222876 T63395 AI004598 T91528 AI582812 AI126013 AI937274 AI031991 AI312045 AA844465 AA743166 AI872897 AA677296 W94703 AI380769 AA843780 AA908172 AA954631 AA864193 AA810948 AI189126 AI348197 AA844566 AI348198 AI299069 AA487231 AA996357 R43924 AA975404 AI138666 R49416 AI809565 AI090030 AA282919 T91499 AI057198 AI932538 AI078631 AI089500 AA973763 AI342332 R68673 W94575 AI363106 AA826054 AA760624 AA514570 AA682652 AI915535 AI224395 AI144333 AI362094 AI985969 AI436458 AA977082 AI335950 AI869230 AW572267 N70240 AA936650 AA827009 AI819708 N62614 W68211 T63952 N89602 AA918662 AI375214 T60000 AA873140 W95475 H73602 AA470367 AA775340 AA507672 BE139205 BE349596 AA903018 BE350901 AI827327 AI281432 AA548365 AI963342 AI985929 AA630102 AI955620 AI744996 AA487172 AA838328 AA658289 AI362589 AA872881 AA470832 AA659748 AA058337 AW512820 AA644662 AA502165 AI720562 AA865348 AA621446 AI267923 T59931 AA864686 AA582752 AA782286 AA768026 AW021729 R49423 AA622952 AA627103 AA913103 AI565188 AI869711 AI335624 AI363105 F02909 AI123813 AI919432 AI560364 AW591804 BE243287 T63540 AW518413 AI142065 T29691 AW963949 C02398 W70329 AI951124 AA747317 AI205593 AA947141 R64116 H73830 AA587498 AA532564 AW815511 AW815773 AW815836 AW815686 AW815435 AW815441 AW815439 AW815826 AW815760 AW815442 AW609595 AW815628 AW391443 AW815775 AW815825 BE254396 R35029 AW946116 T63330 AA886716 AI355072 AI378131 AA812294 |
| 102992 | 24839_13 | M85430 AU076495 R06237 AW604847 AL162086 AA100051 AA158333 R01021 W87566 AA125842 AW503043 H30655 NM_003379 X51521 AA300214 BE293620 BE250025 AW505317 W61195 AA226978 D58824 AW499841 AW163414 AA251998 AI816093 AA152399 BE312481 J05021 BE535236 AA305199 AW407614 AW408681 N77970 AA312609 BE001280 AA877541 BE536355 AI269050 AL048877 BE064504 W39373 AI272023 AI033950 W87471 AW844221 N58381 AA777630 AA069221 AA069234 AW105693 BE174670 AW387283 AW387279 AA772163 AI076246 AA368689 AI247220 AA643529 AI240585 AI870488 AI075769 AA125857 W61147 R06238 H30656 AA159412 H30218 R01022 AA074396 AA355706 BE271450 AW157537 AI830027 AI816134 AI825881 AI688335 AI214071 AW176662 AW732611 BE562933 AI869702 AW997321 BE149700 AW821680 AA627389 AW856162 AW840172 AW856160 AW856164 AW856053 AW840205 AW582458 AW856165 AA340614 AW452775 AW382070 AI032419 BE272692 AW816677 AW816678 BE271792 AA576444 H67217 BE177808 AW816622 AI400391 BE149697 AA594450 AW935536 AW376579 AW364201 AW362605 AW364193 AW848501 AW376626 AW947474 AW376794 |

TABLE 1B-continued

| Pkey | CAT Number | Accessions |
|---|---|---|
| | | AW250260 AW376808 AW376722 AW376787 AA359700 AW848535 AW376771 BE143111 AW848737 AW848747 AW848873 AW376652 AW848530 AW849127 AW848451 AW848531 AW848609 AW848543 AW376670 AW848194 AW848682 AW848669 AW848541 AW848601 AW848394 AW376710 AW848532 AW849125 AW376723 AW376835 AW848605 AW376535 AW848664 AW848684 AW848944 AW848685 AW849095 AW848671 AW376602 AW578344 AW848941 AW376648 AW848198 AW376608 AW848200 AW376589 AW848554 AW848879 AW848323 AW578331 AW848330 AW848319 AW578377 AW849088 AW376793 AW376669 AW578352 AW849126 AW376727 AW848594 AW848251 AW848241 AW578343 AW848434 AW578332 AW849019 AW848889 AW752678 AW376574 AW848545 AW376591 AW578335 AW848466 AW376766 AW376664 AW848529 AW578330 AW578338 AW848524 AW848617 AW376790 AW376634 AW376725 AW376763 AW752659 AW376797 AW376755 AW376673 AW578350 AW848258 AW376760 AW376603 AW848446 AW849139 AW848611 AW376761 AW376611 AW848887 AW376628 AW376716 AW848647 AW376703 AW376714 AW376594 AW376596 AW848457 AW376672 AW848190 AW848606 AW376586 AW848462 AW376742 AW376677 AW376598 AW376746 AW848610 AW848447 AW848683 AW376556 AW856261 AW376638 AW367077 AA068995 AW068772 AL120506 AL120386 AI244494 BE545234 AA159304 AW376599 BE295933 AF187552 AA152400 BE543706 AW578337 AF188896 AA811996 AF189213 AF188897 AW856185 AF190059 BE070163 AA251742 AI750309 BE150151 BE150252 AW848663 BE150159 AW856128 BE150201 AW578313 BE150250 AW381440 AW856074 AW381435 BE150190 AW856179 AW856121 AW856174 AW401844 BE003225 AW856177 AA526169 AA640192 BE314916 AA779712 AI906402 BE537879 AI834242 AI909763 AW845219 AW845215 AI809671 AW997331 AW177044 AW862068 AW993854 BE301919 AI834227 AA071495 AA130320 AW796591 BE179055 BE179234 BE006022 BE171097 BE207582 C17290 D58666 BE541097 BE089932 AW842190 C16922 AW444560 AI909741 AW403131 AW845207 AA092681 F05915 AI909742 AA233232 F08318 AA305354 AA147149 AA356962 AW366642 R14107 BE140572 BE140576 AW390347 AW402485 AA670344 AW408599 AW402702 AW249495 AA376813 AW130853 BE536618 AW338652 AA361509 AA431551 AI758329 AA233156 AW369723 BE185308 AI264242 AA724592 AA159922 AW205121 AI206517 AA305432 AI369749 AW754278 R55893 R34799 F11143 AI198270 AA335689 AW439092 AA577609 AW894217 AI302960 AW406637 C17923 H63348 AI634226 BE177956 AI498384 AW609479 AW950912 BE085889 AW391004 R14402 AI669187 AI758210 AW150328 AW402978 AW474568 AW579293 AW363558 AW369322 AA633069 AW364214 AA557144 AA352699 AW369361 AI625770 AA037067 AW369367 AW369378 AW369383 AW369320 AW369340 AW369334 AW747900 AI452805 AA025994 AW969302 AI471469 AW838332 AA700483 AW575707 AW363552 AW754279 AI538596 N41444 AW369369 AA533573 AI697373 N91447 T63645 AA343413 AW369372 AA329807 AA847288 AW369363 AA009432 BE177210 H43742 AA130321 H05246 AW517890 AW511678 AW198136 AA411576 AW934870 AW131725 N99045 AW190050 W48791 R96149 AW298454 AW051778 AI423040 AA147092 AW438903 AW519147 AI936035 AW747910 AI588900 AI572603 AA854132 AW272152 AI884403 AI689595 AA994684 AA576990 AW837159 AA411440 Z20745 AW369342 AI554272 AW051768 AA865624 AW190197 AW129438 AI590389 AI954048 AI553828 AI000547 AI858437 AA554141 AI017045 U82777 AA431097 AA622202 AA101026 AA890524 AI141907 AA770195 BE000706 AI338886 D20039 BE001103 BE000729 AI093763 AI128438 AI038158 AI014806 AI206804 AI128741 AA731344 AA781650 AA847245 AW977294 AI149018 AA725251 AI073592 AA601940 AA687609 AW001981 AA857855 AA027254 AI696346 AW068510 AA025935 AI288581 AA312064 AI366687 AI123208 AI361102 AA009433 AI375745 AI190304 AI810395 AI061262 AA722843 AA027255 AA693398 AA983511 AI523184 R55808 AI766707 AA723485 AA158005 AA731346 AI860056 AA470452 AI344375 AI052053 AA706704 W49616 W81209 AW058630 W38348 AA648692 AI244933 AA233115 AW803105 N69871 AI357292 W81226 AA676328 AA977264 N69416 AW082751 AI354629 AA843429 AI701333 AA161092 AA226840 AA993389 AW176551 AA243693 AA937997 AA470742 R96150 AA873311 AA282110 AI245104 AA318159 AI648622 T63845 AA972595 AW573031 H63268 C75028 AA523040 F02163 AI221319 F04541 AA708486 F08814 AA550863 AA524127 T28847 AI868107 AA635688 AA282111 AI147151 |
| 102993 | 17554_1 | BE262998 BE245856 BE244814 BE243904 AU077244 AW410227 BE263251 BE313253 BE268009 AA314290 AW407890 AA482209 AA315209 NM_001237 X51688 AA158802 X68303 AA360411 AA001329 AW608728 AI061440 AW875571 AI654232 AW371180 AA608568 AW371208 AA213393 AA306347 AI872410 AA936671 AI763348 AI948484 N41638 AA482297 AI827243 AW276578 AI199011 AI350965 AA158803 AI040688 AA693660 T28292 AW950496 AA001916 AA213394 AA557629 AI872826 BE564910 AA580754 AA459213 AA213538 |
| 112033 | 259080_1 | R49031 AI620424 R43162 R37467 H90387 AA367338 AW955845 |
| 112068 | 611385_1 | AI264847 R43910 AW614197 AI863821 AW467620 AI695292 AI672346 AI302090 N81071 AI611641 AW166600 AI168293 AI313201 R43835 |
| 104204 | 11607_1 | AK001691 R80991 BE207855 AI872457 AI206292 AA223534 AW364783 AW364715 AV645744 H65388 BE170476 U46375 AA234504 AA285262 AA055428 W52943 W78060 AI669713 AI804895 AI056890 AI202008 BE504324 AI638488 AI991279 AW301184 AI990138 AI765837 AI523554 AI735158 AI637794 AA922055 AW069634 AW875295 AW002630 AI089420 AA535017 AI652587 AI657071 AI637803 AA677262 AA865617 AI699986 AA223477 AA554162 AW606040 AI078073 AA573096 AI057436 AI307113 AI983310 AA723619 AI659825 AW275484 AA552067 AW134930 AI038417 AI247714 AI678270 BE139653 AI814032 AI424176 AW874195 AA234118 AA843211 AW136280 AI468611 AI867879 AA495758 AA508603 AW006765 AI825647 AI867777 AI423688 AA037412 AA495818 AW590634 AA883349 AI969113 AW083463 AA054992 |

TABLE 1B-continued

| Pkey | CAT Number | Accessions |
|---|---|---|
| 112098 | 659188_1 | R44714 AI952898 AI623118 AI271632 T10160 Z40968 |
| 134332 | 16633_1 | D86962 Z43779 AA298247 AF073378 AF000017 BE386788 BE146000 AL046008 AW951300 BE328763 AA565135 T17443 AW197239 Z39844 AW149267 R42775 W94026 AA133831 D81179 AW292896 W24533 AA340353 AW964788 R35792 W72778 Z20086 AA129406 AW665655 W94015 AW518912 AW385139 N92349 F28925 C15300 AI239534 AI358889 AI625560 AI936054 AI239416 D60096 AA808160 AA889642 AI360831 AW197699 AA136336 AA807872 H92911 AI123784 W72779 AI146976 AI023919 AI183855 AA298388 R85083 AW085113 R35681 AI560637 AF000018 R85130 D60097 R20996 AW370219 |
| 104254 | 28286_1 | AW411425 AW411256 AW248441 AB011446 AF015254 AF004022 AA071235 AW245199 NM_004217 AB011450 AA070237 AL121492 BE264315 AA356271 BE253249 BE621112 BE256245 BE253568 AF008552 N49806 AW405819 AA352701 T25793 H51697 AI829974 W89058 AA297276 AW170452 AW249658 BE392539 AA070238 H81023 AW339856 N49700 AW406366 AA071486 AA720659 AA847804 AW411426 AW236354 AW411257 AI830139 AI348173 AI092097 AA807548 AI039321 AI280182 AA196757 AI803988 AA976765 H58497 AI953453 BE045492 AW294622 AA883408 H82885 R97912 AA810605 W88963 H81024 AW103189 AI453120 AA738386 T25124 AI582910 AI352050 AI802294 AI348029 BE561223 H57656 AW407129 R97911 AW951023 |
| 134351 | 16763_1 | BE272506 U47721 NM_002997 J05392 BE259935 X60306 AL039256 Z48199 BE149524 AA425123 AA419287 AW630308 AL039215 AA219419 AW374657 BE081779 AW352196 AW602851 AA368110 BE078507 AA299561 AA377906 T58819 BE273643 BE541572 AA367994 AA100094 N93982 R22500 AA375599 AW998547 AW887074 AW631259 AW085777 AI660836 H13083 D58798 AA010621 T39490 AA001108 AA224261 AA366381 AI696816 W79383 N40117 AI219172 AW630029 AW079051 AI829106 AW439517 AI814283 AA579623 AW084866 AW170078 T92786 AI860472 N54556 AW009667 AI333283 AI348031 AA707206 AI831036 AA928681 AW337157 BE160976 AI422988 AA777013 AI691025 AA032042 AI831457 AI921282 T89395 T62508 AI566209 AW516825 AI758659 AI271852 AI677918 H01094 AI829280 AI224622 D59025 AA723113 AA601514 AW192078 AI224154 AI015641 AW182754 R68745 AA031960 AA583770 AA921870 AA632080 H00744 AI148519 BE206146 AA010622 R68690 AI247825 N76636 AA774612 AI078484 AA677405 N22040 AI432009 AA074511 AW662594 AA911301 AI342919 AA863447 AI474153 N26996 AA426099 W74093 AA001637 N69444 AA902587 R01486 AA639804 AA057472 AW050972 H13287 AW273894 AI872681 T47346 AI865585 T29391 AA745902 AA069313 AA443694 R22448 H70273 C00094 D29190 AA918847 AA577952 AW999231 N53786 T97945 AA586967 H00654 AA001255 H01095 AW376447 R70643 T53352 H03335 AA487014 AI346925 AW272885 AA829733 AI002312 AI991128 AI609012 AA917832 AA994510 AW151183 AW044410 T87877 AI744429 T70053 T53353 W96029 W52504 AW074106 AW571586 AA335556 AI355538 AI922244 AW276403 W52688 AA588801 AI493346 R82074 AI343474 AI693962 H95157 AA002260 AI590864 BE049626 AI206365 AI241074 AI610408 AI952089 AI014897 R00830 BE049407 AI820005 AI422564 AW511287 AW591439 AI864028 T58751 AA568360 R81546 AI282671 AI684071 AI950509 AI439380 T71663 W94662 AI678329 T49501 AI079708 AA995106 AA918622 AA502982 AA502632 AA548291 AI354395 AW000944 AW085741 D45578 AI826443 AI810939 AI301212 AI243066 AI699271 T87967 R81545 T53792 H12560 R24884 AI188950 W03268 |
| 110837 | 163104_1 | H03109 AA190569 R27719 R77038 R23789 N41571 N34588 R26033 T94741 AI110626 AF063500 W35141 AA236329 H15136 AW043845 N23362 AA682872 H03110 AI168530 N32346 T94740 AA236561 AA236235 N23955 R27720 N31614 AI814425 AI804857 AW590744 AI080155 N30796 AI341754 AI367163 AI272814 AI332944 AA193683 AI183993 AI183991 Z39979 F04878 AI868457 N26707 BE535358 R23737 AW449959 |
| 134369 | 5386_1 | AF207664 AW163724 AF170084 NM_006988 AF060152 AB037767 AL162080 AW630434 AI148739 AI686088 AW844411 AW163200 AA677116 AA368429 C03600 H27128 N88341 AI126019 AA373718 AW964293 AA345812 AW967361 BE047207 AI571069 AI335849 AI537518 AW168050 W47316 AL355724 R13547 Z43925 AI769318 R19976 W35345 W24878 AW194129 T95373 W07142 H28325 AA634915 T86778 T39243 T10738 AI370696 T36271 AW954313 AA296523 AA029247 AI369552 T40309 AA022997 AA011364 T41144 T41173 C18560 N59612 AA328867 AA040690 AA088617 AW167394 AA028018 AI569560 AW195344 AI089584 AA151507 AA133346 AI692832 R20636 AA031616 N91530 AI369060 AI755040 AI890478 AI985641 AI926525 AI654583 R76276 AW001362 AI887177 H28326 W92831 AI129429 AI719476 N40523 AW474740 AA022464 AA993528 N46572 AA129732 AI342643 AI144408 AA011376 T95293 AA057170 AW613713 AI280406 N95765 AA031474 AI128171 AI097021 AI684137 AI889755 N29991 H89564 W92688 AI953558 H98678 AI168616 W47201 AI690716 AA834490 AI160430 AW207161 AA677837 AW080654 AW104712 AI368138 AW474712 AI559164 H89565 AI185000 R76553 AA662930 AI340202 AA608802 AA757215 AA595069 AI199506 AI765271 AA028027 AA703651 AA918632 AI128696 AA903074 AI027793 AW204001 AI932695 AA846139 AI859558 AI537176 AI040586 AI270245 T40492 AA987460 AI160028 W23529 AA029035 AI827556 AA904875 AA706779 AA807465 AI689182 AW050514 AW150550 AW150472 AI648649 AA781059 Z41664 AA897320 AW050517 R45078 AI933450 |
| 110844 | 26206_1 | AI740792 AI949422 AL079298 AI423046 N31952 AW195192 AV660395 BE543143 AA658285 R89611 R88931 |
| 133731 | 33199_24 | N71725 H73296 T58304 H94803 H71098 R97116 NM_000517 V00488 V00493 R98241 H62729 H02536 H93953 H93849 R83420 R97372 H74255 H73034 R92870 H50844 R91252 H82329 H50974 R73807 R26201 H50967 H81482 H78630 N94123 H69920 R89892 AA340135 R97379 W03876 H19610 T58178 N78051 W25742 H78463 R63791 H63594 R83842 AF097635 H73826 R94380 H47962 T53050 T54718 R64416 R74107 AF147332 T53241 H01120 R69900 R63176 R78653 H81168 R80097 R66776 H66298 H60727 R87144 R99227 T67143 |

TABLE 1B-continued

| Pkey | CAT Number | Accessions |
|---|---|---|
| | | R99448 H52368 H50753 R76757 W01513 T59136 R70829 N77678 R80500 H78988 Z84721 N77683 N49814 N49427 AL038057 T52784 AA176749 N74739 W03863 T56842 N73036 T48014 N58317 N23926 AA766008 AA054580 N27635 R24279 AA458708 T51591 R34838 N63760 T58643 T54776 T56870 T52464 R26296 R48863 R64108 T52509 AI266020 T56462 T52644 AW950562 T54777 T50483 T54790 T53061 N49288 T51607 R52129 T50474 H65397 T55568 H93336 H00452 R81632 N71325 T52168 N71376 AI497856 R39511 R80225 T50668 T52574 AA069455 T52166 R28311 H68765 R89496 AA182860 T54943 T56607 T52370 R68553 H73383 H94478 N74134 T56851 Z20477 H47886 R95766 T50309 H38014 R71482 R26898 H03665 R77486 R82305 R69335 |
| 133740 | 26830_1 | AW162919 AL050259 NM_004761 Z97184 AA640291 AW606692 AW246097 T08669 AL047730 U68142 AA910103 T80173 R17716 R25789 AW367388 AW175613 D85757 C04496 AI686948 AA369649 BE617744 AW129501 AW166092 AI963470 AI199238 AI884759 AI972097 AI143863 AA453509 BE336660 AI811410 AA902192 AW151682 AI688884 AW000804 AI024368 BE047332 AW339091 BE350021 AW338566 AA961769 AW950817 AI823704 AI435442 AI168340 BE047303 AI632056 AA404233 AI634306 AA007622 AW089074 AA916663 AI198501 BE042528 AA845142 AA740795 AI215659 AI312894 R37588 C02440 AA830137 AA453510 AA860919 AI760689 AA828494 AW840260 N80842 T80183 AI192854 AA613311 AW816806 AA135176 AA035367 T49125 AA639686 AA442982 AA402117 T30397 AI078067 AW190739 N27365 AA813552 AA613813 AA505865 AA506506 T08668 AA401972 AA854089 AW132030 R41786 AA526375 AA458470 AA907444 AW339956 N99972 T32323 AA687824 T32376 AA636046 AI401093 AI749004 AI222452 AA569896 AA699480 BE206118 N75044 AI439196 AA454684 AA987257 AI351217 N92937 AA007661 AW389309 AA456333 T87606 D31579 D30835 T49124 BE042568 AI690934 T31165 AA843733 R86012 AA135350 AW389311 C03271 AA345798 R46768 N27045 AA995286 AI572405 |
| 103677 | 41847_1 | Z83806 AJ132091 AJ132090 |
| 133797 | 14537_1 | AL133921 BE389006 NM_005056 S66431 T07054 AW500214 AW604275 AA487706 AA211245 AA247515 AL133922 AA311252 AA487492 AA312860 AW268369 BE328608 AW105357 AW468600 BE535444 AW672876 U25911 AA877356 AI587632 AI609139 AW500785 AW997007 AW847840 AW370915 AW370913 T60896 AA101935 AW191714 AI676232 H06919 T59110 AA665509 AI866620 AI890038 BE301184 AA633020 AI146438 AI088562 AA778271 AA572820 AW182989 AA101936 AA149972 AW373677 AA056587 AI189146 AA194891 AA884333 AA996366 AI972293 AL039952 AL048473 AI693257 AA165428 N42199 R64192 AI682230 AA460756 T55996 AA460157 AA884291 AI654969 AI014993 AI807648 BE044209 AW594737 AI199395 AW296902 AA354250 AA399998 AA327076 AI700672 R64102 T59036 AW014952 AI695952 N20368 AI492362 AA906265 AW300068 AW572973 T29558 AW949803 AA761392 AA128422 AA129842 AI393285 H06876 AI040173 H24862 AI081931 BE467125 BE464863 BE219481 H24863 AW304389 AI221831 AA662088 AI537156 AA662123 AA548129 AA357123 AA635823 AI184593 AA165427 AA056492 N89116 AA249262 AA090888 |
| 133799 | 14540_1 | W24087 AA428006 AA490408 AA337922 AI291297 AL110297 NM_015415 AW160443 AA306892 AV647213 AA341034 AA296279 H80945 AW675361 AA082259 AW406543 AA034979 BE002719 AW373227 AW373260 AW875261 AW991430 AW875387 AW373224 AW580714 AW875373 AW875390 AW875323 AW991424 AW393069 AW576748 AW581565 AW875392 AI192351 AW274556 AW341482 AW674758 AA969478 BE122712 AI457696 AI241221 AA935160 AI073372 AA747666 AA532390 AI150824 AA236527 AA836680 AI126569 AW020703 AA847379 AA034912 AA490310 AI370587 AA427895 AI066462 AI750138 AA476719 AA938503 AA456421 AA281132 T25464 BE222761 AW875310 AW875322 AI191421 AI743446 AI086059 AI421846 AI221065 AW662500 AI569047 AI302685 AI869738 AW162453 AI032331 AA576425 AI286210 AI400077 AA650374 AI025206 AI214417 AA435919 AI264013 AW361280 AI268127 AI143814 AW402014 N92838 AI097003 AA165350 AA862308 AI347735 AA164559 AA490322 AI342201 AI091667 AI074045 BE122708 AA188818 AI342770 AA157009 BE165950 T56385 F21881 AI537284 AA740314 AI866755 AI349589 AA515191 AW291939 AI972418 C02120 AI559371 AA876641 AW197038 N91910 AA807386 AI468060 AA216134 AI630442 R88195 AI525508 AW662869 T56504 AA188876 W25063 AA490426 AA102193 |
| 125924 | 16763_1 | BE272506 U47721 NM_002997 J05392 BE259935 X60306 AL039256 Z48199 BE149524 AA425123 AA419287 AW630308 AL039215 AA219419 AW374657 BE081779 AW352196 AW602851 AA368110 BE078507 AA299561 AA377906 T58819 BE273643 BE541572 AA367994 AA100094 N93982 R22500 AA375599 AW998547 AW887074 AW631259 AW085777 AI660836 H13083 D58798 AA010621 T39490 AA001108 AA224261 AA366381 AI696816 W79383 N40117 AI219172 AW630029 AW079051 AI829106 AW439517 AI814283 AA579623 AW084866 AW170078 T92786 AI860472 N54556 AW009667 AI333283 AI348031 AA707206 AI831036 AA928681 AW337157 BE160976 AI422988 AA777013 AI691025 AA032042 AI831457 AI921282 T89395 T62508 AI566209 AW516825 AI758659 AI271852 AI677918 H01094 AI829280 AI224622 D59025 AA723113 AA601514 AW192078 AI224154 AI015641 AW182754 R68745 AA031960 AA583770 AA921870 AA632080 H00744 AI148519 BE206146 AA010622 R68690 AI247825 N76636 AA774612 AI078484 AA677405 N22040 AI432009 AA074511 AW662594 AA911301 AI342919 AA863447 AI474153 N26996 AA426099 W74093 AA001637 N69444 AA902587 R01486 AA639804 AA057472 AW050972 H13287 AW273894 AI872681 T47346 AI865585 T29391 AA745902 AA069313 AA443694 R22448 H70273 C00094 D29190 AA918847 AA577952 AW999231 N53786 T97945 AA586967 H00654 AA001255 H01095 AW376447 R70643 T53352 H03335 AA487014 AI346925 AW272885 AA829733 AI002312 AI991128 AI609012 AA917832 AA994510 AW151183 AW044410 T87877 AI744429 T70053 T53353 W96029 W52504 AW074106 AW571586 AA335556 AI355538 AI922244 AW276403 W52688 AA588801 AI493346 R82074 AI343474 AI693962 H95157 AA002260 AI590864 BE049626 AI206365 AI241074 AI610408 AI952089 AI014897 R00830 BE049407 AI820005 AI422564 AW511287 |

TABLE 1B-continued

| Pkey | CAT Number | Accessions |
|---|---|---|
| | | AW591439 AI864028 T58751 AA568360 R81546 AI282671 AI684071 AI950509 AI439380 T71663 W94662 AI678329 T49501 AI079708 AA995106 AA918622 AA502982 AA502632 AA548291 AI354295 AW000944 AW085741 D45578 AI826443 AI810939 AI301212 AI243066 AI699271 T87967 R81545 R53792 H12560 R24884 AI188950 W03268 |
| 135015 | 34946_1 | AW301638 AW009334 AA776753 AI580431 AW411290 AA281800 U54999 AA247905 AA249103 AA375000 AA369034 AW951354 W92010 R25539 |
| 112170 | 64558_1 | BE246743 AA436942 AW024744 AW242177 AA975476 AW385185 R07536 R73462 AV654529 T57442 AI399986 R50073 R48743 AI769689 AI863005 AA317806 AI678000 AW189963 AI986207 AW471273 R73463 AI335104 AI590161 AI469257 AI954604 H21954 T25141 AA856793 R50074 AI708253 AI217945 AI224459 AA505828 AI521061 AI651948 AI919161 AI766992 AI287290 AI868191 AW956075 AA335980 AA335672 AI424272 AW572622 AI500040 AI553687 AI932452 AW196184 R48744 |
| 134421 | 17110_1 | AU077196 J04478 NM_000393 Y14690 AW239129 BE018496 AW068123 AI750528 X04758 AI828712 AA577121 AA853106 AA320450 AI750939 U53092 AA334363 AA486225 M10956 W05131 AA373460 AA247709 AA328980 AA092106 AA330038 AA304992 AA386156 AA331327 M11718 AI751005 AA305175 AW955473 AA342316 AW950601 AW849233 N42734 W52306 AL038512 AA332886 AA332661 AA332101 AA853780 R58798 AA040410 AA332339 AA334576 AA091436 AW068455 R09649 AA114947 AI567519 W93869 AW372828 AW372820 AW393330 AW386363 AW393342 AW372817 AW393339 AW393324 AW393333 AW840441 AW840379 AW393335 BE167044 BE070635 AW393329 AW608872 AI963125 R07913 AW608870 AI609225 AA010309 AW840403 AW840445 AW840390 AW840345 BE070633 AW840464 AW840371 AW840436 AA333851 AA092962 AW840569 AI884581 AI953978 AW840566 AA004204 AW393334 AW393343 AA334087 W24174 AW150834 AA095583 AW372823 AW393338 AI858101 AW840529 AW840568 AI281477 N32519 AW840375 T29615 AI814914 AI570898 BE070542 W05395 AA706823 AA599504 AI262822 AA329445 AA330407 AW088731 AI122842 AI128830 AI754803 AA676903 AI127349 AI582477 AA486379 AA600038 AI589319 AA903134 AW840521 AI083555 AI755281 AA035380 AW804130 AI088658 AI143031 AI354707 AW804069 AI580763 AW804101 BE089359 W02000 R95826 AI086998 AA578679 AI346302 J03051 AW088383 AW840365 N68613 AW393337 AI075140 W87515 AI342335 AI417127 W93848 AI935300 AW886342 AA853107 AI147454 AA348035 BE090787 AI750253 H59312 AA232701 AA194797 AW196741 AA040329 AL038513 AA194648 AA328379 AA233015 W57799 AW372121 AA346374 AA706805 AI670785 AI750527 AW792942 AW792970 AW068714 N75508 C00044 AI751004 AA091990 AA723122 AA093252 N87869 N89578 AW068212 AI052797 T49492 AW302579 AI753788 AW069514 AI357733 AW751666 AA505831 AW073493 AI200515 AA974667 AI560062 W87487 R95777 AW780128 R77205 AA058930 AA099728 T27809 AI382841 AI688861 AI589497 R86097 H39522 H45011 N76100 AW385366 AI752198 AW385329 AW385351 AW385359 AW792894 R09536 T31628 T31631 T31612 AW834785 R69515 T24745 D62992 AW605897 AA122291 AA361011 AI341677 AA150616 AA725207 AA127736 AA344504 AA137193 BE153409 AA452231 AW835203 AA442665 AA449381 AA329886 AA330396 AA099729 AW839760 BE049568 BE177845 AW385337 H13571 R27886 AW875656 H87987 AI751983 AW875865 AW875887 AW579855 AW608741 AW069271 AI755045 AI753615 H03527 C02028 AI160667 AA328122 AA121511 AW020206 AA070970 AA343104 AW069115 BE150497 T49493 AI888126 AA993150 AA599273 AW937969 AI654845 AA137194 AW937892 AW191921 D62061 AA334999 AA609330 AW875872 AW771446 BE502145 AI090089 AW780273 AI127162 AI697486 AW439391 AW572213 AW021109 AW008422 AI371826 AA010310 AI692736 AI160542 AW592395 AI127946 AI864906 AI077562 AI304554 AI446310 AI457114 AI214470 H13204 AW074603 BE302102 AI754320 AW875878 AI671130 AW069432 AW291469 N63241 AW340511 AI268892 AI095555 AI754231 AA857098 AA573183 R27794 AI919268 AI039775 H03445 AA142904 H44959 AI094661 AI865506 AW088208 AW235794 AA122386 AA852331 T63108 N64280 AI263967 AA343018 AI569315 AI537624 AA594297 AI751984 AA342315 AA449254 T03859 H88165 AI537635 AW084603 AI564735 AA115948 W30698 AW883468 AA878466 AA096062 AA115524 BE167017 AA703985 AA705256 N43019 AW393341 |
| 134444 | 33247_1 | BE184455 BE396187 AL035660 NM_003064 X04470 AA132992 AI862145 AI564623 AA572950 AA993549 AA026099 AA460433 X04503 X04502 AA026192 AF114471 AI858387 AI885550 AW264225 AI638119 AA564454 AI222907 AA541595 AA587161 AI743345 BE044073 AI742512 AA551908 AW238407 BE392080 AA397776 AA863166 AA587140 AI042208 AA683520 R71834 AA026497 AW081599 AA932864 AI580185 AA316675 AI000873 AW513394 H65171 BE612494 BE612943 AI377093 AA938592 AI148713 AA594366 AI042358 AI282099 AA878509 AI126451 AW302276 AW510396 AA991397 AI066534 AA993550 AI276644 AW305053 AA026264 AA975787 AW103765 AA026420 AI311077 AA903202 AI347358 AA557989 AI300095 AI813709 BE184402 AA460434 AI302183 AI096385 AI024981 AA132956 AI184947 AW470608 AI358410 AI811543 AI418421 AA936659 AI275993 N23232 AI422607 AI628518 AW190157 N27733 AA026641 AW472804 H65117 AI684142 N25032 AA164414 AW167388 AA165295 N23721 AI675729 AA829536 AA169507 AA160175 T68535 BE181364 AW088845 T28664 AI399779 AA643910 AA165296 T68469 AI363937 R49912 AI784193 AI991241 R71785 AI800677 AW794052 AA995549 AA164415 AI718351 AA419259 AA588301 AA401179 AW391622 AA485776 AA485649 AI970057 AA587129 AI685920 AI589995 AA886793 AA478097 AI363962 AI540954 |
| 127229 | 11897_1 | AA316181 BE439545 AC005053 AF186249 AW386101 AC004969 AA730199 AA032221 AI686139 AI167942 AA809228 AI184070 AI394674 AW969977 AA032279 AW079284 AA513174 AA888312 AI453179 AA483363 AA528432 AA579511 |

TABLE 1B-continued

| Pkey | CAT Number | Accessions |
|---|---|---|
| 127236 | 19449_5 | AW661857 AI915426 AI341818 AI204517 |
| 134454 | 35303_1 | NM_013230 L33930 M58664 AI905918 AA434132 AA904758 AA588618 AA594622 AA948567 AA527668 AI907434 AA862503 AI745625 AI189061 BE174316 AA468774 BE002291 AA725505 AW176047 AA894539 AA988737 BE090598 BE090586 AA677897 AA937588 AI348033 AA367135 AW375476 AA385290 AW375573 AI310309 BE148067 BE006010 AW510588 BE002449 AW176070 R45919 AW937774 AW372169 AI005477 AW375919 AA233381 AW363508 AW363501 AA349672 AW376020 AW363574 AW959345 AA362098 AA164354 AA367166 AW873216 BE000889 D87667 BE164344 BE062266 AW607225 BE064576 W39287 AW610129 AI885465 AA445951 D51997 AA411741 AA632836 AA317144 AA058499 AI564540 BE176594 AA371311 AA295400 AW601989 BE090755 D54335 D54370 D53586 D55388 D55061 D54957 R29242 AW864980 D52634 R23787 AA430088 AA962260 AW151335 W06968 AA165306 H04204 T18454 BE612502 D51399 BE168228 D54311 BE004449 AA300121 AA523877 AA430446 AW392680 AW392679 AI300582 AI626053 AA610627 AI810781 AW089838 AI300587 AW371645 AI857812 AI859979 AA729544 AW151626 AA772990 AA845164 AI720288 AI679250 AA831488 AW168119 AA136096 AW162096 AA972782 AA587042 BE172059 AW055310 BE046866 AI986140 AI744399 AI446769 C05711 AI801851 AI925745 AI559460 AI748785 AI801199 AI264631 AI635844 AA299240 AA299241 AA299414 AI275244 AI799457 W31859 AW473701 N78899 AI626045 AI446550 AW946403 AI275112 AA629868 AI948969 BE219021 AW269521 AI245637 AI568016 AI570341 AI687736 AI912508 AW129471 AA446458 AI926301 AI697327 AI796682 AI627199 AI571997 AW005027 AI679826 AI580230 AI610148 AI559396 W60476 AA464857 AW237865 AI683443 AI610541 W73562 AW511411 W73581 AW439864 AW024739 AI569460 AI308094 R77796 T85259 AA209488 AW473796 R96739 AA506567 AA165307 AA136165 H04205 AW191964 AW001833 AA197340 AW473849 AI537898 AW572099 C75355 AI888628 AI537886 AI302906 AA493556 AI973160 AI244703 AI537165 AW272161 AA970748 AI926035 AI341007 C75315 H59916 AI832273 AA583306 AI869784 AW887507 AI669500 AI804770 AI926216 AI701366 AW028195 AA505677 R23736 BE153112 BE139498 AA991452 AW992492 BE153248 AA807755 AI433971 AA164903 AW162585 BE168971 AA732914 AI312727 AA700369 AI619791 AI085826 H45709 AA971080 AA845730 AI654466 AW571969 AA372945 AI671427 AI908193 AI908184 AI908173 AI908183 AI908190 AI908174 AI908185 AI908189 AI908186 AI908187 AI908191 AI244244 AA493617 AI908192 AI972647 AI290408 AI287904 AA631331 AA508879 T32271 AW002782 AI582423 AW517532 AI539148 AI824403 AI302867 AI933821 AI287336 T03913 AI678303 AI470699 AI915702 AI758491 AA977101 AI367376 AI870452 AW496810 AI302938 AI559862 AI468929 AI569907 T03853 T30204 AA662349 AA658971 AW818354 C20918 AI611355 D25554 AA910304 AW198061 AI687539 BE074794 AW995748 T03912 T03852 BE082213 BE174465 AA453342 AW844350 AW603902 BE176743 BE004975 BE074755 BE074661 BE090606 BE176758 BE173074 BE004516 D55070 BE002011 BE172645 BE090594 AW999864 AA339261 AA343589 H59915 AA357314 AI123763 AA453217 AW996441 BE082136 AA384370 AA340742 BE081952 AA384272 R78158 AA367413 BE001850 AW580006 T08552 AA349978 AA610643 BE000015 AI766762 AA300134 AA747175 BE180467 AI905702 AI214104 BE174082 AW376653 AW376759 AW848546 AW376799 D54438 AA384504 AA384911 R81453 D55004 BE613090 BE272356 AA780152 AA761181 AI559700 R91610 |
| 110930 | 127662_1 | BE242691 AA700942 AW242679 AI367403 AA193579 AW016712 AA806667 AW469266 AA194800 N75463 AI350692 AI982662 AA100138 AI017903 AI272803 N48603 AI671216 AI760490 AW510307 AW003140 AI760463 AI492196 AI380897 AI692959 T81970 AA744442 T81542 |
| 110932 | 9346_1 | AA021459 AL157453 N48694 AW898879 H08850 N46609 AW014561 N51002 AA482856 AA482842 AA482868 AA885753 AI628670 |
| 134470 | 17294_1 | X54942 NM_001827 AA419596 BE566311 AA292964 H91988 AA234001 AA306157 AA252386 BE566951 AW172736 AW949804 BE019764 AA745959 W92388 R00665 AA644467 AI160521 AA010065 AI167445 AI375953 AI375935 AI219021 AW172922 W92332 AA526800 AW327300 H89939 AA729171 AA729539 D19699 AA234002 W15179 T29560 AA305796 BE164003 |
| 104394 | 22050_4 | AA129551 H46617 |
| 103739 | 110079_1 | AA115173 AA075221 AA075709 AA076354 AA083101 AA085391 AA070684 AA083368 AA076395 AA076396 AA075779 AA083500 |
| 133820 | 27806_2 | S69681 S69680 M13686 AW502119 AI193546 AA910449 M30838 AA970237 AA928513 AW268995 AW205504 AA491477 T63632 AA488018 AW275908 AW067774 AA969323 AA969402 AA994009 AW662888 AI191424 AW274542 AI185334 AA770654 T60105 AA486609 T59747 T62701 AA315974 AA487660 T39218 T39235 AA775183 T63485 AA487757 AI821350 T63560 AA487056 T39248 AA487096 AW268523 AA630447 AA663970 AW271249 AW262256 AA630518 AA487450 AW276064 AA488089 AA977012 BE328823 AI299538 AA634768 AA634025 D45697 AA926698 T63653 T63908 T94546 S69791 |
| 126645 | 11897_1 | AA316181 BE439545 AC005053 AF186249 AW386101 AC004969 AA730199 AA032221 AI686139 AI167942 AA809228 AI184070 AI394674 AW969977 AA032279 AW079284 AA513174 AA888312 AI453179 AA483363 AA528432 AA579511 |
| 103797 | 109699_1 | AA080912 AA075318 AA083403 AA076594 AA078992 AA084926 AA081881 AA113913 AA113892 AA083821 AA134801 AA082953 AA070343 AA062835 AA075419 AA063293 AA071252 AA078900 AA062836 AW974305 |
| 133886 | 14865_1 | U97276 NM_002826 AW268982 AL042393 AI750566 AW068508 AL042118 AA675908 L42379 AI460098 AA375375 R88085 AW583087 AA634510 AW843402 AW366299 H78270 AA358959 AW959189 AI906500 W51802 N28303 AW362572 AA425481 R12312 AW815562 AW815518 AW815532 BE407187 AW815423 BE540993 BE254859 F13473 T74161 T89894 BE296648 BE299756 R72745 W00849 R17397 AA378713 AI752636 W47068 AW451378 AA291759 AA335801 R22462 AW960615 H78358 W73493 AA631167 AA569359 BE386345 N50154 |

TABLE 1B-continued

| Pkey | CAT Number | Accessions |
|---|---|---|
| | | AI199150 AI986162 R42633 R25868 AI802749 BE222099 AW242272 AI249022 AI798888 AW410048 N53572 W46968 AI750698 AW769273 AI269750 T89619 AW068770 AI991132 H99489 AI829238 AI823721 AI074884 AI359292 AA969412 W73574 AW444839 AA090268 AA368461 R72746 AI678870 AW368846 AW368816 AA311282 AA906143 AA971683 AA744065 AA744106 AI066455 AA846698 N30659 AI983057 AW026585 AI916350 AI677873 AI149001 AW469153 AW081661 AI355535 AI221419 AI085982 AI188675 AW193368 AI333700 AI610674 AI358823 R84988 AA464152 AI077668 AA433854 R88086 AI469130 AI095539 AA947617 AI910564 BE077429 AI301310 AW304341 AI193681 AA947615 N26760 AA292682 AA434375 AI818592 AA826496 AI401585 AA470775 AI187738 AA298131 AI587057 AI536760 AI582920 R37241 AA551891 AI184397 F10241 AA865219 AI250666 AI205923 AA878115 AI891055 AI768178 AA907719 AI687947 AI801778 AI221415 W74434 W79188 AA577088 AI798472 AI559148 AW601460 AW602641 R26680 AI202219 AW602665 AA367691 AA934351 BE410383 BE005882 AL046719 AL041878 AL046353 H44278 R25042 AW410047 AL040884 AL046698 AW815531 AW815383 AW815420 AW815536 AW391301 AW815385 AW815364 T84067 R10965 R10912 AW380777 AA065020 AW371383 AW815728 AA595714 R43801 T86108 T48538 |
| 133893 | 14927_1 | AI434699 X01060 NM_003234 BE256019 BE142860 BE142729 AW500605 AA347570 AL120908 AA082493 AW630459 AW501236 BE009458 AW503924 AA055688 AA216664 AW802703 AA877477 R82301 N85217 AA134422 H02417 AW389909 AW389907 AW389913 AW389877 AL046375 AA488721 R95492 AI189434 AI132910 BE092247 R11868 F05413 N85500 H60074 H02305 W95694 D59086 R82712 AW402489 AI630673 AA132188 AW629714 AA581142 R19476 AA033935 AW862307 F12939 BE536497 F12950 H13379 AW815251 AW861747 AA490726 AW861754 AW858119 AW861737 AW366658 AW858160 AW858110 BE010851 AI630422 AI630188 AW852822 F12235 AW935236 T66396 F07003 F06134 AA279609 W25236 AW904519 AA689397 T93034 AW672879 N27985 W94700 R80466 AW672950 AW815197 N44949 R82022 N36574 BE090822 BE090815 BE090816 AI630083 AA010798 AL039227 AA094713 AW875438 AW875695 R66329 AA095005 AA094771 BE092490 AI630297 AW875916 R36193 R23888 AW875696 D20720 AA252852 H04165 R29433 AW875844 AW575175 AA806223 AA527154 R31997 W42895 AI051604 BE042743 AA740874 AI018806 AW168040 BE220532 AA524174 AI491927 AI473960 AI160447 AI955757 AW613237 BE091026 AW474577 AW301101 AI708141 AI950338 W31163 AI916228 R78012 AI247914 T28012 R82069 AI022814 AW025110 AW073258 AA503534 AW006460 AI367004 AI219035 AI479239 AA570691 AA411603 AA702652 R80666 AW197401 W94572 N21329 AI339784 BE218877 N33166 AI985812 AA206003 AW675538 AA687416 AI190077 AA749258 AA693678 AA045779 AA169605 AI384107 AA011137 AI970642 BE084942 AI242509 AI289875 AI982939 AI565948 AI086958 AA134423 N70819 H98010 AI131217 W01453 AI302356 AI767028 AI083967 AI253739 AI858602 AI274245 AI377075 AI478140 AA252818 AA136170 AA768776 R23889 AI760271 AA055468 AA743650 AI092439 AA487593 AI890879 AA609631 AA903015 AA693892 R31947 R67470 AI499141 AA736415 W42780 AA280009 AA216598 AW513219 AA588311 AI867207 AA132359 AW852302 AA764997 R36097 AI948778 AI287724 AI471581 H69791 AW377519 AW377518 AI399652 AI248512 AW768867 AA677760 AA693569 R66330 AA809708 AW188938 AW971675 AA507029 AI590003 AI087149 F11037 AA701429 AI025587 AA491217 AA594281 AA694002 AA806052 AA938634 AA494325 AA668757 AA507582 H06044 AI763105 AI355107 AA055165 AI630478 AI123155 AI352266 AI565399 AI243061 AI264434 AI524781 AW675559 F02401 AA587442 C75156 AI250240 AI264889 AI084240 AI590022 AI473121 AI275644 F03280 AA747073 AW511815 AI469211 AI873809 AW168304 AW236405 F02400 AI696311 F10538 R19385 AI471302 AI471270 AW265552 AA788973 AW673575 AW150054 AW731723 AI814944 AW818598 AU076796 BE566848 AA527171 H59421 AA045912 N99895 T92920 AW950268 |
| 105011 | 6948_1 | BE091926 NM_006461 AF063308 AW246310 W94875 BE293514 BE091862 BE091863 BE091910 AL041446 BE091916 BE296565 AL137585 W93404 AL039797 AA853256 AA332773 BE391536 AA131484 AA148724 AA115978 BE541379 AL122116 AA070390 AW887577 AW175976 BE619622 AL041841 AW250305 AL041447 AA249507 AI138779 AA598727 AW149054 AA131171 AI631485 AW613280 AA070391 T86847 AW249545 AA886967 AA605095 AA644113 AA115979 AL043729 AL043728 AL043765 AI660376 AI079510 AW250980 AA132223 AA971754 AA541345 AA853255 AI745706 T97349 T86656 AA132327 |
| 105012 | 5687_1 | AF098158 AL120028 AW629818 AB024704 AI206883 AI654707 AA158331 AA310249 AA306686 BE314654 AA379553 AA135066 AA333019 AB027467 AA158654 AA116035 AL044513 AL117534 AW295988 BE066858 AK001391 H69176 H73968 R96494 AW367308 AL046501 BE206847 AW363720 R58761 N55662 AA249322 AA953186 AA134490 AW674890 BE149647 H73329 AA159064 BE244510 R96540 BE081793 H69175 AA303255 H68297 AW408298 AW408297 AI950056 AW838698 AA337269 AW858823 AA218615 AA306617 AW955262 BE256349 BE386559 BE275395 AW513669 BE175417 BE251038 BE395442 AA353109 AW957319 BE619311 AI630209 AW937114 AW361680 AA136254 R29286 BE616205 AI632275 BE615883 BE615281 AW605285 AW604395 AA292987 AA450276 H68298 AA807738 AA158040 AA595755 AA157993 AW731997 AA279247 AW394245 BE150890 AI672701 AW615751 AW977833 AA936183 AW376724 AA861636 AW574838 BE617939 AI355063 AI827709 AW294731 AW069337 AA805397 N52991 BE046370 AW615684 AA218616 AA279210 AI610434 N89268 AW872956 AI670125 AW452411 AA134938 AA581835 AI672735 AI609609 AI922954 AI140381 AI222769 N54313 AI583523 AI024647 AA134491 AW272722 R06239 AI366952 AA135938 AI700357 AA398451 AA678766 AI090872 AA947182 AW674033 AW170336 AA809443 BE045316 AA779113 AA630611 AI288417 AL044514 T51634 AA626627 AW672972 AI936743 AI003531 AL040256 BE536573 AA116036 AW020234 AI696422 AA809459 AW590332 AI824928 AA911039 AA976920 AF244547 AA534688 |

TABLE 1B-continued

| Pkey | CAT Number | Accessions |
|---|---|---|
| 105039 | 137669_1 | AA907305 AA130348 AW277052 AA366056 AW960004 AI243620 AA228511 AA902186 AI572237 AW340595 AA992201 AA602572 AA130349 H50751 R63643 T80979 AA558367 AA588171 BE043192 BE043580 BE043743 BE043768 BE042032 BE043400 AW301377 BE043489 AI344150 AI311691 AI249572 AW274364 AW268772 AI224233 AI590456 AW302913 AI345856 BE138608 AI583641 AW086290 BE042169 AI345938 AW301796 AI224718 AI371551 AI583797 AI349757 AI344002 AI345922 AI250006 AW268755 AI802798 AW269120 AI284680 AI255085 AI311607 AI284643 AI310868 BE043571 BE041781 BE043280 AI343068 AI223469 |
| 105076 | 47218_2 | AI598252 AA448763 AA142858 AA314199 AA056047 AA090265 H60157 W57916 AF086234 F22165 AA056029 BE396782 W57917 F27183 AA975000 AW007218 AI583241 F32178 AI563924 AI500207 F36633 AW051788 AI241216 AA630401 AA448666 AI734878 AI015250 F23448 AW603082 AA708925 AA372713 AA469104 AA304316 AA372977 AA452900 F33453 AA728846 AA933045 AA868287 |
| 135192 | 5741_1 | U83993 U87270 BE439498 NM_002560 Y07684 AA316197 AW954722 AA975735 AF000234 AF012903 T53417 AA452777 AW604427 AI205525 AW959349 AA298113 AA337884 AW024997 AI633687 AA359184 W30955 AW295511 R60723 AI082452 AI032800 AI824276 AA843367 AI190193 AI432157 AA972272 W02801 T53418 AA677220 AA838236 AI765489 AA700841 AA452596 AW136770 AA630980 AA995011 AA977728 AI954259 AI300715 R10377 AA302820 AI797307 AW874145 |
| 133903 | 14969_1 | X63692 NM_001379 AW502857 BE397040 AI798071 AA490926 AA761775 AW183093 AA935652 AI269110 AI830747 AW505569 AA878256 AI991441 AA719875 AW015453 AA417865 AW503606 AW505299 AW503793 AW504938 AW500273 AW503403 AW504614 AA093687 AW500658 AW504739 AW500610 AL135282 AW804511 AW505281 AW503375 AW503302 AI003012 AW503566 AW505245 AW502737 AW407657 AA323060 AW500279 BE088611 AW408532 H51721 AA522689 AI240655 AW407372 R83279 AW501165 AW500841 BE294986 AA305721 C75196 AW402456 H24268 BE267863 R98901 BE297878 BE559932 AW401578 AA424953 AL046576 AA380578 F08260 R17473 H09054 AA121560 AW602088 H05995 AA677275 AA352850 AA769959 AA360481 AA352944 AI418351 AW293021 AI270781 AI952903 AI742433 AI564492 AI625978 AA622973 AI141776 AI499287 AI208257 AA580154 AI188287 AA401450 AA424954 BE222766 AW473899 AA714556 AA743925 AI620072 AI439509 AI033322 AA806335 AW439248 AI003132 H09055 W60515 AW341814 AW190835 AI952396 AI701552 AI701562 AI174310 AW173473 AW272197 T97335 AI078013 N34857 R98675 AA121699 AI084113 AL120771 AI475941 AI422863 R42819 N52989 AW338649 AW575787 AW516098 AW020720 T29495 AW951377 AA887736 AW575686 H05948 H22676 AW574994 H27322 AW576425 F04487 D19819 AA417716 AA832060 AA815271 AI241589 AI003705 T19259 |
| 133908 | 28620_2 | AU076820 M83216 AA971545 H51609 AA092764 AI926727 AI801609 AI888318 AW950682 R99241 N42334 T68396 R24753 AW083647 R01328 H50950 |
| 133944 | 5151_1 | AW068579 AI205108 AL049969 AA249019 AW068578 AA056648 AA056482 R58113 AA056676 F13429 F11610 AW840189 AW948891 AA338450 AW952752 AA056553 AW993964 AW993974 AW993980 AA446789 AA166952 AW993961 N40598 Z42290 AW948852 W01690 T84498 AA284997 T77159 H60865 AA094499 Z43304 BE173592 AL036483 AI972279 H05379 AW292994 AW296424 AA133268 AA131812 AA453323 AA448120 H93597 AA031743 R68125 AA129772 BE172377 BE544374 AW369298 AW901935 AW369297 AW369263 AW369306 AW369270 AA126199 D62661 AA045870 AA131742 AI598238 AI080612 AA216416 AA522741 AA166788 AA904632 AI332596 N27826 AI142437 R37649 AA004512 AA004459 AI492985 AA284971 AA432103 AA614664 AA542827 AI149121 AA669523 AA045803 T83862 AI620824 AI805311 AI074427 AW192347 AI126537 AI858132 AA026983 AI078530 AI916697 AI206829 AI868017 N71661 AA127220 AA447977 AW194084 H05325 AA469189 AA775907 AI597982 AA678720 AI581612 AA469120 T76992 H11520 H60866 AI382065 AA133788 AA503687 AI863713 AA847108 AA031653 AI371363 T32076 AA876618 R68086 Z39378 AI864225 F13741 AA886579 AA887825 AI954531 N55800 N59149 F09246 D79619 AI279779 D62621 AA516488 R57146 AL080032 D20274 AI868600 AI625136 F01813 F09265 AA888263 AI074624 AA888262 AA934459 AA992530 |
| 133968 | 31286_1 | AA355986 AW965776 W07702 W67356 AI373166 AI655916 AI869991 T87392 W86816 R02541 AW770573 AI499318 AW241688 AA975344 N80580 AI051560 W67260 AA826947 AI088230 AI052067 AI367546 W87003 AW297928 R00059 AW293052 AI369468 T79856 AW294224 T85742 BE046326 AA722708 AW191634 AA490795 AW118587 AI127858 AI288493 AI288615 T90835 T90813 AW514553 BE464846 AI610836 AA490690 AW085067 AA687786 AI591345 D15050 R22712 T27043 R22765 W31576 T27044 N26347 T27003 F11195 BE408487 AA773913 R53292 T10113 AA252877 AA033540 AA675918 AA150877 AA490371 AI567864 AW195477 AI567529 AI700749 AI475792 AW803195 AW820137 AV658376 BE439674 AW058046 AI434821 M78443 AA386182 AW338461 AI766237 R87137 AW271729 AI459830 AW340247 AW193806 BE221907 AI760453 AI935475 AA505626 AI149367 AI126214 AI300513 AW473504 AI096818 AW769876 AA628106 AI935110 AA976973 AA827397 AI373541 AI292008 AI572689 AA929080 AI073528 AI968673 AI961943 AA034023 AI492567 AA595290 AI591158 AA150750 AI624901 AW664088 AI225091 AW338771 AA878624 AI335611 BE246155 N23385 AW167453 AI914057 AI566400 AI362466 AW235573 AW205703 AI075112 AW999675 AW236654 W04652 AI700645 AA252899 AW779263 AW291852 T10112 AW207331 R52638 AI962070 H99228 AW183560 AI914628 R87138 AA732161 AI567585 AI418807 F11004 T27004 H46629 AI270118 |
| 120132 | 357774_1 | W57554 D60903 C14589 C15135 H83629 H17143 AI243227 AI475903 Z38839 T34306 AW085505 D60592 H82752 AA886113 AI961641 D59909 D81156 D80799 Z38595 AI028272 AI125908 AI160678 AA774399 AA768768 AI580883 AA574171 AA928320 AW275377 BE243408 AA886081 AA663328 |

TABLE 1B-continued

| Pkey | CAT Number | Accessions |
|---|---|---|
| 105162 | 3913_1 | AL133033 AI095686 AW994533 AW501074 AB028948 AW361914 H85495 AI909786 AW365107 AA226992 AW938788 AW365084 BE300613 AA007546 AL137644 AA348189 AA314006 AW965318 AA332417 AW849166 AW367089 AW849180 AW849703 AW849541 AW367103 AW849545 AW849228 AW082975 T10694 AW337934 AA846773 R99646 AW579773 Z45094 AW964243 AA386023 N99826 H77791 T80893 R95709 AA193217 N55908 AA418656 AA174145 AW368341 AW972060 AA449584 BE550214 AW864463 AW864397 AA910651 R95710 AI131165 R19049 AA810946 BE180116 H77622 AA668778 AW294688 R99104 AI636492 AW805508 AI802090 AW150158 N70687 T70316 AW805502 T72613 Z40829 AA042866 AW242513 AI741829 AA557208 AA418594 AI022383 T10721 AW090786 AA825153 AA551771 AI307392 AI278436 H99707 AA733000 AI122918 AI678973 AA449326 W87001 AA193218 AW262242 AI266651 AW614519 AI351781 AA176690 AA425079 AW964063 AI435168 M85549 AI536622 AA353413 BE466618 BE466662 AA496000 AI702078 AI250775 AW029439 AI659133 AI800652 BE045664 AI342915 AI342681 AI537979 AI827131 R44036 AI783734 AA857374 AI267518 T91175 AA044417 |
| 127435 | 7085_1 | X69086 NM_007124 AW068350 AI276756 AA010522 AA010436 AA096390 AA808926 AW946518 AA092900 AA640706 AI933802 AW467977 X15488 AW837023 AW837028 AW837031 AA984785 AA331662 AW837040 W03101 AI208201 AA558709 AW273144 AI201281 AA634455 H78336 AA676840 AL046945 AL046967 T29210 AW965973 AI275523 AA233855 AI671796 AW451675 AI611085 AW449960 AA358108 AW965864 N98380 D30948 D31284 N45955 N26947 AA384318 H21757 W60040 T94506 AA204703 W84486 AA379354 AW963924 AA046146 W81048 AL046946 AW606721 AA634874 AW976587 AA744739 AI685733 AI949272 N98830 BE048727 AI623170 AW152488 AW029348 AI088454 AI566007 AI202340 AW193549 W81101 N70184 T48264 AI636267 AI735436 AI761576 BE045949 AI290430 AA503827 AI262075 AW236949 AW665647 W80432 AW236700 AW594040 W61339 T58091 AI970837 AA830152 AA830232 AI263107 AA046321 AI832981 AA860669 AI935758 AW770518 AI809597 AI692972 AI241862 AI377719 AI741950 AW057572 W32113 AI972334 AA025239 N36795 W55927 W55906 AI493394 AA765491 AI476244 AI088220 AA026026 AA570074 AA557618 AI978798 BE350227 AI978824 AW172473 AA771924 AI091618 C00337 AW946594 AA912617 AA993456 AI769854 W84563 AI474867 AI014410 AI422587 AW009137 H99081 D63010 AI914435 AI701280 T94419 AI868870 AW081817 W32171 AI829405 W80562 D82777 T48489 |
| 134656 | 17813_1 | AI750878 AA853767 M14326 NM_003246 X14787 M25631 X04665 AA853089 AA773505 AA257124 AA235269 AA404574 AA461130 W16745 AI284148 AA236646 AI812030 AI250909 AI269249 BE465062 AI963323 AW028334 W30751 AI000621 AA291474 AA878172 AA460828 AA884863 AI000849 AI379665 AI263550 AA593663 AA884172 AA878373 AI803562 AI042554 N94526 AW192233 AI086533 AA257020 N77812 AA852575 AI092991 AA235270 AA236145 W52528 BE552472 AI928020 AI086779 BE089560 AW362285 AW362261 AW362367 BE089561 AI866968 AI588960 AI435009 AI804154 AI492979 AI041974 AA527055 AI763324 AA243572 N26247 AA526978 AI750209 AA256369 R52032 AI278172 AI306124 AI572353 AW614480 N35411 H26096 AA256479 AA464532 AA426510 AA243836 H24875 AW576784 N39897 AI753454 AA464630 AA256885 AI751155 AA852234 AA852974 AA256821 N48043 H40049 AW068763 AW067905 BE002241 AW994516 AI750449 AW753655 N42923 N85003 AW389277 AW995299 AA852235 AA852979 AW581273 AW868821 AW868820 AL047248 BE002218 AW068451 AW992583 AW994560 AW068086 AI752766 AW997017 AW752585 BE002552 AW847916 AW604150 AW604145 AA376395 N98278 BE168445 AW601027 BE168043 AI750877 AA027234 AA703916 AA852402 AV653807 AA368984 M99425 AA149184 AI692802 AA081392 AA853378 AA374765 AI281724 AI003785 AA600110 AA853090 AW994576 AI147763 AA149185 AL047409 AI750450 AW996793 AI768560 AA132207 AI765822 W93760 BE087365 W93493 AA027235 AW050808 AA308199 AW068710 AA373772 AA373735 AW954365 AA080998 AA147963 AA372834 BE158021 AA132064 AI597702 AA371272 W47517 N98350 AA853826 BE003134 AA852274 C01864 AA852340 W24155 AV656963 AI750260 AL079948 AA043624 BE158037 AA599373 AI750876 AA188473 BE151310 AW938210 AW938209 AA370310 AW938211 BE122739 AW938212 H62153 BE001303 H77645 AA007557 AW242688 AI752623 AI093436 N99136 AI755232 AW069822 AI754150 W47518 AA343622 AI373733 AA135843 AA373994 N63907 AI077756 AI828265 AL048098 AA164488 AW630665 AA043285 AI358576 AA344995 AI240286 AA056491 AI752508 AA343471 AW963038 AA037609 H98155 AW008151 AA493195 AA225530 AA775913 AA599857 AI659579 AA852724 BE122738 AA344177 AA419134 AI202460 AA329919 AA316388 AW193072 AA056585 AW893058 R78085 AW844061 AW843880 AW068403 AW068811 AA345809 AA313173 AW068176 D45506 AA226117 BE092720 N70154 AI950521 N32982 AW068363 AW068501 AI248597 AW615014 AI752767 AL048099 AA599930 AW068869 AA599790 AI754476 AA007558 AI750259 AI752622 AW613349 AI572033 AI677990 AI139209 AW449199 AI002688 AI678555 AA852401 D29388 AA852975 AW067935 AI753854 AA081394 AA225254 AA080999 H77646 AW769422 AW069887 T28616 AA852725 AI913010 R78033 AI269247 AI263852 AI755103 AL048309 AA853913 AA375073 AA037309 AA373962 AV656566 AA373293 AA327376 AA308864 AA095749 |
| 134671 | 5525_1 | BE263255 AA375265 AA375347 AF089745 BE144775 AA340612 AW368470 AA078072 BE275609 BE019239 N23502 AA315663 BE018874 F01178 BE312941 BE260733 H12936 AW884739 BE388486 AI380264 AA449160 AL050187 BE168320 AA077898 BE394473 AW844396 T75218 F12856 R53231 R79920 H44804 AA206644 AA569056 R76650 R76629 AA369148 AW382899 R69659 W81156 BE019742 W81439 AA150898 AA595020 AW804672 AA487755 H26670 T63664 R43680 W78225 W35266 BE271750 W72678 AI308872 AA527335 AW069284 AA476808 AW768967 W94802 AA151024 W77784 W70296 AA041480 AI193981 AA040125 BE467203 AI073739 AI183617 AA041485 R80221 AA025390 AI031630 R53232 BE208140 AA026036 AI361928 H44805 AI628129 T87579 R80327 AI040016 AI130024 AA011294 AI201502 R69575 W81157 AI088246 W75993 AA010858 AW081802 W49745 R22901 W42936 W81479 AW241250 AI085106 AI471615 AA022556 |

TABLE 1B-continued

| Pkey | CAT Number | Accessions |
|---|---|---|
| | | W49661 AW139857 AA022612 AI869235 F19474 H05524 AA468514 AI652489 AA022613 AA025412 AA599868 T47997 AW009466 H39695 AW020977 AA704514 AI335108 AI566569 N67921 AA040077 AI392932 AA468984 AI971229 AI050694 AI041456 AA636024 F10456 W23588 T63343 R24479 AW572353 N80262 AI720396 AA812602 W70335 BE274013 BE616914 AA022555 BE408628 BE409712 BE275481 R24478 AI497841 |
| 134696 | 124196_1 | BE326276 R33323 H01620 AI267763 AA947123 AA137146 AI347813 AA910386 N21442 N63579 AI741987 AI768933 AI187285 AA099185 AI813768 AI368703 AI636604 AI827186 AW592490 AW058122 AA421778 N71967 BE468018 AW080902 AI216787 T48695 H01514 R33324 W72293 AI671748 AI284779 AA137074 AI418731 H88426 H88413 H88364 H88354 N71975 N36426 AA884242 |
| 103989 | 214327_1 | AA315993 AA316249 AA313200 AA315069 AA316658 AA307590 AA314181 AA314847 AA316848 AA315862 AW957953 AA307789 AA313418 AA308533 AA308019 AA314573 AA315990 AA314779 AI791286 AI791498 AA313549 AA316634 AW363214 U54601 AA581222 AA315757 AI652625 AW854268 AW854267 AW854179 AW853800 AW853962 AW853952 AW853974 AW853961 AA316525 AW753755 AW361114 AW362522 AI318255 AI318551 AI346914 AI307602 AW577859 AW362532 AW351498 AW361468 AA573910 AA573811 AA573904 AI732541 AA573823 AA573762 AA573949 AI925615 AI802703 AA552098 AA508861 AA573769 AW130226 AI446121 AI926615 AA552304 AA552332 AA552106 AA551912 AA574080 AA552253 AA552492 AW351551 AA552296 AA552602 AA552328 AA588112 AI888532 AI691058 AI452604 AA551820 AA527185 AA584947 AW182560 AA612996 AI933755 AA588123 AA581266 AI537454 AA583270 AI282560 AA582738 AI732344 AA535703 AA837983 AW044042 AI470732 AI444965 AI919553 |
| 119637 | 452840_1 | W52448 W52773 AI201922 AA781389 AI651363 BE550487 AW236796 AW304858 AI695978 AI220182 |
| 105200 | 8286_1 | AA328102 AW962379 N45436 AA723896 AK001611 AA190714 N38804 T06386 AW087631 N55928 AW802534 AW817224 AW856722 AW608045 AW385575 AW386762 AW849265 AW849524 AW849534 AW849638 AW849517 BE567079 AA436931 AA251890 AA436944 AA247829 N40287 N40301 AI572210 AA504389 AJ227855 AA353766 AW957541 AI954160 AA954666 AI817235 BE350644 BE464745 AI198945 AI333281 AI275429 AA504130 AW967692 AA830121 AA976543 AW467238 AA281447 AA251798 R33545 R33538 AW337177 AW294018 AA937107 AA262753 AA496033 AA496017 AI499799 AA195399 AI748957 AA856673 AA856672 R33440 R33445 N56497 AI376457 AI333035 T52152 AI080074 AW802493 AW015712 |
| 113098 | 5432_1 | N77737 AA577996 AW610442 AW610391 AW610448 AW862368 AW610397 AW610390 AW610441 AW604909 T78476 AI760643 N74639 AI913746 T91004 T71577 AW450191 R99475 N58369 AI672811 AW444631 T40936 AK000324 AF271790 |
| 105271 | 178880_1 | AA807881 AW975195 AI278781 AA972195 AA719291 AA757944 AI139653 AA629991 AI587372 AA227986 AI978727 AW263583 AI168721 AW043602 AI079906 AI581282 AI381218 AI124883 R73580 R72963 R39512 H92700 AI267571 AI267568 R39513 |
| 104636 | 81639_2 | R82252 AI247742 AA878993 AA845614 R80756 R27710 R24662 R80757 R70100 BE538468 AA707215 AI086207 T52087 R66365 R31131 R80767 R74462 R74561 AA807929 R73819 R66364 H04865 R27709 AI743578 AI221795 AA907388 R70101 AI702271 AI034342 AA912960 AA587102 AI299799 AI401707 AA004415 AA708307 AA771846 AA680118 |
| 134738 | 18022_1 | AU076801 X83228 NM_004063 U07969 AW853021 AW854674 AW609540 AW753432 AW604493 AW391746 AW854701 AW854703 AW604484 AA308216 AW862312 AW753130 AA053188 AW859530 AW859603 AW859550 AW859567 AW859489 AA102326 AI733765 AW859487 AW879361 AW859497 AW351846 AI347909 AW351659 AW375303 AW375298 AW351613 AW578054 AA376878 AA088861 AI732453 AW887172 AI262603 AW375947 AI920859 AI566493 AI623483 AI922856 AA305406 AA056417 AA313526 AW950160 AA565642 AI732393 AA053102 AI688206 AI721059 AI601183 |
| 128180 | 27120_14 | AW949068 AA557891 AW949060 AW973973 AW949103 AA650284 AA654838 M21896 AA504038 AI557338 AI547284 AI557405 AA471075 AI732363 AA588358 AA229713 AA230069 AA587730 AA230054 AA531476 AA226266 AA729111 AA554524 AA579136 AA228773 AW957255 AA230212 AA570800 AA228802 AA655033 AA229145 AA650240 AA653930 AA226143 AA579264 AA244482 AA618514 AA228761 AA533114 |
| 104667 | 82675_1 | AI239923 BE463623 AA007234 AW129672 AI650353 AI805921 N51082 AI564414 AI241833 H52176 H52585 BE220048 |
| 134750 | 1718_1 | L29073 M24069 AW293566 N74869 AA056554 W61342 AA969622 T03509 AI276528 N27150 AI188837 AI276981 AI190223 AW170359 AI423464 AI377756 AI376843 AI224950 AA742399 AA831313 AA789174 H42895 AW149718 AA018222 AI074968 C03891 H85863 H97623 H85342 AA382137 AA340286 H30556 AA815229 AI133115 H25849 H97642 AA380078 AA383380 AA382758 AW401549 AA302052 H84621 AA172330 AI110693 AF063568 AI064745 W52519 AA194531 AI207399 AA194653 AI093343 AA181440 AA095335 H42965 H26227 AA371139 AI133674 AI758803 H30508 AW022165 AW369654 BE545337 AA382315 AW469333 W72165 H43757 AI064935 H57706 F01198 AW130377 AW665530 AA195977 AW151996 AI827460 AA195973 AA075341 T19285 AA641412 T27859 AW385656 F00921 AA602643 AA481461 AI460135 AA194480 AA465019 AA083512 AA369528 AA838327 W69811 AA194485 AA083491 AI440276 AI127381 F21624 AA018321 AA219619 AI150246 AA192243 R94742 H85803 AI205693 W69772 AA195811 W60042 AW058306 AI610407 AI493237 AW189293 AI809631 AA225326 W60705 W94324 N70453 AI280647 N22114 W60766 H99773 AA085931 H99755 H68991 AW589330 AA176478 AA058585 AI752985 C05741 W60043 H56047 F30653 AA609157 F36887 C74985 AA453355 F35981 AA411135 F34676 AI381517 AA868712 AA193213 AI004865 T40507 AA181379 AI567056 F36145 F26023 H26088 H85937 F26845 F00217 AI749873 AI379686 T55289 T40519 F33567 Z19271 F00061 F16551 T40496 F32783 T36062 NM_003651 X95325 AA481696 F33338 F32308 F35188 F00349 AA446787 AA195826 AA278888 |

TABLE 1B-continued

| Pkey | CAT Number | Accessions |
| --- | --- | --- |
| | | AA193214 F18170 AW339081 AI419655 AI017806 AI802747 AI360980 AI337970 AA887521 AA890618 AA915962 AA731163 AI301559 AI263782 AA411503 R80938 AA345996 AA176737 T11362 H57707 AA962809 AW021331 AA173734 AA173887 N86949 AI768644 AA447202 AA769189 F00065 AA807098 AW752413 AA730257 N20020 AI361372 H98942 AA613376 H39898 AI991933 AA013261 AA111995 AA887647 AA641147 AA716360 BE513481 F00644 AA366694 R76927 AW195998 AA225325 R97125 AA196064 AA828578 AA195822 R27861 AA960783 |
| 120328 | 167625_2 | AA923278 AI341975 AI650511 AI961064 AA196979 |
| 113158 | 8286_1 | AA328102 AW962379 N45436 AA723896 AK001611 AA190714 N38804 T06386 AW087631 N55928 AW802534 AW817224 AW856722 AW608045 AW385575 AW386762 AW849265 AW849524 AW849534 AW849638 AW849517 BE567079 AA436931 AA251890 AA436944 AA247829 N40287 N40301 AI572210 AA504389 AJ227855 AA353766 AW957541 AI954160 AA954666 AI817235 BE350644 BE464745 AI198945 AI333281 AI275429 AA504130 AW967692 AA830121 AA976543 AW467238 AA281447 AA251798 R33545 R33538 AW337177 AW294018 AA937107 AA262753 AA496033 AA496017 AI499799 AA195399 AI748957 AA856673 AA856672 R33440 R33445 N56497 AI376457 AI333035 T52152 AI080074 AW802493 AW015712 |
| 105312 | 8029_1 | BE613348 AW504826 R22239 AW083136 AI472084 AW074277 R22188 AI743908 AI094365 AI539568 R74220 AW779999 AI770133 AI261365 AA988975 AI559886 AI436272 AA036678 AA988508 AA830561 R26449 AI867147 AW518513 AI620019 AA232795 AI801919 AI457722 AA233854 AW205320 AA516294 C02356 |
| 135400 | 19618_1 | X78592 NM_000044 M58158 M23263 L29496 M20260 AW951855 T28396 AA229063 AA524966 AA230070 AA229062 AA229714 AI659563 M20132 M27430 M21748 M35851 M58158 AA659567 |
| 111923 | 8585_1 | BE383234 AF038182 BE387559 T78838 BE078306 BE078298 H69993 AA361778 AW370450 AW069649 BE047106 R39995 R52538 |
| 105388 | 55418_2 | AW575008 AI634855 AW798365 AW292001 AA327938 AW961447 AI809376 AI749195 AI160828 AA777529 BE075261 AI979210 AW474781 AW025432 R70001 AA225644 AA780239 AI684492 AA808020 AI183662 R10298 AA811648 AI078793 AI276655 AI091386 AI753563 AI369160 N66265 AI183479 AI749805 AI347536 AA573243 AA961939 AI422111 AI289097 AW103141 AI283662 H99867 AA953017 AA424859 AI376828 AI084532 BE046019 AA721258 AA236972 AI183622 H87991 H65485 H88320 AI001021 AW192437 AA827221 AA962016 AA884293 AA225539 AI610537 T63980 H87924 AW576472 AI205642 AA833586 AA992204 AI055921 R08316 AW295735 AW021168 AW798357 AA505644 AW519135 AW059649 AA807275 AA738385 AA627239 |
| 113231 | 28318_1 | AA278583 AF035315 Z43970 T77122 AA456857 AA558631 AA304851 AW965988 AV655165 AA284581 R65643 AW296957 N77566 AW977803 AI769688 AI708205 AI033689 AI640339 AW014193 AI204896 AW511025 AW090647 AA854954 AI718554 AA814742 AI523677 AA815050 AA884379 AI521876 N62278 AA665606 N62709 AW890035 R67023 AW043800 AI708796 AI041510 AI522236 T61475 AI915764 AI026127 Z40030 N68220 F19093 T16783 |
| 120483 | 2210_15 | BE251623 BE251539 AA312200 AW027314 T84247 AA252993 BE093135 BE093133 T88719 AW014316 AA648913 AI040032 R59705 BE205801 AI597747 AA159574 AA610279 AI049847 AA780111 AI016328 AI381296 AI672628 AI197771 BE504654 AA252994 AI800528 |
| 105402 | 189_1 | AB014680 NM_004267 AB014679 AF083066 AA243229 AL120609 AA301111 BE208539 AA370075 W07003 H50963 AW297253 AA449208 AW084874 AW006712 AI870244 AW026423 AA126782 H89157 T56257 AI290268 H89886 AI356890 N47867 AI784543 AA973890 N80041 AW304895 T48114 H89887 T35895 T31577 AA380245 AW302278 AW732239 AI805387 AW874605 AI440081 AI797262 AI368451 AI003055 AA243167 H88931 AI354485 AA582666 M79009 AA918884 AI805570 AA846040 AI025213 AA449209 AA682637 AA665736 W22029 BE328570 N51129 |
| 105437 | 8396_1 | AF151076 H63353 BE514333 BE397496 AA307614 AA299715 BE269640 BE513907 AA356102 BE262303 BE543973 AA299992 AA252190 NM_016498 AA317879 AW080934 W95235 H87140 AI871908 AI831605 AW167551 AW301113 AA308486 AA610308 AI400607 H06255 AI359438 H08800 H63355 AI640394 AA748535 AA858196 AA613105 AA552239 AI358153 AA865656 AA808351 AA252191 W92610 AI362958 AI206006 AI223781 AI318256 AI349795 AI363160 AW269073 AI094210 AA856552 AW192973 AI313332 AI224288 AI249393 AI348900 AW268739 AA748698 R36895 AA775898 AI142521 AA748697 AI031635 AI220261 AA811788 AW296500 AI246242 AA767679 AA761033 AA299716 AA953952 AW451143 F30133 F36531 AA613122 AI345152 C02485 |
| 106096 | 90631_1 | AW379378 AA852211 AI751036 AA657729 AI751257 AI752526 T59268 AA299257 D31528 D31541 AA319726 AA364833 BE178218 AA336003 AW173315 AW303375 AA384793 AA417652 C04206 C05155 AA455496 AW794702 AI751258 AW794499 AA600736 AA625303 AI090486 AA258414 AW795817 AW631492 AI768270 BE378218 AA599207 AI828437 AI862133 AA421744 AA419609 AA024968 AA446024 AA419525 AI272646 AI148235 AA455497 AA634323 AI092202 AI191710 AA375571 AA593295 AW957682 AA774270 N64555 AI218226 AI754332 AI039656 N67061 AI350380 AA978105 AI084698 AA912802 AI751035 AI673545 AI432010 AA610296 AI754989 AA971661 AI564218 AA478719 AI221431 AA258397 AA936765 AA456579 AW338252 AI075349 AI270416 AA410897 AW572523 AI382511 |
| 106099 | 5801_1 | NM_012068 AB021663 T71531 T67794 AA344893 H46645 AA191110 BE271163 AA513805 AA512936 T67718 T71368 D31104 AI870651 AW629156 BE207819 AA161164 AA292328 AA815137 AA994765 AA191099 AA994766 N59773 AI000315 H46624 W56638 T64935 W56601 R06908 N93059 T85073 AW390226 AA465295 H27386 R99387 H53559 AW971750 AA714781 T73635 AW381810 AW601287 AW601284 BE063948 AW601286 BE063943 BE064022 BE063949 BE063947 AV651606 BE063950 BE063954 AW601282 AA345127 AW601288 |

TABLE 1B-continued

| Pkey | CAT Number | Accessions |
|---|---|---|
| | | BE063945 AW392058 BE064024 AV653635 AW991637 AW393063 R99298 AI658680 BE395604 N34330 H65944 AA496253 AI769302 AW675052 AW803131 BE467506 N25046 AW872383 AI871397 AA421049 AA179101 R71935 AI658606 AW005082 AI380622 AI499815 AI087208 AI434572 AA628172 AA747921 AA987954 Z39409 BE063944 AI720657 AI796847 AI281663 AW594699 AI720641 AW137984 AI142566 H53560 AW674321 AW132070 AA777352 AI245309 AA969757 AI024020 N73650 R07889 BE063951 T67671 R06957 T85072 R07946 T54592 AW393041 AW393028 T32244 BE175298 |
| 105493 | 86044_1 | AL047586 AW840357 AW840354 T31380 AW840504 T35664 AA256196 AA137140 AW954421 Z36755 AW900287 AA247424 AA643796 N78560 AI753144 AI263010 AA626885 AW300273 AA886718 N59865 AW026173 AI748876 AI720838 AI056930 AI634216 BE221138 AW296259 AI675382 AI677769 AW276137 AA977716 AI078134 AI311733 AI004600 AI984095 AI018092 AI862628 AW044703 N73684 AI302589 AA137069 N73806 N73811 AI989816 AW571932 AA256268 AI805872 N73713 AA015867 AA053711 AW150861 AW510935 AA348340 AA018642 |
| 121176 | 276579_1 | AL121523 AL135038 AW263497 AI867872 AA400080 AW020294 |
| 129000 | 37953_1 | AA744902 AI571767 AI097387 AI357779 AW583460 W39645 AW014996 R85139 H39057 AI675368 AI159850 H96718 W05585 N98881 AI038335 AA206790 AA918345 AI536671 H46750 BE350087 AW197014 Z43666 AI080414 AA886382 H98215 AI202597 C15906 C15872 D80812 D60117 D53401 D81322 D52755 H19694 AA688395 C15801 C15411 AA683218 AA991302 AI263272 AW469791 AI570417 AI114878 AF116637 D61286 R84467 H49688 BE077114 H19693 C15829 H23775 AA339499 W31186 H23900 H97800 AI267364 H46831 AW959927 AA206963 H43859 N80428 H45366 H39083 AA425373 AA425465 AA846590 AA046580 D55145 AA621706 T07073 D54657 T08681 M78869 T31825 N75559 W15471 H39034 AW969557 AA844311 N68003 D11866 AA046666 AW028626 AI692215 AA854854 R85088 H89957 AA131299 AA492538 AA989250 F02980 AW162736 AA158136 AI401506 AA890420 AA917393 AI571336 AI869323 AI827967 AI167686 AI198259 AA158135 AA907273 AA775294 AW162846 AW771452 AI697437 AW134528 AW293478 AI636044 AI339786 AW058021 AW241507 AI633980 AW103281 AI972028 AW058445 AI927316 AI656586 AW590352 AI671179 AI814588 AW241452 AW024820 AW090161 AW273560 AW237544 AI678195 |
| 105500 | 47391_1 | AW602166 H27807 AA256985 AI885416 AI424243 AA781512 AA889422 AA694242 H93603 AW339154 AW629590 AI000160 AW613178 AA256986 AI247191 AA224998 AA256485 C01115 R83652 AI380982 AA333630 AA864639 AW026325 W79647 AF086390 AI287672 W74079 AI276664 AI420272 AI342436 AI298488 N90717 AA224927 AI420762 AI686213 AW577102 H44430 |
| 105508 | 28450_1 | AA173942 AW340361 AW051451 Z30152 AI373446 AI205868 AA877392 N77705 N55339 AI267930 AA045814 AI373456 T90642 AA189109 T31714 AL110126 AA370493 F05971 R34427 AI312646 BE044590 AI220003 AI283798 R38259 AA716749 AI143745 R46634 AA630545 AA629608 H42099 F10707 AA716649 H08738 N77345 AA129564 AA630438 AA047635 BE160867 AW953643 AA359126 BE393582 AW607442 AA256679 W80945 AA456404 N58337 BE274974 AA022974 AI186132 W26186 AI091820 AI570515 AI263997 AA232711 AI140312 AI469924 AI276475 AI129610 AI743887 AI924968 AW188027 AI130934 AI266227 AI493333 AI291964 AA455935 AI375107 AI363031 R48960 AI380788 AA047535 AA876373 AA977525 W80824 AA173541 AA661511 AA232209 AI377867 AA777167 AI492854 AA706605 AI144540 H42054 AA884059 AI473346 AI242452 AI968059 AW274832 AI671519 AW002603 AI934064 AI500491 AA876721 AW182176 AA256680 AA910769 AI382571 AA913276 AI453679 AI199434 Z38891 AI680662 AI459275 |
| 129075 | 10385_1 | BE250162 BE296056 NM_002439 U61981 AA421716 AA723916 N32298 H99382 AI817671 AW364509 AW364468 BE250719 AW364498 AW993728 AA382889 AW473270 N44579 BE514508 BE514324 AW069265 AA969963 J00140 AW575796 AA314334 AL040147 R01547 T91432 T29009 W47530 AI242555 AI379077 AI272820 AI467802 AI827163 AI221263 AW592425 AI472183 AI740752 AW044683 BE467755 AA427637 J00146 AA252992 AI784131 AA694127 AI352150 AA290600 AI040148 AI090860 AA215695 AA227746 AI040147 AA401306 AI332971 AI187739 AW013865 AA010576 AA699792 AI131225 AA700469 R91775 AA778381 AA455309 R00884 T91344 AA682438 AW821327 AA290577 AW864100 BE397831 H25209 BE397236 AW821317 BE253372 J00139 X00855 V00507 BE252613 BE250809 BE256056 BE391734 BE295309 AA031848 J04810 AA749344 AA489055 AA129465 AA280816 AA280833 AI803332 AW572941 AW572255 AA725857 AI184392 AI635482 AI186480 AA463881 NM_000791 AA447680 AI830697 H94631 AA129464 BE071304 W23580 AA742541 AA651836 AW885001 AW026548 AI361777 AA665122 AI359154 AI039319 AA423962 AI469383 AI262751 AA134941 AI138260 AI003995 AI096798 N80705 AA292482 AI436158 AI695673 AI141920 AA932994 AI880434 AI131169 AA424790 AW024376 AA707045 AA557160 N73567 AW051136 AI419234 AI423410 AI919237 AI626046 AI359605 AI421996 AI375347 AI394460 AA426588 H79646 AA423961 W07757 AA447831 AA348708 BE566659 AA463389 AW951651 T28939 AA488803 AA307107 AA281033 AA280993 AW408089 F06483 BE541506 W03282 AA454921 N90189 AA701106 AA516401 AA578546 AI093830 AA481792 AW176093 AW845531 AA639142 AI271794 AW104373 AA834961 AA927195 AI274416 AA664231 |
| 129087 | 80800_2 | AI348027 BE502126 AI138711 AI982983 AW873570 AI367855 AI052179 H29060 AA001522 AW419076 R60761 H41440 AW008195 AA019213 H17526 AW873111 AA535480 AI304671 AI609692 AI367495 AI141287 AW025505 R93547 AI279349 AI581275 N27200 AA872715 AA779062 AI471043 AI224904 AI017367 AA872384 AA738315 AI262559 AI742262 AI041676 R91429 AA057567 H86772 AW131262 AI241156 AA678522 AA953998 AW188581 H69217 H95226 AA976949 H56456 N72695 AA725465 H95701 AI264419 AI220672 AI290418 W57713 AW194286 |

TABLE 1B-continued

| Pkey | CAT Number | Accessions |
|---|---|---|
| | | R99866 H85105 AI074855 AA918031 AI864069 AI678424 H14085 AW166317 AA775239 AA015626 AA429622 AA977988 Z38375 AI000910 AI431360 AA524244 |
| 105588 | 16241_1 | L43821 NM_006403 U64317 Z43516 T32960 AW630081 AA311484 AA371958 AW500483 AW843734 AW843732 AA633455 AW367753 AI888130 AA322558 AA486343 BE301275 AI925674 AI084816 AI859264 AA614658 R85808 AI834268 BE220087 T85067 AW007104 N20931 AA578880 AI686498 AI566735 T39292 T39300 T39304 T39336 T39285 AW613847 AW089138 AI968682 AA493210 N88590 AI753359 Z42849 R61431 N71155 AW516368 T40509 AA064805 T40508 AA380175 AW963532 Z44251 H09381 AA279249 AW675199 AA309822 AW960657 H65178 T24972 R73746 AW859590 AW576255 AW392437 AW947102 AA447838 N40318 AA745981 N35758 AW190522 AI338165 AA478437 AI744191 AI423196 H09321 R61386 AW263144 AI627568 AI360799 AI360842 AW674632 AA279215 AI084758 AW572349 AA910809 H65122 R73663 AI091525 AW363913 AA765765 AA740549 AI536885 AA873412 AA122400 AA687921 AA814628 AW576224 AW196743 Z38985 F03394 AI864842 AI200147 N27798 AA157721 R17863 |
| 128453 | 21764_1 | X02761 AL134153 U60067 M27589 H12552 AI750806 AW069698 H00678 T92951 AA156457 T53448 R77777 T47375 AV653325 T60421 W61256 T47700 AI752874 AA116119 AW150500 R46471 R42093 R44355 R62662 R44189 AW813264 T63601 R32764 AW069338 AW023601 AW020233 AA946739 AI752245 AW191877 D58570 AI754285 AI886146 AA342911 AI139349 AW994835 AW263386 AW994830 T65787 C18724 U42404 AW378684 AW580570 BE174525 AA600101 AW750611 AI356556 AI750644 T47699 R81772 T49245 T93048 R36450 T49421 AW390369 AA082805 BE142984 AA129277 N83780 AI370335 H43251 AA330915 R23404 AA367947 AW608529 W25319 AA935923 AA092761 H75833 R15348 AI750474 T78889 R62612 T53447 U41850 U42455 AW947480 W25621 R21374 |
| 104933 | 6451_1 | N94126 AL079277 AW888638 T99290 T66903 AL079297 AA385535 AI904659 C01303 AI672325 N56904 AI690044 T66879 AI459242 AI984028 AI824050 AW150708 AW292114 AI761229 AI744400 AI076075 AW338738 AI473882 AI866270 AI864510 AA148594 AA515264 N69305 AA812099 AI040500 AI367728 AI803898 R40374 AI916038 AW192082 AI866927 AA909946 AI205640 T99244 AA767512 AA977260 AA063070 AA063098 |
| 128472 | 5868_1 | BE241880 AU076460 BE241665 BE245048 BE247391 BE246660 AA298045 BE077209 AA297464 NM_001814 X87212 AA361792 R72967 AA360906 W24402 R66335 BE535303 AA312121 BE397079 U79415 AA305090 AA376522 AA297298 AA383568 AA297907 AA360340 BE069716 AA298339 H46642 H16271 AI142867 N90454 T80468 AA063400 AA298057 AA298101 AA298014 H66230 AW675364 H04403 AW995462 BE161688 R06023 AA295256 AW864340 AW964280 H71749 T60230 AW864485 AA461415 N39480 AA875996 AA055296 T83014 W32011 AI356625 AI697273 AW363586 AA054986 AI804501 AI955203 AI671058 N47562 AW072362 AW589307 N79134 AW474312 AW189479 AI979123 N33847 AI358930 AW131876 AW264203 AI571565 AW517706 AI702005 R33767 BE044262 AA903662 AI758808 AI625339 AI608874 AI859527 AI419415 AW769283 AW519037 AI589797 H50749 AW262906 AW803051 AW190946 AW470124 AW085499 AI151493 AI589155 AI811579 AW071433 AW043903 AA923546 BE349609 AA946567 N28435 AI027551 AI886029 AI218474 AI249095 AI827883 AI262847 AI038312 AA461100 AA516112 AW607922 AI250238 AI587647 AI445709 AA506164 AI095563 AI367751 AW022921 AA594304 AA954399 AI273385 AA644088 AI765475 AW449748 AA054987 AI359314 H04378 AI362797 W68451 N26792 AI346633 AI302865 AI344505 AI347864 AI339769 AI159818 AI191669 AA917866 AI301086 AW468843 AI346628 AI431993 AI139442 AI474061 W31602 AI554488 AI263002 H97738 AW864080 D20107 H72312 AA922712 AI718444 AA609844 BE244914 AA405503 AA872308 T60170 AW392842 AI866248 AA721249 AI274597 AI473654 AI335841 AI244612 AW768467 AI274576 N62365 T90206 R67476 AW518530 N69192 AI146867 AW510462 AA723925 AA736591 AA055178 AI826023 T56326 AA886405 N24975 AI811447 AW496812 AA632074 AI955935 AA342746 AA358975 AA248112 BE397640 AI042227 |
| 104978 | 71799_1 | AI199268 AA088458 AA631057 AA636031 R45651 AW245042 AW250904 AW248620 R46583 AI149606 AW009855 AA577402 AW516086 R02182 AI972338 R54078 BE301440 AI469797 BE301694 AI243919 F03242 AA887808 F09160 F10267 AI739345 AW382169 BE536816 AW472853 AW083578 BE255725 AW377425 AA088457 AA364880 AA307300 BE616509 AA306659 BE617729 AW885240 AW885210 AA294929 AW250558 |
| 104986 | 128798_1 | AW088826 AW293764 AA845265 AW771263 AI934858 AI720358 AA101632 AW151292 AI969728 BE218525 AA779354 AI783721 AW244016 AI802114 AI093360 AI420138 AW024260 F03967 AW026834 AI373133 AI335587 AI832852 W85852 R79192 AI611148 |
| 120649 | 201075_1 | AA687322 AA642329 AI080760 AI039479 AA832416 AA807302 AA854015 AA889829 AW771843 AI608865 AI819500 AW663364 AA905058 AA287115 AW974492 AI312843 AW302499 |
| 120655 | 37998_1 | AA305599 AF161398 AA249640 AF116682 AI133406 N39717 AA449890 AW027019 AW027067 BE145690 AW027058 BE176728 BE176732 AW024795 AW901295 AW024324 AI869647 AA287306 AA480978 AI570577 AW602318 AA772331 AI151440 BE174451 AI469975 AA827541 AA362212 AW964222 AA983471 AA639458 AA287347 AW439509 AI866765 AI216331 AI224047 AI868763 AA658562 |
| 120689 | 88984_1 | AW134519 AI890121 AI675294 AI338111 AI200103 AW993754 AI811317 AA731663 AA731664 AA974904 AA291168 C75353 AA730560 AI810299 AI438987 R22198 AA143793 AA101252 AI583182 AA216611 W31626 AA857679 H99145 AA020980 AI768078 AI862828 H43598 AI866902 H97045 AA465732 AA733134 AI628409 AI581618 AA494109 AI819116 AA176112 AI472513 AW614605 BE045533 AI478195 AI671411 AA581997 AI628367 AI830602 AI394104 R77963 AW576849 AW881857 R22252 BE220138 AI697987 AA026878 AA327229 |

TABLE 1B-continued

| Pkey | CAT Number | Accessions |
|---|---|---|
| | | AW964784 W32118 R78337 AA340274 AW861417 AW964786 AW369487 AW134545 AW139467 AW372198 AW363178 AW604629 AW372211 N24394 AW390678 H44639 BE547625 BE378546 AA021065 AW749075 D79177 BE003143 BE538347 AA148177 AA501786 AA465134 |
| 129113 | 20805_1 | BE543205 AW295679 AW673574 Z42168 H67124 R76663 R34273 AI248588 BE563389 AI110638 AF063512 AA323818 AW451960 R53683 R35469 R76334 AL050159 AW952333 AA985460 N70948 W20094 AI935619 AA299214 AW022621 T87680 BE173489 H28874 R83808 AA480490 BE173429 T47469 H95166 AA385568 AW956798 W31529 AA531109 N50543 N64019 AW182443 AI278631 AI073393 AA526901 AI056406 AA147701 T49984 AI192203 N50194 AW889806 AI971390 R78690 AI956145 AA576727 BE043948 T67476 AI435353 AA256232 AI096758 AI095656 AI765375 AW889828 AW889883 AW898231 AI880696 AI361249 AI956056 AI240407 AI310705 AI660609 AI806066 AI832496 AI494103 H04356 AA740597 AI216050 AA846346 AI014665 AI038130 AA687761 AI640214 AI306435 AW664764 AI032636 AW129290 AI040442 AA256173 AA704713 H68547 R11671 H43562 R51003 H01321 AI050987 R53571 AI240856 AI192395 W04630 AA781781 H04314 AA340769 H95569 R78642 AI087904 AA147646 AI097392 AI869195 N48462 AI565369 AA910379 T50041 AA469240 D62067 AI370195 AI382557 H95131 AA225900 AA574255 AA328752 BE173506 AA782848 AI766294 Z41612 N90433 AW129932 AI269081 AW299810 AI985143 N76125 R83371 H81430 R00098 R93230 AA975698 AW023941 AA237076 |
| 106286 | 34552_1 | AI765107 AK000557 AW250662 AW404558 AW631125 AI474992 H38495 BE259536 AA338808 AW961032 AW375527 AW375519 AA036978 T98407 AA058761 BE394031 AA366003 AI761506 AA587887 AI573291 AI744657 AA588536 AA738047 BE502073 AA700013 AW246799 T85297 AA759011 AI890594 AI148268 AI587531 T15960 AA830722 AI298775 AI200417 R00301 AI798469 AI825338 AI809308 AI436070 AW137267 AI344370 AA838214 AI085034 AA838498 AI537302 AI368583 AI040364 AI341279 AI365563 H78131 AA036979 AW082916 AI248063 AW337164 AW663937 AA683570 AW473394 AI500302 AI357177 AI927184 AI991231 AA365119 AA573353 AW630338 AW872754 AI766544 AW589264 T32118 AA719102 AI370730 AI469218 AI668957 AI263592 AW103958 AA434441 T99954 |
| 128506 | 19818_1 | L40904 NM_005037 X90563 AB005526 H21596 AA088517 |
| 129168 | 20858_1 | AI132988 F30153 AA330234 AW961558 NM_004894 AF054175 AW248089 AA531530 AA654862 AA216025 AA081589 T83147 AA650169 AL046957 H87571 W31005 W15644 AW967334 AA305437 AA341970 AA134307 AA134315 AI190937 AA094070 AA284212 AA953551 D53844 W30743 T84144 AA133509 AA134308 AA308101 F27405 AA134316 W30854 AA983553 AA626444 F36175 F28648 AI305827 AA468556 AA974508 AI066796 AA554533 AA548236 AA742511 AI209154 AI806566 AI582766 AA903485 AI189759 AI186311 AA569869 AW305249 AI148765 AI244424 AI144495 AA279759 AA521064 AA907836 AA552043 AI000083 AI478931 AI128403 AI200568 H95707 F30237 AI302453 N94464 AA557186 F20977 AI491886 AW183938 AA569868 AA852663 AW275122 H91807 N41841 N30742 AW169997 AI038347 AA746065 AA972090 AA654533 AA654036 AI936891 AI807215 AI332537 AA906338 AA115690 AI251732 AW975227 AL046958 AA937615 AA730937 AI420622 AA978142 AW105551 AW182041 AI363204 AA651663 AI057284 N94563 AI827188 T90621 F18332 AA707791 AA635717 AW249748 N80826 T24920 F18565 AI005595 AW592487 AI674940 AA283903 AA084667 AI674878 T89384 AA552449 AI701784 F37912 AA215865 H91708 AI040250 N98724 AI264957 BE391925 N56092 AA369378 N56408 AA092677 F36194 AW023614 AA664664 AA665052 |
| 105643 | 27555_2 | BE621719 AI650848 AI948512 AI565989 AI701100 AI651953 AA400457 AW665046 AA132285 AI384087 AI862666 AW731708 AI492502 AI417121 AI923718 AI368059 AI798646 AI308171 AI920811 AI766803 AI288945 AA904735 AA905267 AW105089 AI914082 AA337906 AA337575 AW961108 AI890117 AI458515 BE552265 AW515686 AA282069 AI273524 F25739 AW512006 AI334601 AI475997 R36636 AA642305 AA737494 T91753 AA132264 AI572422 AW576228 AA093898 |
| 128515 | 5884_1 | BE395085 AW938942 NM_016639 AB035480 AF191148 AW172990 BE304867 BE384718 T74424 N41733 AA386018 AI219327 AI221536 AA610401 AW859588 N83862 AW391445 AW815436 AW815444 AW815514 AW815626 AW815697 AI768116 AI492143 AA149044 AA149043 BE076102 BE076131 BE076032 F25336 BE075966 AA631934 AW204761 AI768403 AW051452 AW338518 AI800959 AW262030 T56712 AA994944 AI827127 AI568941 AI313436 R48167 AI761510 AW628237 H95227 AI718198 R33355 AA576558 AI358289 AW001699 AI796303 AI767239 AW149867 AI911799 AI004154 AI470703 AW166567 AI470484 AI611273 AI270718 AI867518 AI264959 AA970894 AA873480 AI910684 AI701259 BE275042 |
| 128530 | 28930_1 | AI932995 BE064464 AW371902 AW371841 AI885885 BE064457 AA524113 AA721037 AA504343 AA778099 AI800598 AI693112 AI864633 AI690228 AI400990 AW969089 AW371927 AW371912 AW383562 BE151089 AW383568 BE218503 AW383570 AW371899 BE151097 AW371900 AW293095 AW292008 AA434179 AA714780 R45868 W01182 AW957767 AW119223 AI207864 W01578 AA354403 AA805177 AI613299 AW269636 AA481528 AW079101 AF131777 R60489 T81289 AA481594 BE181020 AA465433 AW808125 T84992 AA749191 |
| 112902 | 22861_1 | AL035633 F11794 F11783 H18042 T66089 H29379 R19493 AW134660 AI299437 AL133995 AA057405 N78357 AA917450 AI002692 T09262 T65008 H29290 AI200874 AA894415 AI732887 AI791768 AI733447 AA988785 N62128 T09261 AW956936 |
| 106350 | 29794_1 | AK001404 AL080146 AW408459 AA308006 AA311856 AW245692 AA314336 AA171604 BE255449 AA333688 N86231 BE273256 AA131058 W21555 AB020981 BE255879 BE538183 AF002822 NM_004701 AA448945 R29074 AA296834 AA129846 BE047883 AA127430 AA356440 AW965782 BE081899 BE122764 AI026942 AI885254 AI148662 AI223319 AI566711 AI589694 AW373217 BE079491 BE082260 AW169180 AW467305 AW574879 AA548534 AI209160 AW264460 AW264424 AI863120 AI827718 AI924812 AW197450 AA830281 AI827510 AA171505 |

TABLE 1B-continued

| Pkey | CAT Number | Accessions |
|---|---|---|
| | | AA992158 AW662743 AI630285 AA129847 AA477855 AI916064 N87720 AW002272 AA774665 AI283511 AI151355 AI285079 AA707003 AA812053 BE502584 AW002394 AA127431 AI932735 AA969143 AA033826 W86050 AA033883 AI184396 N95207 AI538607 AI214873 AW105471 AA644331 AI886966 AI274715 AI365259 AI219971 R12588 AI696374 AA449672 AI873551 AI184398 AW473393 AA442763 AI886545 BE464149 AA612786 BE263965 |
| 105713 | 92484_1 | AI122843 Z43800 R19718 R59259 N74752 W20097 N46928 AA215691 AW672684 AW672673 AL044945 H93163 H92772 AW451096 AW675432 AW675425 AA844417 AW674797 AA855104 AA291320 AA770259 AI749837 AA034362 AW370463 AI825998 AA027067 AA744373 AA732336 AW674014 AA291321 AA029285 AA766450 R59201 AA588329 AI168449 AA215692 AI079651 Z39868 R05650 F03066 AA357760 AW955291 AI992075 AW020148 N90519 |
| 129241 | 20936_1 | AI878857 BE314866 AA373626 AW160437 AW249045 AW247563 AW249444 T35944 AW162790 AI815553 AW163007 AF177862 NM_016185 AW163690 T35507 AW163145 AW162789 AW245575 W17086 BE279269 BE295577 BE298775 AW239152 AA081739 BE546064 AW732933 AW452944 AA306955 T19160 R12895 AW248235 AW248163 AW001143 AW162053 AA837536 AI922962 T33996 AI824155 AI201115 AW083153 AI742667 AW161761 AI830108 AI924200 AI076922 AI660564 AW245321 AW247124 AI819687 AA114831 AW245932 AI208988 AA758649 AA815239 AA528116 D51617 T30432 AI262690 AI208987 AI147137 W58364 AA923127 AI192915 T30514 AA873335 AI143959 AI150497 AA812021 AI131067 AA857674 AI088664 AW026844 AI342320 AI028701 AA732838 T31513 AI090663 AI263936 AA460509 AI146489 AA938269 AA121319 T32243 AA682227 AI380081 W74345 AA037001 AA035430 AA157846 AI122814 AA076666 AA043961 AA125824 N95775 T33977 AI278876 AA844703 AI304927 AI199914 AI086895 AA865919 AI208211 AI797337 AA513350 AI081016 AA935218 AI911153 AA659745 AI621133 AA393554 AA922480 AA506591 AA632008 AA151780 AA635844 F35908 AI150406 AA662271 AA581991 AA326722 AA304090 AW168504 C02124 AA083399 AI687982 AA149372 R10687 AW007563 AA435665 AI138385 AA633131 AI311575 AI214715 AA862738 AA876228 AI365039 AI300793 AI204161 AI014594 AW363392 AW021715 T35946 R59637 T34358 T31159 T34597 AA079616 T30357 AA309738 T30263 AA310849 AA114954 H19161 T33803 H15275 N31561 Z41906 W79797 AA083988 AA339429 AA304919 R10776 AI082390 R12632 AI032249 Z38203 AI349445 AI275653 AW161226 AA436135 AW162952 AA121451 AA304897 AA043948 AA082026 AA149371 AA151779 R15250 AA954536 AW087529 R20831 N55671 BE513794 BE072886 AI929127 AA310437 BE272561 AA991963 BE540931 BE256608 AI142628 AA992004 C15158 AI918160 BE621599 AA205696 AW157040 AW250051 AW248606 AI803396 BE378918 R59503 AW162684 AW675726 AW512625 AW162683 AI879413 AI459135 AI341703 AI991009 R41289 H15276 AI743873 AA459865 AI365995 AI573295 AI913981 AA641574 AI570500 AW157362 AI359932 AW246717 AA102348 R49093 AI720459 AI858810 AI871001 AW157171 AW149373 AI818720 AA629793 AI270364 AI816494 AA628527 AA650006 H40297 AA773757 AI339859 T96425 AA687692 AI146986 AI805615 AA324146 AI571241 AI500413 AA219491 AI050833 R33438 AA912263 AA554740 AA629996 AA666193 AA508137 AA583060 AA083362 H23997 AA527418 AI928881 AW075692 AA768434 D59336 AI422921 W32596 AA037871 AA436027 AW075399 AI608809 AI311089 W02203 AA214526 T52777 AA902300 T52778 AA302623 AA731417 N21540 AI000911 AI146570 AA083741 AI869897 AA035429 BE394057 D54813 AA861638 R36011 N34239 T03027 |
| 112941 | 4686_1 | AW163034 NM_004209 AJ002309 T08741 T80472 N48923 R81887 BE313769 H20603 N46419 AW157065 H03872 AW291363 H03873 AA825164 AW104966 AA776642 AA989308 T16232 H20514 AA890072 AA878765 BE314664 |
| 105726 | 5801_1 | NM_012068 AB021663 T71531 T67794 AA344893 H46645 AA191110 BE271163 AA513805 AA512936 T67718 T71368 D31104 AI870651 AW629156 BE207819 AA161164 AA292328 AA815137 AA994765 AA191099 AA994766 N59773 AI000315 H46624 W56638 T64935 W56601 R06908 N93059 T85073 AW390226 AA465295 H27386 R99387 H53559 AW971750 AA714781 T73635 AW381810 AW601287 AW601284 BE063948 AW601286 BE063943 BE064022 BE063949 BE063947 AV651606 BE063950 BE063954 AW601282 AA345127 AW601288 BE063945 AW392058 BE064024 AV653635 AW991637 AW393063 R99298 AI658680 BE395604 N34330 H65944 AA496253 AI769302 AW675052 AW803131 BE467506 N25046 AW872383 AI871397 AA421049 AA179101 R71935 AI658606 AW005082 AI380622 AI499815 AI087208 AI434572 AA628172 AA747921 AA987954 Z39409 BE063944 AI720657 AI796847 AI281663 AW594699 AI720641 AW137984 AI142566 H53560 AW674321 AW132070 AA777352 AI245309 AA969757 AI024020 N73650 R07889 BE063951 T67671 R06957 T85072 R07946 T54592 AW393041 AW393028 T32244 BE175298 |
| 105731 | 183373_1 | AA834664 BE178044 BE177861 AA625539 AA235759 H13061 N50469 R70814 AA464989 AA292969 AW500304 AI935460 AI040324 AI796981 AI890157 AI949973 AI652063 AW996983 AA398376 AA557462 AI078795 AW080589 AI804213 AI887296 AA976310 AI016158 AW241303 AA364617 AA455270 AI635593 AI208885 AA235760 AW959848 AI333957 AA292711 H13268 AA701078 R70764 AA767950 N53058 AA995091 AI566674 R77646 D52194 AW770208 AI208878 AA382439 AA382328 AA587992 N50415 AA382442 AA382502 AA382393 |
| 106390 | 7471_1 | AJ297436 H02338 AA158880 N32011 N32614 AA525838 AA446964 AI677792 AI139599 AW205435 AA640913 AI685741 AI936226 AI094278 AA548812 AI810655 AA702913 AI017464 AA630584 AI597844 AA662112 H96372 AW338346 AA662078 AA543070 AI086213 AW973274 AI221540 AI685668 AW134915 AI696731 R08364 AI391510 AI220820 AA662861 AI623123 AW006591 AI392790 AI972502 AW139444 AI686348 AI801281 AI583077 AI201402 AI674308 AI474807 AA888696 AI972562 NM_005672 AF043498 |

TABLE 1B-continued

| Pkey | CAT Number | Accessions |
|---|---|---|
| 129265 | 27030_11 | AA530892 R46439 R22993 W51996 NM_004417 X68277 AW013822 R65960 AI913774 AW014748 AI184379 AA459716 R22310 AA524040<br>W45617 R62606 AA129573 AA393264 AA884945 AI306629 AA045451 W94005 H01024 AA045069 W45564 AW085536 AI247358 AI799505<br>AA528000 AA614594 AW303637 AW183973 AI081949 AI200726 AI470067 AI741284 AI224392 AI206005 AA515019 AA688356 AI832134<br>AI309942 AI972472 AI685363 AI524312 AI004940 AA769912 AA988747 AI208880 AI972380 AI806713 AA938288 AA618509 AA634477<br>AI469965 R22941 AA573179 AI200581 AI742424 AA468764 AW054732 AI949274 AI432591 AI569661 AA398653 AI343632 AI817705<br>AI343633 AI762374 AI340158 AI126316 AI452473 AI305811 AI885305 AW051547 AW593370 AW663465 AW026301 AW195559 AI369288<br>AI761910 AI937387 AW182408 AI149453 AI685606 AI214909 AI688086 AA588279 AA845361 R66153 AA868062 AA461299 AI031838<br>AA771818 AA524381 AA835016 AA857094 AI200369 AA991172 AI129153 AW001870 AI808287 AI025372 AI743150 R64308 AI471928<br>AW104466 AI200236 AA782178 AI740595 AW665580 AA772161 R26873 AI857638 AA968943 AI148350 AI245001 AI800733 AI190594<br>AA922198 AA974126 AI239837 AI160915 AI274898 AI222293 R24269 AI348161 AA812960 AI923677 AI479438 AI083758 AA968593 R65836<br>H87192 AI199628 AA468744 AA931769 AA905596 R22200 H15820 R73559 AW044544 AA976433 AW172647 AA991246 AI952977 AI674311<br>AI300680 AW167720 AA991370 AI671264 AA782053 AI831017 AI214093 AA953524 R46348 R32661 H87494 H87747 AA502755 AA970591<br>AA994775 AA532536 AA961973 AA620640 AA781046 AA620662 AI147332 AV656322 AI497863 AA938249 AA723917 AA961371 AA614683<br>AI084704 AA863085 AA757840 AI369289 AI419959 AA909338 AA937061 AA652275 W94624 AA909459 AA909047 AA904783 AI635760<br>AI304629 AW339550 BE219181 AW044187 AI261765 AW028682 BE220133 BE465722 BE550216 AI096961 BE351045 AI832186 AI560934<br>AI436091 AI422196 AI418323 AW026158 AI473340 AI422214 AW139728 BE220958 AI087388 BE221950 AW204648 AW014315 AW015004<br>W44534 AA947314 AI151366 AW075231 AI436034 AI392917 AI769090 BE218794 AW130262 AI589205 AW051278 AI250363 AI830804<br>AW262237 AI990168 AI634871 AI638187 AI798152 AI698185 AW000896 AW469265 AI147840 AI783608 AI627742 AW024420 AI872960<br>AW300037 AW025071 AI951547 AI766009 AI768322 AW008501 AI953376 AI022876 AA862834 AI253026 AI417597 AI436621 H86958<br>AA310606 W44533 AV658735 H26694 H26549 AW827303 AA367151 AA385080 R48196 W21976 AW794572 AW887246 W22848 W16674<br>R66637 AA890723 W37557 R31631 AW754289 AW629883 AI983878 AA296041 AA652782 AI956076 AA148831 AA151060 AA149094 H21593<br>AI110578 R68734 AA312698 AI278791 AV646518 AA528324 AA483050 AA013389 AV662286 AJ227912 AA100643 AA534962 AI950801<br>R79387 H04421 AW029283 AA150767 AW960232 R24508 AI342111 AI354486 AI805249 AW152250 AI954157 AA708746 AA885522<br>AW571463 AW136888 AA367810 AI376297 AA554532 BE122873 T27641 R28260 AA149095 AW273246 AA630085 AI205165 AA843403<br>AI538988 AI148236 AI445086 AW304213 AI718052 R68681 AA576126 AW272437 AA947429 AI721016 D25598 AL079997 AA736640<br>AI653854 AA018197 R26087 AI803803 AI151476 AA342527 H85646 AA953048 AI051042 AA988506 AA100642 AA720526 AA976292<br>AA604926 AA875942 AA977949 AA902944 R79388 H86754 AA150431 D56509 AA628144 R67358 AA046912 AA865418 T03811 AW020544<br>R27999 AA381257 AI283880 AA757535 R48371 H13674 R82642 T56972 AA020881 H85864 AA018946 AA074910 AA394169 AW517919<br>R33499 AA074913 AA654385 R48738 AI244700 D58190 AI270427 H04395 R78941 R55504 H86908 BE243618 H86757 BE122905 AI926294<br>AI383760 AW627357 AI089977 AW264875 H64936 R52399 R80807 T17257 F01408 AA044854 H84908 AI540282 W90037 |
| 128610 | 5905_1 | N48373 NM_001627 L38608 Y10183 AA262217 AW753075 N38736 AA262218 AA464900 AA464626 AI692580 R13558 AA214664 AW601683<br>H09189 AI752497 AA160065 AV653517 AW968888 AV660191 AA482188 T68513 R30733 N46489 W33058 AA336413 AW961079 N26375<br>AW993589 AA280339 F06946 R20701 R25706 BE067521 AI239631 AA837433 AI220324 AI473782 AA127889 AW968882 AI445486 AI754377<br>BE465326 BE503131 AI670792 AI685623 R41236 BE348349 AI439167 AW469600 AW172580 R39862 AW130015 AI040222 AA609793<br>AI753801 R88603 AI288562 BE043005 AI693132 AA160883 H09133 AI684835 N57440 W51882 AA482283 AW505289 AI800765 H97982<br>AI807890 AA156810 AA156842 AA085507 AA085490 BE348821 AI932782 AI093768 AA280417 AA214471 T23573 AI857238 AW612154<br>AI351946 N35165 T32021 T31992 T32027 T32022 AA894475 AA877033 AA937480 AW952613 AI285827 AA810590 AW513250 W39699<br>AA304516 T60647 H19723 D58092 AA160066 AA173200 AA029282 D57784 D57901 T68448 AA481804 AL041869 W55951 H16026 N47520<br>AA256441 N42928 R62450 AA770631 W76153 AI027075 AA855080 AA782515 AA156721 AA825251 W72486 AW189607 T31384 AA156604<br>AI752498 T57750 AW119056 AI431803 AW172541 Z40035 AI378630 N94406 AA523778 W73809 AI332387 H05980 N72898 AW172777<br>AI823902 AI753586 AA687259 AA101774 W45054 AA526261 AA719932 AI492249 N29499 AI914417 AI078799 N29839 H99250 AA025656<br>AW512390 AI357817 AI435550 AW270260 AA912141 AA101149 N29787 U30999 AI167331 AA814355 AA745134 AI288890 AI378398<br>AI075396 R38497 N38915 AI082099 AI278455 AA837745 AA256316 H20060 AA917752 AA777157 AI042419 AW117209 AA029426 T31882<br>AA491892 AI050952 AI184339 AI291162 AI218908 AI147696 AW439899 AI628615 AI417598 AA526236 AI186395 AA954458 AW009491<br>AI038346 AW172807 AW022922 AA641089 AI358995 AA703922 AA887149 AW339840 AA678724 AW001023 AI141359 AI381394 AW242676<br>AI424129 AW089435 D30976 AI027975 AI623932 AA888478 AI382482 AA722150 W35209 AA211084 H06029 W02984 AA523581 R46168<br>R14919 |
| 112988 | 4282_1 | NM_014867 AB018254 AW168269 AA862290 AI002757 AL119225 AA304818 AA324034 AA322898 H08070 AF009203 AI879346 Z43673<br>F05558 AA984778 T85590 R89241 R89245 AA331508 AA331454 AI879725 T80266 AA317341 AW952104 AA090797 M85930 AA478713<br>AI809260 AW090486 AW118578 AW467026 AI590195 AW969236 R89242 AW665003 T85591 AI870604 AW872769 R89246 AI798663 |

TABLE 1B-continued

| Pkey | CAT Number | Accessions |
| --- | --- | --- |
| | | AI871447 AI655835 AI914944 AA702544 H08071 AA757719 AA468523 AW070300 AA478578 R40065 AA884358 AI628680 AI434017 AW468683 AW469670 T23475 AA907552 R38728 Z39728 F01826 AI651919 AW779316 AI201359 AI659697 AI623102 D25650 AW511079 AI187759 AW341763 |
| 105772 | 244540_1 | H57111 AI217870 AA347973 |
| 105794 | 257715_1 | H24530 BE504444 AI817593 AI480381 AI681900 AI201883 AI457347 H29265 AI168395 AW291489 N51748 AI474181 AW272366 AI918992 AI138983 AI300295 AI972632 H85951 AI873790 H57432 H40684 AI810327 AI701614 AA365731 AA365541 AW953992 AI640212 AW291292 AI539303 R58955 AA921945 AW969611 |
| 128666 | 94330_2 | AA808466 AW408541 AW057933 AW173219 AI285317 AI285318 AI188887 T86951 AI674065 AI379851 AI285319 AI273248 AA916353 H05974 AI768137 AI924432 AI206831 AI688061 AW070470 R25166 AW663362 H27003 AW274505 AI244682 AA486436 AA131923 AA031343 AA527280 AI925040 F05052 AA970929 AA147751 AW466969 BE090800 AI986086 R27895 R24664 AA131922 AA147517 T52090 T79243 R30911 BE176703 T84523 R62851 H30605 |
| 107059 | 51551_1 | BE614410 BE263285 AA543021 BE077086 BE077057 AW954216 AW603009 AL079372 AA829458 AI971641 AW957537 AA625338 AA216782 BE302152 AW166947 BE253374 AA608603 AA070497 AW298698 AI654312 N70010 AI805421 N70093 AA574256 AW840760 AA232493 AA740836 AI004468 AA662530 AI138924 BE222560 AA991349 AI261529 AI472035 AI351354 AW768756 AA608545 R45352 AW592971 AA480640 AA406170 AA766706 AW769108 AA614571 AA715089 R46394 AA588606 AI097444 AI630548 AF055882 T34050 Z40494 |
| 107071 | 179431_1 | AW385224 AI024086 D63106 D62579 AA609053 AA858077 AI568799 AI904805 AI022798 AW518879 AI040968 AW663654 AI356697 AA610023 AI359240 AA971629 AI873452 W15305 N92610 AW132137 D63105 AA229060 AI363830 |
| 114292 | 29227_1 | AI815395 AL120368 NM_004265 AF126799 BE260421 AA095017 AA478551 AL118803 Z44979 AW881720 AL050118 AW370482 AW581642 BE396506 BE382648 AW246354 BE313171 T08867 AL047548 AW297013 AW296403 H19385 R25719 H17219 T32904 AW961984 M78952 BE261945 AA450134 H74159 AI571182 BE263579 BE266986 R09913 T91440 AW364801 AA339338 AW248385 AW961065 AW793516 AW245703 AA337430 AL046424 AW246567 AI815776 AI205184 AA225658 AW297948 AW516100 AW296357 H17114 AI859217 AI214035 AW008242 BE265979 AA677778 AF009759 AA593565 AW191853 D51256 AI359204 AI973282 AI500208 AW083410 AW194193 R12563 H18943 AW245580 AW247948 AI659973 T91353 N88658 AA225572 AI927559 AI927445 AA642634 AA665550 AA678588 AI698885 D81096 AW732061 D60750 D60749 AA090561 AI817267 AW015750 AA687090 Z40715 AI674941 AA564889 T30121 AW954225 AA775443 AI865553 AI520908 AW149871 AI694877 AI435027 AA777103 AI041194 AW135397 AI597773 T30520 T30521 AI342344 AI572751 AA662525 T15863 AI985606 AI053516 AI312176 BE560905 |
| 113674 | 4406_1 | NM_014214 BE407555 AW672705 BE538245 BE619341 AF014398 AF200432 AA054659 AA350997 R52482 BE257590 BE255436 BE540254 AA352378 AA368117 AA056721 N95677 AI742203 AI184977 AI703196 AI858501 AW190354 BE219864 AW468540 AI264208 AW088250 BE049259 BE222751 BE546756 W60101 AA297285 AW014889 AW675462 AW381525 AW513795 AW675783 AI624316 AA994724 AW468646 AA744893 AI986396 F32627 F28856 AA056571 AI948591 AI934929 R52483 AI291300 F37406 AI673625 F34593 F22307 R42685 N66051 T96137 AI241140 T79151 F34848 F28689 AI904247 W61362 AA027948 AI015559 T96374 AA297793 AW572361 H69939 AW779474 AA812902 AI266392 AW194846 AI765896 AI636703 AI915311 AA731935 BE222765 AI452567 T33938 AA595049 AI890260 AL079610 T17216 BE620004 AA056470 |
| 105811 | 71767_1 | BE617695 H53446 AA337307 R84598 AA336843 AA336805 H30706 R89516 R47841 AI904928 AW510845 AA526070 AA888053 AI885168 C15349 C15673 AW880940 AW881264 AW882124 AW769062 AW884194 AW882123 AI991953 AI626102 AI335884 AI990989 N34316 AA837994 AA552509 AI401049 AA480481 AI912336 AI653454 AI285288 AI955194 AI554150 AI090803 AI888215 AA595258 AI469648 R85487 H53447 N44209 AA916251 AI690777 AA577010 R49981 AI435882 T36285 AW769431 AI004435 AA293626 AA480480 AI400085 AA991155 AW519306 H38297 AW769088 AI833056 AI287574 AI869239 AI769037 AA394121 AW081575 AW661888 AI284876 AW085042 AI673603 AA552555 AA292365 AI721236 AA687930 AI934050 T03674 AA552171 AA922388 AI582103 H28136 AW137358 AI568122 AI220138 AW001520 AI419713 AW301098 AW301080 AW009642 |
| 129389 | 21074_1 | NM_012445 AB027466 BE407510 BE047605 AA047125 AW084003 AA149494 AA149490 AA292528 AA570505 AA526186 AW006250 AW007762 AI341557 AI799666 AI972710 AI377966 AI962810 AI084783 AI458032 AI190971 AW148913 AA372354 AW970032 AW007426 AA650188 AI123203 AI122890 AI280975 W73595 W73495 AI863238 AA374109 AA603986 AW149089 AW957523 AI307748 AI921067 AI336463 F24537 AI380460 AI367500 AI189309 AI814701 AI766921 AW572106 AA037024 AW072576 AA578293 AI288103 AA235464 AW450642 AA574230 AW294024 AI589229 AI580733 AW512227 AA877009 AI660255 AW188597 AA558228 AI572782 AA658397 AI274628 AI866359 AA864573 AI264439 AA621604 AW515493 AW243333 Z39737 AI567038 AA573997 AA573559 AW236431 AI652870 AI684973 AA034505 AA047126 |
| 128789 | 242173_1 | AW368576 AW608042 AW608060 AI698134 AA485294 AW022298 AA486666 AA344857 AW838572 AA345513 AA486567 AW293657 AI085802 AI814184 AL048262 AI087838 AW269513 AI830641 AI627296 AI762868 AW379562 AW471021 AI817002 AI092496 AI800669 BE465358 BE467033 AA721711 H62838 AA721758 |

TABLE 1B-continued

| Pkey | CAT Number | Accessions |
|---|---|---|
| 121503 | 174478_6 | AA412049 AA399074 |
| 107129 | 4002_1 | AC004770 W05005 AA356068 AA094281 H29358 T56781 AW875313 L37374 BE312466 BE311755 BE207106 BE293320 BE018115 AW239090 BE548830 AW247547 AA776062 BE397382 AA486713 T10111 T09340 AW498981 BE547280 AA356003 AW581520 AW875331 AA580720 AW875336 BE276873 BE408229 AW188148 BE255166 BE253761 AW793727 AW373141 AW581548 AA471223 AA305950 BE263976 AA626820 BE257409 AW360962 AA090655 C00312 BE312741 BE407213 AA209352 AW298199 AW248553 AW297794 AW731722 BE300586 AW731972 AW615446 BE301599 AW615520 AA486714 AW440257 AA196516 AA564630 AA618079 AW192592 AW474985 AA604580 AI627461 AA765440 AI680394 AL135548 AI683224 AI581126 AW245096 AW194154 H29274 N70363 AA629758 AA580602 AA862006 AI863841 AI097667 AI928583 AI358774 BE243487 AA620553 AA653297 AA292690 T10110 Z38906 AA908544 AA340930 AI185438 T03328 T28844 AI687010 AI864965 AI872575 BE388740 T56780 AW373138 BE258717 AA699671 |
| 120911 | 168897_1 | AI189754 AA372041 AL044946 AA653367 AI472490 AA204752 |
| 114394 | 20102_1 | T34462 NM_016588 AF136631 T32644 T31288 T31751 BE296947 Z41921 BE562701 W92054 T08180 R51118 H17989 AI807092 AI765692 AI422694 AA337689 AA336543 AW135790 AA346654 AA054618 AA054521 AA054610 AA007469 BE219031 R67704 BE549718 W67749 W68029 AA054558 N90860 AW055077 AW140145 AI742041 AI742772 AI190645 W94890 AI453070 W17083 AI497992 W79385 AA007307 AA928224 AI143163 R15801 AI023751 AW052203 AI919239 AI333466 H17990 W74094 AA505684 R45609 T03721 N94819 T31814 AA054550 AI309605 AA864456 T32643 R66101 AA936245 AI203769 T08179 BE391402 R14623 |
| 113783 | 4882_2 | AL359588 AK001821 AW160980 AW160713 R60610 R59877 H10278 AA344815 AA349679 AW937762 R51499 R20177 R20270 AI935430 N98574 AA557887 AA559968 H57311 AW957511 AI341683 H10222 R60556 N69972 R59878 AI015582 AI814829 AW515396 T33330 AA349678 AI635336 AW243924 AI371168 W19222 T17389 AW965984 R51500 AI358310 AW136265 F02645 R39158 AI269711 AW150587 F34915 AI825735 AW025929 AI989474 BE548407 H57312 C00272 AW578427 AW604365 T75160 |
| 105914 | 5785_1 | AW245680 AW248105 AI929071 NM_006705 AF079806 AA205205 AW672807 R59883 D83023 R21285 C17926 C18579 R19531 H18546 AF078078 H95114 AI952982 T71522 AI763168 BE045174 BE045175 AI660838 AI928149 AW151260 AI826139 AI765444 BE256392 AI675589 AI928803 W38897 AA292919 AW273339 AI707756 AW206044 AW016232 AW055044 AI160785 AI149164 AI338449 AI151410 AI1453079 AI745590 AI570609 AW119208 AI953225 AI356695 AW299857 AI934818 AW170027 AI934809 AW955915 AI978660 AI497791 AI364092 AI936816 AI566894 AI130953 AW119167 AA994955 N95061 AW249764 AA719323 AI200552 AI039364 AI349345 AI500281 AW731845 AI741812 AA745886 AI032009 AA628027 AI199833 AI122835 AW246013 AI055815 AI933218 AI886963 AI219115 T71360 AA976326 AA902359 AA872300 AI185503 T54128 AA679099 AI186651 AA402224 AI766496 AI672982 AI915367 AA308947 AI399731 AI801925 AI828622 AW016236 R45375 R59884 AA205163 AA424495 |
| 106590 | 78874_1 | AI350260 AA988598 Z28548 BE615969 BE616037 AW410647 W94080 BE295816 H84543 AW629493 AW182849 AI092942 W94081 AI972761 AI744086 AI417665 W52625 AW410648 AW071747 AI076797 T35757 AI479793 AI803421 AI005195 AI375750 AA456665 AI827403 AI192342 AA745830 AI096465 AI362083 AA968430 AI079812 AI276080 AI309279 AI934890 AA649155 AA885011 AA525841 AI309206 AW081737 AI918166 AI802432 AI017501 AI298589 AI302399 AW072907 AA665056 AI305216 AA961542 AA769751 AI274718 AI299711 AW087546 BE172780 AA769250 AA383287 BE465779 AW954068 AI742103 AI219146 AA884500 AI668953 AI670703 AA975981 AI630943 D25769 |
| 105953 | 31475_1 | BE410556 AW029110 AJ272057 BE294818 BE294879 AK001248 M78740 BE269104 AA099795 R13768 BE391355 M78739 BE222168 BE272244 R48417 T78577 AF050158 AA114272 AA319781 AI828701 AA369923 AW007503 H71115 AI692370 AA405292 H00411 AA113208 AA580475 AA441914 AI076756 AI690821 AI369797 T24095 AA514779 AW016331 AA731775 F24846 F35784 AA405293 AA431140 AI243672 AI745565 AA432159 AI223089 AW327585 AW273493 AA369922 BE243391 AI598237 AW086438 AW188208 AW440968 BE464350 AW090654 AW088435 R91137 AI799806 W84581 AW235828 AA913249 AW050992 AW327540 W84580 |
| 130080 | 23940_1 | X14850 NM_002105 AW403571 AA252011 BE612408 BE296104 AA287562 W32583 BE278606 BE408067 BE621198 W94174 BE409472 BE409450 W68240 AA293578 AA452974 AA402261 AA425209 AW403349 BE019334 AW402498 AA252266 AA490804 AA641976 AA404737 AA262121 AA641739 AA252330 AI346416 AA410550 AI127894 AA286894 BE266359 AI660653 AW673673 AI739476 AI052545 AI246051 AA425654 AI934493 AI304325 AI992278 AI368129 AI375393 AI401570 AI741839 AW043867 AW977266 AI150741 AI368127 AI814875 AW075943 AI954049 AW134990 AW574780 AI143329 AI318105 AI283241 AW575172 AW081161 AI142073 AW016427 AA741381 W63774 AI346292 AI141089 AI582307 AI283179 AI126730 AW043912 AI571832 AI298341 AI679483 AI521429 AI346394 AI273252 AI880039 AI383700 AI287542 AA632199 AA448204 AI198285 AI869256 AW574781 AI349346 AA713587 AI263944 AI864900 AI273251 AW515501 AI265988 AW780139 AA909952 AA765867 AA465092 AA744588 AA731158 AA814660 AA748723 AA768424 AA235743 AA765706 AA809967 AA632362 AA722465 AA721072 AI739477 AA806084 AI363026 AA252319 AA830765 AA768839 AA780188 AA737659 AA936522 AA251781 AA648959 AA402783 AA452833 AA262136 AA744737 AA458933 AA768945 AW016384 AI073667 AW140044 AI919463 W02122 AA227390 BE393943 AA282805 AI183859 AA830665 AI871369 AI887043 AA286895 AA594349 AA837324 AA214524 AA810962 AA287576 AA490613 AA825316 AA613373 AA761522 AA731427 AA767785 AA733191 AA948512 R32626 AA251671 AI860358 AI424667 AI493334 AA481488 AA252351 AA731499 AA399475 AA737005 AW137326 AI824260 AA465210 AW247312 AW368898 AA302102 AA256564 AA912888 H24558 AA604467 |

TABLE 1B-continued

| Pkey | CAT Number | Accessions |
|---|---|---|
| | | AA252929 R23909 AI572501 AI858741 AI130884 AI538528 AI288244 AI991619 AI131338 AI379888 AI810139 H18623 AA523536 AW517344 AI279546 AI144242 AI379684 AA573326 AA479696 N23081 AA397812 AA262774 AI186536 AI222012 AI192712 AI818719 AW071697 AI805329 AI871755 AI192609 BE220626 BE219396 AI633555 AW104172 AA577335 AI827811 AW007345 AA625830 AI588989 AW770682 AI148337 AI475084 AI123923 BE550812 AA662467 AI360115 AI805170 AI369687 AI193722 AI282176 AA972427 AA236915 AI336153 AI086426 AI222895 BE549696 AI123934 AI085689 AA235489 AI273579 AA564468 AI239466 AI298426 BE220634 AI417179 AI669072 AI187330 AA252247 AA434251 AI342328 AA477824 AI167911 AI417106 AA961041 AA642406 AA233129 AI082559 AA700492 H41441 AI190068 AA854589 AI279528 AA766145 AI580054 AI193551 AA860764 AA897119 AI143445 H40029 AA242933 AW772475 H41460 H95392 AI825262 AW303587 AW274048 AI962152 AA811134 AA948456 AA402162 AA292269 H81731 AW007786 AA570126 AA928634 AA402817 AA284933 AA410695 AA714511 AA478223 AA197317 AA830632 H22464 H51429 H95424 H81730 AA292963 AA262854 AA456794 AA937842 H22504 R23908 H21208 AA836312 AI090132 H40752 AA233697 H40751 AA256563 AA290819 H41014 AA838308 H51472 AA773829 T77989 AI288232 AA443907 AA025611 AI363870 AA293048 T27807 AW403778 AA224587 AI033349 AA496418 H18622 H30359 AA386273 AA386272 AA682686 AI827574 AI554793 AA760862 AA760859 AI816990 AW731660 AA811889 AA806839 AA767410 AA536051 AA287575 AA481173 AA465623 AA455243 AW950018 AW949942 |
| 128896 | 415_1 | T53925 AV654499 AV657714 NM_004467 D14446 AV658061 AA370274 AF075361 AI110862 AA345505 T74363 AA188651 AW297483 AA345286 R10477 T85969 AF114088 H65999 AI174708 N72345 AA776481 R06022 AV662188 N92084 H58205 AV662210 AW665010 AI248425 AA677287 T73668 AI193644 AA693775 AA188754 AA676216 D12418 R05924 AI242950 T86984 AI868468 N68870 T73568 H66000 T28575 R10378 N92944 AF042036 T72498 AI444654 |
| 130094 | 26139_1 | NM_001471 AJ225028 AF099148 AJ012288 AL031983 AJ012185 Y11044 D80024 AL119755 X90543 AI598214 X90542 AW380842 AW380854 AW380862 AW380861 AW380836 AW380767 AW380855 AW380765 AW380851 AW381524 AL042317 AA348199 H51356 H19658 Z44106 AW867915 BE181406 AW896205 AA181004 R71844 AW373750 AW373775 AW373673 AW373686 AW839098 AW373772 N56175 T81224 M78726 AJ741552 H43286 AI371087 AW090617 AW264022 AW081493 AA348198 AI668882 AI435011 H19659 AI078526 R76486 AI808509 H41556 AA992062 AI242458 R71794 AI280436 AA742280 H50397 BE047768 AW517824 AI866545 N70841 AW263371 AI377521 AA908707 T81014 AW380864 AW391804 T99207 R73356 H25821 R76485 W01458 T99208 |
| 115084 | 10376_1 | BE383668 AK001480 AA148764 BE612465 N29908 AI863707 AI803462 AI984336 AI244784 AI202881 AA101937 AA160974 AW672908 R70272 BE502676 AA076294 AI694452 BE466032 AI634396 AA127707 AA317157 AI431745 AI479348 AW298074 AI819738 AW779732 AI636201 AA127644 AI879529 AI929217 AW967042 AI979011 AW999434 AA160975 AI193979 AI261728 AI611182 AI220151 BE041823 AI808476 R70235 AA829482 AA923724 AA101938 AA479944 AI038574 AI037902 AW772390 AA927845 AA148598 BE504061 AA255566 AA291116 AA905133 AA600243 AI580425 AA256550 AI871555 AW028167 F08651 AL049246 N87182 BE172825 AA661699 AI885987 AI684650 AA199704 AA451615 N29043 N36739 H96228 AA417612 AI911722 AA831277 AI218343 AW182865 W79896 AI927944 BE617134 N26100 AI458582 AA332639 AA808190 AI148566 AI016593 AI262141 AA298989 W78011 N20666 W70001 AA837014 Z39634 AA847214 AA969699 AI572503 N44140 AA450212 AW994671 C00243 AW651724 AI909061 AA206767 AA357059 AW959266 AW501282 AA625313 R76944 AI075024 N83752 BE176339 AI909022 BE219994 AA251651 AI701394 BE535538 AI310331 AA659124 AW020466 AA278712 BE537837 H46637 AI632755 H44674 AI627794 AW779883 AW675586 AI417161 AI521744 AA884469 AA448566 AW514918 AW276033 AI978767 AA449711 BE350283 AW301187 AW511119 AW194437 AI991555 AI051324 AW271236 AI168827 AW673185 AI942281 AI168428 BE179474 AA743631 AW967659 AI569095 BE172268 AI281481 AI859112 AW292479 BE041813 AW075626 R58686 H98013 AA433890 AI953954 AI624812 AW591031 AA173614 AA825772 AW518673 AI678624 AI198635 AA865892 AI689529 AA251550 AA452248 AW593588 AI216855 AW243391 AI205697 N66362 AI918718 AA854270 AI570307 AW151445 N36135 AW959355 W70000 |
| 113803 | 37976_1 | AW880709 AW299730 AW242583 H00775 AI479289 AW299787 AW192551 AI566742 AI459679 AI889230 AI983099 R76873 AI679576 AW168845 AI478838 AI399741 AA525911 AA707181 BE049625 AI004255 H16793 AI078326 AI805808 AW299399 AI687323 AI680013 AI624570 AI193114 AW193492 AW591118 AI088396 AI554160 AI476388 AI860582 AA126669 W15544 BE049628 AA845559 AA862493 AI061081 W42789 AI679592 AA985263 AI889586 AA953324 AI924475 AL047591 AI187008 AL047590 AA505452 AI589312 AI923561 AI640475 AW166735 AI245398 AI076257 AI879857 AI565433 AA643547 R93003 AA630199 N68638 AA610614 AI061082 AI365007 AI185613 AI089598 AI632050 AW472823 AI873642 AI565888 AA370319 AI275678 AI969207 AF116660 AI114821 |
| 107252 | 144520_1 | D60745 D52450 D52669 D60886 D60742 BE545209 AA147290 N47211 Z28667 T24540 AA379681 AW954513 N80340 H69538 N64633 AI478640 BE504487 AI608780 AI031931 AI950473 N79962 AI457151 AA625540 AW297097 AA780347 AI659003 Z19752 Z28668 AI400953 N64544 AI354671 AW197824 AI079956 AI783689 AI079934 AI269572 AI206541 C00535 D59840 D59971 D59919 D60741 D80436 D60744 AA912149 AW628867 |
| 113816 | 437168_1 | H46008 AA757630 H45998 H47035 W45499 H18092 H46080 H46068 W40422 H18132 H46498 |
| 106639 | 7493_1 | AV655272 AI382139 AI124646 AW298134 AA652260 T58540 AI337943 AI354941 AW511303 BE501483 AI371627 AI687503 AI693430 AI693871 BE348647 AI091164 AA947682 AA371477 AI014595 AK001478 AA319342 AA775305 AL119130 R13701 AA363659 AW959490 |

TABLE 1B-continued

| Pkey | CAT Number | Accessions |
|---|---|---|
| | | AA460066 T95465 AI161400 F07057 Z42134 AW298014 AA134238 H15216 R19551 AA356614 AW965786 Z43860 AA448444 AA133248 R09023 AA011707 W52631 BE539194 AA404459 BE540061 H77582 R65897 R82856 R77316 R07005 N76954 AA151044 AW237218 N45210 AA602932 AA602716 AA133302 AA758224 AI934546 AA777775 AA313088 AI090189 AI034208 BE179566 AW243921 AA094482 AA503364 AA150954 N55569 AA459974 AA876807 AA877039 H15156 N50021 N59869 AI359768 AA011659 AI082642 R08917 AI057486 N59861 AI159893 AI373105 AI421080 AI342277 AI627170 AI291327 AI248158 AI248401 AW243833 AW302479 AI359914 AW304855 AA134239 AA700701 AA778115 AW590251 N93112 AA523791 BE328612 R77267 AI685130 AI624648 R65802 AI094830 AV649450 AW197384 H77583 AI554805 AW169702 AI018035 AA719149 AA923007 AA522740 Z39926 AI967947 AW002934 AW242790 AW594430 AI471090 R93133 F01671 R37796 AA879223 R82857 AW297212 AA522866 AW014397 AA935208 F03335 N58316 |
| 106654 | 45790_1 | AW075485 AW172725 AI139839 AW016792 AA884849 AA864855 AI074623 AI971498 AI015679 AA460449 AA770565 AA486285 AI743010 AA135421 AA599969 AI827576 AI280003 N51411 N93321 AI033354 N39592 T08378 AI362995 AA706143 N67186 AI914762 AA776948 AA489379 AI582816 AA630687 AA612847 AA604912 AA877918 BE250407 BE089982 AA599941 AI284644 AI244178 AA847692 AW103367 R39987 AA535348 AA195482 AW673066 AI277886 BE465702 AI248419 AI285130 AW166948 AA573153 AA025800 AI183794 T08907 AW627396 AW088806 AA192412 D16935 H17298 AI886836 AA181649 T79405 H11014 AW245363 AI539823 AA922299 AI252815 AI359568 T03411 AW189837 |
| 106689 | 166691_1 | AW296584 AI148476 AA830427 AW274632 AI743693 AA463272 N27950 AA243863 AI435319 H97988 AI858382 AI652245 AA934726 AI524315 AA283019 AI431707 AI081819 N62389 AI124890 AI828768 AA918069 AA644278 AA602331 AW300062 R44785 AA481312 AI698918 N26029 AI990803 BE504851 AI830530 AI264927 AI379553 AA195654 AA234974 N67908 AW514546 N40392 N59013 N40716 N79356 D79707 N55407 AA236195 AW970965 AA233081 R44415 R49013 AA515611 N45671 |
| 129565 | 22779_2 | X77777 NM_004624 |
| 130117 | 5921_6 | U06641 |
| 128920 | 26098_1 | AA622037 AL135416 AA034266 AA156940 AA043774 AA318437 R71425 W07240 R10964 AA452724 AF014955 NM_004708 AA314244 AA115385 AA133412 AA948665 AI264864 AA903227 AA991276 AI125964 AI187865 AA903588 AA903051 AA416757 AI263705 AI200921 R80461 R81019 AA643309 AI264865 R80662 AA887693 AW858813 AA043775 AW858919 AA557190 AW818483 AW819028 R80815 AA032038 AA301901 AA588453 R71082 AA639204 F31415 F35616 R10911 AA580111 AA484160 F19735 AA595406 N78810 AI500147 AA715093 |
| 130135 | 7730_2 | AA311426 AA121371 AA114214 AW498646 AA351817 NM_001070 M61764 BE619846 AI810820 AI925931 AW189057 AW365287 AI858990 AI197888 AI221058 AI269259 AA114177 AI271946 AI655305 AA830364 AA121361 AA857294 AA628775 AA609451 AI246739 AA493146 AA449220 AI261530 AA918335 AA480655 AA255578 AA716045 BE206558 AA828411 AA864423 AI128080 T77733 AW365297 AI139593 AA665796 AI200431 R49038 AI680375 R56440 N92854 AI343939 AI373574 AW003083 AI660758 AI744469 AI339832 R42481 AA824525 AI337024 AI885656 AA400182 AI870955 AW236018 R49068 AI193261 AI004430 AW090097 AA045552 R08801 BE245481 AI819653 AI301689 AI028729 AI867219 AI571384 H77660 R83857 T78017 AW304199 H54282 AA810146 AI208198 H66693 H87155 AA654271 AA810147 N47968 AW135071 AI925926 AI620421 AA887714 AW378844 R33008 AI825098 AA535373 AI375189 BE614215 BE613460 AI886603 AW015522 T78339 AA551679 AA934637 T89970 R45984 T89334 AA255618 H48520 AW275053 AI671890 AI633271 AI627426 AI586954 AI656141 AI873091 AI342499 BE466834 AW365290 AW379133 AA412154 AA281077 AI474805 C01734 |
| 130149 | 27252_1 | AW067805 BE541584 AA306062 NM_005956 AA070303 J04031 BE312280 AW732457 AW503643 AW160327 AL121244 N83260 BE280875 F07914 AA633577 AA191328 AA314240 BE251948 H10778 T50852 AW673457 AW951060 AA306935 BE259246 AA188726 T39294 R11375 R09358 AW130512 AI619438 AA554969 AW386097 AI885437 AI609985 AA989366 R10672 T84718 AW167464 AW162292 AW675779 BE208814 W72174 AA877847 AI280980 AA653627 AI498020 R73302 AA070219 AI127974 AA747737 AI348140 AI128094 AA855156 AA995409 AA847280 T91855 W79427 R72842 AI871107 AI308940 AI300435 AA188564 AI760179 AW067986 AI268893 AA948506 AI056081 T50697 AI174584 AW131532 AI762639 AA776216 AI203778 AW293866 H10779 AW068193 AW388112 AA781203 AW440839 R09242 AI913678 R14873 AA721106 AI865494 F22283 AA569882 AA764727 T91072 AI262978 F17222 T03579 D12225 AA598833 AI582459 W76460 R49780 AW627960 R10673 W79327 R49826 |
| 128959 | 20608_3 | AI580127 AI800539 AA235117 H05805 AA869002 AA886870 AI797540 AI123740 D79791 AA885898 AI768399 AI333984 AW664874 AA128334 AA278483 AA961059 AI382103 AI937434 AA653690 AA934911 R81196 AA652315 W23609 AW952397 AW965860 AW393401 AA418277 AA136349 AA305525 AW393414 AW610096 AA235225 H06098 AI583185 AA278957 BE439716 AI758772 |
| 130173 | 24209_1 | U38847 NM_005646 AI300003 AW169926 AA830228 AW998285 R50615 AW296351 AA313376 AW387767 AW389642 AW389660 AW389664 AA300785 AW389381 AW389361 H60879 H99890 AW176504 AA436765 BE169286 AA367148 N58675 AI741939 AA319787 AA714641 AW467084 AI628831 AI986341 AI986353 AI582175 BE502875 C15414 AI150028 AW130279 AW173482 AI697143 AI700127 AI912354 AI890195 AA173224 AW770681 AI683138 AI702183 AI570149 AW513881 AW129049 AW664244 AA777669 AI762730 BE349576 AI185139 AI312769 AI335351 AI811587 AW515869 AI611405 AI611404 AI955345 N54151 T79602 AI500593 AI273389 T79578 N75526 AA768440 |

TABLE 1B-continued

| Pkey | CAT Number | Accessions |
|---|---|---|
| | | AI168020 AI801736 C14310 D51562 AI026660 AI873986 AI079700 H99891 R52969 AI914734 H10654 AA749201 N62244 AI214876 H60880 AI354872 AW291419 H67903 AI623992 AA705596 H53300 AW008758 AI914113 AI094478 H07144 T92042 AI381266 D51093 F09534 AI470628 AI128792 D59532 D25590 AI207613 AA359818 AI538959 AA323115 AA322879 AA836178 |
| 128987 | 20632_1 | AI339046 AI275145 R53342 R50891 AW936150 AW936176 AW936165 AW936146 AW936167 AA827713 AA971922 AI209089 AI223019 H82579 H16530 BE535743 AW936061 AI751447 AA026573 AW296214 Z44411 F05916 AW953227 AW403893 AW590566 AA350089 H38073 AA642033 N73355 AI630444 AI630593 AW608717 BE168107 BE064507 W42550 AF131838 AW403365 BE064515 AW803021 AI090600 AA459821 H27054 AA326253 BE538474 AA292615 BE348667 AA744747 N28710 W60503 BE467678 AL120648 W38658 AW085263 AA765645 W79406 AA463813 AA150876 AA025284 W03467 AA025509 W56251 AA121005 AA251900 W72220 AA046864 AA652737 AA460117 AA046616 T87823 W77964 AW770864 AW340730 AW274012 AW274585 AW375893 AA838074 BE044582 AA865270 AA758578 W37590 AI093268 N49501 AI809015 AA576920 AA715298 AI469964 W79519 AI359261 AI215777 W44726 AI090504 AA115937 AW779054 AW069815 R45694 AI091875 T71930 AA575900 AI262012 AA195169 AI090622 AI081436 AI086990 AI086986 AA553947 AI688371 AI066619 AI301033 AI025326 AI687571 AI129737 AA666117 T33329 T73883 AA025323 C02044 AA778035 R53947 AW662808 AA935141 N67493 AI263263 AI186363 AI671927 AI811977 AA731247 AI480217 R50774 AA252057 R34874 AI305238 AI358639 AI089304 AA810051 AI751448 T47322 AA150749 AA082082 AA460249 AI798193 AI963475 AA580432 AI610212 AI911053 AI216841 AA749453 AA730902 AA195269 AA863123 AA461469 AA971960 Z32875 AW970342 AA994639 AA743723 Z38836 AA459701 AA838079 AI471442 T73794 AA970479 AA872546 AI269403 AI202176 W42435 AI829322 AI659000 AI190243 AA534925 F03512 AI003577 AA443607 AI027078 W37485 AA055476 AI381856 AA025816 R39020 AI349563 AW592309 AA284253 AA780143 AI216601 AA926781 AA665590 R15006 |
| 121748 | 251592_1 | BE536911 AI015982 AA707645 AW662200 AW001937 AW027095 AA774231 AI081570 AA810133 AI623723 AW130102 AA629353 AI038782 AI208694 AW197999 AA421171 AA812475 AW295098 H89015 AA383718 AA357223 |
| 114530 | 104600_1 | AA601038 AI620259 AA053027 |
| 114542 | 18581_3 | AW970128 AF038452 AW363691 AI922323 AA777025 AW662423 AW972374 BE042577 AW841224 AI859211 AI192986 AA470471 AW192135 AW571539 AI913866 AA055768 AA503343 AA514607 AI924498 AA506763 |
| 113923 | 3869_1 | AW953484 T09475 W16491 AL133116 BE017986 AA496836 AI750502 BE549107 AA359865 AW959704 AA463418 AA452504 AA378409 AA328156 N24393 R55375 H39596 AW879019 AA479551 AA363023 AA358275 W30769 AK000690 AA496878 H25985 W79868 W52767 W80872 AL365371 H98040 AA367475 AI863187 W21074 BE169312 W58424 AA115338 AA150031 AA115298 H97338 AA411955 AA687480 AI174530 W72509 AI741325 N94422 AI688227 AI687489 AW515631 AI925664 AA461615 AW513548 AA563582 AA582573 BE349263 AA569395 AA834079 AI095261 W72139 AA807844 W52661 AI752480 AA779677 AA926794 AA024450 AA988617 AI567500 AI280806 AW273442 AI142563 W02690 AA150123 AI362861 AA553678 AI061428 W74236 H99144 AA477651 W77880 AI312661 AI028169 AA024802 AI298150 BE328724 AW662231 R40403 AI952450 AI037968 BE351012 AI198327 AW004736 AI087245 AW872846 AI870989 AI334346 AI689546 AI349417 AI332748 AW166280 AI357863 AW104147 T32290 AI979074 AI917258 AA461442 AI536791 AA577352 T09474 W80763 AA987427 N79974 AA187662 AI611160 AW770276 AI201782 AA888165 AI918172 AA411956 AA935961 AW768993 AW074526 AI635472 AI612934 AA478489 AI371307 |
| 114598 | 113800_1 | AA075601 AA075485 |
| 106753 | 184227_1 | AI656166 AI350418 AI355271 AI628890 AI628902 AW291921 AW516418 AW612512 AW206730 AI609136 AW450906 AI928342 AI418296 AI810254 AI401797 AI968486 AA449733 AI335248 AI216435 AA476944 AA477121 AA477055 AI972539 T23913 BE222184 AA595001 AI800322 AI612791 AW519286 AA236726 AA976561 AI969887 AW780016 AW473179 AW074828 AA292470 AA858060 AA608660 AI687633 AI339380 AI206912 AI811358 AW440338 AA931265 AI439148 AI203022 AW593924 AI204178 AI208856 AI419422 AA724031 AI979283 AI202715 AA477368 AI206876 AA460792 AA448589 |
| 129626 | 58648_2 | F13272 F13273 R34445 AV647250 BE082008 W19736 W67837 W39444 W44710 AA368308 AA367353 AI089325 T57082 W69088 W67973 AI090480 AW960154 AA807829 AI460130 U48354 AI708050 AI923927 AI810345 AA112633 D25913 D45480 N68138 AA324910 H57121 R38184 AA640108 N56445 AA025514 F11092 AA493903 W95383 W56152 AA367581 F10871 U73507 N46793 W79760 AA447410 AW945206 W16734 AW945337 AW945335 Z41375 T64536 AW945349 AI304372 AA915983 AA447411 R63583 AI334106 AA553997 AI890637 T94632 AI140098 AI192841 AI368815 N40935 R82052 T65959 N70067 AI092317 W52768 W52662 AW371136 W79670 AI700115 W15352 W74132 F34815 AI033747 W95384 BE139634 AI951289 AI051369 AA025422 AA664205 AA664064 AA861945 BE328556 AI028079 AI193663 N89993 AI698848 AA002155 AI695630 AI911625 AI193944 AA878472 AI382314 W32249 AA778270 AI472493 AA854747 AA026061 N71222 N22176 AW945339 |
| 106774 | 44046_3 | AI216748 AA934429 AW135031 AI658617 AI686188 AI005676 AW275800 T79465 AW501146 R41671 AI989757 AA705657 T58684 AI285567 AW503040 AA478112 AW407946 |
| 129642 | 6175_1 | NM_001360 AF034544 BE617055 AL044893 AW806574 BE312456 AW806754 BE313736 AF067127 AW068650 AF096305 AI903797 AF062481 AW248123 AA160454 BE390816 AL118630 AI878957 H09710 AW806469 AW580431 H04989 R61101 BE537695 AA282412 |

TABLE 1B-continued

| Pkey | CAT Number | Accessions |
|---|---|---|
| | | AW939298 BE261725 AA336925 AW955945 AI026700 T67599 AW150953 BE393459 W87472 AA188832 AA683516 AA923356 AA443525 AA471295 AI285221 AA282516 AI034087 AA970494 H09665 AA678013 AL119180 AW997153 W87507 R16081 AW295514 W05001 BE393891 R88150 AA343352 AI968905 AA364447 BE549329 AI669821 AA328114 AI651619 AW006923 AI651625 AI653428 AI567453 BE502142 AA188795 R50008 AA160364 AA357609 AI685468 AW085492 AI435048 AW237004 AA429396 AA737995 AW249784 AI969800 AA398257 BE047742 AI400394 AI190356 AW027451 AI288677 N70359 BE076148 BE076162 T67482 R50345 AA070075 AA070844 AA503528 R61824 AA781972 AA599455 AI690960 AI610807 AI888720 AI200950 AI183635 AI913455 AA017353 H97015 H04990 AW068649 W87479 H69324 AI042444 AI022413 AI359110 AI370888 AA704505 AA313400 AI203117 AA775663 AA627585 AA399209 AA351881 N57922 AA464773 AI689711 AA514515 AA302341 AA464182 AA599359 AA743498 AA566025 AA292187 N68101 AW235924 AA861245 AI192049 AI682081 F08418 R87706 H69421 AA300253 BE293240 H59653 |
| 100114 | 17101_2 | X02308 NM_001071 BE389795 BE280876 BE271611 BE254747 D00596 BE397212 T90837 AW327374 AA397729 AW411088 T52065 AA433840 AA353074 BE546746 AA309516 AI174883 AW149605 W21187 AI954736 AI539850 AW188482 AI439193 AI140108 AA400865 C17075 BE328762 AI559128 AW514981 AW300821 AI758911 AW271761 AI655570 AA614536 AW196807 AA564837 BE538040 AA769948 AA703102 AW411089 AI478280 AA134538 AI247985 AI479879 AI368057 AI825861 AW779873 AA128870 AI479538 AA678389 AI002380 AA678579 N74133 AW079080 AI914714 AI553714 BE041387 AI860444 T51984 BE466640 AI247990 D29210 AA093053 BE042403 AA663310 AA248117 AA699564 BE535555 W86907 W86939 N84557 AA714923 H74065 |
| 100144 | 13999_1 | AL119964 AW160379 BE410219 D13643 AA558185 AW992124 T82834 BE077754 BE077738 AL135438 T06133 AW681208 AW996263 BE297941 BE257104 BE253839 BE005960 H29660 BE005935 AA243118 AW249290 AW602669 BE515052 AA226841 AL046697 BE258559 BE252955 AW996136 AA658492 AW604418 BE258173 T99783 M79232 BE259672 BE312815 AA774904 AI799855 AA341811 BE392475 BE272462 BE314908 BE304719 AA173117 AA345770 T71525 BE514931 H72789 AA113908 AA349104 BE272501 AW801634 AW955486 H29576 AA305374 AA565003 H18011 BE514959 BE314948 BE271929 BE272003 W32723 W68455 AA155872 H62693 BE272270 AI133557 AI752540 W19931 AA482423 AA460472 R66733 BE272820 AA486921 AW732562 AA150551 BE514739 H81348 AI110647 AF063521 AW880963 W19950 W56219 BE336634 AL042717 F12861 N90499 N90397 T75097 BE620272 BE262345 W40234 BE547249 AI270753 H60091 BE392291 N76889 H53330 H53324 H40265 H66248 W92108 AA489271 AA428819 AA341915 BE271759 AW966989 F05336 AA437333 AA531557 AW173783 H53896 N48225 AA287070 AA362089 N28019 R29030 AA501746 AA327943 AW994749 BE392141 AW994762 AW994756 T73126 AW994746 AW994745 AA405908 D54607 AA479601 N64300 R98916 W20481 AA333707 AA299603 AA305667 W52766 H13595 AA349028 AA482324 T60392 BE394527 H47443 AA173221 W52660 Z20420 W95248 AI620891 AI738414 N58098 AI869982 AI887935 N39036 AA602014 T67809 AW247179 AI354878 AW337151 AI761368 AI147214 AI888376 AA284527 W91979 AA699623 AA102612 AI357783 AW206801 W46288 AA948372 AA482572 AW105415 AI970645 AI597913 T94772 AW373551 AI609097 AI708366 AA405722 AA526112 N21356 W46858 AW136070 N78769 C06484 AI362700 AW085796 AA732843 AA428665 AA596004 N57822 AI307238 H96352 AW192944 AA854322 AI346385 AI952034 AI084675 AA482228 H47353 AI718548 AI739473 AW264939 AW070539 AA576093 AI802777 H60831 AI203711 R40924 BE207882 AI567244 AI207176 AA151987 AI799399 N55281 AW248869 AI638601 H13226 R98690 AI653865 AI911706 AI752539 AI567870 AA429344 AI636540 H81292 AI655027 W45469 AI079628 R96879 AI401671 N72013 AI125570 AA833613 AW103977 W47539 AA429268 H71431 W68408 AA724616 AA719984 AI674429 H57506 AI148115 T28591 AI700654 W95151 AW662647 AI631421 H72790 AI128918 H59440 BE221002 AA947249 AA349234 W94138 AA774522 R38963 AA580678 AI867278 H75383 AA548009 AA774588 AA434105 AA989328 F10463 D29605 AA341914 AA783036 R46201 AA349227 H65321 H70321 AI240737 AI364042 AA372013 AI216668 AA304169 AW273684 AI351212 AI613322 N69235 AI695186 AI911981 AA971392 AA331312 AA613281 AA283188 R41216 T73001 AA579228 AA911984 T61892 N91359 AI185338 H41287 AA776356 AL042978 BE515138 BE394988 H67622 H58049 H71430 H53315 H70320 H75271 H60917 H00791 T87383 R13414 C00137 AI557553 BE382608 BE305235 AW994771 AW994748 BE394341 R46294 AA341543 AA349277 AI905938 T62538 T79843 R45485 BE390795 BE392234 W16625 H00536 T62613 AA085443 N99465 T61686 AA380215 W47586 AA650122 H57505 AA370066 AI905930 T27443 BE393074 |
| 100154 | 16656_1 | H60720 D14657 NM_014736 BE567086 BE566463 BE566112 BE379981 BE566068 AW949480 AW949479 BE564672 BE565224 BE567903 AA366593 AA356557 H40371 R91106 AA330579 BE546676 AA315764 AA353277 H93720 W68219 H60726 AA723497 AI335256 AI638837 AW242317 AI192481 AI910143 AI189304 AW406665 R91107 H89485 AW406166 AI140369 AI344272 AI598250 AI799430 AW265718 AW629318 AI538961 AI538962 AI219489 AA993867 BE620012 BE619351 AA330135 AA330343 AW269704 AA631326 AA923666 AI380114 AI538955 R86943 AI199822 AA676608 AA884789 AW630936 W68220 N29873 AA614457 AW294660 AW235202 AA777983 AI538668 T28263 AI538747 N29534 AI435635 AA860746 AI864149 AI808475 AI419616 AA897252 BE296432 BE267841 AA379911 H89631 R79296 N88180 H60719 H60725 AA352708 R39706 H40318 N84253 BE567446 AI655330 AA954784 AW105094 R36629 AI538678 AA778075 AI301288 |
| 100168 | 804_2 | H73444 N57055 W38867 N90468 D14874 NM_001124 AA017572 W73051 F08781 D82211 R08807 C17011 C17019 AI751223 BE273115 AA295188 BE408486 AW239323 AA151224 R33056 H10950 N44786 D43639 S73906 R05567 R51469 AW798021 AW798014 AI356571 AI128041 AA371484 AI560240 AI808369 AA946949 AW118722 BE273459 AI741969 AA936864 AI264261 AI680241 AA573913 AI619441 |

TABLE 1B-continued

| Pkey | CAT Number | Accessions |
|---|---|---|
| | | AI338029 AI038361 AI669339 AI080311 N26013 AI280673 AI565206 AW519004 AI090337 AA876423 N20993 AL359337 AA876254 AA583015 AI023730 AA151225 AI200677 AI375398 AI375399 AI540560 AI912411 AA446120 BE077450 AI375243 AI287300 AA862425 AI283790 AA936868 AI751222 AA845567 AA844428 AA919043 AI261791 AI424089 AA838708 AI079768 N69205 AI673754 N29357 AA705456 AA470391 AI371890 W19284 AI288343 AI188919 AI073777 AI359704 AI952558 N35478 AI025714 N64045 AW389862 AW368140 AW368134 R50989 R08808 R50837 AW998591 H10951 AW951356 AW087554 R40968 AA369219 AA017304 AW089795 AI085975 AI186391 AL037071 H24761 F05068 R51366 AI886896 N92575 AI934118 AI540490 AI752361 AA886325 AI335573 R05462 AA931968 AI858024 AW070521 AI002461 AA622891 AA027780 N27217 N26931 H24806 AI302108 BE265500 N36645 BE544892 R35177 R26474 |
| 100187 | 15283_1 | D17793 AB018580 AL110349 BE292958 BE567235 AA412193 W38438 W52890 BE566465 S68288 AV656520 BE568206 W19989 AF149416 NM_016253 AV658223 T67588 NM_003739 L43839 W37401 F08737 F06575 T27359 F06300 AA364931 BE300124 H58396 W52052 D82112 D82312 AA366446 H73624 AW663269 T27869 AW950054 AA203134 BE000252 W84844 BE617544 AA402153 H24611 AI813686 AW842756 R27884 AA843129 AI831673 AI971401 AI279556 AI091614 W86023 AA902840 BE250738 AI041999 AA486657 AW007495 AI956150 AI859330 AA147163 AA147070 AA557264 AA557379 C75304 AI749277 AI280903 AA085556 AV654599 AI198281 AI630426 AW276014 AI056004 AA098822 AI264609 AI214196 AI911802 AA854250 AI446111 AI269887 AI222719 AI000022 AA771800 AW024597 AA936023 AA873787 AI814714 AA416778 AA838787 AI400736 N49692 AA702577 AA580221 AA916325 AI027016 AI077794 AA782223 AA854223 AI081704 U54719 AI123388 N90416 AW192013 T67427 AI261978 AA843631 AW613665 AA577219 AI127780 AI026020 AI022916 AI127778 AI023938 H95243 AA705974 AI298309 W84497 AA416896 AW069843 AA706857 AA890227 AI167684 C06401 H24575 AI089404 W60596 H58397 R92154 AI358421 AI245164 AI858236 AA860565 AI075141 W60098 H52506 W60468 W86061 F33598 H58768 AI357836 AI358255 W15361 T74050 AI824136 H75805 AA486560 R27792 C06437 W44838 T74879 AI623595 F05022 D57312 AA678168 H42372 C75359 AA865655 AA781648 AA484781 F02592 H73625 AA524157 AA725077 BE250237 AV659233 BE617020 BE568089 BE618951 AA535907 BE304828 BE567782 T18927 T74932 AA701220 AA854881 AI245341 BE566952 W39320 F06576 R95439 BE568236 AI014414 BE566762 AA872597 AI025983 AI269235 W63727 BE565876 AA772525 AI559249 T74425 T67623 AA075352 AA074850 AA084854 AA989309 AA075279 AA075335 T62735 AW997194 AV646269 T73188 T72351 AV653980 AB031085 AV645550 T74919 BE064574 BE568381 AV653860 AV659930 |
| 100199 | 12561_1 | BE562298 D25218 BE208598 BE388561 BE388799 BE387932 BE560834 AA100612 AA100096 AA147503 AA307237 AW027577 AW444723 AI891104 AI632486 BE048325 BE185154 H21250 H22075 AW052129 AI298730 BE185524 BE218256 AW614528 AW471485 AI190957 AI674449 AI471849 AI262311 AA100613 AI659055 AA730555 AI332995 AI766536 AA788769 AW516400 AA564726 AI524497 AI440293 AA630007 AI589107 AI380567 H22006 AI690130 H20293 |
| 130287 | 24547_1 | AA479005 AA291981 AA477941 AI768117 AI742439 AI740612 NM_003311 AF001294 AF035444 AI863726 AW044158 AW084115 AI290356 W30881 R68174 AI452633 AW015740 H68978 AI309294 AF019953 R75643 AI741008 AI741269 AI188588 AI073833 AI832162 AI766545 AI129104 AI077667 AI738908 AA814143 AI337297 AI277523 AI565240 AI422619 AA293320 AA693763 H68885 AI991120 AI492135 AI281966 AI298392 AI669214 BE467215 N29541 AI200143 AI802743 BE220003 AI689894 AA989208 AW084562 AA057186 AI222900 BE219424 AA503237 AA577052 AI802724 AA968817 AA976627 AA502313 AI306416 AI253677 AI991092 R24092 AA056958 AA113149 AA876081 AA976558 AA369394 T35135 T35140 T35134 D20894 AI611274 AI659266 AI417723 |
| 122411 | 300118_1 | AW172356 AI223077 AA446859 AI432375 AI567144 AW274018 AI288165 |
| 121847 | 289608_1 | AA446628 AI888258 AI334335 AI767188 AI651734 AI371154 AI370597 AA425749 AI278618 AW593395 AI803458 AA628659 AA453128 H01726 |
| 115291 | 22325_1 | BE545072 AI540751 AA301103 AI916675 N85422 BE563965 AA327978 AI816094 AK001515 BE501319 AA279943 BE138895 AA343765 AW963051 AW082308 AI823992 AI653752 AI589007 AI816135 AI566535 BE501307 AW272765 AW242239 AA766315 AI014927 AA578848 AI354483 AI476548 AI038579 AA973322 AA992180 AW472921 BE504789 AI392988 AA506076 AA769228 AI370562 AL137710 BE005656 AW965920 |
| 114660 | 685_8 | AA071383 AA071369 AA083800 AA075976 AA116006 AA075667 AA085142 AA085087 AA076496 AA129187 AA122171 AA076367 AA074080 AA085088 AA084663 AA085094 AA112092 AA075668 AA122253 AA122199 AA071140 |
| 107480 | 13160_1 | AF001691 NM_002705 AF013717 AF041004 AB011140 AW379129 BE149649 AW378873 BE168169 AW084902 AA233948 AA158208 T16869 AW372235 AA507188 AA776617 AW379469 AW372236 AW601186 AW991416 BE184815 AW582622 BE184812 BE184811 AW991619 AW991497 AA025674 AW368139 T57706 AW991434 AW749668 AW576740 AW373236 AI681156 AW749667 AW576752 AW576743 AW991422 AW991557 AW577300 AW577322 AW577319 T57667 AA888121 AI703487 AA025675 T29988 AI298486 W58384 AI680568 W58057 AI149765 AI719398 AW991633 AW991569 AW795578 AA632719 D11970 AW265400 AI914109 AA493846 AA233963 AI139713 AA157557 AW749662 T31016 AA909832 AI401181 AA586911 |
| 106849 | 7043_1 | AL137281 BE205870 AI650975 R14487 AA922570 H11891 H29488 H29523 AI206294 AI215425 R38943 R38942 H08943 AA442674 AA306295 AW958068 AW972543 Z19328 AI863078 C02207 BE350493 AA505869 R40812 T93149 H95001 C18110 AA485465 F27445 AI433831 AA557309 AI377747 BE467304 AI139368 BE348511 F20210 AA912949 AW513418 BE327136 AI127681 AI658928 AA587053 T93063 F33088 |

TABLE 1B-continued

| Pkey | CAT Number | Accessions |
| --- | --- | --- |
| | | AI922245 AA971641 AA663936 AW303901 AI537689 AI283036 AI283962 AW510432 AA708783 H08860 AI363857 AA829264 AA507719 AA829344 AI420107 AI283037 Z19327 F23412 AI678514 F30637 AI864155 AA917438 AI439337 AA485308 |
| 129726 | 6269_1 | H15474 R52848 AF035284 F07283 F13380 R12156 T77191 R13138 R96295 AA356763 AW675367 AA343586 AA489509 AW500426 AF009758 AW341341 AI681262 BE252566 BE252163 AA069088 AA010227 AA307348 H66237 AF009757 AA084193 AA083946 AA374100 AW893308 N36736 AA319191 W76142 AW960664 N31425 AA057653 H10662 BE393342 W81053 AA126186 BE392323 AW902076 F12173 T66054 BE255347 BE251382 AA600210 BE393809 H15419 AI114741 BE391404 BE389714 AA057699 AW305118 BE388163 T89453 AW576394 R66422 AF009755 AA489510 H51753 AI497773 W80802 AA778129 AA069023 R52814 AA365686 AW953989 T97693 AI087020 AA732954 R40619 AA633539 R98686 R82999 AI142743 AI038185 H79526 H70618 W72916 R10913 AA704737 AA010104 AW674760 AA011433 AA703446 AA704480 R15088 F03555 AL041978 AA173042 W92755 AA083606 N28538 AI565712 H97486 AI912320 AI027627 AA948084 AI052027 AA432026 AI479405 AW513386 AA630798 AA633546 AA148694 AW130360 AA236623 N22673 AA431773 T65295 AA126080 AI094889 N24124 W92731 AI380076 AI384060 AW130366 N30429 AA112061 AA236999 AA664256 N26096 BE222996 AI028790 AF009756 AA148695 AI356127 AA083858 W86036 AI311581 AA775310 AI239724 AA992636 AA302659 H08702 AA083953 AI240047 H10663 AW263220 H66350 AW975040 AI056000 AA724663 AW016192 AI918300 AI422577 F09805 AI185362 AW148301 AI474974 AA657794 T74199 AI056494 AA468663 T74198 T89542 H79525 AA011652 AA314276 T97793 R82956 T78297 R10967 AA057613 |
| 106868 | 62559_1 | BE185536 AW387821 AA581144 T10391 AI690802 AA345198 AW136974 AI275804 AI348576 AI868133 AA112069 AA487561 AW044496 AA346366 AW272367 T54856 AV652054 |
| 100202 | 19610_1 | BE294407 AL135112 D25328 AA088354 BE273722 BE272668 BE276672 BE514674 BE279911 BE279913 AW239137 H30835 H30695 H39126 AW603879 AA297040 AA853405 AA143274 AA324224 AA102159 BE410931 AA156346 AA143737 T12211 AW178985 W52954 H19449 D21863 AW603930 R47802 R47796 R12860 AW249362 AL121190 AW675029 BE408786 AA374051 BE311615 AA315645 M64784 AA079444 BE076586 AA316113 AA374646 AA324565 AA044376 AA308362 AW951725 AW805242 AA608558 AA384565 AI719345 AW994518 AW891548 AI565573 H30766 H43768 AI813652 AA169712 AW868192 W07368 AI187907 AA247371 AI479642 BE300944 AA946886 AA617959 H39092 AA725570 AA570091 AA603074 AI073609 AW864812 AI498239 AI570920 AW769140 AW300823 AW613145 AA227722 AW338365 AA634394 AI568954 AI865816 AA622467 AA622586 AW571827 AW517726 W35243 AI653786 AI861994 H28131 AI312567 AI913039 AA565609 AW674259 AW166540 AW103808 AA579837 AA827484 AI199670 AI201785 BE536802 R38433 AA503834 AA878031 AI183668 AI539684 AW770004 AA903232 AA847671 AA617688 AA383688 AA383687 AW248638 AI476052 AW469070 AI634941 AA633506 AI192072 AA873200 AI869874 AA121991 AI707457 AI932686 AA984558 AA406517 AA995260 AA406495 AA769419 AI929834 AA406340 AW512235 AI673540 AA406382 AA284665 AI032219 R87480 AI140638 AI653882 N80241 T28549 N90878 AA826472 AI870799 AW069643 AA169166 AI969266 AA199606 AA156311 AI332993 AA223736 AA847238 AA228101 AA079349 W60432 R49952 AW474675 H28156 H28157 AA303532 AI926938 AI370126 H43690 AA834352 AA648144 AA609613 AA730591 AI274501 AW083391 AI309947 AA740393 AA280414 AW191933 AI018583 AL134423 AI367848 AA349442 AA535249 AW009189 AW000717 AA303169 AA543033 AL043513 AW069701 AI038914 AA143275 AA304073 AA688012 T23544 AA923652 AA187749 AA381201 BE122669 AA865053 AA074435 W23575 AA069978 AA143708 AA515580 AI695525 AA044444 BE378739 BE561618 BE535741 BE252119 AL045356 AW572190 H14937 BE386379 W16562 AA554183 BE275809 AW385196 U91917 AA912272 AA988289 N88262 AA187748 AW516465 AI674256 D57241 BE171390 |
| 106889 | 72482_1 | U46258 AA173149 AA206272 AW408375 AA210826 AA342412 AI075920 AW952891 AW070942 AI026835 AW367242 AW602275 AW367332 AI915314 AW104080 AW013923 AW367328 AA287338 AA133979 AL135396 AW978864 AA934545 AA504314 AI630566 AI630392 AI630319 R23055 AA205833 AW673513 AA173276 AA287324 AI004681 AA829651 AA210721 AI376711 AA688155 AI858354 AA126774 AA836121 AA489233 AA598962 R22949 AI206140 AI028632 AA342411 AA599018 R78445 AW593702 AA831728 AW268252 AI343050 BE047778 AA628867 |
| 100235 | 6535_1 | D29954 AW810400 N86381 T27145 AF070553 R24816 H10674 H05886 T81290 BE081440 AA347340 AW502865 W38633 BE081508 BE545197 N78187 AA354376 AW403884 AW949291 AA430545 N94238 AI827148 AA399070 AI796581 AI684155 T29848 AW949862 AW469201 W44737 R40401 AW469198 AW664344 AW192708 H10675 AW615130 AI862188 N59634 AI292183 AI091968 H90537 H42430 AI033530 H30425 AI291364 AA430546 R45546 AJ274765 AA412170 AA574218 R38945 AA778459 R38811 H05779 H42859 BE018564 AI040602 AW505246 AA507084 R13015 AW503464 BE245313 T80046 H44409 AW602308 BE245345 |
| 130336 | 27120_15 | AA535210 X07730 AA659438 M24543 X05332 NM_001648 S75755 U17040 AI525089 AI524893 AI524861 AI546857 AI525128 M26663 AI547285 AI525832 X14810 M27274 AI557591 M21895 AW973948 AW451486 AI547064 AA659534 AA639308 AA654548 AA534235 AI926979 AA579039 AA225115 AA658261 AA640352 AA229599 AA574023 AA573727 AA535453 AA522842 AA657697 AA659319 AA397360 AA654636 AA653755 AA808858 AA535185 AI826164 AA228845 AA259192 AA228999 T29521 AA557838 AI547051 AA622817 AA397452 AI936076 AI826504 AA577955 AA659391 AA650205 AA640736 AA640280 AA640372 AW957256 AA642495 AA579134 AA523902 AA631704 AA228884 AI524856 AI524842 AA657389 AA572896 AA658494 AA569560 AA640510 AA650269 AW083359 AA654754 AA420678 AA569445 AA564886 AI399713 AA572787 AA662137 AI546893 AA595295 AA216409 AA595094 AA572731 AI669143 AA594993 AA658304 AA622211 AA594942 |

TABLE 1B-continued

| Pkey | CAT Number | Accessions |
|---|---|---|
| | | AA613267 AA622228 AA622221 AA640290 AA541668 AA613665 AA570587 AA420606 AA594947 AA631696 AA579361 AA541677 AA244158 AA244159 AA557834 AA225529 AA564089 AA612574 AA513226 AA568528 AA658266 AI524918 AA420532 AA622386 AA742853 AA622399 AA420427 AA614195 AA177118 AA228440 AA229488 AA225114 AA542918 AA602936 AA595415 AA688100 AA654204 AA533337 AA467972 AA573548 AA650351 AA579038 AW969995 AA659194 AA573563 AA630816 AA654970 AA579480 AA658400 AA226567 AA225626 AA531322 AA229759 AA558395 AA525076 AA420783 AA225043 AA650228 AA420818 AA229219 AA226150 AA658911 AA568333 AA420816 AA513597 AA525050 AA579470 AA226161 AA226222 AA602211 AA527907 AA533137 AA230250 AA641190 AA657850 AA687931 AA397400 AA558678 AA467971 AA573729 AA532918 AA229144 AA569723 AA552572 AA809594 AA531371 AA528279 AA603973 AA533547 AA564290 AA650166 AA550936 AA525122 AA640642 AA639894 AA658551 AA531355 AA654373 AA614206 AA569669 AA244246 AA225154 AA604036 AA548289 AA603549 AA527943 AA524601 AA876387 AA657942 AA602158 AA640996 AA535294 AA603978 AA640517 AA554876 AA524889 AA566020 AA564525 AI734071 AA654743 AA225137 AA603981 AA230145 AA659430 AA605005 AA225509 AA602959 AA564506 AA631839 AA653917 AA603284 AA226430 AA225508 AA530919 AA542887 AA642067 AA653961 AA573590 AA524594 AI535889 AA535572 AA687218 AA243984 AA595609 AA534155 AA650133 AA259191 AA886140 AA228722 AA467814 AA578915 AA551615 AI547277 AA657764 AA894884 AA551616 AA522859 AA572918 AA229957 AA229751 AA531199 AA652522 AA229967 AA551461 AA532935 AA601934 AA230032 AA640714 AA535828 AI865511 AA468362 AA226298 AA469419 AA224930 AA652490 AA573554 AA935415 AA876596 AA550775 AA578325 AA602721 AA640881 AA602193 AA470345 AA470329 AA228299 AA659390 AA503922 AA548820 AA631828 AA468363 AA602725 AA558252 AA937840 AA551700 AA504059 AA640677 AA467991 AA687575 AA569519 AA468448 AA533935 AA230163 AA224955 AA559996 AA573534 AA613750 AA659184 AA468034 AA492276 AA533118 AA177132 AA578322 AA229623 AA578410 AA614248 AA604850 AA602011 AA534015 AI867619 AA535585 AA613770 AA557916 AA641176 AA578039 AA573994 AA468942 AA579411 AA657805 AA886046 AA652492 AA516525 AA652252 AA614074 AA467767 AA469019 AA886501 AA226254 AA224856 AA594919 AA559921 AA224855 AA602123 AA469434 AA579405 AA876824 AA573705 AA657775 AA633434 AA622818 AA580256 AA659550 AA687992 AA468140 AA579217 AA470332 AA468160 AA468372 AA555233 AA935098 AA468122 AA551711 AA641183 AA229801 AA224940 AA570202 AA504034 AA468041 AA228397 AA503262 AA535502 AA886623 AA259272 AA228444 AA503911 AA565282 AA658335 AA574401 AA224941 AA652562 AA640888 AA652767 AA935442 AA641051 AA228914 AA934464 AA467738 AA468189 AA595856 AA635384 AA226579 AA657837 AA566022 AA659486 AA572841 AA658248 AA569582 AA639325 AA555126 AA229568 AA578333 AA533825 AA579236 AA508086 AI826974 AA658203 AA888477 AA228966 AA533715 AA886949 AA541337 AA888317 AA661941 AI969953 AA657879 AA550919 AA533343 AA657824 AA554865 AA687194 AA640720 AA569708 X75682 AA559285 AA632441 AA659520 AA533537 AI201973 AI400942 AI417483 AA526834 AI824643 AI805186 AA548801 |
| 130338 | 35749_1 | AI375726 AA375035 AW473735 AF151875 AI027284 N56147 AI969850 AI392955 AI826989 AA558979 R54959 AA613499 AA617721 AA948475 AA662409 AA903501 AI919026 AI018100 AI208510 AA948714 AF151019 AA988645 AA576978 AA609181 AI422638 BE263495 AW974970 AF161460 NM_016391 W38698 AA657709 T98093 BE387588 AA263009 AA152012 BE613491 AA157670 AA167416 BE620899 BE614317 AA625533 BE514747 AA657391 AA410546 AA081898 BE410812 BE385275 W16728 AA369472 AI830127 AI553745 AI188258 AA372444 AW954346 AA167417 AA152086 AA993228 AW084495 AW006707 AW572294 AI871025 AI088800 AW138264 AW298378 AA532375 AA582896 AW102856 AI814112 AI311113 AI554707 AA156529 AI887782 AI022141 AI369659 AI937626 AI056707 N94929 AA661750 AA715119 AA687670 AI553747 AI206081 AI199362 AI206076 AA504814 AA235739 AI150428 AA766830 AA885940 AI865620 AI383724 T98014 AA677906 AI869522 AI242483 AA884650 AI302333 AI799882 AA554885 N90127 AA401040 AI803167 AA564431 AA570164 AA888995 AA860762 AA515287 AA570106 AI760857 AA251834 AA243508 AI493645 AA465658 AA806966 AA768338 AA627255 |
| 100254 | 15085_1 | AA452181 Z99391 D38037 NM_004116 S69815 L37086 AI381398 N47640 AA131963 R08267 AA365884 AW953999 BE464115 Z99392 AA778361 AA535082 AI352461 T92678 AI277339 AA132035 AI079285 AI078220 AA760992 AI350209 A$$94159 AI393630 AI273266 AI242942 AI242927 AA948705 AW801871 T65049 AA831473 F09516 AI002601 N57494 AI208400 AI347804 AW440529 AW955732 |
| 130342 | 24725_3 | U81802 AL134741 AA283598 AA227592 AA282326 |
| 130350 | 31572_1 | AA369601 AA370114 BE613589 W44825 C05670 R84924 AW630592 AV651362 AV651430 NM_005746 U02020 F06443 AA282448 N47287 AA487998 AW754256 AW754257 AW178826 AW754258 AW178831 AW178827 AW178825 AW444796 AW449977 AA047110 C18759 R58104 AW806186 R61438 AA344546 AA344185 AV660602 BE620411 AA345021 AW855446 N45414 AL135656 AI346985 AW991295 AA363420 L29050 AI628246 AA295240 AI738995 AI201110 AI570810 AI937489 AI921237 AA338046 AI703011 AI912186 AI510844 AA312466 AA169649 AW130031 AA367384 AW173546 AW999163 AW747906 W38435 AA570350 BE619498 AA171644 AA171651 AL036971 N32103 BE440116 AI627325 AI380402 AI378189 N48604 AI494582 N50820 AW242962 AI280758 AI347110 AW262932 AI093801 AA047266 AI591314 AI860900 AI347039 AI935963 BE440094 AW081676 AA258153 N47868 H39794 AW611852 AI581358 AW008393 BE144688 AW192805 AI125068 AI709227 D78876 AW796010 AA916659 N86700 R72589 R72584 F02728 N88264 D20842 AI280764 AA345416 AW607652 AW627420 AA255720 AW510528 BE049565 AA371506 AW051170 AW194725 AI739058 AI422995 BE049273 AI970833 AW841868 AI698490 AI796572 |

TABLE 1B-continued

| Pkey | CAT Number | Accessions |
|---|---|---|
| | | AI718085 BE550421 AI640574 AI951047 AW468381 AI362669 AI984216 AI538830 AI498388 AA369993 AA169829 AA594783 AA806075 AA748507 AA169813 AI925828 AW468332 AI610668 R61393 AI282896 AI538572 AI452566 AA281120 D57042 AA169806 AA594385 AA371153 |
| 130356 | 24765_1 | AF127577 AF248484 NM_003489 X84373 AV645706 AA857317 BE082478 BE082541 AA779730 BE143244 AA971761 AI342295 AI928195 D82209 D82512 D82400 D82182 AA081963 AA316125 T65486 R51409 T65476 F11900 Z43988 AA188083 AW455802 AV653072 AV653725 R59543 AA304478 AA206769 AA209222 AA482984 AI824012 AA768896 AW612577 AI400750 AA449520 T65401 AA211913 AW291960 AI911295 AI446344 AA814760 AA677454 C75000 R59544 R51297 AL039130 AA449089 AI086104 AA809866 AA206804 Z40045 C75037 AW440101 AW197032 AA280932 F09547 AI916155 AA743706 BE241778 AI376408 AW753161 R17465 AA359004 AW965881 AW999119 T07281 AA458503 AI224852 AA595767 AA442995 W37099 N49104 AA054374 T91694 AW299549 AI004825 AW299883 AI627839 BE538413 AI762896 AA826259 AW271632 AW518990 AI859278 AW274754 AW664423 AI088568 AA084086 AI536946 AI031603 AI672268 AI280809 AI344726 AI092301 AI678783 AI161136 AA845846 AI799760 AI049949 AW272717 AA814205 AI687186 AI564231 AI368242 AI280221 W37800 AI280217 AA780874 R42811 AI675645 AI432495 AA775158 AA947820 T93292 AA887849 T65412 N50218 D81782 |
| 130380 | 23719_3 | AI949359 AI951632 NM_014498 U55853 AA877669 AI350831 AA594567 AA757313 BE004166 BE004172 AI751019 AA775945 AW900183 BE179065 C75329 AW176764 BE081225 AW841878 BE081243 AW751717 AW176761 AW176760 AI380670 AI150603 AI739640 AI208928 AI351823 AI392887 AI652303 AI570420 AW612023 AI380056 AI739087 AI817139 AI127352 AI760233 AI380993 AI392843 AI916076 AI962401 AW772471 AI569713 AW204685 AW206595 AW452676 AW134712 AI751018 AI638153 AI492220 BE551859 AA627523 AI343520 AA535030 C18867 AA447271 AW366490 AA448760 |
| 130385 | 24861_1 | AW067800 AW089012 AA497040 NM_003714 AF098462 AF055460 AI474188 H98185 AI087984 AI760274 AB012664 AW068334 BE019475 AF031036 AA195455 AA497118 AA456244 AW673699 AA298636 AW068233 AA373922 AW600316 AW731682 AA463548 AW601596 BE219547 AA825343 W46285 AA223294 BE206056 AA704088 AW068001 AA463501 AW068149 W46425 AW068066 AI754129 AW166703 H97088 AA120990 AI906777 AW294872 AA126474 AA506770 AA113396 AA223369 AI908075 BE621311 R50082 AW960175 AA305041 AW601338 |
| 122512 | 19449_1 | AF053305 NM_004336 AF046078 AF047471 AF043294 AW752982 AW500073 AW601961 AF011387 R94348 BE270025 AA383290 AW959418 AA301178 AW374428 AA315653 AI635394 AA430092 AI678046 AA885302 AI184582 AI637516 BE077207 AA913888 AA449311 BE547063 AA806242 AA446462 AW028219 AW576327 AA548086 AA694593 |
| 114795 | 27494_1 | AB037858 AW888417 BE168022 BE297137 AI205125 BE003963 AW965680 AA349466 AA351821 AI492558 BE146202 D31580 AK001199 R45887 AI372674 AI755276 BE168407 AW840238 AA160849 AA027021 T18598 AA161281 AA143489 AI372673 D80801 AI870013 AI460100 AA158252 AI971206 AW071873 AI431911 AI493768 AI439206 AI376927 AI038534 AA678831 AI418906 AI356122 AA789304 AW150270 AI499098 T98883 AA349465 AA330631 D80800 AA158399 AA350488 AI334361 AW338483 AA351820 AA301787 AW753882 AI926390 AA702382 AA376185 AI084962 AA355373 AA102488 AA100840 AA325211 AA425180 BE392668 H50462 AA367255 N94717 AA037160 W89039 AI096627 AI750041 AA102418 AI589918 AA313505 AW951928 AW082735 AW189862 AI567485 AI590590 AI494149 AI422826 AW082999 AA043408 AA043409 AI363488 AW104306 AA877117 AA476207 AI811883 AW026405 H63354 AI992015 W88956 AI190217 AI738539 AI361483 N77542 N62261 AI359937 H41345 AA156068 AA102489 AW339965 AW083453 BE139062 AI937868 AW075493 AA654017 AI094530 AA548969 AI686221 AI961671 AI570099 AA904590 AA631107 AW770217 AW471322 W88756 AW134571 AL042199 |
| 106925 | 10086_1 | AK002011 BE560115 BE244257 AA313857 AA354345 AA481981 AW962091 AA482086 AW440413 AI679439 AA090435 AI868537 AW089582 AW474722 AF038172 T77208 AW856051 AW960758 AW518287 T99228 AI307233 AI262765 BE002408 D81717 AA831090 W16962 T94688 R82725 N75161 AA329959 BE000997 AW471326 AI768878 AI627326 AI016722 AI985651 AA745481 AW166835 AI799250 AI658978 AI392702 AW166451 AI683838 AI049806 AI184623 R66658 AI700203 AW087581 AI022581 AA491261 T94333 AW151396 AW518715 R39449 N89614 AW340791 AI469622 AI583586 AA385922 AW954135 R77484 AA214329 T24555 AA214170 |
| 129823 | 20333_1 | X00949 NM_006911 X00948 NM_005059 V00578 AI004059 |
| 131076 | 142899_1 | AA749230 AA827843 AI584078 AW628529 AW294894 R44598 BE206653 AA136884 AI332945 AI025951 AI809614 AW168575 AI291313 AW631327 AI085768 H96656 AW439344 AW078937 AI656243 N62596 AA280025 AW339047 AI800241 AI094105 AI369449 BE465417 AW769001 AW051849 AA961618 Z40582 AA452517 H44386 H88601 AA454100 AI000264 AI521686 AA136958 N78362 H88600 R88383 R44859 AW382784 AI824802 AA249363 |
| 131083 | 7920_1 | Y09763 Y09765 Y07637 NM_004961 U66661 R07883 AA347289 BE001800 T78142 AA299532 R91732 AW578245 R64082 H83086 AW889734 C17786 H63934 AI963395 H63532 AI432632 AI332325 AI334197 AI400573 AI334196 AW009693 AW014213 R49719 AW070871 AA776409 AI276837 AA677867 R35667 AW316736 AA682288 AA704433 T27014 AI040493 AI682740 AA954089 H25140 AI168466 AW796808 AA634042 AI924717 AA321214 AA677292 U92283 |

TABLE 1B-continued

| Pkey | CAT Number | Accessions |
|---|---|---|
| 131084 | 28427__1 | NM__017413 AB023493 AK001855 T27132 R60088 T51728 AA367598 AA372030 AI871469 R60026 AA099445 AA083736 AA101878 AI149981 AW015212 AI493364 T27131 BE463932 AA083737 AW594286 AA367347 W67823 AF086248 W91937 AI871137 AI932377 T51938 BE465845 AA676726 AA680168 AI419647 W94900 W67638 AA304416 |
| 129890 | 21128__1 | AI868872 AI701282 D00025 AV659396 AA332389 AV653260 NM__000096 M13699 AA873581 AA865338 T61867 AW276926 M13536 T67969 S77464 AV661653 AV652883 H86642 AA166973 AA166820 X04136 AV661909 AA492037 AA333043 AA333248 AV650236 AV650229 X04137 AI064929 AA171809 AW950668 AV656880 AV658013 BE006635 AA172240 AA166902 AI683839 AI687338 AV648674 AA741202 AI921934 H86554 X69706 BE439435 T28653 AV649343 BE065513 AW273276 AA165482 AA171694 AI358150 AI289226 AA172005 AW827499 AV658379 AW419072 T69670 T40113 AW118431 AI288268 AW303836 AI985661 T51148 T71679 AI538280 AW193233 AA165601 AI769578 AW088433 AV655147 AI950030 AI302101 AI889538 AI761095 AA832118 AA402240 AA918982 AW006277 AA661833 AI923375 AI309991 AI924724 AW015771 AW576487 N53433 AI269889 AI458138 R46148 AW244013 R26189 AW474149 AW089848 AI886539 AA953507 AA219354 N69299 AI194079 AI301236 AI277803 AA402701 H04754 H04844 AI128266 AA946849 AI277947 AA283661 AI343881 AI467936 AA169335 AI823730 T69598 AA769673 T68167 AI690616 AI933892 AA344900 AW950671 T67818 T40914 AI857292 T41019 AA603131 AA344899 AA825794 AA171782 AA283660 AA281666 AI648426 AW050523 R26437 BE081066 AA172094 H42697 BE172361 AW839157 AW890922 AW839165 T68242 AA344502 AI922198 T60369 AV656493 AV658487 AV652320 AV648804 AW519214 |
| 100368 | 24424__1 | D79987 NM__012291 AA339975 AW867242 T86767 AA780037 AI023991 AI022797 R21501 AA455415 AA581005 AA548572 AA248889 BE019694 BE467107 AI214569 AA948058 AW008862 AI283098 AI458447 AW009863 AA928961 AI800823 AI127437 AI268609 AI023899 AA694341 AA580948 AI816969 AA456053 AI446360 R42883 AW497592 AW497604 |
| 100372 | 29155__1 | NM__014791 D79997 AA307070 AA436897 AA307476 AW949325 AL135150 AA461263 AI693521 AA626419 AI590871 AA587220 AA903137 AW003353 AI870210 AA460956 AI082492 AA744784 AA744782 W32362 AA768291 AI637653 AI888723 AI753377 AW134936 AA835959 AA664563 |
| 116024 | 17331__1 | AA088767 AF224278 AA128075 AL035541 AA027926 AI761441 AI972096 AW071693 AI742327 AI377498 AI804815 AI640802 AI885001 AI921394 AA595115 N71820 AI921217 AW007283 AI467828 AI369306 AA917446 AI493698 AA088701 AA126899 AI936228 AW204238 AI039567 AI925027 BE138909 AW452945 AW135998 AA310984 AA027860 AW073519 AI537597 AA953976 AI521341 AW273569 AW050740 AA536113 AA559064 AI474392 AW135709 AA535181 AW572959 AA570597 AI905464 AI677810 AI587642 AW975102 AA424310 AA482527 N64192 AA658276 AW889117 AA486591 AW889172 AI381990 AI381991 AI673419 AI990950 AA487031 AI272934 AI150565 AA229168 AW316722 AI142707 BE222396 AA614168 AA122026 AW338227 AA632457 AI968726 AW369662 AA512956 AA541675 AA451748 AI250993 BE146418 AA122025 |
| 116028 | 10381__1 | H59799 AF118652 AI541284 W15560 AW014738 AA452335 BE544743 AW327841 T36308 W01696 AI822071 F07471 F11379 H17884 AW967157 N24488 AI813451 AA307154 T06444 N76641 W58564 BE073341 BE073270 BE073211 AA363862 T10785 W73086 H96310 AI685717 W23637 T06445 AI339481 W42805 N54132 H87931 AI628153 AF118649 R63123 AA157103 BE546263 BE548825 AI902183 BE439583 BE171547 W49685 W73191 AW026315 AI753757 AA777016 BE220574 AA917341 AA929058 BE071872 AI869731 AI743771 AW131831 AA649050 AI830164 AA505418 AI673768 AA757060 AI982692 AW769179 AA723135 AA938577 AA626042 AA046585 AI148193 AI151433 AI352689 AW519307 AA524653 T82269 AA157126 AI362791 AA749429 AI479766 N80791 AI942481 H17885 AA927992 N51867 AA813198 AI346075 W49686 AA983587 N54561 AI200101 AI312837 T81577 AI674397 AI769929 AA877860 AI420811 H17927 H59800 AA169342 H78381 AA452112 AI002089 AA843462 AI301424 AI208478 AA046718 W42717 N71667 AA953967 AA995117 AA055199 AA635544 AI128348 AW900065 AI263939 AA649696 AA652012 F09043 AW273006 W58565 Z40527 AW016738 R58072 H78479 T83390 |
| 130466 | 28127__1 | W19744 R46503 AI743763 BE296731 AA037137 AA355318 AA496829 N44805 AA347090 AW961673 N31086 AW996770 W68522 W19801 AA091353 AA248312 W44357 R11174 W40197 AA158267 W02396 AW274756 AW182379 BE044491 AW953369 AA354227 AI693750 AW996925 W45710 N34412 AA699614 N72570 AA058876 AA548104 N21679 AI038906 AA948551 AI022731 AI032086 W68424 N34645 AI982583 AI797542 AA714340 N35501 AI338224 AI291688 AW294908 AA702282 AA810816 R11175 AI700747 T90012 AA736883 BE243671 AA702898 AA010076 AI473124 AW182231 BE243342 AA312213 AA347089 AI767506 AA890568 R93023 AW812894 AA355137 N90004 W01662 AA491304 H83598 AA400751 R94344 Z42074 R13196 H78499 H77362 AW969134 AA284198 AA284197 AA310528 AA922068 AK000660 AI457629 AI269931 D79173 N67039 BE000260 AA688264 AA400669 AA505197 T99728 AA234296 AA031989 T18591 AW366346 AA256212 AA193119 AA345093 W01844 N90821 AW868490 AW051349 BE047080 AW151955 AA777005 AA059377 AI375089 AI571555 AW172699 AI436645 R82672 AA766813 AA031990 AI332630 AA194249 AA512994 AA775695 AW028098 AI741887 AA604274 AA805247 AA701969 AA262986 T99729 C16696 AI167208 N71636 AI085767 AI472804 AW043907 AA731320 AI367890 N64397 AA806344 AA251120 AA256155 N75337 AI334727 AA284086 T26676 AI382959 AA170845 AW779445 AI270066 AA585248 Z41608 AI193926 |
| 100387 | 13440__1 | D83777 NM__014766 AA333003 BE004425 AL119670 AA323656 BE296006 AL118935 BE256656 AA374227 BE271472 BE296326 AW583557 AW583626 N40409 AW608433 AA324811 AA190746 AW949591 BE000350 AA350275 BE392178 AA430618 AA348536 AA366634 AW818371 AA317886 BE072912 BE072917 AA323887 W38798 AA322171 W46661 AA036818 AA309827 AW583615 AA378262 W25430 H97457 N42389 |

TABLE 1B-continued

| Pkey | CAT Number | Accessions |
|---|---|---|
| | | AA169692 AA364115 H42180 AA081704 AA775719 AI185130 N75656 AW006117 AA984601 AI421198 AA181467 AW511204 AA181639 N64808 AI937715 AA169219 AA088783 AA548717 AW238470 AW662116 AW166218 D51086 AI867027 AA729243 AI923221 AI357913 AI375759 AA967267 AA773569 AW500216 AA191460 AA633234 T34787 AA527048 C75239 N93172 AW129534 N33415 AJ239459 BE328344 AW418717 AI308847 H42999 N24779 AA621221 AI497806 AI418855 AW418718 AI089499 AI332576 AI039047 AW583402 AA430500 AI271939 AI798736 AA612803 AW169919 AI183542 AA843085 C05884 C75127 AW044680 T03756 AW583349 AA082053 AA877439 AI298253 AA010549 AW168981 AI372978 AI039490 AI311909 AI313396 W81554 AI582863 AI566169 AA010548 AA748398 AI092355 AI074928 AA862701 W46570 AI570312 AA582306 AI082069 AI452384 AI498938 AA953378 AA910381 AA987271 AW664437 AW583393 T33340 H50310 AI361354 T15902 AI280310 AW583343 T15989 AA995343 AA718958 AI277293 AI468250 AI860396 AI951938 AA018659 AI590916 AI383915 AI382782 AA844109 AI016130 AA812632 AC004912 AI091734 AW893561 AW893559 AA984413 AA484993 AA491098 AW504790 AA018658 AW902844 T09170 |
| 115414 | 173073_1 | AA662240 AW769037 AW769560 AI913396 AA465182 AA214513 AW511261 AA283832 AI767608 AW510759 AW968608 AW967783 AA766028 |
| 108218 | 107976_1 | W57550 AA057266 AW797200 AI972066 AA058711 AI874259 |
| 115471 | 11801_1 | AK001376 BE386444 BE390867 BE408981 AI126802 AI765051 AI829784 AI810648 AA284708 AW752963 AI380487 AA805701 AA829971 W90692 AI367405 AA693657 AI003180 AA514968 AW972449 AI754241 AA852950 AL121107 AI868791 AI637676 AI760108 AI022771 AI022773 W90758 AI224853 AI246664 AI767311 AI203326 AI378374 AI078556 AA775023 AA856802 AI568198 R85788 AA287138 AW117381 AW242618 BE242067 AI282240 AI077934 AA642983 AI017044 BE263867 BE270147 AA852949 AA223807 |
| 114877 | 58_20 | AW024162 AA215804 N99222 AI215780 AA215639 AA410844 AA089529 D62135 AA366317 AW960045 AI168309 AI620911 BE552423 AI632827 N66253 AI762924 AI344470 AI478305 AA235618 AI824177 AI972356 |
| 101013 | 31218_1 | BE300094 BE384439 AW794648 NM_002305 M57678 AI929016 AU076727 Z83844 Z83844 AI906100 W44519 H98497 AA188069 AA572687 AA035793 W93978 BE409220 AA359751 AA502475 H28319 AA527889 AA432335 AA864762 AA340061 C05180 W68192 AA327811 AA345871 AI750205 N34093 N86639 AA085753 AA603415 AI355561 AA442262 N42135 C04367 N57266 AI038364 AI184846 AI928853 X15256 J04456 AA603552 AA317300 AA588615 AA813495 N40276 AA400624 AW264898 H21418 AA643822 AA603569 AA507955 N44497 AI000869 AW079049 AA614629 AA303987 AA362817 H54502 N85495 W52256 F30575 AA568129 H26935 W93977 AA373651 AA872398 AI332540 AW572787 F20782 AA442263 AW301076 AA558556 AA825366 W23842 AI038829 AA302408 AA374629 AA614477 AA341686 AA374846 AA187091 F24764 AA157099 AA374853 AA991592 F26839 AA744090 AA936881 AA374627 AA329755 AA854398 AA618108 AA973600 AA757956 W44520 AA379779 AA373698 AA369135 AA380039 BE408327 AA375117 AA375744 AA380014 AA373556 AI335987 AA903267 AA828223 F25088 AI246573 AA299386 BE275844 BE275666 BE384214 BE620707 AA975886 AA858048 BE548468 AA193055 BE274324 AI870164 AA129614 AA922761 AA935745 AA374567 AI580916 AA374661 AW239224 AA374466 N52172 F24306 AA300453 AA363443 AA588627 F19159 AA580021 N90877 AA654335 AA679168 AA573071 AW238834 AA988739 AW239423 AA976330 AI074239 AA999911 AI200930 AI971173 AI187321 AA937760 AI016242 AA373684 AI094874 AI302174 AA641237 AI370974 AI971010 AA400379 AA679137 AI096579 AI001918 AA524101 X14829 AA081302 N30374 AI338782 W74444 AA528232 AI734954 AW188024 AA433857 W92348 W94431 AI708356 AI753458 AA494460 AA825257 AA614246 AA039477 AI350213 AI309110 AA745965 AA291936 AW001376 AI066764 W74407 F30627 AA291937 AA480615 AA931667 AA331315 AI936154 AA824332 AA181109 AI017291 AA934736 AA062637 AA599977 H54814 AA635624 AI802655 AA564078 R69997 AA716551 F30469 AA961030 AI126757 AI183943 AI066798 AI419436 AA302095 AA157768 AA953030 AA588476 AA131216 T79619 AI752885 AA614820 AA988962 AI143561 AA493182 AI302481 AA301613 R73520 AA069898 AA374944 AW364221 AA342013 AI244949 F36390 AW050980 N79486 AA101160 T68112 AI750204 AA328787 H02617 AA314734 AA527923 AA307835 AI885112 AI872905 AA534666 AA188363 AI192490 H45772 AI824700 AI184276 AW079473 N29847 AA720843 AA720914 AA573391 H54416 T59424 AI824457 AA304220 AA482553 W72882 AA627932 H27514 H28400 W68050 H20953 AA635786 H21376 AA514046 AI342823 F29905 H25999 AA757144 H21636 F22104 AA428650 F27143 F28346 AA535690 H45771 AA548851 AW170154 H45646 W92274 AI921614 AA176461 AW170153 AI927284 AI161206 AA594439 T28595 H41129 AI497579 AA978015 AA328875 AA373653 AA090973 AA328623 AA328759 AA366468 AA375406 H46976 R86050 H02722 AA328321 AA328205 R62358 AA373717 AA304138 AA304224 AA301603 H54867 AA374783 AA376232 AA373239 AA374917 AA375673 AA303857 AA376466 AA376461 AA302613 AA304082 AA301731 AA357988 AA303328 R25744 AA301587 N78746 H20508 AA659423 R47960 AA825456 AI001806 AI245114 AA729223 AA860271 AI913845 H26296 AA733035 AA340965 AA304291 H27356 H20598 AA129613 R69996 AA157689 H20992 W16630 W16561 H25964 H21754 W01159 W42885 AA176730 H39504 N39788 AA182956 H27585 AA082164 AA328927 AA339934 H61805 H61804 H45580 AA476229 AA714104 AA507471 AI262184 AI139474 AI139476 AI001045 AA614374 AA593153 F33347 F34679 T68225 N25703 AA186999 AI623318 F18313 N72069 AA903161 H38546 H28672 AI880529 AI128960 AA299183 AW768886 F17445 F30433 AA303984 AA303687 AA309366 H28320 AI659479 AA627222 AA064882 AA507447 R53171 AA039476 T79704 R36589 T83222 H26453 AA298798 R53415 N84918 F37846 R94423 AA352679 AA308615 AA375442 BE173864 AA353674 R73519 R62478 T59480 AA089852 AI265789 AI077675 T90770 R54006 H46977 AA187168 |

TABLE 1B-continued

| Pkey | CAT Number | Accessions |
|---|---|---|
| | | AA157123 H21637 R48072 AA814207 R53082 AA305829 R62359 AI818429 AA887755 AA534238 AI813821 AW023928 AA062712 AI698995 F19074 AA345870 AI658776 AA903325 S44881 AA379844 N86780 AW089895 F29687 W52257 AA131229 AA978007 AW953024 R94945 H28332 |
| 131101 | 7970_1 | BE387561 W39108 BE256362 BE049300 AW245546 BE543251 AK000543 AW582924 BE245042 AW247754 AW503237 AA037343 AA380550 AA084266 H85635 AA577694 R83455 AA057499 R20350 BE267698 AW997305 AA336686 AA143370 AA053342 BE257631 AL050225 AA303698 H63274 AA393415 H91368 AW402791 AW389378 AW389358 W89161 AA336560 AW960735 F11549 AI871608 R85234 R90913 AW250312 AA057745 AA215726 AA490431 BE612608 AA458740 AW898429 BE618049 BE077016 BE548871 AW404030 N72514 T27273 H48608 H73019 T30417 AW952016 T27342 AA090165 AA384277 AL038685 BE090366 BE090498 BE090506 N53556 W92357 N22745 AA058527 AW245992 AW519163 AA827565 AA778844 AA609876 AW418554 BE549385 AA865787 AA582451 R43735 BE350564 AA857077 AL041251 AA053343 AI459173 AW271278 AI088812 H56312 AI922985 AA421008 AW273565 AW839472 AA054220 AI983745 AW473566 AA632354 W92321 AI252620 AW075525 AA057754 AA916396 BE244907 H48800 AI276992 AA688188 AA465218 AW089078 AA813504 R90914 AI244608 BE243339 H69697 H77911 AA457479 AA770572 AI094194 AA435687 AI287782 AW074674 R85235 AW074496 AW339961 AA779806 AW339652 H63717 H42212 H85008 M79220 AA777251 H91070 AW236192 D56982 AW103971 AI991944 AW583947 AI690863 AW250987 AW050679 AW196196 AI381358 AW895771 AA282896 AA205662 BE544924 R46159 BE258779 AA053876 H42283 N84165 BE294648 AA465573 BE613259 |
| 101032 | 10618_1 | BE206854 M55674 M18172 NM_000290 BE263723 R58471 J05073 AA192133 AA077207 W21455 AI016327 N47645 AA192732 AI208606 AA781116 C04893 N86080 AA634505 F28198 T28690 AW950710 N57500 F32816 AI338544 AI340296 F24817 AA192659 AI338303 F29892 C05250 F36165 F33897 F22479 AI159928 F35509 F33462 F36911 F24672 F32750 AI018135 F33256 F18881 F26107 F31842 AI200819 AA085861 AA947198 N93414 BE264368 F31524 |
| 101042 | 5921_1 | T46839 BE326864 S82485 T62130 AW129268 AA962194 T67857 AW237578 AW473055 AI914917 BE463520 T62074 AW604423 AW753337 AF016492 NM_001073 H70611 J05428 NM_001074 AI821970 AA746229 AI480418 AV655524 AI433838 AI627658 AI271811 AI245185 AI948812 AI942260 AI860135 AI000188 AW614236 AW025122 AW001836 AW293066 AW241660 AW291676 AI373219 AW779660 AI650317 AI925907 AI702900 AI942430 AW272002 AI209072 AI015557 AI769988 AW294360 AI672484 AI364979 AI783649 AA994828 AW271738 AV654408 H69250 R00611 AA987868 AI866226 |
| 131148 | 52061_1 | AW953575 BE563938 AV651228 AI858629 AW238652 AI811530 AW238464 AA775509 AA639961 AI951020 AA906505 R23723 AA588751 AI278514 AI683943 AI817634 AI023936 AI890265 AI955543 AI985699 AI378931 AI472890 AA076610 AA626034 AI924309 AW302595 AI400768 AI811323 AI291597 AI077673 AI168626 AA843925 AW873776 AW043643 AA186897 AA469417 AA688138 AA844033 R70906 AI167393 AA160381 AI146463 AI828457 AI346389 AW269507 AI890963 AA932817 AW167175 AI092688 AI419413 AI471235 BE544155 H21906 N95055 AW472733 AI858698 AA482254 AW117913 AI682734 AI022434 AI561317 AI075057 AI572472 AA631038 AI283412 AI400366 AI446687 AA253195 AW472934 AA580370 AI587086 AI740811 AW242097 AI383070 R82585 AI830090 AW104925 R63720 AI288461 AA079633 AI475132 AA372564 AI932899 AI474703 AW304099 AA159711 BE348964 AA935864 AA158761 AW510468 H97740 AW268508 AI887113 H99748 AW273008 AW190612 AI369025 N62092 AI860660 AA258377 AA352092 AW591233 AI880674 AI436339 AI913025 AW662621 AA614431 AI679511 AI921444 AA654360 AA159816 AI814625 AI858794 AA506029 AW050524 AI452382 R26913 AA480373 AI493331 AA568164 BE122868 AI816752 R38317 H01942 AW966626 AA086218 AA471074 BE621616 AW675760 AA468424 AW265590 R70940 R32172 BE005080 AA253194 AI004583 W38893 BE185114 BE075317 AI291596 AA258741 AA618219 AA385499 AW238247 BE350407 R23770 R77169 AA468385 AW604657 AA328654 BE000238 AW999382 BE000173 AA482352 R27158 AW798741 H21696 AA296799 R63767 T24990 AA382912 AA328285 BE181673 BE181669 AW384494 N87013 T48546 C00038 AW392769 AA610151 AW604655 AW999091 |
| 100409 | 16383_1 | D86957 R18311 AA355702 BE243986 AA378298 AW949846 AW949836 T23850 H08699 R61058 AA029836 H77466 R16502 T84799 AA002107 AA057630 H47819 AA001632 BE149652 R05744 AW607947 R07807 H94800 AA532723 AA233835 H64311 AA441958 R87603 AW883728 AA618204 AA618218 H13046 R66017 R24618 R66031 AW813015 AW170534 AI739572 AI291141 AA086032 BE244483 AW946851 AW368448 AA057669 AA001633 AI813366 AI148468 AW513472 AW162963 AI419243 AA029296 AA702798 AA452039 AW770879 AW341005 AI131361 AA599261 AI458979 AI745081 AI087126 AI634008 AA446924 AA975358 AI299593 BE504239 R66018 AA025899 AW665186 AI039660 AA235356 AI272907 H47820 AI917947 R34247 H08700 AA025747 H64312 AA002108 R66032 AI864466 AW771345 AI333200 AI765707 AI934756 BE245539 AA508656 R60938 T50028 AI335897 AW022337 H75428 H77467 AA614329 AW194912 AW050786 X84713 AI695534 AI659317 AI217093 AI926884 AA625211 H13256 R24515 T91129 D25728 AW138058 R42287 R16800 AW582016 AW161406 R90781 AA326433 AW163611 BE085910 W22101 AA298217 AA443347 AW470117 AA337340 AW044412 AA445950 AA445927 N59157 AW265503 H46577 H18977 AI538390 H47012 AW105475 AW013946 H51387 AA912311 |

TABLE 1B-continued

| Pkey | CAT Number | Accessions |
|---|---|---|
| 131170 | 8113_1 | NM_014253 AF100772 BE088769 AL022718 BE161779 AW863569 BE161640 AL039060 BE168542 AW296554 AA323193 AA235370 AW779760 N48674 AI375997 R45432 D59344 AI203107 F07491 R35360 R25094 AI913631 AI498402 T61382 AI016320 N45526 T61415 AA331486 |
| 131185 | 8142_1 | BE280074 BE259747 BE410297 AU076544 N86746 AW732908 M25753 BE280182 BE615878 BE271905 BE384456 BE385925 AW732409 AA083535 BE274998 BE279139 BE408605 BE296871 BE304438 AW732806 BE246832 BE410018 BE259803 BE313807 BE298693 BE383966 BE259665 BE280874 BE260503 BE019303 BE312527 AW362034 BE252087 AA373339 AW402329 BE019774 N84498 BE278166 BE393328 BE613489 AA096142 AA632161 AW750366 BE395874 BE166397 AW803394 BE541559 AI393943 BE296197 BE407516 AI631549 AW674149 AA564659 AI436761 AI282926 AW731781 AW009966 AI168792 AA490719 AA126048 AI499551 AW134695 AA933931 AA812470 BE208152 AI093806 AI434469 AI081933 AA937261 AW769696 AI278230 AI358586 AA113936 AI755191 AA968443 AW769706 AA113937 BE463826 AA644601 AA487342 AI379129 AW381794 AI783483 BE512849 BE378992 BE547984 AA628409 AI147317 BE537647 AA126208 BE539131 BE396389 BE281123 BE539644 BE408771 BE396885 BE296373 BE267330 BE260145 BE298872 BE281631 BE294664 BE390179 BE300310 BE281252 BE263828 |
| 100447 | 13274_1 | NM_014767 D87465 AI138758 AJ001453 BE315492 AL119602 AA323454 AA324193 H14434 AI372719 AA349626 AI372720 BE392102 AW503953 BE466278 AW029058 AI492113 H14384 AA349625 AA324192 AA326695 R52857 AA019306 AA021656 Z42668 AA323883 AA378569 AA350904 AI372419 AW404848 AA324503 Z42460 BE379289 BE394456 H15894 AI372421 AW607813 AA341681 AA323752 R88491 R90802 AA350810 AA325142 AA399317 AI952009 AW444587 AI829285 AI985914 AI627590 AI024341 AA398230 AI886803 T59381 AI014310 AI015469 AA080905 T33681 Z42334 T30945 T30906 T33219 H17555 AA776204 AA323721 BE392352 AA326015 BE294053 AA323277 AA341603 AL041008 R55664 BE395340 AA420642 M78925 AA493844 AA296883 BE394689 AA404699 AA806818 AI372420 AI953017 AI953273 R43882 AI356317 BE378447 AI672782 T30918 R90803 AI919449 BE350066 AA021487 AW071828 AI589288 AA635623 AW269658 R55665 AI423403 AI524197 AI333826 AA815454 AI051257 T03448 AI418846 AA814571 AA084339 AI553739 R58899 AI809288 AI221743 AI740981 AA291537 T33644 AI356753 T33610 AI024694 AA912707 AI372418 T16022 AA894697 AI339970 AI797874 AI350316 AW085823 AA678937 AW576501 AA910596 AA628149 AA953514 AI887011 T33218 AW378345 AA782949 AI475040 AW518669 AA805970 Z38828 T33680 F01860 AA019030 AI888030 BE388681 |
| 100452 | 31881_1 | D87742 AL041819 AI690015 AW892874 AW749413 L34688 AW820900 T28972 AW950961 AI280676 BE011098 AL045223 AA985398 BE177291 BE082789 AA321074 W03922 AA233692 AA236265 AA356813 BE089675 BE089691 BE090253 BE090262 AA381354 AA381995 AA381648 AA411613 AI536017 AA257980 AV648480 AV648281 AW001578 AI473648 AI744678 AA633556 AI453775 AA976885 AW444436 AA398095 AV656068 AI572718 AI554850 N53228 AI979021 AW970707 T79641 AI050698 R71379 AI085594 AA872982 AI888200 AA399573 AI888205 AI378463 R31158 T70314 T80069 AW571478 N66352 AA235006 AW474738 AW662311 N73775 AW021225 AA411193 AI240381 AA856575 AA432198 AA902517 AW571651 H15501 AA732554 AA693813 AW591720 AI619790 AI278448 AI093710 AI269162 H57533 H72479 AI291594 AI872714 AA768658 AI805984 AW390750 AI658850 H57534 AI802375 H72880 R32629 Z41949 AI028434 N98415 W39460 R80445 AA319022 AW952141 H69052 AA600042 N52860 AA004740 AA432213 BE467872 BE348422 AI701145 BE549553 BE467054 AA429602 BE219899 H15443 AW300450 AI697659 BE218510 AI689771 H69053 H40963 H23669 AA757277 H40920 AI126093 AA004690 AW080482 R80648 AI299452 AI268905 H23625 AW138577 AI263941 AI873606 R32515 W30703 AA834477 AA886843 N64067 Z38238 D61024 D81376 D81541 D80871 AW998422 AW998416 AA579383 |
| 130553 | 30653_1 | AF062649 AA405947 AW602820 AA075247 AF095287 AA039876 AW957275 AA033896 AA430241 AA249470 AA314652 AA007646 AA380236 AF075242 AA436999 N23584 AA477063 BE544942 AA055311 H64056 AW750040 AI571797 AF095289 AF095288 AI569781 AW750100 R83062 AA081272 AI052735 AA287672 AA781104 N73057 H90483 N76842 AA286786 AW261964 AI870484 AW515957 AI598181 AI073718 AW874587 AA033949 AA081273 N93408 AA781338 H64006 AA706787 H77519 AA074947 AW575580 AA075073 AA007621 AI970768 AI037954 AA705320 AI187853 AW272792 N53693 AI192508 BE184064 AI140876 AI698655 AA861023 N93319 H52544 AA476952 AA812948 AI445235 AI362866 AA693507 R93114 AA442827 AA287855 AA780128 AI302602 AA405385 AA772482 AA992412 AA041520 N55467 R83011 H77520 AA287854 AA430032 AA555210 H58693 AI185954 H67910 R70335 N51912 AW023686 H94652 AA960936 H66067 H60873 R93232 AA627719 H90427 AA764752 AA806062 AI933075 AA287547 AA055312 AW082280 AA404964 H82417 AI498735 C21248 AI910658 BE328455 T25511 BE261824 AA075235 H66113 H82677 AA352192 H60872 H67960 H58303 H67633 H52308 AW796097 AW796134 AW796237 AI811894 AA644227 AJ223953 AA203476 AA383595 AA405133 |
| 116121 | 10887_1 | AK001330 AA356435 BE313393 BE293644 BE251929 AA808340 BE409475 AA331948 N91096 AW402232 AW402994 AW386322 AA004739 AA459479 AW579400 W68758 AW673556 BE313041 AA455698 AL045680 AA134589 AW606254 BE301261 AW976697 AW968467 AW976703 W68453 AA004688 AW976701 AA223724 AA565953 AA215565 AA744555 AW193840 AI086227 AW970769 BE300513 AI458782 AI183406 AI309531 AA455644 AA128908 AA588705 AI138389 AI476292 AA515291 AA524425 AA459254 AA600279 AA614836 AA769786 AA492544 AL045681 AA765178 AI864425 AW780369 BE246640 AA926793 AW054669 N63744 AA206610 AA729135 AA766112 AI553635 |

TABLE 1B-continued

| Pkey | CAT Number | Accessions |
|---|---|---|
| 130567 | 2239_1 | AA383092 AA731398 AA767126 NM_002947 L07493 AI417050 AA856682 AA946979 AI022007 AI417138 AI167442 AA461254 BE559626 AI333471 AW410993 AA345343 AA877170 F35676 AI688239 AA742693 AI688228 AA374937 AA648932 AA372488 AA227786 AI198618 AW016005 AI365028 AI351115 AA682467 H59259 AI250796 AI400330 AI243725 H49351 AA918597 AI243869 AI424112 AI078674 AA975429 AW580421 W93664 AA807487 T27775 F35677 AA743538 AW949994 AW949993 AA677285 AA860111 AI247552 AW043673 AW607047 AI376819 AA918714 AI160787 AI033070 AA757540 AA701935 AW264399 AA227787 AI735761 AI351848 AA705038 AI807505 N33011 R92112 AW515896 AI765604 AW381917 AA015678 AA017653 W93663 AA625139 T95667 F29051 |
| 116130 | 54227_2 | AW183533 AA761728 AI005242 AA460299 AI814341 AI808860 AA460002 AW440254 R30950 |
| 130577 | 500_1 | M69241 AI752220 AW161570 BE313151 M35410 BE382548 S37730 AA838048 AI460348 BE295221 AA780343 AI752281 BE314081 BE262585 AA308676 AA327814 BE295717 BE383255 AW605824 AA621670 AA443563 T61701 AI800143 AI815794 AI499226 BE253473 AI926577 BE262152 AI480193 AA459532 AI870363 AW440417 AI669011 AA573839 W23509 AW300897 AA040562 AI038308 AI859809 AA028959 AA419054 AI149381 AI952277 AA780788 AW161913 AA599831 AI628044 AW874612 AW161619 AI890811 AI954468 AW157695 AW169233 AI798533 AI983887 AI366904 BE383011 BE378790 AA863332 AW593632 AA423811 AI186554 AI434101 AW081907 AA419161 AA680206 AI143192 T61617 AA443564 AA150059 AI537283 AI085531 AA732800 AI394446 AA653631 AW089730 AW262712 AI983583 AA779586 AA035749 AA635910 AW001554 AI635300 AI635690 AA459301 H79047 AI083871 BE464961 AI219769 AW273491 AW264376 AI752280 AI752221 AW172776 AI028334 AW513739 AW089820 AA035641 AI498954 AW151246 AW173425 AI050082 AI984462 AI476359 AW152542 AA603462 AW079056 AA044641 AI401607 AW593618 AI864472 AI751715 AI750245 BE047378 AI366942 AI758265 AW192270 AI660855 AA931338 AA045494 AA290821 AA284935 AI984402 AA404300 AA477419 AA479582 AI368212 AW028374 AI567133 AA479592 AI004075 AW513319 AW513432 AW151185 AI582123 AI937506 T71718 AW590985 AI016670 AW510408 AA877269 AI653495 AA152182 AA356489 BE394794 AI355505 AI817467 AW439578 AI873967 AA477441 AW249502 AI783946 AW088937 T71787 AA404681 T28526 AI669991 AA028960 X16302 AA532924 BE382760 AW662374 AW305187 AA042827 AI937725 AI798575 AI174571 AW131904 AW105698 AW614321 AA630379 |
| 123360 | 333064_1 | AA532718 AI821485 AI791194 AI821930 AA504784 AW969151 F37127 AA654206 F27974 |
| 116158 | 11903_1 | AA381807 AF144755 NM_013332 AA320807 BE264360 BE312752 AW381329 AW381298 BE301024 AI800437 AI309121 AI343669 AI800457 AA054543 AI310162 AI744870 AI769640 AW674287 AA461187 AW151696 AI277620 AI347821 AA035341 AA670144 AI744879 AI760462 AW514880 AI954915 AI696966 AW105694 AW105695 AI948588 AW083071 BE549300 AW082974 AI862078 AW236191 AW241771 AI368420 AI335595 AI765786 AA054583 |
| 115522 | 56371_1 | BE614387 AA379531 AA406456 N53714 AW976696 AW835469 AW835466 AA096093 AW978736 AW835470 BE568486 AI992158 AW070824 AI743202 AI193598 AI831483 BE464933 AW303817 AA939106 AA465473 T24898 AI094155 AA146858 AA648921 AA908739 AI979181 AI346620 AA581615 BE350612 AA749314 AA768709 AA775633 AW614887 AA284818 AA651863 AW769884 AW731659 AI382916 AA586521 AI922877 AI473650 AA406348 N51950 AI351496 AI225213 AA372701 AW389592 AI674283 AW169393 AI382409 AA736861 N95719 AA331393 |
| 116188 | 183141_1 | AA468183 AI859849 AA844370 AI933818 AW472739 AW439820 AW439625 AW628271 AI962973 AW513172 AA464728 AA463944 AA235454 AW966734 |
| 115536 | 61_1 | AK001468 AA190315 AA374980 AW961179 AA307782 AA315295 AA347194 AW953073 AW368190 AW368192 AA280772 AA251247 N85676 AI215522 AI216389 N87835 R12261 R57094 AI660045 AA347193 R16712 AW119006 N55905 N87768 AW900167 AI341261 AI818674 D20285 AI475165 AA300756 R40626 AI122827 AA133250 AI952488 AA970372 AA889845 AW069517 AI524385 AA190314 AI673359 AA971105 AI351088 AI872789 AI919056 AI611216 AK001472 BE568761 AA581004 |
| 108340 | 28366_1 | AA069820 AA070025 AA654583 AA069911 AA070815 |
| 114986 | 23253_2 | AK000361 AA825936 AW296950 AK000490 AW967462 AW298253 AW449701 AA813827 AA251010 AA207224 |
| 101118 | 14941_1 | AA371931 BE266971 AW328354 AA315443 R96442 AA159099 U93305 L09604 NM_002668 AA853553 AA340466 AA293567 AA099121 AA053737 AW752983 AA430611 AW386371 N95686 AW386295 AI346435 AW804779 AI523881 AA320810 AW793920 AI907892 BE393961 AI565163 AI813687 AI904954 AI394235 AW610291 BE620003 AW387616 AA852810 AW387612 AW387610 AW607951 AW387557 AW387688 AW387532 AI814324 AW807818 AI246030 AW807811 AW387624 BE083067 AW387586 AW387528 AW387679 AW807949 AW387601 AW387515 AW609070 AW809048 AW387694 AW387516 AW387648 AW387583 AW387584 AW387539 AW387587 AW387556 AW387595 AW387631 AW387695 AW387533 AW387605 AW807739 AW807895 AW387677 AW387646 AW807817 AW387609 AW807890 AW387559 AW387521 AW387602 AW387625 AW387668 AW387547 AW387580 AW807749 AW387607 AW387634 AW807665 AW387597 AW387611 AW387596 AW387585 AW581867 W17167 AI280907 AW387569 N98676 AW178502 AA477593 AA873099 AI246562 AA402794 AW609074 H47425 AW366120 AA043896 AI523581 AA622341 AA887676 AW581858 AW387558 AA434191 AA574027 AA161137 AW581818 AW387550 AW800226 BE621591 AW387641 BE621337 AW387667 AW387640 AA552244 AA361238 AA379381 AW387545 AA464528 AW387599 AW387627 AW387544 AW387591 AW387702 AW387510 AW581875 AW387687 AW387696 AW387655 AA161115 AW387636 AA826619 |

TABLE 1B-continued

| Pkey | CAT Number | Accessions |
|---|---|---|
| | | W92874 BE149446 AA029924 AA115286 BE048130 T99421 AW387621 N63397 AI332571 AI174284 AA160777 BE393130 AA429353 AA464842 AI819980 AI831467 AA766218 AI720789 AA832420 AW387548 AI273391 AA424522 AA025486 AI857333 AA808470 AI381579 AA629238 AI907826 AA130586 AW951180 N92482 AA856698 AA053217 AI057323 AA777100 AI992166 AA100577 R96443 AA830492 AI935183 AA430526 AA026078 AW579636 AA453201 AA293398 AA421006 H47338 AA159370 N66153 AA029925 AA826723 AW272436 AA999657 F22574 H69012 AI261968 AA086361 AA454167 AW379792 AA921703 AI801083 AW664325 AA429056 AA099122 AW572270 AI347946 AI337894 AI299197 AW328355 AW467641 AW302628 AI125665 AI457944 AI718119 AI091522 AI214251 AA947200 AI830407 AI261532 AI934695 AI923632 AI720333 AW304217 AI089510 AI719846 AI587160 AI498213 AA759077 AW069810 AI304791 AI939998 AA687919 AA852809 T99527 AA527012 AW001996 AI479890 AI863946 AI688036 AA513191 AA853552 N73100 AI368248 AW263462 AA477464 AA617664 AW591651 T29194 AI610373 AI197850 AI364502 AI280917 AI707897 AA290976 D20308 AA285059 AI148183 AA897561 AW406028 AA130549 H75395 AA453330 AA159162 AA158842 BE546820 AA430426 AA428764 AA421577 BE218289 BE540828 BE259495 AI991221 AI800148 BE545935 AA856632 AA402802 AW001345 AA505268 AI831247 AA661521 AW518864 AW193589 AI871010 AA857226 AA758930 AA588803 AA723089 AI719387 AA424374 T95659 AW809033 AW387658 AA761238 AA402306 AA657982 AW609068 AW809046 AW387630 AW387651 AW387554 AA451772 AW609065 AW387608 BE272809 AA464627 AW609555 AW378072 AW579620 AW579594 AA449966 |
| 101148 | 15647_1 | NM_002923 L13391 L13463 AL035407 AL036629 BE569163 F11824 AA370404 AA081962 AA045784 AW802455 AW839121 AW839129 AA024480 AW579329 AW579342 AW385922 AW579349 AW579370 AW802573 AW579362 AW579367 AW385932 AA122107 AW838807 W07429 AA447937 AA054576 AI656059 AI761246 AA035363 R23120 W69610 AI914095 W55965 AW794213 AW580877 AW951385 AA054537 T29501 W55966 AI935457 BE463897 AI750159 BE218280 BE326769 T65391 N27484 AW193673 AW364934 AI813697 AI652515 AW071950 AI989883 AI989708 BE466665 BE066793 AA058867 AW138286 AW779721 AA036732 H15243 AI139398 BE066840 BE066709 BE066779 AW302145 BE066737 BE066731 BE066805 BE500956 AI567516 AA835167 AI913304 N75846 AA917654 AI346555 AA024481 AI970916 BE467277 AW467527 AA122108 AI126225 AI802267 AI675283 AI569765 AI921562 AI830405 AI090227 AA741487 AA596048 AW005502 AI493891 AI291733 AW237817 AA035364 AI804769 AA830268 W69486 AA045785 AI347989 AI272915 AI651216 AI304403 AI675670 AI829243 AI185343 AW001615 AW076046 H05767 AI971761 AW594212 AI291581 AI948917 AW139656 AA834091 AA648362 AA948018 AW204522 AA815078 AA506569 AI582934 AA160026 AA593757 AA448872 AA775569 AI868965 AI313511 AI282765 AI209025 R23121 AI140249 AW439959 AI399711 AA082833 T82268 AI457374 AI288423 AA769947 F09473 AA708846 AA922770 AW449904 AW006543 AI141220 AI950611 AA593717 AI828641 AW295146 BE328155 AI969935 AI350545 F02032 C00527 R45897 AA582633 AA975385 H15242 T65468 |
| 100528 | 45979_1 | BE386801 AU077299 AA143755 BE302747 AA853375 U30162 BE274163 BE277479 BE408180 BE274874 C15000 AA047476 N27099 AI359165 AI638794 AI151283 AI863925 AW444977 AI207392 AA931263 AA443112 R40138 AW068538 AA351008 AA676972 R62503 AA916492 AW001865 H42334 H38280 AA121497 AA114137 AI750938 M17783 AA383786 BE274462 AI753182 C05975 AA347404 AW069298 AI754351 AI754044 AA188808 AA186879 AA565243 AL040655 AA456177 AI750722 AA045756 AA213580 C16936 AW578747 AW753731 H41632 N44761 R58560 R61260 AA039902 N59721 AW992543 R68380 AA149686 T29017 H03739 BE383822 BE387105 BE408251 BE410425 H41560 AA247591 BE389677 AI752233 AI566195 AA868004 AI424523 AW753720 AA852159 BE386803 |
| 130639 | 86510_1 | AI557212 AI245308 AI261985 BE465474 R25408 AW294869 AA862980 AI619809 AW614948 AW768832 AW591097 AW129774 AI784324 AA621589 R85948 AI333148 AW117302 AA404519 AA165508 AI498674 AW662250 AI827162 D59570 AI696923 AW173727 R62539 AA278329 AI689073 AA513300 AW515987 AW779041 AW079702 AI346562 AI358240 AW778903 R80410 AI479216 AI884330 AI273999 AA953430 AA017059 AW118511 D59711 H38124 R73683 AA021464 T93119 H40632 AI493590 T93220 R28435 H11195 AA167402 AI633798 AW182534 R80519 AA743632 R73775 AA743634 AI267413 AA214448 AA279000 AA743859 AW959595 AA300011 R78798 D59748 D80362 R62538 AA165541 D59651 D59712 D59571 H38123 H38360 AW752148 AW352128 AW352124 AW352115 AW352122 AW388317 AW352116 AW388483 AW388478 AW388597 AW375680 BE169597 AA361084 AA017210 AA021463 AW795970 AW838177 AW898617 AA300012 AW963818 AW629985 BE150641 H00388 AA375656 AA831259 R76419 BE150642 N66962 |
| 116202 | 180776_1 | BE159395 AW391285 AW501131 AW501617 AW501412 AW500885 AA232802 AA465508 AI275691 AI336778 AA233836 AA465398 |
| 124083 | 5116_1 | AW195237 AI187391 AI568462 AK000691 AW136148 AL119665 AA493263 D31514 T99094 AW753537 T99699 AW754146 AW754149 AW754148 AA339438 AW956369 AW754141 AW754127 AW754132 AW754133 AW754150 R35692 H07965 AA844230 AA972909 AI971703 AW004033 AI654374 AI992104 AW003839 AI654373 AW470539 W63603 Z45225 R22668 AW003269 F08747 Z46152 T80299 BE552148 AI636930 AW005913 H61625 R49136 AI027685 AW954143 AA303071 W05056 W04283 W86212 W78834 F37004 AI818420 AI042386 AW615424 D56288 W88475 W81448 AI433418 R31263 H07873 F21223 AA844597 Z41728 W94186 AI143520 AI819296 AI699977 W74614 H03616 H03755 R64239 AA644477 AW291424 R22261 R28323 AI867904 AI932981 AW291160 AI742922 AA194807 AW001420 AI601250 R22207 AI912017 AI446649 N70351 AI935693 AA194993 H02860 R79987 AI887164 R28324 AW514975 AI276611 AI362326 AA130638 AW440982 AI989962 AW241941 AI632136 AA772641 AW263832 W86213 R64136 H61061 AI888634 AA565491 T30214 AW440843 AI656484 |

TABLE 1B-continued

| Pkey | CAT Number | Accessions |
|---|---|---|
| | | Z41786 W81449 AI032918 AW445013 AW593849 AW085289 F05032 AI205207 AW027984 R38950 N74344 W80733 C01142 R36054 R31867 N76515 R80090 AA130741 R72958 |
| 100569 | 27120_15 | AA535210 X07730 AA659438 M24543 X05332 NM_001648 S75755 U17040 AI525089 AI524893 AI524861 AI546857 AI525128 M26663 AI547285 AI525832 X14810 M27274 AI557591 M21895 AW973948 AW451486 AI547084 AA659534 AA639308 AA654548 AA534235 AI926979 AA579039 AA225115 AA658261 AA640352 AA229599 AA574023 AA573727 AA535453 AA522842 AA657697 AA659319 AA397360 AA654636 AA653755 AA808858 AA535185 AI826164 AA228845 AA259192 AA228999 T29521 AA557838 AI547051 AA622817 AA397452 AI936076 AI826504 AA577955 AA659391 AA650205 AA640736 AA640280 AA640372 AW957256 AA642495 AA579134 AA523902 AA631704 AA228884 AI524856 AI524842 AA657389 AA572896 AA658494 AA569560 AA640510 AA650269 AW083359 AA654754 AA420678 AA569445 AA564886 AI399713 AA572787 AA662137 AI546893 AA595295 AA216409 AA595094 AA572731 AI669143 AA594993 AA658304 AA622211 AA594942 AA613267 AA622228 AA622221 AA640290 AA541668 AA613665 AA570587 AA420606 AA594947 AA631696 AA579361 AA541677 AA244158 AA244159 AA557834 AA225529 AA564089 AA612574 AA513226 AA568528 AA658266 AI524918 AA420532 AA622386 AA742853 AA622399 AA420427 AA614195 AA177118 AA228440 AA229488 AA225114 AA542918 AA602936 AA595415 AA688100 AA654204 AA533337 AA467972 AA573548 AA650351 AA579038 AW969995 AA659194 AA573563 AA630816 AA654970 AA579480 AA658400 AA226567 AA225626 AA531322 AA229759 AA558395 AA525076 AA420783 AA225043 AA650228 AA420818 AA229219 AA226150 AA658911 AA568333 AA420816 AA513597 AA525050 AA579470 AA226161 AA226222 AA602211 AA527907 AA533137 AA230250 AA641190 AA657850 AA687931 AA397400 AA558678 AA467971 AA573729 AA532918 AA229144 AA569723 AA552572 AA809594 AA531371 AA528279 AA603973 AA533547 AA564290 AA650166 AA550936 AA525122 AA640642 AA639894 AA658551 AA531355 AA654373 AA614206 AA569669 AA244246 AA225154 AA604036 AA548289 AA603549 AA527943 AA524601 AA876387 AA657942 AA602158 AA640996 AA535294 AA603978 AA640517 AA554876 AA524889 AA566020 AA564525 AI734071 AA654743 AA225137 AA603981 AA230145 AA659430 AA605005 AA225509 AA602959 AA564506 AA631839 AA653917 AA603284 AA226430 AA225508 AA530919 AA542887 AA642067 AA653961 AA573590 AA524594 AI535889 AA535572 AA687218 AA243984 AA595609 AA534155 AA650133 AA259191 AA886140 AA228722 AA467814 AA578915 AA551615 AI547277 AA657764 AA894884 AA551616 AA522859 AA572918 AA229957 AA229751 AA531199 AA652522 AA229967 AA551461 AA532935 AA601934 AA230032 AA640714 AA535828 AI865511 AA468362 AA226298 AA469419 AA224930 AA652490 AA573554 AA935415 AA876596 AA550775 AA578325 AA602721 AA640881 AA602193 AA470345 AA470329 AA228299 AA659390 AA503922 AA548820 AA631828 AA468363 AA602725 AA558252 AA937840 AA551700 AA504059 AA640677 AA467991 AA687575 AA569519 AA468448 AA533935 AA230163 AA224955 AA559996 AA573534 AA613750 AA659184 AA468034 AA492276 AA533118 AA177132 AA578322 AA229623 AA578410 AA614248 AA604850 AA602011 AA534015 AI867619 AA535585 AA613770 AA557916 AA641176 AA578039 AA573994 AA468942 AA579411 AA657805 AA886046 AA652492 AA516525 AA652252 AA614074 AA467767 AA469019 AA886501 AA226264 AA224856 AA594919 AA559921 AA224855 AA602123 AA469434 AA579405 AA876824 AA573705 AA657775 AA633434 AA622818 AA580256 AA659550 AA687992 AA468140 AA579217 AA470332 AA468160 AA468372 AA555233 AA935098 AA468122 AA551711 AA641183 AA229801 AA224940 AA570202 AA504034 AA468041 AA228397 AA503262 AA535502 AA886623 AA259272 AA228444 AA503911 AA565282 AA658335 AA574401 AA224941 AA652562 AA640888 AA652767 AA935442 AA641051 AA228914 AA934464 AA467738 AA468189 AA595856 AA635384 AA226579 AA657837 AA566022 AA659486 AA572841 AA658248 AA569582 AA639325 AA555126 AA229568 AA578333 AA533825 AA579236 AA508086 AI826974 AA658203 AA888477 AA228966 AA533715 AA886949 AA541337 AA888317 AA661941 AI969953 AA657879 AA550919 AA533343 AA657824 AA554865 AA687194 AA640720 AA569708 X75682 AA559285 AA632441 AA659520 AA533537 AI201973 AI400942 AI417483 AA526834 AI824643 AI805186 AA548801 |
| 130655 | 7087_3 | AI831962 N46592 N92934 |
| 100589 | 17389_1 | AW247430 BE257319 BE206820 BE252944 BE269373 BE513813 AA171542 D17031 D16995 AA309640 X88562 AA243110 AL137314 AL039225 BE562350 BE256087 BE273919 AA227066 BE273869 BE297736 AA136426 AW378890 AA218777 BE261142 AA173133 N29067 AA179769 AA811740 BE549024 BE271002 AA554953 AW189205 AV654316 AW189206 AA642534 AA620410 BE546921 AI266220 AI566920 AW731962 AW248525 AA548257 AI198353 AA548561 AW075568 AA063180 AA699637 AI525530 AI088293 N76209 N54505 AA232188 AI494445 AI858969 AI829616 AA136339 AI281692 AW166637 AA180443 AA729802 AA921824 AA057714 AA618538 BE270818 BE618295 BE268699 BE397539 T69322 T70457 BE296891 T28038 BE270675 BE560363 BE265705 BE513820 AW378843 L14577 |
| 130680 | 28833_1 | BE567313 AV661214 AA035752 AI458107 F06002 H05883 H04908 AA385543 BE167781 AA035648 BE166316 W37581 AA370624 W31268 AA376875 AA558103 |
| 130693 | 239704_1 | R68537 AA486842 T97103 AA341183 R68243 AW770394 AA487202 AW956414 AA723375 D80566 D60411 |
| 123477 | 40888_1 | AF217515 BE018076 AA702803 AW593351 AI566865 AI803643 AW385923 AW005007 AA766437 AI817677 AA505838 AA512883 AA631295 AA599331 AI826399 AA808767 AA570116 AI016110 AA043795 BE074585 BE265526 |
| 108406 | 113761_1 | AA075424 AA075425 AA130650 |
| 115652 | 54227_1 | BE093589 AA001669 AI081076 AA921830 AA815405 AW511336 AI688161 AI808257 AA176116 AI243527 AA412401 AI018167 AA578594 AI401366 AW007065 AW339942 BE044297 AI016459 AI143157 AA258586 AA455328 AI961391 AI190888 AA137247 AW197882 AA758654 |

TABLE 1B-continued

| Pkey | CAT Number | Accessions |
|---|---|---|
| | | AA431520 AI061050 AA905522 AA977056 AI242598 AW675276 AA913856 AA625645 AA857796 AA431194 H63257 AW183423 AA725761 AA758623 AA883097 AA405098 AA758496 AW081741 AA431741 AA913400 AI630252 |
| 100654 | tigr_HT2969 | A03758 A06977 A15293 D17029 D17107 D17171 L00132 L00133 M12523 M13075 M13076 M92816 U22961 V00494 V00495 X51363 X51364 X51365 |
| 100655 | tigr_HT2970 | A03758 A06977 A15293 D17029 D17107 D17171 L00132 L00133 M12523 M13075 M13076 M92816 U22961 V00494 V00495 X51363 X51364 X51365 |
| 100793 | tigr_HT4191 | S69027 |
| 109251 | genbank_AA194776 | AA194776 |
| 102208 | 6735_9 | U22961 AA203623 AA503337 AI174733 AI192802 C06092 AA035357 AI190619 AI199244 AI828450 AA602296 AI378195 AI209170 AI186653 AI127795 AI183846 H77389 AI589465 AA629390 H94306 AI018388 R68584 AA027196 AI745413 AI685092 AI093426 AI623873 AI074570 N50096 AA047486 N25060 AA327614 AI042512 AI383957 AA156873 AI333101 N70806 AI141254 AI383191 AI401237 AI080709 AI093400 W84549 T90806 R00012 W01413 AA630557 AI378348 AI559265 AA877103 W84464 AA625146 R68379 AI133207 AI132980 AI133214 AI064826 AI061615 AI133473 AI174852 AI133404 AI133272 V00494 M12523 M12523 AI207526 AI133120 AI064802 AI174993 AI114729 AI061645 AI064716 AI064959 H77388 T85706 AF075298 AI110799 D17107 NM_000477 AF190168 R50724 AI248416 AI207432 AI133684 AI133345 AI174710 AI133290 AI133304 AI174948 AI207484 AI110717 AF074624 AI114515 AF063516 AI110642 AI114559 AI114498 AI114759 AI207568 AI064960 AI174753 AI114666 R69184 R00011 AI064997 T60501 AI207701 T71735 AA385318 H73569 T60496 H94399 AI133158 T74675 AA484750 T73413 T55909 R50261 T72061 N80533 T51189 T74936 AI207490 AI132925 AI064701 AI174748 AI114663 AI133104 AI132999 AI133100 AI064925 AI064979 AI133063 AA343347 T69091 AA233989 T39772 AI444620 T52290 D16931 T40012 T48403 T58926 T69195 AI133061 T50850 AI400677 AI091136 AA334608 T57411 Z20979 N56507 T87485 AI133622 AA343370 T40075 T69671 T53849 T74820 AF075316 AI110818 T40121 T57381 AI114468 AA332728 T51362 AI114589 R06691 AI110629 AF063503 AI140543 AA334661 AA332720 AA343262 T73513 T86549 AI114840 T57284 T39981 T61407 T72757 T51749 T56630 AA343125 T72126 R94135 T83028 T39972 T39896 AI174786 AI132926 R09237 AI064836 AI133660 T60398 T88753 T55930 T92126 AI444602 T60996 AI114792 H93911 AI133106 R10779 AI065020 T90925 T50889 D17029 AI133703 AA333805 AI133040 AI133017 AI064857 AI110730 AF074637 AI207567 H71080 T73217 AA343950 AI174743 AA334224 AA334281 R06692 T64739 T40163 T60628 T81661 T73179 R01842 AA501730 T39931 T39662 T40136 AA334904 T71425 H77784 R00874 AI065049 T84512 T55918 AI207595 T39951 AA005016 T60361 T69176 T73356 T58795 T61233 T39955 T60612 AI114676 AI064778 AA035710 W52763 AI114786 T83564 AA341859 T81684 T55769 AI114710 T51776 AA343213 AI114714 T58102 AI110809 R28984 AI174854 AA305675 AA343592 T53836 T46869 T64721 T55508 W05241 T54019 T57945 T60513 T48364 AF075308 W86731 T82851 T48269 H54053 T73211 AI114590 T48317 T55965 T74857 R84226 T56552 T52231 T74946 T76976 R02576 T95666 AI203974 AI189471 AA005147 AI478102 AI207662 AI192792 AI768421 AI064737 AW051713 AA936693 AI133117 AI766232 AI913646 T83962 AI065112 AI207689 AI174684 AI207702 T81475 AI133325 AI032512 AA701169 AI936354 AI114720 AI433289 AA046980 AI823482 AI114536 AA860651 AW242644 R07469 AW300438 AI133416 AW271670 AI991363 T78943 AI823481 AA845518 AA719124 AA883454 T68850 T69115 AI935509 AI150977 T62890 T71374 T68294 AI174774 T67411 T68318 AI064689 T56624 T69010 T68982 T68302 AI332829 T72908 AI064819 AI205880 T62895 T69430 T95111 AA025050 T73330 W52657 T71984 T69118 W92684 AI114860 T62093 T61797 AI522333 T73322 H92981 T56018 T61811 T57232 AI336158 T61821 T69457 T62900 T62912 T72917 T46885 AI702448 T57212 T57203 R94581 T71311 T61819 T89358 T67708 T70918 T59166 AI187111 T64308 T62071 T69427 AI114750 T60430 R09734 T69033 T69141 T69453 T67908 R16809 T69394 AI207729 T55839 T90273 T73339 AW194909 T75486 T71850 T71305 T71287 T53877 T73452 T68852 N75290 AI312890 T67751 AI174983 T51679 T54851 H69880 N73734 AA443453 T73466 H69672 N53869 T68447 D11809 D12412 T64300 T28321 T55864 |
| 102289 | entrez_U32114 | U32114 |
| 118475 | genbank_N66845 | N66845 |
| 132994 | 45292_1 | AA112748 AF090915 AI110856 AF075355 R58494 AA825984 Z45863 T31804 AA430400 AA360936 AW366355 W05653 AW390733 AA357205 AA309629 AW451697 AW372477 H00961 AW517718 AI693023 AA252105 AI298472 AA041512 AA770121 H81681 AL121337 AI143548 AA252073 AA143745 AI076636 AA041459 AI150645 AA620485 N76147 AI383531 AI468649 AA151685 AI024087 AI702342 AI018193 AW131073 AA090352 H11443 AA761698 AA490992 H00962 AA613495 AA599482 AI383751 AA505133 R67964 AI074739 AA885895 AI383750 AI208735 AI687281 AA678631 AA976412 F04726 AW074481 AA653426 AA872316 AW027385 AI275780 AA732728 AA879149 AA148124 AA151633 AA298085 AA491188 N87414 AA356722 Z21234 |
| 118895 | 43362_3 | N69858 AA156271 AA508868 N90667 |
| 120256 | genbank_AA169801 | AA169801 |
| 134921 | 22621_1 | NM_005461 AF134157 AW207661 AW140037 AA233280 AA360894 AA347213 AI869550 T50172 AI299925 AI624055 AI027385 AI298720 AI983835 H73880 N45054 AW378686 AA379135 W56114 AI192800 AW473396 AI954580 AA505246 AI768823 AA932265 N23167 AI361070 AA725032 AI266743 AI040620 N35044 W36290 AW339095 AA379134 AA347212 W52922 AA037402 AW274442 T50121 AA725480 AA232977 |

TABLE 1B-continued

| Pkey | CAT Number | Accessions |
|---|---|---|
| | | H43244 AW135013 AI168227 AI688452 AI290212 N90926 AI708299 AI092862 R14887 AA583143 AI282032 AI393675 T99632 AI631841 AI417601 N21993 AI650671 AI652634 AI770180 R11392 AA976902 AA975289 AA772628 AF086178 W31474 W31937 AA384636 AW138146 AI375644 AA772409 N32635 AA890455 C02406 W17043 AI041504 |
| 120570 | genbank_AA280679 | AA280679 |
| 129523 | 18045_3 | M13231 X15019 X06776 M89838 |
| 108293 | genbank_AA069155 | AA069155 |
| 101045 | entrez_J05614 | J05614 |
| 131164 | 24837_1 | AW013807 AI815696 AI862432 T49092 AA155690 AA159080 AA157922 AA069164 AA143603 AA160598 AA112428 AA160458 AA121056 AA305088 AA113260 AA158778 AA156367 AA155702 AA159785 D82138 W52865 AA159245 Y00503 AA065024 NM_002276 AA102205 AA128752 AA101009 AI927602 AW051958 AA158511 AA161162 AW190396 AW050418 AI696397 AW273416 AW294898 AI142003 AI804018 AI183496 AI220351 AA513107 AW044309 AI739324 AA419031 AI080537 AI990451 AA991542 AI144377 AA580150 AA506169 AA235494 H28435 AA527890 AA528155 R62300 AA496566 R76562 R81818 H44591 H01057 AI798693 H12756 H26311 R53603 AA314451 AA321679 AW382760 H13203 AA368603 AI907784 AA076205 AA159878 AI826856 AI620832 AA074411 AI469760 AA078887 AA665999 AI289457 AI284021 AI805678 H26193 H26997 AI879997 AA464358 U47725 AI902283 AI907204 AI902493 AW393619 AA346319 AA641035 R77163 AA161028 AA101053 AA158042 R24917 AA568362 AA535551 AI680185 R76187 AI921052 AW189063 AA115773 AI357803 AA300035 AW189909 AW089585 AA642993 AI905428 AA160916 AA160884 AI905445 AA151979 AA149947 AA121437 H28900 AA654438 AW375842 AA160877 AA078888 AA146583 AI832408 AA146594 AA079854 AA160510 AW317033 AA113130 AA658048 AA157497 D58772 AA654340 AW084555 AW168281 AA643069 AA573797 AA641631 AA641663 D58487 D59204 AA074471 AA115774 T51053 AA159081 AA552660 AA641467 AA565127 AA635956 AA295952 T64107 T49093 AA720815 AW117874 AI906306 AA641389 AA130962 AI907203 AI921723 AA838212 AA421902 AA837806 AI537867 AI653492 AI370319 AA126264 AA101010 AI539815 AA837910 AA857688 AI002606 AA533815 H26055 AA635234 AA857696 AA826821 AA826740 AA838556 AA064593 AA160369 AA133047 R80112 AA410759 AA159363 AA826804 AA419188 AA812246 AA112418 AA155634 AA056612 T49519 AA857980 AA826982 AI969250 AA315344 AA155647 AA972492 AA811776 AA069165 AA076655 AA513744 AA076637 AA076630 AA159148 R80874 AA076125 AI620804 AA569710 H26011 AA146580 AA157271 AA113167 AA366798 H13570 AA134137 AA132966 AA161163 AA838651 AA079361 T52628 AA055657 AA133467 AA156306 AA157857 AA641842 W60455 AW070825 AA158394 H70723 AA513763 AA128335 AA160881 AA121070 AA654226 H12798 AA076087 AA654089 AA563680 AA079134 AI874181 AI640642 AW272976 AA161228 AI611735 H01810 AI420288 AA158779 R81923 AA834693 H27392 R62299 T50362 AI207979 AA069299 AW051230 AA534349 H01719 AA847556 H30189 H26470 T29401 AI824943 AA973756 AA122331 R51934 AI695462 AW004947 L32014 AA582931 AI832407 AI394676 AA548496 AI420108 AI738888 AA632038 AA300282 AA357315 AA411570 H26192 AA585251 C00069 J03607 AA614720 D58638 AA367222 AI951192 AA806120 AA654457 AI471675 AA158828 AA159789 AA122412 AA366925 AA075964 AA143606 AA101052 AA122141 AA150526 AA143409 AA158168 AA160035 AA079360 AA078768 AA367322 AA134136 AA113843 AA372342 AA126355 AW351823 T49518 R31821 AA079645 AA079604 AA056701 AI906310 AI220108 AI367372 AA552430 R32468 R80875 H28901 R76188 H28454 AA133466 AW270517 AA826236 AA826785 AI569902 AW081578 AA812314 AW517845 H70722 AI240639 AI367195 AI538063 AA641030 AA427590 AA548569 AA837565 AA827046 AA857588 R31775 AA464250 R76286 AA130973 AA157310 AW087347 AA422046 AA099504 AI906815 AI906817 H00979 AA158004 T52627 AA876536 R80004 AI469617 AI381183 AA159089 |
| 122860 | genbank_AA464414 | AA464414 |
| 108466 | genbank_AA079409 | AA079409 |
| 108505 | genbank_AA083376 | AA083376 |
| 101363 | entrez_M11321 | M11321 |
| 108679 | genbank_AA115963 | AA115963 |
| 124357 | genbank_N22401 | N22401 |
| 101544 | entrez_M31169 | M31169 |
| 124777 | genbank_R41933 | R41933 |
| 117789 | genbank_N48294 | N48294 |
| 119071 | genbank_R31180 | R31180 |
| 133512 | 9759_5 | L18861 L18865 AW070431 AA113837 AI632547 AI916703 AI379430 AI202667 AW206642 AW073179 AA113124 AI143432 AW291178 AA194933 AW500449 |
| 105057 | genbank_AA134233 | AA134233 |
| 103804 | AA129196_at | AA129196 |
| 133905 | 19822_1 | AB028974 N23531 AA331997 AA158930 AA330266 AA325667 AA304830 AW207601 AW136577 AA333353 AA332995 AA333306 AA081713 D56427 H59330 Z44112 F12914 R24585 T75069 W60417 AA333649 W80869 AA082655 T87499 AA368194 AA367780 R16648 AA075872 |

TABLE 1B-continued

| Pkey | CAT Number | Accessions |
|---|---|---|
| | | N78127 W79748 R32582 R17262 H06358 AA303224 AA329888 Z20422 AA700131 AA330349 AA702806 H07856 AI418899 AI298519 W94949 R80840 AA027771 R45272 W73894 F11842 AI122604 AI143062 H68745 AI127271 AI150826 T80201 Z45719 AW026367 T35161 H90057 AF038197 F10518 R16649 W56356 AI150600 AI141868 R44390 W72581 AI127233 T32475 W80690 R40165 AA719936 T89274 U21466 AW419154 Z40120 N58536 AW137627 W81401 AW296674 R64069 AA081667 AI378946 R27298 W69539 N42343 Z42781 H82474 H51766 AW379567 AW379582 AW379598 AW379596 AW379581 AW379538 AW379595 AW379601 AW379560 N28313 AW379547 AW379578 H90923 N91738 H83037 R70566 R80825 C01169 H51765 R82732 AI821161 H13650 AI207663 AA128418 AA247218 AA211931 AI681877 AL039882 AA977075 AI126695 AI126694 AA367630 AA367811 N64724 W69455 AA158931 AA328727 AA827266 W76611 AI373519 AA074053 AI802463 D81614 N52762 H03652 H06301 W67203 W67326 H88874 AI266389 D81742 AI362103 W69145 R80841 R69791 N34686 H02523 H88089 W69982 AA911307 H01435 AA648978 AI694410 R63565 H99496 AI076041 AW169361 N33365 N20516 AI698178 AI362095 H82818 N57584 AA987587 T34901 H88873 R75887 AA847080 AW299352 AW291233 AI191664 R79803 AW510720 AI002932 AW517937 AI300422 AI189530 R32477 AA129838 R41877 AI160115 AW241449 R31444 H13651 F10908 AI244779 H03401 AA666067 AW003480 AI796850 F09374 R26520 T34900 AA831195 AA838386 R39543 R78116 T31573 T35052 R24148 T30304 AA923238 AW183443 AA707584 Z41379 H28683 AA902260 AA676402 AA908922 AA223225 H88090 R26990 AA082061 W81411 AL039881 W67883 R00760 AA368364 AW298081 R00761 AA418931 AA418842 AA975973 AI299566 AI131437 AI803495 T84080 U21465 R25322 AA902173 R31765 AA364160 R31427 R31443 W69251 W72649 R70477 R24022 H07946 W01116 W56459 R35644 R76063 R36685 H03653 R80944 T84346 R78115 W76224 T83547 H04100 R37530 T34997 T84579 AA209275 F11716 N88311 N29211 F13518 H39691 AA367956 R67498 R25594 R25212 AA333481 R10023 R79712 AA327621 |
| 119521 | NOT__FOUND__entrez__W38038 | W38038 |
| 119546 | NOT__FOUND__entrez__W38169 | W38169 |
| 119559 | NOT__FOUND__entrez__W38197 | W38197 |
| 128046 | 877605__1 | AA873285 AI025762 |
| 135424 | U67611__at | U67611 |
| 128460 | genbank__T16206 | T16206 |
| 114767 | 20878__4 | AI859865 AA148885 AI805593 AA701342 W74071 AA211366 AI050010 AA641939 AA470717 AA580812 R99175 AA379782 AA379351 |
| 100547 | tigr__HT2219 | M57417 |
| 322035 | 33334__1 | AL137517 BE072492 AI127076 AW196207 AW294979 |
| 321408 | 507890__1 | AW081530 R99042 AI243443 AA912977 AI990404 |
| 321412 | 624592__1 | AI674383 AI865710 AI201451 AI659387 U25919 BE093109 AW366305 BE141926 BE141913 AW854334 AW854342 BE141916 |
| 321415 | 42585__1 | BE621807 AI445461 AI346835 AI453743 AI564644 AI928364 AW984527 BE158214 AI694111 AI591358 C17504 C17476 C17963 C18304 AW071625 AI678712 C17732 D57559 H61762 AI720939 AI262930 H27252 AA479712 AI927769 AA291465 AA155661 AI963432 AI567995 AA421678 AI925607 AA292956 AA192448 AW192593 AI865838 AI696905 AI871950 AI911921 BE619741 BE439796 AI161312 AI597801 AI424384 AI093510 AI246988 AW820230 AI492554 BE044033 AW262737 AW008570 AA043216 AW629505 AA136645 AA037722 AA706057 AA088439 AW806193 AW806183 AA479834 BE501957 AA129574 R38114 AA649494 AA524526 BE327120 AW572531 BE219784 BE349186 AW015724 AA043217 AW772000 AI799814 AI671727 AW779725 AA502832 AI470033 AA129575 W38161 AI972739 AA404570 AA627686 AA723200 AA147228 AA903050 AI990245 AI075878 T32487 C06123 AA157944 AI800106 W60075 AI859160 AA478328 AW673152 AA182640 AI990827 AW275048 AW103470 AI298935 AW471421 R79190 AW085158 W45410 AI333170 AW300456 AA662517 T55840 AI823466 AI692846 AA962397 AW191997 AA136658 AI251817 BE044134 AW339104 AW517762 AA724739 R79933 AA411100 AA191349 AA037696 AA190966 AA757735 AW772283 AA010631 H80983 AI765616 H64985 AI061065 AI950693 AA085492 AI245632 H28594 AW088968 BE156360 AI349390 AI621320 AI738844 AW194272 AA148284 AA953883 C06365 AA487893 AI927217 AI918523 AI453453 AI798502 AI189366 AI261359 AI032569 AW338678 AI972899 AI500576 AI872628 AI693030 Z28771 AI985583 AI363829 AW339301 AA581093 AI650338 W60032 AA603586 AI686240 AW242958 AA719173 AI745717 AW675302 AI582462 AI244845 AI565439 F09579 AI918453 AA035576 AI472527 AW351556 AA191414 AW674145 D57558 AI446740 D57845 AI589264 C05782 AA722206 AI432033 R21752 BE157510 AI829640 AI468237 AW384233 AA989662 AI865912 AW197954 AI344941 X75684 AI344943 AW583310 AA988297 AI334860 AI348877 AI798415 D11921 AI377596 AI983655 AI744233 C06111 AI248307 AA948565 AI224807 |
| 314219 | 193781__1 | AA262331 AI341087 AI948826 AI091645 AI368235 AW023023 AL036001 AI374947 AW880714 |
| 321441 | 10__2 | AF107493 AW292576 AI350197 AF107492 AI087797 AI015215 AI742876 T19232 Z20369 AW901548 AW297633 H74155 AW444856 AI333452 AI218239 AA768303 AW205216 AI681844 AA927661 AA995339 AA814684 AI004759 AI446253 AA037589 AA826043 AA037588 AA629039 AI378841 AI218713 AW204869 AI969043 AI926273 |
| 321489 | 747638__1 | AI459177 H70146 H70145 AW392474 BE007373 |
| 313624 | 107294__1 | AA525775 AA056342 AI538978 AW975281 AA664986 |

TABLE 1B-continued

| Pkey | CAT Number | Accessions |
|---|---|---|
| 320848 | 30102_1 | AB020691 AW363000 |
| 313637 | 22689_1 | AK000742 AW503432 AF195765 NM_016448 AW735743 AK001261 AA354452 W90163 AK001206 AW674785 W90164 BE537327 AW468557 AI360528 AA765212 BE539846 AW780179 AI969579 AI224479 BE552377 AA846697 AA913841 AA505890 AA730175 AI038673 AI800576 AI376958 AI087840 AW069881 AW499674 BE540961 AW576369 AW674003 AW339528 AW440579 R06900 AW371940 AI800751 AA026058 AA580863 AW504533 AA361353 AA581038 AA252192 |
| 313689 | 789607_1 | AI608810 AW469135 AW081685 AW028811 BE328700 |
| 314305 | 199275_1 | AI280112 BE219678 AA643722 AI338397 AI268833 AI268692 AA873024 AA884051 AA908417 AA283730 AA935786 |
| 322189 | 46920_1 | H65014 AF086007 H65015 |
| 315043 | 346288_1 | AA806538 AI005244 AA535437 AW972174 |
| 315052 | 347718_1 | AA876910 AI075041 AW015293 AA548124 AA876653 AW976986 BE178095 |
| 315074 | 349952_1 | AA828284 AA745395 AI921460 AA553390 AI921457 |
| 321636 | 179566_1 | AI820961 AI791838 AI732149 H88053 AA229286 AA230261 H88264 AA229399 AA230205 |
| 314456 | 243606_1 | AI867931 AW295460 AA346767 AW298044 AI659095 AI243606 AI262454 AA928451 AI348190 AI261259 AW590242 BE466091 AI205524 AW025663 AI342069 |
| 314465 | 245252_1 | AA602917 AA884688 AA348814 |
| 321693 | 41829_1 | AA227069 AA098985 AW378687 W40485 T35169 AA169459 AA191260 AA136391 |
| 321696 | 14507_22 | AA628791 AW896351 N87347 AA248228 W07100 |
| 313832 | 189826_1 | AW271106 AI792438 AW086313 AI792626 AW302105 AW470464 AW086409 AW086298 AW268789 BE138591 AI349941 BE049152 AI336511 AI336493 AI336569 AW302938 BE139030 AI349771 AW303044 AI252136 AI345022 AI144108 AI252466 AI733716 AI349804 AW301920 AI251159 AI311063 AW271910 BE138422 BE139406 AI589963 AI289561 AW302671 AI345087 AI251185 AI251536 BE139045 AI690773 AI252721 AI252886 BE138567 AW269115 AI252823 AI053741 AW301523 AI053755 AI053555 AI054200 AI053780 AI053446 AI054095 AI053514 AI053846 AI053940 AI144063 AA613834 BE138636 AW302056 AW271147 AI345640 AW513914 AW378055 AW272025 AW272051 AW271022 |
| 315198 | 363831_1 | AI741506 AA584304 AW337973 |
| 323045 | 145763_1 | AA148950 AA479395 AA479296 AA148951 |
| 315214 | 386196_1 | AI915927 AW510677 AA732008 N25957 H99949 AW975745 AI627844 AI807785 BE550656 AW205418 AI858589 AA633210 D60275 D80860 D60030 D59841 D60620 R99572 |
| 323091 | 235077_1 | AI902456 AW898820 AW813901 AW818676 AW014094 AW818898 AW609933 AW392990 AW582601 AA334825 AI811892 AL119705 R09750 AI864059 AA353695 AW962070 AW977261 AW975827 AI951144 AW393885 |
| 322447 | 89050_1 | AI735759 AW304313 AI188319 AI677654 AI769885 AI769145 AA723627 AA021055 AA781580 AI611167 W56077 BE162225 BE162152 |
| 322463 | 643179_1 | AI242754 W58441 W58427 |
| 321896 | 1507388_1 | C04863 N54200 N54238 |
| 321899 | 68882_1 | AW972832 N55158 AA527642 BE173119 W03745 W03727 AI784523 AI096936 AW975392 N74169 AW876605 AW876602 AV659835 AI140754 AW188519 AI949757 AI803722 AI014812 AA809213 N50836 N62972 AI914731 AA935043 AW191931 AW516924 AA741240 AI000955 AI014777 AI358045 R75839 AW340779 AI095334 AI241826 AA745278 |
| 300258 | 756653_1 | AI478933 AW187989 AI911151 |
| 323131 | 33779_1 | AK002088 AA176982 AW367780 AI290209 AI338705 |
| 322540 | 38950_1 | R76593 AF147390 R76594 |
| 315344 | 372511_1 | AW292176 AA604126 AW058157 |
| 315352 | 373022_1 | AA604799 AI080551 AI037933 AI358915 AI743933 |
| 315353 | 373106_1 | AI373949 AW452608 AW237521 AI640620 AW873743 AW242635 AA993178 AA604921 AI926566 AW873687 AI693504 AW089401 AI978739 BE169646 |
| 315368 | 20289_1 | AB037745 AW994023 AW864381 AA557888 AW392189 AA533583 AI687545 AI906958 AI906948 AA516526 AI812063 AW151024 AI978956 AW291563 AW511693 AI811598 AI699858 AA336964 AA337039 AW966212 AA336849 AW864722 AW864697 AA337833 AA988916 BE550194 AW994408 AW966239 AW139785 |
| 321960 | 23833_1 | AA723883 BE545311 F13535 T65504 AW246035 H39618 BE293221 AL122073 BE393462 AI367256 AW015154 AI874244 AI339548 AW518892 AI148428 AI339560 AA847296 AI261244 AW173770 AI143349 AI346957 AI475948 R52652 AI814098 AI339729 |
| 314785 | 315390_1 | AI538226 AI951161 AW152296 AI497657 AI631380 AW005645 AA471017 D59282 AA552190 AA658155 AI091127 BE251460 |
| 323243 | 140566_2 | W47525 AA134047 BE391212 AA330333 AA376355 BE304871 BE167342 H87402 AA631722 W45724 AA715517 AI925438 AI804849 AW241617 AW403807 AI653435 AA134048 AW747874 AI922327 AI814967 AI935895 AA228865 AW504076 AA225008 AW673858 C03914 |

TABLE 1B-continued

| Pkey | CAT Number | Accessions |
|---|---|---|
| 316042 | 188898_1 | AI469960 AW297979 AW517302 H30516 AW967501 AA251715 AW966877 AA720888 AA765940 AA743170 |
| 323262 | 333733_1 | AL133990 AI128582 AI829770 AW972505 AA505700 |
| 315439 | 164204_1 | T78413 AI128953 AA843097 AA808038 AA694545 H01994 AA730423 AW576123 AI475644 AA987811 AI948528 R19187 AI339951 AI338984 T88696 AI830997 BE349489 AI880004 H02091 R26552 AA575927 AA464693 R24078 W58758 AI189805 AA844323 AI889162 AW731626 AI817046 AW243903 T24484 N68847 AI264219 AA455017 AW731676 AI969578 AI279912 AI446015 AI522034 AA962541 AI128503 D51331 H77926 H48807 AW994256 H48707 AW371368 T78796 Z36733 R24132 H73036 N92060 BE177547 AW953472 H48381 H48616 T85132 R11439 D51512 AW385362 T09302 AA455821 AA887686 T32458 AW673632 AW368929 AI470249 AI248766 AA641833 AI885015 AW182619 AA702943 AA740564 AA700695 AA622697 AA650141 AA654855 AI815704 AW673694 BE003621 BE002736 AW361569 AW503647 H24255 |
| 315498 | 382739_1 | AA628539 AA939273 AW151381 |
| 314881 | 588392_1 | AI095087 AW051857 AI418253 |
| 301015 | 7493_1 | AV655272 AI382139 AI124646 AW298134 AA652260 T58540 AI337943 AI354941 AW511303 BE501483 AI371627 AI687503 AI693430 AI693871 BE348647 AI091164 AA947682 AA371477 AI014595 AK001478 AA319342 AA775305 AL119130 R13701 AA363659 AW959490 AA460066 T95465 AI161400 F07057 Z42134 AW298014 AA134238 H15216 R19551 AA356614 AW965786 Z43860 AA448444 AA133248 R09023 AA011707 W52631 BE539194 AA404459 BE540061 H77582 R65897 R82856 R77316 R07005 N76954 AA151044 AW237218 N45210 AA602932 AA602716 AA133302 AA758224 AI934546 AA777775 AA313088 AI090189 AI034208 BE179566 AW243921 AA094482 AA503364 AA150954 N55569 AA459974 AA876807 AA877039 H15156 N50021 N59869 AI359768 AA011659 AI082642 R08917 AI057486 N59861 AI159893 AI373105 AI421080 AI342277 AI627170 AI291327 AI248158 AI248401 AW243833 AW302479 AI359914 AW304855 AA134239 AA700701 AA778115 AW590251 N93112 AA523791 BE328612 R77267 AI685130 AI624648 R65802 AI094830 AV649450 AW197384 H77583 AI554805 AW169702 AI018035 AA719149 AA923007 AA522740 Z39926 AI967947 AW002934 AW242790 AW594430 AI471090 R93133 F01671 R37796 AA879223 R82857 AW297212 AA522866 AW014397 AA935208 F03335 N58316 |
| 315528 | 584775_1 | R37257 R59060 R51008 AW512988 T16256 T17085 AI091075 Z40598 AI161111 |
| 315566 | 7248_1 | AB037810 AA613585 AA143433 AW292417 AI703130 BE047771 AW856308 AA164855 BE152441 AA263151 W39493 Z41877 R67724 AI866562 AW886795 R58240 AI949477 AI697664 BE468174 W15184 AI291490 AW903944 AW205158 W38386 BE073171 AA151839 AW770804 AW938901 AW938887 BE180851 D80042 AW075286 AI307191 AI142899 AA825269 AW612226 AI912726 AW078999 AL120580 AA248003 AA249641 AA256328 AA035016 AA838179 AA195567 AI267533 AA151840 AA417241 AI436735 AW969461 AI215929 BE467827 AA000998 AA194726 N78677 AA468900 AI889860 BE327986 AW150774 AA527287 AI985620 N70070 AI401246 AA716216 N58944 AW020195 AI290564 AA035484 AI492846 AI422573 AI479863 AI492858 N95814 AA808525 AA464598 AI128011 AI091118 AA256329 AA248931 AI695597 AI913995 AI186382 AI474202 AA483844 AW339194 AI784462 AI189110 AI359376 AA985653 AA634155 Z38179 T24811 T99839 |
| 314915 | 534268_1 | AI673735 AA978066 |
| 314916 | 335944_1 | AA548906 AI351272 AW087522 AW268901 AI215628 AA931650 AA622392 AA512893 AI868907 AA781491 AW973048 AI310053 AI346006 AW192528 AA627385 BE327414 |
| 314943 | 29197_1 | Y00272 NM_001786 X05360 AI798699 AA356724 BE614169 BE613918 AA481617 AA460416 AA502929 AA405362 AA262523 AA278384 AA309053 AW961259 AA278928 AA309870 BE082133 BE620698 BE620344 AF154332 AI608775 BE044519 AI609169 AI336229 AW589947 AA679747 AW051286 AI476797 AI619661 AA936969 AA725015 AI476796 AI719320 AA460417 AA598974 AI801699 AI968016 AA281899 AW768864 AI784302 AI566748 AA678755 AA889424 AW970204 AW497613 AF055880 AA356815 AA377603 AA314704 AA313715 BE252934 AA213845 AI167610 AI246661 AI288902 AI091363 AI559983 AI338883 AA938977 AA261869 AA971654 AA278812 AA906356 AI332362 AI239956 AI039800 AA805603 AA764779 AA761043 AA827942 AA836076 AA806100 AA828529 AA809666 AA835771 AA837406 AA761575 AI806162 BE537294 AA281741 AL037114 AA481551 AA748439 AA406217 AA829653 AA278152 AA026802 BE275968 AI492210 AA505596 R57512 W79096 |
| 314946 | 338282_1 | AI097229 AI242329 AI242439 AA932068 AW196074 AW001485 AA516371 |
| 324047 | 739073_1 | AI433357 AI628543 AW772732 |
| 301182 | 432790_1 | AW291411 AI989588 AW119198 AI699375 AW268984 AA744306 BE349487 AA744319 AA744343 AA744022 AW673026 AI538081 AA936261 AW901168 AI880221 |
| 323410 | 624147_1 | AW118683 AI200954 H30192 AL135542 AI500131 AW021787 D62063 |
| 300551 | 20299_1 | AW408800 AW247286 BE273604 BE384688 BE383679 AW407566 BE535238 AA306655 BE247297 BE256060 AL162048 R58359 BE315109 R97889 AA425243 R84295 AA287784 W25131 W86372 R10781 AW977742 AW182315 BE246157 AA779101 AA828352 AA830694 AA729221 AA805637 AW665290 AI857924 AI739152 AW007712 AI382016 AI022382 AA577188 AA563628 AA993840 AA714213 AA425761 W86308 AI683544 AA837056 AI040484 AA912066 AA639677 T66935 R87657 AI952610 N93289 AW247902 R10692 AA286828 AA905665 BE294545 AA971688 AA700328 AA936181 |

TABLE 1B-continued

| Pkey | CAT Number | Accessions |
|---|---|---|
| 300566 | 833197_1 | R34926 BE241681 BE464839 H86709 AI694038 AI803494 BE241794 |
| 316244 | 245064_1 | AI640761 AW518716 AA348598 AI694415 |
| 322826 | 249229_1 | AI807883 AW025512 AA806939 AA587695 AW445093 AA723744 AA354050 AI694068 AI204307 AI935072 AA836440 AW582751 |
| 315618 | 102491_1 | AI287341 AI561357 AI571458 AW874317 AW157589 AW293749 AI380603 AW166199 AI817052 AW148795 AA045635 AI306119 AW627570 AW513999 AI978963 AI272242 AW161193 AW630809 AI741494 |
| 316345 | 433093_1 | AW139408 AA744532 AW976631 AI806964 AA923075 N68640 |
| 322919 | 124640_1 | AA178955 AI955703 AA093453 |
| 315715 | 397912_1 | AI284219 AA661618 AW631144 AA923594 AI697028 AI190512 |
| 323591 | 209807_1 | AA301270 AA301379 AA301366 |
| 322939 | 128851_1 | AA101697 AI828242 AA101698 |
| 315720 | 54549_1 | AA292998 AW238350 AI676059 AW074092 BE566458 AW078677 AW514801 AW073701 AW170620 AI523736 AI580870 AI923975 AI393326 AI700229 AW450814 AW628452 AI671457 AA937534 AI889694 AW339423 AW291875 AA551874 AI682314 AI926227 AA397375 |
| 315772 | 141422_1 | AW515373 AI378428 AI570315 AA135126 |
| 300702 | 113505_1 | AA075481 AA075480 AA075067 |
| 323620 | 54455_2 | AA306997 AA775676 AW299505 AI660377 AI698467 |
| 323645 | 216757_1 | AW445014 AW902240 AI660713 AA310888 |
| 316465 | 439802_1 | AW574774 AW574775 BE350883 AI349525 AI144210 AA764736 AA774177 AA877426 AI337556 AI911497 |
| 308615 | 33893_1 | AK000142 AW243187 AI738593 AW505395 BE009209 |
| 315841 | 405260_1 | AW136397 AI190461 AA679034 |
| 315843 | 405549_1 | AA679430 AI288325 AW168732 AW365349 AW179172 AW179160 AW179165 AW179167 AW179170 AW179164 AW178268 |
| 302067 | 31663_6 | BE542706 AA228426 AA228353 H93602 R83651 H05698 AI732365 AA574391 AA631694 |
| 324302 | 347430_1 | AW972771 AA543008 AW020052 AI927329 AL080044 H89135 AI240797 AA805682 AA781992 AA654987 |
| 324330 | 300543_1 | AA884766 AW974271 AA592975 AA447312 |
| 323753 | 12462_4 | AK002161 AA327102 AI056868 AI743901 AI139018 AI199114 AI076003 |
| 315901 | 170244_1 | AI521558 AA482964 AA206578 AI371259 AW298746 T70009 AI928914 AI561010 AI879995 AA865374 AW089990 AI961462 AI290111 AW131805 AI923946 AW008328 AW589464 AI823687 AI890645 AI620053 AW516110 AW058236 AI978667 AI352590 BE258572 |
| 315936 | 761946_1 | AW069807 AI499094 AW516301 |
| 302123 | 23805_1 | AB013452 AF067820 AA224982 AW751070 AA319924 AW014224 AA652796 W39181 AL119045 AA814358 AW499864 AI438930 AI798836 W15233 AW362985 AI218581 |
| 302124 | 23806_1 | AA676403 AW609167 AA287084 BE003999 AI221765 AW452395 AI184576 AA486282 AK001685 BE536328 BE000905 BE000900 BE000683 BE000686 BE001093 AL138357 AA748694 AA741478 AW368265 AW368273 AI784060 AW976762 AW296432 AA382900 AA055782 |
| 317202 | 498599_1 | AA894880 AI276231 AI914673 AI791221 AI680137 AA902510 |
| 317224 | 18771_1 | X73608 NM_004598 AF231124 AI208205 AA722985 AA918523 AA040054 AI203645 AA027807 AA628818 AW341349 AA719218 R68656 H51589 H08669 L25221 AA236371 M91505 AC005213 R68707 D56269 T39129 AA325789 AI074652 AI081195 AA253244 R58901 T15998 H08670 AW498685 AA019478 AI142950 H50927 AA082187 D56119 D56136 AA332649 R11993 R11994 AW894947 AW893628 AL120495 AA091445 AW949196 R11796 AW837521 BE142522 R14798 T30912 T05006 T30522 AA046577 T08651 AW381962 Z30311 T30767 F11882 AW904442 AA303296 BE154252 AA322067 AW904198 AW904187 AW904193 AW904201 AW904206 AW904202 AW904196 AA134701 AW904208 AI093233 AW904186 AA148474 AA045381 AA136351 AA244116 R65619 R28122 AA365618 AA046785 AI674088 AA363780 AW271560 AA377745 AI672458 AW628847 AA568297 AI627957 AI597687 W72670 AA046655 AI074414 AA325605 AI637614 AA579447 AI138683 AA045197 AA148475 AI827501 AI741374 AW025784 AI339638 AI200151 AI632080 AA244115 AA815320 AA629333 AA436142 AA757444 AA035654 AA436269 AI274673 AI754962 AI968580 AA777035 AW072910 AI017799 AI057215 AI493834 AA666311 AI088596 AA372733 AI198492 AA046664 AI383480 AI961192 AI342057 AI624747 AA781681 AI754497 AA781870 AA618484 R28012 R67001 M85718 R37716 F09529 R40109 AA911953 AA136263 AI381197 AW022958 AW020985 AI003403 AI480133 AI915945 T65571 N67431 AI886538 AW014340 N67114 T34884 AW020558 AA134702 AA933914 D56760 AI376330 AA027861 T65642 |
| 300942 | 340348_1 | AW301344 AI289542 AI263645 AI223760 AI345609 AI591244 AI581207 AI371620 AI371624 AI308891 AI349682 AI435690 AW268752 AW268734 AW075105 AW274066 AW273964 BE138662 AI341582 AI766474 AW275006 AW024110 |
| 300953 | 347317_1 | AA542845 AA971073 AA782986 AW173084 AW803688 AW183046 BE513408 |
| 300967 | 354154_1 | AA565209 AA565210 |
| 323835 | 506747_1 | AL042005 AL042006 AA911481 |
| 317275 | 503193_1 | AI809444 AA906815 AI699577 |

TABLE 1B-continued

| Pkey | CAT Number | Accessions |
|---|---|---|
| 316625 | 451975_1 | BE540090 AA780307 AI018561 AI017086 AA863480 AW805223 AW363266 AW576899 |
| 310014 | 144520_1 | D60745 D52450 D52669 D60886 D60742 BE545209 AA147290 N47211 Z28667 T24540 AA379681 AW954513 N80340 H69538 N64633 AI478640 BE504487 AI608780 AI031931 AI950473 N79962 AI457151 AA625540 AW297097 AA780347 AI659003 Z19752 Z28668 AI400953 N64544 AI354671 AW197824 AI079956 AI783689 AI079934 AI269572 AI206541 C00535 D59840 D59971 D59919 D60741 D80436 D60744 AA912149 AW628867 |
| 310026 | 194614_1 | AA278233 AI628014 AA555029 AA918926 AA813236 T24895 |
| 310056 | 622647_1 | AI253072 AI793200 AI199238 AI793011 |
| 302235 | 26088_1 | AL049987 AW362842 T78981 AA247541 AI217018 AW961515 AA632986 AA663108 BE326465 AW872412 AI024689 AA453725 BE150456 AA229448 AA442638 AA442648 AI916737 AA460220 AA868553 AI827987 AI005467 R31132 AI742087 AA442379 N56349 AW769479 AI860142 AI917507 AA813604 AI860141 AI459289 AA522837 AI354470 AI921333 BE466760 AW971193 AW103830 AW277065 AW020895 AI187977 N28268 AI084517 R95914 AA833517 AA563934 AA437299 AA436880 AA447794 AA812876 AA663178 R31089 AI472712 R64648 AA600372 AA229164 AA703066 AW270324 AI191725 AA551512 AA493776 |
| 302290 | 27712_1 | AA179949 AL117607 AW162167 AI879018 AW156914 AI879513 AA378584 AW576223 AA457509 AW900231 AW402142 AA457603 R13422 AW401706 AA206711 |
| 323926 | 249618_1 | AA354572 AW062361 AW813419 AW816041 AI744949 |
| 324598 | 331443_1 | AW972227 AA502659 AA502837 BE463981 AA577001 AW135566 AA614316 AI347791 AA714751 AA632758 AA721400 AA888459 |
| 316738 | 461749_1 | AA889055 AW293447 AA868594 AA812611 |
| 302357 | 30107_1 | X03178 L10641 T69098 T60971 T61278 T68211 H65922 AA344752 AA343792 T39954 T61705 M12654 S67527 T82026 AA702451 AA705281 AA701621 AA700699 T62119 AA700045 T87611 T72420 T72411 N50008 T73672 T74480 AV657689 T50959 AV662244 AA345132 AA758473 AI375145 T80195 AA693754 AW881104 R11123 H58064 AW881106 T28663 AI207447 AI133110 AW471264 AI453369 AW001034 AI032548 AA228086 AA968433 AI218121 T68099 AI218125 R11318 AI092243 T69019 AA702371 AI478226 AA702916 T61069 T53887 AI076291 AI269174 AI521340 T69266 T73927 AA676637 T69294 AI097273 AA780013 T72397 AI366751 AI288875 AI760507 AW469534 AI374870 T50796 T74901 AA694251 T60479 T74707 AI244538 T61247 T73320 T62056 T50726 AI338616 T61621 R83003 AA228087 R11319 H58065 AI436703 T74106 T71572 T73571 AA974692 T72156 N49908 T72389 R11066 AW827139 T41010 AI758185 AA935828 T41011 T55900 T40910 T72396 T73316 R85385 T61196 C20921 AI034365 AI034363 AA702473 AI191087 T73959 T72308 T73386 T75002 T60633 T69369 T74828 T61172 T54034 T69340 R29569 T98492 R83053 T55094 T73381 T40102 T50882 T40058 T72421 T54928 AV658208 |
| 301712 | 34465_1 | BE083080 AL035409 F05978 AA071204 R59067 |
| 302380 | 56518_1 | AA325633 AW955338 AA134505 H94836 AW631383 N57361 H29086 H88572 D63256 AI762876 AA130535 AW088798 H88446 AW118230 H98112 AA225686 AI494601 BE328740 AA225168 AA216401 D79750 AA935145 BE440187 AA730383 AI368654 AI868522 AA598873 AA513290 AW516458 H88380 C16196 H88527 AA513285 N31853 H28981 AL120556 BE568637 AW070439 |
| 302385 | 30464_1 | AJ224172 AW015055 AW105434 AW105433 AA335579 AW105483 AW103293 AA299198 AA299023 |
| 317404 | 509763_1 | AI806867 AI701001 AI018370 AA917422 |
| 324666 | 164204_1 | T78413 AI128953 AA843097 AA808038 AA694545 H01994 AA730423 AW576123 AI475644 AA987811 AI948528 R19187 AI339951 AI338984 T88696 AI830997 BE349489 AI880004 H02091 R26552 AA575927 AA464693 R24078 W58758 AI189805 AA844323 AI889162 AW731626 AI817046 AW243903 T24484 N68847 AI264219 AA455017 AW731676 AI969578 AI279912 AI446015 AI522034 AA962541 AI128503 D51331 H77926 H48807 AW994256 H48707 AW371368 T78796 Z36733 R24132 H73036 N92060 BE177547 AW953472 H48381 H48616 T85132 R11439 D51512 AW385362 T09302 AA455821 AA887686 T32458 AW673632 AW368929 AI470249 AI248766 AA641833 AI885015 AW182619 AA702943 AA740564 AA700695 AA622697 AA650141 AA654855 AI815704 AW673694 BE003621 BE002736 AW361569 AW503647 H24255 |
| 324674 | 346953_1 | AA541323 AI791466 AI791312 AI732511 AI686664 |
| 324678 | 347425_1 | AI990739 AI082831 AI990284 AI989475 AI927951 AW295986 BE328405 AI798629 AW590232 AI380475 AI350438 AW194833 AI867928 AW611508 AI478440 AI758120 AI862507 AI307600 AI308018 BE465174 AI953643 |
| 324697 | 22689_1 | AK000742 AW503432 AF195765 NM_016448 AW735743 AK001261 AA354452 W90163 AK001206 AW674785 W90164 BE537327 AW468557 AI360528 AA765212 BE539846 AW780179 AI969579 AI224479 BE552377 AA846697 AA913841 AA505890 AA730175 AI038673 AI800576 AI376958 AI087840 AW069881 AW499674 BE540961 AW576369 AW674003 AW339528 AW440579 R06900 AW371940 AI800751 AA026058 AA580863 AW504533 AA361353 AA581038 AA252192 |
| 317488 | 514611_1 | AW071851 AA928369 AI919409 AW836172 |
| 316868 | 471387_1 | AI660898 AA834538 AI377344 AW043948 AI769408 AI923843 AW798783 |
| 316897 | 474090_1 | AA838114 AW629478 AA883713 AI620552 |
| 310219 | 637034_1 | AI221087 AI698579 AI700118 |

TABLE 1B-continued

| Pkey | CAT Number | Accessions |
|---|---|---|
| 303054 | 35775_1 | BE265848 NM_013326 AF143536 F12757 AA402970 Z44352 R14707 BE177528 AW958512 AA380463 AA424104 AW363411 AW363412 BE066806 AA614320 AA354557 H67001 AA421994 AI679344 AA135564 AW058200 AW664972 AW058056 AA135474 BE220515 BE348437 BE174518 AW058165 AI480045 AI250938 AI811246 AI720372 AA934983 AI498324 AI002130 AW021770 AI299247 AA620416 N51067 AI086016 AI276853 AI436292 AW087667 AI218712 AA788684 R91508 AA714928 AI275852 AI245860 AI095507 AI334292 AI800688 AA767951 AA402027 AI985390 H67002 AW295541 H77654 R45252 AI271551 F10365 AA424047 AW001830 AA810829 AI358357 AW271613 R42429 T74967 H59894 T80841 |
| 302416 | 14686_1 | AL120259 AF070673 AL161976 AF030196 NM_003498 AA663592 H50906 AW139111 AI582741 AI124509 R86835 AI122619 D81997 AI017837 AI480055 AI202048 F11990 T65360 AL134186 F08366 Z44769 F06392 R14463 AW371095 AW947207 AI124893 R19946 H30239 T08167 AW961950 AI124544 W25535 AA985098 W72938 AA448032 AA186495 C01444 AI198135 AA394190 W73248 AI867767 R52255 AA894930 R44756 AW247309 AA082666 AI743791 AW027269 AI066512 AI335979 AW952848 AW151239 AW297787 AA447631 AA341268 BE387731 T65161 AI202044 AI376153 AI095510 AI097397 AA704463 AI198902 AW021978 AI299090 AA262109 T15756 AI984744 AW090208 AW028340 N50631 AI085260 F02682 R52256 AA908658 R40981 AI937275 AI216731 AA101147 AW058083 AA448650 AA604431 H51578 AA883063 H26984 AA907804 AW293804 BE217869 AI521091 W19293 AA187183 AA903305 AI985439 F09637 F03757 AA903293 AI305652 AI306975 AI306000 R86660 H51572 |
| 301804 | 61_1 | AK001468 AA190315 AA374980 AW961179 AA307782 AA315295 AA347194 AW953073 AW368190 AW368192 AA280772 AA251247 N85676 AI215522 AI216389 N87835 R12261 R57094 AI660045 AA347193 R16712 AW119006 N55905 N87768 AW900167 AI341261 AI818674 D20285 AI475165 AA300756 R40626 AI122827 AA133250 AI952488 AA970372 AA889845 AW069517 AI524385 AA190314 AI673359 AA971105 AI351088 AI872789 AI919056 AI611216 AK001472 BE568761 AA581004 |
| 324713 | 357877_1 | AI093930 AW150892 AI683004 AI635756 AW970049 AW340249 AA574295 AA578334 |
| 301872 | 27494_4 | H84730 T73262 |
| 324753 | 375340_1 | AA612626 AW263031 AI131456 AA968971 AI868979 |
| 316905 | 474983_1 | AW138241 AA843479 AI769635 AW271676 AA894822 |
| 324790 | 392494_1 | AI334367 AI379644 AA742788 AA648175 AA745103 |
| 303132 | 39594_1 | AI929819 F28779 AA632963 AF161428 AA658915 AW450807 AI929660 AF161430 AW964378 AA318185 F24885 F37620 F34389 AA602113 F36287 F33311 AA503400 F21165 AA627162 AA844750 F36001 AI832751 AI748847 AW753132 AA513079 AW804971 AA480002 BE149300 |
| 310353 | 652068_1 | AI261700 AI793196 AI469160 AI793007 |
| 310371 | 652857_1 | AI262584 AI733828 AI692683 |
| 303194 | 117948_1 | AA082000 AA101107 |
| 302595 | 213615_2 | AI699372 AA767895 AI925984 AI468911 AA768087 |
| 324804 | 398093_1 | AI692552 AI393343 AI800510 AI377711 F24263 AA661876 |
| 324867 | 127674_1 | AI624707 AI445885 D25670 AA864795 AI952402 AA522853 T47840 R71339 R26278 AW150990 AI446414 AI758983 AI583137 AA723568 R45103 R40973 H11088 AA773734 Z39030 |
| 311013 | 481_1 | AA224760 AA332843 BE271344 AC005058 AA230199 AW934959 AA228766 T59121 BE092989 AW879494 AW805062 T64581 H46088 AA639977 AA159765 AA773078 AW381143 AA934471 AW945282 AA157096 T59775 AA838394 AA622099 U74661 T29058 AW020229 AW975648 AA809246 AI865461 AI567200 AW411471 AW455216 AA886133 AA876597 AA484908 AW006533 AA484797 AA876600 AW241349 AI356351 AA665333 AW827106 AA095917 BE617721 X52967 X57959 NM_000971 L16558 BE546142 BE298465 AA079187 BE619947 AA089872 N40644 AA147085 AI241894 BE385214 T60795 BE408944 BE383181 AA093225 N69952 BE296462 BE252523 AA578005 AA527034 AA527111 BE296142 BE314845 N84513 AA094268 AA091139 BE257271 BE297367 AL031589 AA090328 AL049545 T65841 AW374034 D52104 AI541322 AI092213 AA090217 AI535670 AI536086 AI557362 AI535719 AI535758 AI535696 AA648341 AW885361 AW976501 T50153 AA090124 AA096425 AA978018 AA092117 T60188 AA095024 AA093750 AA096245 AA093716 AI445129 BE568306 AA096158 AA527208 BE388185 AW270341 AA937848 T59643 T53081 AA580838 AI719250 AW881564 AA092762 T12399 AA308000 AA096460 N87260 AA096220 BE169825 T59048 AA083628 BE313409 AA089707 AA603915 X57958 AA888688 BE299530 BE273737 |
| 311034 | 13087_2 | BE567130 AI564023 AI952976 AI567489 |
| 311067 | 786469_1 | AI587332 AW070928 AI924735 AW274522 AI803756 |
| 310430 | 659831_1 | AI670843 AI272378 AI880053 |
| 310438 | 661627_1 | AW022192 AI559500 AI274757 |
| 310455 | 664099_1 | AI277603 AI277601 AI300268 AW195846 AI708510 |

TABLE 1B-continued

| Pkey | CAT Number | Accessions |
|---|---|---|
| 303274 | 61_1 | AK001468 AA190315 AA374980 AW961179 AA307782 AA315295 AA347194 AW953073 AW368190 AW368192 AA280772 AA251247 N85676 AI215522 AI216389 N87835 R12261 R57094 AI660045 AA347193 R16712 AW119006 N55905 N87768 AW900167 AI341261 AI818674 D20285 AI475165 AA300756 R40626 AI122827 AA133250 AI952488 AA970372 AA889845 AW069517 AI524385 AA190314 AI673359 AA971105 AI351088 AI872789 AI919056 AI611216 AK001472 BE568761 AA581004 |
| 303297 | 6537_1 | AF070623 T80072 H08917 R35413 H14948 T80074 C15452 D81744 F05382 F05380 Z45148 R18285 AI634532 BE549752 AW299752 AW090717 AI693471 H08831 BE217766 AI373383 AW137702 AI241235 R49210 R38766 AA757779 R38765 AI498410 AI693124 AI648374 R14143 |
| 302656 | 71764_1 | BE090580 R96998 AA091152 AA488678 AA644573 AA563967 BE090584 AA079122 N79188 R95018 AW958397 AA190398 AA563719 AA379630 AA280050 AA190542 AW328142 AA306992 AA383598 AW293005 BE254231 BE018829 BE207008 AW247508 AW328143 AI888789 AI953071 BE617691 AW245093 AW079089 AI825722 AA102386 AA621823 AA486490 AI286316 AI638634 BE551712 N62469 AA903777 AA991450 AI056209 AA079223 AA707656 AA442421 R94934 AA639374 BE613108 AA056180 AA046427 |
| 324988 | 22162_1 | AK001379 AK001411 AW795711 T06997 AA287540 AA354538 AW957773 AI632268 AI651003 AI689650 AI809332 AW304483 AI805269 AA278506 AA862381 AA287875 AW628545 AI085761 AW025965 AI658615 AW628879 AW139496 AI214278 AA902745 AA991679 BE540102 AW593658 AI745602 AA744687 AI285441 AA807089 AI218314 AA721449 AI202987 AA432129 AI285502 AI281462 AA731319 BE082573 |
| 317777 | 10778_1 | NM_014785 D87447 BE263434 AA400883 AW407881 AI160515 N51680 AW583855 AA844421 AI274202 BE019777 AW998722 AI420586 AI612828 AI765601 AW015434 AI955032 AL133780 AA928914 BE548610 D31490 AL048391 BE552460 AI796059 AW173479 AA341631 AI934611 AI274836 AA373732 AA525028 AI571392 AI392971 AI738589 AI953828 AI061125 AW772523 AI361106 AW883276 R45884 AI356652 AW236104 AI873069 F15747 AI362185 AI360910 AI419573 AA974612 AI143525 AA995238 AI214649 AI591399 BE170850 BE163405 |
| 311137 | 800082_1 | AW207582 AI962335 AI632618 BE504857 |
| 310557 | 681858_1 | AI431798 AW418836 AI307777 BE274992 AI910729 AW751094 |
| 310598 | 690468_1 | AI439136 AI338013 AW204095 AI910519 AW977064 |
| 302767 | 1623718_1 | H94900 N39891 |
| 319080 | 180943_1 | AW967646 AA251431 Z45131 R20502 AI911796 AA234020 AA232982 H29165 |
| 318486 | 810943_1 | T23514 AI655785 |
| 317850 | 363835_1 | AI681545 AI951714 AI570397 AW873588 AA836396 AI359986 AI499790 AA773477 AI951615 T07547 AW304709 AF114041 BE176629 Z44580 T30422 T32690 AW953065 H10602 |
| 311251 | 810826_1 | AI655662 AW014514 AI686482 |
| 319109 | 198008_1 | Z45662 AA282123 H10149 AA505157 W92511 N78341 |
| 318538 | 13064_1 | AI750979 AI690164 AI807700 AI681067 N35860 N28625 R98369 R53158 R56501 AI750292 AA319987 BE122902 AA094362 T36150 Z30223 T34600 H06612 F13507 BE615062 AA332035 T35478 R58469 T35542 AA128518 R58400 H04119 AA329969 AI435429 N31656 AA151326 AA151327 T80239 AF070648 H79097 AA748115 C02997 AA385870 H25456 H48665 H81253 R54555 AA083618 R48014 R48397 BE615503 BE615487 AA328258 BE531052 N45373 W06934 W45683 AA444383 AW369052 AA493867 W93600 R93256 R83439 W67400 AA461434 AA493673 W94180 AA054776 AA151260 AA558674 C03776 C02719 C02874 R32667 W30825 AA463399 AA429967 AA502956 AA973501 C02309 AA037446 H44694 T60011 C05126 AL133639 H96749 AA305810 AA151524 AA304647 AA148902 AA730403 AA303439 T81041 W40357 AA375204 BE122903 R77190 R77048 AF074993 AA034379 R81032 R35976 AW798160 AI807741 AI985921 D61845 C04231 AI709069 AW340655 AI089307 AW072394 W45684 AA054588 AI660784 AI128025 AW006516 AW298028 AA034460 AW166802 AA080891 AI336397 AA149439 N75560 AA578138 AA972868 AA776324 AA662526 AI750291 AI750980 AA461117 AA878326 AA593225 N90728 AA669385 AA373803 AA148903 AI608786 AA034380 AI075666 AI189847 W80762 AI589277 AI983086 AI022289 AI366800 AA484102 AW591160 AA460459 AA618356 AA487560 H07122 N49761 W67254 R98960 H78292 N93866 AW957498 AA618362 AA483979 AA730610 T57690 AA993371 T91713 AA905610 H96215 R76885 AI095319 AA861847 R07587 AI086979 R60588 N32062 AA988759 AA708682 R07495 AA487124 R56108 AI190163 AW514077 AA775533 AJ243236 R98370 H81592 R54556 AW079084 H48499 R36343 AA971353 R38791 T57730 H22262 AI352244 AA613398 R48294 R38927 R53070 AA780476 AA582771 AA502935 T99237 BE542934 N25593 AA773154 AA187193 AA487842 AA719934 F10690 AA320214 AI240597 D61759 AI242923 AA861756 D62069 R80931 AI572686 AI928905 AI432490 AI678565 N24039 R93163 AW952168 AI471081 AW589311 T70254 R28483 AA679545 T96567 R83340 AA779202 T96568 D29206 AA044994 AA557588 AA722546 AA911537 H03416 T63767 AA513897 BE616845 BE615451 BE531169 BE541857 AA669217 T77611 T63803 R98872 H78291 T92479 R07586 R07548 T99281 N98435 AI039878 R36433 R47910 AA652135 AA652076 T80566 |
| 302892 | 43416_1 | AW176909 BE079271 N58545 C05823 C05663 H01168 AW898176 AA872625 AW882394 AA992650 N30218 AI092549 AI343862 AI952705 AI378118 N94915 H92093 AI222138 N94913 H24672 AA232915 AA622464 BE085972 AI275049 R01404 AA553341 AA279297 AI186225 AA670281 AI360384 N92762 AI365417 AA911285 R97413 R06776 N49141 AI274292 N25608 BE004159 R91372 W94420 AI248933 BE166276 |

TABLE 1B-continued

| Pkey | CAT Number | Accessions |
|---|---|---|
| | | AI766590 AI084587 AW628148 AA572751 AW004720 AI246152 AI142874 BE000402 AI199528 AI766610 W23594 AA233333 AW175584 AI347817 AI186388 AA493414 AI761134 BE166252 AI041327 AA844070 AI565852 AW661749 AW751778 N54450 BE002066 AA632179 R21875 BE002042 BE001776 AW016633 AI220671 AW812516 AW812517 H97525 AA679008 AL050210 AI936057 AA065090 AA463254 C05794 AI264499 AI766630 R30816 AI472739 Z40297 AA989267 AA825919 AW009737 BE044883 AA837303 AW275901 AW007967 AI884309 AI808852 AW304265 AW150227 AI872036 AI830999 AW611846 AW264260 AI860579 AI703086 AI564360 AW001961 AI632881 AI564288 AW081856 AW591657 AW236335 AI557412 F35641 AI672381 AA384893 F22489 AI537564 AI521808 AW751780 AW176875 AW581639 |
| 318541 | 1567176_1 | T30290 Z43131 H15301 |
| 317916 | 540437_1 | AI565071 AI521958 AA993566 AI864217 |
| 317939 | 542313_1 | AI986208 AA995791 AW169341 |
| 303502 | 325188_1 | BE174240 AA488528 AL042253 |
| 303506 | 74515_2 | AA340605 AW962461 AI559190 AI076929 AA716150 AI027322 AI927434 AA722847 AA577045 AA533247 AA559906 AI916650 AW167602 AI671915 AI973046 |
| 310787 | 723998_1 | AW262580 AI381876 AI926355 |
| 302943 | 44295_1 | AI581344 AA757285 AW102885 AA865734 AI355317 U31738 |
| 318617 | 13858_1 | AW247252 AA381085 AA381079 N91995 AA296473 BE382459 AA296110 AW673101 AA315735 AA311617 AA326750 NM_000270 AA346143 X00737 BE266250 BE265212 AA376804 AW403290 T95231 T47963 M13953 H82039 AA279899 AA627997 N76320 N99527 BE392764 H37842 AA457308 AW469547 AA724143 H83220 AA319496 W86334 W30892 R89169 R99427 H47286 N41854 AA348094 AA045089 R63016 AI922219 AI024906 AI096488 AW798134 BE270964 N73184 AW798022 AI885005 AA194872 AI452544 N90489 H72411 AA282427 AA430735 R68963 R22453 H13890 AW129369 H70385 AW519082 AW467320 AA345018 AA582183 AI901789 R65918 BE047457 N30611 AI979189 AI280889 AW883321 R66531 AW273191 AW572406 AW673735 AI285845 AW571872 AI675927 AW190879 AI421990 AW662151 H37794 AA954388 AI140048 AA430382 AI204151 AW247864 AA559099 AA548276 AI431420 H64795 AI149466 AA772669 AA724168 AA694388 AA281952 AA779925 AA234760 W86290 AA913603 AW511745 AA814922 AI500697 AA835040 T47964 AA975804 R98710 H53998 N70252 AI077604 R98084 AI597614 AW250171 H69268 AA970746 AA972548 AI377116 R62962 H16737 AA731329 R66532 AI818832 N54354 N71567 H81944 T95122 W86463 AA437095 AI431999 AI915724 N63851 AA457307 AI674743 N64444 AA211475 H72853 AI799146 R99335 H60413 AA156105 AI269937 H64029 H89728 R65819 AI873318 AW470496 AI735713 H82987 C02447 AI478666 T27651 AI699770 AW025156 N69225 AA953577 AI459856 H69719 AI424691 R22404 H13843 AI873796 N70898 AI336002 AI420854 AA346142 AA541792 AI000814 AI828348 AA045090 N90434 T51257 BE311761 AA890720 BE538521 BE262057 W20095 AA781606 R68964 H16845 AI984717 AW966160 AI708083 |
| 302970 | 1027688_1 | W05608 AW118352 AW196215 |
| 319289 | 45090_1 | AA037534 N39809 N41794 W07304 N41487 H83369 F12072 AW387905 AV654341 AW615236 AA174046 N31438 |
| 312073 | 174687_1 | AA682393 T79422 AI819905 AW593218 AA218967 AI961481 T91861 AW935990 R85689 T79508 T84729 AW957463 AA373019 AW839268 AI244432 BE066829 |
| 311422 | 270835_1 | F00677 AW853896 AW361342 AA383426 AW966402 BE180950 AW841639 AW242125 AA806114 BE301605 AI249498 BE219291 AI560615 AI274667 AI972210 Z28533 |
| 311465 | 857586_1 | AI758660 AI758665 AW020810 |
| 303654 | 64558_1 | BE246743 AA436942 AW024744 AW242177 AA975476 AW385185 R07536 R73462 AV654529 T57442 AI399986 R50073 R48743 AI769689 AI863005 AA317806 AI678000 AW189963 AI986207 AW471273 R73463 AI335104 AI590161 AI469257 AI954604 H21954 T25141 AA856793 R50074 AI708253 AI217945 AI224459 AA505828 AI521061 AI651948 AI919161 AI766992 AI287290 AI868191 AW956075 AA335980 AA335672 AI424272 AW572622 AI500040 AI553687 AI932452 AW196184 R48744 |
| 310884 | 740029_1 | AW014684 AW779935 AI434594 AW275353 |
| 312105 | 413562_1 | T81819 AW393709 AA703541 AW370185 |
| 312108 | 202153_1 | T82331 AA973625 H57392 AA953717 AI761465 AA290850 AW270500 AI127126 AW293000 AI298354 |
| 312197 | 280163_1 | T96203 AA405343 T96121 |
| 311587 | 16193_2 | AI828254 AW190862 AW102765 AW835668 |
| 311598 | 903700_1 | AW023595 AW129233 BE350312 AI865094 |
| 310955 | 715902_1 | AI476732 AI560210 BE049559 AW118381 AI859875 AI371924 |
| 319408 | 301280_1 | AA448090 R01572 |
| 303762 | 9344_1 | AF034799 NM_003625 AI002917 AA325780 N45544 H08934 |
| 318814 | 1702210_1 | W07361 R36748 Z42619 R19489 R18800 |

TABLE 1B-continued

| Pkey | CAT Number | Accessions |
|---|---|---|
| 320099 | 21462_1 | AW411307 AA386114 AF081535 AJ223728 T31599 AF053074 NM_003504 T34235 AF062495 AA353437 AW674908 AA356690 BE255146 AA355389 BE087589 BE087469 AI369688 AW063594 AW063720 AW081615 AI768340 AW674262 AI768943 AA700904 AW589431 BE501602 AW339992 AI220589 AA576429 AI248334 AA654267 AI174517 H55633 AI953232 AI824844 AW768868 AI783560 AA973202 AA342014 H55654 AI458783 BE260534 BE262473 |
| 312226 | 220393_1 | AA315703 T99503 AI796815 AI049875 |
| 312240 | 576434_1 | R36475 R28628 AI080520 R75900 R67518 H01236 R79817 R67517 R32555 |
| 312292 | 669283_1 | AW450103 AW451893 H15073 AI286250 AI283763 |
| 303820 | 27494_1 | AB037858 AW888417 BE168022 BE297137 AI205125 BE003963 AW965680 AA349466 AA351821 AI492558 BE146202 D31580 AK001199 R45887 AI372674 AI755276 BE168407 AW840238 AA160849 AA027021 T18598 AA161281 AA143489 AI372673 D80801 AI870013 AI460100 AA158252 AI971206 AW071873 AI431911 AI493768 AI439206 AI376927 AI038534 AA678831 AI418906 AI356122 AA789304 AW150270 AI499098 T98883 AA349465 AA330631 D80800 AA158399 AA350488 AI334361 AW338483 AA351820 AA301787 AW753882 AI926390 AA702382 AA376185 AI084962 AA355373 AA102488 AA100840 AA325211 AA425180 BE392668 H50462 AA367255 N94717 AA037160 W89039 AI096627 AI750041 AA102418 AI589918 AA313505 AW951928 AW082735 AW189862 AI567485 AI590590 AI494149 AI422826 AW082999 AA043408 AA043409 AI363488 AW104306 AA877117 AA476207 AI811883 AW026405 H63354 AI992015 W88956 AI190217 AI738539 AI361483 N77542 N62261 AI359937 H41345 AA156068 AA102489 AW339965 AW083453 BE139062 AI937868 AW075493 AA654017 AI094530 AA548969 AI686221 AI961671 AI570099 AA904590 AA631107 AW770217 AW471322 W88756 AW134571 AL042199 |
| 312313 | 424162_1 | AW293341 AA807690 AA736918 AA743825 AA905001 R31408 AW173322 AA922276 AA780620 AA724578 AW976496 R71334 |
| 312391 | 394292_1 | R43707 AA780139 AI051417 AI628657 AI674282 AW974521 AA651778 |
| 312405 | 765247_1 | AI523875 R45782 R45781 |
| 313070 | 734749_1 | AI422023 AI624442 N47903 |
| 313097 | 820456_1 | AI676164 AI972427 N52328 N75098 |
| 313166 | 177700_1 | AI801098 AA910047 N66834 |
| 313179 | 513995_1 | AA927670 AI076101 N69351 AW196229 |
| 311928 | 251800_1 | T62216 AA357503 AW953611 AW024798 |
| 319808 | 7069_3 | T58960 AA609180 AA621130 AI927236 AA431075 |
| 321023 | 493429_1 | AW294316 AA977516 AW079380 AI972654 AI913755 AI864320 AI380443 AA884643 AI538592 AI685770 AI240179 H25135 |
| 321024 | 126702_1 | AW246216 BE245357 BE247413 AI264325 AI809116 AI198454 AI199757 AI369902 AW136723 AI553879 AI857438 AI500226 AI199726 AA994567 AI536961 AI560412 AW614026 AI720184 AA931957 |
| 319897 | 200730_1 | N46574 AA286737 BE503575 AW613553 H81831 AI458626 T76948 N40525 N26680 |
| 312600 | 88181_1 | AW970985 H38094 AA019335 H86102 AA516342 |
| 313280 | 229754_1 | AW960454 AI285537 U51706 AA700954 AA702720 AA327833 |
| 312689 | 843717_1 | AW450461 AI720166 R85744 D81222 |
| 319926 | 37979_2 | AI820719 AI273515 AW592687 AI263784 AI351926 R46866 |
| 320574 | 25769_1 | AL049443 C01145 AI478278 AI420528 |
| 320654 | 430904_1 | AI160015 AW015237 AA831294 AA749122 AA834580 AA741126 AA946695 AA825481 AI807850 AI419758 AA904637 AW665981 AI911425 AA931308 N73678 AI244699 N48346 AI887929 AW976264 AW263086 AI654504 AW593142 R57253 AW387830 AW387791 AW809206 AW809231 |
| 312800 | 412652_1 | AI248774 H73944 H70813 AA702493 |
| 312803 | 404357_1 | AA677934 AI080992 H71242 |
| 320683 | 234846_1 | AA334511 AW250609 BE265237 AI792758 R59291 |
| 313475 | 83840_1 | AA010200 AA926774 AW316970 AA928372 AW371245 |
| 320697 | 341050_1 | N62937 N63008 N63029 N63016 N63034 R63876 R62588 AA525236 |
| 312821 | 410071_1 | AA699325 AI057455 H75866 |
| 321325 | 28266_1 | AB033100 AA347036 BE260325 AW961669 AL047207 AA347037 AI766894 AA601045 AI559897 AW139033 AW274622 AW172884 AW089070 AA804340 AW798925 |
| 314146 | 183043_1 | AI827237 AW294348 AI682922 AI306704 AA460256 AW151460 AI804404 AA908484 AI553689 AA235344 AI016721 |
| 314171 | 185602_1 | AI821895 AI732057 AA480610 AA661559 AA243967 AW188132 AA244048 AI821242 AI820944 AA244056 AA502471 |

TABLE 1B-continued

| Pkey | CAT Number | Accessions |
|---|---|---|
| 313552 | 110315_1 | AI889208 AW022052 AA525256 AW016601 AW015966 AI802311 AW052192 AA130588 AI571862 AW007997 R51785 AA633153 T55272 H46904 AW070863 AW772654 AI597967 AA947350 T87529 AA629377 AW467155 AI768796 AI347474 N90095 AI347598 R08750 BE217782 N93763 AI536969 AA169871 AI566026 AA169356 AI494412 AA063623 AW168998 AI825776 R09172 AI434882 AI903041 T67439 H66517 R91140 H66322 H42318 |
| 320771 | 210125_1 | R74441 W04256 R86080 AI793266 AI991774 BE327552 AI807726 AW770471 BE326537 AI218667 AI492388 AI241532 AA301750 AI209012 AA886528 N70309 AW582776 |
| 320779 | 74700_2 | AA815354 AW452856 AI972288 AI659767 AI833067 |
| 320787 | 500789_1 | AW088363 R78323 AW628638 AA903902 |
| 312939 | 246486_1 | AA495930 AI470890 H97831 AA350358 BE166712 |
| 329365 | c_x_hs | |
| 336662 | CH22_4138FG_41_1_ | |
| 336684 | CH22_4167FG_46_1_ | |
| 336721 | CH22_4244FG_83_17_ | |
| 338038 | CH22_6535FG___LINK_EM:AC00 | |
| 306999 | AI138628 | |
| 338316 | CH22_6944FG___LINK_EM:AC00 | |
| 338561 | CH22_7294FG___LINK_EM:AC00 | |
| 338562 | CH22_7295FG___LINK_EM:AC00 | |
| 333124 | CH22_353FG_81_8_LINK_EM:A | |
| 333135 | CH22_364FG_83_11_LINK_EM: | |
| 333137 | CH22_366FG_83_13_LINK_EM: | |
| 333138 | CH22_367FG_83_15_LINK_EM: | |
| 333139 | CH22_368FG_83_16_LINK_EM: | |
| 303187 | 487417_1 | AA115962 AA078794 |
| 326213 | c17_hs | |
| 333516 | CH22_772FG_173_1_LINK_EM: | |
| 333517 | CH22_773FG_173_2_LINK_EM: | |
| 333743 | CH22_1009FG_264_1_LINK_EM | |
| 333795 | CH22_1063FG_275_1_LINK_EM | |
| 333796 | CH22_1065FG_275_3_LINK_EM | |
| 335044 | CH22_2367FG_480_1_LINK_EM | |
| 333808 | CH22_1077FG_279_2_LINK_EM | |
| 333809 | CH22_1078FG_280_2_LINK_EM | |
| 333845 | CH22_1114FG_290_3_LINK_EM | |
| 333849 | CH22_1118FG_290_8_LINK_EM | |
| 335149 | CH22_2484FG_499_5_LINK_EM | |
| 305096 | AA642964 | |
| 335289 | CH22_2631FG_527_2_LINK_EM | |
| 335290 | CH22_2632FG_527_3_LINK_EM | |
| 335293 | CH22_2635FG_527_6_LINK_EM | |
| 326816 | c20_hs | |
| 303951 | AW475081 | |
| 305232 | AA670052 | |
| 328164 | c_6_hs | |
| 305503 | AA759177 | |
| 335682 | CH22_3043FG_595_2_LINK_EM | |
| 305612 | AA782347 | |
| 335753 | CH22_3120FG_604_2_LINK_EM | |
| 335755 | CH22_3122FG_604_4_LINK_EM | |
| 335756 | CH22_3123FG_604_5_LINK_EM | |

TABLE 1B-continued

| Pkey | CAT Number | Accessions |
|---|---|---|
| 335809 | CH22__3181FG__617__6__LINK__EM | |
| 335810 | CH22__3182FG__617__7__LINK__EM | |
| 335824 | CH22__3197FG__619__11__LINK__E | |
| 328648 | c__7__hs | |
| 337182 | CH22__5204FG__570__2__ | |
| 307111 | AI174528 | |
| 330032 | c16__p2 | |
| 330033 | c16__p2 | |
| 337603 | CH22__5896FG__LINK__C20H12. | |
| 337674 | CH22__6005FG__LINK__EM:AC00 | |
| 337675 | CH22__6006FG__LINK__EM:AC00 | |
| 337755 | CH22__6105FG__LINK__EM:AC00 | |
| 339186 | CH22__8120FG__LINK__DA59H18 | |
| 309390 | AW080585 | |
| 309575 | AW168096 | |
| 332792 | CH22__8FG__3__2__LINK__C4G1.GE | |
| 334101 | CH22__1379FG__327__59__LINK__E | |
| 304049 | T58155 | |
| 334221 | CH22__1504FG__360__1__LINK__EM | |
| 334222 | CH22__1506FG__360__3__LINK__EM | |
| 334282 | CH22__1571FG__369__12__LINK__E | |
| 302910 | 386182__1 | N77976 W03184 |
| 325889 | c16__hs | |
| 327110 | c21__hs | |
| 304263 | AA062837 | |
| 304275 | AA070605 | |
| 304309 | AA112147 | |
| 334502 | CH22__1802FG__397__18__LINK__E | |
| 334578 | CH22__1883FG__406__1__LINK__EM | |
| 304521 | AA464716 | |
| 334616 | CH22__1923FG__411__15__LINK__E | |
| 304541 | AA482561 | |
| 336054 | CH22__3440FG__683__3__LINK__DJ | |
| 304735 | AA576453 | |
| 334891 | CH22__2208FG__452__5__LINK__EM | |
| 334899 | CH22__2216FG__452__13__LINK__E | |
| 306011 | AA896986 | |
| 334900 | CH22__2217FG__452__14__LINK__E | |
| 334902 | CH22__2219FG__452__16__LINK__E | |
| 334905 | CH22__2222FG__452__20__LINK__E | |
| 334906 | CH22__2223FG__452__21__LINK__E | |
| 334951 | CH22__2272FG__465__20__LINK__E | |
| 327821 | c__5__hs | |
| 330415 | 13440__1 | D83777 NM__014766 AA333003 BE004425 AL119670 AA323656 BE296006 AL118935 BE256656 AA374227 BE271472 BE296326 AW583557 AW583626 N40409 AW608433 AA324811 AA190746 AW949591 BE000350 AA350275 BE392178 AA430618 AA348536 AA366634 AW818371 AA317886 BE072912 BE072917 AA323887 W38798 AA322171 W46661 AA036818 AA309827 AW583615 AA378262 W25430 H97457 N42389 AA169692 AA364115 H42180 AA081704 AA775719 AI185130 N75656 AW006117 AA984601 AI421198 AA181467 AW511204 AA181639 N64808 AI937715 AA169219 AA088783 AA548717 AW238470 AW662116 AW166218 D51086 AI867027 AA729243 AI923221 AI357913 AI375759 AA987267 AA773569 AW500216 AA191460 AA633234 T34787 AA527048 C75239 N93172 AW129534 N33415 AJ239459 BE328344 AW418717 AI308847 H42999 N24779 AA621221 AI497806 AI418855 AW418718 AI089499 AI332576 AI039047 AW583402 AA430500 |

TABLE 1B-continued

| Pkey | CAT Number | Accessions |
| --- | --- | --- |
| | | AI271939 AI798736 AA612803 AW169919 AI183542 AA843085 C05884 C75127 AW044680 T03756 AW583349 AA082053 AA877439 AI298253 AA010549 AW168981 AI372978 AI039490 AI311909 AI313396 W81554 AI582863 AI566169 AA010548 AA748398 AI092355 AI074928 AA862701 W46570 AI570312 AA582306 AI082069 AI452384 AI498938 AA953378 AA910381 AA987271 AW664437 AW583393 T33340 H50310 AI361354 T15902 AI280310 AW583343 T15989 AA995343 AA718958 AI277293 AI468250 AI860396 AI951938 AA018659 AI590916 AI383915 AI382782 AA844109 AI016130 AA812632 AC004912 AI091734 AW893561 AW893559 AA984413 AA484993 AA491098 AW504790 AA018658 AW902844 T09170 |
| 330506 | 4584_1 | AI130740 AI131523 AW016460 N27986 M61906 AL047197 D59003 N21330 AA318688 AA318491 AA075494 AA091104 F05655 W26855 F05451 AA349939 T78213 AA343626 R19868 R14467 AA349896 AA354917 N87834 AW369592 AW369698 AW369619 T86645 T79490 AW291079 R12202 R57144 R58203 AA972249 AA370777 AW894884 AA334448 AW591414 AW444493 H42359 H42094 AI921874 AI446498 H22289 AI679268 R68159 AW080204 N94253 AI569748 AA196023 T29126 AW951130 AW242337 AW131735 AA678725 AI679842 AW131714 T79404 AI683195 AW172868 AW072767 AI491992 H41227 AI114698 AW440607 AI569428 R40336 AI823887 T86837 AI799345 R45961 AI925160 H95622 H95629 H95628 AI363016 BE245861 AI038569 AI493526 N69643 R40985 AW516092 T15783 H43128 N68131 AI362599 R68112 F01911 R54050 H22253 F01712 AA055113 AI934473 H46343 AW270067 AI334281 AI937186 AA713487 AA723162 AA810839 H46272 AA055114 AI190793 Z44767 F11517 F11518 AI630833 H19191 AA657810 AI560484 AA309103 AW952385 AW630519 AW662985 W81164 AI124626 Z41962 R20606 BE018740 AI491998 AI540623 |
| 330541 | 33584_2 | NM_002038 U22970 U22970 BE407364 |
| 330601 | 17051_1 | U90916 Z43999 R11903 R35836 AI002816 AW953298 AW499839 AW499842 BE612866 R52743 R12215 AV652701 N92044 W86382 W87694 W01902 AW403961 AV651788 N45261 AV651755 AA370875 BE081705 AI003010 AW900132 BE081502 BE074256 AW138351 AA776585 AV658700 AW629228 N46668 AI289333 AA858365 AA702489 AW195744 AI827700 AA533051 AI885483 H11624 AA975525 AI979228 AI659992 AI359183 AI420739 AI554830 AI423186 AA132369 AI457832 R82659 AA564441 AI339778 R49546 AW512718 N39193 AI554295 N68831 AW337784 AI095041 AI687203 N71007 AI274126 AI470999 AI621324 T33590 AI224462 AI468105 AA907448 AA424516 AA669297 BE164956 R44735 T15980 AA553897 Z39667 H88696 AI358248 F02927 R39937 T93875 AW591245 AA480284 H29820 AA772510 AA492079 N39224 AW591255 F03227 H88651 T25741 AI146573 AI869149 T30872 H64366 F06653 Z43605 R19934 H16349 H12134 BE242391 AV657794 AV657769 AV657422 AV651458 AV651476 AV651475 AV651936 T77196 |
| 330694 | 80816_1 | AI741617 R63241 AW085539 AL043992 AI265801 AA745252 AA765098 AI687211 H60519 AW189337 AI338215 AA469964 AW088916 R83278 N93819 AI436357 F09306 AA001546 AA865939 AW662082 AA904018 AA019806 R92394 H86093 H86068 F09624 AA829574 H67463 AW975945 AA420980 R63295 AW753877 W44970 AA746749 H51720 |
| 330706 | 8280_1 | AF097994 NM_016228 AA404282 AI798980 AW166135 AI219254 AI219351 AA059063 AI219062 AI799069 AA401238 AA434578 BE543192 AA333897 H12165 F11219 R06274 H72204 AW974068 AI819354 AI393635 AI560690 AI024796 AI580846 AI242427 AI393644 AW020098 R40205 AA568464 F08882 AA121140 AA059294 H92545 H72102 N74993 AW472959 |
| 330714 | 8276_1 | AA263143 NM_006479 AF006259 AA221023 BE244869 AA311615 AA307025 AW960332 AA356040 AA356154 AA626685 AW977244 AW864107 AI424788 AA730059 R78075 AW002924 AI961178 AA190203 AW974223 AA585449 AI435212 AI682005 BE464128 W86577 AI032099 AA968418 AI022750 AW418754 AA609817 AI951262 AI374767 BE046375 BE568801 AI086264 AA600301 AA577374 AA928747 AW592917 BE046813 AA232231 AW864160 |
| 330728 | 188037_1 | AI905520 R78058 AA250728 AI953914 AI332355 AI656637 N39605 AI419721 AI910726 AI278952 AI825136 AI187770 AI151140 BE245117 AI522210 AW050707 N49605 AI350645 AA976383 AA253432 R77725 |
| 330760 | 122430_2 | H04588 AW293409 AA448663 AA569143 AI856823 AA935374 T19666 T19667 D62239 |
| 330776 | 202879_1 | AW953805 AA651785 AI027526 AI022110 AA364304 N66168 AI669957 R68607 AA291713 R54971 AW971448 AW969070 AA736719 N98692 AA480126 AA912621 AW269453 H61262 AA504597 D25926 AA291817 R68606 AA291783 R14993 AI674879 AA504513 AA482095 H61266 |
| 330786 | 53973_3 | BE379594 AI192455 AL039862 AI744012 AI761735 AW243181 AI743687 AI928223 AI423022 AI627855 AI636059 AI651571 AW802044 AI826995 AI431733 AI539125 AA863056 AW270910 AI768930 AW008835 AW615183 AW591147 AI695294 AI672106 AA506358 AI308060 AA011556 AA962437 AI935488 BE219625 AI004356 AW151394 AI218466 N66178 AI419784 AW242519 AW946907 D60374 AA989263 AI698799 AA470460 AI824167 |
| 330814 | 85936_1 | AI955040 AA017064 AW151704 AA015730 AA054643 AW946327 BE088702 BE088898 BE088969 |
| 330824 | 11887_1 | AB037732 AW503898 AA215297 BE547488 AW177355 AA046224 AA361664 AA773328 AW512704 AI283330 AI307357 AI138263 AA046116 AI219874 AA315431 AW169999 AA492006 AW298002 AA043140 AA131781 AA292383 AA031721 AA027867 R31381 AW023352 AI686186 AW467416 AA493914 AA483019 AA483081 AA040871 AA558288 AW070397 AW572828 AA693439 AW206584 AA761354 AA907254 AI671019 BE221791 AI915828 AA744724 AA027815 AA131769 AA031641 AA837286 AA737401 AI765196 AW086076 AW873024 AI567164 AA744556 AA888910 AI572276 |

TABLE 1B-continued

| Pkey | CAT Number | Accessions |
|---|---|---|
| 330859 | 118662_1 | AA082977 AA082955 AA082956 |
| 330867 | 28286_7 | AW978991 AA831014 AA825706 AW139028 AA081819 AA112247 |
| 331022 | 163104_1 | H03109 AA190569 R27719 R77038 R23789 N41571 N34588 R26033 T94741 AI110626 AF063500 W35141 AA236329 H15136 AW043845 N23362 AA682872 H03110 AI168530 N32346 T94740 AA236561 AA236235 N23955 R27720 N31614 AI814425 AI804857 AW590744 AI080155 N30796 AI341754 AI367163 AI272814 AI332944 AA193683 AI183993 AI183991 Z39979 F04878 AI868457 N26707 BE535358 R23737 AW449959 |
| 331028 | 770043_1 | AI539652 AW576543 AI800374 N48793 AW195209 AI969934 AI565252 C01574 R62583 BE468212 |
| 331046 | 143843_1 | N66563 R02024 |
| 331050 | 1335173_1 | BE007967 R66103 N68542 BE007971 |
| 331053 | 123927_1 | AI949841 AA092378 N70242 |
| 331131 | genbank_R54797 | R54797 |
| 331180 | 499249_1 | R44692 AI989555 AI990018 AI678955 AI479353 AI453159 AI424114 AI865174 AA897714 T32446 T16534 AA928817 D63033 AW952921 |
| 331278 | 685_8 | AA071383 AA071369 AA083800 AA075976 AA116006 AA075667 AA085142 AA085087 AA076496 AA129187 AA122171 AA076367 AA074080 AA085088 AA084663 AA085094 AA112092 AA075668 AA122253 AA122199 AA071140 |
| 331283 | 141490_1 | AA467736 AA135210 AW968166 AA467804 |
| 331306 | 12044_1 | AF102546 AL079278 NM_004392 AJ005670 AW779087 AI003686 AW579053 AW862365 AW604900 AA909203 AF069509 AK001000 T11719 R11546 AA219450 AW772082 AW592446 AW664022 AI375131 AA677921 AI002524 AI355380 BE549771 AI220096 D80570 AA219327 AA252130 R19271 AI522192 AA252079 AI498677 AI680922 AA911675 R25458 AI201756 AI741454 BE550851 AW204718 AI204557 AI936340 AI002220 AW135139 R26283 AI240507 R74591 |
| 331313 | 16353_2 | AA761094 H41336 AI902687 AI807720 AW510795 AI806133 AW005818 BE327107 AW005636 AI630970 BE550777 AI436308 AI287598 AI188425 AI273679 AI202140 AA255824 AA701863 AA233858 AA252898 AW090104 AW474094 AW206913 AW960534 N86020 H41583 AA303374 AA256521 AA585335 AI797149 AL120920 AA490520 AA720591 AA236827 AA760777 AA515110 AI188075 AA680139 AA677413 W93115 AA282549 AA249038 |
| 331336 | genbank_AA287450 | AA287450 |
| 331337 | 169430_1 | N74392 N74444 AA287662 AA205513 AA287862 W02641 W03156 |
| 331341 | 172787_1 | BE541042 AW069774 AW664160 AW189935 R27296 AI872737 H04753 R67040 AA687583 R78627 AA214158 W02221 AA303125 AI865269 R46578 AI571977 |
| 331353 | 191360_2 | AA953006 AI276403 AI277578 AA256327 AA406577 AA479917 |
| 331363 | 18581_1 | AW582256 AW956284 AF038451 NM_006408 AA316115 AA315629 AW369360 AA314225 AF007791 AA421527 BE072059 AI817063 AW194118 AW192785 AI075324 AA298537 AI634717 AI380637 AW151674 AI888294 AW190856 AW364247 AI080640 AW152548 AW002338 AW614754 AI445913 AI828325 AA573742 AI436796 AA909945 AI735767 AW304001 AI475938 AW303846 AA582017 BE076995 BE049240 AI678847 AW471069 AI720013 AW951790 AI888914 AW272720 AI801054 AA582851 AW073291 AA583091 AA315049 AI828251 AI801784 AI805627 AI025266 AA776960 AI559391 AI800431 AI800451 AA838499 AI378681 AA884931 AI242802 AW769127 AI184843 AA316874 AA565996 AA442829 AA593818 AW027843 AI249798 AI378390 AI277266 AA552670 AA970336 AI473626 AI275085 AA622524 AI610106 AI291994 AI476691 AA838482 AI925030 AI146786 AI582452 AI537173 AI040152 AI678427 AI469656 AI445130 AI916480 AI285429 AW602019 AI358508 AA687567 AA421562 AA425142 AW190915 AA570785 AI888732 AA632103 AI924494 AW152169 AI891014 AA565444 AW191880 AW591300 AA581848 AI473553 AI675714 AA501945 AI685830 AI469613 AI933636 AI972701 AI972499 AI581525 AA526975 AI623264 AA639696 AA513297 AI400863 AW080588 AA558986 AI926128 AI537212 AI695291 AA327356 AA625485 AF088867 AA298527 T24475 AA476675 AA055880 AA314206 AA315408 AA316508 AA307697 AW844413 AA314052 AW370274 AW582421 AW364225 AI815198 AW166169 BE072073 AI675865 AA315613 AA426228 AA314146 AA437001 AA307795 AA316233 AA314372 AA316967 AA315724 AA313235 AW369331 AA244356 T86663 AW868072 |
| 331393 | 7091_1 | AW976438 AF227899 AL079586 AW242991 AA296993 AF083249 AA743290 AA082927 H38607 AA046204 AI458928 AA810515 AI985329 AW450239 AA279595 AI632699 AI091806 BE221365 AI130893 AA082926 AI017851 AI474175 AA669471 AA169631 AA248905 AL133594 H08612 AA247824 AA399016 AI268687 AA479433 BE467082 AA961159 AW890022 AW890015 AW899450 AW890140 AW890016 AI656542 AI656530 AI284462 AW590370 T61838 AA478729 AA047401 N53320 AA834839 AW264473 AW007865 AA249450 AA167427 AI365221 AI701000 AI680921 AA385375 AW954119 AI860823 C75362 AI492007 AI539819 AW014989 AW628976 AI473662 AW276150 AA047467 N67246 H08613 AI559629 AI811077 AI039475 AI431949 AA907555 AI915180 AW148492 AI242862 AI365222 BE018520 AA412178 BE302119 AI823337 AA905198 N83376 AI382420 AA776507 T94766 W67770 AW369401 AA262427 W84569 AW968527 R20183 AA485189 F06553 BE080982 AW995604 BE080849 BE080826 BE080978 AA167428 BE080830 AW995687 AA171673 AW995686 |

TABLE 1B-continued

| Pkey | CAT Number | Accessions |
|---|---|---|
| 331406 | 8041_1 | BE176893 BE176888 AA397686 AI620405 AI299697 AI702708 AA987446 AI693106 AW889017 AA442537 AI922509 AI653242 AW237517 AW418517 AA806072 AI968500 AI760938 AI537876 AI811401 AW244033 AL046630 AI143522 AW263905 AI985159 AI962850 AI202886 AW300419 AA251838 AA861778 AI025639 AA399033 AI924740 AI800259 AA179395 AA610064 AI865176 AI289921 AA565722 AW770029 AW439544 AI025969 AW380171 AW080913 AW749363 AA496833 R58228 H09840 AA836330 AA764813 AI352142 T31439 Z43462 F08407 H47178 AI114660 N48131 AI061591 N48117 BE167338 AW384456 T19719 R23036 AW384458 N38985 T19720 AA075344 AI671613 AW842474 BE550608 AA778899 AA279243 AA496875 AI888310 AI088077 AI493142 AI338275 AW872997 AI459760 AA909786 AI292044 AA136299 H09755 AA279929 AA279124 AI871819 AI924804 N38971 AI000293 AW022179 AA952968 R22931 AI244527 AI003708 Z39538 F04624 H47088 AF180425 W56074 AA287344 H96262 W19197 AA456123 W38634 AA428762 AA485167 W24739 AW368029 AA236691 BE075101 AA136180 AA075597 AI217101 R81770 AA410581 |
| 331432 | 193887_1 | AA262451 AA760878 H67704 AA748621 |
| 331442 | 48779_-2 | H77381 |
| 331492 | 11196_1 | AK001114 AI949698 AI694727 BE501500 AI436121 AI769868 AI298375 AA026113 AA723068 F13681 AA908961 AW821352 AA976618 AI814359 AW070254 AA933772 AW298059 AI829001 AW515661 AI346450 AW664032 AA909492 AA961461 N34017 AW371083 AA918350 AI346671 AI337550 T86138 AI128634 AI738898 AI738907 AA026199 AA089670 |
| 331517 | 288032_1 | AA765603 AI675581 AI355934 AW166822 AI566925 AA767454 AA814384 AA730044 AW070292 N48610 AI341862 AI683402 AA424064 N23063 N23090 N38898 AI627249 AW339549 AI281421 AA708329 AW976803 |
| 331661 | 452840_1 | W52448 W52773 AI201922 AA781389 AI651363 BE550487 AW236796 AW304858 AI695978 AI220182 |
| 331686 | 1153509_1 | AW474960 W88502 H70430 W86162 |
| 331919 | 300127_1 | AA446869 AI368257 BE550153 AI080424 AW590470 AI478438 H46178 AW975073 AI701561 AW204114 BE165640 AA658113 AI214533 AW206932 AW885560 AW607277 AA446983 R49782 |
| 332002 | 188158_1 | AI579909 AW967587 AA766314 AW173502 AA831027 AA991192 AW407403 AW299333 AI356937 AA761270 AI979179 AW207045 AA482009 AW070877 AA280294 AW469832 AA250879 AA251072 |
| 332043 | 262097_1 | AA371307 AW968802 AA988769 AA642428 AA490831 W96347 AA649036 |
| 332120 | 374423_1 | AA609684 AA758732 |
| 332256 | 349165_1 | AW975028 AA551969 AA644028 AA689303 AI220334 AI220090 AI925480 N66393 |
| 332265 | 1028361_1 | AW770320 AW119114 D61961 N74375 N74427 |
| 332314 | 477192_1 | R41396 T25915 H23454 AA846250 H42125 D62549 H18484 C00804 AI446466 AW206738 AI445643 T25862 AI339005 |
| 332340 | 22951_1 | AP000692 NM_005128 AJ237839 R82151 AB023150 AW410488 AJ003273 AW379450 AA322182 R82140 AJ001857 BE004377 AW083855 AI096738 AW070676 AA678924 AW085802 W15495 BE551040 AI699147 AI510780 R82143 R82122 |
| 332386 | 399_1 | NM_000481 D14686 D13811 AU076448 BE293629 BE305090 BE250035 AA341258 F11299 F07978 AI129601 N85119 W79101 C18828 R09579 AW850108 N78273 AW950618 H79161 BE008484 AI081517 AA534975 AI290815 AA741122 AA921395 AW591508 AI885347 AI348172 N59532 W79815 AA947150 AW074248 AW751377 AI057053 AI346712 AI193862 H85887 AA983969 AA804465 AA886299 AI217497 AI351816 F08959 AA503087 AA993107 F04230 AA550742 AA962122 AA969722 AI625176 T28574 AI767567 |
| 332397 | 35955_1 | AB027249 AF237709 BE245643 AW403476 AB027250 AF189722 AA353579 BE537775 W25389 AW962279 AW818197 AA449542 AA448898 AW974523 AW195611 AI393315 AI738792 AW665895 AW574679 AA913471 AA651780 AA737663 AI015407 AI366737 AI285359 BE245537 AA740847 AW513628 AI278471 AA405512 AI955022 AI276896 AI932328 AA971676 AI002631 AW193686 AW118095 AI969593 BE466775 AI375878 AI911763 AW269502 AA476576 AA768652 AI300231 AI216689 AI287319 |
| 332430 | 53900_1 | H25350 H28544 AI955873 N29952 N29938 R12730 AA229527 H25302 AA854239 AW051288 AA598738 H62306 AI337901 AI056386 T18606 H82372 AI761586 AI889010 AW043582 AI765252 AA620587 AI190510 AI494128 AI161119 AI457908 AI420691 AW236132 AI917195 AI949791 AI433283 AI146385 AI074325 H62210 AA846154 AI344715 AI982957 AA524256 R39782 AI360821 AI124983 AA723581 AI289068 AW137304 AW073116 W37495 AI335838 AL121074 AW264699 AA865259 AI089458 AA782578 AA788618 AA595002 AI167549 W07131 AL120665 |
| 332530 | 2356_1 | M31669 M31682 M13437 AW370612 F00759 AI659282 W44452 AA600841 W44338 AA608807 AW973553 AW973542 AA505620 AI458719 AA936480 AA973451 T29876 AA577032 AI874161 AA670038 AA469911 AW006085 AI693790 AA872040 BE467580 BE467714 BE467700 AW971179 AA431428 AA938692 AA416873 AA493619 AI671596 AW590794 AW016444 AI971108 BE077433 C02533 AA593753 |
| 332567 | 8509_1 | AW939251 NM_005252 AU076596 V01512 V01512 AW579056 AA249247 AI590359 AW510478 AW518282 BE046054 AW874080 AI268596 AA996237 AI695592 AI244117 AA290764 AA401957 AA505878 AA428304 W74018 W74016 AA040944 AI272071 AA745909 AA620979 AA019816 AI245094 AW009706 AA662536 AW024264 AI268601 AA932024 AW513222 AW024169 AI659705 AA932526 AA975329 AI567603 AI889320 AA514238 AA020837 AI623966 AA843677 AA477453 AA496353 AW372625 AV656426 K00650 W96348 N62388 R95977 AA434270 AI093633 T27639 AW960245 AW881177 R15253 N36936 F07701 AA319315 AA337290 AA284642 AA344052 F05184 AA351062 AA378451 AW794233 AW884380 N36951 R49879 AB022276 AA300350 AW839435 AW191708 BE220350 AA280404 AA485546 AW794235 AV654223 |

TABLE 1B-continued

| Pkey | CAT Number | Accessions |
|---|---|---|
| | | AW838891 AA295986 N72823 AA335648 AA371089 AW845414 H63166 R12840 AA379680 AA477579 R13148 H71003 H71015 AA362156 AW750674 AW845415 AA366924 AW608044 AI570388 R31511 R33906 R33921 AW663022 AW360985 AI207838 AW607239 AI672451 AI573282 AW794752 AA370328 AW998896 AW797239 AW998912 AW794742 AI954543 AI810067 AW073373 AA370325 AW195330 C18106 AW998736 R79476 AA429721 AI891081 AI381534 AW022137 AW020000 AI630329 N99428 AI870222 AI971257 AI922196 AI857753 AW579397 D56749 AI925005 AI685727 AW805573 AI982678 AI784604 AI005625 AW877772 AI634947 AI950829 AA493243 BE166086 AI801820 AI925643 AI627992 AW316704 AI261318 D57757 AA887178 AW770406 AI972075 AI222254 AI675794 D58060 AI701954 D58166 AI799500 AW805669 AW276098 AW874253 AI962991 AI248184 AW996924 AI017462 AW022260 AI885957 BE176841 AA878863 AI697419 AW662094 AI479529 BE177025 D57403 AA507952 AW664593 AW800998 AI985773 AA566089 AA442759 AI624670 AI460284 AI800205 AI537788 AI537593 AI244382 AA583463 AA922678 AA864382 AI610837 D58070 AA844283 AA947992 N73801 AI453821 D58184 AI678887 AW243755 AA746085 D57742 AA757380 R44148 AA496403 BE180303 AW363528 BE006616 D57395 AW805507 AW805511 AA617991 AI373585 H30122 D57744 AW805501 D57691 D58148 AW873164 AW768483 D57601 AA777812 AA837997 BE180123 D57599 AA485387 AW022208 D58096 N67917 W95944 AW805506 D57518 D57990 AI074096 D56521 D58151 AA428720 D56648 D57778 AW805504 D57750 D58108 AW021706 D57449 D57041 D58277 D56935 AI356974 D57023 AA018712 H27631 D57851 D57514 D57268 D57468 AW805646 AI278945 D57323 D56986 D57539 D57829 D58078 AW805515 AI348684 D57772 R74449 BE041558 D56746 AW798485 D56640 AA985597 D56702 D56849 D56874 AW581419 AA470397 D57591 AW798984 T27640 N66497 D56803 AA618186 AW805647 D57945 N23726 D56637 N23730 D56992 BE176882 BE176839 BE176909 D56757 N68137 D56987 AI559806 AA631437 D57464 D56718 C17030 T29278 D57377 AW021936 AW118330 AA515358 D56610 AA494092 D56934 T97774 AI473546 R74350 R84834 AA579200 D56616 C03207 D57391 N52416 D56928 R79209 D56925 AA020879 D45546 AI858769 R20750 T09381 F01435 AW627906 D58202 AI933993 F01912 H27552 AA174191 T16515 AW023216 AA434146 H83387 AI346751 V01512 V01512 AA576407 AW365140 AA937471 BE174681 AI568829 AI274663 R85530 AL048225 H83388 AW798734 |
| 332577 | 89088_2 | AI826268 AW248872 H69511 AI748806 AW779557 AI992254 AI890377 AW151271 AI356374 AI634503 AA777065 AI590131 H37767 AI889058 H69512 AA046480 N27343 AI573008 AW130925 AI635838 AW594603 AW000790 AI208239 AI275835 AW090294 AA021587 AW273456 AA505726 AW469424 AI400222 AI025723 BE046148 AI128668 BE350462 AW302601 AI299977 AA284809 AI640358 AW470364 AI241794 AA650048 AW090027 H15377 AW615318 D60021 AI934336 AW118536 AI041281 AA614238 R85918 AW571741 AW516692 AW572232 AW515188 AI798585 AI392825 Z40518 AI869580 AA469975 AI537819 AI810684 AI701744 AI370410 BE383083 Z44676 BE002481 BE002532 AA456765 N44196 D60022 C14604 AA021099 AA284872 BE266647 AW249292 |
| 332640 | 4172_1 | BE568452 BE297396 AA449593 AW732490 AW069736 BE548667 AA207229 AF044588 NM_003981 BE268994 AW444578 AA471151 BE250747 AW732555 AA074582 BE336856 AW408764 AA191159 BE092129 AA310614 AW958677 AA312276 AW750027 AW750046 AW750032 AW750024 AA188893 AW750054 AW408409 AW750030 BE151875 AA478509 N58721 AA195614 H70079 H75580 BE250401 AA454518 AA007263 AA626405 AA417152 AA004230 AA557354 AW863151 AW863181 AA702179 AI924143 AI671185 BE006198 AA190630 AI638795 AI609113 AI056239 BE537023 BE464668 AA634413 BE208066 BE208833 AW250803 AI337375 AA478510 BE501624 AI814763 AW594726 AI091408 AA827285 AA189108 AW594169 BE618589 BE618040 AL135398 AA632206 AI080026 AI638180 AA725439 AI379107 AI288872 H14801 AI679151 AI263619 AI559213 AI679722 W93249 AA552345 AA417030 AI969543 AA534494 AI038181 AA766364 AA573241 AI754325 AW043937 BE207865 AI291838 N73585 N73539 AW805051 AA808510 AI699813 AW166044 AW104716 H05808 AA248270 BE538022 N56013 AA621586 AA149737 D19671 AW192890 N54283 H73339 AA910989 BE273424 BE560082 AW959012 AA313552 AW750034 BE072537 BE297947 AW732361 AA449336 D29574 |
| 332732 | 5436_1 | AF191019 NM_015516 BE546494 AL110276 R13844 BE313586 BE336912 R18704 R18703 AA045868 T70952 BE336901 T60387 BE149749 BE271848 BE271902 AA489929 Z45402 T64360 AA305745 AA009451 T95706 H14907 AA299901 C03221 T72431 AW471185 AA335297 AI269100 AA345072 AW965160 H27581 R48910 H25380 AA335281 AW973283 T79590 AW183447 T64172 AI744097 AI342358 AA336102 AA335299 BE208375 AI140834 AA088181 AI860314 AI738613 T70902 R42077 AI884558 AA489798 AI130828 AA009735 H25381 AW612425 R48801 H27507 H30105 H44671 AI631362 AA558470 AW014412 AA552059 AA045801 AW589435 AI039657 H14614 AA974256 R42078 AI245758 T61886 AI559202 AI074139 AI817313 AI041484 AA437138 AI613032 AI147891 AI457945 AW197727 AI074399 AI758636 AI598048 AA972077 M85390 R36989 R71936 AI867492 T40081 Z41115 AA772775 T41013 AI695691 T40996 AI826822 N93464 AW955524 AA088651 |

Pkey: Unique Eos probeset identifier number
CAT number: Gene cluster number
Accession: Genbank accession numbers

TABLE 1C

| Pkey | Ref | Strand | Nt_position |
|---|---|---|---|
| 332792 | Dunham, I. et.al. | Plus | 73381-73768 |
| 333135 | Dunham, I. et.al. | Plus | 3361208-3361369 |
| 333137 | Dunham, I. et.al. | Plus | 3367643-3367726 |
| 333138 | Dunham, I. et.al. | Plus | 3369205-3369323 |
| 333139 | Dunham, I. et.al. | Plus | 3369495-3369571 |
| 333516 | Dunham, I. et.al. | Plus | 5570204-5570390 |
| 333517 | Dunham, I. et.al. | Plus | 5570729-5570925 |
| 333795 | Dunham, I. et.al. | Plus | 7807688-7807795 |
| 333796 | Dunham, I. et.al. | Plus | 7808253-7808319 |
| 333808 | Dunham, I. et.al. | Plus | 7880600-7880775 |
| 333809 | Dunham, I. et.al. | Plus | 7880600-7880775 |
| 333845 | Dunham, I. et.al. | Plus | 8005832-8005945 |
| 333849 | Dunham, I. et.al. | Plus | 8018323-8018472 |
| 334101 | Dunham, I. et.al. | Plus | 9973413-9973550 |
| 334616 | Dunham, I. et.al. | Plus | 15176123-15176470 |
| 334891 | Dunham, I. et.al. | Plus | 19299770-19299944 |
| 334899 | Dunham, I. et.al. | Plus | 19315168-19315311 |
| 334900 | Dunham, I. et.al. | Plus | 19315678-19315743 |
| 334902 | Dunham, I. et.al. | Plus | 19317083-19317195 |
| 334905 | Dunham, I. et.al. | Plus | 19322553-19322680 |
| 334906 | Dunham, I. et.al. | Plus | 19323493-19323590 |
| 335044 | Dunham, I. et.al. | Plus | 20842088-20842682 |
| 335149 | Dunham, I. et.al. | Plus | 21497441-21497587 |
| 335809 | Dunham, I. et.al. | Plus | 26310772-26310909 |
| 335810 | Dunham, I. et.al. | Plus | 26314767-26314849 |
| 335824 | Dunham, I. et.al. | Plus | 26376860-26376942 |
| 336054 | Dunham, I. et.al. | Plus | 29161685-29161937 |
| 336721 | Dunham, I. et.al. | Plus | 3371522-3371586 |
| 337182 | Dunham, I. et.al. | Plus | 23934889-23934962 |
| 337674 | Dunham, I. et.al. | Plus | 3332616-3332697 |
| 337675 | Dunham, I. et.al. | Plus | 3335368-3335505 |
| 337755 | Dunham, I. et.al. | Plus | 3971764-3971900 |
| 338038 | Dunham, I. et.al. | Plus | 8138219-8138392 |
| 338316 | Dunham, I. et.al. | Plus | 17089711-17089988 |
| 333124 | Dunham, I. et.al. | Minus | 3318017-3317932 |
| 333743 | Dunham, I. et.al. | Minus | 7573218-7573060 |
| 334221 | Dunham, I. et.al. | Minus | 12730944-12730387 |
| 334222 | Dunham, I. et.al. | Minus | 12732417-12732289 |
| 334282 | Dunham, I. et.al. | Minus | 13285293-13285178 |
| 334502 | Dunham, I. et.al. | Minus | 14488605-14488526 |
| 334578 | Dunham, I. et.al. | Minus | 15004462-15004304 |
| 334951 | Dunham, I. et.al. | Minus | 20147708-20147502 |
| 335289 | Dunham, I. et.al. | Minus | 22305950-22305708 |
| 335290 | Dunham, I. et.al. | Minus | 22309950-22309891 |
| 335293 | Dunham, I. et.al. | Minus | 22316408-22316275 |
| 335682 | Dunham, I. et.al. | Minus | 25421215-25421093 |
| 335753 | Dunham, I. et.al. | Minus | 25761535-25761444 |
| 335755 | Dunham, I. et.al. | Minus | 25763806-25763747 |
| 335756 | Dunham, I. et.al. | Minus | 25764330-25764251 |
| 336662 | Dunham, I. et.al. | Minus | 2158060-2157993 |
| 336684 | Dunham, I. et.al. | Minus | 2158060-2157993 |
| 337603 | Dunham, I. et.al. | Minus | 1299296-1299194 |
| 338561 | Dunham, I. et.al. | Minus | 22311966-22311856 |
| 338562 | Dunham, I. et.al. | Minus | 22312594-22312465 |
| 339186 | Dunham, I. et.al. | Minus | 32339211-32339097 |
| 325889 | 5867087 | Plus | 223829-223891 |
| 330032 | 6682596 | Plus | 85177-85237 |
| 330033 | 6682596 | Plus | 86663-86723 |
| 326213 | 5867224 | Minus | 60751-60927 |
| 326816 | 6552458 | Plus | 198354-198436 |
| 327110 | 6117842 | Plus | 94608-94785 |
| 327821 | 5867968 | Plus | 131060-131232 |

TABLE 1C-continued

| Pkey | Ref | Strand | Nt_position |
|---|---|---|---|
| 328164 | 5868068 | Minus | 27080-27226 |
| 328648 | 6004473 | Plus | 424829-424959 |
| 329365 | 5868838 | Minus | 107687-107765 |

Pkey: Unique number corresponding to an Eos probeset

Ref: Sequence source. The 7 digit numbers in this column are Genbank Identifier (GI) numbers. "Dunham I. et al." refers to the publication entitled "The DNA sequence of human chromosome 22." Dunham I. et al. (1999) Nature 402: 489-495.

Strand: Indicates DNA strand from which exons were predicted.

Nt_position: Indicates nucleotide positions of predicted exons.

Table 2A lists about 1165 genes selected to have an interesting expression pattern during androgen withdrawal of prostate cancer tissue. These genes were selected by analysis of variance, such that the P value is less than 0.01, the 90th percentile exhibits a minimum of 100 average intensity across all samples, and a comparison of any group means shows a minimum 3 fold change. The interesting expression patterns can be broadly defined into the following categories:

1. Genes that are expressed early in the time course of androgen withdrawal, then drop off in expression, and then express again with emergence of androgen-independence (hi-lo-lo-hi pattern in table 2A).
2. Genes that are expressed early in the time course, then drop off in expression immediately after androgen-withdrawal, and do sot express again with emergence of androgen-independence (hi-lo-lo-lo pattern in table 2A).
3. Genes that are expressed early in the time course, then drop off in expression after several days of androgen withdrawal, and do not express again with emergence of androgen-independence (hi-hi-lo-lo pattern in table 2A).
4. Genes that are not expressed early in the time course, but express only with emergence of androgen-independence (lo-lo-lo-hi pattern in table 2A).
5. Genes that are not expressed early in the time course, but then express as androgen is withdrawn and continue to express with emergence of androgen-independence (lo-lo-hi-hi pattern in table 2A).
6. Genes that are not expressed early in the time course, but then express as androgen is withdrawn and drop off again with emergence of androgen-independence (lo-lo-hi-lo pattern in table 2A).

Table 2B lists accession numbers for primekeys lacking a unigeneID in table 2A. For each probeset is listed a gene cluster number from which oligonucleotides were designed. Gene clusters were compiled using sequences derived from Genbank ESTs and mRNAs. These sequences were clustered based on sequence similarity using Clustering and Alignment Tools (Double Twist, Oakland Calif.). Genbank accession numbers for sequences comprising each cluster are listed in the "Accession" column.

Table 2C lists genomic positioning for primekeys lacking unigene ID's and accession numbers in table 2A. For each predicted exon is listed genomic sequence source used for prediction. Nucleotide locations of each predicted exon are also listed

TABLE 2A

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 433412 | AV653729 | Hs.8185 | CGI-44 protein; sulfide dehydrogenase li | lo—lo-hi-lo |
| 429097 | AK001270 | Hs.196086 | hypothetical protein FLJ10408 | lo—lo-hi-lo |
| 442731 | AI868167 | Hs.131044 | ESTs | lo—lo-hi-lo |
| 420820 | W26096 | Hs.336635 | *Homo sapiens*, clone IMAGE: 4179482, mRNA | lo—lo-hi-lo |
| 422267 | AB033044 | Hs.114012 | KIAA1218 protein | lo—lo-hi-lo |
| 416953 | N31537 | Hs.269046 | ESTs | lo—lo-hi-lo |
| 413277 | H24177 | Hs.75262 | cathepsin O | lo—lo-hi-lo |
| 410209 | AI583661 | Hs.60548 | hypothetical protein PRO1635 | lo—lo-hi-lo |
| 428523 | AW974540 | Hs.98626 | ESTs | lo—lo-hi-lo |
| 435847 | W93821 | Hs.39780 | CDA017 protein | lo—lo-hi-lo |
| 443967 | AW294013 | Hs.200942 | ESTs | lo—lo-hi-lo |
| 440838 | AA907075 | Hs.131307 | ESTs | lo—lo-hi-lo |
| 404054 | | | Target Exon | lo—lo-hi-lo |
| 431697 | H66740 | Hs.38540 | ESTs, Weakly similar to ALU4_HUMAN ALU S | lo—lo-hi-lo |
| 432114 | AL036021 | Hs.8934 | ESTs | lo—lo-hi-lo |
| 446397 | AW275603 | Hs.200712 | ESTs | lo—lo-hi-lo |
| 414094 | H15088 | Hs.31433 | ESTs | lo—lo-hi-lo |
| 424005 | AB033041 | Hs.137507 | vang (van gogh, *Drosophila*)-like 2 | lo—lo-hi-lo |
| 424401 | H67220 | Hs.169681 | death effector domain-containing | lo—lo-hi-lo |
| 449749 | AI668611 | Hs.49760 | ESTs | lo—lo-hi-lo |
| 458368 | BE504731 | Hs.138827 | ESTs | lo—lo-hi-lo |
| 427221 | L15409 | Hs.174007 | von Hippel-Lindau syndrome | lo—lo-hi-lo |
| 432715 | AA247152 | Hs.200483 | ESTs, Weakly similar to KIAA1074 protein | lo—lo-hi-lo |
| 425980 | AA366951 | | gb: EST77963 Pancreas tumor III *Homo sapi* | lo—lo-hi-lo |
| 412492 | AW962604 | | gb: EST374677 MAGE resequences, MAGG *Homo* | lo—lo-hi-lo |
| 438882 | AA827695 | | gb: od56c02.s1 NCI_CGAP_GCB1 *Homo sapiens* | lo—lo-hi-lo |
| 422473 | U94780 | Hs.117242 | meningioma expressed antigen 6 (coiled-c | lo—lo-hi-lo |
| 404211 | | | NM_005936: *Homo sapiens* myeloid/lymphoid | lo—lo-hi-lo |
| 423019 | AI640185 | Hs.283626 | ESTs | lo—lo-hi-lo |
| 443559 | AI076765 | Hs.269899 | ESTs, Moderately similar to ALU8_HUMAN A | lo—lo-hi-lo |
| 444291 | AI598022 | Hs.193989 | TAR DNA binding protein | lo—lo-hi-lo |
| 428065 | AI634046 | Hs.157313 | ESTs | lo—lo-hi-lo |
| 442566 | R37337 | Hs.12111 | ESTs | lo—lo-hi-lo |
| 442202 | BE272862 | Hs.106534 | hypothetical protein FLJ22625 | lo—lo-hi-lo |
| 439456 | AI752409 | Hs.109314 | hypothetical protein FLJ20980 | lo—lo-hi-lo |
| 423476 | AL035633 | | Human DNA sequence from clone RP5-1046G1 | lo—lo-hi-lo |
| 437952 | D63209 | Hs.5944 | solute carrier family 11 (proton-coupled | lo—lo-hi-lo |
| 451987 | AA815092 | Hs.77554 | *Homo sapiens* cDNA FLJ14967 fis, clone TH | lo—lo-hi-lo |
| 453408 | AI804732 | Hs.295963 | ESTs | lo—lo-hi-lo |
| 444004 | N39842 | Hs.301444 | KIAA1673 | lo—lo-hi-lo |
| 452691 | AA164842 | Hs.192619 | KIAA1600 protein | lo—lo-hi-lo |
| 434865 | AW050449 | Hs.116507 | ESTs | lo—lo-hi-lo |
| 440819 | AI809444 | Hs.202108 | ESTs | lo—lo-hi-lo |
| 419526 | AI821895 | Hs.193481 | ESTs | lo—lo-hi-lo |
| 422072 | AB018255 | Hs.111138 | KIAA0712 gene product | lo—lo-hi-lo |
| 453459 | BE047032 | Hs.257789 | ESTs | lo—lo-hi-lo |
| 419038 | AW134924 | Hs.190325 | ESTs | lo—lo-hi-lo |
| 413243 | AA769266 | Hs.193657 | ESTs | lo—lo-hi-lo |
| 432079 | AW972746 | | gb: EST384840 MAGE resequences, MAGL *Homo* | lo—lo-hi-lo |
| 441328 | AI982794 | Hs.159473 | ESTs | lo—lo-hi-lo |
| 416508 | R39769 | | ESTs, Moderately similar to ALU8_HUMAN A | lo—lo-hi-lo |
| 451066 | AI758660 | Hs.206132 | ESTs | lo—lo-hi-lo |
| 446017 | N98238 | Hs.55185 | ESTs | lo—lo-hi-lo |
| 447104 | R19085 | Hs.210706 | *Homo sapiens* cDNA FLJ13182 fis, clone NT | lo—lo-hi-lo |
| 447211 | AL161961 | Hs.17767 | KIAA1554 protein | lo—lo-hi-lo |
| 447765 | AW014112 | Hs.161390 | ESTs | lo—lo-hi-lo |
| 429540 | M85776 | | gb: EST02297 Fetal brain, Stratagene (cat | lo—lo-hi-lo |
| 444314 | AI140497 | | gb: ow76b09.s1 Soares_fetal_liver_spleen_ | lo—lo-hi-lo |
| 414555 | N98569 | Hs.76422 | phospholipase A2, group IIA (platelets, | lo—lo-hi-lo |
| 432677 | NM_004482 | Hs.278611 | UDP-N-acetyl-alpha-D-galactosamine: polyp | lo—lo-hi-lo |
| 422091 | AI906339 | Hs.97927 | ESTs | lo—lo-hi-lo |
| 423028 | H90946 | | gb: yu86c02.r1 Soares fetal liver spleen | lo—lo-hi-lo |
| 444040 | AF204231 | Hs.182982 | golgin-67 | lo—lo-hi-lo |
| 441111 | AI806867 | Hs.126594 | ESTs | lo—lo-hi-lo |
| 418838 | AW385224 | Hs.35198 | ectonucleotide pyrophosphatase/phosphodi | lo—lo-hi-lo |
| 415999 | AA172179 | Hs.294029 | ESTs | lo—lo-hi-lo |
| 429615 | AF258627 | Hs.211562 | ATP-binding cassette, sub-family A (ABC1 | lo—lo-hi-lo |
| 427774 | AA278583 | Hs.180737 | *Homo sapiens* clone 23664 and 23905 mRNA | lo—lo-hi-lo |
| 438585 | AA811371 | Hs.123362 | ESTs | lo—lo-hi-lo |
| 424776 | AI867931 | Hs.164595 | ESTs | lo—lo-hi-lo |
| 413786 | AW613780 | Hs.13500 | ESTs | lo—lo-hi-lo |
| 421077 | AK000061 | Hs.101590 | hypothetical protein | lo—lo-hi-lo |
| 445837 | AI261700 | Hs.145544 | ESTs | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 449282 | AL048056 | Hs.23437 | *Homo sapiens* cDNA FLJ13555 fis, clone PL | lo—lo-hi-lo |
| 414065 | AW515373 | Hs.271249 | *Homo sapiens* cDNA FLJ13580 fis, clone PL | lo—lo-hi-lo |
| 432527 | AW975028 | Hs.102754 | ESTs | lo—lo-hi-lo |
| 412093 | BE242691 | Hs.14947 | ESTs | lo—lo-hi-lo |
| 457121 | AI743770 | Hs.180513 | ESTs, Weakly similar to KIAA0822 protein | lo—lo-hi-lo |
| 417280 | AW173116 | Hs.250103 | ESTs | lo—lo-hi-lo |
| 452445 | AB002438 | Hs.29596 | *Homo sapiens* mRNA from chromosome 5q21-2 | lo—lo-hi-lo |
| 438624 | AA889055 | Hs.123468 | ESTs | lo—lo-hi-lo |
| 442343 | AA992480 | Hs.129874 | ESTs | lo—lo-hi-lo |
| 401416 | | | C14000338*: gi\|7459502\|pir\|\|S74665 outer | lo—lo-hi-lo |
| 437176 | AW176909 | Hs.42346 | calcineurin-binding protein calsarcin-1 | lo—lo-hi-lo |
| 451663 | AI872360 | Hs.209293 | ESTs | lo—lo-hi-lo |
| 449295 | AW137268 | Hs.270954 | ESTs | lo—lo-hi-lo |
| 426848 | H72531 | Hs.36190 | ESTs | lo—lo-hi-lo |
| 445467 | AI239832 | Hs.15617 | ESTs, Weakly similar to ALU4_HUMAN ALU S | lo—lo-hi-lo |
| 418662 | AI801098 | Hs.151500 | ESTs | lo—lo-hi-lo |
| 416239 | AL038450 | Hs.48948 | ESTs | lo—lo-hi-lo |
| 428054 | AI948688 | Hs.266619 | ESTs | lo—lo-hi-lo |
| 435284 | AA879470 | Hs.96849 | *Homo sapiens* cDNA FLJ11492 fis, clone HE | lo—lo-hi-lo |
| 424332 | AA338919 | Hs.101615 | ESTs | lo—lo-hi-lo |
| 442369 | AI565071 | Hs.159983 | ESTs | lo—lo-hi-lo |
| 420717 | AA284447 | Hs.271887 | ESTs | lo—lo-hi-lo |
| 439584 | AA838114 | Hs.221612 | ESTs | lo—lo-hi-lo |
| 440260 | AI972867 | Hs.7130 | copine IV | lo—lo-hi-lo |
| 426269 | H15302 | Hs.168950 | *Homo sapiens* mRNA; cDNA DKFZp566A1046 (f | lo—lo-hi-lo |
| 428398 | AI249368 | Hs.98558 | ESTs | lo—lo-hi-lo |
| 407276 | AI951118 | Hs.326736 | *Homo sapiens* breast cancer antigen NY-BR | lo—lo-hi-lo |
| 409339 | AB020686 | Hs.54037 | ectonucleotide pyrophosphatase/phosphodi | lo—lo-hi-lo |
| 442150 | AJ368158 | Hs.70983 | PTPL1-associated RhoGAP 1 | lo—lo-hi-lo |
| 415787 | H01463 | Hs.93534 | ESTs | lo—lo-hi-lo |
| 430685 | AI690234 | Hs.191666 | ESTs, Weakly similar to GNMSLL retroviru | lo—lo-hi-lo |
| 443794 | N94104 | Hs.29280 | ESTs | lo—lo-hi-lo |
| 446215 | AW821329 | Hs.14368 | SH3 domain binding glutamic acid-rich pr | lo—lo-hi-lo |
| 441285 | NM_002374 | Hs.167 | microtubule-associated protein 2 | lo—lo-hi-lo |
| 448738 | BE614081 | | gb: 601503815F1 NIH_MGC_71 *Homo sapiens* c | lo—lo-hi-lo |
| 403746 | | | ENSP00000226812*: KIAA1494 protein (Fragm | lo—lo-hi-lo |
| 434022 | R18374 | Hs.117956 | ESTs | lo—lo-hi-lo |
| 435714 | AA699325 | Hs.269880 | ESTs | lo—lo-hi-lo |
| 439848 | AW979249 | | gb: EST391359 MAGE resequences, MAGP *Homo* | lo—lo-hi-lo |
| 421974 | AA301270 | | gb: EST14192 Testis tumor *Homo sapiens* cD | lo—lo-hi-lo |
| 433332 | AI367347 | Hs.44898 | *Homo sapiens* clone TCCCTA00151 mRNA sequ | lo—lo-hi-lo |
| 449919 | AI674685 | Hs.200141 | ESTs | lo—lo-hi-lo |
| 407192 | AA609200 | | gb: af12e02.s1 Soares_testis_NHT *Homo sap* | lo—lo-hi-lo |
| 436169 | AA888311 | Hs.17602 | *Homo sapiens* cDNA FLJ12381 fis, clone MA | lo—lo-hi-lo |
| 418624 | AI734080 | Hs.104211 | ESTs | lo—lo-hi-lo |
| 432432 | AA541323 | Hs.115831 | ESTs | lo—lo-hi-lo |
| 426172 | AA371307 | Hs.125056 | ESTs | lo—lo-hi-lo |
| 401093 | | | C12000586*: gi\|6330167\|dbj\|BAA86477.1\| (A | lo—lo-hi-lo |
| 426716 | NM_006379 | Hs.171921 | sema domain, immunoglobulin domain (Ig), | lo—lo-hi-lo |
| 439569 | AW602166 | Hs.222399 | CEGP1 protein | lo—lo-hi-lo |
| 451720 | AW970985 | Hs.290853 | ESTs | lo—lo-hi-lo |
| 429163 | AA884766 | | gb: am20a10.s1 Soares_NFL_T_GBC_S1 *Homo s* | lo—lo-hi-lo |
| 432435 | BE218886 | Hs.282070 | ESTs | lo—lo-hi-lo |
| 408170 | AW204516 | Hs.31835 | ESTs | lo—lo-hi-lo |
| 433530 | BE349534 | Hs.281789 | ESTs | lo—lo-hi-lo |
| 425776 | U25128 | Hs.159499 | parathyroid hormone receptor 2 | lo—lo-hi-lo |
| 430068 | AA464964 | | gb: zx80f10.s1 Soares ovary tumor NbHOT H | lo—lo-hi-lo |
| 422725 | AA315703 | Hs.199993 | ESTs, Weakly similar to ALUB_HUMAN !!!! | lo—lo-hi-lo |
| 432314 | AA533447 | Hs.312989 | ESTs | lo—lo-hi-lo |
| 434609 | R76593 | | gb: yi60c11.r1 Soares placenta Nb2HP *Homo* | lo—lo-hi-lo |
| 448760 | AA313825 | Hs.21941 | AD036 protein | lo—lo-hi-lo |
| 417381 | AF164142 | Hs.82042 | solute carrier family 23 (nucleobase tra | lo—lo-hi-lo |
| 456334 | T50392 | Hs.271745 | ESTs | lo—lo-hi-lo |
| 435445 | AA737345 | Hs.294041 | ESTs | lo—lo-hi-lo |
| 411928 | AA888624 | Hs.197289 | rab3 GTPase-activating protein, non-cata | lo—lo-hi-lo |
| 438869 | AF075009 | | gb: *Homo sapiens* full length insert cDNA | lo—lo-hi-lo |
| 423932 | T95633 | Hs.189703 | ESTs | lo—lo-hi-lo |
| 422222 | AI699372 | Hs.193247 | hypothetical protein DKFZp434A171 | lo—lo-hi-lo |
| 434941 | AW073202 | Hs.334825 | *Homo sapiens* cDNA FLJ14752 fis, clone NT | lo—lo-hi-lo |
| 415736 | AA827082 | Hs.291872 | ESTs | lo—lo-hi-lo |
| 432722 | AA830532 | Hs.326150 | ESTs | lo—lo-hi-lo |
| 435511 | AA683336 | Hs.189046 | ESTs | lo—lo-hi-lo |
| 432242 | AW022715 | Hs.162160 | ESTs, Weakly similar to ALU4_HUMAN ALU S | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 451141 | AW772713 | Hs.247186 | ESTs | lo—lo-hi-lo |
| 450546 | AA010200 | Hs.175551 | ESTs | lo—lo-hi-lo |
| 413351 | BE086815 | | ESTs | lo—lo-hi-lo |
| 439324 | AF086134 | Hs.94309 | ESTs | lo—lo-hi-lo |
| 452688 | AA721140 | Hs.49930 | ESTs, Weakly similar to putative p150 [H | lo—lo-hi-lo |
| 415669 | NM_005025 | Hs.78589 | serine (or cysteine) proteinase inhibito | lo—lo-hi-lo |
| 450164 | AI239923 | Hs.63931 | ESTs | lo—lo-hi-lo |
| 417169 | R13550 | Hs.246773 | ESTs | lo—lo-hi-lo |
| 443645 | R36475 | Hs.24321 | *Homo sapiens* cDNA FLJ12028 fis, clone HE | lo—lo-hi-lo |
| 424878 | H57111 | Hs.221132 | ESTs | lo—lo-hi-lo |
| 449618 | AI076459 | Hs.15978 | KIAA1272 protein | lo—lo-hi-lo |
| 432572 | AI660840 | Hs.191202 | ESTs, Weakly similar to ALUE_HUMAN !!!! | lo—lo-hi-lo |
| 400293 | N51002 | Hs.306480 | *Homo sapiens* mRNA; cDNA DKFZp761E2112 (f | lo—lo-hi-lo |
| 431474 | AL133990 | Hs.190642 | CEGP1 protein | lo—lo-hi-lo |
| 421674 | T10707 | Hs.296355 | hypothetical protein FLJ23138 | lo—lo-hi-lo |
| 438494 | AA908678 | Hs.130183 | ESTs | lo—lo-hi-lo |
| 425332 | AA633306 | Hs.127279 | ESTs | lo—lo-hi-lo |
| 451411 | AA017492 | Hs.135655 | EST | lo—lo-hi-lo |
| 419972 | AL041465 | Hs.182982 | golgin-67 | lo—lo-hi-lo |
| 434804 | AA649530 | Hs.348148 | gb: ns44f05.s1 NCI_CGAP_Alv1 *Homo sapiens* | lo—lo-hi-lo |
| 442832 | AW206560 | Hs.253569 | ESTs | lo—lo-hi-lo |
| 408660 | AA525775 | | ESTs, Moderately similar to PC4259 ferri | lo—lo-hi-lo |
| 432674 | AA641092 | Hs.257339 | ESTs, Weakly similar to I38022 hypotheti | lo—lo-hi-lo |
| 448150 | AI472167 | | ESTs | lo—lo-hi-lo |
| 450468 | AW379075 | Hs.141742 | *Homo sapiens* cDNA FLJ12211 fis, clone MA | lo—lo-hi-lo |
| 452874 | AK001061 | Hs.30925 | hypothetical protein FLJ10199 | lo—lo-hi-lo |
| 412088 | AI689496 | Hs.108932 | ESTs | lo—lo-hi-lo |
| 443451 | AI057404 | Hs.58698 | ESTs | lo—lo-hi-lo |
| 453853 | AL040600 | Hs.188083 | ESTs | lo—lo-hi-lo |
| 419863 | AW952691 | Hs.93485 | *Homo sapiens* mRNA; cDNA DKFZp761D191 (fr | lo—lo-hi-lo |
| 420729 | AW964897 | Hs.290825 | ESTs | lo—lo-hi-lo |
| 440801 | AA906366 | Hs.190535 | ESTs | lo—lo-hi-lo |
| 407284 | AI539227 | Hs.214039 | hypothetical protein FLJ23556 | lo—lo-hi-lo |
| 428279 | AA425310 | Hs.155766 | ESTs, Weakly similar to A47582 B-cell gr | lo—lo-hi-lo |
| 436862 | AI821940 | | ESTs, Moderately similar to ALU8_HUMAN A | lo—lo-hi-lo |
| 432340 | AA534222 | | gb: nj21d02.s1 NCI_CGAP_AA1 *Homo sapiens* | lo—lo-hi-lo |
| 442048 | AA974603 | | gb: op34f05.s1 Soares_NFL_T_GBC_S1 *Homo s* | lo—lo-hi-lo |
| 418781 | T41160 | Hs.8404 | ESTs | lo—lo-hi-lo |
| 450642 | R39773 | Hs.7130 | copine IV | lo—lo-hi-lo |
| 451661 | AB020650 | Hs.26777 | *Homo sapiens*, Similar to KIAA0843 protei | lo—lo-hi-lo |
| 435812 | AA700439 | Hs.188490 | ESTs | lo—lo-hi-lo |
| 448065 | AI459177 | Hs.172759 | ESTs, Moderately similar to ALU7_HUMAN A | lo—lo-hi-lo |
| 453486 | AL039201 | Hs.173554 | ubiquinol-cytochrome c reductase core pr | lo—lo-hi-lo |
| 414312 | AA155694 | Hs.191060 | ESTs | lo—lo-hi-lo |
| 438980 | AW502384 | | gb: UI-HF-BR0p-aka-f-12-0-UI.r1 NIH_MGC_5 | lo—lo-hi-lo |
| 408001 | AA046458 | Hs.95296 | ESTs | lo—lo-hi-lo |
| 421476 | AW953805 | Hs.21887 | ESTs | lo—lo-hi-lo |
| 414426 | D60745 | Hs.25925 | *Homo sapiens*, clone MGC: 15393, mRNA, com | lo—lo-hi-lo |
| 444563 | N57057 | Hs.284163 | ANKHZN protein | lo—lo-hi-lo |
| 418771 | AA807881 | Hs.25329 | ESTs | lo—lo-hi-lo |
| 417843 | W07361 | Hs.22545 | *Homo sapiens* cDNA FLJ12935 fis, clone NT | lo—lo-hi-lo |
| 415565 | AA642449 | Hs.48994 | ESTs, Weakly similar to AF151800 1 CGI-4 | lo—lo-hi-lo |
| 419229 | AI827237 | Hs.282884 | ESTs | lo—lo-hi-lo |
| 419905 | AW248229 | Hs.93659 | protein disulfide isomerase related prot | lo—lo-hi-lo |
| 452870 | AW502761 | Hs.30909 | KIAA0430 gene product | lo—lo-hi-lo |
| 449059 | AK000566 | Hs.98135 | hypothetical protein FLJ20559 | lo—lo-hi-lo |
| 416157 | NM_003243 | Hs.342874 | transforming growth factor, beta recepto | lo—lo-hi-lo |
| 439305 | AW393883 | Hs.98968 | hypothetical protein FLJ23058 | lo—lo-hi-lo |
| 419235 | AW470411 | Hs.288433 | neurotrimin | lo—lo-hi-lo |
| 416640 | BE262478 | Hs.79404 | neuron-specific protein | lo—lo-hi-lo |
| 434938 | AW500718 | Hs.8115 | *Homo sapiens*, clone MGC: 16169, mRNA, com | lo—lo-hi-lo |
| 408177 | AI241733 | Hs.43871 | ESTs | lo—lo-hi-lo |
| 438459 | T49300 | Hs.35304 | *Homo sapiens* cDNA FLJ13655 fis, clone PL | lo—lo-hi-lo |
| 418381 | AA682393 | Hs.119237 | ESTs | lo—lo-hi-lo |
| 432161 | AK000400 | Hs.341181 | ESTs, Weakly similar to envelope [*H. sapi* | lo—lo-hi-lo |
| 418283 | S79895 | Hs.83942 | cathepsin K (pycnodysostosis) | lo—lo-hi-lo |
| 421443 | BE550141 | Hs.156148 | hypothetical protein FLJ13231 | lo—lo-hi-lo |
| 416619 | AF013168 | Hs.79393 | tuberous sclerosis 1 | lo—lo-hi-lo |
| 449802 | AW901804 | Hs.23984 | hypothetical protein FLJ20147 | lo—lo-hi-lo |
| 446714 | W73818 | Hs.110028 | ESTs | lo—lo-hi-lo |
| 413195 | AA127382 | Hs.22404 | protease, serine, 12 (neurotrypsin, moto | lo—lo-hi-lo |
| 438233 | W52448 | Hs.56147 | ESTs | lo—lo-hi-lo |
| 416051 | AA835868 | Hs.25253 | mannosidase, alpha, class 1A, member 1 | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 438855 | AW946276 | Hs.6441 | *Homo sapiens* mRNA; cDNA DKFZp586J021 (fr | lo—lo-hi-lo |
| 425907 | AA365752 | Hs.155965 | ESTs | lo—lo-hi-lo |
| 451295 | AI557212 | Hs.17132 | ESTs, Moderately similar to I54374 gene | lo—lo-hi-lo |
| 415443 | T07353 | Hs.7948 | ESTs | lo—lo-hi-lo |
| 422366 | T83882 | Hs.97927 | ESTs | lo—lo-hi-lo |
| 435163 | AA668884 | Hs.19155 | ESTs | lo—lo-hi-lo |
| 426559 | AB001914 | Hs.170414 | paired basic amino acid cleaving system | lo—lo-hi-lo |
| 448988 | Y09763 | Hs.22785 | gamma-aminobutyric acid (GABA) A recepto | lo—lo-hi-lo |
| 453655 | AW960427 | Hs.342874 | transforming growth factor, beta recepto | lo—lo-hi-lo |
| 414516 | AI307802 | Hs.135560 | ESTs, Weakly similar to T43458 hypotheti | lo—lo-hi-lo |
| 420028 | AB014680 | Hs.8786 | carbohydrate (N-acetylglucosamine-6-O) s | lo—lo-hi-lo |
| 430223 | NM_002514 | Hs.235935 | nephroblastoma overexpressed gene | lo—lo-hi-lo |
| 425887 | AL049443 | Hs.161283 | *Homo sapiens* mRNA; cDNA DKFZp586N2020 (f | lo—lo-hi-lo |
| 442577 | AA292998 | Hs.163900 | ESTs | lo—lo-hi-lo |
| 424940 | AA985308 | Hs.283902 | ESTs | lo—lo-hi-lo |
| 428839 | AI767756 | Hs.82302 | *Homo sapiens* cDNA FLJ14814 fis, clone NT | lo—lo-hi-lo |
| 443868 | W88483 | Hs.293650 | *Homo sapiens* mRNA for RGPR-p117, complet | lo—lo-hi-lo |
| 430334 | AI824719 | Hs.328700 | ESTs | lo—lo-hi-lo |
| 439686 | W40445 | Hs.235857 | ESTs, Weakly similar to I38022 hypotheti | lo—lo-hi-lo |
| 423754 | NM_016181 | Hs.132526 | melanoma antigen | lo—lo-hi-lo |
| 415205 | H71616 | Hs.135233 | ESTs | lo—lo-hi-lo |
| 426413 | AA377823 | | gb: EST90805 Synovial sarcoma *Homo sapien* | lo—lo-hi-lo |
| 407204 | R41933 | Hs.140237 | ESTs, Weakly similar to ALU1_HUMAN ALU S | lo—lo-hi-lo |
| 430234 | N29317 | Hs.236463 | KIAA1238 protein | lo—lo-hi-lo |
| 437143 | AW204056 | Hs.8917 | ESTs | lo—lo-hi—hi |
| 445162 | AB011131 | Hs.12376 | piccolo (presynaptic cytomatrix protein) | lo—lo-hi—hi |
| 415083 | AI632683 | Hs.27179 | *Homo sapiens* cDNA FLJ12933 fis, clone NT | lo—lo-hi—hi |
| 442924 | AA533513 | Hs.93659 | protein disulfide isomerase related prot | lo—lo-hi—hi |
| 429536 | AA873016 | Hs.206097 | oncogene TC21 | lo—lo-hi—hi |
| 458584 | AF217518 | Hs.324136 | PTD012 protein | lo—lo-hi—hi |
| 419647 | AA348947 | Hs.91816 | hypothetical protein | lo—lo-hi—hi |
| 427201 | AB037860 | Hs.173933 | nuclear factor I/A | lo—lo-hi—hi |
| 428030 | AI915228 | Hs.11493 | *Homo sapiens* cDNA FLJ13536 fis, clone PL | lo—lo-hi—hi |
| 411779 | AA292811 | Hs.72050 | non-metastatic cells 5, protein expresse | lo—lo-hi—hi |
| 442482 | NM_014039 | Hs.8360 | PTD012 protein | lo—lo-hi—hi |
| 417458 | NM_005655 | Hs.82173 | TGFB inducible early growth response | lo—lo-hi—hi |
| 438021 | AV653790 | Hs.324275 | WW domain-containing protein 1 | lo—lo-hi—hi |
| 409799 | D11928 | Hs.76845 | phosphoserine phosphatase-like | lo—lo-hi—hi |
| 440676 | NM_004987 | Hs.112378 | LIM and senescent cell antigen-like doma | lo—lo-hi—hi |
| 421437 | AW821252 | Hs.104336 | hypothetical protein | lo—lo-hi—hi |
| 456362 | AW973003 | Hs.179909 | hypothetical protein FLJ22995 | lo—lo-hi—hi |
| 407686 | AW901268 | Hs.126043 | chromosome 21 open reading frame 51 | lo—lo-hi—hi |
| 431129 | AL137751 | Hs.263671 | *Homo sapiens* mRNA; cDNA DKFZp434I0812 (f | lo—lo-hi—hi |
| 431874 | AW610031 | Hs.323914 | translocase of inner mitochondrial membr | lo—lo-hi—hi |
| 448072 | AI459306 | Hs.24908 | ESTs | lo—lo-hi—hi |
| 436860 | H12751 | Hs.5327 | PRO1914 protein | lo—lo-hi—hi |
| 448770 | AA326683 | Hs.21992 | likely ortholog of mouse variant polyade | lo—lo-hi—hi |
| 428044 | AA093322 | Hs.301404 | RNA binding motif protein 3 | lo—lo-hi—hi |
| 451468 | AW503398 | Hs.293663 | ESTs, Moderately similar to I38022 hypot | lo—lo-hi—hi |
| 440278 | BE560870 | Hs.9052 | ESTs, Weakly similar to 2004399A chromos | lo—lo-hi—hi |
| 441102 | AA973905 | | intermediate filament protein Syncoilin | lo—lo-hi—hi |
| 423942 | AF209704 | Hs.135723 | glycolipid transfer protein | lo—lo-hi—hi |
| 425254 | U91985 | Hs.105658 | DNA fragmentation factor, 45 kD, alpha p | lo—lo-hi—hi |
| 409324 | W76202 | Hs.343812 | lipoic acid synthetase | lo—lo-hi—hi |
| 431707 | R21326 | Hs.267905 | hypothetical protein FLJ10422 | lo—lo-hi—hi |
| 423335 | AB018337 | Hs.127287 | KIAA0794 protein | lo—lo-hi—hi |
| 429200 | AA447871 | Hs.194215 | ESTs, Weakly similar to I38022 hypotheti | lo—lo-hi—hi |
| 429898 | AW117322 | Hs.42366 | ESTs | lo—lo-hi—hi |
| 409604 | AW444448 | Hs.49124 | ESTs | lo—lo-hi—hi |
| 431797 | BE169641 | Hs.270134 | hypothetical protein FLJ20280 | lo—lo-hi—hi |
| 437576 | BE514383 | | prothymosin, alpha (gene sequence 28) | lo—lo-hi—hi |
| 415992 | C05837 | Hs.145807 | hypothetical protein FLJ13593 | lo—lo-hi—hi |
| 458537 | W24704 | Hs.54773 | ESTs | lo—lo-hi—hi |
| 417665 | AW852858 | Hs.22862 | ESTs | lo—lo-hi—hi |
| 422292 | AI815733 | Hs.114360 | transforming growth factor beta-stimulat | lo—lo-hi—hi |
| 421501 | M29971 | Hs.1384 | O-6-methylguanine-DNA methyltransferase | lo—lo-hi—hi |
| 457952 | U25750 | | Human chromosome 17q21 mRNA clone 1046: 1 | lo—lo-hi—hi |
| 414630 | BE410857 | Hs.16064 | gb: 601301177F1 NIH_MGC_21 *Homo sapiens* c | lo—lo-hi—hi |
| 421990 | T31811 | Hs.110480 | DC12 protein | lo—lo-hi—hi |
| 404956 | | | C1003210*: gi\|6912582\|ref\|NP_036524.1\| pe | lo—lo-hi—hi |
| 436829 | AW297958 | Hs.163109 | ESTs | lo—lo-hi—hi |
| 402106 | AK002178 | | hypothetical protein FLJ11316 | lo—lo-hi—hi |
| 404384 | | | NM_020632*: *Homo sapiens* ATPase, H(+)-tra | lo—lo-hi—hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 445123 | AI762911 | Hs.145369 | ESTs | lo—lo-hi—hi |
| 401757 | | | Target Exon | lo—lo-hi—hi |
| 439502 | AA836672 | Hs.130694 | ESTs | lo—lo-hi—hi |
| 400111 | | | Eos Control | lo—lo-hi—hi |
| 405446 | AI015709 | | *Homo sapiens* mRNA; cDNA DKFZp586I2022 (f | lo—lo-hi—hi |
| 401563 | | | C15001262: gi\|7304981\|ref\|NP_038528.1\| ca | lo—lo-hi—hi |
| 402786 | | | C1000887*: gi\|12732453\|ref\|XP_011474.1\| C | lo—lo-hi—hi |
| 426484 | AA379658 | Hs.272759 | KIAA1457 protein | lo—lo-hi—hi |
| 414343 | AL036166 | Hs.323378 | coated vesicle membrane protein | lo—lo-hi—hi |
| 421970 | AF227156 | Hs.110103 | RNA polymerase\|transcription factor RR | lo—lo-hi—hi |
| 422592 | BE081857 | Hs.94211 | rcd1 (required for cell differentiation, | lo—lo-hi—hi |
| 413431 | AW246428 | Hs.75355 | ubiquitin-conjugating enzyme E2N (homolo | lo—lo-hi—hi |
| 426746 | J03626 | Hs.2057 | uridine monophosphate synthetase (orotat | lo—lo-hi—hi |
| 400237 | | | NM_001087*: *Homo sapiens* angio-associated | lo—lo-hi—hi |
| 402532 | | | Target Exon | lo—lo-hi—hi |
| 402396 | | | Target Exon | lo—lo-hi—hi |
| 459649 | AW298364 | Hs.289292 | ESTs | lo—lo-hi—hi |
| 401512 | | | NM_014080: *Homo sapiens* dual oxidase-like | lo—lo-hi—hi |
| 448622 | AL046508 | Hs.270607 | ESTs, Weakly similar to STK2_HUMAN SERIN | lo—lo-hi—hi |
| 400501 | | | ENSP00000251912*: KIAA1617 protein (Fragm | lo—lo-hi—hi |
| 452324 | W81486 | Hs.58648 | ESTs | lo—lo-hi—hi |
| 453146 | AI338952 | Hs.32194 | ESTs | lo—lo-hi—hi |
| 430445 | AW892432 | Hs.65307 | ESTs | lo—lo-hi—hi |
| 401750 | | | NM_012448*: *Homo sapiens* signal transduce | lo—lo-hi—hi |
| 435236 | T03890 | Hs.157208 | ESTs, Highly similar to ARX MOUSE HOMEOB | lo—lo-hi—hi |
| 400375 | NM_014115 | | NM_014115*: *Homo sapiens* PRO0113 protein | lo—lo-hi—hi |
| 412151 | AA100529 | Hs.286232 | *Homo sapiens* cDNA: FLJ23190 fis, clone L | lo—lo-hi—hi |
| 410498 | AA355749 | | gb: EST64459 Jurkat T-cells VI Homo sapie | lo—lo-hi—hi |
| 405044 | | | NM_014630*: *Homo sapiens* KIAA0211 gene pr | lo—lo-hi—hi |
| 413169 | AW161061 | Hs.62954 | ESTs, Weakly similar to zinc finger prot | lo—lo-hi—hi |
| 402101 | | | ENSP00000217725*: Laminin alpha-1 chain p | lo—lo-hi—hi |
| 455019 | AW850818 | | gb: IL3-CT0220-091199-026-A03 CT0220 *Homo* | lo—lo-hi—hi |
| 446826 | AK000626 | Hs.16230 | hypothetical protein FLJ20619 | lo—lo-hi—hi |
| 412180 | AW898791 | Hs.118837 | gb: CM0-NN0075-130400-332-f06 NN0075 *Homo* | lo—lo-hi—hi |
| 407273 | AJ132560 | | gb: *Homo sapiens* mRNA for immunoblobulin | lo—lo-hi—hi |
| 452895 | BE389229 | Hs.30954 | phosphomevalonate kinase | lo—lo-hi—hi |
| 416117 | H19480 | Hs.268787 | ESTs | lo—lo-hi—hi |
| 430934 | AI792302 | Hs.248141 | potassium inwardly-rectifying channel, s | lo—lo-hi—hi |
| 416309 | R84694 | Hs.79194 | cAMP responsive element binding protein | lo—lo-hi—hi |
| 444578 | T80795 | Hs.193702 | ESTs | lo—lo-hi—hi |
| 401966 | | | C17000574: gi\|8923190\|ref\|NP_060178.1\| hy | lo—lo-hi—hi |
| 444850 | AW444882 | Hs.148483 | ESTs | lo—lo-hi—hi |
| 403885 | | | Target Exon | lo—lo-hi—hi |
| 405435 | | | Target Exon | lo—lo-hi—hi |
| 422694 | C06003 | Hs.23782 | hypothetical protein FLJ12847 | lo—lo-hi—hi |
| 422912 | AW405973 | Hs.11637 | ESTs | lo—lo-hi—hi |
| 412748 | BE083158 | Hs.10862 | *Homo sapiens* cDNA: FLJ23313 fis, clone H | lo—lo-hi—hi |
| 403704 | | | Target Exon | lo—lo-hi—hi |
| 440507 | H06994 | | gb: yl81b07.r1 Soares infant brain 1NIB H | lo—lo-hi—hi |
| 405503 | | | C7000609*: gi\|628012\|pir\|\|A53933 myosin\| | lo—lo-hi—hi |
| 456123 | R00602 | | gb: ye74c04.r1 Soares fetal liver spleen | lo—lo-hi—hi |
| 454261 | AF216077 | Hs.48376 | *Homo sapiens* clone HB-2 mRNA sequence | lo—lo-hi—hi |
| 458956 | BE220675 | | gb: ht98f11.x1 NCI_CGAP_Lu24 *Homo sapiens* | lo—lo-hi—hi |
| 418367 | AA326035 | Hs.59236 | hypothetical protein DKFZp434L0718 | lo—lo-hi—hi |
| 444553 | AI167530 | Hs.149380 | ESTs | lo—lo-hi—hi |
| 405811 | | | NM_024810: *Homo sapiens* hypothetical prot | lo—lo-hi—hi |
| 429461 | AI188219 | Hs.99311 | ESTs, Weakly similar to HSJ2_HUMAN DNAJ | lo—lo-hi—hi |
| 423378 | BE313601 | Hs.164866 | hypothetical protein FLJ22558 | lo—lo-hi—hi |
| 458516 | BE010749 | Hs.255097 | ESTs | lo—lo-hi—hi |
| 404039 | | | ENSP00000247650*: Hypothetical 177.6 kDa | lo—lo-hi—hi |
| 454148 | AW732837 | Hs.42390 | nasopharyngeal carcinoma susceptibility | lo—lo-hi—hi |
| 412678 | AA115575 | Hs.114914 | ESTs | lo—lo-hi—hi |
| 449298 | AI911333 | Hs.171689 | ESTs | lo—lo-hi—hi |
| 405525 | | | NM_002439*: *Homo sapiens* mutS (*E. coli*) h | lo—lo-hi—hi |
| 424576 | BE154142 | Hs.96833 | ESTs | lo—lo-hi—hi |
| 451601 | N92100 | Hs.97437 | centrosomal protein 1 | lo—lo-hi—hi |
| 422395 | AA310177 | Hs.103931 | DKFZP434B0335 protein | lo—lo-hi—hi |
| 434333 | AA186733 | Hs.292154 | stromal cell protein | lo—lo-hi—hi |
| 413509 | BE145419 | | gb: IL5-HT0198-291099-009-E01 HT0198 *Homo* | lo—lo-hi—hi |
| 419504 | AI088585 | Hs.118904 | ESTs | lo—lo-hi—hi |
| 448586 | AF285120 | Hs.283734 | CGI-204 protein | lo—lo-hi—hi |
| 401209 | | | C12000519: gi\|7710046\|ref\|NP_057914.1\| ki | lo—lo-hi—hi |
| 423554 | M90516 | Hs.1674 | glutamine-fructose-6-phosphate transamin | lo—lo-hi—hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 439803 | AA001021 | Hs.6685 | thyroid hormone receptor interactor 8 | lo—lo-hi—hi |
| 424593 | AA343729 | | gb: EST49730 Gall bladder\|*Homo sapiens* | lo—lo-hi—hi |
| 408122 | AI432652 | Hs.42824 | hypothetical protein FLJ10718 | lo—lo-hi—hi |
| 409958 | NM_001523 | Hs.57697 | hyaluronan synthase 1 | lo—lo-hi—hi |
| 408214 | AL120445 | Hs.77823 | hypothetical protein FLJ21343 | lo—lo-hi—hi |
| 421911 | AL041520 | | gb: DKFZp434G2317_s1 434 (synonym: htes3) | lo—lo-hi—hi |
| 407813 | AL120247 | Hs.40109 | KIAA0872 protein | lo—lo-hi—hi |
| 425211 | M18667 | Hs.1867 | progastricsin (pepsinogen C) | lo—lo-hi—hi |
| 442772 | AW503680 | Hs.5957 | *Homo sapiens* clone 24416 mRNA sequence | lo—lo-hi—hi |
| 419733 | AW362955 | Hs.224961 | *Homo sapiens* cDNA FLJ14415 fis, clone HE | lo—lo-hi—hi |
| 428260 | AW290886 | Hs.86999 | ESTs, Weakly similar to S65657 alpha-1C- | lo—lo-hi—hi |
| 427083 | NM_006363 | Hs.173497 | Sec23 (*S. cerevisiae*) homolog B | lo—lo-hi—hi |
| 418583 | AA604379 | Hs.86211 | hypothetical protein | lo—lo-hi—hi |
| 407355 | AA846203 | Hs.193974 | ESTs, Weakly similar to ALU1_HUMAN ALU S | lo—lo-hi—hi |
| 454003 | AA058944 | Hs.116602 | *Homo sapiens*, clone IMAGE: 4154008, mRNA, | lo—lo-hi—hi |
| 425322 | U63630 | Hs.155637 | protein kinase, DNA-activated, catalytic | lo—lo-hi—hi |
| 402240 | | | Target Exon | lo—lo-hi—hi |
| 421867 | AA481078 | Hs.109045 | hypothetical protein FLJ10498 | lo—lo-hi—hi |
| 408603 | R25283 | Hs.326416 | *Homo sapiens* mRNA; cDNA DKFZp564H1916 (f | lo—lo-hi—hi |
| 437389 | AL359587 | Hs.271586 | hypothetical protein DKFZp762M115 | lo—lo-hi—hi |
| 457148 | AF091035 | Hs.184627 | KIAA0118 protein | lo—lo-hi—hi |
| 400277 | | | Eos Control | lo—lo-hi—hi |
| 400995 | | | C11000295*: gi\|12737279\|ref\|XP_012163.1\| | lo—lo-hi—hi |
| 400818 | | | Target Exon | lo—lo-hi—hi |
| 402758 | | | C1001899*: gi\|12722636\|ref\|XP_010672.1\| e | lo—lo-hi—hi |
| 403708 | | | Target Exon | lo—lo-hi—hi |
| 405610 | | | ENSP00000241065*: CDNA | lo—lo-hi—hi |
| 414242 | AA749230 | Hs.26433 | dolichyl-phosphate (UDP-N-acetylglucosam | lo—lo-hi—hi |
| 420757 | X78592 | Hs.99915 | androgen receptor (dihydrotestosterone r | lo—lo-hi—hi |
| 400965 | | | C11002190*: gi\|12737279\|ref\|XP_012163.1\| | lo—lo-hi—hi |
| 401192 | | | Target Exon | lo—lo-hi—hi |
| 404407 | | | Target Exon | lo—lo-hi—hi |
| 401405 | | | Target Exon | lo—lo-hi—hi |
| 403055 | | | C2002219*: gi\|12737280\|ref\|XP_006682.2\| k | lo—lo-hi—hi |
| 404661 | | | C9000306*: gi\|12137280\|ref\|XP_006682.2\| k | lo—lo-hi—hi |
| 433627 | AF078666 | Hs.284296 | *Homo sapiens* cDNA: FLJ22993 fis, clone K | lo—lo-hi—hi |
| 410204 | AJ243425 | Hs.326035 | early growth response 1 | lo—lo-hi—hi |
| 432642 | BE297635 | Hs.3069 | heat shock 70 kD protein 98 (mortalin-2) | lo—lo-hi—hi |
| 400769 | | | Target Exon | lo—lo-hi—hi |
| 433980 | AA137152 | Hs.286049 | phosphoserine aminotransferase | lo—lo-hi—hi |
| 403725 | | | Target Exon | lo—lo-hi—hi |
| 413587 | AA156164 | Hs.286241 | protein kinase, cAMP-dependent, regulato | lo—lo-hi—hi |
| 422614 | AI908006 | Hs.295362 | *Homo sapiens* cDNA FLJ14459 fis, clone HE | lo—lo-hi—hi |
| 400275 | | | NM_006513*: *Homo sapiens* seryl-tRNA synth | lo—lo-hi—hi |
| 402810 | | | NM_004930*: *Homo sapiens* capping protein | lo—lo-hi—hi |
| 452049 | BE268289 | Hs.27693 | peptidylprolyl isomerase (cyclophilin)-I | lo—lo-hi—hi |
| 445677 | H96577 | Hs.6838 | ras homolog gene family, member E | lo—lo-hi—hi |
| 428770 | AK001667 | Hs.193128 | hypothetical protein FLJ10805 | lo—lo-hi—hi |
| 428403 | AI393048 | Hs.326159 | leucine rich, repeat (in FLJI) interactin | lo—lo-hi—hi |
| 434647 | W74158 | Hs.103189 | lipopolysaccharide specific response-68 | lo—lo-hi—hi |
| 402807 | | | ENSP00000235229: SEMB. | lo—lo-hi—hi |
| 413992 | W26276 | Hs.136075 | RNA, U2 small nuclear | lo—lo-hi—hi |
| 407191 | AA608751 | | gb: ae56h07.s1 Stratagene lung carcinoma | lo—lo-hi-lo |
| 403328 | | | Target Exon | lo—lo-hi—hi |
| 411984 | NM_005419 | Hs.72988 | signal transducer and activator of trans | lo—lo-hi-lo |
| 451017 | BE391847 | Hs.181173 | hypothetical protein MGC10771 | lo—lo-hi—hi |
| 404108 | | | C7000911*: gi\|4235142\|gb\|AAD14470.1\| (AC0 | lo—lo-hi—hi |
| 407819 | R42185 | Hs.102720 | ESTs | lo—lo-hi—hi |
| 435876 | AW612586 | Hs.160271 | G protein-coupled receptor 48 | lo—lo-hi—hi |
| 436716 | AI433540 | | gb: ti69g05.x1 NCI_CGAP_Kid11 *Homo sapien* | lo—lo-hi—hi |
| 401419 | | | Target Exon | lo—lo-hi—hi |
| 424363 | AW512144 | Hs.346947 | ESTs, Weakly similar to A48809 carboxyle | lo—lo-hi—hi |
| 408866 | AW292096 | Hs.255036 | ESTs | lo—lo-hi—hi |
| 415516 | F11411 | | gb: HSC2WF081 normalized infant brain cDN | lo—lo-hi—hi |
| 423144 | AW851527 | Hs.253677 | ESTs, Weakly similar, to I38022 hypotheti | lo—lo-hi—hi |
| 452560 | BE077084 | Hs.99969 | ESTs | lo—lo-hi—hi |
| 439827 | AA846538 | Hs.187389 | ESTs | lo—lo-hi—hi |
| 419709 | AA255592 | Hs.347973 | ESTs, Weakly similar to alternatively sp | lo—lo-hi—hi |
| 413672 | BE156536 | | gb: QV0-HT0368-310100-091-h10 HT0368 *Homo* | lo—lo-hi—hi |
| 425291 | AA354572 | | gb: EST62857 Jurkat T-cells V *Homo sapien* | lo—lo-hi—hi |
| 427403 | AA402107 | Hs.257146 | ESTs, Moderately similar to I38022 hypot | lo—lo-hi—hi |
| 436911 | AW937461 | Hs.255377 | ESTs | lo—lo-hi—hi |
| 435293 | AI040777 | Hs.117170 | ESTs | lo—lo-hi—hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 448490 | AI523897 | Hs.271692 | ESTs, Weakly similar to I38022 hypotheti | lo—lo-hi—hi |
| 449539 | W80363 | Hs.58446 | ESTs | lo—lo-hi—hi |
| 458082 | AW978611 | Hs.314451 | ESTs, Weakly similar ALU1_HUMAN ALU S | lo—lo-hi—hi |
| 459407 | N92114 | | gb: za22h11.r1 Soares fetal liver spleen | lo—lo-hi—hi |
| 423231 | AA323486 | Hs.271273 | *Homo sapiens* cDNA FLJ12335 fis, clone MA | lo—lo-hi—hi |
| 450628 | AW382884 | Hs.204715 | ESTs | lo—lo-hi—hi |
| 411690 | AA669253 | Hs.136075 | RNA, U2 small nuclear | lo—lo-hi—hi |
| 414739 | U83867 | Hs.77196 | spectrin, alpha, non-erythrocytic 1 (alp | lo—lo-hi—hi |
| 444169 | AV648170 | Hs.58756 | ESTs | lo—lo-hi—hi |
| 420911 | U77413 | Hs.100293 | O-linked N-acetytglusosamine (GlcNAC) tr | lo—lo-hi—hi |
| 422195 | AB007903 | Hs.113082 | KIAA0443 gene product | lo—lo-hi—hi |
| 452704 | AA027823 | Hs.149424 | *Homo sapiens* PNAS-130 mRNA, complete cds | lo—lo-hi—hi |
| 425074 | AA495930 | | *Homo sapiens* cDNA: FLJ22165 fis, clone H | lo—lo-hi—hi |
| 426376 | N46752 | Hs.302985 | ESTs | lo—lo-hi—hi |
| 447754 | AW073310 | Hs.163533 | *Homo sapiens* cDNA FLJ14142 fis, clone MA | lo—lo-hi—hi |
| 413686 | AI469213 | Hs.71404 | ESTs | lo—lo-hi—hi |
| 449000 | U69560 | Hs.3826 | kelch-like protein C3IP1 | lo—lo-hi—hi |
| 430064 | AK000091 | Hs.231436 | hypothelical protein FLJ20084 | lo—lo-hi—hi |
| 412205 | N33818 | Hs.20274 | ESTs, Weakly similar to unnamed protein | lo—lo-hi—hi |
| 423955 | AI420582 | Hs.136164 | cutaneous T-cell lymphoma-associated turn | lo—lo-hi—hi |
| 455619 | BE063853 | | gb: QV3-BT0296-011299-022-g09 BT0296 *Homo* | lo—lo-hi—hi |
| 408722 | AA487860 | Hs.298102 | ESTs | lo—lo-hi—hi |
| 459710 | AI701596 | Hs.121592 | ESTs | lo—lo-hi—hi |
| 417918 | AA209205 | Hs.163754 | hypothetical protein FLJ12606 | lo—lo-hi—hi |
| 402964 | | | NM_022095*: *Homo sapiens* hypothetical C2H | lo—lo-hi—hi |
| 424387 | AI739312 | Hs.284163 | ANKHZN protein | lo—lo-hi—hi |
| 427220 | AF069517 | Hs.173993 | RNA binding motif protein 6 | lo—lo-hi—hi |
| 410451 | BE065687 | | gb: RC3-BT0316-270400-016-f10 BT0316 *Homo* | lo—lo-hi—hi |
| 400713 | | | NM_006165*: *Homo sapiens* nuclear factor r | lo—lo-hi—hi |
| 407218 | AA095473 | Hs.28505 | ubiquitin-conjugating enzyme E2H (homolo | lo—lo-hi—hi |
| 449312 | N71673 | Hs.223666 | ESTs | lo—lo-hi—hi |
| 419612 | AI498267 | Hs.110613 | KIAA0421 protein | lo—lo-hi—hi |
| 455272 | BE148152 | | gb: RC4-HT0231-041199-012-b04 HT0231 *Homo* | lo—lo-hi—hi |
| 401839 | | | NM_005177*: *Homo sapiens* ATPase, H+ trans | lo—lo-hi—hi |
| 440422 | AW452696 | Hs.130760 | myosin phosphatase, target subunit 2 | lo—lo-hi—hi |
| 436819 | AA731746 | Hs.120232 | ESTs | lo—lo-hi—hi |
| 413644 | BE154910 | Hs.278793 | ESTs, Weakly similar to Z195_HUMAN ZINC | lo—lo-hi—hi |
| 413939 | AL047051 | Hs.199961 | ESTs, Weakly similar to ALU7_HUMAN ALU S | lo—lo-hi—hi |
| 448198 | BE622100 | Hs.209406 | ESTs, Weakly similar to I38600 zinc fing | lo—lo-hi—hi |
| 450488 | AA009999 | Hs.59159 | ESTs, Moderately similar to HPV16 E1 pro | lo—lo-hi—hi |
| 433507 | AI817336 | Hs.191791 | ESTs | lo—lo-hi-lo |
| 438996 | AW748336 | Hs.110613 | KIAA0421 protein | lo—lo-hi-lo |
| 442789 | AW904361 | Hs.131191 | ESTs, Weakly similar to ALU7_HUMAN ALU S | lo—lo-hi-lo |
| 407251 | U67611 | | transaldolase 1 | lo—lo-hi-lo |
| 409051 | AA080912 | | gb: zn04d03.r1 Stratagene hNT neuron (937 | lo—lo-hi-lo |
| 409123 | AA063403 | | gb: zm04d12.s1 Stratagene corneal stroma | lo—lo-hi-lo |
| 416225 | AA577730 | Hs.188684 | ESTs, Weakly similar to PC4259 ferritin | lo—lo-hi-lo |
| 433735 | AA608955 | Hs.109653 | ESTs | lo—lo-hi-lo |
| 434404 | AW445034 | Hs.256578 | ESTs | lo—lo-hi-lo |
| 446667 | BE161878 | Hs.224805 | ESTs | lo—lo-hi-lo |
| 447982 | H22953 | Hs.137551 | ESTs | lo—lo-hi-lo |
| 438890 | AA827756 | Hs.135049 | ESTs, Weakly similar to ALU7_HUMAN ALU S | lo—lo-hi-lo |
| 427882 | AA640987 | Hs.193767 | ESTs | lo—lo-hi-lo |
| 459680 | H96982 | Hs.42321 | ESTs | lo—lo-hi-lo |
| 416632 | H69480 | Hs.141304 | ESTs | lo—lo-hi-lo |
| 453876 | AW021748 | Hs.110406 | ESTs, Weakly similar to I38022 hypotheti | lo—lo-hi-lo |
| 414528 | AA148950 | Hs.188836 | ESTs | lo—lo-hi-lo |
| 419902 | AA804409 | Hs.118920 | ESTs | lo—lo-hi-lo |
| 409542 | AA503020 | Hs.36563 | hypothetical protein FLJ22418 | lo—lo-hi-lo |
| 433560 | AI925195 | Hs.130891 | hypothetical protein MGC4400 | lo—lo-hi-lo |
| 447499 | AW262580 | Hs.147674 | protocadherin beta 16 | lo—lo-hi-lo |
| 435023 | AI692552 | | gb: wd73f12.x1 NCI_CGAP_Lu24 *Homo sapiens* | lo—lo-hi-lo |
| 412156 | H29487 | Hs.17110 | *Homo sapiens* mRNA: cDNA DKFZp434C2016 (f | lo—lo-hi-lo |
| 414505 | R45389 | Hs.23558 | ESTs, Weakly similar to A8042 lysosomal | lo—lo-hi-lo |
| 404277 | | | NM_019111*: *Homo sapiens* major histocompa | lo—lo-hi-lo |
| 414662 | AL036058 | Hs.76807 | major histocompatibility complex, class | lo—lo-hi-lo |
| 444430 | AI611153 | Hs.6093 | *Homo sapiens* cDNA: FLJ22783 fis, clone K | lo—lo-hi-lo |
| 445612 | N94126 | Hs.12969 | hypothetical protein | lo—lo-hi-lo |
| 403739 | | | ENSP00000251563*: UDP-glucuronosyltransfe | lo—lo-hi-lo |
| 403740 | | | NM_001076*: *Homo sapiens* UDP glycosyltran | lo—lo-hi-lo |
| 411084 | T18987 | Hs.125472 | ESTs, Moderately similar to KIAA0877 pro | lo—lo-hi-lo |
| 429143 | AA333327 | Hs.197335 | plasma glutamate carboxypeptidase | lo—lo-hi-lo |
| 443060 | D78874 | Hs.8944 | procollagen C-endopeptidase enhancer 2 | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 422749 | W01076 | Hs.278573 | CD59 antigen p18-20 (antigen identified | lo—lo-hi-lo |
| 429441 | AJ224172 | Hs.204096 | lipophilin B (uteroglobin family member) | lo—lo-hi-lo |
| 414382 | AW380339 | Hs.8068 | hematopoietic PBX-interacting protein | lo—lo-hi-lo |
| 441560 | F13386 | Hs.7888 | *Homo sapiens* clone 23736 mRNA sequence | lo—lo-hi-lo |
| 446106 | AA377165 | Hs.44833 | ESTs | lo—lo-hi-lo |
| 452239 | AW379378 | Hs.170121 | protein lyrosine phosphatase, receptor t | lo—lo-hi-lo |
| 446874 | AW968304 | Hs.56156 | ESTs | lo—lo-hi-lo |
| 412795 | BE241753 | Hs.74592 | special AT-rich sequence binding protein | lo—lo-hi-lo |
| 430325 | AF004562 | Hs.239356 | syntaxin binding protein 1 | lo—lo-hi-lo |
| 426392 | AW968324 | Hs.17384 | ESTs | lo—lo-hi-lo |
| 447448 | BE244285 | | F-box only protein 29 | lo—lo-hi-lo |
| 415743 | AA167664 | Hs.14333 | ESTs, Weakly similar to Z195__HUMAN ZINC | lo—lo-hi-lo |
| 431607 | AB033097 | Hs.183669 | KIAA1271 protein | lo—lo-hi-lo |
| 411979 | X85134 | Hs.72984 | retinoblastoma-binding protein 5 | lo—lo-hi-lo |
| 453620 | BE396163 | Hs.25005 | ESTs, Weakly similar to ALU5__HUMAN ALU S | lo—lo-hi-lo |
| 431099 | Y13367 | Hs.249235 | phosphoinositide-3-kinase, class 2, alph | lo—lo-hi-lo |
| 421687 | AL035306 | Hs.106823 | hypothetical protein MGC14797 | lo—lo-hi-lo |
| 439565 | AF086386 | Hs.145599 | ESTs | lo—lo-hi-lo |
| 442349 | W40516 | Hs.132355 | *Homo sapiens* cDNA: FLJ22119 fis, clone H | lo—lo-hi-lo |
| 410096 | AW245200 | Hs.267400 | hypothetical protein MGC5540 | lo—lo-hi-lo |
| 429447 | AW812452 | Hs.83286 | ESTs, Weakly similar to S14747 sphingomy | lo—lo-hi-lo |
| 431802 | AL133570 | Hs.270571 | *Home sapiens* mRNA; cDNA DKFZp434L201 (fr | lo—lo-hi-lo |
| 441715 | AI929453 | Hs.342655 | *Homo sapiens* cDNA FLJ13289 fis, clone OV | lo—lo-hi-lo |
| 458230 | BE311851 | Hs.6639 | KIAA1624 protein | lo—lo-hi-lo |
| 428788 | AF082283 | Hs.193516 | B-cell CLL/lymphoma 10 | lo—lo-hi-lo |
| 450818 | AI740573 | Hs.142827 | P311 protein | lo—lo-hi-lo |
| 419576 | AK002060 | Hs.91251 | hypothetical protein FLJ11198 | lo—lo-hi-lo |
| 400401 | AF159093 | | *Homo sapiens* endogenous retrovirus RAN1 | lo—lo-hi-lo |
| 427004 | AI921573 | HS.213107 | ESTs | lo—lo-hi-lo |
| 401178 | AA046772 | | RNA binding motif protein, X chromosome | lo—lo-hi-lo |
| 423749 | U09848 | Hs.132390 | zinc finger protein 36 (KOX 18) | lo—lo-hi-lo |
| 428898 | AB033070 | Hs.194408 | KIAA1244 protein | lo—lo-hi-lo |
| 458258 | AW406546 | Hs.127971 | ESTs | lo—lo-hi-lo |
| 429521 | BE048708 | Hs.50949 | ESTs | lo—lo-hi-lo |
| 402185 | | | Target Exon | lo—lo-hi-lo |
| 415961 | H10983 | Hs.155919 | ESTs | lo—lo-hi-lo |
| 457265 | AB023212 | Hs.225967 | KIAA0995 protein | lo—lo-hi-lo |
| 412419 | AW948630 | | gb: QV0-FT0001-050500-226-g05 FT0001 *Homo* | lo—lo-hi-lo |
| 438397 | AA806478 | Hs.123206 | ESTs | lo—lo-hi-lo |
| 440509 | BE410132 | Hs.134202 | ESTs, Weakly similar to T17279 hypotheti | lo—lo-hi-lo |
| 423895 | AA332215 | | gb: EST36124 Embryo, 8 week I Homo sapien | lo—lo-hi-lo |
| 400251 | | | NM__004651*: *Homo sapiens* ubiquitin specif | lo—lo-hi-lo |
| 445094 | AW296163 | Hs.147296 | ESTs | lo—lo-hi-lo |
| 432323 | AK001409 | Hs.274356 | hypothetical protein FLJ10547 | lo—lo-hi-lo |
| 444290 | AA262496 | | gb: zs20f11.r1 NCI__CGAP__GCB1 *Homo sapiens* | lo—lo-hi-lo |
| 435803 | Z44194 | Hs.4994 | transducer of ERBB2, 2 | lo—lo-hi-lo |
| 436905 | N31273 | Hs.42380 | ESTs | lo—lo-hi-lo |
| 401849 | | | Target Exon | lo—lo-hi-lo |
| 402249 | | | C19000553*: gi\|12741444\|ref\|XP__008888.2\| | lo—lo-hi-lo |
| 406180 | AB018249 | | small inducible cytokine subfamily A (Cy | lo—lo-hi-lo |
| 448176 | AI672546 | Hs.170507 | ESTs | lo—lo-hi-lo |
| 409259 | AW608930 | Hs.52184 | hypothetical protein FLJ20618 | lo—lo-hi-lo |
| 457335 | AW969834 | Hs.303303 | ESTs | lo—lo-hi-lo |
| 452444 | BE144022 | | gb: MR0-HT0165-191199-004-f05 HT0165 *Homo* | lo—lo-hi-lo |
| 405429 | | | Target Exon | lo—lo-hi-lo |
| 430103 | AA465259 | | gb: aa33b03.r1 NCI__CGAP__GCB1 *Homo sapiens* | lo—lo-hi-lo |
| 439944 | AA856767 | Hs.124623 | ESTs | lo—lo-hi-lo |
| 411283 | AW852754 | | gb: PM1-CT0247-180100-009-c05 CT0247 *Homo* | lo—lo-hi-lo |
| 458195 | R10085 | Hs.130370 | ESTs | lo—lo-hi-lo |
| 452654 | BE004783 | | gb: MR2-BN0114-270400-004-e11 BN0114 *Homo* | lo—lo-hi-lo |
| 425684 | AF000989 | Hs.159201 | thymosin, beta 4, Y chromosome | lo—lo-hi-lo |
| 29452 | AI949495 | Hs.133998 | *Homo sapiens* cDNA FLJ13202 fis, clone NT | lo—lo-hi-lo |
| 431709 | AF220185 | Hs.267923 | uncharacterized hypothalamus protein HT0 | lo—lo-hi-lo |
| 411701 | BE181659 | | gb: QV1-HT0638-070500-191-g07 HT0636 *Homo* | lo—lo-hi-lo |
| 430729 | AI572560 | Hs.301283 | KIAA0793 gene product | lo—lo-hi-lo |
| 447476 | BE293466 | Hs.20880 | ESTs, Weakly similar to I38022 hypotheti | lo—lo-hi-lo |
| 450436 | AW293661 | Hs.131887 | ESTs | lo—lo-hi-lo |
| 405365 | | | CX001212*: gi\|7861932\|gb\|AAF70445.1\| (AF2 | lo—lo-hi-lo |
| 419555 | AA244416 | | gb: nc07d11.s1 NCI__CGAP__Pr1 *Homo sapiens* | lo—lo-hi-lo |
| 448103 | U90918 | Hs.13804 | hypothetical protein dJ462O23.2 | lo—lo-hi-lo |
| 400986 | | | NM__024085*: *Homo sapiens* hypothetical pro | lo—lo-hi-lo |
| 424194 | BE245833 | Hs.169854 | gb: TCBAP1E1908 Pediatric pre-B cell acut | lo—lo-hi-lo |
| 400210 | | | Eos Control | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 400234 | | | NM_005336: *Homo sapiens* high density lipo | lo—lo-hi-lo |
| 400235 | | | NM_005336: *Homo sapiens* high density lipo | lo—lo-hi-lo |
| 405387 | | | NM_022170*: *Homo sapiens* Williams-Beuren | lo—lo-hi-lo |
| 433075 | NM_002959 | | sortilin 1 | lo—lo-hi-lo |
| 406302 | | | C16000922: gi\|7499103\|pir\|\|T20903 hypothe | lo—lo-hi-lo |
| 428181 | AA423976 | | gb: zv62h06.s1 Soares_testis_NHT *Homo sap* | lo—lo-hi-lo |
| 456629 | AW891965 | Hs.279789 | histone deacetylase 3 | lo—lo-hi-lo |
| 426940 | AA393537 | Hs.98347 | ESTs, Weakly similar to JC5308 testis-sp | lo—lo-hi-lo |
| 433555 | AA535902 | Hs.146211 | *Homo sapiens* HERC2P7 pseudogene, partial | lo—lo-hi-lo |
| 421431 | AA650117 | Hs.283107 | ESTs | lo—lo-hi-lo |
| 448631 | AI554923 | | gb: te53h12.x1 Soares_NFL_T_GBC_S1 *Homo s* | lo—lo-hi-lo |
| 433521 | T66087 | Hs.112482 | *Homo sapiens* unknown mRNA sequence | lo—lo-hi-lo |
| 407187 | AA446971 | | gb: zw85f11.s1 Soares_total_fetus_Nb2HF8_ | lo—lo-hi-lo |
| 450739 | AI732707 | Hs.116506 | ESTs, Weakly similar to ALU7_HUMAN ALU S | lo—lo-hi-lo |
| 440004 | BE397117 | Hs.120824 | hypothetical protein FLJ21845 | lo—lo-hi-lo |
| 403947 | NM_005032 | | plastin 3 (T isoform) | lo—lo-hi-lo |
| 405529 | AW410458 | | chromosome 11 open reading frame2 | lo—lo-hi-lo |
| 402163 | | | C19001075*: gi\|4567179\|gb\|AAD23607.1\|AC00 | lo—lo-hi-lo |
| 404663 | | | ENSP00000251884: KIAA1521 protein (Fragme | lo—lo-hi-lo |
| 400220 | | | Eos Control | lo—lo-hi-lo |
| 401444 | | | Target Exon | lo—lo-hi-lo |
| 455824 | BE143703 | | gb: MR0-HT0164-191199-004-f03 HT0164 *Homo* | lo—lo-hi-lo |
| 400206 | | | Eos Control | lo—lo-hi-lo |
| 458659 | AW749895 | Hs.332520 | *Homo sapiens* mRNA; cDNA DKFZp434A1014 (f | lo—lo-hi-lo |
| 428866 | AL080190 | Hs.189242 | *Homo sapiens* mRNA4; cDNA DKFZp434A202 (fr | lo—lo-hi-lo |
| 428442 | AA428638 | Hs.98606 | ESTs | lo—lo-hi-lo |
| 440151 | AA868167 | | gb: ak38e07.s1 Soares_testis_NHT *Homo sap* | lo—lo-hi-lo |
| 431046 | AW854382 | Hs.249126 | *Home sapiens* clone 24894 mRNA sequence | lo—lo-hi-lo |
| 443914 | AI091173 | Hs.222362 | ESTs, Weakly similar to p40 [*H. sapiens*] | lo—lo-hi-lo |
| 402469 | | | Target Exon | lo—lo-hi-lo |
| 418155 | R45481 | Hs.23719 | ESTs, Weakly similar to I38022 hypotheti | lo—lo-hi-lo |
| 446893 | AI610818 | Hs.7110 | ESTs | lo—lo-hi-lo |
| 442336 | AW340958 | Hs.7572 | ESTs | lo—lo-hi-lo |
| 421290 | NM_014368 | Hs.103137 | LIM homeobox protein 6 | lo—lo-hi-lo |
| 450374 | AA397540 | Hs.60293 | *Homo sapiens* clone 122482 unknown mRNA | lo—lo-hi-lo |
| 402347 | | | Target Exon | lo—lo-hi-lo |
| 415184 | AA380436 | Hs.211973 | homolog of Yeast RRP4 (ribosomal RNA pro | lo—lo-hi-lo |
| 415632 | U67085 | Hs.78524 | TcD37 homolog | lo—lo-hi-lo |
| 423718 | AL119520 | Hs.180737 | *Homo sapiens* clone 23664 and 23905 mRNA | lo—lo-hi-lo |
| 449140 | AW013840 | Hs.202092 | ESTs | lo—lo-hi-lo |
| 431241 | AA496799 | Hs.36958 | ESTs | lo—lo-hi-lo |
| 416631 | H69466 | | gb: yr88f07.r1 Soares fetal liver spleen | lo—lo-hi-lo |
| 424168 | L29277 | Hs.321677 | signal transducer and activator of trans | lo—lo-hi-lo |
| 401600 | BE247275 | | U5 snRNP-specific protein, 116 kD | lo—lo-hi-lo |
| 420588 | AF000982 | Hs.147916 | DEAD/H (Asp-Glu-Ala-Asp/His) box polypep | lo—lo-hi-lo |
| 414111 | BE047679 | Hs.152982 | hypothetical protein FLJ13117 | lo—lo-hi-lo |
| 417138 | AA193646 | Hs.65771 | *Homo sapiens* chromosome 19, BAC CIT-HSPC | lo—lo-hi-lo |
| 424318 | AA476515 | Hs.172723 | ESTs | lo—lo-hi-lo |
| 455653 | BE154075 | | gb: PM0-HT0339-200400-010-E05 HT0339 *Homo* | lo—lo-hi-lo |
| 451493 | H38656 | Hs.32854 | ESTs | lo—lo-hi-lo |
| 457015 | AA688058 | Hs.261544 | ESTs | lo—lo-hi-lo |
| 403654 | | | NM_003071: *Homo sapiens* SWI/SNF related, | lo—lo-hi-lo |
| 435203 | AW957127 | Hs.294027 | ESTs | lo—lo-hi-lo |
| 409322 | BE091159 | Hs.22687 | ESTs, Moderately similar to unnamed prot | lo—lo-hi-lo |
| 437764 | AA767795 | Hs.166832 | ESTs | lo—lo-hi-lo |
| 432542 | AW083920 | Hs.16098 | claudin 2 | lo—lo-hi-lo |
| 436125 | AA765895 | Hs.152895 | ESTs | lo—lo-hi-lo |
| 403217 | AL134878 | | ribosomal protein, large P2 | lo—lo-hi-lo |
| 434023 | AI277883 | Hs.146141 | ESTs | lo—lo-hi-lo |
| 442419 | AI749893 | Hs.270532 | ESTs, Weakly similar to I38022 hypotheti | lo—lo-hi-lo |
| 443667 | AI129066 | Hs.135457 | ESTs | lo—lo-hi-lo |
| 451445 | AA017609 | Hs.343449 | gb: ze37e01.r1 Soares retina N2b4HR *Homo* | lo—lo-hi-lo |
| 454775 | BE160229 | | gb: QV1-HT0413-090200-062-a12 HT0413 *Homo* | lo—lo-hi-lo |
| 411053 | AW815061 | | gb: CM0-ST0209-271099-082-d10 ST0209 *Homo* | lo—lo-hi-lo |
| 435312 | AJ243396 | Hs.4865 | voltage-gated sodium channel beta-3 subu | lo—lo-hi-lo |
| 450875 | AK000724 | Hs.301553 | karyopherin alpha 6 (importin alpha 7) | lo—lo-hi-lo |
| 451180 | H61899 | Hs.171937 | steroid dehydrogenase like | lo—lo-hi-lo |
| 427327 | AW501456 | Hs.288283 | *Homo sapiens* cDNA: FLJ22355 fis, clone H | lo—lo-hi-lo |
| 444321 | AW204210 | Hs.122275 | *Homo sapiens* mRNA; cDNA DKFZp564N1623(f | lo—lo-hi-lo |
| 405109 | N47812 | | CGI-35 protein | lo—lo-hi-lo |
| 450182 | AI796400 | Hs.240767 | Human DNA sequence from clone RP1-12G14 | lo—lo-hi-lo |
| 424990 | AU076896 | Hs.154095 | zinc finger protein 143 (clone pHZ-1) | lo—lo-hi-lo |
| 428997 | AF065391 | Hs.194718 | zinc finger protein 265 | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 402602 | | | NM_021186*: *Homo sapiens* zona pellucida g | lo—lo-hi-lo |
| 428772 | AI524039 | Hs.192524 | ESTs | lo—lo-hi-lo |
| 423759 | AI142358 | Hs.184361 | ESTs, Moderately similar to ALU7_HUMAN A | lo—lo-hi-lo |
| 434350 | AL042940 | Hs.93872 | KIAA1682 protein | lo—lo-hi-lo |
| 442274 | AI733484 | Hs.129182 | ESTs | lo—lo-hi-lo |
| 442884 | AI076570 | Hs.134053 | ESTs | lo—lo-hi-lo |
| 400481 | | | Target Exon | lo—lo-hi-lo |
| 407283 | T51008 | | gb: yb55e08.s1 Stratagene ovary (937217) | lo—lo-hi-lo |
| 408859 | AW291672 | Hs.258981 | ESTs | lo—lo-hi-lo |
| 455615 | BE045344 | Hs.274923 | ESTs, Moderately similar to unnamed prot | lo—lo-hi-lo |
| 427315 | AA179949 | Hs.175563 | *Homo sapiens* mRNA; cDNA DKFZp564N0763 (f | lo—lo-hi-lo |
| 449375 | R07114 | Hs.271224 | ESTs | lo—lo-hi-lo |
| 419937 | AB040959 | Hs.93836 | DKFZP434N014 protein | lo—lo-hi-lo |
| 422231 | AA443512 | Hs.101383 | ESTs | lo—lo-hi-lo |
| 437210 | AA311443 | Hs.293563 | *Homo sapiens* mRNA; cDNA DKFZp586E2317 (f | lo—lo-hi-lo |
| 418056 | AA524886 | | gb: nh34f02.s1 NCI_CGAP_Pr3 *Homo sapiens* | lo—lo-hi-lo |
| 446586 | N58790 | Hs.268820 | ESTs | lo—lo-hi-lo |
| 407949 | W21874 | Hs.247057 | ESTs, Weakly similar to 2109260A B cell | lo—lo-hi-lo |
| 440296 | D30829 | Hs.180610 | splicing factor proline/glutamine rich ( | lo—lo-hi-lo |
| 422260 | AA315993 | Hs.105484 | regenerating gene type IV | lo—lo-hi-lo |
| 434685 | AA642445 | Hs.287467 | *Homo sapiens* cDNA FLJ11948 fis, clone HE | lo—lo-hi-lo |
| 412657 | AW976165 | | gb: EST388274 MAGE resequences, MAGN *Homo* | lo—lo-hi-lo |
| 405188 | | | Taget Exon | lo—lo-hi-lo |
| 416954 | AI222358 | | gb: qh04c12.x1 Soares_NFL_T_GBC_S1 *Homo s* | lo—lo-hi-lo |
| 423700 | AA232375 | Hs.58606 | SNRPN upstream reading frame | lo—lo-hi-lo |
| 430288 | BE394943 | Hs.13804 | hypothetical protein dJ462O23.2 | lo—lo-hi-lo |
| 435184 | T67162 | Hs.135127 | ESTs, Weakly similar to unnamed protein | lo—lo-hi-lo |
| 431475 | AI567669 | Hs.40342 | putative nuclear protein | lo—lo-hi-lo |
| 445239 | AI217375 | Hs.170023 | ESTs, Weakly similar to CA36_HUMAN COLLA | lo—lo-hi-lo |
| 436151 | AK000801 | Hs.324271 | *Homo sapiens* cDNA FLJ20794 fis, clone CO | lo—lo-hi-lo |
| 448489 | AI523875 | | gb: tg97d04.x1 NCI_CGAP_CLL1 *Homo sapiens* | lo—lo-hi-lo |
| 424470 | BE244261 | Hs.323502 | *Homo sapiens* cDNA: FLJ23539 fis, clone L | lo—lo-hi-lo |
| 434733 | AI334367 | Hs.159337 | ESTs | lo—lo-hi-lo |
| 409469 | AW517236 | Hs.335762 | ESTs | lo—lo-hi-lo |
| 414034 | U89277 | Hs.305985 | early development regulator 1 (homolog o | lo—lo-hi-lo |
| 420382 | AW959165 | Hs.270034 | *Homo sapiens*, Similar to nuclear localiz | lo—lo-hi-lo |
| 430433 | AA478883 | Hs.273766 | ESTs | lo—lo-hi-lo |
| 435351 | T80177 | Hs.118064 | similar to rat nuclear ubiquitous casein | lo—lo-hi-lo |
| 403218 | AL134878 | | ribosomal protein, large P2 | lo—lo-hi-lo |
| 420678 | AW593288 | Hs.3530 | TLS-associated serine-arginine protein 2 | lo—lo-hi-lo |
| 445808 | AV655234 | | ESTs, Moderately similar to PC4259 ferri | lo—lo-hi-lo |
| 429933 | AA765596 | Hs.187691 | ESTs | lo—lo-hi-lo |
| 419802 | AA250950 | Hs.154334 | ESTs | lo—lo-hi-lo |
| 425155 | W26522 | Hs.75890 | gb: 32g2 Human retina cDNA randomly prime | lo—lo-hi-lo |
| 417314 | N68168 | | gb: za11c01.s1 Soares fetal liver spleen | lo—lo-hi-lo |
| 428290 | AI932995 | Hs.183475 | *Homo sapiens* clone 25061 mRNA sequence | lo—lo-hi-lo |
| 422128 | AW881145 | | gb: QV0-OT0033-010400-182-a07 OT10033 *Homo* | lo—lo-hi-lo |
| 432014 | H66741 | Hs.38540 | ESTs, Weakly similar to ALU4_HUMAN ALU S | lo—lo-hi-lo |
| 407351 | AW383165 | | gb: PM3-HT0344-151299-004-f07 HT0344 *Homo* | lo—lo-hi-lo |
| 443231 | W87548 | Hs.132932 | ESTs | lo—lo-hi-lo |
| 444001 | AI095087 | Hs.152299 | ESTs, Moderately similar to S65857 alpha | lo—lo-hi-lo |
| 435064 | T70740 | Hs.31433 | ESTs | lo—lo-hi-lo |
| 435173 | AW295645 | Hs.255451 | ESTs | lo—lo-hi-lo |
| 411831 | AW994394 | | gb: RC3-BN0036-060400-014-h12 BN0036 *Homo* | lo—lo-hi-lo |
| 446572 | AV659151 | Hs.282961 | ESTs | lo—lo-hi-lo |
| 428114 | AI821548 | Hs.98363 | ESTs, Weakly similar to I38022 hypotheti | lo—lo-hi-lo |
| 406207 | | | Target Exon | lo—lo-hi-lo |
| 405011 | | | Target Exon | lo—lo-hi-lo |
| 409451 | AF012626 | Hs.54472 | fragile X mental retardation 2 | lo—lo-hi-lo |
| 411233 | AW833793 | | gb: QV4-TT0008-130100-080-a06 TT0008 *Homo* | lo—lo-hi-lo |
| 455729 | BE072092 | | gb: PM4-BT0532-160200-003-b11 B10532 *Homo* | lo—lo-hi-lo |
| 439454 | AA836120 | Hs.258958 | ESTs | lo—lo-hi-lo |
| 445124 | AI806403 | Hs.143942 | ESTs | lo—lo-hi-lo |
| 410324 | AW292539 | Hs.30177 | ESTs | lo—lo-hi-lo |
| 446548 | AI769392 | Hs.200215 | ESTs | lo—lo-hi-lo |
| 416999 | AW195747 | Hs.21122 | hypothetical protein FLJ11830 similar to | lo—lo-hi-lo |
| 414553 | AI813865 | Hs.164478 | hypothetical protein FLJ21939 similar to | lo—lo-hi-lo |
| 444647 | H14718 | Hs.11506 | Human clone 23589 mRNA sequence | lo—lo-hi-lo |
| 418271 | NM_000919 | Hs.83920 | peptidylglycine alpha-amidating monooxyg | lo—lo-hi-lo |
| 407939 | W05608 | Hs.312679 | ESTs, Weakly similar to A49019 dynein he | lo—lo-hi-lo |
| 432676 | AI187366 | | gb: qf29c01.x1 Soares_testis_NHT *Homo sap* | lo—lo-hi-lo |
| 415156 | X84908 | Hs.78060 | phosphorylase kinase, beta | lo—lo-hi-lo |
| 432679 | AI146956 | Hs.146723 | ESTs, Weakly similar to A53950 transcrip | lo—lo-hi-lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 412121 | AB033061 | Hs.73287 | KIAA1235 protein | lo—lo-hi-lo |
| 418858 | AW961605 | Hs.21145 | hypothetical protein RG083M05.2 | lo—lo-hi-lo |
| 425204 | NM_002436 | Hs.1861 | membrane protein, palmitoylated 1 (55 kD) | lo—lo-hi-lo |
| 418348 | AI537167 | Hs.96322 | hypothetical protein FLJ23560 | lo—lo-hi-lo |
| 410765 | AI694972 | Hs.66180 | nucleosome assembly protein 1-like 2 | lo—lo-hi-lo |
| 445594 | AW058463 | Hs.12940 | zinc-fingers and homeoboxes 1 | lo—lo-hi-lo |
| 416503 | H98502 | Hs.269853 | ESTs | lo—lo-hi-lo |
| 426167 | AF039023 | Hs.167496 | RAN binding protein 6 | lo—lo-hi-lo |
| 451752 | AB032997 | Hs.26966 | KIAA1171 protein | lo—lo-hi-lo |
| 447124 | AW976438 | Hs.17428 | RBP1-like protein | lo—lo-hi-lo |
| 419872 | AI422951 | Hs.146162 | ESTs | lo—lo-hi-lo |
| 443161 | AI038316 | | gb: ox48c08.x1 Soares_total_fetus_Nb2HF8_ | lo—lo-hi-lo |
| 445391 | T92576 | Hs.191168 | ESTs | lo—lo-hi-lo |
| 443801 | AW206942 | Hs.253594 | intron of: trichorhinophalangeal syndro | lo—lo-hi-lo |
| 446706 | AW807631 | Hs.190488 | *Homo sapiens*, Similar to nuclear localiz | lo—lo-hi-lo |
| 428172 | U09367 | Hs.182828 | zinc finger protein 136 (clone pHZ-20) | lo—lo-hi-lo |
| 421021 | AA808018 | Hs.109302 | ESTs | lo—lo-hi-lo |
| 431749 | AL049263 | Hs.306292 | *Homo sapiens* mRNA; cDNA DKFZp564F133 (fr | lo—lo-hi-lo |
| 423784 | AK000039 | Hs.132826 | *Homo sapiens* cDNA FLJ14913 fis, clone PL | lo—lo-hi-lo |
| 419479 | AI288348 | Hs.23450 | mitochondrial ribosomal protein S25 | lo—lo-hi-lo |
| 450900 | H61005 | Hs.37902 | ESTs | lo—lo-hi-lo |
| 423396 | AI382555 | Hs.127950 | bromodomain-containing 1 | lo—lo-hi-lo |
| 426137 | AL040683 | Hs.167031 | DKFZP566D133 protein | lo—lo-hi-lo |
| 442012 | AI733277 | Hs.128321 | ESTs | lo—lo-hi-lo |
| 452271 | AA025976 | Hs.34569 | ESTs | lo—lo-hi-lo |
| 414882 | D79994 | Hs.77546 | *Homo sapiens* cDNA: FLJ21983 fis, clone H | lo—lo-hi-lo |
| 432195 | AJ243669 | Hs.8127 | KIAA0144 gene product | lo—lo-hi-lo |
| 430217 | N47863 | Hs.180450 | ribosomal protein S24 | lo—lo-hi-lo |
| 429567 | R35606 | Hs.326800 | Human EST done 53125 mariner transposon | lo—lo-hi-lo |
| 438810 | AW897846 | Hs.6421 | hypothetical protein DKFZp761N09121 | lo—lo-hi-lo |
| 436796 | BE515260 | Hs.5320 | hypothetical protein | lo—lo-hi-lo |
| 426352 | N72324 | Hs.55098 | ESTs | lo—lo-hi-lo |
| 415308 | F05251 | | gb: HSC04H101 normalized infant brain cDN | lo—lo-hi-lo |
| 420148 | U34227 | Hs.95361 | myosin VIIA (Usher syndrome 10 (autosoma | lo—lo-hi-lo |
| 434442 | AA737415 | Hs.152826 | ESTs | lo—lo-hi-lo |
| 449429 | AA054224 | Hs.59847 | ESTs | lo—lo-hi-lo |
| 410245 | C17908 | Hs.194125 | ESTs | lo—lo-hi-lo |
| 421168 | AF182277 | Hs.330780 | cytochrome P450, subfamily IIB (phenobar | lo—lo-hi-lo |
| 436237 | R11528 | Hs.271968 | ESTs | lo—lo-hi-lo |
| 440668 | AI989538 | Hs.191074 | ESTs | lo—lo-hi-lo |
| 422068 | AI807519 | Hs.104520 | *Homo sapiens* cDNA FLJ13694 fis, clone PL | lo—lo-hi-lo |
| 410216 | BE061839 | | gb: RC1-BT0254-290100-015-a05 BT0254 *Homo* | lo—lo-hi-lo |
| 439437 | AI207788 | Hs.343628 | sialyltransferase 4B (beta-galactosidase | lo—lo-hi-lo |
| 417061 | AI675044 | Hs.188691 | *Homo sapiens* cDNA FLJ12033 fis, clone HE | lo—lo-hi-lo |
| 403046 | | | NM_005656*: *Homo sapiens* transmembrane pr | lo—lo-hi-lo |
| 404528 | AI912555 | | peptide YY, 2 (seminalplasmin) | lo—lo-hi-lo |
| 439734 | AC005013 | Hs.149 | cAMP response element-binding protein CR | lo—lo-hi-lo |
| 452997 | N64777 | Hs.44656 | ESTs | lo—lo-hi-lo |
| 403745 | | | ENSP00000226812*: KIAA1494 protein (Fragm | lo—lo-hi-lo |
| 411448 | AA178955 | Hs.271439 | ESTs, Weakly similar to I38022 hypotheti | lo—lo-hi-lo |
| 422460 | AW445014 | Hs.197746 | ESTs | lo—lo-hi-lo |
| 404058 | | | Target Exon | lo—lo-hi-lo |
| 436184 | BE154067 | Hs.136660 | ESTs, Weakly similar to ZN91_HUMAN ZINC | lo—lo-hi-lo |
| 427702 | N76589 | Hs.14454 | ESTs, Weakly similar to TFIID subunit TA | lo—lo-hi-lo |
| 440695 | AW088363 | Hs.246240 | ESTs | lo—lo-hi-lo |
| 424881 | AL119690 | Hs.153618 | HCGVIII-1 protein | lo—lo-hi-lo |
| 440573 | BE550891 | Hs.270624 | ESTs | lo—lo-hi-lo |
| 416659 | W22048 | Hs.64753 | gb: 61A12 Human retina cDNA Tsp509I-cleav | lo—lo-hi—hi |
| 436731 | AA580691 | Hs.180789 | S164 protein | lo—lo-hi—hi |
| 405102 | | | C15001220*: gi\|4469558\|gb\|AAD21311.1\|(AF | lo—lo-hi—hi |
| 450219 | AI826999 | Hs.224624 | ESTs | lo—lo-hi—hi |
| 404527 | AI912555 | | peptide YY, 2 (seminalplasmin) | lo—lo-hi—hi |
| 439158 | R60323 | Hs.193888 | ESTs | lo—lo-hi—hi |
| 431952 | Z70695 | Hs.272240 | *Homo sapiens* cDNA FLJ11086 fis, clone PL | lo—lo-hi—hi |
| 418584 | NM_004606 | Hs.1179 | TATA box binding protein (TBP)-associate | lo—lo-hi—hi |
| 424241 | AW995948 | Hs.182339 | *Homo sapiens* pyruvate dehydrogenase kina | lo—lo-hi—hi |
| 410124 | AW962229 | Hs.128927 | *Homo sapiens* cDNA FLJ13903 fis, clone TH | lo—lo-hi—hi |
| 435955 | AA830515 | Hs.222917 | ESTs | lo—lo-hi—hi |
| 424001 | W67883 | Hs.137476 | paternally expressed 10 | hi—hi-lo—lo |
| 441399 | AI630844 | Hs.126919 | ESTs | hi—hi-lo—lo |
| 440184 | AB002297 | Hs.7022 | dedicator of cyto-kinesis 3 | hi—hi-lo—lo |
| 421996 | AW583807 | Hs.1460 | glucagon | hi—hi-lo—lo |
| 444252 | R21135 | Hs.54985 | ESTs | hi—hi-lo—lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 402082 | | | C18000743*: gi\|6678363\|ref\|NP_033416.1\|t | hi—hi-lo—lo |
| 405396 | | | C22000452*: gi\|6981522\|ref\|NP_036781.1\|r | hi—hi-lo—lo |
| 412457 | T32587 | Hs.170414 | paired basic amino acid cleaving system | hi—hi-lo—lo |
| 415808 | R21439 | Hs.334578 | *Homo sapiens*, clone IMAGE: 3929520, mRNA | hi—hi-lo—lo |
| 441494 | AW452344 | Hs.129977 | ESTs | hi—hi-lo—lo |
| 437330 | AL353944 | Hs.50115 | *Homo sapiens* mRNA; cDNA DKFZp761J1112 (f | hi—hi-lo—lo |
| 452784 | BE463857 | Hs.151258 | hypothetical protein FLJ21062 | hi—hi-lo—lo |
| 410037 | AB020725 | Hs.58009 | KIAA0918 protein | hi—hi-lo—lo |
| 449145 | AI632122 | Hs.198408 | ESTs | hi—hi-lo—lo |
| 452487 | AW207659 | Hs.6630 | *Homo sapiens* cDNA FLJ13329 fis, clone OV | hi—hi-lo—lo |
| 431031 | AA830335 | Hs.105273 | ESTs | hi—hi-lo—lo |
| 427209 | H06509 | Hs.92423 | KIAA1566 protein | hi—hi-lo—lo |
| 434280 | BE005398 | | gb: CM1-BN0116-150400-189-h02 BN0116 *Homo* | hi—hi-lo—lo |
| 418236 | AW994005 | Hs.337534 | ESTs | hi—hi-lo—lo |
| 429201 | X03178 | Hs.198246 | group-specific component (vitamin D bind | hi—hi-lo—lo |
| 416653 | AA768553 | Hs.193145 | metallothionein 1E (functional) | hi—hi-lo—lo |
| 422501 | AA354690 | Hs.144967 | ESTs | hi—hi-lo—lo |
| 425087 | R62424 | Hs.126059 | ESTs | hi—hi-lo—lo |
| 426798 | AA385062 | Hs.130260 | ESTs | hi—hi-lo—lo |
| 443798 | R07848 | Hs.188522 | ESTs | hi—hi-lo—lo |
| 427254 | AL121523 | Hs.97774 | ESTs | hi—hi-lo—lo |
| 431657 | AI345227 | Hs.105448 | ESTs, Weakly similar to B34087 hypotheti | hi—hi-lo—lo |
| 409963 | AA133590 | Hs.250857 | calcium/calmodulin-dependent protein kin | hi—hi-lo—lo |
| 446006 | NM_004403 | Hs.13530 | deafness, autosomal dominant 5 | hi—hi-lo—lo |
| 418259 | AA215404 | | ESTs | hi—hi-lo—lo |
| 410173 | AA706017 | Hs.119944 | ESTs | hi—hi-lo—lo |
| 436023 | T81819 | Hs.302251 | ESTs | hi—hi-lo—lo |
| 448428 | AF282874 | Hs.21201 | nectin 3; DKFZP566B0846 protein | hi—hi-lo—lo |
| 430665 | BE350122 | Hs.157367 | ESTs, Weakly similar to I78885 serine/th | hi—hi-lo—lo |
| 432559 | AW452948 | Hs.257631 | ESTs | hi—hi-lo—lo |
| 451572 | AA018556 | Hs.268691 | ESTs, Moderately similar to ALU2_HUMAN A | hi—hi-lo—lo |
| 456032 | AW957446 | Hs.301711 | ESTs | hi—hi-lo—lo |
| 438209 | AL120659 | Hs.6111 | aryl-hydrocarbon receptor nuclear transl | hi—hi-lo—lo |
| 438337 | AK002058 | Hs.6166 | hypothetical protein FLJ11196 | hi—hi-lo—lo |
| 431795 | AK002088 | Hs.270124 | *Homo sapiens* cDNA FLJ11226 fis, clone PL | hi—hi-lo—lo |
| 421114 | AW975051 | Hs.293156 | ESTs, Weakly similar to I78885 serine/th | hi—hi-lo—lo |
| 431843 | AA516420 | | ESTs, Weakly similar to I38022 hypotheti | hi—hi-lo—lo |
| 440948 | AW188311 | Hs.128619 | ESTs | hi—hi-lo—lo |
| 430105 | X70297 | Hs.2540 | cholinergic receptor, nicotinic, alpha p | hi—hi-lo—lo |
| 439046 | AA947354 | | gb: od86e11.s1 NCI_CGAP_Ov2 *Homo sapiens* | hi—hi-lo—lo |
| 451491 | AI972094 | Hs.286221 | *Homo sapiens* cDNA FLJ13741 fis, clone PL | hi—hi-lo—lo |
| 452789 | AW081626 | Hs.242561 | ESTs | hi—hi-lo—lo |
| 419829 | AI924228 | Hs.115185 | ESTs, Moderately similar to PC4259 ferri | hi—hi-lo—lo |
| 449567 | AI990790 | Hs.188614 | ESTs | hi—hi-lo—lo |
| 407787 | N21307 | Hs.13477 | ESTs, Weakly similar to 1207289A reverse | hi—hi-lo—lo |
| 409091 | AW970386 | Hs.269423 | ESTs | hi—hi-lo—lo |
| 435354 | AA678267 | Hs.117115 | ESTs | hi—hi-lo—lo |
| 444809 | BE207568 | Hs.208219 | oculospanin | hi—hi-lo—lo |
| 422170 | AI791949 | Hs.112432 | anti-Mullerian hormone | hi—hi-lo—lo |
| 453582 | AW854339 | Hs.33476 | hypothetical protein FLJ11937 | hi—hi-lo—lo |
| 435905 | AW997484 | Hs.5003 | KIAA0456 protein | hi—hi-lo—lo |
| 443884 | N20617 | Hs.194397 | leptin receptor | hi—hi-lo—lo |
| 430027 | AB023197 | Hs.227743 | KIAA0980 protein | hi—hi-lo—lo |
| 432582 | AI623817 | Hs.168457 | ESTs | hi—hi-lo—lo |
| 417993 | AW963705 | Hs.301183 | molecule possessing ankyrin repeats indu | hi—hi-lo—lo |
| 444930 | BE185536 | Hs.301183 | molecule possessing ankyrin repeats indu | hi—hi-lo—lo |
| 427794 | AA709186 | Hs.99070 | ESTs | hi—hi-lo—lo |
| 410913 | AL050367 | Hs.66762 | *Homo sapiens* mRNA; cDNA DKFZp564A026 (fr | hi—hi-lo—lo |
| 431992 | NM_002742 | Hs.2891 | protein kinase C, mu | hi—hi-lo—lo |
| 447846 | AA324057 | Hs.77955 | *Homo sapiens* cDNA: FLJ23527 fis, clone L | hi—hi-lo—lo |
| 430439 | AL133561 | | DKFZP434B061 protein | hi—hi-lo—lo |
| 432621 | AI298501 | Hs.12807 | ESTs, Weakly similar to T46428 hypotheti | hi—hi-lo—lo |
| 431427 | AK000401 | Hs.252748 | *Homo sapiens* cDNA FLJ20394 fis, clone KA | hi—hi-lo—lo |
| 408872 | AI476139 | Hs.13921 | ESTs | hi—hi-lo—lo |
| 453200 | AA033832 | Hs.212433 | ESTs | hi—hi-lo—lo |
| 411529 | AA430348 | Hs.317596 | *Homo sapiens* cDNA FLJ12927 fis, clone NT | hi—hi-lo—lo |
| 414483 | R25513 | Hs.10683 | ESTs | hi—hi-lo—lo |
| 451273 | NM_014811 | Hs.26163 | KIAA0649 gene product | hi—hi-lo—lo |
| 437052 | AA861697 | Hs.120591 | ESTs | hi—hi-lo—lo |
| 440049 | R06699 | Hs.19769 | hypothetical protein MGC4174 | hi—hi-lo—lo |
| 429483 | AA974832 | Hs.128708 | ESTs | hi—hi-lo—lo |
| 411296 | BE207307 | Hs.10114 | growth suppressor 1 | hi—hi-lo—lo |
| 425188 | AK002052 | Hs.155071 | hypothetical protein FLJ11190 | hi—hi-lo—lo |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 436315 | BE390513 | Hs.27935 | hypothetical protein MGC4837 | hi—hi-lo—lo |
| 400297 | AI127076 | Hs.306201 | hypothetical protein DKFZp564O1278 | hi—hi-lo—lo |
| 431089 | BE041395 | | ESTs, Weakly similar to unknown protein | hi—hi-lo—lo |
| 418824 | AW751661 | Hs.53542 | choreoacanthocytosis gene; KIAA0986 prot | hi—hi-lo—lo |
| 449226 | AB002365 | Hs.23311 | KIAA0367 protein | hi—hi-lo—lo |
| 450149 | AW969781 | Hs.132863 | Zic family member 2 (odd-paired *Drosophi* | hi—hi-lo—lo |
| 418443 | NM_005239 | Hs.85146 | v-ets avian erythroblastosis virus E26 o | hi—hi-lo—lo |
| 458692 | BE549905 | Hs.231754 | ESTs | hi—hi-lo—lo |
| 410102 | AW248508 | Hs.279727 | ESTs; homologue of PEM-3 [*Ciona savignyi* | hi—hi-lo—lo |
| 451062 | AL110125 | Hs.25910 | *Homo sapiens* mRNA; cDNA DKFZp564C1416 (f | hi—hi-lo—lo |
| 407633 | NM_007069 | Hs.37189 | similar to rat HREV107 | hi—hi-lo—lo |
| 418941 | AA452970 | Hs.239527 | E1B-55 kDa-associated protein 5 | hi—hi-lo—lo |
| 407059 | X95406 | | gb: *H. sapiens* cyclin E gene. | hi—hi-lo—lo |
| 455956 | BE162704 | | gb: PM1-HT0454-301299-001-d08 HT0454 *Homo* | hi—hi-lo—lo |
| 437763 | AA469369 | Hs.5831 | tissue inhibitor of metalloproteinase 1 | hi—hi-lo—lo |
| 451404 | AA460775 | Hs.6295 | ESTs, Weakly similar to T17248 hypotheti | hi—hi-lo—lo |
| 428494 | AA233439 | Hs.184634 | hypothetical protein FLJ20005 | hi—hi-lo—lo |
| 414957 | D61283 | Hs.45206 | ESTs | hi—hi-lo—lo |
| 456415 | AI734051 | Hs.277102 | ESTs, Weakly similar to ALU1_HUMAN ALU S | hi—hi-lo—lo |
| 400183 | | | Eos Control | hi—hi-lo—lo |
| 400158 | | | ENSP00000244302*: CDNA FLJ11591 fis, clon | hi—hi-lo—lo |
| 403893 | | | ENSP00000237068*: Protocadherin alpha 6 p | hi—hi-lo—lo |
| 423809 | AI223833 | Hs.154483 | ESTs | hi—hi-lo—lo |
| 400170 | | | Eos Control | hi—hi-lo—lo |
| 403291 | | | Target Exon | hi—hi-lo—lo |
| 422026 | U80736 | Hs.110826 | trinucleotide repeat containing 9 | hi—hi-lo—lo |
| 417130 | AW276858 | Hs.81256 | S100 calcium-binding protein A4 (calcium | hi—hi-lo—lo |
| 432472 | AA548781 | Hs.136418 | ESTs | hi—hi-lo—lo |
| 405231 | | | C2001066: gi\|10257425\|ref\|NP_033892.1\| CD | hi—hi-lo—lo |
| 400141 | | | Eos Control | hi—hi-lo—lo |
| 428971 | BE278404 | Hs.285813 | hypothetical protein FLJ11807 | hi—hi-lo—lo |
| 422390 | AW450893 | Hs.121830 | ESTs, Weakly similar to T42682 hypotheti | hi—hi-lo—lo |
| 425538 | BE270918 | Hs.164026 | *Home sapiens*, clone IMAGE: 3534875, mRNA, | hi—hi-lo—lo |
| 456972 | AI054347 | Hs.2017 | ribosomal protein L38 | hi—hi-lo—lo |
| 456622 | AF205849 | Hs.107740 | Kruppel-like factor 2 (lung) | hi—hi-lo—lo |
| 418515 | AI568453 | Hs.19487 | ESTs, Weakly similar to CNIH_HUMAN CORNI | hi—hi-lo—lo |
| 448439 | BE613082 | Hs.28229 | ARG99 protein | hi—hi-lo—lo |
| 445418 | AW139377 | Hs.127179 | cryptic gene | hi—hi-lo—lo |
| 402559 | Z23024 | | Rho GTPase activating protein 1 | hi—hi-lo—lo |
| 402575 | Z23024 | | Rho GTPase activating protein 1 | hi—hi-lo—lo |
| 420811 | AA807544 | | ESTs, Weakly similar to B34323 GTP-bindi | hi—hi-lo—lo |
| 446627 | AI973016 | Hs.15725 | hypothetical protein SBBI48 | hi—hi-lo—lo |
| 400247 | | | Eos Control | hi—hi-lo—lo |
| 430289 | AK001952 | Hs.238039 | hypothetical protein FLJ11090 | hi—hi-lo—lo |
| 400133 | | | Eos Control | hi—hi-lo—lo |
| 418816 | T29621 | Hs.88778 | carbonyl reductase 1 | hi—hi-lo—lo |
| 433579 | BE264473 | Hs.284297 | hypothetical protein from EUROIMAGE 1967 | hi—hi-lo—lo |
| 401952 | | | Target Exon | hi—hi-lo—lo |
| 410349 | AW663021 | Hs.323445 | ESTs, Weakly similar to T2D3_HUMAN TRANS | hi—hi-lo—lo |
| 417558 | AF045229 | Hs.82280 | regulator of G-protein signalling 10 | hi—hi-lo—lo |
| 446851 | AW007332 | Hs.10450 | *Homo sapiens* cDNA: FLJ22063 fis clone H | hi—hi-lo—lo |
| 404489 | | | Target Exon | hi—hi-lo—lo |
| 405802 | | | Target Exon | hi—hi-lo—lo |
| 456266 | L29073 | Hs.198726 | cold shock domain protein A | hi—hi-lo—lo |
| 457133 | M54968 | | v-Ki-ras2 Kirsten rat sarcoma 2 viral on | hi—hi-lo—lo |
| 459330 | C16931 | | gb: C16931 Clontech human aorta polyA mRN | hi—hi-lo—lo |
| 433041 | BE265848 | Hs.289080 | colon cancer-associated protein Mic1 | lo—lo—lo-hi |
| 446545 | AI431798 | Hs.164192 | ESTs, Weakly similar to Y161_HUMAN HYPOT | lo—lo—lo-hi |
| 414911 | NM_000107 | Hs.77602 | damage-specific DNA binding protein 2 (4 | lo—lo—lo-hi |
| 414682 | AL021154 | Hs.76884 | inhibitor of DNA binding 3, dominant neg | lo—lo—lo-hi |
| 422311 | AF073515 | Hs.114948 | cytokine receptor-like factor 1 | lo—lo—lo-hi |
| 447329 | BE090517 | | ESTs, Moderately similar to ALU8_HUMAN A | lo—lo—lo-hi |
| 412942 | AL120344 | Hs.75074 | mitogen-activated protein kinase-activat | lo—lo—lo-hi |
| 420747 | BE294407 | Hs.99910 | phosphofructokinase, platelet | lo—lo—lo-hi |
| 431912 | AI660552 | Hs.76549 | ESTs, Weakly similar to A56154 Abl subst | lo—lo—lo-hi |
| 446506 | AI123118 | Hs.15159 | chemokine-like factor, alternatively spl | lo—lo—lo-hi |
| 408633 | AW963372 | Hs.46677 | PRO2000 protein | lo—lo—lo-hi |
| 433675 | AW977653 | Hs.75319 | ribonucleotide reductase M2 polypeptide | hi-lo—lo-hi |
| 424560 | AA158727 | Hs.150555 | protein predicted by clone 23733 | hi-lo—lo-hi |
| 425234 | AW152225 | Hs.165909 | ESTs, Weakly similar to I38022 hypotheti | hi-lo—lo-hi |
| 439815 | AA206079 | Hs.6693 | hypothetical protein FLJ20420 | hi-lo—lo-hi |
| 410174 | AA306007 | Hs.59461 | DKFZP434C245 protein | hi-lo—lo-hi |
| 410442 | X73424 | Hs.63788 | propionyl Coenzyme A carboxylase, beta p | hi-lo—lo-hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 429190 | H18650 | Hs.92602 | ESTs | hi-lo—lo-hi |
| 423619 | T48691 | Hs.249159 | adrenergic, alpha-2A-, receptor | hi-lo—lo-hi |
| 433764 | AW753676 | Hs.39982 | ESTs | hi-lo—lo-hi |
| 421998 | R74441 | Hs.117176 | poly(A)-binding protein, nuclear 1 | hi-lo—lo-hi |
| 451593 | AF151879 | Hs.26706 | CGI-121 protein | hi-lo—lo-hi |
| 452092 | BE245374 | Hs.27842 | hypothetical protein FLJ11210 | hi-lo—lo-hi |
| 447425 | AI963747 | Hs.18573 | acylphosphatase 1, erythrocyte (common) | hi-lo—lo-hi |
| 421654 | AW163267 | Hs.106469 | suppressor of var1 (*S. cerevisiae*) 3-like | hi-lo—lo-hi |
| 432502 | NM_014641 | Hs.277585 | KIAA0170 gene product | hi-lo—lo-hi |
| 429597 | NM_003816 | Hs.2442 | a disintegrin and metalloproteinase doma | hi-lo—lo-hi |
| 434203 | BE262677 | Hs.283558 | hypothetical protein PRO1855 | hi-lo—lo-hi |
| 438461 | AW075485 | Hs.286049 | phosphoserine aminotransferase | hi-lo—lo-hi |
| 409142 | AL136877 | Hs.50758 | SMC4 (structural maintenance of chromoso | hi-lo—lo-hi |
| 439574 | AI469788 | Hs.165190 | ESTs | hi-lo—lo-hi |
| 438182 | AW342140 | Hs.182545 | ESTs, Weakly similar to ALU1_HUMAN ALU S | hi-lo—lo-hi |
| 449103 | T24968 | Hs.23038 | HSPC071 protein | hi-lo—lo-hi |
| 421059 | AI654133 | Hs.30212 | thyroid receptor interacting protein 15 | hi-lo—lo-hi |
| 446939 | AL133353 | Hs.16606 | CGI-32 protein | hi-lo—lo-hi |
| 408576 | NM_003542 | Hs.46423 | H4 histone family, member G | hi-lo—lo-hi |
| 410073 | AW408163 | Hs.58488 | catenin (cadherin-associated protein), a | hi-lo—lo-hi |
| 450912 | AW939251 | Hs.25647 | v-fos FBJ murine osteosarcoma viral onco | hi-lo—lo-hi |
| 434701 | AA460479 | Hs.321707 | KIAA0742 protein | hi-lo—lo-hi |
| 450455 | AL117424 | Hs.25035 | chloride intracellular channel 4 | hi-lo—lo-hi |
| 451144 | AW956103 | Hs.61712 | pyruvate dehydrogenase kinase, isoenzyme | hi-lo—lo-hi |
| 427390 | AI432163 | Hs.268231 | *Homo sapiens* cDNA: FLJ23111 fis, clone L | hi-lo—lo-hi |
| 451831 | NM_001674 | Hs.460 | activating transcription factor 3 | hi-lo—lo-hi |
| 406776 | T16206 | Hs.237164 | ESTs, Highly similar to LDHH_HUMAN L-LAC | hi-lo—lo-hi |
| 428157 | AI738719 | Hs.198427 | hexokinase 2 | hi-lo—lo-hi |
| 408096 | BE250162 | Hs.83765 | dihydrofolate reductase | hi-lo—lo-hi |
| 418203 | X54942 | Hs.83758 | CDC28 protein kinase 2 | hi-lo—lo-hi |
| 449338 | H73444 | Hs.394 | adrenomeduilin | hi-lo—lo-hi |
| 422082 | AA016188 | Hs.111244 | hypothetical protein | hi-lo—lo-hi |
| 407907 | AI752235 | Hs.41270 | procollagen-lysine, 2-oxoglutarate 5-dio | hi-lo—lo-hi |
| 416655 | AW968613 | Hs.79428 | BCL2/adenovirus E1B 19 kD-interacting pro | hi-lo—lo-hi |
| 419551 | AW582256 | Hs.91011 | anterior gradient 2 (*Xenepus laevis*) hom | hi-lo—lo-hi |
| 434094 | AA305599 | Hs.238205 | hypothetical protein PRO2013 | hi-lo—lo-hi |
| 443951 | F13272 | Hs.111334 | ferritin, light polypeptide | hi-lo—lo-hi |
| 422975 | AA347720 | Hs.122669 | KIAA0264 protein | hi-lo—lo-hi |
| 430314 | AA369601 | Hs.239138 | pre-B-cell colony-enhancing factor | hi-lo—lo-hi |
| 412664 | AA421404 | Hs.346868 | nucleolar protein p40; homolog of yeast | hi-lo—lo-hi |
| 408089 | H59799 | Hs.42644 | thioredoxin-like | hi-lo—lo-hi |
| 409690 | W45393 | Hs.55888 | activating transcription factor 7 | hi-lo—lo-hi |
| 442332 | AI693251 | Hs.8248 | Target CAT | hi-lo—lo-hi |
| 408388 | AF091086 | Hs.44563 | hypothetical protein | hi-lo—lo-hi |
| 441252 | AW360901 | Hs.183047 | hypothetical protein MGC4399 | hi-lo—lo-hi |
| 433069 | X76732 | Hs.3164 | nucleobindin 2 | hi-lo—lo-hi |
| 443837 | AI984625 | Hs.9884 | spindle pole body protein | hi-lo—lo-hi |
| 426108 | AA622037 | Hs.166468 | programmed cell death 5 | hi-lo—lo-hi |
| 441181 | AA416925 | Hs.121076 | peptidylprolyl isomerase (cyclophilin)-I | hi-lo—lo-hi |
| 447397 | BE247676 | Hs.18442 | E-1 enzyme | hi-lo—lo-hi |
| 427505 | AA361562 | Hs.178761 | 26S proteasome-associated pad1 homolog | hi-lo—lo-hi |
| 430287 | AW182459 | Hs.125759 | ESTs, Weakly similar to LEU5_HUMAN LEUKE | hi-lo—lo-hi |
| 415857 | AA866115 | Hs.127797 | *Homo sapiens* cDNA FLJ1381 fis, clone HE | hi-lo—lo-hi |
| 423198 | M81933 | Hs.1634 | cell division cycle 25A | hi-lo—lo-hi |
| 407687 | AK002011 | Hs.37558 | hypothetical protein FLJ11149 | hi-lo—lo-hi |
| 431374 | BE258532 | Hs.251871 | CTP synthase | hi-lo—lo-hi |
| 413273 | U75679 | Hs.75257 | stem-loop (histone) binding protein | hi-lo—lo-hi |
| 442799 | AI564739 | Hs.68505 | ESTs | hi-lo—lo-hi |
| 443881 | R64512 | Hs.237146 | hypothetical protein FLJ12752 | hi-lo—lo-hi |
| 416209 | AA236776 | Hs.79078 | MAD2 (mitotic arrest deficient, yeast, h | hi-lo—lo-hi |
| 421834 | BE543205 | Hs.288771 | DKFZP586A0522 protein | hi-lo—lo-hi |
| 411263 | BE297802 | Hs.69360 | kinesin-like 6 (mitotic centromere-assoc | hi-lo—lo-hi |
| 413924 | AL119964 | Hs.75616 | seladin-1 | hi-lo—lo-hi |
| 450598 | AF151076 | Hs.25199 | hypothetical protein | hi-lo—lo-hi |
| 439453 | BE264974 | Hs.6566 | thyroid hormone receptor interactor 13 | hi-lo—lo-hi |
| 429612 | AF062649 | Hs.252587 | pituitary tumor-transforming 1 | hi-lo—lo-hi |
| 443426 | AF098158 | Hs.9329 | chromosome 20 open reading frame 1 | hi-lo—lo-hi |
| 452353 | C18825 | Hs.29191 | epithelial membrane protein 2 | hi-lo—lo-hi |
| 419879 | Z17805 | Hs.93564 | Homer, neuronal immediate early gene, 2 | hi-lo—lo-hi |
| 422363 | T55979 | Hs.115474 | replication factor C (activator 1) 3 (38 | hi-lo—lo-hi |
| 416065 | BE267931 | Hs.78996 | proliferating cell nuclear antigen | hi-lo—lo-hi |
| 424308 | AW975531 | Hs.154443 | minichromosome maintenance deficient (S. | hi-lo—lo-hi |
| 447519 | U46258 | Hs.339665 | ESTs | hi-lo—lo-hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 437679 | NM_014214 | Hs.5753 | inositol(myo)-1(or 4)-monophosphatase 2 | hi-lo—lo-hi |
| 446636 | AC002563 | Hs.15767 | citron (rho-interacting, serine/threonin | hi-lo—lo-hi |
| 422094 | AF129535 | Hs.272027 | F-box only protein 5 | hi-lo—lo-hi |
| 440334 | BE276112 | Hs.7165 | zinc finger protein 259 | hi-lo—lo-hi |
| 421921 | H83363 | Hs.6820 | translocase of inner mitochondrial membr | hi-lo—lo-hi |
| 422938 | NM_001809 | Hs.1594 | centromere protin A (17 kD) | hi-lo—lo-hi |
| 427719 | AI393122 | Hs.134726 | ESTs | hi-lo—lo-hi |
| 422283 | AW411307 | Hs.114311 | CDC45 (cell division cycle 45, S. cerevis | hi-lo—lo-hi |
| 424840 | D79987 | Hs.153479 | extra spindle poles, *S. cerevisiae*, *Homo* | hi-lo—lo-hi |
| 418216 | AA662240 | Hs.283099 | AF15q14 protein | hi-lo—lo-hi |
| 412140 | AA219691 | Hs.73625 | RAB6 interacting, kinesin-like (rabkines | hi-lo—lo-hi |
| 418322 | AA284166 | Hs.84113 | cyclin-dependent kinase inhibitor 3 (CDK | hi-lo—lo-hi |
| 428479 | Y00272 | Hs.334562 | cell division cycle 2, G1 to S and G2 to | hi-lo—lo-hi |
| 449722 | BE280074 | Hs.23960 | cyclin B1 | hi-lo—lo-hi |
| 417933 | X02308 | Hs.82962 | thymidylate synthetase | hi-lo—lo-hi |
| 433001 | AF217513 | Hs.279905 | clone HQ0310 PRO0310p1 | hi-lo—lo-hi |
| 413943 | AW294416 | Hs.144687 | *Homo sapiens* cDNA FLJ12981 fis, clone NT | hi-lo—lo-hi |
| 424905 | NM_002497 | Hs.153704 | NIMA (never in mitosis gene a)-related k | hi-lo—lo-hi |
| 422765 | AW409701 | Hs.1578 | baculoviral IAP repeat-containing 5 (sur | hi-lo—lo-hi |
| 425397 | J04088 | Hs.156346 | topoisomerase (DNA) II alpha (170 kD) | hi-lo—lo-hi |
| 444371 | BE540274 | Hs.239 | forkhead box M1 | hi-lo—lo-hi |
| 422956 | BE545072 | Hs.122579 | ECT2 protein (Epithelial cell transformi | hi-lo—lo-hi |
| 444783 | AK001468 | Hs.62180 | anillin (*Drosophila* Scraps homolog), act | hi-lo—lo-hi |
| 453884 | AA355925 | Hs.36232 | KIAA0186 gene product | hi-lo—lo-hi |
| 416980 | AA381133 | Hs.80684 | high-mobility group (nonhistone chromoso | hi-lo—lo-hi |
| 442432 | BE093589 | Hs.38178 | hypothetical protein FLJ23468 | hi-lo—lo-hi |
| 417308 | H60720 | Hs.81892 | KIAA0101 gene product | hi-lo—lo-hi |
| 433133 | AB027249 | Hs.104741 | PDZ-binding kinase; T-cell originated pr | hi-lo—lo-hi |
| 432626 | AA471098 | Hs.278544 | acetyl-Coenzyme A acetyltransferase 2 (a | hi-lo—lo-hi |
| 441020 | W79283 | Hs.35962 | ESTs | hi-lo—lo-hi |
| 412281 | AI810054 | Hs.14119 | ESTs | hi-lo—lo-hi |
| 435602 | AF217515 | Hs.283532 | uncharacterized bone marrow protein BM03 | hi-lo—lo-hi |
| 400882 | | | Target Exon | hi-lo—lo-hi |
| 446269 | AW263155 | Hs.14559 | hypothetical protein FLJ10540 | hi-lo—lo-hi |
| 417847 | AI521558 | Hs.7331 | hypothetical protein FLJ22316 | hi-lo—lo-hi |
| 400881 | | | NM_025080: *Homo sapiens* hypothetical prot | hi-lo—lo-hi |
| 419356 | AI656166 | Hs.7331 | hypothetical protein FLJ22316 | hi-lo—lo-hi |
| 400292 | AA250737 | Hs.72472 | BMP-R1B | hi-lo—lo-hi |
| 415539 | AI733881 | Hs.72472 | BMP-R1B | hi-lo—lo-hi |
| 453935 | AI633770 | Hs.42572 | ESTs | hi-lo—lo-hi |
| 420005 | AW271106 | Hs.133294 | ESTs | hi-lo—lo-hi |
| 428450 | NM_014791 | Hs.184339 | KIAA0175 gene product | hi-lo—lo-hi |
| 436291 | BE568452 | Hs.344037 | protein regulator of cytokinesis 1 | hi-lo—lo-hi |
| 441362 | BE614410 | Hs.23044 | RAD51 (*S. cerevisiae*) homolog (*E coli* Re | hi-lo—lo-hi |
| 428484 | AF104032 | Hs.184601 | solute carrier family 7 (cationic amino | hi-lo—lo-hi |
| 418526 | BE019020 | Hs.85838 | solute carrier family 16 (monocarboxylic | hi-lo—lo-hi |
| 458809 | AW972512 | Hs.20985 | sin3-associated polypeptide, 30 kD | hi-lo—lo-hi |
| 444984 | H15474 | Hs.132898 | fatty acid desaturase 1 | hi-lo—lo-hi |
| 447342 | AI199268 | Hs.19322 | *Homo sapiens*, Similar to RIKEN cDNA 2010 | hi-lo—lo-hi |
| 428330 | L22524 | Hs.2256 | matrix metalloproteinase 7 (matrilysin, | hi-lo—lo-hi |
| 428336 | AA503115 | Hs.183752 | microseminoprotein, beta- | hi-lo—lo-hi |
| 430389 | AL117429 | Hs.240845 | DKFZP434D146 protein | hi-lo—lo-hi |
| 417318 | AW953937 | Hs.240845 | ESTs | hi-lo—lo-hi |
| 422545 | X02761 | Hs.287820 | fibronectin 1 | hi-lo—lo-hi |
| 417640 | D30857 | Hs.82353 | protein C receptor, endothelial (EPCR) | hi-lo—lo-hi |
| 422809 | AK001379 | Hs.121028 | hypothetical protein FLJ10549 | hi-lo—lo-hi |
| 425580 | L11144 | Hs.1907 | galanin | hi-lo—lo-hi |
| 416836 | D54745 | Hs.80247 | cholecystokinin | hi-lo—lo-hi |
| 434170 | AA626509 | Hs.122329 | ESTs | hi-lo—lo-hi |
| 427958 | AA418000 | Hs.98280 | potassium intermediate/small conductance | hi-lo—lo-hi |
| 439706 | AW872527 | Hs.59761 | ESTs, Weakly similar to DAP1_HUMAN DEATH | hi-lo—lo-hi |
| 450088 | AW292933 | Hs.254110 | ESTs | hi-lo—lo-hi |
| 414219 | W20010 | Hs.75823 | ALL1-fused gene from chromosome 1q | hi-lo—lo-hi |
| 419201 | M22324 | Hs.1239 | alanyl (membrane) aminopeptidase (aminop | hi-lo—lo-hi |
| 426263 | AI908774 | Hs.259785 | carnitine palmitoyltransferase I, liver | hi-lo—lo-hi |
| 456236 | AF045229 | Hs.82280 | regulator of G-protein signalling 10 | hi-lo—lo-hi |
| 456607 | AI660190 | Hs.106070 | cyclin-dependent kinase inhibitor 1C (p5 | hi-lo—lo-hi |
| 408437 | AW957744 | Hs.278469 | lacrimal proline rich protein | hi-lo—lo-hi |
| 421180 | BE410992 | Hs.258730 | heme-regulated initiation factor 2-alpha | hi-lo—lo-hi |
| 413437 | BE313164 | Hs.75361 | gene from NF2/meningioma region of 22q12 | hi-lo—lo-hi |
| 432415 | T16971 | Hs.289014 | ESTs, Weakly similar to A43932 mucin 2 p | hi-lo—lo-hi |
| 449230 | BE613348 | Hs.211579 | melanoma cell adhesion molecule | hi-lo—lo-hi |
| 417979 | AU077284 | Hs.83081 | GTP cyclohydrolase I feedback regulatory | hi-lo—lo-hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 421877 | AW250380 | Hs.109059 | mitochondrial ribosomal protein L12 | hi-lo—lo-hi |
| 412482 | AI499930 | Hs.334885 | mitochondrial GTP binding protein | hi-lo—lo-hi |
| 428423 | AU076517 | Hs.184276 | solute carrier family 9 (sodium/hydrogen | hi-lo—lo-hi |
| 422947 | AA306782 | Hs.122552 | G-2 and S-phase expressed 1 | hi-lo—lo-hi |
| 441072 | AW275480 | Hs.39504 | hypothetical protein MGC4308 | hi-lo—lo-hi |
| 415938 | BE383507 | Hs.78921 | A kinase (PRKA) anchor protein 1 | hi-lo—lo-hi |
| 432278 | AL137506 | Hs.274256 | hypothetical protein FLJ23563 | hi-lo—lo-hi |
| 446651 | AA393907 | Hs.97179 | ESTs | hi-lo—lo-hi |
| 431515 | NM_012152 | Hs.258583 | endothelial differentiation, lysophospha | hi-lo—lo-hi |
| 445345 | AW003850 | Hs.12532 | chromosome 1 open reading frame 21 | hi-lo—lo-hi |
| 458965 | AA010319 | Hs.60389 | ESTs | hi-lo—lo-hi |
| 438321 | AA576635 | Hs.6153 | CGI-48 protein | hi-lo—lo-hi |
| 416783 | AA206186 | Hs.79889 | monocyte to macrophage differentiation-a | hi-lo—lo-hi |
| 453563 | AW608906 | Hs.181163 | hypothetical protein MGC5629 | hi-lo—lo-hi |
| 432393 | AW205863 | Hs.133988 | hypothetical protein FKSG28 | hi-lo—lo-hi |
| 433914 | AF108138 | Hs.112160 | *Homo sapiens* DNA helicase homolog (PIF1) | hi-lo—lo-hi |
| 414907 | X90725 | Hs.77597 | polo (*Drosophia*)-like kinase | hi-lo—lo-hi |
| 432375 | BE536069 | Hs.2962 | S100 calcium-binding protein P | hi-lo—lo-hi |
| 440773 | AA352702 | Hs.37747 | *Homo sapiens*, Similar to RIKEN cDNA 2700 | hi-lo—lo-hi |
| 415994 | NM_002923 | Hs.78944 | regulator of G-protein signalling 2, 24k | hi-lo—lo-hi |
| 412722 | AI343300 | Hs.15091 | ESTs | hi-lo—lo-hi |
| 446839 | BE091926 | Hs.16244 | mitotic spindle coiled-coil related prot | hi-lo—lo-hi |
| 428862 | NM_000346 | Hs.2316 | SRY (sex determining region Y)-box 9 (ca | hi-lo—lo-hi |
| 439108 | AW163034 | Hs.6467 | synaptogyrin 3 | hi-lo—lo-hi |
| 430178 | AW449612 | Hs.152475 | ESTs | hi-lo—lo-hi |
| 421733 | AL119671 | Hs.1420 | fibroblast growth factor receptor 3 (ach | hi-lo—lo-hi |
| 452410 | AL133619 | | *Homo sapiens* mRNA; cDNA DKFZp434E2321 (f | hi-lo—lo-hi |
| 430132 | AA204686 | Hs.234149 | hypothetical protein FLJ20647 | hi-lo—lo-hi |
| 428297 | AA236291 | Hs.183583 | serine (or cysteine) proteinase inhibito | hi-lo—lo-hi |
| 413142 | M81740 | Hs.75212 | ornithine decarboxylase 1 | hi-lo—lo-hi |
| 427239 | BE270447 | Hs.174070 | ubiquitin carrier protein | hi-lo—lo-hi |
| 409738 | BE222975 | Hs.56205 | insulin induced gene 1 | hi-lo—lo-hi |
| 410748 | BE383816 | Hs.12532 | chromosome 1 open reading frame 21 | hi-lo—lo-hi |
| 424506 | AF220490 | Hs.149623 | group III secreted phospholipase A2 | hi-lo—lo-hi |
| 447333 | BE090580 | Hs.70704 | hypothetical protein dJ616B8.3 | hi-lo—lo-hi |
| 414761 | AU077228 | Hs.77256 | enhancer of zeste (*Drosophila*) homolog 2 | hi-lo—lo-hi |
| 419602 | AW248434 | Hs.91521 | hypothetical protein | hi-lo—lo-hi |
| 411669 | BE612676 | Hs.303116 | stromal cell-derived factor 2-like 1 | hi-lo—lo-hi |
| 452322 | BE566343 | Hs.28988 | glutaredoxin (thioltransferase) | hi-lo—lo-hi |
| 426006 | R49031 | Hs.22627 | ESTs | hi-lo—lo-hi |
| 457465 | AW301344 | Hs.122908 | DNA replication factor | hi-lo—lo-hi |
| 406867 | AA157857 | Hs.182265 | keratin 19 | hi-lo—lo-hi |
| 407230 | AA157857 | Hs.182265 | keratin 19 | hi-lo—lo-hi |
| 446681 | AJ003624 | Hs.15896 | kendrin | hi-lo—lo-hi |
| 408493 | BE206854 | Hs.46039 | phosphoglycerate mutase 2 (muscle) | hi-lo—lo-hi |
| 439186 | AI697274 | Hs.105435 | GDP-mannose 4,6-dehydratase | hi-lo—lo-hi |
| 424544 | M88700 | Hs.150403 | dope decarboxylase (aromatic L-amino aci | hi-lo—lo-hi |
| 431325 | AW026751 | Hs.5794 | ESTs, Weatly similar to 2109260A B cell | hi-lo—lo-hi |
| 414922 | D00723 | Hs.77631 | glycine cleavage system protein H (amino | hi-lo—lo-hi |
| 438291 | BE514605 | Hs.289092 | *Homo sapiens* cDNA: FLJ22380 fis, clone H | hi-lo—lo-hi |
| 418574 | N28754 | | M-phase phosphoprotein 9 | hi-lo—lo-hi |
| 409342 | AU077058 | Hs.54089 | BRCA1 associated RING domain 1 | hi-lo—lo-hi |
| 432734 | AA837396 | Hs.263925 | LIS1-interacting protein NUDE1, rat *Homo* | hi-lo—lo-hi |
| 436087 | BE300296 | Hs.5054 | CGI-133 protein | hi-lo—lo-hi |
| 420309 | AW043637 | Hs.21766 | ESTs, Weakly similar to ALU5_HUMAN ALU S | hi-lo—lo-hi |
| 411619 | AI418609 | Hs.71040 | hypothetical protein FLJ20425 | hi-lo—lo-hi |
| 424381 | AA285249 | Hs.146329 | protein kinase Chk2 | hi-lo—lo-hi |
| 442547 | AA306997 | Hs.217484 | ESTs, Weakly similar to ALU1_HUMAN ALU S | hi-lo—lo-hi |
| 430376 | AW292053 | Hs.12532 | chromosome 1 open reading frame 21 | hi-lo—lo-hi |
| 434666 | AF151103 | Hs.112259 | T cell receptor gamma locus | hi-lo—lo-hi |
| 412330 | NM_005100 | Hs.788 | A kinase (PRKA) anchor protein (gravin) | hi-lo—lo-hi |
| 452123 | AI267615 | Hs.38022 | ESTs | hi-lo—lo-hi |
| 424893 | AW295112 | Hs.153648 | *Homo sapiens* cDNA FLJ13303 fis, clone OV | hi-lo—lo-hi |
| 428057 | AI343641 | Hs.185798 | ESTs | hi-lo—lo-hi |
| 431566 | AF176012 | Hs.260720 | J domain containing protein 1 | hi-lo—lo-hi |
| 439979 | AW600291 | Hs.6623 | hypothetical protein FLJ10430 | hi-lo—lo-hi |
| 418836 | AI655499 | Hs.161712 | ESTs | hi-lo—lo-hi |

TABLE 2A-continued

ABOUT 1165 GENES SELECTED TO HAVE AN INTERESTING EXPRESSION PATTERN DURING ANDROGEN WITHDRAWAL OF PROSTATE CANCER TISSUE

| Pkey | ExAccn | UnigeneID | Unigene Title | Pattern |
|---|---|---|---|---|
| 433757 | AI949974 | Hs.152670 | ESTs | hi-lo—lo-hi |
| 425236 | AW067800 | Hs.155223 | stanniocalcin 2 | hi-lo—lo-hi |
| 426215 | AW963419 | Hs.155223 | stanniocalcin 2 | hi-lo—lo-hi |

Pkey: Unique Eos probeset identifier number
ExAccn: Exemplar Accession number, Genbank Accession number
UnigeneID: Unigene number
Unigene Title: Unigene gene title
Pattern: Broadly defined expression patterns during androgen withdrawal

TABLE 2B

| Pkey | CAT Number | Accession |
|---|---|---|
| 408660 | 107294_1 | AA525775 AA056342 AI538978 AW975281 AA664986 |
| 409051 | 109699_1 | AA080912 AA075318 AA083403 AA076594 AA078992 AA084926 AA081881 AA113913 AA113892 AA083821 AA134801 AA082953 AA070343 AA062835 AA075419 AA063293 AA071252 AA078900 AA062836 AW974305 |
| 409123 | 110143_1 | AA063403 AA070823 AA070050 |
| 410216 | 1184664_1 | BE061839 AW859863 AW606085 |
| 410451 | 1204118_1 | BE065687 BE065637 AW749002 H73690 |
| 410498 | 120611_1 | AA355749 AA085520 AW966333 AA340319 BE170936 |
| 411053 | 1230446_1 | AW815061 H71965 AW815072 AW815048 AW815041 AW815047 BE152831 BE152490 BE149043 BE149075 BE149035 BE149067 |
| 411233 | 1236369_1 | AW833793 AW833799 AW833346 AW833371 AW833795 AW833562 AW833667 AW833377 |
| 411283 | 1237666_1 | AW852754 AW852897 AW852757 AW852617 BE172755 AW835444 |
| 411701 | 1254466_1 | BE181659 AW890576 AW857638 |
| 411831 | 1260400_1 | AW994394 AW865900 AW865905 AW865891 AW866014 AW865898 |
| 412419 | 1293418_1 | AW948630 AW948626 AW948634 AW948616 AW948627 AW948615 AW948631 AW948605 AW948611 AW948610 AW948633 AW948623 AW948628 AW948604 AW948602 AW948607 |
| 412492 | 130082_1 | AW962604 AA368639 AA112257 |
| 412657 | 1318507_1 | AW976165 C04000 |
| 413351 | 1363660_1 | BE086815 BE086823 R81218 R69229 |
| 413509 | 1374313_1 | BE145419 BE145433 |
| 413672 | 1382512_1 | BE156536 BE156439 BE156700 BE156449 BE156653 BE156533 BE156524 BE156670 BE156721 BE156723 |
| 415308 | 1533673_1 | F05251 R13748 Z44028 H14747 |
| 415516 | 1539185_1 | F11411 R15237 Z43915 H20760 |
| 416508 | 1597894_1 | R39769 T53143 H60012 |
| 416631 | 1605019_1 | H69466 H93884 N59684 |
| 416954 | 163427_1 | AI222358 N73390 D61648 AA243520 AA190953 |
| 417314 | 1666649_1 | N68168 N69188 N90450 |
| 418056 | 171841_1 | AA524886 AW971347 AA211537 |
| 418259 | 173388_1 | AA215404 AI990909 BE464132 AW271459 N74332 AI262061 |
| 418574 | 17690_1 | N28754 N28747 AI568146 AI979339 AA322671 AA322672 AW955043 AI990326 AA776406 AI016250 AA843678 AW451882 N23137 N23129 W70051 AI038748 AA831327 AI925845 AW945895 |
| 419555 | 185884_1 | AA244416 AA244401 |
| 420811 | 196677_1 | AA807544 AA280648 AI243056 AI022744 AA705288 AA829425 AW452095 AI929317 R19039 AA282024 |
| 421911 | 208987_1 | AL041520 AA300086 |
| 421974 | 209807_1 | AA301270 AA301379 AA301366 |
| 422128 | 211994_1 | AW881145 AA490718 M85637 AA304575 T06067 AA331991 |
| 423028 | 224062_1 | H90946 AA320597 AW954970 BE143680 |
| 423476 | 22861_1 | AL035633 F11794 F11783 H18042 T66089 H29379 R19493 AW134660 AI299437 AL133995 AA057405 N78357 AA917450 AI002692 T09262 T65008 H29290 AI200874 AA894415 AI732887 AI791768 AI733447 AA988785 N62128 T09261 AW956936 |
| 423895 | 233006_1 | AA332215 AA403110 AW965299 |
| 424593 | 241234_1 | AA343729 AA345779 AA344370 |
| 425074 | 246486_1 | AA495930 AI470890 H97831 AA350358 BE166712 |
| 425291 | 249618_1 | AA354572 AW062361 AW813419 AW816041 AI744949 |
| 425980 | 258778_1 | AA366951 AA470999 AA469425 |
| 426413 | 266650_1 | AA377823 AW954494 AI022688 |
| 428181 | 287953_1 | AA423976 AA437075 BE006469 |
| 429163 | 300543_1 | AA884766 AW974271 AA592975 AA447312 |
| 429540 | 305828_1 | M85776 AA454535 AA456208 H90189 |
| 430068 | 312849_1 | AA464964 M85405 AA947566 |
| 430103 | 313089_1 | AA465259 AW897142 AW897144 |
| 430439 | 31808_1 | AL133561 AL041090 AL117481 AL122069 AW439292 AI968826 |
| 431089 | 327825_1 | BE041395 AA491826 AA621946 AA715980 AA666102 |
| 431843 | 338324_1 | AA516420 C14818 C14815 C15161 C15068 D80763 D60656 AW970134 AA543007 D81004 D60184 AI498371 D60382 D60181 C15876 |

TABLE 2B-continued

| Pkey | CAT Number | Accession |
|---|---|---|
| 432079 | 341114_1 | AW972746 AA525323 AI150314 |
| 432340 | 345248_1 | AA534222 AA632632 T81234 |
| 432676 | 352582_2 | AI187366 AA558869 AA618478 |
| 433075 | 35820_1 | NM_002959 X98248 AA233278 AA846376 AI470560 AI470533 BE327147 AW291971 AA017125 AI198417 AI365213 AI168442 AI337018 AI475049 H86459 AA969895 AA888000 AA418326 AA418378 N71981 AL043634 AA426361 AA418275 AA232975 AL036861 BE277220 BE387505 N99710 AW375004 AA418268 AL079651 H85743 AW902319 AW805907 AA984366 T92310 AA405425 AA421732 AI656841 AW300968 AW593418 T92267 BE464032 AW473548 AI359502 BE552306 AI990196 AW518351 AI239559 AW590963 AA018359 AI273737 AL042658 AA411308 AA402810 H38111 AW013931 AW366432 AW752435 AW376124 AI292020 AI292121 AA340647 BE613672 BE409874 AA351915 BE617026 BE019588 AW402692 AW247466 R59233 AA134761 BE254019 BE265105 D63316 BE313080 BE547713 BE536578 BE546749 AA324185 H17386 BE253377 R87598 H29072 AA350980 BE076629 BE253957 AA532613 BE252486 AW804459 D30966 R87959 AA091832 |
| 434280 | 382816_1 | BE005398 AA626622 AA994155 |
| 434609 | 38950_1 | R76593 AF147390 R76594 |
| 435023 | 398093_1 | AI692552 AI393343 AI800510 AI377711 F24263 AA661876 |
| 436716 | 425440_1 | AI433540 AA728984 AA804981 |
| 436862 | 42814_2 | AI821940 N67106 AI744264 AA808846 AA643417 AA643416 Z70715 |
| 437576 | 43892_1 | BE514383 AA071273 AW247987 AW673286 BE312102 AW749824 BE071985 AW577383 BE071945 BE072005 AW577355 BE071965 AW239231 BE072000 BE071960 AW577360 AW749830 AW373020 X97303 AW999522 BE000192 BE562219 BE266655 BE264970 |
| 438869 | 46651_1 | AF075009 R63109 R63068 |
| 438882 | 466649_1 | AA827695 AA833754 AW978946 |
| 438980 | 467544_1 | AW502384 AI982587 AA828822 |
| 439046 | 468133_1 | AA947354 AA829660 AI687296 |
| 439848 | 477806_1 | AW979249 D63277 AA846968 |
| 440151 | 487109_1 | AA868167 F21558 F31418 F35624 |
| 440507 | 495677_1 | H06994 BE147898 |
| 441102 | 509604_1 | AA973905 AI299888 AA917019 H63235 T90771 |
| 442048 | 531432_1 | AA974603 AI984319 AW340495 |
| 443161 | 561305_1 | AI038316 AI344631 AI261653 |
| 444290 | 59994_1 | AA262496 AV648929 AA305356 D61644 D78724 |
| 444314 | 600667_1 | AI140497 AW749625 AW749626 AW749644 |
| 445808 | 65133_1 | AV655234 AW966332 AA340239 |
| 447329 | 71759_1 | BE090517 AW970792 AW264490 AW014985 F27436 AA947336 F15843 H89338 AA563626 F17712 BE546579 AA421821 AA284952 AA477751 AW025245 |
| 447448 | 722246_1 | BE244285 C18429 H42373 AI820706 AI379786 R55439 AW276142 |
| 448150 | 752165_1 | AI472167 AI990315 R32175 |
| 448489 | 765247_1 | AI523875 R45782 R45781 |
| 448631 | 772996_1 | AI554923 AI902356 |
| 448738 | 77790_1 | BE614081 W01988 AW500790 |
| 452410 | 9163_1 | AL133619 AA468118 AA383064 AI476447 T09430 AI673758 AA524895 AI581345 AI300820 AW498812 AA256162 AI559724 AI685732 AA602400 AA905453 AI204595 AW166541 AA157456 AA156269 AA383652 AA431072 AW592707 AI435410 AW272464 AI215594 AA622747 R74039 N35031 AI804128 AW513621 AA868351 AI026826 AI493388 AA614641 W81604 AI567080 AI214351 AA730140 AI125754 AI200813 AI269603 AI565082 AI807095 AI476629 AA505909 AI368449 AI686077 AI582930 AW085038 AA757863 AA730154 AI767072 AA468316 AI734130 AI734138 AA426284 AA433997 AI741241 AW043563 AI732741 AI732734 AA437369 AA425820 AA664048 R74130 |
| 452444 | 918078_1 | BE144022 BE143969 BE143915 |
| 452654 | 925931_1 | BE004783 BE004947 AI911790 |
| 454775 | 1234106_1 | BE160229 AW819879 AW820179 AW819882 AW819876 AW820169 BE153201 AW993736 BE152911 |
| 455019 | 1249138_1 | AW850818 AW850833 AW851100 |
| 455272 | 1271871_1 | BE148152 BE148133 BE148159 BE148132 AW885107 |
| 455619 | 1346387_1 | BE063853 BE063955 BE063866 BE063705 BE063846 BE061416 BE063844 |
| 455653 | 1348742_1 | BE154075 BE153973 BE064861 BE153852 BE153847 BE064684 BE153602 BE065075 BE154018 BE064772 BE064842 BE153557 BE153509 |
| 455729 | 1353792_1 | BE072092 BE072106 BE072086 BE072098 BE072103 |
| 455824 | 1372880_1 | BE143703 BE143631 BE143629 BE143702 |
| 455956 | 1387163_1 | BE162704 BE162705 BE162732 BE162702 BE162694 |
| 456123 | 1534442_1 | R00602 Z42921 F06132 |
| 457133 | 29066_1 | M54968 NM_004985 AI808924 AL135130 AW242010 AA476848 AI740449 M17087 K03210 M35505 M35504 L00049 AI186585 W35273 X01669 X02825 W23635 AI554920 AI539465 AA425263 AI469981 W21091 T28976 AW977922 BE550180 AW664973 AI148939 AW117295 AA811229 AI343010 AA766141 BE219368 N95249 AA280396 AW504574 AA232870 AI770018 AA262948 AW450230 AW362890 AW609417 AW499941 AA425857 AW380665 AA830647 AA282180 T27356 H85307 AA861543 AA356548 AA356410 AW860656 AW860647 AW938103 AW860649 AI567016 N70374 AW474707 AA505084 AA082195 AW949515 AA361728 N33863 AA411821 AA401640 AW594461 AL120766 AI500024 |

TABLE 2B-continued

| Pkey | CAT Number | Accession |
|---|---|---|
| | | AW771891 H84567 D51551 AA330460 R14184 AI301629 N64676 AV659669 AI697660 AI004579 AA287927 AW453052 AW601642 AA676681 AA737010 AA872481 AA281094 AA564243 BE464958 BE049265 AW167917 AA843916 AA525301 AI015987 N25230 AI889481 AW173466 AA937541 AI334416 AI676214 AI281159 AA553559 AA582189 AA255527 AW160515 AA670007 H08199 AA808271 AA281015 W47527 AA649252 AI364302 AA889246 R40473 H02312 AA648116 AA342730 AA243624 R99351 R41588 R49696 AA854442 F01713 AA213685 AA721296 R79833 H84241 R70668 H85554 AA223758 N95349 AI374913 AI306683 AA015609 AA918548 AI453570 AA772321 AI692775 AA195733 AI474563 AW873048 AI209133 AI028182 AI374920 AW572807 AA406223 AA833684 T97255 H69138 AA382906 AW119162 N31974 AI890584 N39418 AA864877 AA679469 BE350651 N41020 AI050915 F00075 AA864878 N26970 AA828898 AW019991 AW796631 AW993262 N48532 BE564662 AV654063 AI754461 AW945712 C03289 AV655314 AV659070 AV659808 AV660435 H70113 C05323 R91984 H96949 AV658936 AV658879 H69137 AA384411 AA412584 C02749 W32014 R58168 C05526 BE536017 N24354 AA287991 N80109 F05452 R12740 H08297 AL138354 AW020801 BE178443 BE178018 BE178336 BE178360 BE178107 BE178385 BE178215 BE178186 BE178447 BE178352 BE178422 BE178424 BE178043 BE178093 BE178460 BE178356 BE178441 BE178438 BE178467 AI091259 BE177839 BE178094 R28455 BE177844 BE178100 AA262387 R70669 W80934 W93668 AA256711 BE178141 BE177893 BE178449 AA167718 H69694 BE178017 BE178029 BE177999 BE177936 AA095144 N32462 AA281203 AA281183 W47526 W05015 R34165 R35306 T97366 R79640 W25258 R99450 AW368425 BE178196 R26447 C03146 C03683 |
| 457952 | 44256_1 | U25750 AI792472 AA487379 AI872282 AA487262 R22383 AI865750 R21832 AA593628 AW571869 AA377191 R78814 T27193 |
| 458956 | 83645_1 | BE220675 AA345621 AA009992 |

Pkey: Unique Eos probeset identifier number
CAT number: Gene cluster number
Accession: Genbank accession numbers

TABLE 2C

| Pkey | Ref | Strand | Nt_position |
|---|---|---|---|
| 400481 | 8439853 | Plus | 112433-112541 |
| 400501 | 9796227 | Minus | 12479-12619 |
| 400713 | 8118874 | Minus | 43185-43394 |
| 400769 | 8131628 | Plus | 28671-29795 |
| 400818 | 8569994 | Plus | 172644-172765, 173085-173200 |
| 400881 | 2842777 | Minus | 91446-91603, 92123-92265 |
| 400882 | 2842777 | Minus | 110431-110708 |
| 400965 | 7770576 | Minus | 173043-173564 |
| 400986 | 8085497 | Minus | 63140-63319 |
| 400995 | 8099094 | Plus | 141186-141601 |
| 401093 | 8516137 | Minus | 22335-23166 |
| 401178 | 9438616 | Minus | 133663-133812 |
| 401192 | 9719502 | Minus | 69559-70101 |
| 401209 | 7712287 | Plus | 164932-165112 |
| 401405 | 7768126 | Minus | 69276-69452, 69548-69958 |
| 401416 | 7452889 | Minus | 121456-121626 |
| 401419 | 7452889 | Minus | 136389-136508 |
| 401444 | 8346725 | Plus | 90895-90994, 93070-93213 |
| 401512 | 7622346 | Plus | 136399-136557 |
| 401563 | 8247910 | Plus | 91395-91763 |
| 401600 | 4388746 | Minus | 27363-27518, 28727-28891, 29526-29731 |
| 401750 | 9828651 | Plus | 82143-82270, 89284-89373, 90596-90770, 95822-96001, 96688-96775, 96870-96992, 98046-98138 |
| 401757 | 7239630 | Plus | 88641-88751 |
| 401839 | 7656637 | Plus | 1016-1086, 2751-2967, 3241-3348, 26677-26831 |
| 401849 | 7770425 | Plus | 129375-129483, 129597-129720 |
| 401952 | 3319121 | Minus | 53770-53979 |
| 401966 | 3126781 | Plus | 29397-29918 |
| 402082 | 8117478 | Minus | 190046-190183 |
| 402101 | 8117697 | Plus | 134308-134487, 135402-135587, 136421-136548 |
| 402106 | 8131652 | Plus | 3717-3848 |
| 402163 | 8568936 | Plus | 166996-167119 |
| 402185 | 8576002 | Plus | 25486-25639 |
| 402240 | 7690131 | Plus | 104382-104527, 106136-106372 |
| 402249 | 7704953 | Minus | 107636-107813, 108694-108824, 110435-110502, 113182-113386 |
| 402347 | 8099267 | Minus | 13714-15440 |
| 402396 | 1905896 | Plus | 4426-4648 |
| 402469 | 9797107 | Minus | 71266-72351 |

TABLE 2C-continued

| Pkey | Ref | Strand | Nt_position |
|---|---|---|---|
| 402532 | 9800951 | Minus | 180240-180558 |
| 402559 | 9864273 | Plus | 33539-33715 |
| 402575 | 9884830 | Minus | 109742-109883 |
| 402602 | 7239666 | Plus | 6785-6972, 7478-7575 |
| 402758 | 9213869 | Plus | 87638-87924 |
| 402786 | 9715046 | Plus | 47624-47795 |
| 402807 | 6456148 | Minus | 101542-101660, 103476-103656 |
| 402810 | 6010110 | Plus | 12715-12856, 13527-13643 |
| 402964 | 9581599 | Minus | 46624-46784 |
| 403046 | 3540153 | Minus | 55707-55859, 56369-56511 |
| 403055 | 8748904 | Minus | 109532-110225 |
| 403217 | 7630969 | Plus | 54089-54163, 55427-55623 |
| 403218 | 7630969 | Plus | 58039-58149 |
| 403291 | 7230870 | Plus | 95177-95435 |
| 403328 | 8469086 | Minus | 120428-120703 |
| 403654 | 8736093 | Minus | 28634-28758 |
| 403704 | 4982546 | Minus | 8850-8996 |
| 403708 | 5705981 | Minus | 134394-134812 |
| 403725 | 7534031 | Plus | 86737-86843 |
| 403739 | 7630882 | Plus | 44563-44766, 48209-48483, 52255-52495 |
| 403740 | 7630882 | Plus | 86504-87227 |
| 403745 | 7652036 | Minus | 67610-68002 |
| 403746 | 7652036 | Plus | 93612-93887 |
| 403885 | 7710403 | Minus | 53259-53524 |
| 403893 | 7710581 | Minus | 5435-7846 |
| 403947 | 7711923 | Plus | 38657-38817 |
| 404039 | 8698763 | Plus | 81889-82011 |
| 404054 | 3548785 | Plus | 66713-69175 |
| 404058 | 3548785 | Plus | 99397-101808 |
| 404108 | 8247074 | Minus | 63603-64942 |
| 404211 | 5006246 | Plus | 185728-185885, 194575-194686 |
| 404277 | 1834458 | Minus | 91665-91946 |
| 404384 | 8887028 | Minus | 38055-38156, 42175-42391, 43435-43553 |
| 404407 | 7329316 | Minus | 48154-48499 |
| 404489 | 8113772 | Plus | 98183-98480 |
| 404527 | 8152087 | Plus | 127737-127796, 128080-128210, 129888-130054, 132545-132869 |
| 404528 | 8152087 | Plus | 135325-135486 |
| 404661 | 9797073 | Plus | 33374-33675, 33769-34008 |
| 404663 | 9797133 | Plus | 29885-30514 |
| 404956 | 7387343 | Plus | 55883-56203 |
| 405011 | 6139150 | Plus | 117359-117612 |
| 405044 | 7596797 | Minus | 98903-101141 |
| 405102 | 8076881 | Minus | 120922-121296 |
| 405109 | 8096886 | Minus | 30301-30518 |
| 405188 | 6649489 | Plus | 134573-134678 |
| 405231 | 7249032 | Minus | 109793-109969 |
| 405365 | 2275192 | Minus | 119867-120372, 120481-120824, 121029-121357 |
| 405387 | 6587915 | Minus | 3769-3833, 5708-5895 |
| 405396 | 6624129 | Minus | 89965-90273 |
| 405429 | 7321905 | Minus | 51577-51723 |
| 405435 | 7408068 | Minus | 51704-51841, 53581-53767 |
| 405446 | 7582529 | Plus | 99136-99313 |
| 405503 | 9211311 | Minus | 51198-51314 |
| 405525 | 9558552 | Minus | 19699-19828 |
| 405529 | 9581957 | Minus | 38944-39213 |
| 405610 | 5757553 | Minus | 71907-72080 |
| 405802 | 5924004 | Minus | 27743-28264 |
| 405811 | 4902753 | Plus | 5128-5248 |
| 406180 | 7283201 | Minus | 38923-39107 |
| 406207 | 5923650 | Minus | 162607-162800 |
| 406302 | 8575868 | Plus | 168961-169150, 169610-169769 |

Pkey: Unique number corresponding to an Eos probeset

Ref: Sequence source. The 7 digit numbers in this column are Genbank Identifier (GI) numbers. "Dunham I. et al." refers to the publication entitled "The DNA sequence of human chromosome 22." Dunham I. et al. (1999) Nature 402: 489-495.

Strand: Indicates DNA strand from which exons were predicted.

Nt_position: Indicates nucleotide positions of predicted exons.

| Pkey | ExAccn | UnigeneID | Unigene Title | Seq ID No |
|---|---|---|---|---|
| 415539 | AI733881 | Hs.72472 | BMP-R1B | Seq ID No 1 & 2 |
| 448988 | Y09763 | Hs.22785 | gamma-aminobutyric acid (GABA) A recepto | Seq ID No 3-10 |
| 403740 | | | NM_001076*: *Homo sapiens* UDP glycosyltran | Seq ID No 11 & 12 |
| 408633 | AW963372 | Hs.46677 | PRO2000 protein | Seq ID No 13 & 14 |
| 408660 | AA525775 | | ESTs, Moderately similar to PC4259 ferri | Seq ID No 15 & 16 |
| 409051 | AA080912 | | gb: zn04d03.r1 Stratagene hNT neuron (937 | Seq ID No 17 |
| 409123 | AA063403 | | gb: zm04d12.s1 Stratagene corneal stroma | Seq ID No 18 |
| 415787 | H01463 | Hs.93534 | ESTs | Seq ID No 19-21 |
| 415999 | AA172179 | Hs.294029 | ESTs | Seq ID No 22 |
| 416225 | AA577730 | Hs.188684 | ESTs, Weakly similar to PC4259 ferritin | Seq ID No 23 |
| 420757 | X78592 | Hs.99915 | androgen receptor (dihydrotestosterone r | Seq ID No 24 & 25 |
| 429163 | AA884766 | | gb: am20a10.s1 Soares_NFL_T_GBC_S1 *Homo s* | Seq ID No 26 |
| 429441 | AJ224172 | Hs.204096 | lipophilin B (uteroglobin family member) | Seq ID No 27 & 28 |
| 431099 | Y13367 | Hs.249235 | phosphoinositide-3-kinase, class 2, alph | Seq ID No 29 & 30 |
| 432432 | AA541323 | Hs.115831 | ESTs | Seq ID No 31 |
| 432435 | BE218886 | Hs.282070 | ESTs | Seq ID No 32 & 33 |
| 432527 | AW975028 | Hs.102754 | ESTs | Seq ID No 34 |
| 435876 | AW612586 | Hs.160271 | G protein-coupled receptor 48 | Seq ID No 35 & 36 |
| 438233 | W52448 | Hs.56147 | ESTs | Seq ID No 37-40 |
| 439569 | AW602166 | Hs.222399 | CEGP1 protein | Seq ID No 41 & 42 |
| 440819 | AI809444 | Hs.202108 | ESTs | Seq ID No 43 |
| 442832 | AW206560 | Hs.253569 | ESTs | Seq ID No 44 |
| 447342 | AI199268 | Hs.19322 | *Homo sapiens*, Similar to RIKEN cDNA 2010 | Seq ID No 45 & 46 |
| 447499 | AW262580 | Hs.147674 | protocadherin beta 16 | Seq ID No 47 & 48 |
| 451411 | AA017492 | Hs.135655 | EST | Seq ID No 49 |
| 451720 | AW970985 | Hs.290853 | ESTs | Seq ID No 50 & 51 |

Pkey: Unique Eos probeset identifier number
ExAccn: Exemplar Accession number, Genbank accession number
UnigeneID: Unigene number
Unigene Title: Unigene gene title
Seq ID No: Seq ID number correlation for those sequences in Table 4

| Pkey | CAT Number | Accession |
|---|---|---|
| 408660 | 107294_1 | AA525775 AA056342 AI538978 AW975281 AA664986 |
| 409051 | 109699_1 | AA080912 AA075318 AA083403 AA076594 AA078992 AA084926 AA081881 AA113913 AA113892 AA083821 AA134801 AA082953 AA070343 AA062835 AA075419 AA063293 AA071252 AA078900 AA062836 AW974305 |

-continued

| Pkey | CAT Number | Accession |
|---|---|---|
| 409123 | 110143_1 | AA063403 AA070823 AA070050 |
| 429163 | 300543_1 | AA884766 AW974271 AA592975 AA447312 |

| Pkey | Ref | Strand | Nt_position |
|---|---|---|---|
| 403740 | 7630882 | Plus | 86504-87227 |

TABLE 4

```
Seq ID NO: 1 DNA sequence
Nucleic Acid Accession #: NM_001203
Coding sequence 274..1782
1          11         21         31         41         51
|          |          |          |          |          |
CGCGDGGCGC GGAGTCGGCG GGGCCTCGCG GGACGCGGCC AGTGCGGAGA CCGCGGCCCT    60
GAGGACGCGG GAGCCGGGAG CGCACGCGCG GGGTGGAGTT CAGCCTACTC TTTCTTAGAT   120
GTGAAAGGAA AGGAAGATCA TTTCATGCCT TGTTGATAAA GGTTCAGACT TCTGCTGATT   180
CATAACCATT TGGCTCTGAG CTATGACAAG AGAGGAAACA AAAAGTTAAA CTTACAAGCC   240
TGCCATAAGT GAGAAGCAAA CTTCCTTGAT AACATGCTTT TGCGAAGTGC AGDAAAATTA   300
AATGTGGGCA CCAAGAAAGA CCATGGTGAG AGTACAGCCC CCACCCCCCG TCCAAAGGTC   360
TTGCGTTGTA AATGCCACCA CCATTGTCCA GAAGACTCAG TCAACAATAT TTGCAGCACA   420
GACGGATATT GTTTCACGAT GATAGAAGAG GATGACTCTG GGTTGCCTGT GGTCACTTCT   480
GGTTGCCTAG GACTAGAAGG CTCAGATTTT CAGTGTCGGG ACACTCCCAT TCCTCATCAA   640
AGAAGATCAA TTGAATGCTG CACAGAAAGG AACGAATGTA ATAAAGACCT ACACCCTACA   600
CTGCCTCCAT TGAAAAACAG AGATTTTGTT GATGGACGTA TACACCACAG GGCTTTACTT   660
ATATCTGTGA CTGTCTGTAG TTTGCTCTTG GTCCTTATCA TATTATTTTG TTACTTCCGG   720
TATAAAAGAC AAGAAACCAG ACCTCGATAC AGCATTGGGT TAGAACAGGA TGAAACTTAC   780
ATTCCTCCTG GAGAATCCCT GAGAGACTTA ATTGAGCAGT CTCAGAGCTC AGGAAGTGGA   840
TCAGGCCTCC CTCTGCTGGT CCAAAGGACT ATAGCTAAGC AGATTCAGAT GGTGAAACAG   900
ATTGGAAAAG GTCGCTATGG GGAAGTTTGG ATGGGAAAGT GGCGTGGCGA AAAGGTAGCT   960
```

TABLE 4-continued

| | | | | | | |
|---|---|---|---|---|---|---|
| GTGAAAGTGT | TCTTCACCAC | AGAGGAAGCC | AGCTCGTTCA | GAGAGACAGA | AATATATCAG | 1020 |
| ACAGTGTTGA | TGAGGCATGA | AAACATTTTG | GGTTTCATTG | CTGCAGATAT | CAAAGGGACA | 1080 |
| GGGTCCTGGA | CCCAGTTGTA | CCTAATCACA | GACTATCATG | AAAATGGTTC | CCTTTATGAT | 1140 |
| TATCTGAAGT | CCACCACCCT | AGACGCTAAA | TCAATGCTGA | AGTTAGCCTA | CTCTTCTGTC | 1200 |
| AGTGGCTTAT | GTCATTTACA | CACAGAAATC | TTTAGTACTC | AAGGCAAACC | AGCAATTGCC | 1260 |
| CATCGAGATC | TGAAAAGTAA | AAACATTCTG | GTGAAGAAAA | ATGGAACTTG | CTGTATTGCT | 1320 |
| GACCTGGGCC | TGGCTGTTAA | ATTTATTAGT | GATACAAATG | AAGTTGACAT | ACCACCTAAC | 1380 |
| ACTCGAGTTG | GCACCAAACG | CTATATGCCT | CCAGAAGTGT | TGGACGAGAG | CTTGAACAGA | 1440 |
| AATCACTTCC | AGTCTTACAT | CATGGCTGAC | ATGTATAGTT | TTGGCCTCAT | CCTTTGGGAG | 1600 |
| GTTGCTAGGA | GATGTGTATC | AGGAGGTATA | GTGGAAGAAT | ACCAGCTTCC | TTATCATGAC | 1560 |
| CTAGTGCCCA | GTGACCCCTC | TTATGAGGAC | ATGAGGGAGA | TTGTGTGCAT | CAAGAAGTTA | 1620 |
| CGCCCCTCAT | TCCCAAACCG | GTGGAGCAGT | GATGAGTGTC | TAAGGCAGAT | GGGAAAACTC | 1680 |
| ATGACAGAAT | GCTGGGCTCA | CAATCCTGCA | TCAAGGCTGA | CAGCCCTGCG | GGTTAAGAAA | 1740 |
| ACACTTGCCA | AAATGTCAGA | GTCCCAGGAC | ATTAAACTCT | GATAGGAGAG | GAAAAGTAAG | 1800 |
| CATCTCTGCA | GAAAGCCAAC | AGGTACTCTT | CTGTTTGTGG | GCAGAGCAAA | AGACATCAAA | 1860 |
| TAAGCATCCA | CAGTACAAGC | CTTGAACATC | GTCCTGCTTC | CCAGTGGGTT | CAGACCTCAC | 1920 |
| CTTTCAGGGA | GCGACCTGGG | CAAAGACAGA | GAAGCTCCCA | GAAGGAGAGA | TTGATCCGTG | 1380 |
| TCTGTTTGTA | GGCGGAGAAA | CCGTTGGGTA | ACTTGTTCAA | GATATGATGC | AT | |

Seq ID NO: 2 Protein sequence
Protein Accession #: NP_001184

| 1 | 11 | 21 | 31 | 41 | 51 | |
|---|---|---|---|---|---|---|
| \| | \| | \| | \| | \| | \| | |
| MLLRSAGKLN | VGTKKEDGES | TAPTPRPKVL | RCKCHHHCPE | DSVNNICSTD | GYCFTMIEED | 60 |
| DSGLPVVTSG | CLGLEGSDFQ | CRDTPIPHQR | RSIECCTERN | ECNKDLNPTL | PPLKNRDFVD | 120 |
| GPIHHRALLI | SVTVCSLLLV | LIILFCYPRY | KRQETRPRYS | IGLEQDETYI | PPGESLRDLI | 180 |
| EQSQSSGSGS | GLPLLVQRTI | AKQIQMVKQI | GKGRYGEVWM | GKWRGEKVAV | KVFFTTEEAS | 240 |
| WFRETEIYQT | VLMRHEMTLG | FIAADIKGTG | SWTQLYLITD | YHENGSLYDY | LKSTTLDAKS | 300 |
| MLKLAYSSVS | GLGNLHTEIF | STQGKPAIAH | RDLKSNKILV | KKNGTCCIAD | LGLAVKFISD | 380 |
| TNEVDIPPNT | RVGTKRYMPP | EVLDESLNRN | HFQSYIMADM | YSFGLILWEV | ARRCVSGGIV | 420 |
| EEYQLPYHDL | VPSDPSYEDM | REIVCIKKLR | PSFPNRWSSD | ECLRQMGKLM | TECWAHNPAS | 480 |
| RLTALRVKKT | LAKMSESQDI | KL | | | | |

Seq ID NO: 3 DNA sequence
Nucleic Acid Accession #: NM_004981.2
Coding sequence: 55..1575

| 1 | 11 | 21 | 31 | 41 | 51 | |
|---|---|---|---|---|---|---|
| \| | \| | \| | \| | \| | \| | |
| GCCAGAGCGT | GAGCCGCGAC | CTCCGCGCAG | GTGGTCGCGC | CGGTCTCCGC | GGAAATGTTG | 60 |
| TCCAAAGTTC | TTCCAGTCCT | CCTAGGCATC | TTATTGATCC | TCCAGTCGAG | GGTCGAGGGA | 120 |
| CCTCAGACTG | AATCAAAGAA | TGAAGCCTCT | TCCCGTGATG | TTGTCTATGG | CCCCCAGCCC | 180 |
| CAGCCTCTGG | AAAATCAGCT | CCTCTCTGAG | GAAACAAAGT | CAACTGAGAC | TGAGACTGGG | 240 |
| AGCAGAGTTG | GCAAACTGCC | AGAAGCCTCT | CGCATCCTGA | ACACTATCCT | GAGTAATTAT | 300 |
| GACCACAAAC | TGCGCCCTGG | CATTGGAGAG | AAGCCCACTG | TGGTCACTGT | TGAGATCGCC | 360 |
| GTCAACAGCC | TTGGTCCTCT | CTCTATCCTA | GACATGGAAT | ACACCATTGA | CATCATCTTC | 420 |
| TCCCAGACCT | GGTACGACGA | ACGCCTCTGT | TACAACGACA | CCTTTGAGTC | TCTTGTTCTG | 480 |
| AATGGCAATG | TGGTGAGCCA | GCTATGGATC | CCGGACACCT | TTTTTAGGAA | TTCTAAGAGG | 540 |
| ACCCACGAGC | ATGAGATCAC | CATGCCCAAC | CAGATGGTCC | GCATCTACAA | GGATGGCAAG | 800 |
| GTGTTGTACA | CAATTAGGAT | GACCATTGAT | GCCGGATGCT | CACTCCACAT | GCTCAGATTT | 860 |
| CCAATGGATT | CTCACTCTTG | CCCTCTATCT | TTCTCTAGCT | TTTCCTATCC | TGAGAATGAG | 720 |
| ATGATCTACA | AGTGGGAAAA | TTTCAAGCTT | GAAATCAATG | AGAAGAACTC | CTGGAAGCTC | 780 |
| TTCCAGTTTG | ATTTTACAGG | AGTGAGCAAC | AAAACTGAAA | TAATCACAAC | CCCAGTTGGT | 840 |
| GACTTCATGG | TCATGACGAT | TTTCTTCAAT | GTGAGCAGGC | GGTTTGGCTA | TGTTGCCTTT | 900 |
| CAAAACTATG | TCCCTTCTTC | CGTGACCACG | ATGCTCTCCT | GGGTTTCCTT | TTGGATCAAG | 960 |
| ACAGAGTCTG | CTCCAGCCCG | GACCTCTCTA | GGGATCACCT | CTGTTCTGAC | CATGACCACG | 1020 |
| TTGGGCACCT | TTTCTCGTAA | GAATTTCCCG | CGTGTCTCCT | ATATCACAGC | CTTGGATTTC | 1080 |
| TATATCGCCA | TCTGCTTCGT | CTTCTGCTTC | TGCGCTCTGT | TGGAGTTTGC | TGTGCTCAAC | 1140 |
| TTCCTGATCT | ACAACCAGAC | AAAAGCCCAT | GCTTCTCCTA | AACTCCGCCA | TCCTCGTATC | 1200 |
| GATAGCCGTG | CCCATGCCCG | TACCCGTGCA | CGTTCCCGAG | CCTGTGCCCG | CCAACATCAG | 1260 |
| GAAGCTTTTC | TGTGCCAGAT | TGTCACCACT | GAGGGAAGTG | ATGGAGAGGA | GCGCCCGTCT | 1320 |
| TGCTCAGCCC | AGCAGCCCCC | TACCCCAGGT | AGCCCTGAGG | GTCCCCGCAG | CCTCTGCTCC | 1380 |
| AAGCTGGCCT | GCTGTGAGTG | GTGCAAGCGT | TTTAAGAAGT | ACTTCTGCAT | GGTCCCCGAT | 1440 |
| TGTGAGGGCA | GTACCTGGCA | GCAGGGCCGC | CTCTGCATCC | ATGTCTACCG | CCTGGATAAC | 1500 |
| TACTCGAGAG | TTGTTTTCCC | AGTGACTTTC | TTCTTCTTCA | ATGTGCTCTA | CTGGCTTGTT | 1560 |
| TGCCTTAACT | TGTAGGTACC | AGCTGGTACC | CTGTGGGGCA | ACCTCTCCAG | TTCCCCAGGA | 1620 |
| GGTCCAAGCC | CCTTGCCAAG | GGAGTTGGGG | GAAAGCAGCA | GCAGCAGCAG | GAGCGACTAG | 1680 |
| AGTTTTTCCT | GCCCCATTCC | CCAAACAGAA | GCTTGCAGAG | GGTTTGTCTT | TGCTGCCCCT | 1740 |
| CTCCCCTACC | TGGCCCATTC | ACTGAGTCTT | CTCAGCAGAC | CATTTCAAAT | TATTAATAAA | 1800 |
| TGGGCCACCT | CCCTCTTCTT | CAAGGAGCAT | CCGTGATGCT | CAGTGTTCAA | AACCACACCC | 1860 |
| ACTTAGTGAT | CACCTCCCTA | AAACCATGCC | TAAGTACACC | CGJATTAGCT | ATCTTCCAAC | 1920 |
| AATGCTGACC | ACCAGACAAT | TACTGCATTT | TTCCAGAACC | CCACTATTGC | CTTTGTAGTG | 1980 |
| CTTTCGGCCC | AGTTCTGGCC | TCACCCTCAA | AGTGCACCGA | CTAGTTGCTT | GCCTATACCT | 2040 |
| GGCACCTCAT | TAAGATGCTG | GGCAGCAGTA | TAACAGGAGG | AAGAGATCCC | TCTCCTTTGG | 2100 |
| TCAGATTATT | ATCTTCTCAG | TTCTCTCTCC | CTGCTACCCC | TTTCTCTGCA | GATAGATAGA | 2160 |
| CACTGGCATT | ATCCCTTTAG | GAAGAGGGGG | GGGCAGCAAG | AGAGCCTATT | TGGGACAGCA | 2220 |
| TTCCTCTCTC | TCTGCTGCTG | TGACATCTCC | CTCTCCTTGC | TGGCTCCATC | TTTCGTCTGC | 2280 |
| ACTACCAATT | CAATGCCCTT | CATCCAATGG | GTATCTATTT | TTGTGTGTGA | TTATAGTAAC | 2340 |
| TACTCCCTGC | TTTATATGCC | ACCCTCTTCC | TTCTCTTTGA | CCCCTGTGAC | TCTTTCTGTA | 2400 |
| ACTTTCCCAG | TGACTTCCCC | TAGCCCTGAC | CCAGGCACTA | GGCCTTGGTG | ACTTCCTGGG | 2460 |

TABLE 4-continued

| | | | | | | |
|---|---|---|---|---|---|---|
| GCCAAGAAAC | TAAGGAAACT | CGGCTTTGCA | ACAGGCATTA | CTCGCCATTG | ATTGGTGCCC | 2520 |
| ACCCAGGGCA | CACTGTCGGA | GTTCTATCAC | TTGCTTGACC | CCTGGACCCA | TAAACCAGTC | 2580 |
| CACTGTTATA | CCCGGGGCAC | TCTAACCATC | ACAATCAATC | AATCAAATTC | CCTTAAATTT | 2640 |
| GTATGGCACT | GGAACTTTGG | CAAAGCACTT | TTGACAAGTT | GTGTCTGATT | GGAGCTTCAT | 2700 |
| GATAGCCTTG | TGACATCTTT | AGGGGAGGAT | TCTTATCCCC | ATTTTGCAGA | TGAAAACCCT | 2760 |
| GAGTCACAGA | TTTCTGTGGG | ACTGTGGATC | TCACTGGAAG | CTATCCAAGA | GCCCACTGTC | 2820 |
| ACCTTCTAGA | CCACATGATA | GGGCTAGACA | GCTCAGTTCA | CCATGATTCT | CTTCTGTCAC | 2880 |
| CTCTGCTGGC | ACACCAGTGG | CAAGGCCCAG | AATGGCGACC | TCTCTTTAGC | TCAATTTCTG | 2940 |
| GGCCTGAGGT | GCTCAGACTG | CCCCCAAGAT | CAAATCTCTC | CTGGCTGTAG | TAACCCAGTG | 3000 |
| GAATGAATTT | GGACATGCCC | CAATGCTTCT | ATATGCTAAG | TGAAATCTGT | GTCTGTAATT | 3060 |
| TGTTGGGGGG | TGGATAGGGT | GGGGTCTCCA | TCTACTTTTT | GTCACCATCA | TCTGAAATGG | 3120 |
| GGAAATATGT | AAATAAATAT | ATCAGCAAAG | CAAAAAGAAA | AAAAAAAA | | |

Seq ID NO 4 Protein sequence
Protein Accession #: NP_004952.1

| 1 | 11 | 21 | 31 | 41 | 51 | |
|---|---|---|---|---|---|---|
| \| | \| | \| | \| | \| | \| | |
| MLSKVLPVLL | GILLILQSRV | EGPQTESKNE | ASSRDVVYGP | QPQPLENQLL | SEETKSTETE | 60 |
| TGSRVGKLPE | ASRILNTILS | NYDNKLRPGI | GEKPTVVTVE | IAVNSLGPLS | ILDMEYTIDI | 120 |
| IFSQTWYDER | LCYNDTFESL | VLNGNVVSQL | WIPDTFPRNS | KRTNENEITN | PNQMVRIYKD | 180 |
| GKVLYTIRMT | IDAGCSLHML | RPPMDSNSCP | LSPSSPSYPE | NENIYKMENF | KLEINEKNSW | 240 |
| KLFQFDFTGV | SNKTEIITTP | VGDFMVMTIF | PNVSRRFGYV | APDNYVPSSV | TTMLSWVSFW | 300 |
| IKTESAPART | SLGITSVLTM | TTLGTFSRKN | PPRVSYITAL | DFYIAICFVF | CFCALLEFAV | 360 |
| LNFLIYNQTK | ANASPKLRHP | RINSRAHART | RARSRACARQ | HQEAPVCQIV | TTEGSDGEER | 420 |
| PSCSAQQPPS | PGSPEGPRSL | CSKLACCEMC | KRFKKYPCMV | PDCEGSTWQQ | GRLCINVYRL | 480 |
| DNYSRVVFPV | TFFFFNVLYW | LVCLNL | | | | |

Seq ID NO 5 DNA sequence
Nucleic Acid Accession #: NM_021984.1
Coding Sequence: 572..1753

| 1 | 11 | 21 | 31 | 41 | 51 | |
|---|---|---|---|---|---|---|
| \| | \| | \| | \| | \| | \| | |
| GCCAGAGCGT | GAGCCGCGAC | CTCCGCGCAG | GTGGTCGCGC | CGGTCTCCGC | GGAAATGTTG | 60 |
| TCCAAAGTTC | TTCCAGTCCT | CCTAGGCATC | TTATTGATCC | TCCAGTCGAG | AACATGTATA | 120 |
| CAGAGAAGTG | CTCAAATCAT | AAGTGTACAG | CTGATGAGTT | GTCAAAAAAT | GACCACAGCG | 180 |
| GTGTAAAGAA | AGCCAAATCA | AGGACCCGAA | TGTGAGCAGG | ACCGCAGAAG | CCCCCTTTGT | 240 |
| CACTGCCTCC | CAGCAAAGGC | AGCACTATCC | GGACTTCTAA | CACCATCGGG | TCGAGGGACC | 300 |
| TCAGACTGAA | TCAAAGAATG | AAGCCTCTTC | CCGTGATGTT | GTCTATGGCC | CCCAGCCCCA | 360 |
| GCCTCTGGAA | AATCAGCTCC | TCTCTGAGGA | AACAAAGTCA | ACTGAGACTG | AGACTGGGAG | 420 |
| CAGAGTTGGC | AAACTGCCAG | AAGCCTCTCG | CATCCTGAAC | ACTATCCTGA | GTAATTATGA | 480 |
| CCACAAACTG | CGCCCTGGCA | TTGGAGAGAA | GCCCACTGTG | GTCACTGTTG | AGATCTCCGT | 540 |
| CAACAGCCTT | GGTCCTCTCT | CTATCCTAGA | CATGGAATAC | ACCATTGACA | TCATCTTCTC | 600 |
| CCAGACCTGG | TACGACGAAC | GCCTCTGTTA | CAACGACACC | TTTGAGTCTC | TTGTTCTGAA | 660 |
| TGGCAATGTG | GTGAGCCAGC | TATGGATCCC | GGACACCTTT | TTTAGGAATT | CTAAGAGGAC | 720 |
| CCACGAGCAT | GAGATCACCA | TGCCCAACCA | GATGGTCCGC | ATCTACAAGG | ATGGCAAGGT | 780 |
| GTTGTACACA | ATTAGGATGA | CCATTGATGC | CGGATGCTCA | CTCCACATGC | TCAGATTTCC | 840 |
| AATGGATTCT | CACTCTTGCC | CTCTATCTTT | CTCTAGCTTT | TCCTATCCTG | AGAATGAGAT | 900 |
| GATCTACAAG | TGGGAAAATT | TCAAGCTTGA | AATCAATGAG | AAGAACTCCT | GGAAGCTCTT | 960 |
| CCAGTTGGAT | TTTACAGGAG | TGAGCAACAA | AACTGAAATA | ATCACAACCC | CAGTTGGTGA | 1020 |
| CTTCATGGTC | ATGACGATTr | TCTTCAATGT | GAGCAGGCGG | TTTGGCTATG | TTGCCTTTCA | 1080 |
| AAACTATGTC | CCTTCTTCCG | TGACCACGAT | GCTCTCCTGG | GTTTCCTTTT | GGATCAAGAC | 1140 |
| AGAGTCTGCT | CCAGCCCGGA | CCTCTCTAGG | GATCACCTCT | GTTCTGACCA | TGACCACGTT | 1200 |
| GGGCACCTTT | TCTCGTAAGA | ATTTCCCGCG | TGTCTCCTAT | ATCACAGCCT | TGGATTTCTA | 1260 |
| TATCGCCATC | TGCTTCGTCT | TCTGCTTCTG | CGCTCTGTTG | GAGTTTGCTG | TGCTCAACTT | 1320 |
| CCTGATCTAC | AACCAGACAA | AAGCCCATGC | TTCTCCTAAA | CTCCGCCATC | CTCGTATCAA | 1380 |
| TAGCCGTGCC | CATGCCCGTA | CCCGTGCACG | TTCCCGAGCC | TGTGCCCGCC | AACATCAGGA | 1440 |
| AGCTTTTGTG | TGCCAGATTG | TCACCACTGA | GGGAAGTGAT | GGAGAGGAGC | GCCCGTCTTG | 1500 |
| CTCAGCCCAG | CAGCCCCCTA | GCCCAGGTAG | CCCTGAGGGT | CCCCGCAGCC | TCTGCTCCAA | 1560 |
| GCTGGCCTGC | TGTGAGTGGT | GCAAGCGTTT | TAAGAAGTAC | TTCTGCATGG | TCCCCGATTG | 1620 |
| TGAGGGCAGT | ACCTGGCAGC | AGGCCCGCCT | CTGCATCCAT | GTCTACCGCC | TGGATAACTA | 1680 |
| GTCGAGAGTT | GTTTTCCCAG | TGACTTTCTT | CTTCTTCAAT | GTGCTCTACT | GGCTTGTTTG | 1740 |
| CCTTAACTTG | TAGGTACCAG | CTGGTACCCT | GTGGGGCAAC | CTCICCAGTT | CCCCAGGAGG | 1800 |
| TCCAAGCCCC | TTCCCAAGGG | AGTTGGGGGA | AAGCAGCAAC | AGCAGCAGGA | GCGACTAGAG | 1860 |
| TTTTTCCTGC | CCCATTCCCC | AAACAGAAGC | TTGCAGAGGG | TTTGTCTTTG | CTCCCCCTCT | 1920 |
| CCCCTACCTG | GCCCATTCAC | TGAGTTTTCT | CASCAGACCA | TTTCAAATTA | TTAATAAATG | 1980 |
| GGCCACCTCC | CTCTTCTTCA | AGGAGCATCC | GTGATCCTCA | GTGTTCAAAA | CCACAGCCAC | 2040 |
| TTAGTGATCA | GCTCCCTAAA | ACCATGCCTA | AGTACAGGCC | CATTAGCTAT | CTTCCAACAA | 2100 |
| TGCTCACCAC | CAGACAATTA | CTGCATTTTT | CCAGAAGCCC | ACTATTCCCT | TTGCAGTGCT | 2160 |
| TTCGGCCCAG | TTCTCGCCTC | AGCCTCAAAD | TCCACCGACT | AGTTGCTTGC | CTATACCTGG | 2220 |
| CACCTCATTA | ACATGCTGGG | CAGCAGTATA | ACAGGAGGAA | CAGATCCCTC | TCCTTTGGTC | 2280 |
| AGATTATTAT | GTTCTCAGTT | CTCTCTCCCT | GCTACCCCTT | TCTCTGCAGA | TAGATAGACA | 2340 |
| CTGGCATTAT | CCCTTTAGGA | AGAGGGGGGG | GCAGCAAGAG | ACCCTATTTG | GGACAGCATT | 2400 |
| CCTCTCTCTC | TGCTGCTGTG | ACATCTCCCT | CTCCTTGCTG | GCTCCATCTT | TCGTCTGCAC | 2460 |
| TACCAATTCA | ATGCCCTTCA | TCCAATGGGT | ATCTATTTTT | GTGTGTGATT | ATAGTAACTA | 2520 |
| CTCCCTGCTT | TATATGCCAC | CCTCTTCCTT | CTCTTTGACC | CCTGTGACTC | TTTCTGTAAC | 2580 |
| TTTCCCAGTG | ACTTCCCCTA | GCCCTGACCC | AGGCACTAGG | CCTTGGTGAC | TTCCTGGGGC | 2640 |
| CAAGAAACTA | AGGAAACTCG | GCTTTGCAAC | AGGCATTACT | CGCCATTGAT | TGGTGCCCAC | 2700 |
| CCAGGGCACA | CTGTCGGAGT | TCTATCACTT | GCTTGACCCC | TGGACCCATA | AACCAGTCCA | 2760 |
| CTGTTATACC | CGGGGCACTC | TAACCATCAC | AATCAATCAA | TCAAATTCCC | TTAAATTTGT | 2820 |

TABLE 4-continued

```
ATGGCACTGG   AACTTTGGCA   AAGCACTTTT   GACAAGTTGT   GTCTGATTGG   AGCTTCATGA   2880
TAGCCTTGTG   ACATCTTTAG   GGCAGGATTC   TTATCCCCAT   TTTGCAGATG   AAAACCCTGA   2940
GTCACAGATT   TCTGTGGGAC   TGTGGATCTC   ACTGGAAGCT   ATCCAAGAGC   CCACTGTCAC   3000
CTTCTAGACC   ACATGATAGG   GCTAGACAGC   TCAGTTCACC   ATGATTCTCT   TCTGTCACCT   3060
CTGCTGGCAC   ACCAGTGGCA   AGGCCCAGAA   TGGCGACCTC   TCTTTAGCTC   AATTTCTGGG   3120
CCTGAGGTGC   TCAGACTGCC   CCCAAGATCA   AATCTCTCCT   GGCTGTAGTA   ACCCAGTGGA   3180
ATGAATTTGG   ACATGCCCCA   ATGCTTCTAT   ATGCTAAGTG   AAATCTGTGT   CTGTAATTTG   3240
TTGGGGGGTG   GATAGGGTGG   GGTCTCCATC   TACTTTTTGT   CACCATCATC   TGAAATGGGG   3300
AAATATGTAA   ATAAATATAT   CAGCAAAGC
```

Seq ID NO 6 Protein sequence
Protein Accession #: NP_068819.1

```
1            11           21           31           41           51
|            |            |            |            |            |
MEYTIDIIPS   QTWYDERLCY   NDTFESLVLN   GNVVSQLWIP   DTFFRNSKRT   HENEITNPNQ     60
MVRIYKDGKV   LYTIRNTIDA   GCSLNNLRFP   MDSNSCPLSP   SSPSYPENEM   IYKWENFKLE    120
INEKNSWKLF   QLDFTGVSNK   TEIITTPVGD   FNVMTIFFNV   SRRFGYVAFQ   NYVPSSVTTM    180
LSWVSFWIKT   ESAPARTSLG   ITSVLTMTTL   GTPSRNMPPR   VSYITALDFY   IAICPVFCFC    240
ALLEPAVLNF   LIYNQTKANA   SPKLPNPRIN   SRAHARTRAR   SRACARQHQE   AFVCQIVTTE    300
GSDGEERPSC   SAQQPPSPGS   PEGPESLCSK   LACCEWCKRF   KKYPCMVPDC   EGSTWQQARL    360
CINVYRLDNY   SRVVFPVTFP   FPNVLYWLVC   LNL
```

Seq ID NO 7 DNA sequence
Nucleic Acid Accession #: NM_021987.1
Coding sequence 672..1657

```
1            11           21           31           41           51
|            |            |            |            |            |
GCCAGAGCGT   GAGCCGCGAC   CTCCGCGCAG   GTGGTCGCGC   CGGTCTCCGC   GGAAATGTTG     60
TCCAAAGTTC   TTCCAGTCCT   CCTAGGCATC   TTATTGATCC   TCCAGTCGAG   AACATGTATA    120
CAGAGAAGTG   CTCAAATCAT   AAGTGTACAG   CTGATGAGTT   GTCAAAAAAT   GACCACAGCG    180
GTGTAAAGAA   AGGCAAATCA   AGGACCCGAA   TGTGAGCAGG   ACCTCAGAAG   CCCCCTTTGT    240
CACTGCCTCC   CAGCAAAGGC   AGCACTATCC   GGACTTCTAA   CACCATCGGG   TCGAGGGACC    300
TCAGACTGAA   TCAAAGAATG   AAGCCTCTTC   CCGTGATGTT   GTCTATGGCC   CCCAGCCCCA    360
GCCTCTGGAA   AATCAGCTCC   TCTCTGAGGA   AACAAAGTCA   ACTGAGACTG   AGACTGGGAG    420
CAGAGTTGGC   AAACTGCCAG   AAGCCTCTCG   CATCCTGAAC   ACTATCCTGA   GTAATTATGA    480
CCACAAACTG   CGCCCTGGCA   TTGGAGAGAA   GCCCACTGTG   GTCACTGTTG   AGATCTCCGT    540
CAACAGCCTT   GGTCCTCTCT   CTATCCTAGA   CATGGAATAC   ACCATTGACA   TCATCTTCTC    600
CCAGACCTGG   AATTCTAAGA   GGACCCACGA   GCATGAGATC   ACCATGCCCA   ACCAGATGGT    660
CCGCATCTAC   AAGGATGGCA   AGGTGTTGTA   CACAATTAGG   ATGACCATTG   ATGCCGGATG    720
CICACTCCAC   ATGCTCAGAT   TTCCAATGGA   TTCTCACTCT   TGCCCTCTAT   CTTTCTCTAG    780
CTTTTCCTAT   CCTGAGAATG   AGATGATCTA   CAAGTGGGAA   AATTTCAAGC   TTGAAATCAA    840
TGAGAAGAAC   TCCTGGAAGC   TCTTCCAGTT   TGATITTACA   GGAGTGAGCA   ACAAAACTGA    900
AATAATCACA   ACCCCAGTTG   GTGACTTCAT   GGTCATGACG   ATTTTCTTCA   ATGTGAGCAG    960
GCGGTTTGGC   TATGTTGCCT   TTCAAAACTA   TGTCCCTTCT   TCCGTGACCA   CGATGCTCTC   1020
CTGGGTTTCC   TTTTGGATCA   AGACAGAGTC   TGCTCCAGGC   CGGACCTCTC   TAGGGATCAC   1080
CTCTGTTCTG   ACCATGACCA   CGTTGGGCAC   CTTTTCTCGT   AAGAATTTCC   CGCGTGTCTC   1140
CTATATCACA   GCCTTGGATT   TCTATATCGC   CATCTGCTTC   GTCTTCTGCT   TCTGCGCTCT   1200
GTTGGAGTTT   GCTGTGGTCA   ACTTCCTGAT   CTACAACCAG   ACAAAAGCCC   ATGCTTCTCC   1260
TAAACTCCGC   CATCCTCGTA   TCAATAGCCG   TGCCCATGCC   CGTACCCGTG   CACGTTCCCG   1320
AGCCTGTGCC   CGCCAACATC   AGGAAGCTTT   TGTGTDCCAG   ATTGTCACCA   CTGAGGGAAG   1380
TGATGGAGAG   GAGCGCCCGT   CTTGCTCAGC   CCAGCAGCCC   CCTAGCCCAG   GTAGCCCTGA   1440
GGGTCCCCGC   AGCCTCTGCT   CCAAGCTGGC   CTGCTGTGAG   TGGTGCAAGC   GTTTTAAGAA   1500
GTACTTCTGC   ATGGTCCCCG   ATTGTGAGGG   CAGTACCTGG   CAGCAGGGCC   GCCTCTGCAT   1560
CCATGTCTAC   CGCCTGGATA   ACTACTCGAG   AGTTGTTTTC   CCAGTGACTT   TCTTCTTCTT   1620
CAATGTGCTC   TACTGGCTTG   TTTGCCTTAA   CTTGTAGGTA   CCAGCTGGTA   CCCTGTGGGG   1680
CAACCTCTCC   AGTTCCCCAG   GAGGTCCAAG   CCCCTTGCCA   AGGGAGTTGG   GGGAAAGCAG   1740
CAGCAGCAGC   AGGAGGGACT   AGAGTTTTTC   CTGCCCCATT   CCCCAAACAG   AAGCTTGCAG   1800
AGGGTTTGTC   TTTGCTGCCC   CTCTCCCCTA   CCTGGCCCAT   TCACTGAGTT   TTCTCAGCAG   1860
ACCATTTCAA   ATTATTAATA   AATGGGCCAC   CTCCCTCTTC   TTCAAGGAGC   ATCCGTGATG   1920
CTCAGTGTTC   AAAACCACAG   CCACTTAGTG   ATCAGCTCCC   TAAAACCATG   CCTAAGTACA   1980
GGCGGATTAG   CTATCTTCCA   ACAATGCTGA   CCACCAGACA   ATTACTGCAT   TTTTCCAGAA   2040
GCCCACTATT   GCCTTTGCAG   TGCTTTCGGC   CCAGTTCTGG   CCTGAGCCTC   AAAGTGCACC   2100
GACTAGTTGC   TTGCCTATAC   CTGGCACCTC   ATTAAGATGC   TCGGCAGCAG   TATAACAGGA   2160
GGAAGAGATC   CCTCTCCTTT   GGTCAGATTA   TTATGTTCTC   AGTTCTCTCT   CCCTGCTACC   2220
CCTTTCTCTG   CAGATAGATA   GACACTGGCA   TTATCCCTTT   AGGAAGACGG   GGGGGCAGCA   2280
AGAGAGCCTA   TTTGGGACAG   CATTCCTCTC   TCTCTGCTGC   TGTGACATCT   CCCTCTCCTT   2340
GCTGGCTCCA   TCTTTCGTCT   GCACTACCAA   TTCAATGCCC   TTCATCCAAT   GGGTATCTAT   2400
TTTTGTGTGT   GATTATAGTA   ACTACTCCCT   GCTTTATATG   CCACCCTCTT   CCTTCTCTTT   2460
GACCCCTGTG   ACTCTTTCTG   TAACTTTCCC   AGTGACTTCC   CCTAGCCCTG   ACCAGGCACT   2520
AGGCCTTGGT   GACTTCCTGG   GGCCAACAAA   CTAAGGAAAC   TCGGCTTTGC   AACAGGCATT   2580
ACTCGCCATT   GATTGGTGCC   CACCGAGGGC   ACACTGTCGG   AGTTCTATCA   CTTGCTTGAC   2640
CCCTGGACCC   ATAAACCAGT   GCACTGTTAT   ACCCGGGGCA   CTCTAACCAT   CACAATCAAT   2700
CAATCAAATT   CCCTTAAATT   TGTATGGCAC   TGGAACTTTG   GCAAAGCACT   TTTGACAAGT   2760
TGTGTCTGAT   TGGAGCTTCA   TGATAGCCTT   GTGACATCTT   TAGGGCAGGA   TTCTTATCCC   2820
CATTTTGCAG   ATGAAAACCC   TGAGTCACAG   ATTTCTGTGG   GACTGTGGAT   CTCACTGGAA   2880
GCTATCCAAG   AGCCCACTGT   CACCTTCTAG   ACCACATGAT   AGGGCTAGAC   AGCTCAGTTC   2940
ACCATGATTC   TCTTCTGTCA   CCTCTGCTGG   CACACCACTG   GCAAGGCCCA   GAATGGCGAC   3000
CTCTCTTTAG   CTCAATTTCT   GGGCCTGAGG   TGCTCAGACT   GCCCCCAAGA   TCAAATCTCT   3060
CCTGGCTGTA   GTAACCCAGT   GGAATGAATT   TGGACATGCC   CCAATGCTTC   TATATGCTAA   3120
```

TABLE 4-continued

| | | | | | | |
|---|---|---|---|---|---|---|
| GTGAAATCTG | TGTCTGTAAT | TTGTTGGGGG | GTGGATAGGG | TGGGGTCTCC | ATCTACTTTT | 3180 |
| TGTCACCATC | ATCTGAAATG | GGGAAATATG | TAAATAAATA | TATCAGCAAA | GC | |
| Seq ID NO: 8 Protein sequence | | | | | | |
| Protein Accession #: NP_068822.1 | | | | | | |
| 1 | 11 | 21 | 31 | 41 | 51 | |
| \| | \| | \| | \| | \| | \| | |
| MEYTIDIIFS | QTWNSKRTHE | HEITNPNQMV | RIYKDGKVLY | TIRMTIDAGC | SLHMLRFPMD | 60 |
| SHSCPLSFSS | FSYPENNMIY | KWENFKLEIN | EKNSWKLFQF | DFTGVSNKTE | IITTPVGDFM | 120 |
| VMTIFFNVSR | RFGYVAFQNY | VPSSVTTMLS | WVSFWIKTES | APARTGLGIT | SVLTMTTLGT | 180 |
| FSRKNFPRVS | YITALDFYIA | ICFVFCFCAL | LEPAVLNFLI | YNQTKAHASP | KLRHPRINSN | 240 |
| AHARTPARSN | ACARQHQEAF | VCQIVTTEGS | DGEERPSCSA | QQPPSPGSPE | GPRSLCSKLA | 300 |
| CCEWCKRFKK | YFCMVPDCEG | STWQQGRLCI | HVYRLDNYSR | VVFPVTFFFF | NVLYWLVCLN | 360 |
| L | | | | | | |
| Seq ID NO: 9 DNA sequence | | | | | | |
| Nucleic Acid Accession #: NM_021990.1 | | | | | | |
| Coding sequence: 1309..2490 | | | | | | |
| 1 | 11 | 21 | 31 | 41 | 51 | |
| \| | \| | \| | \| | \| | \| | |
| GCCAGAGGGT | GAGCCGCGAC | CTCCGCGCAG | GTGGTCGCGC | CGGTCTCCGC | GGAAATGTTG | 60 |
| TCCAAAGTTC | TTCCAGTCCT | CCTAGGCATC | TTATTGATCC | TCCAGTCGAG | AACATGTATA | 120 |
| CAGAGAAGTG | CTCAAATCAT | AAGTGTACAG | CTGATGAGTT | GTCAAAAAAT | GACCACAGCG | 180 |
| GTGTAAAGAA | AGCCAAATCA | AGGACCCGAA | TGTGAGCAGG | ACCTCAGAAG | CCCCCTTTGT | 240 |
| CACTGCCTCC | CAGCAAAGGC | AGCACTATCC | GGACTTCTAA | CACCATCGGT | GAGTTTCATA | 300 |
| CCTTGGCAGA | TGGCCTTTAA | CATTTTTGTT | TAATTCAATT | ATTCTTACTA | ATCTTCTTCT | 360 |
| TTTTCTTGGC | TGTGGTGCAT | GGCTGTGGAG | CTCAGGGTGG | ACTCCTGTTG | GGCAGCCAGT | 420 |
| TCCTGGATGG | CTGTCTGTGG | GTGGAGGACT | CCTGCCTTTC | CTGTTTAGAC | ACCCACAAAG | 480 |
| GCTGCTCTTT | AGCCTCCTTC | CCTTCATCCC | CTTCCCCtGC | CCCCAGTGCA | ACGAGTATTA | 540 |
| CACAACCAAC | AAAACCGCAA | AATATTCCCA | CAATTTTGTG | GTCCTCTCTG | GGAGAGGCCG | 600 |
| CTCTGGCTTT | TCCTCTCAGC | CCTGGCCCTC | TGCCTGCTCC | TCACTCCTGG | TTGGTGCTGG | 660 |
| TCAGGCTGAC | TAGAGGCCAA | GGCGACCAAC | ACTAGGCAAA | CGCGGCCAGC | GCTCAGACAT | 720 |
| AAATGCCCTC | TTCATTTCAC | GTGTAACATT | CTTTTAAAAT | GTAGGTCTTG | GTTTTGTTGA | 780 |
| TTTTTTCTTA | AATAAAAGAG | TGATCATAAA | AGAGGGACAG | CATAGAAAGT | CCCCAAAGAG | 840 |
| CAGCAAGGTT | TTAAAGAAAT | TCACAAGCCT | AATCTGTGAC | TGTCTTATAA | TTTGCTATTA | 900 |
| CCAGTCACAA | TTTAACTAGG | TTTTGTGTTG | AAAACTTGTT | TTGGTTTGCT | TCTGTCCCAA | 960 |
| GAGGCACTAG | CTGGGGCCCC | TACAGAGTGC | AGGGCAGAGC | TTCATTTTTC | GTTTGAATGT | 1020 |
| TCTAGGGTCG | AGGGACCTCA | GACTGAATCA | AAGAATGAAG | CCTCTTCCCG | TGATGTTGTC | 1080 |
| TATGGCCCCC | AGCCCCAGCC | TCTGGAAAAT | CAGCTCCTCT | CTGAGGAAAC | AAAGTCAACT | 1140 |
| GAGACTGAGA | CTGGGAGCAG | AGTTGGCAAA | CTGCCAGAAG | CCTCTCGCAT | CCTGAACACT | 1200 |
| ATCCTGAGTA | ATTATGACCA | CAAACTGCGC | CCTGGCATTG | GAGAGAAGCC | CACTGTGGTC | 1260 |
| ACTGTTGAGA | TCTCCGTCAA | CAGCCTTGGT | CCTCTCTCTA | TCCTAGACAT | GGAATACACC | 1320 |
| ATTGACATCA | TCTTCTCCCA | GACCTGGTAC | GACGAACGCC | TCTGTTACAA | CGACACCTTT | 1380 |
| GAGTCTCTTG | TTCTGAATGG | CAATGTGGTG | AGCCAGCTAT | GGATCCCGGA | CACCTTTTTT | 1440 |
| AGGAATTCTA | AGAGGACCCA | CGAGCATGAG | ATCACCATGC | CCAACCAGAT | GGTCCGCATC | 1000 |
| TACAAGGATG | GCAAGGTGTT | GTACACAATT | AGGATGACCA | TTGATGCCGG | ATGCTCACTC | 1560 |
| CACATGCTCA | GATTTCCAAT | GGATTCTCAC | TCTTGCCCTC | TATCTTTCTC | TAGCTTTTCC | 1620 |
| TATCCTGAGA | ATGAGATGAT | CTACAAGTGG | GAAAATTTCA | AGCTTGAAAT | CAATGAGAAG | 1680 |
| AACTCCTGGA | AGCTCTTCCA | GTTTGATTTT | ACAGGAGTGA | GCAACAAAAC | TGAAATAATC | 1740 |
| ACAACCCCAG | TTGGTGACTT | CATGGTCATG | ACGATTTTCT | TCAATGTGAG | CAGGCGGTTT | 1800 |
| GGCTATGTTG | CCTTTCAAAA | CTATGTCCCT | TCTTCCGTGA | CCACGATGCT | CTCCTGGGTT | 1860 |
| TCCTTTTGGA | TCAAGACAGA | GTCTGCTCCA | GCCCGGACCT | CTCTAGGGAT | CACCTCTGTT | 1920 |
| CTGACCATGA | CCACGTTGGG | CACCTTTTCT | CGTAAGAATT | TCCCGCGTGT | CTCCTATATC | 1980 |
| ACAGCCTTGG | ATTTCTATAT | CGCCATCTGC | TTCGTCTTCT | GCTTCTGCGC | TCTGTTGGAG | 2040 |
| TTTGCTGTGC | TCAACTTCCT | GATCTACAAC | CAGACAAAAG | CCCATGCTTC | TCCTAAACTC | 2100 |
| CGCCATCCTC | GTATCAATAG | CCGTGCCCAT | GCCCGTACCC | GTGCACGTTC | CCGAGCCTGT | 2160 |
| GCCCGCCAAC | ATCAGGAAGC | TTTTGTGTGC | CAGATTGTCA | CCACTGAGGG | AAGTGATGGA | 2220 |
| GAGGAGCGCC | CGTCTTGCTC | AGCCCAGCAG | CCCCCTAGCC | CAGGTAGCCC | TGAGGGTCCC | 2280 |
| CGCAGCCTCT | GCTCCAAGCT | GGCCTGCTGT | GAGTGGTGCA | AGCGTTTTAA | GAAGTACTTC | 2340 |
| TGCATGGTCC | CCGATTGTGA | GGGCAGTACC | TGGCAGCAGG | GCCGCCTCTG | CATCCATGTC | 2400 |
| TACCGCCTGG | ATAACTACTC | GAGAGTTGTT | TTCCCAGTGA | CTTTCTTCTT | CTTCAATGTG | 2460 |
| CTCTACTGGC | TTGTTTGCCT | TAACTTGTAG | GTACCAGCTG | GTACCCTGTG | GGGCAACCTC | 2520 |
| TCCAGTTCCC | CAGGAGGTCC | AAGCCCCTTG | CCAAGGGAGT | TGGGGGAAAG | CAGCAGCAGC | 2580 |
| AGCAGGAGCG | ACTAGAGTTT | TTCCTGCCCC | ATTCCCCAAA | CAGAAGCTTG | CAGAGGGTTT | 2640 |
| GTCTTTGCTG | CCCCTCTCCC | CTACCTGGCC | CATTCACTCA | GTTTTCTCAG | CAGACCATTT | 2700 |
| CAAATTATTA | ATAAATGGGC | CACCTCCCTC | TTCTTCAAGG | AGCATCCGTG | ATGCTCAGTC | 2760 |
| TTCAAAACCA | CAGCCACTTA | GTGATCAGCT | CCCTAAAACC | ATGCCTAAGT | ACAGGCGGAT | 2820 |
| TAGCTATCTT | CCAACAATGC | TGACCACCAG | ACAATTACTG | CATTTTTCCA | GAAGCCCACT | 2880 |
| ATTGCCTTTG | CAGTGCTTTC | GGCCCAGTTC | TGGCCTCAGC | CTCAAAGTGC | ACCCACTAGT | 2940 |
| TGCTTGCCTA | TACCTGGCAC | CTCAATAAGA | TGCTGGGCAG | CAGTATAACA | CCAGGAAGAG | 3000 |
| ATCCCTCTCC | TTTGGTCAGA | TTATTATGTT | CTCAGTTCTC | TCTCCCTGCT | ACCCCTTTCT | 3060 |
| CTGCAGATAG | ATAGACACTG | GCATTATCCC | TTTAGGAAGA | GGGGGGGGCA | GCAAGAGAGC | 3120 |
| CTATTTGGGA | CAGCATTCCT | CTCTCTCTGC | TGCTGTGACA | TCTCCCTCTC | CTTGCTGGCT | 3180 |
| CCATCTTTCG | TCTGCACTAC | CAATTCAATG | CCCTTCATCC | AATGGGTATC | TATTTTTGTG | 3240 |
| TGTGATTATA | GTAACTACTC | CCTGCTTTAT | ATGCCACCCT | CTTCCTTCTC | TTTCACCCCT | 3300 |
| GTGACTCTTT | CTGTAACTTT | CCCAGTGACT | TCCCCTAGCC | CTGACCAGGC | ACTAGGCCTT | 3360 |
| GGTGACTTCC | TGGGGCCAAG | AAACTAAGGA | AACTCGGCTT | TGCAACAGGC | ATTACTCGCC | 3420 |
| ATTGATTGGT | GCCCACCCAG | CCCACACTGT | CGGAGTTCTA | TCACTTGCTT | GACCCCTGGA | 3480 |
| CCCATAAACC | AGTCCACTGT | TATACCCGGG | GCACTCTAAC | CATCACAATC | AATCAATCAA | 3540 |

TABLE 4-continued

| | | | | | | |
|---|---|---|---|---|---|---|
| ATTCCCTTAA | ATTTGTATGG | CACTGGAACT | TTGGCAAAGC | ACTTTTGACA | AGTTGTGTCT | 3600 |
| CATTGGAGCT | TCATGATAGC | CTTGTGACAT | CTTTAGGGCA | GGATTCTTAT | CCCCATTTTG | 3660 |
| CAGATGAAAA | CCCTGAGTCA | CAGATTTCTG | TGGGACTGTG | GATCTCACTG | GAAGCTATCC | 3720 |
| AAGAGCCCAC | TGTCACCTTC | TAGACCACAT | GATAGGGCTA | GACAGCTCAG | TTCACCATGA | 3780 |
| TTCTCTTCTG | TCACCTCTGC | TGGCACACCA | GTGGCAAGGC | CCAGAATGGC | GACCTCTCTT | 3840 |
| TAGCTCAATT | TCTGGGCCTG | AGGTGCTCAG | AGTGCCCCGA | AGATCAAATC | TCTCCTGGCT | 3900 |
| GTAGTAACCC | AGTGGAATGA | ATTTGGACAT | GCCCCAATGC | TTCTATATGC | TAAGTGAAAT | 3960 |
| CTGTGTCTGT | AATTTGTTGG | GGGGTGGATA | GGGTGGGGTC | TCCATCTACT | TTTTGTCACC | 4020 |
| ATCATCTGAA | ATGGGGAAAT | ATGTAAATAA | ATATATCAGC | AAAGC | | |

Seq ID NO: 10 Protein sequence
Protein Accession #: NP_068830.1

| 1 | 11 | 21 | 31 | 41 | 51 | |
|---|---|---|---|---|---|---|
| \| | \| | \| | \| | \| | \| | |
| MEYTIDIIPS | QTWYDERLCY | NDTFESLVLN | GNVVSQLWIP | DTFFRNSKRT | HENEITNPNQ | 60 |
| MVRIYKIGKV | LYTIRMTIDA | GCSLHNLRFP | MDSNSCPLSF | SSFSYPENEM | IYKWENFKLE | 120 |
| INEKNSWKLF | QFDFTGVSNK | TEIITTPVGD | FMVMTIFFNV | SRRFGYVAFQ | NYVPSSVTTM | 180 |
| LSWVSFWIKT | ESAPARTSLG | ITSVLTMTTL | GTFSRKNFPR | VSYITALDFY | IAICFVFCFC | 240 |
| ALLEFAVLNF | LIYNQTKANA | SPKLRNPRIN | SPAHARTEAR | SRACARQNQE | AFVCQIVTTE | 300 |
| GSDGEERPSC | SAQOPPSPGS | PEGPRSLCSK | LACCEWCKRF | KKYFCMVPDC | EGSTWQQGRL | 360 |
| CINVYRLDNY | SRVVFPVTPF | FFNVLYWLVC | LNL | | | |

Seq ID NO: 11 DNA sequence
Nucleic Acid Accession #: NM_001076.1
Coding sequence: 22..1614

| 1 | 11 | 21 | 31 | 41 | 51 | |
|---|---|---|---|---|---|---|
| \| | \| | \| | \| | \| | \| | |
| TTCGGCACGA | GTAAGACCAG | GATGTCTCTG | AAATGGACGT | CAGTCTTTCT | GCTGATACAG | 60 |
| CTCAGTTGTT | ACTTTAGCTC | TGGAAGCTGT | GGAAAGGTGC | TAGTGTGGCC | CACACAATAC | 120 |
| AGCCATTGGA | TAAATATGAA | GACAATCCTG | GAAGAGCTTG | TTCAGAGGGG | TCATGAGGTG | 180 |
| ACTGTGTTGA | CATCTTCGGC | TTCTACTCTT | GTCAATGCCA | GTAAATCATC | TGCTATTAAA | 240 |
| TTAGAAGTTT | ATCCTACATC | TTTAACTAAA | AATGATTTGG | AAGATTCTCT | TCTGAAAATT | 300 |
| CTCGATAGAT | GGATATATGG | TGTTTCAAAA | AATACATTTT | GGTCATATTT | TTCACAATTA | 360 |
| CAAGAATTGT | GTTGGGAATA | TTATGACTAC | AGTAACAAGC | TCTGTAAAHA | TGCAGTTTTG | 420 |
| AATAAGAAAC | TTATGATGAA | ACTACAAGAG | TCAAAGTTTG | ATGTCATTCT | GGCAGATGCC | 480 |
| CTTAATCCCT | GTGGTGAGCT | ACTGGCTGAA | CTATTTAACA | TACCCTTTCT | GTACAGTCTT | 540 |
| CGATTCTCTG | TTGGCTACAC | ATTTGAGAAG | AATGGTGGAG | GATTTCTGTT | CCCTCCTTCC | 600 |
| TATGTACCTG | TTGTTATGTC | AGAATTAAGT | GATCAAATGA | TTTTCATGGA | GAGGATAAAA | 660 |
| AATATGATAC | ATATGCTTTA | TTTTGACTTT | TGGTTTCAAA | TTTATGATCT | GAAGAAGTGG | 720 |
| GACCAGTTTT | ATAGTGAAGT | TCTAGGAAGA | CCCACTACAT | TATTTGAGAC | AATGGGGAAA | 780 |
| GCTGAAATGT | GGCTCATTCG | AACCTATTGG | GATTTTGAAT | TTCCTCGCCC | ATTCTTACCA | 840 |
| AATGTTGATT | TTGTTGGAGG | ACTTCACTGT | AAACCAGCCA | AACCCCTGCC | TAAGGAAATG | 900 |
| GAAGAGTTTG | TGCAGAGCTC | TGGAGAAAAT | GGTATTGTGG | TGTTTTCTCT | GGGGTCGATG | 960 |
| ATCAGTAACA | TGTCAGAAGA | AAGTGCCAAC | ATGATTGCAT | CAGCCCTTGC | CCAGATCCCA | 1020 |
| CAAAAGGTTC | TATGGAGATT | TGATGGGAAG | AAGCCAAATA | CATTAGGTTC | CAATACTCGA | 1080 |
| CTGTACAAGT | GGTTACCCCA | GAATGACCTT | CTTGGTCATC | CCAAAACCAA | AGCTTTTATA | 1140 |
| ACTCATGGTG | GAACCAATGG | CATCTATGAG | GCGATCTACC | ATGGGATCCC | TATGGTGGTC | 1200 |
| ATTCCCTTGT | TTGCGGATCA | ACATGATAAC | ATTGCTCACA | TGAAAGCCAA | GGGAGCAGCC | 1260 |
| CTCAGTGTGG | ACATCAGGAC | GATGTCAAGT | AGAGATTTGC | TCAATGCATT | GAAGTCAGTC | 1320 |
| ATTAATGACC | CTGTCTATAA | AGAGAATGTC | ATGAAATTAT | CAAGAATTCA | TCATGACCAA | 1380 |
| CCAATGAAGC | CCCTGGATCG | AGCAGTCTTC | TGGATTGAGT | TTGTCATGCG | CCACAAAGGA | 1440 |
| GCCAAGCACC | TTCGAGTCGC | AGCTCACAAC | CTCACCTGGA | TCGAGTACCA | CTCTTTGGAT | 1500 |
| GTGATAGCAT | TCCTGCTGGC | CTGCGTGGCA | ACTGTGATAT | TTATCATCAC | AAAATTTTGC | 1560 |
| CTGTTTTGTT | TCCGAAAGCT | TGCCAAAACA | GGAAAGAAGA | AGAAAAGAGA | TTAGTTATAT | 1620 |
| CAAAAGCCTG | AAGTGGAATG | ACTGAAAGAT | GGGACTCCTC | CTTTATTTCA | GCATGGAGGG | 1680 |
| TTTTAAATGG | AGGATTTCCT | TTTTCCTGTG | ACAAAACATC | TTTTCACAAC | TTACCTTGTT | 1740 |
| AAGACAAAAT | TTATTTTCCA | GGGATTTAAT | ACGTACTTTA | GTTGGAATTA | TTCTATGTCA | 1800 |
| ATGATTTTTA | AGCTATGAAA | AATACAATGG | GGGGAAGGAT | AGCATTTGGA | GATATACCTA | 1860 |
| ATGTTAAATG | ACGAGTTACT | GGATGCAGGA | CGCAACATGG | CACATGTGTA | TACATATGTA | 1920 |
| GCTAACCCTT | CGTTGTGCAC | ATGTACCCTA | AAACTTAAAG | TATAATTTAA | AAAAAGCAAA | 1980 |
| AAAAAAAAAT | ACCAACTCTT | TTTTTTAAAC | CAGGAAGGAA | AATGTGAACA | TGGAAACAAC | 2040 |
| TTCTAGTATT | GGATCTGAAA | ATAAAGTGTC | ATCCAAGCCA | TAAAAAAAAA | | |

Seq ID NO: 12 Protein sequence
Protein Accession #: NP_001067.1

| 1 | 11 | 21 | 31 | 41 | 51 | |
|---|---|---|---|---|---|---|
| \| | \| | \| | \| | \| | \| | |
| MSLKWTSVFL | LIQLSCYFSS | GSCGKVLVWP | TEYSHWINMK | TILEELVQRG | HEVTVLTSSA | 60 |
| STLVNASKSS | AIKLEVYPTS | LTKNDLEDGL | LKILDRWIYG | VSKNTFWSYF | SQLQELCWEY | 120 |
| YDYSNKLCKD | AVLNKKLMMK | LGEGKFDVIL | ADALNPCGEL | LAELFNIPFL | YSLRFSVGYT | 180 |
| FEKNGGGGFL | PPSYVPVVNS | ELSDQMIFME | RIKNMINMLY | FDFWFQIYDL | KKWDQFYSEV | 240 |
| LGRPTTLFET | MGKAEMWLIR | TYWDFEFPRP | FLPNVDFVGG | LNCKPAKPLP | KENEEFVQSS | 300 |
| GENGIVVFSL | GSMISNNSEE | SANMIASALA | QIPQKVLWRF | DGKKPNTLCS | NTRLYKWLPQ | 360 |
| NDLLGNPKTK | AFITNGGTNG | IYSAIYNGIP | MVGIPLFADQ | HDNIAHMKAK | GAALSVDIRT | 420 |
| NSSRDLLNAL | KSVINDPVYK | ENVMKLSRIN | NDQPMKPLDR | AVFWIEFVMR | HKGAKHLRVA | 480 |
| AHNLTWIQYN | SLDVIAFLLA | CVATVIFIIT | KFCLFCPRKL | AKTGKKKKRD | | |

TABLE 4-continued

Seq ID NO 13 DNA sequence
Nucleic Acid Accession #: NN_014109 1
Coding sequence: 651..1739

| 1 | 11 | 21 | 31 | 41 | 51 | |
|---|---|---|---|---|---|---|
| CTGTCATTCA | TGCTTTGGAA | AAGTTTACTG | TATATACATT | AGACATTCCT | GTTCTTTTTG | 60 |
| GAGTTAGTAC | TACATCCCCT | GAAGAAACAT | GTGCCCAGGT | GATTCGTGAA | GCTAAGAGAA | 120 |
| CAGCACCAAG | TATAGTGTAT | GTTCCTCATA | TCCACGTGTG | GTGGGAAATA | GTTGGACCGA | 180 |
| CACTTAAAGC | CACATTTACC | ACATTATTAC | AGAATATTCC | TTCATTTGCT | CCAGTTTTAC | 240 |
| TACTTGCAAC | TTCTGACAAA | CCCCATTCCG | CTTTGCCAGA | AGAGGTGCAA | GAATTGTTTA | 300 |
| TCCGTGATTA | TGGAGAGATT | TTTAATGTCC | AGTTACCGGA | TAAADAAGAA | CGGACAAAAT | 360 |
| TTTTTGAAGA | TTTAATTCTA | AAACAAGCTG | CTAAGCCTCC | TATATCAAAA | AAGAAAGCAG | 420 |
| TTTTGCAGGC | TTTGGAGGTA | CTCCCAGTAG | CACCACCACC | TGAGCCAAGA | TCACTGACAG | 480 |
| CAGAAGAAGT | GAAACGACTA | GAAGAACAAG | AAGAAGATAC | ATTTAGAGAA | CTGAGGATTT | 540 |
| TCTTAAGAAA | TGTTACACAT | AGGCTTGCTA | TTGACAAGCG | ATTCCGAGTG | TTTACTAAGC | 800 |
| CTGTTGACCC | TGATGAGGTT | CCTGATTATG | TCACTGTAAT | AAAGCAACCA | ATGGACCTTT | 680 |
| CATCTGTAAT | CAGTAAAATT | GATCTACACA | AGTATcTGAC | TGTGAAAGAC | TATTTGAGAG | 720 |
| ATATTGATCT | AATCTGTAGT | AATGCCTTAG | AATACAATCC | AGATAGAGAT | CCTGGAGATC | 780 |
| GTCTTATTAG | GCATAGAGCC | TGTGCTTTAA | GAGATACTGC | CTATGCCATA | ATTAAAGAAG | 840 |
| AACTTGATGA | AGACTTTGAG | CAGCTCTGTG | AAGAAATTCA | GGAATCTAGA | AAGAAAAGAG | 900 |
| GTTGTAGCTC | CTCCAAATAT | GCCCCGTCTT | ACTACCATGT | GATGCCAAAG | CAAAATTCCA | 960 |
| CTCTTGTTGG | TGATAAAAGA | TCAGACCCAG | AGCAGAATGA | AAAGCTAAAG | ACACCGAGTA | 1020 |
| CTCCTGTGGC | TTGCAGCACT | CCTGCTCAGT | TGAAGAGGAA | AATTCGCAAA | AAGTCAAACT | 1080 |
| GGTACTTAGG | CACCATAAAA | AAGCGAAGGA | AGATTTCACA | GGCAAAGGAT | GATAGCCAGA | 1140 |
| ATGCCATAGA | TCACAAAATT | GAGAGTGATA | CAGAGGAAAC | TCAAGACACA | AGTGTAGATC | 1200 |
| ATAATGAGAC | CGGAAACACA | GGAGAGTCTT | CGGTGGAAGA | AAATGAAAAA | CAGCAAAATG | 1260 |
| CCTCTGAAAG | CAAACTGGAA | TTGAGAAATA | ATTCAAATAC | TTGTAATATA | GAGAATGAGC | 1320 |
| TTGAAGACTC | TAGGAAGACT | ACAGCATGTA | CAGAATTGAG | AGACAAGATT | GCTTGTAATG | 1380 |
| GAGATGCTTC | TAGCTCTCAG | ATAATACATA | TTTCTGATGA | AAATGAAGGA | AAAGAAATGT | 1440 |
| GTGTTCTGCG | AATGACTCGA | GCTAGACGTT | CCCAGGTAGA | ACAGCAGCAG | CTCATCACTG | 1500 |
| TTGAAAAGGC | TTTGGCAATT | CTTTCVCAGC | CTACACCCTC | ACTTGTTGTG | GATCATGAGC | 1560 |
| GATTAAAAAA | TCTTTTGAAG | ACTGTTGTTA | AAAAAAGTCA | AAACTACAAC | ATATTTCAGT | 1820 |
| TGGAAAATTT | GTATGCAGTA | ATCAGCCAAT | GTATTTATCG | GCATCGCAAG | GACCATGATA | 1880 |
| AAACATCACT | TATTCAGAAA | ATGGAGCAAG | AGGTAGAAAA | CTTCAGTTGT | TCCAGATGAT | 1740 |
| GATGTCATGG | TATCGAGTAT | TCTTTATATT | CAGTTCCTAT | TTAAGTCATT | TTTGTCATGT | 1800 |
| CCGCCTAATT | GATGTAGTAT | GAAACCCTGC | ATCTTTAAGG | AAAAGATTAA | AATAGTAAAA | 1880 |
| TAAAAGTATT | TAAACTTTCC | TGATATTTAT | GTACATATTA | AGATAAATGT | CATGTGTAAG | 1920 |
| ATAACTGATA | AATA | | | | | |

Seq ID NO: 14 Protein sequence
Protein Accession #: NP_054828.1

| 1 | 11 | 21 | 31 | 41 | 51 | |
|---|---|---|---|---|---|---|
| MDLSSVISKI | DLNKYLTVKD | YLRDIDLICS | NALEYNPDRD | PGDRLIRNRA | CALRDTAYAI | 60 |
| IKEELDEDEE | QLCEEIQESS | KKRGCSSSKY | APSYYHVNPK | QNSTLVGDKR | SDPEQNEKLK | 120 |
| TPSTPVACST | PAQLRRKIRK | KSNWTYGTIE | KRRKISOAKD | DSQNAIDNKI | ESDTEETQDT | 180 |
| SVDHNETGNT | GESSVEENEK | QQNASESKLE | LRNNSNTGNI | ENELEDSRKT | TACTELEDRI | 240 |
| ADNGDASSSQ | IINISDENEG | KEMCVLRNTR | ARRSQVEQQQ | LITVEKALAI | LSQPTPSLVV | 300 |
| DNERLEELLK | TVVKRSQNYN | IFQLENLYAV | ISQCIYRNRK | DHDKTSLIQK | NEQEVENFSC | 360 |
| SR | | | | | | |

Seq ID NO: 15 DNA sequence
Nucleic Acid Accession #: AK001538

| 1 | 11 | 21 | 31 | 41 | 51 | |
|---|---|---|---|---|---|---|
| TATATGTGAC | CTTTTTAAAA | AATGAGCTGT | AAGCAGTCTC | CCAGACAGTA | GCTCAGCCTC | 60 |
| CAGAACTCTC | TTTCTGCATA | GTTGAAGACC | CCTCTTCACA | CAAGATGGTA | GCAACAAATC | 120 |
| ATAGGTGCAA | TTGCACCAAA | TTCACAGAAG | ATCAATTGAA | AATCCTCATC | AATACCTTCA | 180 |
| CTCAAAAACC | TTACCCAGGT | TATGCTACCA | AACAAAAACT | TGCTTTAGCA | ATCAATGCAG | 240 |
| AAGAGTCCAG | AATCCAGATT | TGGTTTCAGA | ATCAAAGAGC | TAGGCATGGA | TTCCAGAAAA | 300 |
| CACCAGAACC | TGACTTTAGA | TTTAAGCCAC | AGCCATGGAC | AAGATTAACC | TGGTGTGGAG | 360 |
| TTTCAAAATA | GAGAAGCCAG | ATGGTGTTGT | ACCACCTATA | GCACCTTTCA | ATTACACACA | 420 |
| ATCATCCATG | CATTTATGAA | AAACCCATAC | CCTGGGATTG | ATTCCGGAGA | ACAACTTGCT | 480 |
| GAAGAAATTG | GTGCTTCAGA | GTCAAGAGTC | CAAATTTGGT | TCCAAAATCA | AAGATCTAGA | 540 |
| TTTCATCTCC | AGAGAAAAAG | AGAACCTGTT | ATGTCCTTAG | AATGAGAAGA | CCAGAGAAGA | 600 |
| CCAGGGGCAA | GGTTTCTGAG | GGACTTCAAG | GTACAGAAGA | TACACAAAGT | GGCACCAGCC | 860 |
| TCACTAGCAC | TCTCATTTCT | CAAGAGCCAG | AACATGGTGA | ATACAGTCAA | GTTCAGTGTA | 720 |
| TTTGATAATA | TCAATTTGGG | CCCCAAATCT | CTCTCACAGT | CTTCCTGGGA | GTCTATTCTT | 780 |
| CTTCCAAAAG | TGCAAGCTAA | GCCTTCTGAA | GATGGTAAAG | AACTTGGGGA | CGTGTGGTGG | 840 |
| CTCATGCCTG | TAATCCCAGC | ACTTTAGGAG | CCTGAGGCTG | CAAGATTGCT | TCAGCCTAGC | 900 |
| AGTTTGAAAC | CAGTCTGAGC | AACATAGTAA | GACCCTGTCT | CTATTCTAAA | AAACAAAATA | 900 |
| AGTAAAAAGG | ACTGTAGGAG | GCCAAGACAG | GTACAGGAOG | CACCACACTA | CCCTGTTGAC | 1020 |
| ACAGCCTGGA | TCCAGAGTTC | AGCAGACCTT | CAGACAATGA | AAACAAACTT | AGTAATAATC | 1080 |
| ATTTTTCAAT | CATTGCAGTA | ATTATTGATT | TGGACAAAAA | TCAATTGACC | TCAAAACCTT | 1140 |
| AAAGTGACGT | TTCTCTGCCT | ATGGAGTGGT | CATTCTTTTA | TTCCTTTAGT | TTCATAATAA | 1200 |
| ATTTTCTTTT | ACTTAAAAAA | ACTTATAGTT | TGATGAAGAG | TGAGATATAT | ACCTCATCTC | 1260 |

TABLE 4-continued

| | | | | | | |
|---|---|---|---|---|---|---|
| AAAGAATCTT | CACACACACA | CTTATTAATT | ACAAAAGGAA | AATCAGTAAT | TTTGCAGTGG | 1320 |
| AGACATATGG | CCAACTCCAC | CTTACCCAAG | TGGCTGAAAG | TCACTGCACC | ACTAATGGCA | 1380 |
| CAAACCAATG | TGAGATCATT | CCTCATATDA | TACACTAAAA | AGGGCACTGT | CTCTTCTGCA | 1440 |
| TGTTGCAGAC | AAAAAGTGGC | TAAGCTGACA | CTGAAACTAA | TAATTAGGCA | ATGTCAAGCA | 1900 |
| AATACAAATT | CAAGTTGACA | GTCTGCAAAG | TAACATCCAT | GTACTCTTCA | ACAATGGATC | 1560 |
| CACCCTAGCT | ACTCAGGAGG | CTGAGGTGGA | ATAATTGTTT | GAGGCCAGGA | CTTCCAGATC | 1620 |
| AGCCTCGGCA | ACATCATGCG | ACCCCATCTC | TAAAAACATC | TTTTTAAAAA | TCAGCCAGGT | 1680 |
| GTGGTAGCAT | GCACCCGTAG | TCTCAGCTAC | TCAGGACCCT | GAGOCAGGAG | CATGGTTTCA | 1740 |
| ACATAGGAGA | TCGAGGCTGC | TGTGAGCTAT | GATCGTGCTA | CTGCACTCCA | GCCTGGGTGA | 1800 |
| CACAGCAAGT | TCCTGTTTCC | AAACAACAAC | AAGAAAACAA | AACAAAACAA | AACAAAAAAT | 1860 |
| AGATAGAATA | GTGACAATAA | AAATGGAGAA | AAAGTAGGCT | GACTCAGGAA | ATGCTTAGAA | 1920 |
| AGTACAGCCA | TACCTCAAAG | ATATTGTAGA | TTTGATTCGA | GACCACCACA | ATPAAGCAGA | 1980 |
| TATTGCTACA | AAGTGAGTCA | CACAAATTGT | TTTGTTTCCT | TGTGAATATG | AAGTTATATT | 2040 |
| GGCTGGGTGT | GATGGCTCAT | GCCTATAATC | CCAGTACTTT | AGGAGACGGA | GGCGGGAGGG | 2100 |
| TCACTTGAGC | CCAGGAATTG | TGAGATCAAC | CTGGGCATAT | AGGGAGATCC | TGTCTCTATT | 2160 |
| TAAAAAAAGA | AGCTATGTTT | ACACTACACT | ATAGTCTATT | TAAAGTGTGA | AATGGCGTTA | 2220 |
| TGTCCTTAAT | TTTAAAACTC | TTGATGCTGG | CTGGGTTCGG | TGGCTCATAC | CTGTAATCCC | 2280 |
| ATCACTTTGG | GAGGCCAAGA | CAGGTTGATT | ACTTGAATTC | AGGAGTTCAA | GACCAGCCTG | 2340 |
| GACAACATGG | CAAAACACGT | CTTTAAAAAA | AGAAAAGAAA | AAAGAAAAAC | AGAAAGAAAA | 2400 |
| AGAAGAAAPA | CTACTTGCTG | CCCTTACTTG | AAGCTCAATT | ATTTAAAAC | | |

Seq ID NO: 16 DNA sequence
Nucleic Acid Accession #: CAT cluster

| 1 | 11 | 21 | 31 | 41 | 51 | |
|---|---|---|---|---|---|---|
| \| | \| | \| | \| | \| | \| | |
| CTTTTTTTTT | TTTTTTTTTT | TAGTAGAGAC | AGGGTTTCAC | CATGTTAGCC | AGGATGGTCT | 60 |
| CGATCTCCTG | ACCTCATGAT | CTTCCTGCTT | TGGCCTCCCA | AAGTGCTGCG | ATTACAGGCG | 120 |
| TGAGCCACTG | CACCCAGCCC | AGAGTTTTTT | TTAACAAGGT | TCTTCTCAGC | AATTCTAGTA | 180 |
| TCCAGATATA | GGCCCATCAT | AGACATCACA | CAAGCGTGTA | CTTCATAATC | CTGGTGAATA | 240 |
| CAGAAGTTTC | CTGGACTCCT | TGATGAGCTA | CTGCTTTCGC | TCCTATATCA | GTGTTTTCAG | 300 |
| CTGATGTCAT | TTGTGATTGT | GTTTCTGACT | TTCTGTAGGC | AGAAAAAAAC | TTTCATTTTT | 360 |
| TTTTTGCTTA | CATGCACATA | AATGTAAGCG | CTAATTCTTA | TATTAAACTG | TTTATTTCTA | 420 |
| TAATACTTAA | TTGGCTGTTT | TCCTGGCTGA | ACCAAACCAA | GAGCATAAGG | AATGATAACC | 480 |
| TTCAAAACTG | ATTAAATTAG | AGATCAATAA | ATGGAGCTGT | TTTAATTCTA | TTATTCTTCT | 540 |
| TTCATAGATT | AAATAGAAAA | TTTTT | | | | |

Seq ID NO: 17 DNA sequence
Nucleic Acid Accession #: CAT cluster

| 1 | 11 | 21 | 31 | 41 | 51 | |
|---|---|---|---|---|---|---|
| \| | \| | \| | \| | \| | \| | |
| GGCACGAGAA | GACGCCACAT | CCCCTATTAT | AGAATAGCTA | ATAAATTTCC | ATGATCACAC | 60 |
| ACTAATAATT | GTTTTCCTAA | TTAGCTCCTT | AGTCCTCTAT | ATCATCTCGC | TAATATTAAC | 120 |
| AACAAAACTA | ACACATACAA | GCACAATAGA | TGCACAATAA | GTTGAAACCA | TTTGAACTAT | 180 |
| TCTACCAGCT | GTAATCCTTA | TCATAATTGC | TCTCCCCTCT | CTACGCATTC | TATATATAAT | 240 |
| AGACGAAATC | AACAACCCCG | TATTAACCGT | TAAAACCATA | GGGCACCAAT | GATACTGAAG | 300 |
| CTACGAATAT | ACTGACTATG | AAGACCTATG | CTTTGATTCA | TATATAATCC | CAACAAACGA | 380 |
| CCTAAAACCT | GGTGAACTAC | GACTGCTAGA | AGTTGATAAC | CGAGTCGTTC | TGCCAATAGA | 420 |
| ACTTCCAATC | CGTATATTAA | TTTCATCTGA | AGACGTCCTC | CACTCATGAG | CAGTCCCCTC | 480 |
| CCTAGGACTT | AAAACTGATG | CCATCCCAGG | CCGACTAAAT | CCAGCACAGT | ACATCAACCG | 540 |
| ACCAGGGTTA | TTCTATGGCC | AATGTCTGAA | TTTGTGGTCT | TACCATAGCT | TTTTGCCATT | 600 |
| GTCCTAGAAT | GGGTCCCTAA | AATATTTCGG | NACTGGTCTG | | | |

Seq ID NO: 18 DNA sequence
Nucleic Acid Accession #: CAT cluster

| 1 | 11 | 21 | 31 | 41 | 51 |
|---|---|---|---|---|---|
| \| | \| | \| | \| | \| | \| |
| GTGTACATCA | GAGCAAAAAT | ACAGAGTATT | TATTCATTTC | TTCCCACTAG | 60 |
| | | | | AGGGACACAC | |
| TGTTCTTGGA | CAGACAAATG | AATCATCAGT | TGTCAGGAGT | TGCCTTTGGA | 120 |
| | | | | GAATGATCAA | |
| TGAACTCCTT | TTCAGGGGTT | GGAAATTGAT | ACCAGGGTCC | ATCACCTCGG | 180 |
| | | | | GCACGCATCA | |
| GCCTTCGAAC | TTCCTGCTCC | TTTAACCGTA | ACTCAGCCTT | TTCAGATTCA | 240 |
| | | | | ATCTGGAGGA | |
| TAGCCAGGGT | TTTCTCGTAG | TTCTTTTCAG | GGCCATCATA | GAAATTCCGG | 300 |
| | | | | GCGATCCATC | |
| TTGATATCGG | ATGCTTGTAA | TACTCCCAGT | GTTCAGGGAT | GTAGCCTTCT | 360 |
| | | | | GGGATTTCTG | |
| CAAGCTCGGC | TTCACCAATA | AATATGTTCA | CCAGTGTTAT | GCCAATTATA | 420 |
| | | | | ACTGGGATCC | |
| CAGTCAACAT | AAGGTAGAAT | TTCATTAACC | TCAAGAAGCG | AGCGTCATAG | 480 |
| | | | | TATAAAGAAG | |
| GCTTGACGAC | AAACAGTCTC | TTGCCATGTC | CCCACTGTGC | CGCACAGGAG | 540 |
| | | | | CGACAGTCTT | |
| CGGAAANTCC | GCGTGAGAAA | ACTTCCGACT | CCGAGTCTAG | GACCAGCGCG | 600 |
| | | | | GCGGCAAGAC | |
| CACGCTGTCA | GCGCGGAGAC | CGAANCCGCT | GCAGCAGCTC | ATGGCCGCCA | |
| | | | | TGG | |

TABLE 4-continued

Seq ID ND: 19 DNA sequence
Nucleic Acid Accession #: CAT cluster

| 1 | 11 | 21 | 31 | 41 | 51 | |
|---|---|---|---|---|---|---|
| TAGTCCAGTN | AATTACTTTA | ATTTCGCTTT | TCCATAATAC | TGGTATTCCA | TAGAAGAAAA | 60 |
| TCTTTTATTA | ATATTCTATA | CTACTACATC | CGACACCAGA | TGACTAAAGT | TTGCAATGGT | 120 |
| CCAAAATTCT | GTAAACCCAT | TAAATGCAAT | TCATACTTTA | TTTTGGCAGT | ATTCATTTCA | 160 |
| TCATTACTTT | ATTTGGATGC | TAACGCAAGT | ACTTCTAAGG | AAAAGCTGTC | ATATAATTAC | 240 |
| TTTAGTCAAG | CATTCAGTAG | AGGCAATAAT | CAAACCTCTA | TCCCAACATT | TTACACTTGT | 300 |
| AACAGAATGA | AGGATGAGGT | ACAACATACA | TTTTTGGCAA | TTTACTATTA | AGGGCCATAA | 360 |
| TCATTTTAGG | GGCGCTTAGG | GCCCATATAT | ATATATATAT | ATTTTTGGAC | A | |

Seq ID NO: 20 DNA sequence
Nucleic Acid Accession #: U92072
Coding sequence: 351..3701

| 1 | 11 | 21 | 31 | 41 | 51 | |
|---|---|---|---|---|---|---|
| CCCGGGCGGC | TGCGCTGAGC | AGAGGCCCAG | CCCGGGACGC | GCCGAGGGAC | TGCGGGGCTG | 60 |
| CGGGTCATGG | ATGCGGCGGC | AGCGGCGCGG | GACGGCCGGA | GCCCGGCCGC | GACCAGGTGA | 120 |
| GGAGGCGGCG | TCCGGCGCCA | CTGCAGCCGC | AGCGGCCTCG | GAGGAAGAGG | GCTCGCCGCC | 180 |
| GCGCGCCCGC | CCGCCGTCTC | TGCCCTTCCT | GTTGGGATTA | TCTTCTGCTC | CCCGCTGCTT | 240 |
| CTTCGCTCCC | CGCGGTCGAA | GCCGCCTCTA | GGCTTCAGCG | GCTCGGACTC | CTTGGCAGCC | 300 |
| GGTGCCTCTG | CTACCTGGGC | CTCGTAGCTG | GGAGACCCTT | GGGCGAGACC | ATGAGGAAAT | 360 |
| TCAACATCAG | GAAGGTGCTG | GACGGCCTGA | CCGCAGTCTC | GTCCTCGGCC | TCGCAACAGC | 420 |
| AGCAACAGCA | GCAGCACCCG | CCTGGGAACC | GGGAGCCCGA | GATCCAGGAG | ACGCTCCAGT | 480 |
| CCGAGCACTT | CCAACTCTGC | AAGACTGTTC | GCCATGGATT | TCCCTATCAG | CCCTCAGCCC | 540 |
| TGGCCTTTGA | TCCCGTTCAG | AAGATCCTGG | CGGTAGGAAC | CCAGACTGGT | GCTTTAAGGC | 600 |
| TCTTTGGTCG | TCCAGGGGTG | GAATGTTATT | GCCAGCACGA | CAGCGGAGCG | GCAGTGATTC | 660 |
| AACTCCAGTT | CCTGATTAAT | GAGGGAGCCC | TTGTGAGTGC | CTTGGCTGAT | GACACCTTAC | 720 |
| ACTTGTGGAA | TTTACGTCAG | AAAAGGCCTG | CTGTGCTACA | TTCACTCAAA | TTTTGCAGAD | 780 |
| AAAGGGTTAC | ATTTTGCCAT | CTGCCTTTCC | AGAGTAAGTG | GCTCTATGTG | GGCACGGAAC | 840 |
| GAGGTAATAT | ACATATTGTC | AATGTGGAGT | CCTTCACACT | CTCAGGCTAC | QTCATTATGT | 900 |
| GGAATAAAGC | CATCGAACTG | TCATCTAAAT | CTCACCCAGG | ACCTGTTGTC | CATATAAGTG | 960 |
| ATAATCCCAT | GGACGAGGGG | AAGCTTCTGA | TTGGCTTTGA | ATCTGGAACA | GTAGTCTTAT | 1020 |
| GGGACCTTAA | GTCAAAGAAG | GCTGACTACA | GATACACTTA | CGACGAGGCT | ATTCACTCTG | 1080 |
| TGGCTTGGCA | TCATGAAGGA | AAACAGTTTA | TTTGCAGTCA | TTCTGATGGT | ACATTGACCA | 1140 |
| TATGGAATGT | GAGGTCCCCT | ACTAAACCTG | TACAGACCAT | CACTCCTCAC | GGAAAACAGT | 1200 |
| TAAAGGATGG | GAAGAAACCC | GAGCCGTGCA | AGCCTATCCT | CAAGGTGGAG | TTCAAGACAA | 1260 |
| CAAGATCGGG | GGAACCTTTT | ATTATTTTGT | CGGGAGGCTT | ATCATATGAT | ACCGTGGGAA | 1320 |
| CAAGACCTTG | CTTAACAGTG | ATGCATCGGA | AAAGCACGGC | AGTGCTGGAA | ATGGACTATT | 1380 |
| CAATTGTCGA | CTTTCTCACA | CTCTGTGAAA | CGCCATATCC | AAATGATTTT | CAGGAGCCGT | 1440 |
| ATGCTGTGGT | TGTTCTCCTG | GAGAAGGATT | TAGTGCTGAT | AGACCTGGCA | CAGAATGGAT | 1500 |
| ACCCTATATT | TGAGAATCCC | TACCCTTTGA | GTATACACGA | GTCCCCTGTT | ACATGTTGTG | 1560 |
| AATATTTTGC | TGATTGTCCT | GTGGACCTTA | TTCCTGCACT | TTATTCTGTT | GGAGCTAGAC | 1620 |
| AGAAACGTCA | AGGTTACAGC | AAAAAGGAAT | GGCCCATCAA | TGGTGGTAAT | TGGGGCTTGG | 1680 |
| GTGCTCAAAG | TTACCCAGAA | ATAATTATTA | CAGGGCATGC | TGATGGCTCA | ATTAAATTCT | 1740 |
| GGGATGCTTC | TGCAATAACT | CTACAAGTAC | TGTATAAATT | AAAAACATCT | AAAGTATTTG | 1800 |
| AAAAGTCAAG | AAATAAAGAT | GACAGACAGA | ACACCGACAT | TGTAGATGAA | GATCCATATG | 1880 |
| CCATTCAGAT | CATCTCCTGG | TGCCCAGAGA | GCAGAATGCT | GTGCATAGCC | GGAGTGTCGG | 1920 |
| CTCATGTCAT | CATTTATAGA | TTCAGCAAGC | AGGAAGTGGT | TACAGAAGTC | ATCCCGATGC | 1980 |
| TTGAAGTCCG | ACIGTTATAT | GAAATAAATG | ATGTGGAAAC | GCCGGAGGGT | GAGCAGCCAC | 2040 |
| CCCCTTTGTC | CACTCCCGTG | GGCAGCTCCA | CCTCTCAGCC | CATCCCCCCT | CAGTCTCATC | 2100 |
| CGTCTACCAG | CAGCAGCTCA | TCGGACGGGC | TTCGAGATAA | TGTACCGTGT | TTAAAAGTTA | 2180 |
| AAAACTCACC | ACTTAAACAG | TCTCCCGGCT | ATCAAACAGA | GCTAGTCATC | CAGTTGGTGT | 2220 |
| GGGTGGGTGG | ACAACCCCCG | CAGCAGATCA | CCAGCCTAGC | ACTCAACTCT | TCCTACGGAT | 2280 |
| TGGTGGTTTT | GGGCAACTCC | AATGGCATTG | CAATGGTTGA | CTACCTCCAG | AAAGCAGTGC | 2140 |
| TGCTCAACCT | CAGCACCATT | GAACTATACG | GCTCAAATGA | TCCTTATCGG | AGAGAACCGA | 2400 |
| GGTCGCCCCG | CAAATCTCGA | CAGCCTTCAG | GAGCGGGCCT | GTGTGATATT | ACCGAAGGAA | 2460 |
| CTGTCGTCCC | AGAGGATCGC | TGCAAATCTC | CGACTTCCGC | AAAGATGTCA | AGGAAATTAA | 2520 |
| GCTTGCCAAC | TGATCTAAAG | CCTGATTTAG | ATGTGAAAGA | CAATTCCTTC | AGCAGATCTC | 2580 |
| GGAGTTCAAG | TGTGACCAGC | ATTGACAAAG | AGTCCCGGGA | AGCCATTTCT | GCTCTTCATT | 2640 |
| TCTGTGAGAC | TTTCACAAGG | AAGGCAGACT | CCTCCCCCTC | CCCGTGCCTG | TGGGTGGGAA | 2700 |
| CCACAGTGGG | AACTGCCTTT | GTCATCACGC | TGAATCTCCC | CCTGGGGCCT | GAGCAGAGAC | 2760 |
| TGCTTCAGCC | AGTGATTGTG | TCTCCAAGCG | GTACTATATT | GAGGTTAAAA | GGTGCGATCT | 2820 |
| TGAGAATGGC | ATTTCTGGAT | GCCGCGGGCT | GCTTAATGCC | ACCTGCATAC | GAACCCTGGA | 2880 |
| CAGAGCACAA | CGTTCCTGAA | GAAAAAGACG | AAAAGGAGAA | ATTGAAAAAG | CGGCGACCTG | 2940 |
| TCTCAGTGTC | CCCCTCCTCT | TCTCAGGAAA | TTAGTGAAAA | CCAGTACGCA | GTGATATGTT | 3000 |
| CTGAAAAGCA | AGCAAAGGTC | ATCTCACTGC | CAACCCAGAA | CTGTGCATAC | AAGCAGAACA | 3080 |
| TCACTGAGAC | GTCCTTCGTG | CICCGTGGAG | ACATTGTCGC | CCTGAGTAAC | AGTGTCTGCC | 3120 |
| TCGCCTGCTT | CTGTGCCAAC | GGCCACATTA | TGACTTTCAG | TTTGCCGAGC | TTGAGGCCTC | 3180 |
| TGCTGGATGT | CTACTACCTG | CCCCTTACCA | ACATGCGGAT | AGCCAGGACA | TTCTGCTTCG | 3240 |
| CCAACAGTGG | GCAAGCCTTA | TACCTTGTTT | CACCTACCGA | AATCCAGAGA | CTCACCTACA | 3300 |
| GTCAGGAGAC | GTGTGAAAAC | CTTCAGGAGA | TGCTTGGTGA | GCTCTTCACG | CCTGTAGAAA | 3360 |
| CACCAGAAGC | ACCAAACAGA | GGGTTCTTCA | AAGGCTTATT | TGGAGGTGGT | GCACAATCTC | 3420 |
| TTGATAGAGA | ACAACTGTTT | GGAGAGTCAT | CCTCGGGAAA | GGCGTCAAGG | AGCCTTGCAC | 3480 |
| AGCACATCCC | GGGTCCTGGC | GGGATCGAAG | GTGTGAAGGG | AGCCGCGTCG | GGAGTGGTGG | 3540 |
| GAGAACTGGC | CCGAGCCAGG | CTGGCCCTCG | ACGAAAGAGG | ACAGAAGCTC | AGCGACTTGG | 3600 |
| AAGAGAGGAC | TGCAGCCATG | ATGTCCAGTG | CAGACTCGTT | TTCCAAACAT | GCTCATGAGA | 3660 |
| TGATGCTGAA | ATACAAAGAT | AAGAAGTGGT | ACCAGTTCTG | ACAAGTAGCA | CTCAGTAAGT | 3720 |

TABLE 4-continued

| | | | | | | |
|---|---|---|---|---|---|---|
| CCAGCTTCAA | CCAGAAGGAA | AAAGACGTTT | CCTTGTTGAG | GTCACTGATG | TATTTGGGAA | 3780 |
| AGATAACATA | AAAGGGATGC | ACACTGCTGA | CAGCGTCTTT | CCCAGCACAA | TCATGCACTT | |

Seq ID NO: 21 Protein sequence
Protein Accession #: AAD04756

| 1 | 11 | 21 | 31 | 41 | 51 | |
|---|---|---|---|---|---|---|
| \| | \| | \| | \| | \| | \| | |
| MRKFNIRKVL | DGLTAGSSSA | SQQGGQQQNP | PGNREPEIQE | TLQSEHFQLC | ETVRNGPPYQ | 60 |
| PSALAFDPVQ | KILAVGTQTG | ALRLFGPPGV | ECYCQHDSGA | AVIQLGFLIN | EGALVSALAD | 120 |
| DTLHLWNLRQ | KRPAVLHSLK | FCRERVTFCH | LPFQSKWLYV | GTERGNINIV | NVESFTLSGY | 180 |
| VIMWNKAIEL | SSKSHPGPVV | HISDNPMDEG | ELLIGFESGT | VVLWDLKSKK | AnYRYTYGSA | 240 |
| IHSVAWHHEG | KQFICSHSDG | TLTIWNVRSP | TKPVQTGTPN | GKQLIGGKKP | ESCEPILEVE | 300 |
| FKTTRSGEPP | TILSGGLSYD | TVGRRPCLTV | MHGKSTAVLE | MGYSIVGELT | LCETPYPNDF | 360 |
| QEPYAVVVLL | EKDLVLIDLA | GNGYPIFENP | YPLSIHESPV | TCCEYFADCP | VDLIPALYSV | 420 |
| CARQKRQGYS | KEEMPINGGN | WGLGAQSYPE | IIITGHADGS | IKFWDASAIT | LQVLYKLKTS | 480 |
| KVFEKSRNKD | DRQNTDIVDE | DPYAIQIISW | CRESRELCIA | GVSAHVIIYR | FSRQEVVTEV | 540 |
| IPMLEVRLLY | EINDVETPEG | EQPPPLSTPV | GSSTSQPIPP | QSHPSTSSSS | SDGLRDNVPC | 600 |
| LKVKNSPLKQ | SPGYQTELVI | QLVWVGGEPP | QQITSLALNS | SYGLVVFGNS | NGIAMVDYLG | 660 |
| KAVLLNLSTI | SLYGSNDPYR | REPRSPSKSR | QPSGAGLGDI | TEGTVVPEDR | CKSPTSARES | 720 |
| RKLSLPTDLK | PGLDVKDNSF | SRSRSSSVTS | IDEESREAIS | ALHPCETFTR | KADSSPSPCL | 780 |
| WVGTTVGTAF | VITLNLPLGP | EQRLLQPVIV | SPSGTGLRLE | GAILRMASLD | AAGCLMPPAY | 840 |
| EPWTEHNVPE | EKDEKEKLKE | RRPVSVSPSS | SQEISENQYA | VICSEKQAKV | ISLPTQNCAY | 900 |
| KQNITETSFV | LEGGIVALSE | SVCLACFCAN | GHIMTFSLPS | LRPLLDVYYL | PLTNNRIART | 960 |
| ECEANSGQAL | YLVSPTEIQR | LTYSQETCEN | LQEMLGELET | PVETPEAPNR | CFFKGLFGGG | 1020 |
| AQSLDREELF | GESSSGKASR | SLAQNGPGPG | GIEGVKGAAS | GVVGELAPAR | LALDERGQEL | 1080 |
| SDLEERTAAM | MSSADSFSKH | AHEMNLKYKD | KEWYQE | | | |

Seq ID NO 22 DNA sequence
Nucleic Acid Accession #: CAT cluster

| 1 | 11 | 21 | 31 | 41 | 51 | |
|---|---|---|---|---|---|---|
| \| | \| | \| | \| | \| | \| | |
| TCCCATCGGG | TGAACCGTGG | TCTTGTTCCG | TCCGCCCACA | ATCGCTCTCC | AGCTTTGACG | 60 |
| CCCCCGGCAA | AGCCIGGCTC | GTTCACAGCT | CTCTCGCACC | TCCTGGAGCT | TCAGCTTCTT | 120 |
| CCGTTGCAGA | GAAGCTTTAT | GGGCCAATTC | GTTCGGCATC | CCGGGGGCAG | GTGCGCGGTG | 180 |
| CGCGGGGAAG | AAGAGGATTT | GACTGCGGTT | CTCCACCCCC | GGCGCCCAAC | CTCCACCCCG | 240 |
| GTGCGCGCGC | TCTTCCAGGC | TCCTGCTGGT | CCCACTTGCC | AGGAGTTAGG | TCTCAGGTCA | 300 |
| GCCTGAGCTC | CTGAGACGCC | CACGCCCGGA | AAGACACGTA | GGGGAAACCA | TCTGCTCACT | 360 |
| TCTGTCCTGT | CCGGAAGGGA | TCCCTTTCTG | ACGGGAAAGA | AAGGCGCTAA | ACAAGCACTG | 420 |
| GCCTTGAGAT | AAGCAATGCT | GAAGCACTTG | CAGCTCACCT | ATTACCATAA | ACTGACTGAG | 480 |
| CCCTCCCTAC | ACAAGCCGTA | ACTACTGCTT | TGATTGGACA | AGAGATTGAT | TTCAGTAGTT | 540 |
| TTCTCTTGAT | AAGAGACCAC | TGGCCGTGGG | CGGGTTCTGG | ACAGTTTACA | GAAGCTATGC | 600 |
| ACTTGATTGC | CTTTGTGTCC | CTGCTTCACC | TTTTGAAGCA | TAGGGCCTAA | TTATAATGTA | 860 |
| TTTAAATGTT | GTCTCCACCC | CAAAGTGAAC | ATGGGTTGCA | TGTAACAGGC | ATGTTTACTC | 720 |
| AGCATGCATG | CAGCAGGATC | CCTTCACAAA | TATTCAGAGC | TCCCCCTATT | CCCTGTTGAA | 780 |
| TATGTATATG | TGGCCAGCCA | GATCAACGTA | AATCACTATT | CGCCCTCCCC | TCCCTGGAAA | 840 |
| CCTACTTTTC | GGGTTTCAGC | AGGAAGCTAT | GCCTCCCAGG | CTTGTCGAAG | AGGGCCCATT | 900 |
| TTCGGGCTTG | ATAACCCCTT | TATAAAAAAA | TAAAATCTCC | TTTCTAAATT | TAAAATACAA | 960 |
| CCACACCACC | GGCCCGCAAC | TATTGGGGGG | GAAAAAGAAT | GAAGACACAC | GGTACATAGT | 1020 |
| TTCATGCACA | TTGTTAAGGA | GACAGGTGCC | CCCAAGCAGG | COGACATCAC | GCAGTACGCA | 1080 |
| GCTTGAGCAT | GCCGAAGACG | CGAGCGACTC | ATAGAACACG | ACGACGCTCG | CAAGGCACTA | 1140 |
| AGCATAGCTA | CTACCACTCG | TCGAAGAGTC | ATACACAGAT | TTCTATTGGC | GA | |

Seq ID NO 23 DNA sequence
Nucleic Acid Accession #: CAT cluster

| 1 | 11 | 21 | 31 | 41 | 51 |
|---|---|---|---|---|---|
| \| | \| | \| | \| | \| | \| |
| CTATGAATCT | CGGAAATTAC | 60 | | | |
| | TCAAACCATC | | | | |
| | AGCCTCTGCA | | | | |
| | AGAAGCAAAG | | | | |
| | TGGACGGCCG | | | | |
| GGCGCGGTGG | CTCACTCCTG | 120 | | | |
| | GAATCCCAGC | | | | |
| | ACTTTGGGAG | | | | |
| | CCCGAGGTGG | | | | |
| | CGGGATCACG | | | | |
| AGGTCAGGAG | ATCGAGACTG | 180 | | | |
| | TTCTGGCTAA | | | | |
| | ACCAGTGAAA | | | | |
| | CCCCCTCTCT | | | | |
| | ACTAAAAAAA | | | | |
| TAAGAAAAGC | GAAGTGCATC | 240 | | | |
| | TCCCATAAAC | | | | |
| | GAGGTACTGC | | | | |
| | AGGAAGAAAG | | | | |
| | CAGAAAATGA | | | | |

TABLE 4-continued

| | | |
|---|---|---|
| GACCCGAGTA | CACACATGCA | 300 |
| | CGCGGGCGCC | |
| | GCACACACAC | |
| | ACCAGAAGAA | |
| | ATGAACCAAG | |
| AGGAAAGGAA | ACATTTTCAA | 360 |
| | ATAAGCATTT | |
| | GGAGATOGGA | |
| | AAAACACCTT | |
| | GAAACAGAAA | |
| TTCATAAAGT | ACAGAATTTT | 420 |
| | TTTTTAAGTT | |
| | AAAAAAGGAA | |
| | CAATAATAGA | |
| | CAGAAAATGA | |
| ATGAAAAATT | AAATGTCATA | 480 |
| | TCAGAAGTGA | |
| | AGATAAATTA | |
| | AAAGTGGTCA | |
| | AAGGAGAAGA | |
| GATCTAAATG | CAAACTTAAG | 640 |
| | AAGGGGCAAT | |
| | TTTTTTTTTT | |
| | TTTTTTTTTG | |
| | AGACGCAGCC | |
| TCACTCTGTC | GC | |

Seq ID NO: 24 DNA sequence
Nucleic Acid Accession #: NM_000044.1
Coding sequence: 1115..3874

| 1 | 11 | 21 | 31 | 41 | 51 | |
|---|---|---|---|---|---|---|
| \| | \| | \| | \| | \| | \| | |
| CGAGATCCCG | GGGAGCCAGC | TTGCTGGGAG | AGCGGGACGG | TCCGGAGCAA | GCCCACAGGC | 60 |
| AGAGGAGGCG | ACAGAGGGAA | AAAGGGCCGA | GCTAGCCGCT | CCAGTGCTGT | ACAGGAGCCG | 120 |
| AAGGGACGCA | CCACGCCAGC | CCCAGCCCGG | CTCCAGCGAC | AGCCAACGCC | TCTTGCAGCG | 180 |
| CGGCGGCTTC | GAAGCCGCCG | CCCGGAGCTG | CCCTTTCCTC | TTCGGTGAAG | TTTTTAAAAG | 240 |
| CTGCTAAAGA | CTCGGAGGAA | GCAAGGAAAG | TGCCTGGTAG | GACTGACGGC | TGCCTTTGTC | 300 |
| CTCCTCCTCT | CCACCCCGCC | TCCCCCCACC | CTGCCTTCCC | CCCCTCCCCC | GTCTTCTCTC | 360 |
| CCGCAGCTGC | CTCAGTCGGC | TACTCTCAGC | CAACCCCCCT | CACCACCCTT | CTCCCCACCC | 420 |
| GCCCCCCCGC | CCCCGTCGGC | CCAGCGCTGC | CAGCCCGAGT | TTGCAGAGAG | GTAACTCCCT | 480 |
| TTGGCTGCGA | GCGGGCGAGC | TAGCTGCACA | TTGCAAAGAA | GGCTCTTAGG | AGCCAGGCGA | 540 |
| CTGGGGAGCG | GCTTCAGCAC | TGCAGCCACG | ACCCGCCTGG | TTAGAATTCC | GGCGGAGAGA | 600 |
| ACCCTCTGTT | TTCCCCCACT | CTCTCTCCAC | CTCCTCCTGC | CTTCCCCACC | CCGAGTGCGG | 660 |
| AGCAGAGATC | AAAAGATGAA | AAGGCAGTCA | GGTCTTCAGT | AGCCAAAAAA | CAAAACAAAC | 720 |
| AAAAACAAAA | AAGCCGAAAT | AAAAGAAAAA | GATAATAACT | CAGTTCTTAT | TTGCACCTAC | 780 |
| TTCAGTGGAC | ACTGAATTTG | GAAGGTGGAG | GATTTTGTTT | TTTTCTTTTA | AGATCTGGGC | 840 |
| ATCTTTTGAA | TCTACCCTTC | AAGTATTAAG | AGACAGACTG | TGAGCCTAGC | AGGGCAGATC | 900 |
| TTGTCCACCG | TGTGTCTTCT | TCTGCACGAG | ACTTTGAGGC | TGTCAGAGCG | CTTTTTGCGT | 1020 |
| ACTACCGCAT | CATCACAGCC | TGTTGAACTC | TTCTGAGCAA | GAGAAGGGGA | GGCGGGGTAA | 1080 |
| GGGAAGTAGG | TGGAAGATTC | AGCCAAGCTC | AAGGATGGAA | GTGCAGTTAG | GGCTGGGAAG | 1140 |
| GGTCTACCCT | CGGCCGCCGT | CCAAGACCTA | CCGAGGAGCT | TTCCAGAATC | TGTTCCAGAG | 1200 |
| CGTGCGCGAA | GTGATCCAGA | ACCCGGGCCC | CAGGCACCCA | GAGGCCGCGA | GCGCAGCACC | 1260 |
| TCCCGGCGCC | AGTTTGCTGC | TGCTGCAGCA | GCAGCAGCAG | CAGCAGCAGC | AGCAGCAGCA | 1320 |
| GCAGCAGCAG | CAGCAGCAGC | AGCAGCAAGA | GACTAGCCCC | AGGCAGCAGC | AGCAGCAGCA | 1380 |
| GGGTGAGGAT | GGTTCTCCCC | AAGCCCATCG | TAGAGGCCCC | ACAGGCTACC | TGGTCCTGGA | 1440 |
| TGAGGAACAG | CAACCTTCAC | AGCCGCAGTC | GGCCCTGGAG | TGCCACCCCG | AGAGAGGTTG | 1500 |
| CGTCCCAGAG | CCTGGAGCCG | CCGTGGCCGC | CAGCAAGGGG | CTGCCGCAGC | AGCTGCCAGC | 1560 |
| ACCTCCGGAC | GAGGATGACT | CAGCTGCCCC | ATCCACGTTG | TCCCTGCTGG | GCCCCACTTT | 1620 |
| CCCCGGCTTA | AGCAGCTGCT | CCGCTGACCT | TAAAGACATC | CTGAGCGAGG | CCAGCACCAT | 1680 |
| GCAACTCCTT | CAGCAACAGC | AGCAGGAAGC | AGTATCCGAA | GGCAGCAGCA | GCGGGAGGGC | 1740 |
| GAGGGAGGCC | TCGGGGGCTC | CCACTTCCTC | CAAGGACAAT | TACTTAGGGG | GCACTTCGAC | 1800 |
| CATTTCTGAC | AACGCCAAGG | AGTTGTGTAA | GGCAGTGTCG | GTGTCCATGG | GCCTGGGTGT | 1860 |
| GGAGGCGTTG | GAGCATCTGA | GTCCAGGGGA | ACAGCTTCGG | GGGGATTGCA | TGTACGCCCC | 1920 |
| ACTTTTGGGA | GTTCCACCCG | CTGTGCGTCC | CACTCCTTGT | GCCCCATTGG | CCGAATGCAA | 1980 |
| AGGTTCTCTG | CTAGACGACA | GCGCAGGCAA | GAGCACTGAA | GATACTGCTG | AGTATTCCCC | 2040 |
| TTTCAAGGGA | GGTTACACCA | AAGGGCTAGA | AGGCGAGAGC | CTAGGCTGCT | CTGGCAGCGC | 2100 |
| TGCAGCAGGG | AGCTCCGGGA | CACTTGAACT | GCCGTCTACC | CTGTCTCTCT | ACAAGTCCGG | 2160 |
| AGCACTGGAC | GAGGCAGCTG | CGTACCAGAG | TCGCGACTAC | TACAACTTTC | CACTGGCTCT | 2220 |
| GGCCGGACCG | CCGCCCCCTC | CGCCGCCTCC | CCATCCCCAC | GCTCGCATCA | AGCTGGAGAA | 2280 |
| CCCGCTGGAC | TACGGCAGCG | CCTGGGCGGC | TGCGGCGGCG | CAGTGCCGCT | ATGGGGACCT | 2340 |
| GGCGAGCCTG | CATGGCGCGG | GTGCAGCGGG | ACCCGGTTCT | GGGTCACCCT | CAGCCGCCGC | 2400 |
| TTCCTCATCC | TGGCACACTC | TCTTCACAGC | CGAAGAAGGC | CAGTTGTATG | GACCGTGTGG | 2460 |
| TGGTGGTGGG | GGTGGTGGCG | GCGGCGGCGG | CGGCGGCGGC | GGCGGCGGCG | GCGGCGGCGG | 2520 |
| CGGCGGCGGC | GAGGCGGGAG | CTGTAGCCCC | CTACGGCTAC | ACTCGGCCCC | CTCAGGGGCT | 2580 |
| GGCGGGCCAG | GAAAGCGACT | TCACCGCACC | TGATGTGTGG | TACCCTGGCG | GCATGGTGAG | 2640 |
| CAGAGTGCCC | TATCCCAGTC | CCACTTGTGT | CAAAAGCGAA | ATGGGCCCCT | GGATGGATAG | 2700 |
| CTACTCCGGA | CCTTACGGGG | ACATGCGTTT | GGAGACTGCC | AGGGACCATG | TTTTGCCCAT | 2760 |
| TGACTATTAC | TTTCCACCCC | AGAAGACCTG | CCTGATCTGT | GGAGATGAAG | CTTCTGGGTG | 2820 |
| TCACTATGGA | GCTCTCACAT | GTGGAAGCTG | CAAGGTCTTC | TTCAAAAGAG | CCGCTGAAGG | 2880 |

TABLE 4-continued

| | | | | | | |
|---|---|---|---|---|---|---|
| GAAACAGAAG | TACCTGTGCG | CCAGCAGAAA | TGATTGCACT | ATTGATAAAT | TCCGAAGGAA | 2940 |
| AAATTGTCCA | TCTTGTCGTC | TTCGGAAATG | TTATGAAGCA | GGGATGACTC | TGGGAGCCCG | 3000 |
| GAAGCTGAAG | AAACTTGGTA | ATCTGAAACT | ACAGGAGGAA | GGAGAGGCTT | CCAGCACCAC | 3060 |
| CAGCCCCACT | GAGGAGACAA | CCCAGAAGCT | GACAGTGTCA | CACATTGAAG | GCTATGAATG | 3120 |
| TCAGCCCATC | TTTCTGAATG | TCCTGGAAGC | CATTGAGCCA | GGTGTAGTGT | GTGCTGGACA | 3180 |
| CGACAACAAC | CAGCCCGACT | CCTTTGCAGC | CTTGCTCTCT | AGCCTCAATG | AACTGGGAGA | 3240 |
| GAGACAGCTT | GTACACGTGG | TCAAGTGGGC | CAAGGCCTTG | CCTGGCTTCC | GCAACTTACA | 3300 |
| CGTGGACGAC | CAGATGGCTG | TCATTCAGTA | CTCCTGGATG | GGGCTCATGG | TGTTTGCCAT | 3360 |
| GGGCTGGCGA | TCCTTCACCA | ATGTCAACTC | CAGGATGCTC | TACTTCGCCC | CTGATCTGGT | 3420 |
| TTTCAATGAG | TACCGCATGC | ACAAGTCCCG | GATGTACAGC | CAGTGTGTCC | GAATGAGGCA | 3480 |
| CCTCTCTCAA | GAGTTTGGAT | GGCTCCAAAT | CACCCCCCAG | GAATTCCTGT | GCATGAAAGC | 3540 |
| ACTGCTACTC | TTCAGCATTA | TTCCAGTGGA | TGGGCTGAAA | AATCAAAAAT | TCTTTGATGA | 3600 |
| ACTTCGAATG | AACTACATCA | AGGAACTCGA | TCGTATCATT | GCATGCAAAA | GAAAAAATCC | 3660 |
| CACATCCTGC | TCAAGACGCT | TCTACCAGCT | CACCAAGCTC | CTGGACTCCG | TGCAGCCTAT | 3720 |
| TGCGAGAGAG | CTGCATCAGT | TCACTTTTGA | CCTGCTAATC | AAGTCACACA | TGGTGAGCGT | 3780 |
| GGACTTTCCG | GAAATGATGG | CAGAGATCAT | CTCTGTGCAA | GTGCCCAAGA | TCCTTTCTGG | 3840 |
| GAAAGTCAAG | CCCATCTATT | TCCACACCCA | GTGAAGCATT | GGAAACCCTA | TTTCCCCACC | 3900 |
| CCAGCTCATG | CCCCCTTTCA | GATGTCCTCT | GCCTGTTATA | ACTCTGCACT | ACTCCTCTGC | 3960 |
| AGTGCCTTGG | GGAATTTCCT | CTATTGATGT | ACAGTCTGTC | ATGAACATGT | TCCTGAATTC | 4020 |
| TATTTGCTGG | GCTTTTTTTT | TCTCTTTCTC | TCCTTTCTTT | TTCTTCTTCC | CTCCCTATCT | 4080 |
| AACCCTCCCA | TGGCACCTTC | AGACTTTGCT | TCCCATTGTG | GCTCCTATCT | GTGTTTTGAA | 4140 |
| TGGTGTTGTA | TGCCTTTAAA | TCTGTGATGA | TCCTCATATG | GCCCAGTGTC | AAGTTGTGCT | 4200 |
| TGTTTACAGC | ACTACTCTGT | GCCAGCCACA | CAAACGTTTA | CTTATCTTAT | GCCACGGGAA | 4260 |
| GTTTAGAGAG | CTAAGATTAT | CTGGGGAAAT | CAAAACAAAA | AACAAGCAAA | CAAAAAAAAA | 4320 |
| A | | | | | | |

Seq ID NO: 25 Protein Sequence
Protein Accession #: NP_000035.1

| | | | | | | |
|---|---|---|---|---|---|---|
| 1 | 11 | 21 | 31 | 41 | 51 | |
| \| | \| | \| | \| | \| | \| | |
| MEVQLGLGRV | YPRPPSKTYR | GAFQNLFQSV | REVIQNPGPR | HPEAASAAPP | GASLLLLQQQ | 60 |
| QQQQQQQQQQ | QQQQQQQQET | SPRQQQQQQG | EDGSPQAHRR | GPTGYLVLDE | EQQPSQPQSA | 120 |
| LECHPERGCV | PEPGAAVAAS | KGLPQQLPAP | PDEDDSAAPS | TLSLLGPTFP | GLSSCSADLK | 180 |
| DILSEASTMQ | LLQQQQQEAV | SEGSSSGRAR | EASGAPTSSK | DNYLGGTSTI | SDNAKELCKA | 240 |
| VSVSMGLGVE | ALEHLSPGEQ | LRGDCMYAPL | LGVPPAVRPT | PCAPLAECKG | SLLDDSAGKS | 300 |
| TEDTAEYSPF | KGGYTKGLEG | ESLGCSGSAA | AGSSGTLELP | STLSLYKSGA | LDEAAAYQSR | 360 |
| DYYNFPLALA | GPPPPPPPPH | PHARIKLENP | LDYGSAWAAA | AAQCRYGDLA | SLHGAGAAGP | 420 |
| GSGSPSAAAS | SSWHTLFTAE | EGQLYGPCGG | GGGGGGGGGG | GGGGGGGGGG | GGEAGAVAPY | 480 |
| GYTRPPQGLA | GQESDFTAPD | VWYPGGMVSR | VPYPSPTCVK | SEMGPWMDSY | SGPYGDMRLE | 540 |
| TARDHVLPID | YYFPPQKTCL | ICGDEASGCH | YGALTCGSCK | VFFKRAAEGK | QKYLCASRND | 600 |
| CTIDKFRRKN | CPSCRLRKCY | EAGMTGAGRK | LKKLGNLKLQ | EEGEASSTTS | PTEETTQKLT | 660 |
| VSHIEGYECQ | PIFLNVLEAI | EPGVVCAGHD | NNQPDSFAAL | LSSLNELGER | QLVHVVKWAK | 720 |
| ALPGFRNLHN | DDQMAVIQYS | WMGLMVFAMG | WRSFTNVNSR | MLYFAPDLVF | NEYRMHKSRM | 780 |
| YSQCVRMRHL | SQEFGWLQIT | PQEFLCMKAL | LLFSIIPVDG | LKNQKFFDEL | RMNYIKELDR | 840 |
| IIACKRKNPT | SCSRRFYQLT | KLLDSVQPIA | RELHQFTFDL | LIKSHMVSVD | FPEMMAEIIS | 900 |
| VQVPKILSGK | VKPIYFHTQ | | | | | |

Seq ID NO: 26 DNA sequence
Nucleic Acid Accession #: CAT cluster

| | | | | | | |
|---|---|---|---|---|---|---|
| 1 | 11 | 21 | 31 | 41 | 51 | |
| \| | \| | \| | \| | \| | \| | |
| AGCATTATCC | ATGGCCAGTG | ATTGATGGAC | TTGTTGAGGT | CCTATGCAGA | GTGCTTCATA | 60 |
| TATCTCATCT | CAATCCTCTA | AATAACCATG | AAAGTTGATG | ATTATCTCAT | GGTACAGATG | 120 |
| GGAGGCTAAG | AGTGTTTAAT | TTTCCCCAAG | TTCCAGTGCT | AGTAAGTGTT | GNNNNNNNNN | 180 |
| NNTGAACTGG | TGTTAATGGT | GTTTCTAGTC | GATGCTGTTA | TCTGTTGCAC | CACATTTTGA | 240 |
| ATAATCTTGG | ACTTTCAGAG | TATGAAGGAC | GATTAAATAT | AACCCTTTGG | TATAAATGTT | 300 |
| CTCTCTCTCG | CTCCTCTGTA | ACAATTGGAG | AAACAGAGTT | CTAACAATAT | TAAAATCAGC | 360 |
| CATAGACAGA | GAGTAGTGAG | AAATATACTT | TTTTTAATAC | AGAAGGTTCC | CTGAAGTACT | 420 |
| TTTAGTATTA | TTCTAAATTA | AGCAATAACC | AATGAACAAT | TTTGGTCATA | AGCAGTTTCT | 480 |
| CTCCAGAAAA | AAAAAAAAAA | AGTCGAC | | | | |

Seq ID NO: 27 DNA sequence
Nucleic Acid Accession #: NM_006551.2
Coding sequence: 64..336

| | | | | | | |
|---|---|---|---|---|---|---|
| 1 | 11 | 21 | 31 | 41 | 51 | |
| \| | \| | \| | \| | \| | \| | |
| AATTCTAGAA | GTCCAAATCA | CTCATTGTTT | GTGAAAGCTG | AGCTCACAGC | AAAACAAGCC | 60 |
| ACCATGAAGC | TGTCGGTGTG | TCTCCTGCTG | GTCACGCTGG | CCCTCTGCTG | CTACCAGGCC | 120 |
| AATGCCGAGT | TCTGCCCAGC | TCTTGTTTCT | GAGCTGTTAG | ACTTCTTCTT | CATTAGTGAA | 180 |
| CCTCTGTTCA | AGTTAAGTCT | TGCCAAATTT | GATGCCCCTC | AACGAAGCCT | CATTGCGGAA | 240 |
| TTAGGAGTGA | AGAGATGCAC | GGATCAGATG | TCCCTTCAGA | AACGAAGCCT | CATTGCGGAA | 300 |
| GTCCTGGTGA | AAATATTGAA | GAAATGTAGT | GTGTGACATG | TAAAAACTTT | CATCCTGGTT | 360 |
| TCCACTGTCT | TTCAATGACA | CCCTGATCTT | CACTGCAGAA | TGTAAAGGTT | TCAACGTCTT | 420 |
| GCTTTAATAA | ATCACTTGCT | CTAC | | | | |

TABLE 4-continued

Seq ID NO: 28 Protein sequence
Protein Accession #: NP_006542.1

| | | | | | | |
|---|---|---|---|---|---|---|
| 1 | 11 | 21 | 31 | 41 | 51 | |
| \| | \| | \| | \| | \| | \| | |
| MKLSVCLLLV | TLALCCYQAN | AEFCPALVSE | LLDFFFISEP | LFKLSLAKFD | APPEAVAAKL | 60 |
| GVKRCTDQMS | LQKRSLIAEV | LVKILKKCSV | | | | |

Seq ID NO: 29 DNA sequence
Nucleic Acid Accession #: NM_002645.1
Coding sequence: 1..5061

| | | | | | | |
|---|---|---|---|---|---|---|
| 1 | 11 | 21 | 31 | 41 | 51 | |
| \| | \| | \| | \| | \| | \| | |
| ATGGCTCAGA | TATTTAGCAA | CAGCGGATTT | AAAGAATGTC | CATTTTCACA | TCCGCAACCA | 60 |
| ACAAGAGCAA | AAGATGTGGA | CAAAGAAGAA | GCATTACAGA | TGGAAGCAGA | GGCTTTAGCA | 120 |
| AAACTGCAAA | AGGATAGACA | AGTGACTGAC | AATCAGAGAG | GCTTTGAGTT | GTCAAGCAGC | 180 |
| ACCAGAAAAA | AAGCACAGGT | TTATAACAAG | CAGGATTATG | ATCTCATGGT | GTTTCCTGAA | 240 |
| TCAGATTCCC | AAAAAAGAGC | ATTAGATATT | GATGTAGAAA | AGCTCACCCA | AGCTGAACTT | 300 |
| GAGAAACTAT | TGCTGGATGA | CAGTTTCGAG | ACTAAAAAAA | CACCTGTATT | ACCAGTTACT | 360 |
| CCTATTCTGA | GCCCTTCCTT | TTCAGCACAG | CTCTATTTTA | GACCTACTAT | TCAGAGAGGA | 420 |
| CAGTGGCCAC | CTGGATTACC | TGGGCCTTCC | ACTTATGCTT | TACCTTCTAT | TTATCCTTCT | 480 |
| ACTTACAGTA | AACAGGCTGC | ATTCCAAAAT | GGCTTCAATC | CAAGAATGCC | CACTTTTCCA | 540 |
| TCTACAGAAC | CTATATATTT | AAGTCTTCCG | GGACAATCTC | CATATTTCTC | ATATCCTTTG | 600 |
| ACACCTGCCA | CACCCTTTCA | TCCACAAGGA | AGCTTACCTA | TCTATCGTCC | AGTAGTCAGT | 660 |
| ACTGACATGG | CAAAACTATT | TGACAAAATA | GCTAGTACAT | CAGAATTTTT | AAAAAATGGG | 720 |
| AAAGCAAGGA | CTGATTTGGA | GATAACAGAT | TCAAAAGTCA | GCAATCTACA | GGTATCTCCA | 780 |
| AAGTCTGAGG | ATATCAGTAA | ATTTGACTGG | TTAGACTTGG | ATCCTCTAAG | TAAGCCTAAG | 840 |
| GTGGATAATG | TGGAGGTATT | AGACCATGAG | GAAGAGAAAA | ATGTTTCAAG | TTTGCTAGCA | 900 |
| AAGGATCCTT | GGGATGCTGT | TCTTCTTGAA | GAGAGATCGA | CAGCAAATTG | TCATCTTGAA | 960 |
| AGAAAGGTGA | ATGGAAAATC | CCTTTCTGTG | GCAACTGTTA | CAAGAAGCCA | GTCTTTAAAT | 1020 |
| AATCGAACAA | CTGAGCTTGC | AAAAGCCCAG | GGCCATATAT | CTCAGAAAGA | CCCAAATGGG | 1080 |
| ACCAGTAGTT | TGCCAACTGG | AAGTTCTCTT | CTTCAAGAAG | TTGAAGTACA | GAATGAGGAG | 1140 |
| ATGGCAGCTT | TTTGTCGATC | CATTACAAAA | TTGAAGACCA | AATTTCCATA | TACCAATCAC | 1200 |
| CGCACAAACC | CAGGCTATTT | GTTAAGTCCA | GTCACAGCGC | AAAGAAACAT | ATGCGGAGAA | 1260 |
| AATGCTAGTG | TGAAGGTCTC | CATTGACATT | GAAGGATTTC | AGCTACCAGT | TACTTTTACG | 1320 |
| TGTGATGTGA | GTTCTACTGT | AGAAATCATT | ATAATGCAAG | CCCTTTGCTG | GGTACATGAT | 1380 |
| GACTTGAATC | AAGTAGATGT | TGGCAGCTAT | GTTCTAAAAG | TTTGTGGTCA | AGAGGAAGTG | 1440 |
| CTGCAGAATA | ATCATTGCCT | TGGAAGTCAT | GAGCATATTC | AAAACTGTCA | AAAATGGGAC | 1500 |
| ACAGAAATTA | GACTACAACT | CTTGACCTTC | AGTGCAATGT | GTCAAAATCT | GGCCCGAACA | 1560 |
| GCAGAAGATG | ATGAAACACC | CGTGGATTTA | AACAAACACC | TGTATCAAAT | AGAAAAACCT | 1620 |
| TGCAAAGAAG | CCATGACGAG | ACACCCTGTT | GAAGAACTCT | TAGATTCTTA | TCACAACCAA | 1680 |
| GTAGAACTGG | CTCTTCAAAT | TGAAAACCAA | CACCGAGCAG | TAGATCAAGT | AATTAAAGCT | 1740 |
| GTAAGAAAAA | TCTGTAGTGC | TTTAGATGGT | GTCGAGACTC | TTGCCATTAC | AGAATCAGTA | 1800 |
| AAGAAGCTAA | AGAGAGCAGT | TAATCTTCCA | AGGAGTAAAA | CTGCTGATGT | GACTTCTTTG | 1860 |
| TTTGGAGGAG | AAGACACTAG | CAGGAGTTCA | ACTAGGGGCT | CACTTAATCC | TGAAAATCCT | 1820 |
| GTTCAAGTAA | GCATAAACCA | ATTAACTGCA | GCAATTTATG | ATCTTCTCAG | ACTCCATGCA | 1980 |
| AATTCTGGTA | GGAGTCCTAC | AGACTGTGCC | CAAAGTAGCA | AGAGTGTCAA | GGAAGCATGG | 2040 |
| ACTACAACAG | AGCAGCTCCA | GTTTACTATT | TTTGCTGCTC | ATGGAATTTC | AAGTAATTGG | 2100 |
| GTATCAAATT | ATGAAAAATA | CTACTTGATA | TGTTCACTGT | CTCACAATGG | AAAGGATCTT | 2160 |
| TTTAAACCTA | TTCAATCAAA | GAAGGTTGGC | ACTTACAAGA | ATTTCTTCTA | TCTTATTAAA | 2220 |
| TGGGATGAAC | TAATCATTTT | TCCTATCCAG | ATATCACAAT | TGCCATTAGA | ATCAGTTCTT | 2280 |
| CACCTTACTC | TTTTTGGAAT | TTTAAATCAG | AGCAGTGGAA | GTTCCCCTGA | TTCTAATAAG | 2340 |
| CAGAGAAAGG | GACCAGAAGC | TTTGGGCAAA | GTTTCTTTAC | CTCTTTGTGA | CTTTAGACGG | 2400 |
| TTTTTAACAT | GTGGAACTAA | ACTTCTATAT | CTTTGGACTT | CATCACATAC | AAATTCTGTT | 2460 |
| CCTGGAACAG | TTACCAAAAA | AGGATATGTC | ATGGAAAGAA | TAGTGCTACA | GGTTGATTTT | 2520 |
| CCTTCTCCTG | CATTTGATAT | TATTTATACA | ACTCCTCAAG | TTGACAGAAG | CATTATACAG | 2580 |
| CAACATAACT | TAGAAACACT | AGAGAATGAT | ATAAAAGGGA | AACTTCTTGA | TATTCTTCAT | 2640 |
| AAAGACTCAT | CACTTGGACT | TTCTAAAGAA | GATAAAGCTT | TTTTATGGGA | GAAACGTTAT | 2700 |
| TATTGCTTCA | AACACCCAAA | TTGTCTTCCT | AAAATATTAG | CAAGCGCCCC | AAACTGGAAA | 2760 |
| TGGGGTAATC | TTGCCAAAAC | TTACTCATTG | CTTCACCAGT | GGCCTGCATT | GTACCCACTA | 2820 |
| ATTGCATTGG | AACTTCTTGA | TTCAAAATTT | GCTGATCAGG | AAGTAAGATC | CCTAGCTGTG | 2880 |
| ACCTGGATTG | AGGCCATTAG | TGATGATGAG | CTAACAGATC | TTCTTCCACA | GTTTGTACAA | 2940 |
| GCTTTGAAAT | ATGAAATTTA | CTTGAATAGT | TCATTAGTGC | AATTCCTTTT | GTCCAGGGCA | 3000 |
| TTGGGAAATA | TCCAGATAGC | ACACAATTTA | TATTGGCTTC | TCAAAGATGC | CCTGCATGAT | 3060 |
| GTACAGTTTA | GTACCCGATA | CGAACATGTT | TTGGGTGCTC | TCCTGTCAGT | AGGAGGAAAA | 3120 |
| CGACTTAGAG | AAGAACTTCT | AAAACAGACG | AAACTTGTAC | AGCTTTTAGG | AGGAGTAGCA | 3180 |
| GAAAAAGTAA | GGCAGGCTAG | TGGATCAGCC | AGACAGGTTG | TTCTCCAAAG | AAGTATGGAA | 3240 |
| CGAGTACAGT | CCTTTTTTCA | GAAAAATAAA | TGCCGTCTCC | CTCTCAAGCC | AAGTCTAGTG | 3300 |
| GCAAAAGAAT | TAAATATTAA | GTCGTGTTCC | TTCTTCAGTT | CTAATGCTGT | CCCCCTAAAA | 3360 |
| GTCACAATGG | TGAATGCTGA | CCCTCTGGGA | GAAGAAATTA | ATGTCATGTT | TAAGGTTGGT | 3420 |
| GAAGATCTTC | GGCAAGATAT | GTTAGCTTTA | CAGATGATAA | AGATTATGGA | TAAGATCTGG | 3480 |
| CTTAAAGAAG | GACTAGATCT | GAGGATGGTA | ATTTTCAAAT | GTCTCTCAAC | TGGCAGAGAT | 3540 |
| CGAGGCATGG | TGGAGCTGGT | TCCTGCTTCC | GATACCCTCA | GGAAAATCCA | AGTGAAATAT | 3600 |
| GGTGTGACAG | GATCCTTTAA | AGATAAACCA | CTTGCAGAGT | GGCTAAGGAA | ATACAATCCC | 3660 |
| TCTGAAGAAG | AATATGAAAA | GGCTTCAGAG | AACTTTATCT | ATTCCTGTGC | TGGATGCTGT | 3720 |
| GTAGCCACCT | ATGTTTTAGG | CATCTGTGAT | CGACACAATG | ACAATATAAT | GCTTCGAAGC | 3780 |
| ACGGGACACA | TGTTTCACAT | TGACTTTGGA | AAGTTTTTGG | GACATGCACA | GATGTTTGGC | 3840 |
| AGCTTCAAAA | GGGATCGGGC | TCCTTTTGTG | CTGACCTCTG | ATATGGCATA | TGTCATTAAT | 3900 |
| GGGGGTGAAA | AGCCCACCAT | TGCTTTTCAG | TTGTTTGTGG | ACCTCTGCTG | TCAGGCCTAC | 3960 |
| AACTTGATAA | GAAAGCAGAC | AAACCTTTTT | CTTAACCTCC | TTTCACTGAT | GATTCCTTCA | 4020 |

TABLE 4-continued

| | | | | | | |
|---|---|---|---|---|---|---|
| GGGTTACCAG | AACTTACAAG | TATTCAAGAT | TTGAAATACG | TTAGAGATGC | ACTTCAACCC | 4080 |
| CAAACTACAG | ACGCAGAAGC | TACAATTTTC | TTTACTAGGC | TTATTGAATC | AAGTTTGGGA | 4140 |
| AGCATTGCCA | CAAAGTTTAA | CTTCTTCATT | CACAACCTTG | CTCAGCTTCG | TTTTTCTGGT | 4200 |
| CTTCCTTCTA | ATGATGAGCC | CATCCTTTCA | TTTTCACCTA | AAACATACTC | CTTTAGACAA | 4260 |
| GATGGTCGAA | TCAAGGAAGT | CTCTGTTTTT | ACATATCATA | AGAAATACAA | CCCAGATAAA | 4320 |
| CATTATATTT | ATGTAGTCCG | AATTTTGTGG | GAAGGACAGA | TTGAACCATC | ATTTGTCTTC | 4380 |
| CGAACATTTG | TCGAATTTCA | GGAACTTCAC | AATAAGCTCA | GTATTATTTT | TCCACTTTGG | 4440 |
| AAGTTACCAG | GCTTTCCTAA | TAGGATGGTT | CTAGGAAGAA | CACACATAAA | AGATGTAGCA | 4500 |
| GCCAAAAGGA | AAATTGAGTT | AAACAGTTAC | TTACAGAGTT | TGATGAATGC | TTCAACGGAT | 4560 |
| GTAGCAGAGT | GTGATCTTGT | TTGTACTTTC | TTCCACCCTT | TACTTCGTGA | TGAGAAAGCT | 4620 |
| GAAGGGATAG | CTAGGTCTGC | AGATGCAGGT | TCCTTCAGTC | CTACTCCAGG | CCAAATAGGA | 4680 |
| GGAGCTGTGA | AATTATCCAT | CTCTTACCGA | AATGGTACTC | TTTTCATCAT | GGTGATGCAT | 4740 |
| ATCAAAGATC | TTGTTACTGA | AGATGGAGCT | GACCCAAATC | CATATGTCAA | AACATACCTA | 4800 |
| CTTCCAGATA | ACCACAAAAC | ATCCAAACGT | AAAACCAAAA | TTTCACGAAA | AACGAGGAAT | 4860 |
| CCGACATTCA | ATGAAATGCT | TGTATACAGT | GGATATAGCA | AAGAAACCCT | AAGACAGCGA | 4920 |
| GAACTTCAAC | TAAGTGTACT | CAGTGCAGAA | TCTCTGCGGG | AGAATTTTTT | CTTGGGTGGA | 4980 |
| GTAACCCTGC | CTTTGAAAGA | TTTCAACTTG | AGCAAAGAGA | CGGTTAAATG | GTATCAGCTG | 5040 |
| ACTGCGGCAA | CATACTTGTA | A | | | | |

Seq ID NO: 30 Protein sequence
Protein Acceseion #: NP_002636.1

| | | | | | | |
|---|---|---|---|---|---|---|
| 1 | 11 | 21 | 31 | 41 | 51 | |
| \| | \| | \| | \| | \| | \| | |
| MAQIFSNSGF | KECPFSHPEP | TRAKDVDKEE | ALQMEAEALA | KLQKDRQVTD | NQRGFELSSS | 60 |
| TRKKAQVYNK | QDYDLMVFPE | SDSQKRALDI | DVEKLTQAEL | EKLLLDSSFE | TKKTPVLPVT | 120 |
| PILSPSFSAQ | LYFRPTIQRG | QWPPGLPGPS | TYALPSIYPS | TYSKQAAPQN | GFNPRMPTFP | 180 |
| STEPIYLSLP | GQSPYPSYPL | TPATPPNPQG | SLPIYRPVVS | TDMAKLFDKI | ASTSEPLKNG | 240 |
| KARTDLEITD | SKVSNLQVSP | KSEDISKFDW | LDLDPLSKPK | VDNVEVLDHE | EEKNVSSLLA | 300 |
| KDPWDAVLLE | ERSTANCNLE | RKVNGKSLSV | ATVTRSQSLN | IRTTQLAKAQ | GHISQKDPNG | 360 |
| TSSLPTGSSL | LQEVEVQNEE | MAAFCRSITR | LKTKFPYTNH | RTNPGYLLSP | VTAQRNICGE | 420 |
| NASVKVSIDI | EGFQLPVTFT | CDVSSTVEII | IMQALCWVHD | DLNQVDVGSY | VLKVCGQEEV | 480 |
| LQNNNCLGSN | EHIQNCRKWD | TEIRLQLLTF | SANCQNLART | AEDDETPVDL | NKNLYQIEKP | 540 |
| CKEAMTRHPV | EELLDSYHNQ | VELALQIENQ | HEAVDQVIKA | VRKICSALDG | VETLAITESV | 600 |
| KKLKRAVNLP | RSKTAGVTSL | FGGEDTSRSS | TRGSLNPENP | VQVSINQLTA | AIYDLLELNA | 660 |
| NSGRSPTDCA | QSSKSVKEAW | TTTEQLQFTI | FAANGISSNW | VSNYEKYYLI | CSLSNNGKDL | 720 |
| FKPIQSKKVG | TYKNFFYLIK | WDELIIFPIQ | ISQLPLESVL | HLTLFGILNQ | SSGSSPDSNK | 780 |
| QRKGPEALGK | VSLPLCDFRR | FLTCGTKLLY | LWTSSHTNSV | PGTVTKKGYV | MERIVLQVDP | 840 |
| PSPAFDIIYT | TPQVDRSIIQ | QINLETLEND | IKGKLLDILN | KDSSLGLSKE | DKAFLWEKRY | 900 |
| YCFKHPNCLP | KOLASAPNNK | WGNLAKTYSL | LHQWPALYPL | IALELLDSKF | ADQEVRSLAV | 960 |
| TWIEAISDDE | LTDLLPQFVQ | ALKYEIYLNS | SLVQFLLSRA | LGNIQIAHNL | YWLLKDALND | 1020 |
| VQFSTRYENV | LGALLSVGGK | RLREELLKQT | KLVQLLGGVA | EKVRQASGSA | RQVVLQRSME | 1080 |
| RVQSFFQKNK | CRLPLKPSLV | AKELNIKSCS | PFSSNAVPLK | VTMVNADPLG | EEINVMFKVG | 1140 |
| EDLPQDMLAL | QMIKIMDKIW | LKEGLDLRNV | IFKCLSTGRD | RGMVELVPAS | DTLRKIQVEY | 1200 |
| GVTGSFKDKP | LAEWLRKYNP | SEEEYEKASE | NFIYSCAGCC | VATYVLGIGD | RHNDNIMLRS | 1260 |
| TGNMFHIDPG | KFLGNAQMPG | SFKRDRAPFV | LTSDMAYVIN | GGEKPTIRFQ | LFVDLCCQAY | 1320 |
| NLIRKQTNLP | LNLLSLMIPS | GLPELTSIQD | LKYVRDALQP | QTTDAEATIF | FTELIESSLG | 1380 |
| SIATKFNFFI | HNLAQLRFSG | LPSNDEPILS | FSPKTYSFRQ | DGRIKEVEVE | TYNKKYNPDK | 1440 |
| HYIYVVRILW | EGQIEPSFVF | RTFVEFQELH | NKLSIIPPLW | KLPGPPNRNV | LGRTHIKDVA | 1500 |
| AERKIELNSY | LQSLMNASTD | VAECDLVCTP | PHPLLRDEKA | EGIARSADAG | SFSPTPGQIG | 1560 |
| GAVKLSISYR | NGTLFIMVMH | IKDLVTEDGA | DPNPYVKTYL | LPDNNKTSKR | KTKISRKTRN | 1620 |
| PTFNEMLVYS | GYSKETLRQR | ELQLSVLSAE | SLRENFFLGG | VTLPLKDFNL | SKETVKWYQL | 1680 |
| TAATYL | | | | | | |

Seq ID NO: 31 DNA sequence
Nucleic Acid Accession #: CAT cluster

| | | | | | | |
|---|---|---|---|---|---|---|
| 1 | 11 | 21 | 31 | 41 | 51 | |
| \| | \| | \| | \| | \| | \| | |
| TTTTTTTTAG | AGACTAAACC | ATAGCAAGGA | GTTTGTGATC | ACTGTATAGC | GCTGAGTGAA | 60 |
| ACCTCAAAAT | ACATTCTGGA | ATTTGTAAGG | GATGCTTTCG | TCGACTTTTT | TTTTTTTTTT | 120 |
| TTGGTATTTT | CACTGTCAAT | TATGCCTCGT | ATTATTTATT | TATTTGCCAA | AATACGACTG | 180 |
| TATGAAAAAA | AGCTACCTCA | TAGAGCTCAT | GACACATAAT | AGGTATTCAC | TGAGCATTTG | 240 |
| GTGATTTGTT | AAGCACTCAC | ATCAATAAAA | TATTTCAGCT | CAACAGGCAC | ACTAGGGGCC | 300 |
| AGATGAGCAC | TGACTTTCCC | CATTGAGGAG | TCTCGATTAC | CTCATGTCTC | ACTTCAAACA | 360 |
| ATTTATTTTT | CTTGTATGCA | TAGCTGGGTT | CAAGAGTTCT | TTCTTGTTTT | GTCGGATATA | 420 |
| TTCTTTTTCT | TTTGTTTTTG | TAGGTCCTAT | AATACAGTAA | AGACATCAAA | TAGACC | |

Seq ID NO: 32 DNA sequence
Nucleic Acid Accession #: CAT cluster

| | | | | | | |
|---|---|---|---|---|---|---|
| 1 | 11 | 21 | 31 | 41 | 51 | |
| \| | \| | \| | \| | \| | \| | |
| CAGTCAGATT | TTTTTTTTGC | TTAACTAAGA | CAAAGTGAAT | AATTCACTGT | GAGCCAAATT | 60 |
| CTTTCTTGAT | TCCTCTTTTT | GGAGCAGTCC | ATCTTTATGG | GAAAACCAGC | CTAGAATGGT | 120 |
| GATTTCAGTT | TCAGGTGATT | TCGATAGAAT | TGTATTTGGC | TCAGAAATGA | TAAGACTGGG | 180 |
| GCCAAGAAAA | ATTTTAAACT | TTTTTTTTTG | TAATCATATT | ACTAGTTTGA | TTTCATATGA | 240 |
| ACTTCCTTTG | TTGACTTTCT | TTGCCATTAA | TTTAAAAGTT | CCAGTATCCT | CAATATTTGA | 300 |
| TGTCTTATAT | GTACAGAATC | CTTTCCAGCT | GTAAGTCATC | AGCAAGTAAA | AAATTTAGTA | 360 |
| TGGCAATAGT | TTTCATAAGA | GGTTTTTTAA | AACAGAAAAA | TGTTGACATT | GCCAGCCTCT | 420 |
| GGGTTGCATT | TTGGGATATG | CTACATTTCA | AAGGTATCTT | TTAAATCTGA | AGGCAAAGAC | 480 |
| TTTTTCAACA | TCTGAATATT | CTGATTTACA | GAAATTATAA | AAAAAAAAGT | CGACGCG | |

TABLE 4-continued

Seq ID NO: 33 DNA sequence
Nucleic Acid Accession #: AK026418.1

```
1          11         21         31         41         51
|          |          |          |          |          |
TTTTAAGATG GAGTTTTCGC TCTTGTTGCC CAGGCTGGAG TGCAGTGGTG CAATCTTGGC   60
TCACTGCAAC CTCTGCCCCC CGGGTTCAGG CGATTCTCTC CTCTCAGTCT CTCAAGTAAC  120
TGGGATTACA GGCACACACC ACCACGGCCA GCTAATTATT TTGTATTTTG AGTCGAGAGG  180
AGAATTCACC ATATTGGCCT CAGGTAATCC GCCCGCCTCG GCCTCCCAAA GTGTTGGGAT  240
TATGGGCGTG AGCCAGCCAC GGTGCCCGGC CCGTTTTATT GTTTGAAAAA CAAGTACAGG  300
TTGTTATTAT CCAAGAATTG TTGATAGAGT ATATACTGTA TTTGAAGTGT AGAACTGAGG  360
CAGAGGCTGA TTAATATAAC TAGTTTACAT TTGTTAGCCT TTCACATCTG TGAAGGAATA  420
AAGTACAGAC AAAAGTGGAA AACAAACCAG AAAAAAAAAA ATTGTGAAGC ACAGAGCTGC  480
TTAAAAGAGT GGTGTCACAT TAAAAGAAAA AAGTCACAGA AATAAGTCAG TATTTTGTTT  540
AGAGACTAGA ACTCCAACTG CTAGCCAACT GCCTAGAATA TAGTAAATAT TTTCTAGTTT  600
CTTAAATGAC TAGTAATATT CCTACATTAT GTGATGGCAT TTCCCAAACT GTTTAATTAG  660
ATGTTAGATT TGTAGCCAAA TATGTCTAGG AAATGCTTAA ACAATATAAA ACAGTTTTAA  720
TGATTGGCTT TTTAGAACGT TATATATTAG TGTGCTTTAT GCATATCCAA GAGGTGAGTG  780
AGGTATTTGG GGTTTTTCAG ACTTACTTGA TTACAGATCT GGAGTATCTC AAAACAGTTG  840
TTTTGTGGAA AACACTTTGG CAAACTCTGA GTCTTAGTCA TTAAAAATAG TTTTTGGGTA  900
AACAACAGTG TAATAGAAAT GGAAATTACT GATTCACATT GAGCCATGAA GAATTTATTT  960
TCAGCGATTT TTATAGAAGT TGCTTTATGA CAAAGAAAGC TTTGGTTAAC TGGCATTTGG 1020
CATTTCACAC CCCTAAATTT TCTACATGAG GATTTATTTC TCTGGTTCTC TCACTTTCTC 1080
ACTCAGTTAT ACTGAATTCA TTTATGATGA GCGCTCTCAA CCATTCTTAT TCATCAAAGC 1140
TGAAGTTGGC AGAGCCCTCT CTGGTACCTG ATTAGAAGTC CGTCTTCCGT CTCATAGGGA 1200
AGTGTTAGAG ATGGATAATG TTTCTGTGTA GCAGAAGTAG TCATTATGTC CCCTTAAATT 1260
CGGTCACTTT GACTGCAGTA GAGCTTCTTA GTGAGCAGTC TGTGATGGAG TATACTTTCG 1320
GAGAAGCTCA TGGTGGGGGA AACCTGGAAT TTATCTAAAT ATTTCATTTC TTTGATAAAT 1380
TACATTAAAA AATTAATAAG AGTATCTATT TGGTGAAATC ATTTTCCTCC ACGTGACCAA 1440
ATGAGAAATT TAGTGAAAGA TTTAAAATCA TTTTTCAGAC TTTTTCCACA TTAGTTGGGA 1500
AGCAAACCCC TTTTTTAAGG CAATGTCAGT TATTAAGCTT TAGGGAACCA CATGCCACTT 1560
TAGGTAACAC ATGATTGGAG AGATTGAAGA GTGAAGTCCC TGCTTTAAAG TGTACTCCTG 1620
TGGACACAGT AATGCATATA TTTAAAATGG TTCATGTTAA GAGTAGGTAT ATTTCTATCT 1680
AAATACTCTG TAGCTTTTGT GATTCAGGGA AATGAGTGGA GCCTCACAGG CACAAGAATC 1740
TAGTAAATTC TAGGTTTCTT GTGTGGAACT CAGTGGGCAA AATCTTAACT GAGTGAATTC 1800
TTGATTATTG GTATCACATT TATTAGTCTG TATGTATCTG TGTCATCGAT CTCCTTAAGA 1860
AGAGACTCGT AGATATTGAC TGGGAGACCC AAGCTGAATG CTAAAATCTG CTCCATGGAT 1920
ATAAGCTGAT GCAGTCATCA TTTCACATTA AAATGTACCA CAGCTATATA TGCCGCAAAA 1980
AAAAAAAAAA AAAA
```

Seq ID NO: 34 DNA sequence
Nucleic Acid Accession #: CAT cluster

```
1          11         21         31         41         51
|          |          |          |          |          |
CTACTACTAA ATTCGCGGCC GCGTCGACTT TTTTTTTTTT TTGTCTTATG TCTCTAATCT   60
GCACTGTTCA GCTCTTTTAG GCACTGCAAA GTTGTCTTGA ATTAGGAAAG AGGTGCTAGA  120
ATGTGGGCGT GGGTGTTGAC CTACATCTGA ACAATTTACA TATGATTCAC CACAATTAAA  180
CAATTTGGTT TGAAATAGCT ATAATTAAGT TATTATCAGA GAAGTATTTA CTAGTCTAGA  240
AATTCTAAAT TTATCTTCAC ATACACCCTA ACTGAGAAAA GGGCCACATT TTCTGCACTC  300
TATTAAGTAA AGCAAATGCT GAACTAAATG CCTCCATGTT AACATTTATA TTGTTAAGTT  360
ACTGACAGCA TATTCTATGA ATGATTACGT TAGTCGTTTC TTTAAAAATT ATAGGTTTGA  420
AATAGCAAGA AAAATATGAA ATGATGGTAG ACAAAAAAGA GTTTCAGTTT CTAACTTCTA  480
ACTATATATA TACACACACA CATGCACACA GAATTGCCTT CCCGGATGTA TAGAAATTAT  540
ATACAGCCAT GTCCAGGCNC GATGGAAATT ATGGGGGAAT ATCCAANTTA GGATACNCGT  600
GCCGAATCGC CGGGTNTAAA TAATACNGGT CNATCCACCA TCCTGGTTTA
```

Seq ID NO: 35 DNA sequence
Nucleic Acid Accession #: NM_018490.1
Coding sequence: 445..3300

```
1          11         21         31         41         51
|          |          |          |          |          |
CCGCGGCTGG GAGACAGCGA GCCAGAGTCT GGGTGTTTGT GCGAGAGCCA CGGCGGGGGC   60
TGGGGCGAGT GGCCGGCATG GCTGAAGGCT GCGCTCTGCA ACCTTGAAGA GCCGCTGCAT  120
TGAGAGGCCA GGGACAGGGA GACCGGTGCG ATGGCAGAGC GCGGCCCCCG CCGCTGCGCC  180
GGGCCGGCCC GGCTGGCCTG AGCCGCCGGA GGAGCGGGGC TGCCTCTGCG CGTCCATGGA  240
GCAGCGGGAA GGGCGAAACT CCGGAGCGCC GCGTCCCTGC GCCGCTGCGG CGGACTGCTG  300
AAGGGGCCGA GCCCGCGCGG ACCGCCGAGG AAGAGACCCC CGCTCCAGCC CGCAGGCCGG  360
CTGCCCGGGG GCGGCGGGGG ACATCGGAGG GCAGCGGAGC GAGCAGCGCC GCGGGAGAGG  420
CCGGCGCGGG AGGCGGCCGC AGCAATGCCG GGCCCGCTAG GGCTGCTCTG CTTCCTCGGC  480
CTGGGGCTGC TCGGCTCGGC CGGGCCCAGC GGCGCGGCGC CGCCTCTCTG CGCGGCGCCC  540
TGCAGCTGCG ACGGCGACCG TCGGGTGGAC TGCTCCGGGA AGGGGCTGAC GGCCGTGCCC  600
GAGGGGCTCA GCGCCTTCAC CCAAGCGCTG GATATCAGTA TGAACAACAT TACTCAGTTG  660
CCAGAAGATG CATTTAAGAA CTTTCCTTTT CTAGAAGAGC TACAATTGGC GGGCAACGAC  720
CTTTCTTTTA TCCACCCAAA GGCCTTGTCT GGGTTGAAAG AACTCAAAGT TCTAACGCTC  780
CAGAATAATC AGTTGAAAAC AGTACCCAGT GAAGCCATTC GAGGGCTGAG TGCTTTGCAG  840
TCTTTGCGTT TAGATGCCAA CCATATTACC TCAGTCCCCG AGGACAGTTT TGAAGGACTT  900
GTTCAGTTAC GGCATCTGTG GCTGGATGAC AACAGCTTGA CGGAGGTGCC TGTGCACCCC  960
CTCAGGAACT TGCCCACCCT ACAGGCGCTG ACCCTGGCTC TCAACAAGAT CTCAAGCATC 1020
```

TABLE 4-continued

| | | | | | | |
|---|---|---|---|---|---|---|
| CCTGACTTTG | CATTTACCAA | CCTTTCAAGC | CTGGTAGTTC | TGCATCTTCA | TAACAATAAA | 1080 |
| ATTAGAGGCC | TGAGTCAACA | CTGTTTTGAT | GGACTAGATA | ACCTGGAGAC | CTTAGACTTG | 1140 |
| AGTTATAATA | ACTTGGGGGA | ATTTCCTCAG | GCTATTAAAG | CCCGTCCTAG | CCTTAAAGAG | 1200 |
| CTAGGATTTC | ATAGTAATTC | TATTTCTGTT | ATCCCTGATG | GAGCATTTGA | TGGTAATCCA | 1260 |
| CTCTTAAGAA | CTATACATTT | GTATGATAAT | CCTCTGTCTT | TTGTGGGGAA | CTCAGCATCT | 1320 |
| CACAATTTAT | CTGATCTTCA | TTCCCTAGTC | ATTCGTGGTG | CAAGCATGGT | GCAGCAGTTC | 1380 |
| CCCAATCTTA | CAGGAACTGT | CCACCTGGAA | AGTCTGACTT | TGACAGGTAC | AAAGATAAGC | 1440 |
| AGCATACCTA | ATAATTTGTG | TCAAGAACAA | AAGATGCTTA | GGACTTTGGA | CTTGTCTTAC | 1500 |
| AATAATATAA | GAGACCTTCC | AAGTTTTAAT | GGTTGCCATG | CTCTGGAAGA | AATTTCTTTA | 1560 |
| CAGCGTAATC | AAATCTACCA | AATAAAGGAA | GGCACCTTTC | AAGGCCTGAT | ATCTCTAAGG | 1620 |
| ATTCTAGATC | TGAGTAGAAA | CCTGATACAT | GAAATTCACA | GTAGAGCTTT | TGCCACACTT | 1680 |
| GGGCCAATAA | CTAACCTAGA | TGTAAGTTTC | AATGAATTAA | CTTCCTTTCC | TACGGAAGGC | 1740 |
| CCGAATGGGC | TAAATCAACT | GAAACTTGTG | GGCAACTTCA | AGCTGAAAGA | AGCCTTAGCA | 1800 |
| GCAAAAGACT | TTGTTAACCT | CAGGTCTTTA | TCGGTACCAT | ATGCTTATCA | GTGCTGTGCA | 1860 |
| TTTTGGGGTT | GTGACTCTTA | TGCAAATTTA | AACACAGAAG | ATAACAGCCT | CCAGGACCAC | 1920 |
| AGTGTGGCAC | AGGAGAAAGG | TACTGCTGAT | GCAGCAAATG | TCACAAGCAC | TCTTGAAAAT | 1980 |
| GAAGAACATA | GTCAAATAAT | TATCCATTGT | ACACCTTCAA | CAGGTGCTTT | TAAGCCCTGT | 2040 |
| GAATATTTAC | TGGGAAGCTG | GATGATTCGT | CTTACTGTGT | GGTTCATTTT | CTTGGTTGCA | 2100 |
| TTATTTTTCA | ACCTGCTTGT | TATTTTAACA | ACATTTGCAT | CTTGTACATC | ACTGCCTTCG | 2160 |
| TCCAAATTGT | TTATAGGCTT | GATTTCTGTG | TCTAACTTAT | TCATGGGAAT | CTATACTGGC | 2220 |
| ATCCTAACTT | TTCTTGATGC | TGTGTCCTGG | GGCAGATTCG | CTGAATTTGG | CATTTGGTGG | 2280 |
| GAAACTGGCA | GTGGCTGCAA | AGTAGCTGGG | TTTCTTGCAG | TTTTCTCCTC | AGAAAGTGCC | 2340 |
| ATATTTTTAT | TAATGCTAGC | AACTGTCGAA | AGAAGCTTAT | CTGCAAAAGA | TATAATGAAA | 2400 |
| AATGGGAAGA | GCAATCATCT | CAAACAGTTC | CGGGTTGCTG | CCCTTTCGGC | TTTCCTAGGT | 2460 |
| GCTACAGTAG | CAGGCTGTTT | TCCCCTTTTC | CATAGAGGGG | AATATTCTGC | ATCACCCCTT | 2520 |
| TGTTTGCCAT | TTCCTACAGG | TGAAACGCCA | TCATTAGGAT | TCACTGTAAC | GTTAGTGCTA | 2580 |
| TTAAACTCAC | TAGCATTTTT | ATTAATGGCC | GTTATCTACA | CTAAGCTATA | CTGCAACTTG | 2640 |
| GAAAAAGAGG | ACCTCTCAGA | AAACTCACAA | TCTAGCATGA | TTAAGCATGT | CGCTTGGCTA | 2700 |
| ATCTTCACCA | ATTGCATCTT | TTTCTGCCCT | GTGGCGTTTT | TTTCATTTGC | TTTTCCATTG | 2820 |
| CCTGCTTGCC | TGAATCCAGT | CCTGTATGTT | TTCTTCAACC | CAAAGTTTAA | AGAAGACTGG | 2880 |
| AAGTTACTGA | AGCGACGTGT | TACCAAGAAA | AGTGGATCAG | TTTCAGTTTC | CATCAGTAGC | 2940 |
| CAAGGTGGTT | GTCTGGAACA | GGATTTCTAC | TACGACTGTG | GCATGTACTC | ACATTTGCAG | 3000 |
| GGCAACCTGA | CTGTTTGCGA | CTGCTGCGAA | TCGTTTCTTT | TAACAAAGCC | AGTATCATGC | 3060 |
| AAACACTTGA | TAAAATCACA | CAGCTGTCCT | GCATTGGCAG | TGGCTTCTTG | CCAAAGACCT | 3120 |
| GAGGGCTACT | GGTCCGACTG | TGGCACACAG | TCGGCCCACT | CTGATTATGC | AGATGAAGAA | 3180 |
| GATTCCTTTG | TCTCAGACAG | TTCTGACCAG | GTGCAGGCCT | GTGGACGAGC | CTGCTTCTAC | 3240 |
| CAGAGTAGAG | GATTCCCTTT | GGTGCGCTAT | GCTTACAATC | TACCAAGAGT | TAAAGACTGA | 3300 |
| ACTACTGTGT | GTGTAACCGT | TTCCCCCGTC | AACCAAAATC | AGTGTTTATA | GAGTGAACCC | 3360 |
| TATTCTCATC | TTTCATCTGG | GAAGCACTTC | TGTAATCACT | GCCTGGTGTC | ACTTAGAAGA | 3420 |
| AGGAGAGGTG | GCAGTTTATT | TCTCAAACCA | GTCATTTTCA | AAGAACAGGT | GCCTAAATTA | 3480 |
| TAAATTGGTG | AAAAATGCAA | TGTCCAAGCA | ATGTATGATC | TGTTTGAAAC | AAATATATGA | 3540 |
| CTTGAAAAGG | ATCTTAGGTG | TAGTAGAGCA | ATATAATGTT | AGTTTTTTCT | GATCCATAAG | 3600 |
| AAGCAAATTT | ATACCTATTT | GTGTATTAAG | CACAAGATAA | AGAACAGCTG | TTAATATTTT | 3660 |
| TTAAAAATCT | ATTTTAAAAT | GTGATTTTCT | ATAACTGAAG | AAAATATCTT | GCTAATTTTA | 3720 |
| CCTAATGTTT | CATCCTTAAT | CTCAGGACAA | CTTACTGCAG | GGCCAAAAAA | GGGACTGTCC | 3780 |
| CAGCTAGAAC | TGTGAGAGTA | TACATAGGCA | TTACTTTATT | ATGTTTTCAC | TTGCCATCCT | 3840 |
| TGACATAAGA | GAACTATAAA | TTTTGTTTAA | GCAATTTATA | AATCTAAAAC | CTGAAGATGT | 3900 |
| TTTTAAAACA | ATATTAACAG | CTGTTAGGTT | AAAAAAATAG | CTGGACATTT | GTTTTCAGTC | 3960 |
| ATTATACATT | GCTTTGGTCC | AATCAGTAAT | TTTTTCTTAA | GTGTTTTGTG | ATTACACTAC | 4020 |
| TAGAAAAAAA | GTAAAAGGCT | AATTGCTGTG | TGGGTTTAGT | CGATTTGGCT | AAACTACTAA | 4080 |
| CTAATGTGGG | GGTTTAATAG | TATCTGAGGG | ATTTGGTGGC | TTCATGTAAT | GTTCTCATTA | 4140 |
| ATGAATACTT | CCTAATATCG | TTGGCTCTAC | TAATATTTTC | CAATTTGCTG | GGATGTCACC | 4200 |
| TAGCAATAGC | TTGGATTATA | TAGAAAGTAA | ACTGTGGTCA | ATACTTGCAT | TTAATTAGAC | 4260 |
| GAAACGGGGA | GTAATTATGA | CACGAAGTAC | TTATGTTTAT | TTCTTAGTGA | GCTGGATTAT | 4320 |
| CTTGAACCTG | TGCTATTAAA | TGGAAATTTC | CATACATCTT | CCCCATACTA | TTTTTTATAA | 4380 |
| AAGAGCCTAT | TCAATAGCTC | AGAGGTTGAA | CTCTGGTTAA | ACAAGATAAT | ATGTTATTAA | 4440 |
| TAAAAATAGA | AGAAGAAAGA | ATAAAGCTTA | GTCCTGTGTC | TTTAAAAATT | AAAAATTTTA | 4500 |
| CTTGATTCCC | ATCTATGGGC | TTTAGACCTA | TTACTGGGTG | GAGTCTTAAA | GTTATAATTG | 4560 |
| TTCAATATGT | TTTTTGAACA | GTGTGCTAAA | TCAATAGCAA | ACCCACTGCC | ATATTAGTTA | 4620 |
| TTCTGAATAT | ACTAAAAAAA | TCCAGCTAGA | TTGCAGTTTA | ATAATTAAAC | TGTACATACT | 4680 |
| GTGCATATAA | TGAATTTTTA | TCTTATGTAA | ATTATTTTTA | GAACACAAGT | TGGGAAATGT | 4740 |
| GGCTTCTGTT | CATTTCGTTT | AATTAAAGCT | ACCTCCTAAA | CATAAGTGGC | TGCCAGTAGC | 4800 |
| AGACTGTTAA | ATTGTGGTTT | ATATACTTTT | TGCATTGTAA | ATAGTCTTTG | TTGTACATTG | 4860 |
| TCAGTGTAAT | AAAAACAGAA | TCTTTGTATA | TCAAAATCAT | GTAGTTTGTA | TAAAATGTGG | 4920 |
| GAAGGATTTA | TTTACAGTGT | GTTGTAATTT | TGTAAGGCCA | ACTATTTACA | AGTTTTAAAA | 4980 |
| ATTGCTATCA | TGTATATTTA | CACATCTGAT | AAATATTAAA | TCATAACTTG | GTAAGAAACT | 5040 |
| CCTAATTAAA | AGGTTTTTTC | CAAAATTCAG | GTTATTGAAA | ATTTTTCATT | TTATTCATTT | 5100 |
| AAAAACTAGA | ATAACAGATA | TATAAAAGTG | TTAATCTTTG | TGCTATATGG | TATGAAATAC | 5160 |
| AATATTGTAC | TCAGTGTTTT | GAATTATTAA | AGTTTCTAGA | AAGCAAAAAA | A | |
| Seq ID NO: 36 Protein sequence | | | | | | |
| Protein Accession #: NP_060960.1 | | | | | | |
| 1 | 11 | 21 | 31 | 41 | 51 | |
| \| | \| | \| | \| | \| | \| | |
| MPGPLGLLCG | LALGLLGSAG | PSGAAPPLCA | APCSCDGDRR | VDCSGKGLTA | VPEGLSAFTQ | 60 |
| ALDISMNNIT | QLPEDAFKNF | PFLEELQLAG | NDLSFIGPKA | LSGLKELKVL | TLQNNQLKTV | 120 |
| PSEAIRGLSA | LQSLRLDANH | ITSVPEDSFE | GLVQLRHLWL | DDNSLTEVPV | HPLSNLPTLQ | 180 |
| ALTLALNKIS | SIPDFAFTNL | SSLVVLHLHN | NKIRGLSQHC | FDGLDNLETL | DLSYNNLGEF | 240 |
| PQAIKARPSL | KELGPHSNSI | SVIPDGAFDG | NPLLRTIGLY | DNPLSFVGNS | ASHNLSDLHS | 300 |

TABLE 4-continued

| | | | | | | |
|---|---|---|---|---|---|---|
| LVIRGASMVQ | QFPNLTGTVH | LESLTLTGTK | ISSIPNNLCQ | EQKMLRTLDL | SYNNIRDLPS | 360 |
| FNGCHALEEI | SLQRNQIYQI | KEGTFQGLIS | LRILDLSRNL | IHEIHSRAFA | TLGPITNLDV | 420 |
| SFNELTSFPT | EGPNGLNQLK | LVGNFKLKEA | LAAKDFVNLR | SLSVPYAYQC | CAFWGCDSYA | 480 |
| NLNTEDNSLQ | DHSVAQEKGT | ADAANVTSTL | ENEEHSQIII | HCTPSTGAFK | PCEYLLGSWM | 540 |
| IRLTVWFIFL | VALFFNLLVI | LTTFASCTSL | PSSKLFIGLI | SVSNLFMGIY | TGILTFLDAV | 600 |
| SWGRFAEFGI | WWETGSGCKV | AGFLAVFSSE | SAIFLLMLAT | VERSLSAKDI | MKNGKSNHLK | 660 |
| QFRVAALSAF | LGATVAGCFP | LFHRGEYSAS | PLCLPFPTGE | TPSLGFTVTL | VLLNSLAFLL | 720 |
| MAVIYTKLYC | NLEKEDLSEN | SQSSMIKHVA | WLIFTNCIFF | CPVAFFSFAP | LITAISISPE | 780 |
| IMKSVTLIFF | PLPACLNPVL | YVFFNPKFKE | DWKLLDRRVT | KKSGSVSVSI | SSQGGCLEQD | 840 |
| FYYDCGMYSH | LQGNLTVCDC | CESFLLTKPV | SCKHLIKSHS | CPALAVASCQ | RPEGYWSDCG | 900 |
| TQSAHSDYAD | EEDSFVSDSS | DQVQACGRAC | FYQSRGFPLV | RYAYNLPRVK | D | |

Seq ID NO:37 DNA sequence
Nucleic Acid Accession #: AF144648.1
Coding sequence: 1..1884

| 1 | 11 | 21 | 31 | 41 | 51 | |
|---|---|---|---|---|---|---|
| \| | \| | \| | \| | \| | \| | |
| ATGCTGCGAG | CCGCAGTGAT | CCTGCTGCTC | ATCAGGACCT | GGCTCGCGGA | GGGCAACTAC | 60 |
| CCCAGTCCCA | TCCCGAAATT | CCACTTCGAG | TTCTCCTCTG | CTGTGCCCGA | AGTCGTCCTG | 120 |
| AACCTCTTCA | ACTGCAAAAA | TTGTGCAAAT | GAAGCTGTGG | TTCAAAAGAT | TTTGGACAGG | 180 |
| GTGCTGTCAA | GATACGATGT | CCGCCTGAGA | CCGAATTTTG | GAGGTGCCCC | TGTGCCTGTG | 240 |
| AGAATATCTA | TTTATGTCAC | GAGCATTGAA | CAGATCTCAG | AAATGAATAT | GGACTACACG | 300 |
| ATCACGATGT | TTTTTCATCA | GACTTGGAAA | GATTCACGCT | TAGCATACTA | TGAGACCACC | 360 |
| CTGAACTTGA | CCCTGGACTA | TCGGATGCAT | GAGAAGTTGT | GGGTCCCTGA | CTGCTACTTT | 420 |
| TTGAACAGCA | AGGATGCTTT | CGTGCATGAT | GTGACTGTGG | AGAATCGCGT | GTTTCAGCTT | 480 |
| CACCCAGATG | GAACGGTGCG | GTACGGCATC | CGACTCACCA | CTACAGCAGC | TTGTTCCCTG | 540 |
| GATCTGCATA | AATTCCCTAT | GGACAAGCAG | GCCTGCAACC | TGGTGGTAGA | GAGCTATGGT | 600 |
| TACACGGTTG | AAGACATCAT | ATTATTCTGG | GATGACAATG | GGAACGCCAT | CCACATGACT | 660 |
| GAGGAGCTGC | ATATCCCTCA | GTTCACTTTC | CTGGGAAGGA | CGATTACTAG | CAAGGAGGTG | 720 |
| TATTTCTACA | CAGGTTCCTA | CATACGCCTG | ATACTGAAGT | TCCAGGTTCA | GAGGGAAGTT | 780 |
| AACAGCTACC | TTGTGCAAGT | CTACTGGCCT | ACTGTCCTCA | CCACTATTAC | CTCTTGGATA | 840 |
| TCGTTTTGGA | TGAACTATGA | TTCCTCTGCA | GCCAGGGTGA | CAATTGGCTT | AACTTCAATG | 900 |
| CTCATCCTGA | CCACCATCGA | CTCACATCTG | CGGGATAAGC | TCCCCAACAT | TTCCTGTATC | 960 |
| AAGGCCATTG | ATATCTATAT | CCTCGTGTGC | TTGTTCTTTG | TGTTCCTGTC | CTTGCTGGAG | 1020 |
| TATGTCTACA | TCAACTATCT | TTTCTACAGT | CGAGGACCTC | GGCGCCAGCC | TAGGCGACAC | 1080 |
| AGGAGACCCC | GAAGAGTCAT | TGCCCGCTAC | CGCTACCAGC | AAGTGGTGGT | AGGAAACGTG | 1140 |
| CAGGATGGCC | TGATTAACGT | GGAAGACGGA | GTCAGCTCTC | TCCCCATCAC | CCCAGCGCAG | 1200 |
| GCCCCCCTGG | CAAGCCCGGA | AAGCCTCGGT | TCTTTGACGT | CCACCTCCGA | GCAGGCCCAG | 1260 |
| CTGGCCACCT | CGGAAAGCCT | CAGCCCACTC | ACTTCTCTCT | CAGGCCAGGC | CCCCCTGGCC | 1320 |
| ACTGGAGAAA | GCCTGAGCGA | TCTCCCCTCC | ACCTCAGAGC | AGGCCCGGCA | CAGCTATGGT | 1380 |
| GTTCGCTTTA | ATGGTTTCCA | GGCTGATGAC | AGTATTTTTC | CTACCGAAAT | CCGCAACCGT | 1440 |
| GTCGAAGCCC | ATGGCCATGG | TGTTACCCAT | GACCATGAAG | ATTCCAATGA | GAGCTTGAGC | 1500 |
| TCGGATGAGC | GCCATGGCCA | TGGCCCCAGT | GGGAAGCCCA | TGCTTCACCA | TGGCGAGAAG | 1560 |
| GGTGTGCAAG | AAGCAGGCTG | GGACCTTGAT | GACAACAATG | ACAAGAGCGA | CTGCCTTGCC | 1620 |
| ATTAAGGAGC | AATTCAAGTG | TGATACTAAC | AGTACCTGGG | GCCTTAATGA | TGATGAGCTC | 1680 |
| ATGGCCCATG | GCCAAGAGAA | GGACAGTAGC | TCAGAGTCTG | AGGATAGTTG | CCCCCCAAGC | 1740 |
| CCTGGGTGCT | CCTTCACTGA | AGGGTTCTCC | TTCGATCTCT | TTAATCCTGA | CTACGTCCCA | 1800 |
| AAGGTCGACA | AGTGGTCCCG | GTTCCTCTTC | CCTCTGGCCT | TTGGGTTGTT | CAACATTGTT | 1860 |
| TACTGGGTAT | ACCATATGTA | TTAG | | | | |

Seq ID NO: 38 Protein sequence
Protein Accession #: AAD51172.1

| 1 | 11 | 21 | 31 | 41 | 51 | |
|---|---|---|---|---|---|---|
| \| | \| | \| | \| | \| | \| | |
| MLRAAVILLL | IRTWLAEGNY | PSPIPKFHFE | FSSAVPEVVL | NLFNCKNCAN | EAVVQKILDR | 60 |
| VLSRYDVRLR | PNFGGAPVPV | RISIYVTSIE | QISEMNMDYT | ITMFFHQTWK | DSRLAYYETT | 120 |
| LNLTLDYRMN | EKLWVPDCYF | LNSKDAFVHD | VTVENRVFQL | HPDGTVRYGI | RLTTTAACSL | 180 |
| DLHKFPMDKQ | ACNLVVESYG | YTVEDIILFW | DDNGNAIHMT | EELHIPQFTF | LGRTITSKEV | 240 |
| YFYTGSYIRL | ILKFQVQREV | NSYLVQVYWP | TYLTTITSWI | SFWMNYDSSA | ARVTIGLTSM | 300 |
| LILTTIDSHL | RDKLPNISCI | KAIDIYILVC | LFFVFLSLLE | YVYINYLFYS | RGPRRQPRRH | 360 |
| RRPRRVIARY | RYQQVVVGNV | QDGLINVEDG | VSSLPITPAQ | APLASPESLG | SLTSTSEQAQ | 420 |
| LATSESLSPL | TSLSGQAPLA | TGESLSDLPS | TSEQARHSYG | VRFNGFQADD | SIFPTEIRNR | 480 |
| VEAHGHGVTH | DHEDSNESLS | SDERHGHGPS | GKPMLHHGEK | GVQEAGWDLD | DNNDKSDCLA | 540 |
| IKEQFKCDTN | STWGLNDDEL | MAHGQEKDSS | SESEDSCPPS | PGCSFTEGFS | FDLFNPDYVP | 600 |
| KVDKWSRFLF | PLAFGLFNIV | YWVYHMY | | | | |

Seq ID NO: 39 DNA sequence
Nucleic Acid Accession #: U47334.1
Coding sequence: 1..331

| 1 | 11 | 21 | 31 | 41 | 51 | |
|---|---|---|---|---|---|---|
| \| | \| | \| | \| | \| | \| | |
| CAAAAATTGT | GCAAATGAAG | CTGTGGTTCA | AAAGATTTTG | GACAGGGTGC | TGTCAAGATA | 60 |
| CGATGTCCGC | CTGAGACCGA | ATTTTGGANN | NATGCTTGCT | ACTAACAGTA | CCCGGGGCCT | 120 |
| TAATGAAGAT | GAGCTCATGG | CCCATGGCCA | AGAGAAGGAC | AGTAGCTCAG | AGTCTGAGGA | 180 |
| TAGTTGCCCC | CCAAGCCCTG | GGTGCTCCTT | CACTGAAGGG | TTCTCCTTCG | ATCTCCTTAA | 240 |
| TCCTGACTAC | GTCCCAAAGG | TCGACAAGTG | GTCCCGGTTC | CTCTTCCCTC | TGGCCTTTGG | 300 |
| GTTGTTCAAC | ATTGTAGCGG | CCGAACGATG | C | | | |

TABLE 4-continued

```
Seq ID NO: 40 Protein sequence
Protein Accession #: AAC50559.1
1          11         21         31         41         51
|          |          |          |          |          |
KNCANEAVVQ KILDRVLSRY DVRLRPNFGX MLATNSTRGL NEDELMAHGQ EKDSSSESED   60
SCPPSPGCSF TEGFSFDLLN PDYVPKVDKW SRFLFPLAFG LFNIVAAERC

Seq ID NO: 41 DNA sequence
Nucleic Acid Accession #: NM_020974
Coding sequence: 81..3080
1          11         21         31         41         51
|          |          |          |          |          |
GGCGTCCGCG CACACCTCCC CGCGCCGCCG CCGCCACCGC CCGCACTCCG CCGCCTCTGC   60
CCGCAACCGC TGAGCCATCC ATGGGGGTCG CGGGCCGCAA CCGTCCCGGG GCGGCCTGGG  120
CGGTGCTGCT GCTGCTGCTG CTGCTGCCGC CACTGCTGCT GCTGGCGGGG GCCGTCCCGC  180
CGGGTCGGGG CCGTGCCGCG GGGCCGCAGG AGGATGTAGA TGAGTGTGCC CAAGGGCTAG  240
ATGACTGCCA TGCCGACGCC CTGTGTCAGA ACACACCCAC CTCCTACAAG TGCTCCTGCA  300
AGCCTGGCTA CCAAGGGGAA GGCAGGCAGT GTGAGGACAT CGATGAATGT GGAAATGAGC  360
TCAATGGAGG CTGTGTCCAT GACTGTTTGA ATATTCCAGG CAATTATCGT TGCACTTGTT  420
TTGATGGCTT CATGTTGGCT CATGACGGTC ATAATTGTCT TGATGTGGAC GAGTGCCTGG  480
AGAACAATGG CGGCTGCCAG CATACCTGTG TCAACGTCAT GGGGAGCTAT GAGTGCTGCT  540
GCAAGGAGGG GTTTTTCCTG AGTGACAATC AGCACACCTG CATTCACCGC TCGGAAGAGG  600
GCCTGAGCTG CATGAATAAG GATCACGGCT GTAGTCACAT CTGCAAGGAG GCCCCAAGGG  660
GCAGCGTCGC CTGTGAGTGC AGGCCTGGTT TTGAGCTGGC CAAGAACCAG AGAGACTGCA  720
TCTTGACCTG TAACCATGGG AACGGTGGGT GCCAGCACTC CTGTGACGAT ACAGCCGATG  780
GCCCAGAGTG CAGCTGCCAT CCACAGTACA AGATGCACAC AGATGGGAGG AGCTGCCTTG  840
AGCGAGAGGA CACTGTCCTG GAGGTGACAG AGAGCAACAC CACATCAGTG GTGGATGGGG  900
ATAAACGGGT GAAACGGCGG CTGCTCATGG AAACGTGTGC TGTCAACAAT GGAGGCTGTG  960
ACCGCACCTG TAAGGATACT TCGACAGGTG TCCACTGCAG TTGTCCTGTT GGATTCACTC 1020
TCCAGTTGGA TGGGAAGACA TGTAAAGATA TTGATGAGTG CCAGACCCGC AATGGAGGTT 1080
GTGATCATTT CTGCAAAAAC ATCGTGGGCA GTTTTGACTG CGGCTGCAAG AAAGGATTTA 1140
AATTATTAAC AGATGAGAAG TCTTGCCAAG ATGTGGATGA GTGCTCTTTG GATAGGACCT 1200
GTGACCACAG CTGCATCAAC CACCCTGGCA CATTTGCTTG TGCTTGCAAC CGAGGGTACA 1260
CCCTGTATGG CTTCACCCAC TGTGGAGACA CCAATGAGTG CAGCATCAAC AACGGAGGCT 1320
GTCAGCAGGT CTGTGTGAAC ACAGTGGGCA GCTATGAATG CCAGTGCCAC CCTGGGTACA 1380
AGCTCCACTG GAATAAAAAA GACTGTGTGG AAGTGAAGGG GCTCCTGCCC ACAAGTGTGT 1440
CACCCCGTGT GTCCCTGCAC TGCGGTAAGA GTGGTGGAGG AGACGGGTGC TTCCTCAGAT 1500
GTCACTCTGG CATTCACCTC TCTTCAGATG TCACCACCAT CAGGACAAGT GTAACCTTTA 1560
AGCTAAATGA AGGCAAGTGT AGTTTGAAAA ATGCTGAGCT GTTTCCCGAG GGTCTGCGAC 1620
CAGCACTACC AGAGAAGCAC AGCTCAGTAA AAGAGAGCTT CCGCTACGTA AACCTTACAT 1680
GCAGCTCTGG CAAGCAAGTC CCAGGAGCCC CTGGCCGACC AAGCACCCCT AAGGAAATGT 1740
TTATCACTGT TGAGTTTGAG CTTGAAACTA ACCAAAAGGA GGTGACAGCT TCTTGTGACC 1800
TGAGCTGCAT CGTAAAGCGA ACCGAGAAGC GGCTCCGTAA AGCCATCCGC ACGCTCAGAA 1860
AGGCCGTCCA CAGGGAGCAG TTTCACCTCC AGCTGTCAGG CATGAACCTC GACGTGGCTA 1920
AAAAGCCTCC CAGAACATCT GAACGCCAGG CAGAGTCCTG TGGAGTGGGC CAGGGTCATG 1980
CAGAAAACCA ATGTGTCAGT TGCAGGGCTG GGACCTATTA TGATGGAGCA CGAGAACGCT 2040
GCATTTTATG TCCAAATGGA ACCTTCCAAA ATGAGGAAGG ACAAATGACT TGTGAACCAT 2100
GCCCAAGACC AGGAAATTCT GGGGCCCTGA AGACCCCAGA AGCTTGGAAT ATGTCTGAAT 2160
GTGGAGGTCT GTGTCAACCT GGTGAATATT CTGCAGATGG CTTTGCACCT TGCCAGCTCT 2220
GTGCCCTGGG CACGTTCCAG CCTGAAGCTG GTCGAACTTC CTGCTTCCCC TGTGGAGGAG 2280
GCCTTGCCAC CAAACATCAG GGAGCTACTT CCTTTCAGGA CTGTGAAACC AGAGTTCAAT 2340
GTTCACCTGG ACATTTCTAC AACACCACCA CTCACCGATG TATTCGTTGC CCAGTGGGAA 2400
CATACCAGCC TGAATTTGGA AAAAATAATT GTGTTTCTTG CCCAGGAAAT ACTACGACTG 2460
ACTTTGATGG CTCCACAAAC ATAACCCAGT GTAAAAACAG AAGATGTGGA GGGGAGCTGG 2520
GAGATTTCAC TGGGTACATT GAATCCCCAA ACTACCCAGG CAATTACCCA GCCAACACCG 2580
AGTGTACGTG GACCATCAAC CCACCCCCCA AGCGCCGCAT CCTGATCGTG GTCCCTGAGA 2640
TCTTCCTGCC CATAGAGGAC GACTGTGGGG ACTATCTGGT GATGCGGAAA ACCTCTTCAT 2700
CCAATTCTGT GACAACATAT GAAACCTGCC AGACCTACGA ACGCCCCATC GCCTTCACCT 2760
CCAGGTCAAA GAAGCTGTGG ATTCAGTTCA AGTCCAATGA AGGGAACAGC GCTAGAGGGT 2820
TCCAGGTCCC ATACGTGACA TATGATGAGG ACTACCAGGA ACTCATTGAA GACATAGTTC 2880
GAGATGGCAG GCTCTATGCA TCTGAGAACC ATCAGGAAAT ACTTAAGGAT AAGAAACTTA 2940
TCAAGGCTCT GTTTGATGTC CTGGCCCATC CCCAGAACTA TTTCAAGTAC ACAGCCCAGG 3000
AGTCCCGAGA GATGTTTCCA AGATCGTTCA TCCGATTGCT ACGTTCCAAA GTGTCCAGGT 3060
TTTTGAGACC TTACAAATGA CTCAGCCCAC GTGCCACTCA ATACAAATGT TCTGCTATAG 3120
GGTTGGTGGG ACAGAGCTGT CTTCCTTCTG CATGTCAGCA CAGTCGGGTA TTGCTGCCTC 3180
CCGTATCAGT GACTCATTAG AGTTCAATTT TTATAGATAA TACAGATATT TTGGTAAATT 3240
GAACTTGGTT TTTCTTTCCC AGCATCGTGG ATGTAGACTG AGAATGGCTT TGAGTGGCAT 3300
CAGCTTCTCA CTGCTGTGGG CGGATGTCTT GGATAGATCA CGGGCTGGCT GAGCTGGACT 3360
TTGGTCAGCC TAGGTGAGAC TCACCTGTCC TTCTGGGGTC TTACTCCTCC TCAAGGAGTC 3420
TGTAGTGGAA AGGAGGCCAC AGAATAAGCT GCTTATTCTG AAACTTCAGC TTCCTCTAGC 3480
CCGGCCCTCT CTAAGGGAGC CCTCTGCACT CGTGTGCAGG CTCTGACCAG GCAGAACAGG 3540
CAAGAGGGGA GGGAAGGAGA CCCCTGCAGG CTCCCTCCAC CCACCTTGAG ACCTGGGAGG 3600
ACTCAGTTTC TCCACAGCCT TCTCCAGCCT GTGTGATACA AGTTTGATCC CAGGAACTTG 3660
AGTTCTAAGC AGTGCTCGTG AAAAAAAAAA GCAGAAAGAA TTAGAAATAA ATAAAAACTA 3720
AGCACTTCTG GAGACAT
```

TABLE 4-continued

Seq ID NO: 42 Protein sequence
Protein Accession #: NP_066025

| 1 | 11 | 21 | 31 | 41 | 51 | |
|---|---|---|---|---|---|---|
| MGVAGRNRPG | AAWAVLLLLL | LLPPLLLLAG | AVPPGRGRAA | GPQEDVDECA | QGLDDCHADA | 60 |
| LCQNTPTSYK | CSCKPGYQGE | GRQCEDIDEC | GNELNGGCVH | DCLNIPGNYR | CTCFDGFMLA | 120 |
| HDGHNCLDVD | ECLENNGGCQ | HTCVNVMGSY | ECCCKEGFFL | SDNQHTCIHR | SEEGLSCMNK | 180 |
| DHGCSHICKE | APRGSVACEC | RPGFELAKNQ | RDCILTCNHG | NGGCQHSCDD | TADGPECSCH | 240 |
| PQYKMHTDGR | SCLEREDTVL | EVTESNTTSV | VDGDKRVKRR | LLMETCAVNN | GGCDRTCKDT | 300 |
| STGVHCSCPV | GRTLQLDGKT | CKDIDECQTR | NGGCDHFCKN | IVGSFDCGCK | KGFKLLTDEK | 360 |
| SCQDVDECSL | DRTCDHSCIN | HPGTFACACN | RGYTLYGFTH | CGDTNECSIN | NGGCQQVCVN | 420 |
| TVGSYECQCH | PGYKLHWNKK | DCVEVKGLLP | TSVSPRVSLH | CGKSGGGDGC | FLRCHSGIHL | 480 |
| SSDVTTIRTS | VTFKLNEGKC | SLKNAELFPE | GLRPALPEKH | SSVKESFRYV | NLTCSSGKQV | 540 |
| PGAPGRPSTP | KRMFITVEFE | LETNQKEVTA | SCDLSCIVKR | TEKRLRKAIR | TLRKAVHREQ | 600 |
| FHLQLSGMNL | DVAKKPPRTS | ERQAESCGVG | QGHAENQCVS | CRAGTYYDGA | RERCILCPNG | 660 |
| TFQNEEGQMT | CEPCPRPGNS | GALKTPEAWN | MSECGGLCQP | GEYSADGFAP | CQLCALGTFQ | 720 |
| PEAGRTSCFP | CGGGLATKHQ | GATSFQDCET | RVQCSPGHFY | NTTTHRCIRC | PVGTYQPEFG | 780 |
| KNNCVSCPGN | TTTDFDGSTN | ITQCKNRRCG | GELGDFTGYI | ESPNYPGNYP | ANTECTWTIN | 840 |
| PPPKRRILIV | VPEIFLPIED | DCGDYLVMRK | TSSSNSVTTY | ETCQTYERPI | AFTSRSKKLW | 900 |
| IQFKSNEGNS | ARGFQVPYVT | YDEDYQELIE | DIVRDGRLYA | SENHQEILKD | KKLIKALFDV | 960 |
| LAHPQNYFKY | TAQESREMFP | RSFIRLLRSK | VSERLRPYK | | | |

Seq ID NO: 43 DNA sequence
Nucleic Acid Accession #: CAT cluster

| 1 | 11 | 21 | 31 | 41 | 51 | |
|---|---|---|---|---|---|---|
| TTTCTTCATT | TTATGCTTTT | CTCCCCTTTA | TATATACTGG | GCGGTTTTTC | CTTGAGAAAT | 60 |
| TTTCCATCTC | ATTAATTCTC | CTGCAGCAAT | TCATAACTCT | TTGGGGGCAT | TCCTTTGTTT | 120 |
| TTTGATATGA | CTACTACCTG | ACTGTATATA | GTTTCCCTTT | TTTTTTTTTC | CTCCCAGATT | 180 |
| CTCTCCTTTC | TACTGGCATC | CTTTTCCATT | TTACTCAATT | TTCCTCAGTT | AGGTTGACTT | 240 |
| GCTTTTATAC | CTGTGTGATG | CTCCTTGCCA | GATATCTAGC | AAATGCCCCC | AGGATCCAAT | 300 |
| CATTTTTTTC | CTAAGAAAAC | TGAAAAGAAG | CATGGCAAAT | AACAGAGCTT | GGAAAATAGG | 360 |
| AAACTTTAAA | ATACAAAGCC | CAGTGAAATC | TACTTGGAAG | CCAATGCTTA | GAGGCAAGAG | 420 |
| ACAGTGATTC | AAATAGGTGT | TGANNNNNNN | NNNNNNNNNN | NATGATCAGC | ATAGCAAAGA | 480 |
| TCACTTTCCA | ACATTGGAAA | GTTATGCATA | TTCCAATTGA | GCTAGCCCTT | TTAAACAGCC | 540 |
| TTAAAATTGT | ATAAAAGAGA | AGAAATTTAA | GATATTGAAA | ACTGGTAGAT | AATAAAACCT | 600 |
| AAATAAAGCT | GGTTTTGGAA | GAGCAGTGGC | CACTGTGATT | GACAATGGGG | GCACTTACTG | 660 |
| TTAAGGGGAT | TTATAACAGA | AGTACTTGAG | CAGAATTGTG | AAGAGAATAG | AATTGTGCAT | 720 |
| TCTTTTATCT | GCCCAGAACC | ACAGCTCCCA | TGGGAAATAC | TCCACCTCAT | TCTACAACCT | 780 |
| TCTGGCTGCA | ACAAAAGCAG | TCAAATTAAA | ACATAACCCA | AAGGGGGTAC | CTAACCCAAC | 840 |
| TTGAGAAAAT | CATAGCATNC | TCCCTTTGGC | TATAACTNTT | TCCACATGAA | ATACATTCAA | 900 |
| ATGCCTT | | | | | | |

Seq ID NO: 44 DNA sequence
Nucleic Acid Accession #: CAT cluster

| 1 | 11 | 21 | 31 | 41 | 51 | |
|---|---|---|---|---|---|---|
| TTTTTTTTTT | TTTTTTTGGA | TTTTAGTATG | CCTTGCAATT | TTTTCCCTTT | ATTCTGATGC | 60 |
| ATGAAGTACC | CACTAAAAGT | GACTGCTGTT | AGTATAGCTT | CAGTAATGAG | GTGATGAGGT | 120 |
| GACAGGGCAG | GTGATGCTCT | CTTAGTCTCT | TTAGGCTACT | ATTACAAAAT | ACTTCAGACT | 180 |
| GAGTAATTCA | TAAACAACAG | AGATTATTGT | TCACAGATCT | GGAGGCTGGA | AAGTACAAGA | 240 |
| CTAAAGGGCC | AGAATATTTG | GTGTTTGGTG | AAGGTCAAAC | ATTCAGACAC | TCTCAACGAC | 300 |
| TATAGCGACA | GCAGCAGTCT | TCAGGAATCC | TATGTGAGGG | ACAAACACTC | AGAAGCCAGC | 360 |
| TGGAGTGTTC | TAGAATCCTA | TGTGAGGGAC | AAACATTCAG | ACCCCAGCAG | TAGTGTTGTG | 420 |
| GAATCCTATG | TGAGGGACAA | ACTTTCAAAC | CCTTGTAGCA | GTGTTCTGGA | ATCCTATGTG | 480 |
| AGGGACAAAA | ATTCAGAACC | TTGTAGCAGT | GTTCTGGAAT | CCTATGTGAG | GAACAATCA | |

Seq ID NO; 45 DNA sequence
Nucleic Acid Accession #: Eos sequence
Coding sequence: 31..1092

| 1 | 11 | 21 | 31 | 41 | 51 | |
|---|---|---|---|---|---|---|
| GCCAAGCACG | AAGGGTTCCG | CGCGCCTTCC | TCAGAGCCTG | CGCACCCTGT | TCGACATCCT | 60 |
| GACGACCGGC | GGCGCGGCTG | CGTGCACCTG | CGCACCTCCT | TCTTGAAGCG | CCGACGGCGG | 120 |
| GCCCCCCGGG | ACCCCACGCG | CGCCCCGGCC | CGGCCCGGGG | ATCAGCCGCC | GCCGCCGCCG | 180 |
| CAAGCGCCTT | GGTGTTCGCT | CCGGCCGACG | AGCCGCGGAC | GGTCCTGGAG | AGGAAGCCCC | 240 |
| TGCCCCTGGG | CGTGCGCGCC | CCTCTGGCCG | GTCCCAGCGC | CGCCGCCCGC | AGCCCGGAGC | 300 |
| AGCTGTGCGC | CCCGGCTGAG | GCGGCGCCCT | GCCCCGCGGA | GCCCGAGCGG | TCCCAGAGCG | 360 |
| CGGCGCTGGA | ACCGAGCTCC | AGCGCGGACG | CAGGGACGGG | ACCGGGGAGC | GGCTCTTCGT | 420 |
| GGACTCCGGA | TCCTGGAGGG | CGCCTCGGCG | GGTCTGGAGG | GAAAGGGCTT | CATGCTTGTC | 480 |
| GCGGTGCAGT | GGCGTGCAGG | GCCCTGGAGC | GGACTCAGGG | GATGCCCGGC | GGGCTCCCCG | 540 |
| TGCCCGAGGG | GAACGTCGGA | GGCACACCAT | CGCCAGCGGC | GTGGACTGCG | GCCTGCTGAA | 600 |
| GCAGATGAAG | GAGCTGGAGC | AGGAGAAGGA | GGTGCTGCTG | CAGGGTTTGG | AGATGATGGC | 660 |
| GCGGGGCCGC | GACTGGTACC | AGCAGCAGCT | GCAACGAGTG | CAGGAGCGCC | AGCGCCGCCT | 720 |
| GGGCCAGAGC | AGAGCCAGCG | CCGACTTTGG | GGCTGCAGGG | AGCCCCCGCC | CACTGGGGCG | 780 |
| GCTACTGCCC | AAGGTACAAG | AGGTGGCCCG | GTGCCTGGGG | GAGCTGCTGG | CTGCAGCCTG | 840 |
| TGCCAGCCGG | GCCCTGCCCC | CGTCCTCCTC | CGGGCCCCCC | TGCCCTGCCC | TGACGTCCAC | 900 |
| CTCACCCCCG | GTCTGGCAGC | AGCAGACCAT | CCTCATGCTG | AAGGAGCAGA | ACCGACTCCT | 960 |
| CACCCAGGAG | GTGACCGAGA | AGAGTGAGCG | CATCACGCAG | CTGGAGCAGG | AGAAGTCGGC | 1020 |

TABLE 4-continued

| | | | | | | |
|---|---|---|---|---|---|---|
| GCTCATTAAG | CAGCTGTTTG | AGGCCCGCGC | CCTGAGCCAG | CAGGACGGGG | GACCTCTGGA | 1080 |
| TTCCACCTTC | ATCTAGTCCT | TGTGGGCCGC | GTGGGCCCCC | AGGGCCAGCC | TGGCACTCAG | 1140 |
| CCCTTCGAGG | GTGGGCGCCC | CATCGCACCC | ACCCTCTCTG | GCTGGAGACC | CCCGGCAGGC | 1200 |
| CCAGGCACAG | TCCCGGAGTG | GGCGCCTTCC | TGCCGCCCTT | GCCAGATGGG | CTCCCCAGGC | 1260 |
| CTGCCCCCGG | CTGGTCCCCG | CACCGAGCGC | TTGACTCCGT | TTTGGCTCCT | GGTTGYTGAC | 1320 |
| ATGGGCTGGG | GGCTCTCTTG | AGTCCGCATC | GTCCGCAGCT | ACTACTGGCC | GCTGTCAGTG | 1380 |
| GACAGTGGGG | TACCCCTCCA | TGAGTTAGCG | TCCCCCCGTT | TCCAGCGGTG | CCGCCCTGGG | 1440 |
| TCCCATCTTC | AGGGAAAGGC | ACTGCCCACG | CCAGGCTGCA | CTTCCAACAA | CGGGCAGCAG | 1500 |
| AGGGCGCGGG | GCGGCTCCGA | CGCGGGTCCA | AGGGCAGCTT | CCCGCTCAAC | CAGGGCACCA | 1560 |
| GGACGAGGTG | GCTGTAGCTC | GGACGGACGG | AAGTAGATGG | AGGGGGTGGG | GACGGCCTGT | 1620 |
| AAGCGGGGGG | TGCCTGCCTG | GCTGGGGAGC | CCCAGGGATA | GCGGTCGGAC | TTCAGGTTCT | 1680 |
| GGCCAAGGCT | GAGGGACCCT | GGCTGCAGCG | GATCGGCACG | CCGGGTGGGC | GAGAGCTTGG | 1740 |
| CCTGCATGTG | CCTCCCACAG | ACCCTGGGGT | GATGGCCTTC | CCCCTCTTGG | CCGGGACGTT | 1800 |
| GCCCCACGTT | GAGTCCCACA | CAACATCCTG | TGAGCCTGGC | TCCCCAGGAG | GGCCCCCAGA | 1860 |
| CAGCTCCCAG | GCACGTCATA | GGCAAAGCCT | GTTTCCCCCG | ACTCAGGATT | TCCAAGGCCT | 1920 |
| GGGGTCCTGC | TCACCCCCCT | TTGCTCTCAC | GCCCAGCCTG | TCCCCAGGTT | TCAGCTGGGA | 1980 |
| GAGGCCACCT | CCCTCAGCCA | AGGAAAACGA | GAACCCCCAG | GGTACAGGAG | GAGGCTGGGG | 2040 |
| CAGGTCCCCT | TGGGTGTCAC | TCCCTCAGCC | CCTGCCCAGG | CCCACTCCCG | CTGGTGCTGG | 2100 |
| AGTACGCACT | GGTGGGGGGG | CCCTGCTCAG | CCCAACCTGG | AGGGTCCCAG | TGTCACCAGA | 2160 |
| ACCAGGGGCA | CGGCAACAGC | ATCGATGGGT | TCTGCAGCCC | AGGGCCCCCG | ATGCGGGGTC | 2220 |
| AGTGTGTGTG | GGGCGCAGGG | CCTCCGATGC | GGGGTCAGTG | CGTGGGGGGC | GCAGGGCCCC | 2280 |
| CGATGCGGGG | TCAGTGCGTG | GGGGGCGCAG | GGCCCCCTCG | TGTCCAGGGC | ACTTTGGTAC | 2340 |
| ACTGTCCCAC | AAGGCACCTG | TCTCAGAGGA | GGGGCCCTGG | CAGGCAGCGT | GGCAACTCCT | 2400 |
| TCCGGAGCCC | AGCTCCATGC | TAACCTGCCC | ACAGCAACCC | CACAGAGCCA | CATTCCCTGC | 2460 |
| TGCACCTGGT | CTGCAGGGTG | TCCCAGGACA | GGCCCAAGTC | AGCCCAGCAT | GCAGCTGCCC | 2520 |
| TCCTACCCTG | AAGATGGGAG | TGGGCTTTCC | AGGGGACATA | AGGATGTCAG | GCCTGGACCT | 2580 |
| CCTGGGCAGG | AAAGGGTGCA | GGTCCTGAGG | GCCTGTGCCC | CACAGCCCCA | GCACCCAGGT | 2640 |
| GGACTGCAGC | GCAGTGGGTG | GGCCAGTGGC | AGCCAGGGAG | AAGCCCCCCG | TCAGCAGGCT | 2700 |
| GGGGTCTGCC | CACCAGGGCC | TCCCCACGTC | TGCCTTTGAG | GGTGCCTGCC | ATGCCCTGGG | 2760 |
| GGATCCTGGC | ATCTTTACTG | GACTGGAAGC | AGGAGACAGA | ACAGTGTCTG | TCCCGGGGTG | 2820 |
| ACTTCATCAG | GAGACCGCCC | ACATAGAGCT | GGACCCCGCA | GCTGAAGCGG | AAATGTGAGA | 2880 |
| CAGGCTGGCA | CCTCCGGAAA | AACTGCCTTT | CAGCCTTGGT | GTTCCGTGCA | AGGTGAAAAG | 2940 |
| AAATAGGTCC | TCCCAGTTTA | CAGCTTGAAA | TCAGGCTAGT | GAGTGGCCCT | GGAGACCACG | 3000 |
| AGGGGAGAAT | TTAAAGGCCC | CGGCTGGCAG | GGTCTAGGTG | GCTGGCAGAG | GCACATGCAG | 3060 |
| ACCCTGCCTG | GAGCCTGCCC | TAGGACGCTG | GGCGGGTCAG | TCTCCGTGCA | GGATGTGAGC | 3120 |
| AGCGTCCCTG | GGCTCTATCC | GCGAGGTGCC | AGTAGCGTGT | GCAGGTACAT | ACACGTGCGT | 3180 |
| GCACACTGTG | ATGACACCCG | GAAATGTCTC | AGGATGTTGA | AATGTGTCCT | TGGGGGCAGA | 3240 |
| AGTGTCCCCA | GTTGAGAATC | TGCCCCAGAG | GAACACACCC | ACACCAGGCC | TCAGGATTTT | 3300 |
| GTGTTGATCA | AGTTCCAAGG | AAAAGGAACA | TCTCAGCCGG | GCGTGGTGGT | TCACGCCTGG | 3360 |
| AATCCCAGCA | CTTGAGGCCA | GGAGTTCCAG | AGCAGCCTGG | GCAACGCAGT | GAGAGACCCC | 3420 |
| ATCTCTACAA | AAAAAAAAAA | AGAAAGAAAG | AAAATGAGAG | ATCCAGGTTT | AAAAATTCAT | 3480 |
| AAACACCACA | AGGAAACAAT | ACACTATGAG | ACCCAGCAGA | AGCAACAGAT | TGACTCTAGA | 3540 |
| CCCAGATACT | AGAATTATCA | GAGAGAATAT | AAAGTAACAG | TGTTTTATAT | ATCTAAAGAA | 3600 |
| ATAAAAGAGA | TTTCTGGAAA | CATGAAAAAA | AA | | | |

Seq ID NO: 46 Protein sequence
Protein Accession #: Eso sequence

| | | | | | | |
|---|---|---|---|---|---|---|
| 1 | 11 | 21 | 31 | 41 | 51 | |
| \| | \| | \| | \| | \| | \| | |
| MKVESRGPPS | CWLRARASNS | CLMSADFSCS | SCVMRSLFSV | TSWVRSRFCS | FSMRMVCCCQ | 60 |
| TGGEVDVRAG | QGGPEEDGGR | ARLAQAAASS | SPRHRATSCT | LGSSRPSGRG | LPAAPKSALA | 120 |
| LLWPRRRWRS | CTRCSCCWYQ | SRPRAIISKP | CSSTSFSCSS | SFICFSRPQS | TPLAMVCLRR | 180 |
| SPRARGARRA | SPESAPGPCT | PLHRDKHEAL | SLQTRRGALQ | DPESTKSRSP | VPSLRPRWSS | 240 |
| VPAPRSGTAR | APRGRAPPQP | GRTAAPGCGR | RRWDRPEGRA | RPGAGASSPG | PSAARRPERT | 300 |
| PRRLRRRRRL | IPGPGRGARG | VPGGPPSALQ | EGGAQVHAAA | PPVVRMSNRV | RRL | |

Seq ID NO: 47 DNA sequence
Nucleic Acid Accession #: NM_020957.1
Coding sequence: 1156..3486

| | | | | | | |
|---|---|---|---|---|---|---|
| 1 | 11 | 21 | 31 | 41 | 51 | |
| \| | \| | \| | \| | \| | \| | |
| CAAAGCTCTA | AGTATGCTGG | GACAGATACT | ACAAATGAAC | TTTATGATGA | GCGAATTAAC | 60 |
| CTGATTTATA | GTCCTGTACT | TTCTCTACGT | GCGATATCCA | TTATTAAAGA | AATGAGTCTA | 120 |
| AGTAGGAAGT | AGAGTTAACC | TATAGTTTCA | TTTCTTGAAT | TTCTTATTCT | CTTTCTTCAG | 180 |
| TCTTTTTCAG | TTAACCTACA | CACACACACA | CACACACACA | CACACACACA | CACATATGTT | 240 |
| TATAAGTGGG | ATGGGAGAAC | GGGTACGGTG | ATAATTAAAA | TGAATATATT | AAAAGCCATT | 360 |
| GAAATGAAAA | AAGGGTGGGG | GGAATCCAAA | AGTGTAGCAG | ACCCAACCTT | GAGATTTGCT | 420 |
| TGTTTGGGAA | TGAATTTTCC | AATAACTTGA | AAGTTGTAAA | AACTCACACT | TCTCAGGGTT | 480 |
| AGGTGTCAGA | AAGAAAAGGA | AGTAATTTAT | TCTTTAATAA | AGCAATTGTT | AAATACTCTT | 540 |
| TAGAACTACC | ACTGATTGCA | ATTTTGCAGT | GTCTACTCAT | AGTGTCTATA | TAGGTACCAT | 600 |
| GAAAAAGATG | TACTTGTGAA | ACTGTTCTCA | TGTTACTTCA | GAAAAATTTT | GCTTCTAAGT | 660 |
| GTGTATTCTA | TGTCTGGTTA | AATGTTCATT | GAATTTTATT | TAATCATTAA | TCTCAACAGC | 720 |
| ATTAAACAGT | CAATAACATA | AATGACAGTC | TTCTCTTTGT | ACTCCTCCCT | GTACAACATC | 780 |
| ACAGAGCTCC | ATCTGTATAC | ACGAAAGTCA | CATGAAAATA | GAACTCAGTG | TTTTGTATTA | 840 |
| CATAGTCTAT | TCAGTACATT | TAGAAGTATT | TTGCCTCCAA | TATTCAACCA | CAGTAAAAGA | 900 |
| CTCAGTGAGA | ACGCGTGGTG | GCGCTGCAGG | TTAAGATGAC | GGAAAATACA | ACTGCCTACG | 960 |
| CAGCTCCAGG | ATCCAGCAAA | CCGTTTCCCA | AAGCCTGGAA | GCAAAAGAAT | AGCTGAGCCA | 1020 |
| GAGCGAACGT | GAGTGTGAAA | CCTCTTTAAG | ACACCGTTGG | GCTGCTTGGT | TCTGACATTC | 1080 |
| TGGACTGCAA | AACAGTTCTA | CTAGGATCCT | GGGGATACAT | GAAGCTTCTG | TGAACCAACT | 1140 |

TABLE 4-continued

| | | | | | | |
|---|---|---|---|---|---|---|
| TTTCAAGAAA | AAGCAATGGA | GATTGGATGG | ATGCACAATC | GGAGACAAAG | GCAAGTCCTT | 1200 |
| GTTTTCTTTG | TTTTGCTGAG | CTTGTCTGGG | GCGGGCGCCG | AGTTGGGGTC | CTATTCCGTA | 1260 |
| GTGGAAGAAA | CGGAGAGAGG | CTCTTTTGTG | GCAAATCTAG | GAAAAGACCT | GGGGTTGGGG | 1320 |
| TTGACAGAGA | TGTCCACCCG | CAAGGCCAGG | ATCATTTCCC | AGGGGAACAA | ACAGCATTTG | 1380 |
| CAGCTCAAGG | CTCAAACTGG | GGATTTGCTC | ATAAATGAGA | AGCTAGATCG | AGAGGAGCTA | 1440 |
| TGCGGTCCCA | CTGAGCCTTG | CATACTACAT | TTCCAAGTGT | TAATGGAAAA | CCCTTTAGAA | 1500 |
| ATATTTCAGG | CTGAACTGAG | GGTGATAGAT | ATAAATGACC | ATTCTCCCAT | GTTCACTGAA | 1560 |
| AAGGAAATGA | TTCTAAAAAT | ACCGGAAAAC | AGTCCTCTAG | GAACTGAGTT | CCCTCTGAAT | 1620 |
| CATGCTTTGG | ACTTGGACGT | AGGAAGCAAT | AATGTTCAAA | ACTATAAAAT | CAGCCCAAGC | 1680 |
| TCTCATTTCC | GGGTTCTAAT | CCATGAATTC | AGAGATGGCA | GGAAATACCC | TGAGCTAGTG | 1740 |
| TTGGATAAAG | AGCTGGATCG | GGAGGAGGAG | CCTCAACTAA | GATTAACCCT | GACAGCGCTG | 1800 |
| GATGGTGGCT | CTCCACCGCG | ATCTGGAACT | GCTCAGGTCC | GTATTGAAGT | GGTGGACATC | 1860 |
| AATGATAACG | CTCCTGAGTT | TGAGCAGCCC | ATCTACAAAG | TGCAGATTCC | AGAGAACAGT | 1920 |
| CCTCTTGGCT | CCCTGGTTGC | CACCGTCTCC | GCCAGGGATT | TAGACGGCGG | AGCCAATGGA | 1980 |
| AAAATATCAT | ACACACTCTT | TCAGCCTTCG | GAGGATATTA | GTAAAACTTT | GGAGGTAAAT | 2040 |
| CCTATGACAG | GGGAAGTTCG | ACTGAGAAAG | CAAGTAGATT | TCGAAATGGT | TACGTCTTAT | 2100 |
| GAAGTGCGCA | TCAAAGCCAC | AGATGGGGGA | GGTCTTTCAG | GAAAGTGCAC | TCTTCTCCTG | 2160 |
| CAGGTGGTGG | ACGTGAATGA | CAATCCCCCA | CAGGTGACCA | TGTCTGCACT | CACCAGCCCC | 2220 |
| ATCCCAGAGA | ACTCGCCTGA | GATAGTAGTT | GCTGTTTTCA | GCGTTTCAGA | TCCTGACTCC | 2280 |
| GGAAACAATG | GGAAGACGAT | TTCCTCCATC | CAGGAAGACC | TTCCCTTTCT | TCTAAAACCT | 2340 |
| TCAGTCAAGA | ACTTTTACAC | CTTGGTAACG | GAGAGAGCAC | TCGACAGAGA | AGCAAGAGCT | 2400 |
| GAATATAATA | TCACCCTCAC | CGTCACAGAT | ATGGGGACTC | CAAGGCTGAA | AACGGAGCAC | 2460 |
| AACATAACAG | TGCAGATATC | AGATGTCAAT | GATAACGCCC | CCACTTTCAC | CCAAACCTCC | 2520 |
| TACACCCTGT | TCGTCCGCGA | GAACAACAGC | CCCGCCCTGC | ACATCGGCAG | CGTCAGCGCC | 2580 |
| ACAGACAGAG | ACTCAGGCAC | CAACGCCCAG | GTCACCTACT | CGCTGCTGCC | GCCCCAGGAC | 2640 |
| CCGCACCTGC | CCCTCGCCTC | CCTGGTCTCC | ATCAACGCAG | ACAACGGCCA | CCTGTTCGCC | 2700 |
| CTCAGGTCGC | TGGACTACGA | GGCCCTGCGG | GAGTTCGAGT | TCCGCGTGAG | CGCCACAGAC | 2760 |
| CGCGGCTCCC | CGGCTTTGAG | CAGCGAGGCG | CTGGTGCGCG | TGCTGGTGCT | GGACGCCAAC | 2820 |
| GACAACTCGC | CCTTCGTGCT | GTACCCGCTG | CAGAACGGCT | CCGCGCCCTG | CACTGAGCTG | 2880 |
| GTGCCCCGGG | CGGCCGAGCC | GGGCTACCTG | GTGACCAAGG | TGGTGGCGGT | GGACGGCGAC | 2940 |
| TCGGGCCAGA | ATGCCTGGCT | GTCGTACCAG | CTGCTCAAGG | CCAGGGAGCC | CGGGCTGTTC | 3000 |
| GGTGTGTGGG | CGCACAATGG | CGAGGTGCGC | ACCGCCAGGC | TGCTGAGCGA | GCGCGACGCA | 3060 |
| GCCAAGCAGA | GGCTGGTGGT | GCTGGTCAAG | GACAATGGCG | AGCCTCCGCG | CTCGGCCACC | 3120 |
| GCCACGCTGC | ACGTGCTCCT | GGTGGACGGC | TTCTCCCAGC | CCTTCCTGCC | GCTCCCAGAG | 3180 |
| GCGGCCCCCG | GCCAGACCCA | GGCCAACTCG | CTCACTGTCT | ACCTGGTGGT | GGCGTTGGCC | 3240 |
| TCGGTGTCGT | CGCTCTTCCT | CTTTTCGGTG | CTCCTGTTCG | TGGCGGTGCG | GCTGTGCAGG | 3300 |
| AGGAGCAGGG | CGGCCTCGGT | GGGCCGCTGC | TCGATGCCTG | AGGGCCCCTT | TCCAGGGCGT | 3360 |
| CTGGTGGACG | TAAGCGGCAC | CGGGACCCTG | TCCCAGAGCT | ACCAATACGA | GGTGTGTCTG | 3420 |
| ACAGGAGGCT | CAGAAACAAG | TGAGTTCAAG | TTCCTGAAGC | CGATTATCCC | CAACTTCTCT | 3480 |
| CCTTAGGGCA | CTAGGAAAGA | AATAGATTAA | AATTCCACCC | TTCACAATAG | CTTTGGATTT | 3540 |
| AATTATTGAT | AGGAACCCAT | TTGATAAATT | CCTTAACTTC | TTATGATTGT | CTTGTTGATT | 3600 |
| AAATTGTTCA | TGCTCACCAC | CACCAATAAG | GTATTTTTCT | CTGATTGTTA | GTTCAAATTA | 3660 |
| TATTGTTAAT | TCCAGTTTCC | CTTTTCCTCA | TATTTACCCC | GAAGAGGTGT | TGCATATAGA | 3720 |
| ATCCCAATTA | ACAAAATATA | CTTTATCTTC | AAAGTTGATG | TCATTTAAAA | TTTTTCCGTC | 3780 |
| TTTATATTTT | ATTTACTTCC | TATTCATTTT | TTGCTCCATT | TTTCATGTTA | CTTCTCAGTT | 3840 |
| TCCTAGAACT | TCAAGTATTA | AAATAACCTG | TTGCATGTAT | TAGGCATATT | TCCTATGTTA | 3900 |
| CATTTCTTTT | GTCTATTTTC | CTTTCAAAAT | TGGTATTTTT | GTTGGGCTCA | ATTTTCATTA | 3960 |
| TAATACTTTT | CTTAAAGTTT | CTTTCTTTCT | TTTCTTTTCT | TTCTTTTTTT | TTTTTTCCTT | 4020 |
| TTTGAGACAG | GGTCTTACTC | TTGTCACCCA | GGCTGGAGTG | CAGTGGCACA | ATCTTGGCTC | 4080 |
| ACTGCAACCT | CTGCCTCCTG | GGCTCAACGG | ATCCTTCCAC | CTGAGCCTCC | CAAGTAGCTT | 4140 |
| GGACTATAGG | TGCATGCCAC | CATGCCTGGC | TAATCTTTTG | CAGCGATGAG | ATTTTGCCAA | 4200 |
| GTTGCCCAGG | CTGATCTTGA | ACTCCTGGGC | TCAAGCCATC | CTCCCTCCTC | AGCCTCCCAA | 4260 |
| AATTCTGGGA | TTACAGGCAT | AAGCCAATGT | GCCCATCCAA | AGTTTTATTT | ATTTATTTTT | 4320 |
| TTGAGATGGA | GTCTCGTAAA | GTTACCTTTA | AAAAAAAAGT | TCTATTTTCC | CTGTATTGGT | 4380 |
| ATCTCCTTAA | ATAAAATAAA | ATATTCCTAT | TGTAAGTGAT | ATGAGAAATC | TTTAACCAGC | 4440 |
| CTTATCTAAA | AATAAAAAGA | GAAGCCATTG | TAAGACATTC | AGTATGTGTA | AATGTGTTTG | 4500 |
| TGTTTGTAGA | CAAAAGGCAA | AGGTATTATG | TAAAAATATT | TAATAATTTA | TTCTTTCTAT | 4560 |
| TACTGAATTA | AAAAATCAGA | GGTCCCTGTT | ATATTTTTAA | TGGCTAACAA | CTCAATCTCA | 4620 |
| TTAAGTTGGA | AAAAAAACTT | ATCAAAGAGA | CATTTACATG | GTTTGGCTTT | TATATTCATC | 4680 |
| ATAGTATACA | TTGGCGGTAT | CTAGCCCTTT | CTCTGTAAAA | TATCCCTATG | TTTAATCTGT | 4740 |
| ATTTCTTGCT | TATTATATGT | AAAGTTGAGC | TTCTTTCTAG | ATATTAGGCC | TTTGAATAAA | 4800 |
| ATTCTATGTG | AGTCAGAAAA | AAAAAAA | | | | |

Seq ID NO: 48 Protein sequence
Protein Accession #: NP_066008.1

| 1 | 11 | 21 | 31 | 41 | 51 | |
|---|---|---|---|---|---|---|
| \| | \| | \| | \| | \| | \| | |
| MEIGWMHNRR | QRQVLVFFVL | LSLSGAGAEL | FSYSVVETTE | RGSFVANLGK | DLGLGLTEMS | 60 |
| TRKARIISQG | NKQHLQLKAQ | TGDLLINEKL | DREELCGPTE | PCILHFQVLM | ENPLEIFQAE | 120 |
| LRVIDINDHS | PMFTEKEMIL | KIPENSPLGT | EFFLNHALDL | DVGSNNVQNY | KISPSSHFRV | 180 |
| LIHEFRDGRK | YPELVLDKEL | DREEEPQLRL | TLTALDGGSP | PRSGTAQVRI | EVVDINDNAP | 240 |
| EFEQPIYKVQ | IPENSPLGSL | VATVSARDLD | GGANGKISYT | LFQPSEDISK | TLEVNPMTGE | 300 |
| VRLEKQVDFE | MVTSYEVRIK | ATDGGGLSGK | CTLLLQVVDV | NDNPPQVTMS | ALTSIPIENS | 360 |
| PEIVVAVFSV | SDPDSGNNGK | TISSIQEDLP | FLLKPSVKNF | YTLVTERALD | REARAEYNIT | 420 |
| LTVTDMGTPR | LKTEHNITVQ | ISDVNDNAPT | FTQTSYTLFV | RENNSPALHI | GSVSATDRDS | 480 |
| GTNAQVTYSL | LPPQDPHLPL | ASLVSINADN | GHLFALRSLD | YEALREFEFR | VSATDRGSPA | 540 |

TABLE 4-continued

| | | | | | | |
|---|---|---|---|---|---|---|
| LSSEALVRVL | VLDANDNSPF | VLYPLQNGSA | PCTELVPRAA | EPGYLVTKVV | AVDGDSGQNA | 600 |
| WLSYQLLKAT | EPGLFGVWAH | NGEVRTARLL | SERKAAKQRL | VVLVKDNGEP | PRSATATLHV | 660 |
| LLVDGFSQPF | LPLPEAAPGQ | TQANSLTVYL | VVALASVSSL | FLFSVLLFVA | VRLCRRSRAA | 720 |
| SVGRCSMPEG | PRPGRLVDVS | GTGTLSQSYQ | YEVCLTGGSE | TSEFKFLKPI | IPNFSP | |

Seq ID NO: 49 DNA sequence
Nucliec Acid Accession #: CAT cluster

| 1 | 11 | 21 | 31 | 41 | 51 | |
|---|---|---|---|---|---|---|
| \| | \| | \| | \| | \| | \| | |
| TTTTTTTTTG | ATAATACACA | GACTTTAATT | AAAATTGTAC | TAAAATTAAA | TGTCTAAATA | 60 |
| AATTAGAATG | GTACATGGTA | CATCTAAATG | TATGTTTATA | TATTTTATTT | GTGCATTTTA | 120 |
| TTCCTAGGGT | TGCTTTTGCT | TTAGTTTGTA | AAACGTTCTT | ATTTTTATGA | TAATGTAGTA | 180 |
| TATACTAAAT | AAAGAAAAAT | CAGGAAATAG | AAAATGAAGA | AGAAAACATT | AGCTATTGTC | 240 |
| AACCAAATAA | AAATTGTGCA | ATCTCTAAGC | ACATGAACTA | TGTATTATTT | GTACAGCATG | 300 |
| TACAATGTTT | ATGCTTCACA | GGGTGAGGTA | GAGACTGCAA | AACATTGAAC | CTGGGACAAA | 360 |
| TAAGAAAGTA | AGGAAATTTT | CACAACATAT | TAATATTATA | GAAAATGTTG | AACTTAACAG | 420 |
| TTAAGATACA | AGTAGTGAAA | AATGATAGTA | TTTAAGGAGA | TCTAGAAAAT | TTA | |

Seq ID NO: 50 DNA sequence
Nucleic Acid Accession #: AF034799.1
Coding sequence: 170..3943

| 1 | 11 | 21 | 31 | 41 | 51 | |
|---|---|---|---|---|---|---|
| \| | \| | \| | \| | \| | \| | |
| GATTCCGGGA | GGCAAGTGAG | GAGAGAAGAT | GCTGTAGCGT | CCTCACCGGC | TGCCAGCAGG | 60 |
| GAAATGGTCC | AGGAGTGCTG | GGTGTGAGCC | TCCCTTCTCC | TCAAGCCGGA | GACTGCGGTT | 120 |
| GTCATTGATC | AATTGAAGAA | GCAAGGACCC | GAAATCACAG | ACATTAGCAA | TGATGTGTGA | 180 |
| AGTGATGCCC | ACGATTAATG | AGGACACCCC | AATGAGCCAA | AGGGGGTCCC | AAAGCAGTGG | 240 |
| CTCGGACTCA | GACTCCCATT | TTGAGCAGCT | GATGGTGAAT | ATGCTAGATG | AAAGGGATCG | 300 |
| TCTTCTAGAC | ACCCTTCGGG | AGACCCAGGA | AAGCCTCTCA | CTTGCCCAGC | AAAGACTTCA | 360 |
| GGATGTCATC | TATGACCGAG | ACTCACTCCA | GAGACAGCTC | AATTCAGCCC | TGCCACAGGA | 420 |
| TATCGAATCC | CTAACAGGAG | GGCTGGCTGG | TTCTAAGGGG | GCTGATCCAC | CGGAATTTGC | 480 |
| TGCACTGACA | AAAGAATTAA | ATGCCTGCAG | GGAACAACTT | CTAGAAAAGG | AAGAAGAAAT | 540 |
| CTCTGAACTT | AAAGCTGAAA | GAAACAACAC | AAGACTATTA | CTGGAGCATT | TGGAGTGCCT | 600 |
| TGTGTCACGA | CATGAAAGAT | CACTAAGAAT | GACGGTGGTA | AAACGGCAAG | CCCAGTCTCC | 660 |
| CTCAGGAGTA | TCCAGTGAAG | TTGAAGTTCT | CAAGGCACTG | AAATCTTTGT | TTGAGCACCA | 720 |
| CAAGGCCTTG | GATGAAAAGG | TAAGGGAGCG | ACTGAGGGTT | TCTTTAGAAA | GAGTCTCTGC | 780 |
| ACTGGAAGAA | GAACTAGCTG | CTGCTAATCA | GGAGATTGTT | GCCTTGCGTG | AACAAAATGT | 840 |
| TCATATACAA | AGAAAAATGG | CATCAAGCGA | GGGATCCACA | GAGTCAGAAC | ATCTTGAAGG | 900 |
| GATGGAACCT | GGACAGAAAG | TCCATGAGAA | GCGTTTGTCC | AATGGTTCTA | TAGACTCAAC | 960 |
| CGATGAAACT | AGTCAAATAG | TTGAACTACA | AGAATTGCTT | GAAAAGCAAA | ACTATGAAAT | 1020 |
| GGCCCAGATG | AAAGAACGTT | TAGCAGCCCT | TTCTTCCCGA | GTGGGAGAGG | TGGAACAGGA | 1080 |
| AGCAGAGACA | GCAAGAAAGG | ATCTCATTAA | AACAGAAGAA | ATGAACACCA | AGTATCAAAG | 1140 |
| GGACATTAGG | GAGGCCATGG | CACAAAAGGA | AGATATGGAA | GAAAGAATTA | CAACCCTTGA | 1200 |
| AAAGCGTTAC | CTCAGTGCTC | AGAGAGAATC | TACCTCCATA | CATGACATGA | ATGATAAACT | 1260 |
| AGAAAATGAG | TTAGCAAATA | AAGAAGCTAT | CCTACGGCAG | ATGGAAGAGA | AAAACAGACA | 1320 |
| GTTACAAGAA | CGTCTTGAGC | TAGCTGAAGA | AAAGTTGCAG | CAGACCATGA | GAAAGGCTGA | 1380 |
| AACCTTGCCT | GAAGTAGAGG | CTGAACTGGC | TCAGAGAATT | GCAGCCCTAA | CCAAGGCTGA | 1440 |
| AGAGACACAT | GGAAATATTG | AAGAACGTAT | GAGACATTTA | GAGGGTCAAC | TTGAAGAGAA | 1500 |
| GAATCAAGAA | CTTCAAAGAG | CTAGGCAAAG | AGAGAAAATG | AATGAGGAGC | ATAACAAGAG | 1560 |
| ATTATCGGAT | ACGGTTGATA | GACTTCTGAC | TGAATCCAAT | GAACGCCTAC | AACTACACTT | 1620 |
| AAAGGAAAGA | ATGGCTGCTC | TAGAAGAAAA | GAATGTTTTA | ATTCAAGAAT | CAGAAACTTT | 1680 |
| CAGAAAGAAT | CTTGAAGAAT | CTTTACATGA | TAAGGAAAGC | TTAGCAGAAG | AAATTGAAAA | 1740 |
| GCTGAGATCT | GAACTTGACC | AATTGAAAAT | GAGAACTGGC | TCTTTAATTG | AACCCACATT | 1800 |
| ACCAAGAACT | CATCTAGACA | CCTCAGCTGA | GTTGCGGTAC | TCAGTGGGAT | CCCTAGTGGA | 1860 |
| CAGCCAGTCT | GATTACAGAA | CAACTAAAGT | AATAAGAAGA | CCAAGGAGAG | GCCGCATGGG | 1920 |
| TGTGCGAAGA | GATGAGCCAA | AGGTGAAATC | TCTTGGGGAT | CACGAGTGGA | ATAGAACTCA | 1980 |
| ACAGATTGGA | GTACTAAGCA | GCCACCCTTT | TGAAAGTGAC | ACTGAAATGT | CTGATATTGA | 2040 |
| TGATGATGAC | AGAGAAACAA | TTTTTAGCTC | AATGGATCTT | CTCTCTCCAA | GTGGTCATTC | 2100 |
| CGATGCCCAG | ACGCTAGCCA | TGATGCTTCA | GGAACAATTG | GATGCCATCA | ACAAAGAAAT | 2160 |
| CAGGCTAATT | CAGGAAGAAA | AAGAATCTAC | AGAGTTGCGT | GCTGAAGAAA | TTGAAAATAG | 2220 |
| AGTGGCTAGT | GTGAGCCTCG | AAGGCCTGAA | TTTGGCAATG | GTCCACCCAG | GTACCTCCAT | 2280 |
| TACTGCCTCT | GTTACAGCTT | CATCGCTGGC | CAGTTCATCT | CCCCCCAGTG | GACACTCAAC | 2340 |
| TCCAAAGCTC | ACCCCTCGAA | GCCCTGCCAG | GGAAATGGAT | CGGATGGGAG | TCATGACACT | 2400 |
| GCCAAGTGAT | CTGAGGAAAC | ATCGGAGAAA | GATTGCAGTT | GTGGAAGAAG | ATGGTCGAGA | 2460 |
| GGACAAAGCA | ACAATTAAAT | GTGAAACTTC | TCCTCCTCCT | ACCCCTAGAG | CCCTCAGAAT | 2520 |
| GACTCACACT | CTCCCTTCTT | CCTACCACAA | TGATGCTCGA | AGTAGTTTAT | CTGTCTCTCT | 2580 |
| TGAGCCAGAA | AGCCTCGGGC | TTGGTAGTGC | CAACAGCAGC | CAAGACTCTC | TTCACAAAGC | 2640 |
| CCCCAAGAAG | AAAGGAATCA | AGTCTTCAAT | AGGACGTTTG | TTTGGTAAAA | AAGAAAAAGC | 2700 |
| TCGACTTGGG | CAGCTCCGAG | GCTTTATGGA | GACTGAAGCT | GCAGCTCAGG | AGTCCCTGGG | 2760 |
| GTTAGGCAAA | CTCGGAACTC | AAGCTGAGAA | GGATCGAAGA | CTAAAGAAAA | AGCATGAACT | 2820 |
| TCTTGAAGAA | GCTCGGAGAA | AGGGATTACC | TTTTGCCCAG | TGGGATGGGC | CAACTGTGGT | 2880 |
| CGCATGGCTA | GAGCTTTGGT | TGGGAATGCC | TGCGTGGTAC | GTGGCAGCCT | GCCGAGCCAA | 2940 |
| CGTGAAGAGT | GGTGCCATCA | TGTCTGCTTT | ATCTGACACT | GAGATCCAGA | GAGAAATTGG | 3000 |
| AATCAGCAAT | CCACTGCATC | GCTTAAAACT | TCGATTAGCA | ATCCAGGAGA | TGGTTTCCCT | 3060 |
| AACAAGTCCT | TCAGCTCCTC | CAACATCTCG | AACTCCTTCA | GGCAACGTTT | GGGTGACTCA | 3120 |
| TGAAGAAATG | GAAAATCTTG | CAGCTCCAGC | AAAAACGAAA | GAATCTGAGG | AAGGAAGCTG | 3180 |
| GGCCCAGTGT | CCGGTTTTTC | TACAGACCCT | GGCTTATGGA | GATATGAATC | ATGAGTGGAT | 3240 |
| TGGAAATGAA | TGGCTTCCCA | GCTTGGGGTT | ACCTCAGTAC | AGAAGTTACT | TTATGGAATG | 3300 |
| CTTGGTAGAT | GCAAGAATGT | TAGATCACCT | AACAAAAAAA | GATCTCCGTG | TCCATTTAAA | 3360 |

TABLE 4-continued

| | | | | | | |
|---|---|---|---|---|---|---|
| AATGGTGGAT | AGTTTCCATC | GAACAAGTTT | ACAATATGGA | ATTATGTGCT | TAAAGAGGTT | 3420 |
| GAATTATGAC | AGAAAAGAAC | TAGAAAGAAG | ACGGGAAGCA | AGCCAACATG | AAATAAAAGA | 3480 |
| CGTGTTGGTG | TGGAGCAATG | ACCGAGTTAT | TCGCTGGATA | CAAGCAATTG | GACTTCGAGA | 3540 |
| ATATGCAAAT | AATATACTTG | AGAGCGGTGT | GCATGGCTCA | CTTATAGCCC | TGGATGAAAA | 3600 |
| CTTTGACTAC | AGCAGCTTAG | CTTTATTATT | ACAGATTCCA | ACACAGAACA | CCCAGGCAAG | 3660 |
| GCAGATTCTT | GAAAGAGAAT | ACAATAACCT | CTTGGCCCTG | GGAACTGAAA | GGCGACTGGA | 3720 |
| TGAAAGTGAT | GACAAGAACT | TCAGACGTGG | ATCAACCTGG | AGAAGGCAGT | TTCCTCCTCG | 3780 |
| TGAAGTACAT | GGAATCAGCA | TGATGCCTGG | GTCCTCAGAA | ACATTACCAG | CTGGATTTAG | 3840 |
| GTTAACCACA | ACCTCTGGGA | AGTCAAGAAA | AATGACAACA | GATGTTGCTT | CATCAAGACT | 3900 |
| GCAGAGGTTA | GACAACTCCA | CTGTTCGCAC | ATACTCATGT | TGACCAGCCA | CTCAAAGGAG | 3960 |
| GCAGCACTGA | CCTGCTATGG | CGTCTTTTCA | GTCTACTCTA | CCTAAAGTGC | ACTACCATCT | 4020 |
| AAGAAGACGA | GCAGTGAAAA | CCTTTGTGAA | AACTGAATTC | | | |

Seq ID NO: 51 Protein sequence
Protein Accession #: AAC26100.1

| 1 | 11 | 21 | 31 | 41 | 51 | |
|---|---|---|---|---|---|---|
| MMCEVMPTIN | EDTPMSQRGS | QSSGSDSDSH | FEQLMVNMLD | ERDRLLDTLR | ETQESLSLAQ | 60 |
| QRLQDVIYDR | DSLQRQLNSA | LPQDIESLTG | GLAGSKGADP | PEFAALTKEL | NACREQLLEK | 120 |
| EEEISELKAE | RNNTRLLLEH | LECLVSRHER | SLRMTVVKRQ | AQSPSGVSSE | VEVLKALKSL | 180 |
| FEHHKALDEK | VRERLRVSLE | RVSALEEELA | AANQEIVALR | EQNVHIQRKM | ASSEGSTESE | 240 |
| HLEGMEPGQK | VHEKRLSNGS | IDSTDETSQI | VELQELLEKQ | NYEMAQMKER | LAALSSRVGE | 300 |
| VEQEAETARK | DLIKTEEMNT | KYQRKIREAM | AQKEDMEERI | TTLEKRYLSA | QRESTSIHDM | 360 |
| NDKLENELAN | KEAILRQMEE | KNRQLQERLE | LAEEKLQQTM | RKAETLPEVE | AELAQRIAAL | 420 |
| TKAEETHGNI | EERMRHLEGQ | LEEKNQELQR | ARQREKMNEE | HNKRLSDTVD | RLLTESNERL | 480 |
| QLHLKERMAA | LEEKNVLIQE | SETFRKNLEE | SLHDKESLAE | EIEKLRSELD | QLKMRTGSLI | 540 |
| EPTIPRTHLD | TSAELRYSVG | SLVDSQSDYR | TTKVIRRPRR | GRMGVRRDEP | KVKSLGDHEW | 600 |
| NRTQQIGVLS | SHPFESDTEM | SDIDDDDRET | IFSSMDLLSP | SGHSDAQTLA | MMLQEQLDAI | 660 |
| NKEIRLIQEE | KESTELRAEE | IENRVASVSL | EGLNLAMVHP | GTSITASVTA | SSLASSSPPS | 720 |
| GHSTPKLTPR | SPAREMDRMG | VMTLPSDLRK | HRRKIAVVEE | DGREDKATIK | CETSPPPTPR | 780 |
| ALRMTHTLPS | SYHNDARSSL | SVSLEPESLG | LGSANSSQDS | LHKAPKKKGI | KSSIGRLEGK | 840 |
| KEKARLGQLR | GFMETEAAAQ | ESLGLGKLGT | QAEKDRRLKK | KHELLEEARR | KGLPFAQWDG | 900 |
| PTVVAWLELW | LGMPAWYVAA | CRANVKSGAI | MSALSDTEIQ | REIGISNPLH | RLKLRLAIQE | 960 |
| MVSLTSPSAP | PTRSTPSGNV | WVTHEEMENL | AAPAKTKESE | EGSWAQCPVF | LQTLAYGDMN | 1020 |
| HEWIGNEWLP | SLGLPQYSY | FMECLVDARM | LGHLTKKDLR | VHLKMVDSFH | RSTLQYGIMC | 1080 |
| LKRLNYDRKE | LERRREASQH | EIKDVLVWSN | DRVIRWIQAI | GLREYANNIL | ESGVHGSLIA | 1140 |
| LDENFDYSSL | ALLLQIPTON | TQARQILERE | YNNLLALGTE | RRLDESDDKN | FRRGSTWRRQ | 1200 |
| FPPREVHGIS | MMPGSSETLP | AGFRLTTTSG | QSRKMTTDVA | SSRLQRLDNS | TVRTYSC | |

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

What is claimed is:

1. A method of detecting an androgen-independent prostate cancer cell in a sample comprising prostate cells from a patient having undergone androgen ablation therapy, the method comprising:

obtaining the sample comprising prostate cells from the patient having undergone androgen ablation therapy;

determining in the sample the presence or absence of two or more nucleic acids selected from the group consisting of SEQ. ID NO. 24, SEQ. ID NO. 3, SEQ. ID NO. 5, SEQ. ID NO. 7, SEQ. ID NO. 9, SEQ. ID NO. 53, SEQ. ID NO. 29, SEQ. ID NO. 54, SEQ. ID NO. 55, SEQ. ID NO. 56, SEQ. ID NO. 57, and SEQ. ID NO. 58, and correlating the presence of a nucleic acid comprising the sequence of SEQ. ID NO. 24 to the presence of said androgen-independent prostate cancer cell, and the absence of a nucleic acid comprising the sequence of SEQ. ID NO. 3, SEQ. ID NO. 5, SEQ. ID NO. 7, SEQ. ID NO. 9, SEQ. ID NO. 53, SEQ. ID NO. 29, SEQ. ID NO. 54, SEQ. ID NO. 55, SEQ. ID NO. 56, SEQ. ID NO. 57, or SEQ. ID NO. 58 to the presence of said androgen-independent prostate cancer cell.

2. The method of claim 1, wherein said determining is by hybridizing with two or more polynucleotides that selectively hybridizes to said two or more nucleic acids.

3. The method of claim 1, wherein the sample:

a) is a tissue sample; or b) comprises isolated nucleic acids.

4. The method of claim 3:

a) wherein the nucleic acids are mRNA; or b) further comprising amplifying nucleic acids and contacting the sample with a two or more polynucleotides capable of selectively hybridizing to said two or more nucleic acids.

5. The method of claim 2, wherein the two or more polynucleotides:

a) comprise two or more sequences complementary to sequences selected from the group consisting of SEQ. ID NO. 24, SEQ. ID NO. 3, SEQ. ID NO. 5, SEQ. ID NO. 7, SEQ. ID NO. 9, SEQ. ID NO. 53, SEQ. ID NO. 29, SEQ. ID NO. 54, SEQ. ID NO. 55, SEQ. ID NO. 56, SEQ. ID NO. 57,and SEQ. ID NO. 58;

b) are labeled, including a fluorescent label; or c) are immobilized on a solid surface.

6. The method according to claim 1, wherein said sample is contacted with two or more polynucleotides that each selectively hybridizes to said two or more nucleic acids.

7. The method according to claim 6, wherein said two or more polynucleotides are immobilized on a solid surface.

8. A method for quantitation of a prostate cancer-associated transcript in a biological sample comprising prostate cells from a patient having undergone androgen ablation therapy to determine the presence of an androgen-independent prostate cancer cell, the method comprising:

contacting the biological sample from the patient with two or more polynucleotides that selectively hybridize to two or more nucleic acids selected from the group consisting of SEQ. ID NO. 24, SEQ. ID NO. 3, SEQ. ID NO. 5, SEQ. ID NO. 7, SEQ. ID NO. 9, SEQ. ID NO. 53, SEQ. ID NO. 29, SEQ. ID NO. 54, SEQ. ID NO. 55, SEQ. ID NO. 56, SEQ. ID NO. 57, and SEQ. ID NO. 58;

measuring the amount of said two or more polynucleotides that selectively hybridize to said two or more nucleic acids to determine two or more transcript levels; and comparing the two or more transcript levels to a plurality of transcript levels during androgen ablation therapy to determine the presence of said androgen-independent prostate cancer cell, wherein a transcript level of SEQ. ID NO. 24 higher than the transcript level during the androgen ablation therapy indicates the presence of said androgen-independent prostate cancer cell, and a transcript level of SEQ. ID NO. 3, SEQ. ID NO. 5, SEQ. ID NO. 7, SEQ. ID NO. 9, SEQ. ID NO. 53, SEQ. ID NO. 29, SEQ. ID NO. 54, SEQ. ID NO. 55, SEQ. ID NO. 56, SEQ. ID NO. 57, or SEQ. ID NO. 58 lower than the transcript level during the androgen ablation therapy indicates the presence of said androgen-independent prostate cancer cell.

9. The method of claim 8, wherein:

a) the biological sample comprises isolated nucleic acids;

b) the nucleic acids are mRNAs;

c) the method further comprises the step of amplifying nucleic acids before the step of contacting the biological sample with the two or more polynucleotides;

d) the two or more polynucleotides are complementary to sequences selected from the group consisting of SEQ. ID NO. 24, SEQ. ID NO. 3, SEQ. ID NO. 5, SEQ. ID NO. 7, SEQ. ID NO. 9, SEQ. ID NO. 53, SEQ. ID NO. 29, SEQ. ID NO. 54, SEQ. ID NO. 55, SEQ. ID NO. 56, SEQ. ID NO. 57,and SEQ. ID NO. 58;

e) the two or more polynucleotides are labeled, including a fluorescent label; or f) the two or more polynucleotides are immobilized on a solid surface.

* * * * *

SEQUENCE LISTING

```
<160> NUMBER OF SEQ ID NOS: 58

<210> SEQ ID NO 1
<211> LENGTH: 2032
<212> TYPE: DNA
<213> ORGANISM: Homo sapiens

<400> SEQUENCE: 1

cgcggggcgc ggagtcggcg gggcctcgcg ggacgcgggc agtgcggaga ccgcggcgct      60

gaggacgcgg gagccgggag cgcacgcgcg gggtggagtt cagcctactc tttcttagat     120

gtgaaaggaa aggaagatca tttcatgcct tgttgataaa ggttcagact tctgctgatt     180

cataaccatt tggctctgag ctatgacaag agaggaaaca aaaagttaaa cttacaagcc     240

tgccataagt gagaagcaaa cttccttgat aacatgcttt tgcgaagtgc aggaaaatta     300

aatgtgggca ccaagaaaga ggatggtgag agtacagccc ccaccccccg tccaaaggtc     360

ttgcgttgta aatgccacca ccattgtcca gaagactcag tcaacaatat ttgcagcaca     420

gacggatatt gtttcacgat gatagaagag gatgactctg ggttgcctgt ggtcacttct     480

ggttgcctag gactagaagg ctcagatttt cagtgtcggg acactcccat tcctcatcaa     540
```

-continued

```
agaagatcaa ttgaatgctg cacagaaagg aacgaatgta ataaagacct acaccctaca    600
ctgcctccat tgaaaaacag agattttgtt gatggaccta tacaccacag ggctttactt    660
atatctgtga ctgtctgtag tttgctcttg gtccttatca tattattttg ttacttccgg    720
tataaaagac aagaaaccag acctcgatac agcattgggt tagaacagga tgaaacttac    780
attcctcctg gagaatccct gagagactta attgagcagt ctcagagctc aggaagtgga    840
tcaggcctcc ctctgctggt ccaaaggact atagctaagc agattcagat ggtgaaacag    900
attggaaaag gtcgctatgg ggaagtttgg atgggaaagt ggcgtggcga aaaggtagct    960
gtgaaagtgt tcttcaccac agaggaagcc agctggttca gagagacaga aatatatcag   1020
acagtgttga tgaggcatga aaacattttg ggtttcattg ctgcagatat caaagggaca   1080
gggtcctgga cccagttgta cctaatcaca gactatcatg aaaatggttc cctttatgat   1140
tatctgaagt ccaccaccct agacgctaaa tcaatgctga agttagccta ctcttctgtc   1200
agtggcttat gtcatttaca cacagaaatc tttagtactc aaggcaaacc agcaattgcc   1260
catcgagatc tgaaaagtaa aaacattctg gtgaagaaaa atggaacttg ctgtattgct   1320
gacctgggcc tggctgttaa atttattagt gatacaaatg aagttgacat accacctaac   1380
actcgagttg gcaccaaacg ctatatgcct ccagaagtgt tggacgagag cttgaacaga   1440
aatcacttcc agtcttacat catggctgac atgtatagtt ttggcctcat cctttgggag   1500
gttgctagga gatgtgtatc aggaggtata gtggaagaat accagcttcc ttatcatgac   1560
ctagtgccca gtgacccctc ttatgaggac atgagggaga ttgtgtgcat caagaagtta   1620
cgcccctcat tcccaaaccg gtggagcagt gatgagtgtc taaggcagat gggaaaactc   1680
atgacagaat gctgggctca caatcctgca tcaaggctga cagccctgcg ggttaagaaa   1740
acacttgcca aaatgtcaga gtcccaggac attaaactct gataggagag gaaaagtaag   1800
catctctgca gaaagccaac aggtactctt ctgtttgtgg gcagagcaaa agacatcaaa   1860
taagcatcca cagtacaagc cttgaacatc gtcctgcttc ccagtgggtt cagacctcac   1920
ctttcaggga gcgacctggg caaagacaga gaagctccca gaaggagaga ttgatccgtg   1980
tctgtttgta ggcggagaaa ccgttgggta acttgttcaa gatatgatgc at           2032

<210> SEQ ID NO 2
<211> LENGTH: 502
<212> TYPE: PRT
<213> ORGANISM: Homo sapiens

<400> SEQUENCE: 2

Met Leu Leu Arg Ser Ala Gly Lys Leu Asn Val Gly Thr Lys Lys Glu
  1               5                  10                  15

Asp Gly Glu Ser Thr Ala Pro Thr Pro Arg Pro Lys Val Leu Arg Cys
             20                  25                  30

Lys Cys His His His Cys Pro Glu Asp Ser Val Asn Asn Ile Cys Ser
         35                  40                  45

Thr Asp Gly Tyr Cys Phe Thr Met Ile Glu Glu Asp Asp Ser Gly Leu
     50                  55                  60

Pro Val Val Thr Ser Gly Cys Leu Gly Leu Glu Gly Ser Asp Phe Gln
 65                  70                  75                  80

Cys Arg Asp Thr Pro Ile Pro His Gln Arg Arg Ser Ile Glu Cys Cys
                 85                  90                  95

Thr Glu Arg Asn Glu Cys Asn Lys Asp Leu His Pro Thr Leu Pro Pro
            100                 105                 110
```

-continued

```
Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
        355                 360                 365

Asn Thr Arg Val Gly Thr Lys Arg Tyr Met Pro Pro Glu Val Leu Asp
    370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
    450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500
```

<210> SEQ ID NO 3
<211> LENGTH: 3168

-continued

<212> TYPE: DNA
<213> ORGANISM: Homo sapiens

<400> SEQUENCE: 3
gccagagcgt gagccgcgac ctccgcgcag gtggtcgcgc cggtctccgc ggaaatgttg 60
tccaaagttc ttccagtcct cctaggcatc ttattgatcc tccagtcgag ggtcgaggga 120
cctcagactg aatcaaagaa tgaagcctct tcccgtgatg ttgtctatgg cccccagccc 180
cagcctctgg aaaatcagct cctctctgag gaaacaaagt caactgagac tgagactggg 240
agcagagttg gcaaactgcc agaagcctct cgcatcctga acactatcct gagtaattat 300
gaccacaaac tgcgccctgg cattggagag aagcccactg tggtcactgt tgagatcgcc 360
gtcaacagcc ttggtcctct ctctatccta gacatggaat acaccattga catcatcttc 420
tcccagacct ggtacgacga acgcctctgt tacaacgaca cctttgagtc tcttgttctg 480
aatggcaatg tggtgagcca gctatggatc ccggacacct tttttaggaa ttctaagagg 540
acccacgagc atgagatcac catgcccaac cagatggtcc gcatctacaa ggatggcaag 600
gtgttgtaca caattaggat gaccattgat gccggatgct cactccacat gctcagattt 660
ccaatggatt ctcactcttg ccctctatct ttctctagct tttcctatcc tgagaatgag 720
atgatctaca agtgggaaaa tttcaagctt gaaatcaatg agaagaactc ctggaagctc 780
ttccagtttg attttacagg agtgagcaac aaaactgaaa taatcacaac cccagttggt 840
gacttcatgg tcatgacgat tttcttcaat gtgagcaggc ggtttggcta tgttgccttt 900
caaaactatg tcccttcttc cgtgaccacg atgctctcct gggtttcctt ttggatcaag 960
acagagtctg ctccagcccg gacctctcta gggatcacct ctgttctgac catgaccacg 1020
ttgggcacct tttctcgtaa gaatttcccg cgtgtctcct atatcacagc cttggatttc 1080
tatatcgcca tctgcttcgt cttctgcttc tgcgctctgt tggagtttgc tgtgctcaac 1140
ttcctgatct acaaccagac aaaagcccat gcttctccta aactccgcca tcctcgtatc 1200
aatagccgtg cccatgcccg tacccgtgca cgttcccgag cctgtgcccg ccaacatcag 1260
gaagcttttg tgtgccagat tgtcaccact gagggaagtg atggagagga gcgcccgtct 1320
tgctcagccc agcagccccc tagcccaggt agccctgagg gtccccgcag cctctgctcc 1380
aagctggcct gctgtgagtg gtgcaagcgt tttaagaagt acttctgcat ggtccccgat 1440
tgtgagggca gtacctggca gcagggccgc ctctgcatcc atgtctaccg cctggataac 1500
tactcgagag ttgttttccc agtgactttc ttcttcttca atgtgctcta ctggcttgtt 1560
tgccttaact tgtaggtacc agctggtacc ctgtggggca acctctccag ttccccagga 1620
ggtccaagcc ccttgccaag ggagttgggg gaaagcagca gcagcagcag gagcgactag 1680
agtttttcct gccccattcc ccaaacagaa gcttgcagag ggtttgtctt tgctgcccct 1740
ctcccctacc tggcccattc actgagtctt ctcagcagac catttcaaat tattaataaa 1800
tgggccacct ccctcttctt caaggagcat ccgtgatgct cagtgttcaa aaccacagcc 1860
acttagtgat cagctcccta aaaccatgcc taagtacagg cggattagct atcttccaac 1920
aatgctgacc accagacaat tactgcattt ttccagaagc ccactattgc ctttgtagtg 1980
ctttcggccc agttctggcc tcagcctcaa agtgcaccga ctagttgctt gcctatacct 2040
ggcacctcat taagatgctg ggcagcagta taacaggagg aagagatccc tctcctttgg 2100
tcagattatt atgttctcag ttctctctcc ctgctacccc tttctctgca gatagataga 2160
cactggcatt atccctttag gaagaggggg gggcagcaag agagcctatt tgggacagca 2220

-continued

```
ttcctctctc tctgctgctg tgacatctcc ctctccttgc tggctccatc tttcgtctgc   2280

actaccaatt caatgccctt catccaatgg gtatctattt ttgtgtgtga ttatagtaac   2340

tactccctgc tttatatgcc accctcttcc ttctctttga cccctgtgac tctttctgta   2400

actttcccag tgacttcccc tagccctgac ccaggcacta ggccttggtg acttcctggg   2460

gccaagaaac taaggaaact cggctttgca acaggcatta ctcgccattg attggtgccc   2520

acccagggca cactgtcgga gttctatcac ttgcttgacc cctggaccca taaaccagtc   2580

cactgttata cccggggcac tctaaccatc acaatcaatc aatcaaattc ccttaaattt   2640

gtatggcact ggaactttgg caaagcactt ttgacaagtt gtgtctgatt ggagcttcat   2700

gatagccttg tgacatcttt agggcaggat tcttatcccc attttgcaga tgaaaaccct   2760

gagtcacaga tttctgtggg actgtggatc tcactggaag ctatccaaga gcccactgtc   2820

accttctaga ccacatgata gggctagaca gctcagttca ccatgattct cttctgtcac   2880

ctctgctggc acaccagtgg caaggcccag aatggcgacc tctctttagc tcaatttctg   2940

ggcctgaggt gctcagactg cccccaagat caaatctctc ctggctgtag taacccagtg   3000

gaatgaattt ggacatgccc caatgcttct atatgctaag tgaaatctgt gtctgtaatt   3060

tgttgggggg tggatagggt ggggtctcca tctacttttt gtcaccatca tctgaaatgg   3120

ggaaatatgt aaataaatat atcagcaaag caaaaagaaa aaaaaaaa               3168
```

<210> SEQ ID NO 4
<211> LENGTH: 506
<212> TYPE: PRT
<213> ORGANISM: Homo sapiens

<400> SEQUENCE: 4

```
Met Leu Ser Lys Val Leu Pro Val Leu Leu Gly Ile Leu Leu Ile Leu
  1               5                  10                  15

Gln Ser Arg Val Glu Gly Pro Gln Thr Glu Ser Lys Asn Glu Ala Ser
             20                  25                  30

Ser Arg Asp Val Val Tyr Gly Pro Gln Pro Gln Pro Leu Glu Asn Gln
         35                  40                  45

Leu Leu Ser Glu Glu Thr Lys Ser Thr Glu Thr Glu Thr Gly Ser Arg
     50                  55                  60

Val Gly Lys Leu Pro Glu Ala Ser Arg Ile Leu Asn Thr Ile Leu Ser
 65                  70                  75                  80

Asn Tyr Asp His Lys Leu Arg Pro Gly Ile Gly Glu Lys Pro Thr Val
                 85                  90                  95

Val Thr Val Glu Ile Ala Val Asn Ser Leu Gly Pro Leu Ser Ile Leu
            100                 105                 110

Asp Met Glu Tyr Thr Ile Asp Ile Ile Phe Ser Gln Thr Trp Tyr Asp
        115                 120                 125

Glu Arg Leu Cys Tyr Asn Asp Thr Phe Glu Ser Leu Val Leu Asn Gly
    130                 135                 140

Asn Val Val Ser Gln Leu Trp Ile Pro Asp Thr Phe Phe Arg Asn Ser
145                 150                 155                 160

Lys Arg Thr His Glu His Glu Ile Thr Met Pro Asn Gln Met Val Arg
                165                 170                 175

Ile Tyr Lys Asp Gly Lys Val Leu Tyr Thr Ile Arg Met Thr Ile Asp
            180                 185                 190

Ala Gly Cys Ser Leu His Met Leu Arg Phe Pro Met Asp Ser His Ser
        195                 200                 205
```

-continued

Cys Pro Leu Ser Phe Ser Ser Phe Ser Tyr Pro Glu Asn Glu Met Ile
    210                 215                 220

Tyr Lys Trp Glu Asn Phe Lys Leu Glu Ile Asn Glu Lys Asn Ser Trp
225                 230                 235                 240

Lys Leu Phe Gln Phe Asp Phe Thr Gly Val Ser Asn Lys Thr Glu Ile
                245                 250                 255

Ile Thr Thr Pro Val Gly Asp Phe Met Val Met Thr Ile Phe Phe Asn
            260                 265                 270

Val Ser Arg Arg Phe Gly Tyr Val Ala Phe Gln Asn Tyr Val Pro Ser
        275                 280                 285

Ser Val Thr Thr Met Leu Ser Trp Val Ser Phe Trp Ile Lys Thr Glu
    290                 295                 300

Ser Ala Pro Ala Arg Thr Ser Leu Gly Ile Thr Ser Val Leu Thr Met
305                 310                 315                 320

Thr Thr Leu Gly Thr Phe Ser Arg Lys Asn Phe Pro Arg Val Ser Tyr
                325                 330                 335

Ile Thr Ala Leu Asp Phe Tyr Ile Ala Ile Cys Phe Val Phe Cys Phe
            340                 345                 350

Cys Ala Leu Leu Glu Phe Ala Val Leu Asn Phe Leu Ile Tyr Asn Gln
        355                 360                 365

Thr Lys Ala His Ala Ser Pro Lys Leu Arg His Pro Arg Ile Asn Ser
    370                 375                 380

Arg Ala His Ala Arg Thr Arg Ala Arg Ser Arg Ala Cys Ala Arg Gln
385                 390                 395                 400

His Gln Glu Ala Phe Val Cys Gln Ile Val Thr Thr Glu Gly Ser Asp
                405                 410                 415

Gly Glu Glu Arg Pro Ser Cys Ser Ala Gln Gln Pro Pro Ser Pro Gly
            420                 425                 430

Ser Pro Glu Gly Pro Arg Ser Leu Cys Ser Lys Leu Ala Cys Cys Glu
        435                 440                 445

Trp Cys Lys Arg Phe Lys Lys Tyr Phe Cys Met Val Pro Asp Cys Glu
    450                 455                 460

Gly Ser Thr Trp Gln Gln Gly Arg Leu Cys Ile His Val Tyr Arg Leu
465                 470                 475                 480

Asp Asn Tyr Ser Arg Val Val Phe Pro Val Thr Phe Phe Phe Phe Asn
                485                 490                 495

Val Leu Tyr Trp Leu Val Cys Leu Asn Leu
            500                 505

<210> SEQ ID NO 5
<211> LENGTH: 3329
<212> TYPE: DNA
<213> ORGANISM: Homo sapiens

<400> SEQUENCE: 5
gccagagcgt gagccgcgac ctccgcgcag gtggtcgcgc cggtctccgc ggaaatgttg 60
tccaaagttc ttccagtcct cctaggcatc ttattgatcc tccagtcgag aacatgtata 120
cagagaagtg ctcaaatcat aagtgtacag ctgatgagtt gtcaaaaaat gaccacagcg 180
gtgtaaagaa agccaaatca aggacccgaa tgtgagcagg acctcagaag ccccctttgt 240
cactgcctcc cagcaaaggc agcactatcc ggacttctaa caccatcggg tcgagggacc 300
tcagactgaa tcaaagaatg aagcctcttc ccgtgatgtt gtctatggcc cccagcccca 360
gcctctggaa aatcagctcc tctctgagga aacaaagtca actgagactg agactgggag 420

-continued

```
cagagttggc aaactgccag aagcctctcg catcctgaac actatcctga gtaattatga    480
ccacaaactg cgccctggca ttggagagaa gcccactgtg gtcactgttg agatctccgt    540
caacagcctt ggtcctctct ctatcctaga catggaatac accattgaca tcatcttctc    600
ccagacctgg tacgacgaac gcctctgtta caacgacacc tttgagtctc ttgttctgaa    660
tggcaatgtg gtgagccagc tatggatccc ggacaccttt tttaggaatt ctaagaggac    720
ccacgagcat gagatcacca tgcccaacca gatggtccgc atctacaagg atggcaaggt    780
gttgtacaca attaggatga ccattgatgc cggatgctca ctccacatgc tcagatttcc    840
aatggattct cactcttgcc ctctatcttt ctctagcttt tcctatcctg agaatgagat    900
gatctacaag tgggaaaatt tcaagcttga aatcaatgag aagaactcct ggaagctctt    960
ccagttggat tttacaggag tgagcaacaa aactgaaata atcacaaccc cagttggtga   1020
cttcatggtc atgacgattt tcttcaatgt gagcaggcgg tttggctatg ttgcctttca   1080
aaactatgtc ccttcttccg tgaccacgat gctctcctgg gtttcctttt ggatcaagac   1140
agagtctgct ccagcccgga cctctctagg gatcacctct gttctgacca tgaccacgtt   1200
gggcaccttt tctcgtaaga atttcccgcg tgtctcctat atcacagcct tggatttcta   1260
tatcgccatc tgcttcgtct tctgcttctg cgctctgttg gagtttgctg tgctcaactt   1320
cctgatctac aaccagacaa aagcccatgc ttctcctaaa ctccgccatc ctcgtatcaa   1380
tagccgtgcc catgcccgta cccgtgcacg ttcccgagcc tgtgcccgcc aacatcagga   1440
agcttttgtg tgccagattg tcaccactga gggaagtgat ggagaggagc gcccgtcttg   1500
ctcagcccag cagcccccta gcccaggtag ccctgagggt ccccgcagcc tctgctccaa   1560
gctggcctgc tgtgagtggt gcaagcgttt taagaagtac ttctgcatgg tccccgattg   1620
tgagggcagt acctggcagc aggcccgcct ctgcatccat gtctaccgcc tggataacta   1680
ctcgagagtt gttttcccag tgactttctt cttcttcaat gtgctctact ggcttgtttg   1740
ccttaacttg taggtaccag ctggtaccct gtggggcaac ctctccagtt ccccaggagg   1800
tccaagcccc ttgccaaggg agttggggga aagcagcagc agcagcagga gcgactagag   1860
tttttcctgc cccattcccc aaacagaagc ttgcagaggg tttgtctttg ctgcccctct   1920
cccctacctg gcccattcac tgagttttct cagcagacca tttcaaatta ttaataaatg   1980
ggccacctcc ctcttcttca aggagcatcc gtgatgctca gtgttcaaaa ccacagccac   2040
ttagtgatca gctccctaaa accatgccta agtacaggcg gattagctat cttccaacaa   2100
tgctgaccac cagacaatta ctgcattttt ccagaagccc actattgcct ttgcagtgct   2160
ttcggcccag ttctggcctc agcctcaaag tgcaccgact agttgcttgc ctatacctgg   2220
cacctcatta agatgctggg cagcagtata acaggaggaa gagatccctc tcctttggtc   2280
agattattat gttctcagtt ctctctccct gctacccctt tctctgcaga tagatagaca   2340
ctggcattat ccctttagga agaggggggg gcagcaagag agcctatttg ggacagcatt   2400
cctctctctc tgctgctgtg acatctccct ctccttgctg gctccatctt tcgtctgcac   2460
taccaattca atgcccttca tccaatgggt atctattttt gtgtgtgatt atagtaacta   2520
ctccctgctt tatatgccac cctcttcctt ctctttgacc cctgtgactc tttctgtaac   2580
tttcccagtg acttccccta gccctgaccc aggcactagg ccttggtgac ttcctggggc   2640
caagaaacta aggaaactcg gctttgcaac aggcattact cgccattgat tggtgcccac   2700
ccagggcaca ctgtcggagt tctatcactt gcttgacccc tggacccata aaccagtcca   2760
ctgttatacc cggggcactc taaccatcac aatcaatcaa tcaaattccc ttaaatttgt   2820
```

-continued atggcactgg aactttggca aagcactttt gacaagttgt gtctgattgg agcttcatga 2880
tagccttgtg acatctttag ggcaggattc ttatccccat tttgcagatg aaaaccctga 2940
gtcacagatt tctgtgggac tgtggatctc actggaagct atccaagagc ccactgtcac 3000
cttctagacc acatgatagg gctagacagc tcagttcacc atgattctct tctgtcacct 3060
ctgctggcac accagtggca aggcccagaa tggcgacctc tctttagctc aatttctggg 3120
cctgaggtgc tcagactgcc cccaagatca aatctctcct ggctgtagta acccagtgga 3180
atgaatttgg acatgcccca atgcttctat atgctaagtg aaatctgtgt ctgtaatttg 3240
ttggggggtg gatagggtgg ggtctccatc tactttttgt caccatcatc tgaaatgggg 3300
aaatatgtaa ataaatatat cagcaaagc 3329

<210> SEQ ID NO 6
<211> LENGTH: 393
<212> TYPE: PRT
<213> ORGANISM: Homo sapiens

<400> SEQUENCE: 6

Met Glu Tyr Thr Ile Asp Ile Ile Phe Ser Gln Thr Trp Tyr Asp Glu
1 5 10 15

Arg Leu Cys Tyr Asn Asp Thr Phe Glu Ser Leu Val Leu Asn Gly Asn
20 25 30

Val Val Ser Gln Leu Trp Ile Pro Asp Thr Phe Phe Arg Asn Ser Lys
35 40 45

Arg Thr His Glu His Glu Ile Thr Met Pro Asn Gln Met Val Arg Ile
50 55 60

Tyr Lys Asp Gly Lys Val Leu Tyr Thr Ile Arg Met Thr Ile Asp Ala
65 70 75 80

Gly Cys Ser Leu His Met Leu Arg Phe Pro Met Asp Ser His Ser Cys
85 90 95

Pro Leu Ser Phe Ser Ser Phe Ser Tyr Pro Glu Asn Glu Met Ile Tyr
100 105 110

Lys Trp Glu Asn Phe Lys Leu Glu Ile Asn Glu Lys Asn Ser Trp Lys
115 120 125

Leu Phe Gln Leu Asp Phe Thr Gly Val Ser Asn Lys Thr Glu Ile Ile
130 135 140

Thr Thr Pro Val Gly Asp Phe Met Val Met Thr Ile Phe Phe Asn Val
145 150 155 160

Ser Arg Arg Phe Gly Tyr Val Ala Phe Gln Asn Tyr Val Pro Ser Ser
165 170 175

Val Thr Thr Met Leu Ser Trp Val Ser Phe Trp Ile Lys Thr Glu Ser
180 185 190

Ala Pro Ala Arg Thr Ser Leu Gly Ile Thr Ser Val Leu Thr Met Thr
195 200 205

Thr Leu Gly Thr Phe Ser Arg Lys Asn Phe Pro Arg Val Ser Tyr Ile
210 215 220

Thr Ala Leu Asp Phe Tyr Ile Ala Ile Cys Phe Val Phe Cys Phe Cys
225 230 235 240

Ala Leu Leu Glu Phe Ala Val Leu Asn Phe Leu Ile Tyr Asn Gln Thr
245 250 255

Lys Ala His Ala Ser Pro Lys Leu Arg His Pro Arg Ile Asn Ser Arg
260 265 270

Ala His Ala Arg Thr Arg Ala Arg Ser Arg Ala Cys Ala Arg Gln His

-continued

```
        275                 280                 285

Gln Glu Ala Phe Val Cys Gln Ile Val Thr Thr Glu Gly Ser Asp Gly
    290                 295                 300

Glu Glu Arg Pro Ser Cys Ser Ala Gln Gln Pro Pro Ser Pro Gly Ser
305                 310                 315                 320

Pro Glu Gly Pro Arg Ser Leu Cys Ser Lys Leu Ala Cys Cys Glu Trp
                325                 330                 335

Cys Lys Arg Phe Lys Lys Tyr Phe Cys Met Val Pro Asp Cys Glu Gly
            340                 345                 350

Ser Thr Trp Gln Gln Ala Arg Leu Cys Ile His Val Tyr Arg Leu Asp
        355                 360                 365

Asn Tyr Ser Arg Val Val Phe Pro Val Thr Phe Phe Phe Phe Asn Val
    370                 375                 380

Leu Tyr Trp Leu Val Cys Leu Asn Leu
385                 390


<210> SEQ ID NO 7
<211> LENGTH: 3232
<212> TYPE: DNA
<213> ORGANISM: Homo sapiens

<400> SEQUENCE: 7

gccagagcgt gagccgcgac ctccgcgcag gtggtcgcgc cggtctccgc ggaaatgttg     60

tccaaagttc ttccagtcct cctaggcatc ttattgatcc tccagtcgag aacatgtata    120

cagagaagtg ctcaaatcat aagtgtacag ctgatgagtt gtcaaaaaat gaccacagcg    180

gtgtaaagaa agccaaatca aggacccgaa tgtgagcagg acctcagaag cccccctttgt   240

cactgcctcc cagcaaaggc agcactatcc ggacttctaa caccatcggg tcgagggacc    300

tcagactgaa tcaaagaatg aagcctcttc ccgtgatgtt gtctatggcc cccagcccca    360

gcctctggaa aatcagctcc tctctgagga aacaaagtca actgagactg agactgggag    420

cagagttggc aaactgccag aagcctctcg catcctgaac actatcctga gtaattatga    480

ccacaaactg cgccctggca ttggagagaa gcccactgtg gtcactgttg agatctccgt    540

caacagcctt ggtcctctct ctatcctaga catggaatac accattgaca tcatcttctc    600

ccagacctgg aattctaaga ggacccacga gcatgagatc accatgccca accagatggt    660

ccgcatctac aaggatggca aggtgttgta cacaattagg atgaccattg atgccggatg    720

ctcactccac atgctcagat ttccaatgga ttctcactct tgccctctat ctttctctag    780

cttttcctat cctgagaatg agatgatcta caagtgggaa aatttcaagc ttgaaatcaa    840

tgagaagaac tcctggaagc tcttccagtt tgattttaca ggagtgagca acaaaaactga   900

aataatcaca accccagttg gtgacttcat ggtcatgacg attttcttca atgtgagcag    960

gcggtttggc tatgttgcct ttcaaaacta tgtcccttct tccgtgacca cgatgctctc   1020

ctgggtttcc ttttggatca agacagagtc tgctccagcc cggacctctc tagggatcac   1080

ctctgttctg accatgacca cgttgggcac cttttctcgt aagaatttcc cgcgtgtctc   1140

ctatatcaca gccttggatt tctatatcgc catctgcttc gtcttctgct tctgcgctct   1200

gttggagttt gctgtgctca acttcctgat ctacaaccag acaaaagccc atgcttctcc   1260

taaactccgc catcctcgta tcaatagccg tgcccatgcc cgtacccgtg cacgttcccg   1320

agcctgtgcc cgccaacatc aggaagcttt tgtgtgccag attgtcacca ctgagggaag   1380

tgatggagag gagcgcccgt cttgctcagc ccagcagccc cctagcccag gtagccctga   1440
```

-continued

```
gggtccccgc agcctctgct ccaagctggc ctgctgtgag tggtgcaagc gttttaagaa   1500

gtacttctgc atggtccccg attgtgaggg cagtacctgg cagcagggcc gcctctgcat   1560

ccatgtctac cgcctggata actactcgag agttgttttc ccagtgactt tcttcttctt   1620

caatgtgctc tactggcttg tttgccttaa cttgtaggta ccagctggta ccctgtgggg   1680

caacctctcc agttccccag gaggtccaag ccccttgcca agggagttgg gggaaagcag   1740

cagcagcagc aggagcgact agagtttttc ctgccccatt ccccaaacag aagcttgcag   1800

agggtttgtc tttgctgccc ctctccccta cctggcccat tcactgagtt ttctcagcag   1860

accatttcaa attattaata aatgggccac ctccctcttc ttcaaggagc atccgtgatg   1920

ctcagtgttc aaaaccacag ccacttagtg atcagctccc taaaaccatg cctaagtaca   1980

ggcggattag ctatcttcca acaatgctga ccaccagaca attactgcat tttccagaa   2040

gcccactatt gcctttgcag tgctttcggc ccagttctgg cctcagcctc aaagtgcacc   2100

gactagttgc ttgcctatac ctggcacctc attaagatgc tgggcagcag tataacagga   2160

ggaagagatc cctctccttt ggtcagatta ttatgttctc agttctctct ccctgctacc   2220

cctttctctg cagatagata gacactggca ttatcccttt aggaagaggg gggggcagca   2280

agagagccta tttgggacag cattcctctc tctctgctgc tgtgacatct ccctctcctt   2340

gctggctcca tctttcgtct gcactaccaa ttcaatgccc ttcatccaat gggtatctat   2400

ttttgtgtgt gattatagta actactccct gctttatatg ccaccctctt ccttctcttt   2460

gacccctgtg actctttctg taactttccc agtgacttcc cctagccctg accaggcact   2520

aggccttggt gacttcctgg ggccaagaaa ctaaggaaac tcggctttgc aacaggcatt   2580

actcgccatt gattggtgcc cacccagggc acactgtcgg agttctatca cttgcttgac   2640

ccctggaccc ataaaccagt ccactgttat acccggggca ctctaaccat cacaatcaat   2700

caatcaaatt cccttaaatt tgtatggcac tggaactttg gcaaagcact tttgacaagt   2760

tgtgtctgat tggagcttca tgatagcctt gtgacatctt tagggcagga ttcttatccc   2820

cattttgcag atgaaaaccc tgagtcacag atttctgtgg gactgtggat ctcactggaa   2880

gctatccaag agcccactgt caccttctag accacatgat agggctagac agctcagttc   2940

accatgattc tcttctgtca cctctgctgg cacaccagtg gcaaggccca gaatggcgac   3000

ctctctttag ctcaatttct gggcctgagg tgctcagact gcccccaaga tcaaatctct   3060

cctggctgta gtaacccagt ggaatgaatt tggacatgcc ccaatgcttc tatatgctaa   3120

gtgaaatctg tgtctgtaat ttgttggggg gtggataggg tggggtctcc atctactttt   3180

tgtcaccatc atctgaaatg gggaaatatg taaataaata tatcagcaaa gc           3232
```

<210> SEQ ID NO 8
<211> LENGTH: 361
<212> TYPE: PRT
<213> ORGANISM: Homo sapiens

<400> SEQUENCE: 8

```
Met Glu Tyr Thr Ile Asp Ile Ile Phe Ser Gln Thr Trp Asn Ser Lys
  1               5                  10                  15

Arg Thr His Glu His Glu Ile Thr Met Pro Asn Gln Met Val Arg Ile
             20                  25                  30

Tyr Lys Asp Gly Lys Val Leu Tyr Thr Ile Arg Met Thr Ile Asp Ala
         35                  40                  45

Gly Cys Ser Leu His Met Leu Arg Phe Pro Met Asp Ser His Ser Cys
     50                  55                  60
```

-continued

```
Pro Leu Ser Phe Ser Ser Phe Ser Tyr Pro Glu Asn Glu Met Ile Tyr
 65                  70                  75                  80

Lys Trp Glu Asn Phe Lys Leu Glu Ile Asn Glu Lys Asn Ser Trp Lys
                 85                  90                  95

Leu Phe Gln Phe Asp Phe Thr Gly Val Ser Asn Lys Thr Glu Ile Ile
            100                 105                 110

Thr Thr Pro Val Gly Asp Phe Met Val Met Thr Ile Phe Phe Asn Val
        115                 120                 125

Ser Arg Arg Phe Gly Tyr Val Ala Phe Gln Asn Tyr Val Pro Ser Ser
    130                 135                 140

Val Thr Thr Met Leu Ser Trp Val Ser Phe Trp Ile Lys Thr Glu Ser
145                 150                 155                 160

Ala Pro Ala Arg Thr Ser Leu Gly Ile Thr Ser Val Leu Thr Met Thr
                165                 170                 175

Thr Leu Gly Thr Phe Ser Arg Lys Asn Phe Pro Arg Val Ser Tyr Ile
            180                 185                 190

Thr Ala Leu Asp Phe Tyr Ile Ala Ile Cys Phe Val Phe Cys Phe Cys
        195                 200                 205

Ala Leu Leu Glu Phe Ala Val Leu Asn Phe Leu Ile Tyr Asn Gln Thr
    210                 215                 220

Lys Ala His Ala Ser Pro Lys Leu Arg His Pro Arg Ile Asn Ser Arg
225                 230                 235                 240

Ala His Ala Arg Thr Arg Ala Arg Ser Arg Ala Cys Ala Arg Gln His
                245                 250                 255

Gln Glu Ala Phe Val Cys Gln Ile Val Thr Thr Glu Gly Ser Asp Gly
            260                 265                 270

Glu Glu Arg Pro Ser Cys Ser Ala Gln Gln Pro Pro Ser Pro Gly Ser
        275                 280                 285

Pro Glu Gly Pro Arg Ser Leu Cys Ser Lys Leu Ala Cys Cys Glu Trp
    290                 295                 300

Cys Lys Arg Phe Lys Lys Tyr Phe Cys Met Val Pro Asp Cys Glu Gly
305                 310                 315                 320

Ser Thr Trp Gln Gln Gly Arg Leu Cys Ile His Val Tyr Arg Leu Asp
                325                 330                 335

Asn Tyr Ser Arg Val Val Phe Pro Val Thr Phe Phe Phe Phe Asn Val
            340                 345                 350

Leu Tyr Trp Leu Val Cys Leu Asn Leu
        355                 360


<210> SEQ ID NO 9
<211> LENGTH: 4065
<212> TYPE: DNA
<213> ORGANISM: Homo sapiens

<400> SEQUENCE: 9

gccagagcgt gagccgcgac ctccgcgcag gtggtcgcgc cggtctccgc ggaaatgttg     60

tccaaagttc ttccagtcct cctaggcatc ttattgatcc tccagtcgag aacatgtata    120

cagagaagtg ctcaaatcat aagtgtacag ctgatgagtt gtcaaaaaat gaccacagcg    180

gtgtaaagaa agccaaatca aggacccgaa tgtgagcagg acctcagaag ccccctttgt    240

cactgcctcc cagcaaaggc agcactatcc ggacttctaa caccatcggt gagtttcata    300

ccttggcaga tggcctttaa cattttttgtt taattcaatt attcttacta atcttcttct    360

ttttcttggc tgtggtgcat ggctgtggag ctcagggtgg actcctgttg ggcagccagt    420
```

-continued

```
tcctggatgg ctgtctgtgg gtggaggact cctgcctttc ctgtttagac acccacaaag    480
gctgctcttt agcctccttc ccttcatccc cttcccctgc ccccagtgca acgagtatta    540
cacaaccaac aaaaccgcaa aatattccca caattttctg gtcctctctg ggagaggccg    600
ctctggcttt tcctctcagc cctggccctc tgcctgctcc tcactcctgg ttggtgctgg    660
tcaggctgac tagaggccaa ggcgaccaac actaggcaaa cgcggccagc gctcagacat    720
aaatgccctc ttcatttcac gtgtaacatt cttttaaaat ctaggtcttg gttttgttga    780
ttttttctta aataaaagag tgatcataaa agagggacag catagaaagt ccccaaagag    840
cagcaaggtt ttaaagaaat tcacaagcct aatctgtcac tgtcttataa tttgctatta    900
ccagtcacaa tttaactagg ttttgtgttg aaaacttgtt ttggtttgct tctgtcccaa    960
gaggcactag ctggggcccc tacagagtgc agggcagagc ttcatttttc gtttgaatgt   1020
tctagggtcg agggacctca gactgaatca aagaatgaag cctcttcccg tgatgttgtc   1080
tatggccccc agccccagcc tctggaaaat cagctcctct ctgaggaaac aaagtcaact   1140
gagactgaga ctgggagcag agttggcaaa ctgccagaag cctctcgcat cctgaacact   1200
atcctgagta attatgacca caaactgcgc cctggcattg gagagaagcc cactgtggtc   1260
actgttgaga tctccgtcaa cagccttggt cctctctcta tcctagacat ggaatacacc   1320
attgacatca tcttctccca gacctggtac gacgaacgcc tctgttacaa cgacaccttt   1380
gagtctcttg ttctgaatgg caatgtggtg agccagctat ggatcccgga cacctttttt   1440
aggaattcta agaggaccca cgagcatgag atcaccatgc ccaaccagat ggtccgcatc   1500
tacaaggatg gcaaggtgtt gtacacaatt aggatgacca ttgatgccgg atgctcactc   1560
cacatgctca gatttccaat ggattctcac tcttgccctc tatctttctc tagcttttcc   1620
tatcctgaga atgagatgat ctacaagtgg gaaaatttca agcttgaaat caatgagaag   1680
aactcctgga agctcttcca gtttgatttt acaggagtga gcaacaaaac tgaaataatc   1740
acaaccccag ttggtgactt catggtcatg acgattttct tcaatgtgag caggcggttt   1800
ggctatgttg cctttcaaaa ctatgtccct tcttccgtga ccacgatgct ctcctgggtt   1860
tccttttgga tcaagacaga gtctgctcca gcccggacct ctctagggat cacctctgtt   1920
ctgaccatga ccacgttggg caccttttct cgtaagaatt tcccgcgtgt ctcctatatc   1980
acagccttgg atttctatat cgccatctgc ttcgtcttct gcttctgcgc tctgttggag   2040
tttgctgtgc tcaacttcct gatctacaac cagacaaaag cccatgcttc tcctaaactc   2100
cgccatcctc gtatcaatag ccgtgcccat gcccgtaccc gtgcacgttc ccgagcctgt   2160
gcccgccaac atcaggaagc ttttgtgtgc cagattgtca ccactgaggg aagtgatgga   2220
gaggagcgcc cgtcttgctc agcccagcag ccccctagcc caggtagccc tgagggtccc   2280
cgcagcctct gctccaagct ggcctgctgt gagtggtgca agcgttttaa gaagtacttc   2340
tgcatggtcc ccgattgtga gggcagtacc tggcagcagg gccgcctctg catccatgtc   2400
taccgcctgg ataactactc gagagttgtt ttcccagtga ctttcttctt cttcaatgtg   2460
ctctactggc ttgtttgcct taacttgtag gtaccagctg gtaccctgtg ggcaacctc    2520
tccagttccc caggaggtcc aagccccttg ccaagggagt tgggggaaag cagcagcagc   2580
agcaggagcg actagagttt ttcctgcccc attccccaaa cagaagcttg cagagggttt   2640
gtctttgctg cccctctccc ctacctggcc cattcactga gttttctcag cagaccattt   2700
caaattatta ataaatgggc cacctccctc ttcttcaagg agcatccgtg atgctcagtg   2760
```

-continued

```
ttcaaaacca cagccactta gtgatcagct ccctaaaacc atgcctaagt acaggcggat   2820

tagctatctt ccaacaatgc tgaccaccag acaattactg catttttcca gaagcccact   2880

attgcctttg cagtgctttc ggcccagttc tggcctcagc ctcaaagtgc accgactagt   2940

tgcttgccta tacctggcac ctcattaaga tgctgggcag cagtataaca ggaggaagag   3000

atccctctcc tttggtcaga ttattatgtt ctcagttctc tctccctgct accccttttct   3060

ctgcagatag atagacactg gcattatccc tttaggaaga ggggggggca gcaagagagc   3120

ctatttggga cagcattcct ctctctctgc tgctgtgaca tctccctctc cttgctggct   3180

ccatctttcg tctgcactac caattcaatg cccttcatcc aatgggtatc tatttttgtg   3240

tgtgattata gtaactactc cctgctttat atgccaccct cttccttctc tttgacccct   3300

gtgactcttt ctgtaacttt cccagtgact tcccctagcc ctgaccaggc actaggcctt   3360

ggtgacttcc tggggccaag aaactaagga aactcggctt tgcaacaggc attactcgcc   3420

attgattggt gcccacccag ggcacactgt cggagttcta tcacttgctt gacccctgga   3480

cccataaacc agtccactgt tatacccggg gcactctaac catcacaatc aatcaatcaa   3540

attcccttaa atttgtatgg cactggaact ttggcaaagc acttttgaca agttgtgtct   3600

gattggagct tcatgatagc cttgtgacat ctttagggca ggattcttat ccccattttg   3660

cagatgaaaa ccctgagtca cagatttctg tgggactgtg gatctcactg gaagctatcc   3720

aagagcccac tgtcaccttc tagaccacat gatagggcta gacagctcag ttcaccatga   3780

ttctcttctg tcacctctgc tggcacacca gtggcaaggc ccagaatggc gacctctctt   3840

tagctcaatt tctgggcctg aggtgctcag actgccccca agatcaaatc tctcctggct   3900

gtagtaaccc agtggaatga atttggacat gccccaatgc ttctatatgc taagtgaaat   3960

ctgtgtctgt aatttgttgg ggggtggata gggtggggtc tccatctact ttttgtcacc   4020

atcatctgaa atggggaaat atgtaaataa atatatcagc aaagc                   4065


<210> SEQ ID NO 10
<211> LENGTH: 393
<212> TYPE: PRT
<213> ORGANISM: Homo sapiens

<400> SEQUENCE: 10

Met Glu Tyr Thr Ile Asp Ile Ile Phe Ser Gln Thr Trp Tyr Asp Glu
1               5                   10                  15

Arg Leu Cys Tyr Asn Asp Thr Phe Glu Ser Leu Val Leu Asn Gly Asn
            20                  25                  30

Val Val Ser Gln Leu Trp Ile Pro Asp Thr Phe Phe Arg Asn Ser Lys
        35                  40                  45

Arg Thr His Glu His Glu Ile Thr Met Pro Asn Gln Met Val Arg Ile
    50                  55                  60

Tyr Lys Asp Gly Lys Val Leu Tyr Thr Ile Arg Met Thr Ile Asp Ala
65                  70                  75                  80

Gly Cys Ser Leu His Met Leu Arg Phe Pro Met Asp Ser His Ser Cys
                85                  90                  95

Pro Leu Ser Phe Ser Ser Phe Ser Tyr Pro Glu Asn Glu Met Ile Tyr
            100                 105                 110

Lys Trp Glu Asn Phe Lys Leu Glu Ile Asn Glu Lys Asn Ser Trp Lys
        115                 120                 125

Leu Phe Gln Phe Asp Phe Thr Gly Val Ser Asn Lys Thr Glu Ile Ile
    130                 135                 140
```

-continued

Thr Thr Pro Val Gly Asp Phe Met Val Met Thr Ile Phe Phe Asn Val
145 150 155 160

Ser Arg Arg Phe Gly Tyr Val Ala Phe Gln Asn Tyr Val Pro Ser Ser
165 170 175

Val Thr Thr Met Leu Ser Trp Val Ser Phe Trp Ile Lys Thr Glu Ser
180 185 190

Ala Pro Ala Arg Thr Ser Leu Gly Ile Thr Ser Val Leu Thr Met Thr
195 200 205

Thr Leu Gly Thr Phe Ser Arg Lys Asn Phe Pro Arg Val Ser Tyr Ile
210 215 220

Thr Ala Leu Asp Phe Tyr Ile Ala Ile Cys Phe Val Phe Cys Phe Cys
225 230 235 240

Ala Leu Leu Glu Phe Ala Val Leu Asn Phe Leu Ile Tyr Asn Gln Thr
245 250 255

Lys Ala His Ala Ser Pro Lys Leu Arg His Pro Arg Ile Asn Ser Arg
260 265 270

Ala His Ala Arg Thr Arg Ala Arg Ser Arg Ala Cys Ala Arg Gln His
275 280 285

Gln Glu Ala Phe Val Cys Gln Ile Val Thr Thr Glu Gly Ser Asp Gly
290 295 300

Glu Glu Arg Pro Ser Cys Ser Ala Gln Gln Pro Pro Ser Pro Gly Ser
305 310 315 320

Pro Glu Gly Pro Arg Ser Leu Cys Ser Lys Leu Ala Cys Cys Glu Trp
325 330 335

Cys Lys Arg Phe Lys Lys Tyr Phe Cys Met Val Pro Asp Cys Glu Gly
340 345 350

Ser Thr Trp Gln Gln Gly Arg Leu Cys Ile His Val Tyr Arg Leu Asp
355 360 365

Asn Tyr Ser Arg Val Val Phe Pro Val Thr Phe Phe Phe Asn Val
370 375 380

Leu Tyr Trp Leu Val Cys Leu Asn Leu
385 390

<210> SEQ ID NO 11
<211> LENGTH: 2090
<212> TYPE: DNA
<213> ORGANISM: Homo sapiens

<400> SEQUENCE: 11
ttcggcacga gtaagaccag gatgtctctg aaatggacgt cagtctttct gctgatacag 60
ctcagttgtt actttagctc tggaagctgt ggaaaggtgc tagtgtggcc cacagaatac 120
agccattgga taaatatgaa gacaatcctg gaagagcttg ttcagagggg tcatgaggtg 180
actgtgttga catcttcggc ttctactctt gtcaatgcca gtaaatcatc tgctattaaa 240
ttagaagttt atcctacatc tttaactaaa aatgatttgg aagattctct tctgaaaatt 300
ctcgatagat ggatatatgg tgtttcaaaa aatacatttt ggtcatattt ttcacaatta 360
caagaattgt gttgggaata ttatgactac agtaacaagc tctgtaaaga tgcagttttg 420
aataagaaac ttatgatgaa actacaagag tcaaagtttg atgtcattct ggcagatgcc 480
cttaatccct gtggtgagct actggctgaa ctatttaaca taccctttct gtacagtctt 540
cgattctctg ttggctacac atttgagaag aatggtggag gatttctgtt ccctccttcc 600
tatgtacctg ttgttatgtc agaattaagt gatcaaatga ttttcatgga gaggataaaa 660
aatatgatac atatgcttta ttttgacttt tggtttcaaa tttatgatct gaagaagtgg 720

-continued

```
gaccagtttt atagtgaagt tctaggaaga cccactacat tatttgagac aatggggaaa    780
gctgaaatgt ggctcattcg aacctattgg gattttgaat ttcctcgccc attcttacca    840
aatgttgatt ttgttggagg acttcactgt aaaccagcca aacccctgcc taaggaaatg    900
gaagagtttg tgcagagctc tggagaaaat ggtattgtgg tgttttctct ggggtcgatg    960
atcagtaaca tgtcagaaga aagtgccaac atgattgcat cagcccttgc ccagatccca   1020
caaaaggttc tatggagatt tgatggcaag aagccaaata cattaggttc caatactcga   1080
ctgtacaagt ggttacccca gaatgacctt cttggtcatc ccaaaaccaa agcttttata   1140
actcatggtg gaaccaatgg catctatgag gcgatctacc atgggatccc tatggtgggc   1200
attcccttgt ttgcggatca acatgataac attgctcaca tgaaagccaa gggagcagcc   1260
ctcagtgtgg acatcaggac catgtcaagt agagatttgc tcaatgcatt gaagtcagtc   1320
attaatgacc ctgtctataa agagaatgtc atgaaattat caagaattca tcatgaccaa   1380
ccaatgaagc ccctggatcg agcagtcttc tggattgagt ttgtcatgcg ccacaaagga   1440
gccaagcacc ttcgagtcgc agctcacaac ctcacctgga tccagtacca ctctttggat   1500
gtgatagcat tcctgctggc ctgcgtggca actgtgatat ttatcatcac aaaatttttgc  1560
ctgttttgtt tccgaaagct tgccaaaaca ggaaagaaga agaaaagaga ttagttatat   1620
caaaagcctg aagtggaatg actgaaagat gggactcctc ctttatttca gcatggaggg   1680
ttttaaatgg aggatttcct ttttcctgtg acaaaacatc ttttcacaac ttaccttgtt   1740
aagacaaaat ttattttcca gggatttaat acgtacttta gttggaatta ttctatgtca   1800
atgattttta agctatgaaa aatacaatgg ggggaaggat agcatttgga gatataccta   1860
atgttaaatg acgagttact ggatgcagca cgcaacatgg cacatgtgta tacatatgta   1920
gctaaccctt cgttgtgcac atgtacccta aaacttaaag tataatttaa aaaaagcaaa   1980
aaaaaaaaat accaactctt ttttttaaac caggaaggaa aatgtgaaca tggaaacaac   2040
ttctagtatt ggatctgaaa ataaagtgtc atccaagcca taaaaaaaaa              2090
```

<210> SEQ ID NO 12
<211> LENGTH: 530
<212> TYPE: PRT
<213> ORGANISM: Homo sapiens

<400> SEQUENCE: 12

```
Met Ser Leu Lys Trp Thr Ser Val Phe Leu Leu Ile Gln Leu Ser Cys
  1               5                  10                  15

Tyr Phe Ser Ser Gly Ser Cys Gly Lys Val Leu Val Trp Pro Thr Glu
             20                  25                  30

Tyr Ser His Trp Ile Asn Met Lys Thr Ile Leu Glu Glu Leu Val Gln
         35                  40                  45

Arg Gly His Glu Val Thr Val Leu Thr Ser Ser Ala Ser Thr Leu Val
     50                  55                  60

Asn Ala Ser Lys Ser Ser Ala Ile Lys Leu Glu Val Tyr Pro Thr Ser
 65                  70                  75                  80

Leu Thr Lys Asn Asp Leu Glu Asp Ser Leu Leu Lys Ile Leu Asp Arg
                 85                  90                  95

Trp Ile Tyr Gly Val Ser Lys Asn Thr Phe Trp Ser Tyr Phe Ser Gln
            100                 105                 110

Leu Gln Glu Leu Cys Trp Glu Tyr Tyr Asp Tyr Ser Asn Lys Leu Cys
        115                 120                 125
```

-continued

```
Lys Asp Ala Val Leu Asn Lys Lys Leu Met Met Lys Leu Gln Glu Ser
    130                 135                 140

Lys Phe Asp Val Ile Leu Ala Asp Ala Leu Asn Pro Cys Gly Glu Leu
145                 150                 155                 160

Leu Ala Glu Leu Phe Asn Ile Pro Phe Leu Tyr Ser Leu Arg Phe Ser
                165                 170                 175

Val Gly Tyr Thr Phe Glu Lys Asn Gly Gly Gly Phe Leu Phe Pro Pro
            180                 185                 190

Ser Tyr Val Pro Val Val Met Ser Glu Leu Ser Asp Gln Met Ile Phe
        195                 200                 205

Met Glu Arg Ile Lys Asn Met Ile His Met Leu Tyr Phe Asp Phe Trp
    210                 215                 220

Phe Gln Ile Tyr Asp Leu Lys Lys Trp Asp Gln Phe Tyr Ser Glu Val
225                 230                 235                 240

Leu Gly Arg Pro Thr Thr Leu Phe Glu Thr Met Gly Lys Ala Glu Met
                245                 250                 255

Trp Leu Ile Arg Thr Tyr Trp Asp Phe Glu Phe Pro Arg Pro Phe Leu
            260                 265                 270

Pro Asn Val Asp Phe Val Gly Gly Leu His Cys Lys Pro Ala Lys Pro
        275                 280                 285

Leu Pro Lys Glu Met Glu Glu Phe Val Gln Ser Ser Gly Glu Asn Gly
    290                 295                 300

Ile Val Val Phe Ser Leu Gly Ser Met Ile Ser Asn Met Ser Glu Glu
305                 310                 315                 320

Ser Ala Asn Met Ile Ala Ser Ala Leu Ala Gln Ile Pro Gln Lys Val
                325                 330                 335

Leu Trp Arg Phe Asp Gly Lys Lys Pro Asn Thr Leu Gly Ser Asn Thr
            340                 345                 350

Arg Leu Tyr Lys Trp Leu Pro Gln Asn Asp Leu Leu Gly His Pro Lys
        355                 360                 365

Thr Lys Ala Phe Ile Thr His Gly Gly Thr Asn Gly Ile Tyr Glu Ala
    370                 375                 380

Ile Tyr His Gly Ile Pro Met Val Gly Ile Pro Leu Phe Ala Asp Gln
385                 390                 395                 400

His Asp Asn Ile Ala His Met Lys Ala Lys Gly Ala Ala Leu Ser Val
                405                 410                 415

Asp Ile Arg Thr Met Ser Ser Arg Asp Leu Leu Asn Ala Leu Lys Ser
            420                 425                 430

Val Ile Asn Asp Pro Val Tyr Lys Glu Asn Val Met Lys Leu Ser Arg
        435                 440                 445

Ile His His Asp Gln Pro Met Lys Pro Leu Asp Arg Ala Val Phe Trp
    450                 455                 460

Ile Glu Phe Val Met Arg His Lys Gly Ala Lys His Leu Arg Val Ala
465                 470                 475                 480

Ala His Asn Leu Thr Trp Ile Gln Tyr His Ser Leu Asp Val Ile Ala
                485                 490                 495

Phe Leu Leu Ala Cys Val Ala Thr Val Ile Phe Ile Ile Thr Lys Phe
            500                 505                 510

Cys Leu Phe Cys Phe Arg Lys Leu Ala Lys Thr Gly Lys Lys Lys Lys
        515                 520                 525

Arg Asp
    530
```

-continued

<210> SEQ ID NO 13
<211> LENGTH: 1934
<212> TYPE: DNA
<213> ORGANISM: Homo sapiens

<400> SEQUENCE: 13
ctgtcattca tgctttggaa aagtttactg tatatacatt agacattcct gttctttttg 60
gagttagtac tacatcccct gaagaaacat gtgcccaggt gattcgtgaa gctaagagaa 120
cagcaccaag tatagtgtat gttcctcata tccacgtgtg gtgggaaata gttggaccga 180
cacttaaagc cacatttacc acattattac agaatattcc ttcatttgct ccagttttac 240
tacttgcaac ttctgacaaa ccccattccg ctttgccaga agaggtgcaa gaattgttta 300
tccgtgatta tggagagatt tttaatgtcc agttaccgga taaagaagaa cggacaaaat 360
tttttgaaga tttaattcta aaacaagctg ctaagcctcc tatatcaaaa aagaaagcag 420
ttttgcaggc tttggaggta ctcccagtag caccaccacc tgagccaaga tcactgacag 480
cagaagaagt gaaacgacta gaagaacaag aagaagatac atttagagaa ctgaggattt 540
tcttaagaaa tgttacacat aggcttgcta ttgacaagcg attccgagtg tttactaagc 600
ctgttgaccc tgatgaggtt cctgattatg tcactgtaat aaagcaacca atggaccttt 660
catctgtaat cagtaaaatt gatctacaca agtatctgac tgtgaaagac tatttgagag 720
atattgatct aatctgtagt aatgccttag aatacaatcc agatagagat cctggagatc 780
gtcttattag gcatagagcc tgtgctttaa gagatactgc ctatgccata attaaagaag 840
aacttgatga agactttgag cagctctgtg aagaaattca ggaatctaga aagaaaagag 900
gttgtagctc ctccaaatat gccccgtctt actaccatgt gatgccaaag caaaattcca 960
ctcttgttgg tgataaaaga tcagacccag agcagaatga aaagctaaag acaccgagta 1020
ctcctgtggc ttgcagcact cctgctcagt tgaagaggaa aattcgcaaa aagtcaaact 1080
ggtacttagg caccataaaa aagcgaagga agatttcaca ggcaaaggat gatagccaga 1140
atgccataga tcacaaaatt gagagtgata cagaggaaac tcaagacaca agtgtagatc 1200
ataatgagac cggaaacaca ggagagtctt cggtggaaga aaatgaaaaa cagcaaaatg 1260
cctctgaaag caaactggaa ttgagaaata attcaaatac ttgtaatata gagaatgagc 1320
ttgaagactc taggaagact acagcatgta cagaattgag agacaagatt gcttgtaatg 1380
gagatgcttc tagctctcag ataatacata tttctgatga aaatgaagga aaagaaatgt 1440
gtgttctgcg aatgactcga gctagacgtt cccaggtaga acagcagcag ctcatcactg 1500
ttgaaaaggc tttggcaatt ctttctcagc ctacaccctc acttgttgtg gatcatgagc 1560
gattaaaaaa tcttttgaag actgttgtta aaaaaagtca aaactacaac atatttcagt 1620
tggaaaattt gtatgcagta atcagccaat gtatttatcg gcatcgcaag gaccatgata 1680
aaacatcact tattcagaaa atggagcaag aggtagaaaa cttcagttgt tccagatgat 1740
gatgtcatgg tatcgagtat tctttatatt cagttcctat ttaagtcatt tttgtcatgt 1800
ccgcctaatt gatgtagtat gaaaccctgc atctttaagg aaaagattaa aatagtaaaa 1860
taaaagtatt taaactttcc tgatatttat gtacatatta agataaatgt catgtgtaag 1920
ataactgata aata 1934

<210> SEQ ID NO 14
<211> LENGTH: 362
<212> TYPE: PRT
<213> ORGANISM: Homo sapiens -continued

<400> SEQUENCE: 14

```
Met Asp Leu Ser Ser Val Ile Ser Lys Ile Asp Leu His Lys Tyr Leu
  1               5                  10                  15

Thr Val Lys Asp Tyr Leu Arg Asp Ile Asp Leu Ile Cys Ser Asn Ala
            20                  25                  30

Leu Glu Tyr Asn Pro Asp Arg Asp Pro Gly Asp Arg Leu Ile Arg His
        35                  40                  45

Arg Ala Cys Ala Leu Arg Asp Thr Ala Tyr Ala Ile Ile Lys Glu Glu
    50                  55                  60

Leu Asp Glu Asp Phe Glu Gln Leu Cys Glu Glu Ile Gln Glu Ser Arg
 65                  70                  75                  80

Lys Lys Arg Gly Cys Ser Ser Ser Lys Tyr Ala Pro Ser Tyr Tyr His
                 85                  90                  95

Val Met Pro Lys Gln Asn Ser Thr Leu Val Gly Asp Lys Arg Ser Asp
            100                 105                 110

Pro Glu Gln Asn Glu Lys Leu Lys Thr Pro Ser Thr Pro Val Ala Cys
        115                 120                 125

Ser Thr Pro Ala Gln Leu Lys Arg Lys Ile Arg Lys Lys Ser Asn Trp
    130                 135                 140

Tyr Leu Gly Thr Ile Lys Lys Arg Arg Lys Ile Ser Gln Ala Lys Asp
145                 150                 155                 160

Asp Ser Gln Asn Ala Ile Asp His Lys Ile Glu Ser Asp Thr Glu Glu
                165                 170                 175

Thr Gln Asp Thr Ser Val Asp His Asn Glu Thr Gly Asn Thr Gly Glu
            180                 185                 190

Ser Ser Val Glu Glu Asn Glu Lys Gln Gln Asn Ala Ser Glu Ser Lys
        195                 200                 205

Leu Glu Leu Arg Asn Asn Ser Asn Thr Cys Asn Ile Glu Asn Glu Leu
    210                 215                 220

Glu Asp Ser Arg Lys Thr Thr Ala Cys Thr Glu Leu Arg Asp Lys Ile
225                 230                 235                 240

Ala Cys Asn Gly Asp Ala Ser Ser Ser Gln Ile Ile His Ile Ser Asp
                245                 250                 255

Glu Asn Glu Gly Lys Glu Met Cys Val Leu Arg Met Thr Arg Ala Arg
            260                 265                 270

Arg Ser Gln Val Glu Gln Gln Gln Leu Ile Thr Val Glu Lys Ala Leu
        275                 280                 285

Ala Ile Leu Ser Gln Pro Thr Pro Ser Leu Val Val Asp His Glu Arg
    290                 295                 300

Leu Lys Asn Leu Leu Lys Thr Val Val Lys Lys Ser Gln Asn Tyr Asn
305                 310                 315                 320

Ile Phe Gln Leu Glu Asn Leu Tyr Ala Val Ile Ser Gln Cys Ile Tyr
                325                 330                 335

Arg His Arg Lys Asp His Asp Lys Thr Ser Leu Ile Gln Lys Met Glu
            340                 345                 350

Gln Glu Val Glu Asn Phe Ser Cys Ser Arg
        355                 360
```

<210> SEQ ID NO 15
<211> LENGTH: 2449
<212> TYPE: DNA
<213> ORGANISM: Homo sapiens

<400> SEQUENCE: 15

-continued

```
tatatgtgac ctttttaaaa aatgagctgt aagcagtctc ccagacagta gctcagcctc     60
cagaactctc tttctgcata gttgaagacc cctcttcaca caagatggta gcaacaaatc    120
ataggtgcaa ttgcaccaaa ttcacagaag atcaattgaa aatcctcatc aataccttca    180
ctcaaaaacc ttacccaggt tatgctacca aacaaaaact tgctttagca atcaatgcag    240
aagagtccag aatccagatt tggtttcaga atcaaagagc taggcatgga ttccagaaaa    300
caccagaacc tgactttaga tttaagccac agccatggac aagattaacc tggtgtggag    360
tttcaaaata gagaagccag atggtgttgt accacctata gcacctttca attacacaca    420
atcatccatg catttatgaa aaacccatac cctgggattg attccggaga acaacttgct    480
gaagaaattg gtgcttcaga gtcaagagtc caaatttggt tccaaaatca aagatctaga    540
tttcatctcc agagaaaaag agaacctgtt atgtccttag aatgagaaga ccagagaaga    600
ccaggggcaa ggtttctgag ggacttcaag gtacagaaga tacacaaagt ggcaccagcc    660
tcactagcac tctcatttct caagagccag aacatggtga atacagtcaa gttcagtgta    720
tttgataata tcaatttggg ccccaaatct ctctcacagt cttcctggga gtctattctt    780
cttccaaaag tgcaagctaa gccttctgaa gatggtaaag aacttggccg ggtgtggtgg    840
ctcatgcctg taatcccagc actttaggag gctgaggctg gaagattgct tgagcctagg    900
agtttgaaac cagtctgagc aacatagtaa gaccctgtct ctattctaaa aaacaaaata    960
agtaaaaagg actgtaggag gccaagacag gtacaggagg caccacacta ccctgttgac   1020
acagcctgga tccagagttc agcagacctt gagacaatga aaacaaactt agtaataatc   1080
atttttcaat cattgcagta attattgatt tggacaaaaa tcaattgacg tcaaaacctt   1140
aaagtgacgt ttctctgcct atggagtggt cattctttta ttcctttagt ttcataataa   1200
attttctttt acttaaaaaa acttatagtt tgatgaagag tgagatatat acctcatctc   1260
aaagaatctt cacacacaca cttattaatt acaaaaggaa aatcagtaat tttgcagtgg   1320
agacatatgg ccaactccac cttacccaag tggctgaaag tcactgcacc agtaatggca   1380
caaaccaatg tgagatgatt cctgatatga tacactaaaa agggcactgt ctcttctgca   1440
tgttgcagac aaaaagtggg taagctgaca ctgaaactaa taattaggca atgtcaagca   1500
aatacaaatt caagttgaca gtctgcaaag taacatccat gtactcttca acaatggatc   1560
gaccctagct actcaggagg ctgaggtgga ataattgttt gaggccagga gttccagatc   1620
agcctgggca acatcatgcg accccatctc taaaaacatc tttttaaaaa tgagccaggt   1680
gtggtagcat gcacccgtag tctcagctac tcaggagcct gaggcaggag gatggtttca   1740
acataggaga tcgaggctgc tgtgagctat gatcgtgcta ctgcactcca gcctgggtga   1800
cacagcaagt tcctgtttcc aaacaacaac aagaaaacaa aacaaaacaa aacaaaaaat   1860
agatagaata gtgacaataa aaatggagaa aaagtaggct gactcaggaa atgcttagaa   1920
agtacagcca tacctcaaag atattgtaga tttgattcga gaccaccaca ataaagcaga   1980
tattgctaca aagtgagtca cacaaattgt tttgtttcct tgtgaatatg aagttatatt   2040
ggctgggtgt gatggctcat gcctataatc ccagtacttt aggagacgga ggcgggaggg   2100
tcacttgagc ccaggaattg tgagatcaac ctgggcatat agggagatcc tgtctctatt   2160
taaaaaaaga agctatgttt acactacact atagtctatt taaagtgtga aatggcgtta   2220
tgtccttaat tttaaaactc ttgatgctgg ctgggttcgg tggctcatac ctgtaatccc   2280
atcactttgg gaggccaaga caggttgatt acttgaattc aggagttcaa gaccagcctg   2340
gacaacatgg caaaacacgt ctttaaaaaa agaaaagaaa aaagaaaaac agaaagaaaa   2400
```

-continued agaagaaaaa ctacttgctg cccttacttg aagctcaatt atttaaaac 2449

<210> SEQ ID NO 16
<211> LENGTH: 565
<212> TYPE: DNA
<213> ORGANISM: Homo sapiens

<400> SEQUENCE: 16
cttttttttt tttttttttt tagtagagac agggtttcac catgttagcc aggatggtct 60
cgatctcctg acctcatgat cttcctgctt tggcctccca aagtgctgcg attacaggcg 120
tgagccactg cacccagccc agagtttttt ttaacaaggt tcttctcagc aattctagta 180
tccagatata ggcccatcat agacatcaca caagcgtgta cttcataatc ctggtgaata 240
cagaagtttc ctggactcct tgatgagcta ctgctttcgc tcctatatca gtgttttcag 300
ctgatgtcat ttgtgattgt gtttctgact ttctgtaggc agaaaaaaac tttcattttt 360
tttttgctta catgcacata aatgtaagcg ctaattctta tattaaactg tttatttcta 420
taatacttaa ttggctgttt tcctggctga accaaaccaa gagcataagg aatgataacc 480
ttcaaaactg attaaattag agatcaataa atggagctgt tttaattcta ttattcttct 540
ttcatagatt aaatagaaaa ttttt 565

<210> SEQ ID NO 17
<211> LENGTH: 640
<212> TYPE: DNA
<213> ORGANISM: Homo sapiens
<220> FEATURE:
<221> NAME/KEY: modified_base
<222> LOCATION: (631)
<223> OTHER INFORMATION: a, g, c, t, unknown or other

<400> SEQUENCE: 17
ggcacgagaa gacgccacat cccctattat agaagagcta ataaatttcc atgatcacac 60
actaataatt gttttcctaa ttagctcctt agtcctctat atcatctcgc taatattaac 120
aacaaaacta acacatacaa gcacaataga tgcacaagaa gttgaaacca tttgaactat 180
tctaccagct gtaatcctta tcataattgc tctcccctct ctacgcattc tatatataat 240
agacgaaatc aacaaccccg tattaaccgt taaaaccata gggcaccaat gatactgaag 300
ctacgaatat actgactatg aagacctatg ctttgattca tatataatcc caacaaacga 360
cctaaaacct ggtgaactac gactgctaga agttgataac cgagtcgttc tgccaataga 420
acttccaatc cgtatattaa tttcatctga agacgtcctc cactcatgag cagtcccctc 480
cctaggactt aaaactgatg ccatcccagg ccgactaaat ccagcacagt acatcaaccg 540
accagggtta ttctatggcc aatgtctgaa tttgtggtct taccatagct ttttgccatt 600
gtcctagaat gggtccctaa aatatttcgg nactggtctg 640

<210> SEQ ID NO 18
<211> LENGTH: 653
<212> TYPE: DNA
<213> ORGANISM: Homo sapiens
<220> FEATURE:
<221> NAME/KEY: modified_base
<222> LOCATION: (547)
<223> OTHER INFORMATION: a, g, c, t, unknown or other
<220> FEATURE:
<221> NAME/KEY: modified_base
<222> LOCATION: (625)
<223> OTHER INFORMATION: a, g, c, t, unknown or other -continued

<400> SEQUENCE: 18
gtgtacatca gagcaaaaat acagagtatt tattcatttc ttcccactag agggacacac 60
tgttcttgga cagacaaatg aatcatcagt tgtcaggagt tgcctttgga gaatgatcaa 120
tgaactcctt ttcaggggtt ggaaattgat accagggtcc atcacctcgg gcacgcatca 180
gccttcgaac ttcctgctcc tttaaccgta actcagcctt ttcagattca atctggagga 240
tagccagggt tttctcgtag ttcttttcag ggccatcata gaaattccgg gcgatccatc 300
ttgatatcgg atgcttgtaa tactcccagt gttcagggat gtagccttct gggatttctg 360
caagctcggc ttcaccaata aatatgttca ccagtgttat gccaattata actgggatcc 420
cagtcaacat aaggtagaat ttcattaacc tcaagaagcg agcgtcatag tataaagaag 480
gcttgacgac aaacagtctc ttgccatgtc cccactgtgc cgcacaggag cgacagtctt 540
cggaaantcc gcgtgagaaa acttccgact ccgagtctag gaccagcgcg gcggcaagac 600
cacgctgtca gcgcggagac cgaanccgct gcagcagctc atggccgcca tgg 653

<210> SEQ ID NO 19
<211> LENGTH: 411
<212> TYPE: DNA
<213> ORGANISM: Homo sapiens
<220> FEATURE:
<221> NAME/KEY: modified_base
<222> LOCATION: (10)
<223> OTHER INFORMATION: a, g, c, t, unknown or other

<400> SEQUENCE: 19
tagtccagtn aattacttta atttcgcttt tccataatac tggtattcca tagaagaaaa 60
tcttttatta atattctata ctactacatc cgacaccaga tgactaaagt ttgcaatggt 120
ccaaaattct gtaaacccat taaatgcaat tcatacttta ttttggcagt attcatttca 180
tcattacttt atttggatgc taacgcaagt acttctaagg aaaagctgtc atataattac 240
tttagtcaag cattcagtag aggcaataat caaacctcta tcccaacatt ttacacttgt 300
aacagaatga aggatgaggt acaacataca tttttggcaa tttactatta agggccataa 360
tcattttagg ggcgcttagg gcccatatat atatatatat atttttggac a 411

<210> SEQ ID NO 20
<211> LENGTH: 3840
<212> TYPE: DNA
<213> ORGANISM: Homo sapiens

<400> SEQUENCE: 20
gccgggcggc tgcgctgagc agaggccgag cccgggacgc gccgagggac tgcggggctg 60
cgggtcatgg atgcggcggc agcggcgcgg gacggcggga gcccggccgc gaccaggtga 120
ggaggcggcg tccggcgcca ctgcagccgc agcggcctcg gaggaagagg gctcgccgcc 180
gcgcgcccgc ccgccgtcgc tgcccttcct gttgggatta tcttctgctc cccgctgctt 240
cttcgctccc cgcggtcgaa gccgcctcta ggcttcagcg gctcggactc cttggcagcc 300
ggtgcctctg ctacctgggc ctcgtagctg ggagaccctt gggcgagacc atgaggaaat 360
tcaacatcag gaaggtgctg gacggcctga ccgcaggctc gtcctcggcc tcgcaacagc 420
agcaacagca gcagcacccg cctgggaacc gggagcccga gatccaggag acgctccagt 480
ccgagcactt ccaactctgc aagactgttc gccatggatt tccctatcag ccctcagccc 540
tggcctttga tcccgttcag aagatcctgg cggtaggaac ccagactggt gctttaaggc 600
tctttggtcg tccaggggtg gaatgttatt gccagcacga cagcggagcg gcagtgattc 660

-continued

```
aactccagtt cctgattaat gagggagccc ttgtgagtgc cttggctgat gacaccttac    720
acttgtggaa tttacgtcag aaaaggcctg ctgtgctaca ttcactcaaa ttttgcagag    780
aaagggttac attttgccat ctgcctttcc agagtaagtg gctctatgtg ggcacggaac    840
gaggtaatat acatattgtc aatgtggagt ccttcacact ctcaggctac gtcattatgt    900
ggaataaagc catcgaactg tcatctaaat ctcacccagg acctgttgtc catataagtg    960
ataatcccat ggacgagggg aagcttctga ttggctttga atctggaaca gtagtcttat   1020
gggaccttaa gtcaaagaag gctgactaca gatacactta cgacgaggct attcactctg   1080
tggcttggca tcatgaagga aaacagttta tttgcagtca ttctgatggt acattgacca   1140
tatggaatgt gaggtcccct actaaacctg tacagaccat cactcctcac ggaaaacagt   1200
taaaggatgg gaagaaaccc gagccgtgca agcctatcct caaggtggag ttcaagacaa   1260
caagatcggg ggaacctttt attattttgt cgggaggctt atcatatgat accgtgggaa   1320
gaagaccttg cttaacagtg atgcatggga aaagcacggc agtgctggaa atggactatt   1380
caattgtcga ctttctcaca ctctgtgaaa cgccatatcc aaatgatttt caggagccgt   1440
atgctgtggt tgttctcctg gagaaggatt tagtgctgat agacctggca cagaatggat   1500
accctatatt tgagaatccc taccctttga gtatacacga gtcccctgtt acatgttgtg   1560
aatattttgc tgattgtcct gtggacctta ttcctgcact ttattctgtt ggagctagac   1620
agaaacgtca aggttacagc aaaaaggaat ggcccatcaa tggtggtaat tggggcttgg   1680
gtgctcaaag ttacccagaa ataattatta cagggcatgc tgatggctca attaaattct   1740
gggatgcttc tgcaataact ctacaagtac tgtataaatt aaaaacatct aaagtatttg   1800
aaaagtcaag aaataaagat gacagacaga acaccgacat tgtagatgaa gatccatatg   1860
ccattcagat catctcctgg tgcccagaga gcagaatgct gtgcatagcc ggagtgtcgg   1920
ctcatgtcat catttataga ttcagcaagc aggaagtggt tacagaagtc atcccgatgc   1980
ttgaagtccg actgttatat gaaataaatg atgtggaaac gccggagggt gagcagccac   2040
ccccttttgtc cactcccgtg ggcagctcca cctctcagcc catccccccct cagtctcatc   2100
cgtctaccag cagcagctca tcggacgggc ttcgagataa tgtaccgtgt ttaaaagtta   2160
aaaactcacc acttaaacag tctcccggct atcaaacaga gctagtcatc cagttggtgt   2220
gggtgggtgg agaacccccg cagcagatca ccagcctagc actcaactct tcctacggat   2280
tggtggtttt cggcaactcc aatggcattg caatggttga ctacctccag aaagcagtgc   2340
tgctcaacct cagcaccatt gaactatacg gctcaaatga tccttatcgg agagaaccga   2400
ggtcgccccg caaatctcga cagccttcag gagcgggcct gtgtgatatt accgaaggaa   2460
ctgtcgtccc agaggatcgc tgcaaatctc cgacttccgc aaagatgtca aggaaattaa   2520
gcttgccaac tgatctaaag cctgatttag atgtgaaaga caattccttc agcagatctc   2580
ggagttcaag tgtgaccagc attgacaaag agtcccggga agccatttct gctcttcatt   2640
tctgtgagac tttcacaagg aaggcagact cctccccctc cccgtgcctg tgggtgggaa   2700
ccacagtggg aactgccttt gtcatcacgc tgaatctccc cctggggcct gagcagagac   2760
tgcttcagcc agtgattgtg tctccaagcg gtactatatt gaggttaaaa ggtgcgatct   2820
tgagaatggc atttctggat gccgcgggct gcttaatgcc acctgcatac gaaccctgga   2880
cagagcacaa cgttcctgaa gaaaaagacg aaaaggagaa attgaaaaag cggcgacctg   2940
tctcagtgtc cccctcctct tctcaggaaa ttagtgaaaa ccagtacgca gtgatatgtt   3000
```

-continued

```
ctgaaaagca agcaaaggtc atctcactgc caacccagaa ctgtgcatac aagcagaaca   3060

tcactgagac gtccttcgtg ctccgtggag acattgtcgc cctgagtaac agtgtctgcc   3120

tcgcctgctt ctgtgccaac ggccacatta tgactttcag tttgccgagc ttgaggcctc   3180

tgctggatgt ctactacctg ccccttacca acatgcggat agccaggaca ttctgcttcg   3240

ccaacagtgg gcaagcctta taccttgttt cacctaccga aatccagaga ctcacctaca   3300

gtcaggagac gtgtgaaaac cttcaggaga tgcttggtga gctcttcacg cctgtagaaa   3360

caccagaagc accaaacaga gggttcttca aaggcttatt tggaggtggt gcacaatctc   3420

ttgatagaga agaactgttt ggagagtcat cctcgggaaa ggcgtcaagg agccttgcac   3480

agcacatccc gggtcctggc gggatcgaag gtgtgaaggg agccgcgtcg ggagtggtgg   3540

gagaactggc ccgagccagg ctggccctcg acgaaagagg acagaagctc agcgacttgg   3600

aagagaggac tgcagccatg atgtccagtg cagactcgtt ttccaaacat gctcatgaga   3660

tgatgctgaa atacaaagat aagaagtggt accagttctg acaagtagca ctcagtaagt   3720

ccagcttcaa ccagaaggaa aaagacgttt ccttgttgag gtcactgatg tatttgggaa   3780

agataacata aaagggatgc acactgctga cagcgtcttt cccagcacaa tcatgcactt   3840
```

<210> SEQ ID NO 21
<211> LENGTH: 1116
<212> TYPE: PRT
<213> ORGANISM: Homo sapiens

<400> SEQUENCE: 21

```
Met Arg Lys Phe Asn Ile Arg Lys Val Leu Asp Gly Leu Thr Ala Gly
  1               5                  10                  15

Ser Ser Ser Ala Ser Gln Gln Gln Gln Gln Gln Gln His Pro Pro Gly
             20                  25                  30

Asn Arg Glu Pro Glu Ile Gln Glu Thr Leu Gln Ser Glu His Phe Gln
         35                  40                  45

Leu Cys Lys Thr Val Arg His Gly Phe Pro Tyr Gln Pro Ser Ala Leu
     50                  55                  60

Ala Phe Asp Pro Val Gln Lys Ile Leu Ala Val Gly Thr Gln Thr Gly
 65                  70                  75                  80

Ala Leu Arg Leu Phe Gly Arg Pro Gly Val Glu Cys Tyr Cys Gln His
                 85                  90                  95

Asp Ser Gly Ala Ala Val Ile Gln Leu Gln Phe Leu Ile Asn Glu Gly
            100                 105                 110

Ala Leu Val Ser Ala Leu Ala Asp Asp Thr Leu His Leu Trp Asn Leu
        115                 120                 125

Arg Gln Lys Arg Pro Ala Val Leu His Ser Leu Lys Phe Cys Arg Glu
    130                 135                 140

Arg Val Thr Phe Cys His Leu Pro Phe Gln Ser Lys Trp Leu Tyr Val
145                 150                 155                 160

Gly Thr Glu Arg Gly Asn Ile His Ile Val Asn Val Glu Ser Phe Thr
                165                 170                 175

Leu Ser Gly Tyr Val Ile Met Trp Asn Lys Ala Ile Glu Leu Ser Ser
            180                 185                 190

Lys Ser His Pro Gly Pro Val Val His Ile Ser Asp Asn Pro Met Asp
        195                 200                 205

Glu Gly Lys Leu Leu Ile Gly Phe Glu Ser Gly Thr Val Val Leu Trp
    210                 215                 220

Asp Leu Lys Ser Lys Lys Ala Asp Tyr Arg Tyr Thr Tyr Asp Glu Ala
```

-continued

```
225                 230                 235                 240

Ile His Ser Val Ala Trp His His Glu Gly Lys Gln Phe Ile Cys Ser
                245                 250                 255

His Ser Asp Gly Thr Leu Thr Ile Trp Asn Val Arg Ser Pro Thr Lys
            260                 265                 270

Pro Val Gln Thr Ile Thr Pro His Gly Lys Gln Leu Lys Asp Gly Lys
        275                 280                 285

Lys Pro Glu Pro Cys Lys Pro Ile Leu Lys Val Glu Phe Lys Thr Thr
    290                 295                 300

Arg Ser Gly Glu Pro Phe Ile Ile Leu Ser Gly Gly Leu Ser Tyr Asp
305                 310                 315                 320

Thr Val Gly Arg Arg Pro Cys Leu Thr Val Met His Gly Lys Ser Thr
                325                 330                 335

Ala Val Leu Glu Met Asp Tyr Ser Ile Val Asp Phe Leu Thr Leu Cys
            340                 345                 350

Glu Thr Pro Tyr Pro Asn Asp Phe Gln Glu Pro Tyr Ala Val Val Val
        355                 360                 365

Leu Leu Glu Lys Asp Leu Val Leu Ile Asp Leu Ala Gln Asn Gly Tyr
    370                 375                 380

Pro Ile Phe Glu Asn Pro Tyr Pro Leu Ser Ile His Glu Ser Pro Val
385                 390                 395                 400

Thr Cys Cys Glu Tyr Phe Ala Asp Cys Pro Val Asp Leu Ile Pro Ala
                405                 410                 415

Leu Tyr Ser Val Gly Ala Arg Gln Lys Arg Gln Gly Tyr Ser Lys Lys
            420                 425                 430

Glu Trp Pro Ile Asn Gly Gly Asn Trp Gly Leu Gly Ala Gln Ser Tyr
        435                 440                 445

Pro Glu Ile Ile Ile Thr Gly His Ala Asp Gly Ser Ile Lys Phe Trp
    450                 455                 460

Asp Ala Ser Ala Ile Thr Leu Gln Val Leu Tyr Lys Leu Lys Thr Ser
465                 470                 475                 480

Lys Val Phe Glu Lys Ser Arg Asn Lys Asp Asp Arg Gln Asn Thr Asp
                485                 490                 495

Ile Val Asp Glu Asp Pro Tyr Ala Ile Gln Ile Ile Ser Trp Cys Pro
            500                 505                 510

Glu Ser Arg Met Leu Cys Ile Ala Gly Val Ser Ala His Val Ile Ile
        515                 520                 525

Tyr Arg Phe Ser Lys Gln Glu Val Val Thr Glu Val Ile Pro Met Leu
    530                 535                 540

Glu Val Arg Leu Leu Tyr Glu Ile Asn Asp Val Glu Thr Pro Glu Gly
545                 550                 555                 560

Glu Gln Pro Pro Pro Leu Ser Thr Pro Val Gly Ser Ser Thr Ser Gln
                565                 570                 575

Pro Ile Pro Pro Gln Ser His Pro Ser Thr Ser Ser Ser Ser Ser Asp
            580                 585                 590

Gly Leu Arg Asp Asn Val Pro Cys Leu Lys Val Lys Asn Ser Pro Leu
        595                 600                 605

Lys Gln Ser Pro Gly Tyr Gln Thr Glu Leu Val Ile Gln Leu Val Trp
    610                 615                 620

Val Gly Gly Glu Pro Pro Gln Gln Ile Thr Ser Leu Ala Leu Asn Ser
625                 630                 635                 640

Ser Tyr Gly Leu Val Val Phe Gly Asn Ser Asn Gly Ile Ala Met Val
                645                 650                 655
```

-continued

```
Asp Tyr Leu Gln Lys Ala Val Leu Leu Asn Leu Ser Thr Ile Glu Leu
            660                 665                 670

Tyr Gly Ser Asn Asp Pro Tyr Arg Arg Glu Pro Arg Ser Pro Arg Lys
        675                 680                 685

Ser Arg Gln Pro Ser Gly Ala Gly Leu Cys Asp Ile Thr Glu Gly Thr
    690                 695                 700

Val Val Pro Glu Asp Arg Cys Lys Ser Pro Thr Ser Ala Lys Met Ser
705                 710                 715                 720

Arg Lys Leu Ser Leu Pro Thr Asp Leu Lys Pro Asp Leu Asp Val Lys
                725                 730                 735

Asp Asn Ser Phe Ser Arg Ser Arg Ser Ser Ser Val Thr Ser Ile Asp
            740                 745                 750

Lys Glu Ser Arg Glu Ala Ile Ser Ala Leu His Phe Cys Glu Thr Phe
        755                 760                 765

Thr Arg Lys Ala Asp Ser Ser Pro Ser Pro Cys Leu Trp Val Gly Thr
    770                 775                 780

Thr Val Gly Thr Ala Phe Val Ile Thr Leu Asn Leu Pro Leu Gly Pro
785                 790                 795                 800

Glu Gln Arg Leu Leu Gln Pro Val Ile Val Ser Pro Ser Gly Thr Ile
                805                 810                 815

Leu Arg Leu Lys Gly Ala Ile Leu Arg Met Ala Phe Leu Asp Ala Ala
            820                 825                 830

Gly Cys Leu Met Pro Pro Ala Tyr Glu Pro Trp Thr Glu His Asn Val
        835                 840                 845

Pro Glu Glu Lys Asp Glu Lys Glu Lys Leu Lys Lys Arg Arg Pro Val
    850                 855                 860

Ser Val Ser Pro Ser Ser Ser Gln Glu Ile Ser Glu Asn Gln Tyr Ala
865                 870                 875                 880

Val Ile Cys Ser Glu Lys Gln Ala Lys Val Ile Ser Leu Pro Thr Gln
                885                 890                 895

Asn Cys Ala Tyr Lys Gln Asn Ile Thr Glu Thr Ser Phe Val Leu Arg
            900                 905                 910

Gly Asp Ile Val Ala Leu Ser Asn Ser Val Cys Leu Ala Cys Phe Cys
        915                 920                 925

Ala Asn Gly His Ile Met Thr Phe Ser Leu Pro Ser Leu Arg Pro Leu
    930                 935                 940

Leu Asp Val Tyr Tyr Leu Pro Leu Thr Asn Met Arg Ile Ala Arg Thr
945                 950                 955                 960

Phe Cys Phe Ala Asn Ser Gly Gln Ala Leu Tyr Leu Val Ser Pro Thr
                965                 970                 975

Glu Ile Gln Arg Leu Thr Tyr Ser Gln Glu Thr Cys Glu Asn Leu Gln
            980                 985                 990

Glu Met Leu Gly Glu Leu Phe Thr Pro Val Glu Thr Pro Glu Ala Pro
        995                 1000                1005

Asn Arg Gly Phe Phe Lys Gly Leu Phe Gly Gly Gly Ala Gln Ser Leu
   1010                 1015                1020

Asp Arg Glu Glu Leu Phe Gly Glu Ser Ser Ser Gly Lys Ala Ser Arg
1025                1030                1035                1040

Ser Leu Ala Gln His Ile Pro Gly Pro Gly Gly Ile Glu Gly Val Lys
               1045                1050                1055

Gly Ala Ala Ser Gly Val Val Gly Glu Leu Ala Arg Ala Arg Leu Ala
           1060                1065                1070
```

-continued

```
Leu Asp Glu Arg Gly Gln Lys Leu Ser Asp Leu Glu Glu Arg Thr Ala
       1075                1080                1085

Ala Met Met Ser Ser Ala Asp Ser Phe Ser Lys His Ala His Glu Met
   1090                1095                1100

Met Leu Lys Tyr Lys Asp Lys Lys Trp Tyr Gln Phe
1105               1110                1115
```

<210> SEQ ID NO 22
<211> LENGTH: 1192
<212> TYPE: DNA
<213> ORGANISM: Homo sapiens

<400> SEQUENCE: 22

```
tcccatcggg tgaaccgtgg tcttgttccg tccgcccaca atcgctctcc agctttgacg     60
gccccggcaa agcctggctc gttcacagct ctctcgcacc tcctggagct tcagcttctt    120
ccgttgcaga gaagctttat gggccaattc gttcggcatc ccgggggcag gtgcgcggtg    180
cgcggggaag aagaggattt gactgcggtt ctccaccccc ggcgcccaac ctccaccccg    240
gtgcgcgcgc tcttccaggc tcctgctggt cccacttgcc aggagttagg tctcaggtca    300
gcctgagctc ctgagacgcc caggcccgga aagacacgta ggggaaacca tctgctcact    360
tctgtcctgt ccggaaggga tccctttctg acgggaaaga aaggcgctaa acaagcactg    420
gccttgagat aagcaatgct gaagcacttg cagctcacct attaccataa actgactgag    480
ccctccctac acaagccgta actactgctt tgattggaca agagactgat ttcagtagtt    540
ttctcttgat aagagaccac tggccgtggg cgggttctgg acagtttaca gaagctatgc    600
acttgattgc ctttgtgtcc ctgcttcacc ttttgaagca tagggcctaa ttataatgta    660
tttaaatgtt gtctccaccc caaagtgaac atgggttgca tgtaacaggc atgtttactc    720
agcatgcatg cagcaggatc ccttcacaaa tattcagagc tccccctatt ccctgttgaa    780
tatgtatatg tggccagcca gatcaacgta aatcactatt cgccctcccc tccctggaaa    840
cctacttttc gggtttcagc aggaagctat gcctcccagg cttgtcgaag agggcccatt    900
ttcgggcttg ataacccctt tataaaaaaa taaaatctcc tttctaaatt taaaatacaa    960
ccacaccacc ggcccgcaac tattgggggg gaaaaagaat gaagacacac ggtacatagt   1020
ttcatgcaca ttgttaagga gacaggtgcc cccaagcagg cggacatcac gcagtacgca   1080
gcttgagcat gccgaagacg cgagcgactc atagaacacg acgacgctcg caaggcacta   1140
agcatagcta ctaccactcg tcgaagagtc atacacagat ttctattggc ga           1192
```

<210> SEQ ID NO 23
<211> LENGTH: 552
<212> TYPE: DNA
<213> ORGANISM: Homo sapiens

<400> SEQUENCE: 23

```
ctatgaatct cggaaattac tcaaaccatc agcctctgca agaagcaaag tggacggccg     60
ggcgcggtgg ctcactcctg gaatcccagc actttgggag cccgaggtgg cgggatcacg    120
aggtcaggag atcgagactg ttctggctaa accagtgaaa ccccctctct actaaaaaaa    180
taagaaaagc gaagtgcatc tcccataaac gaggtactgc aggaagaaag cagaaaatga    240
gacccgagta cacacatgca cgcgggcgcc gcacacacac accagaagaa atgaaccaag    300
aggaaaggaa acattttcaa ataagcattt ggagatggga aaaacacctt gaaacagaaa    360
ttcataaagt acagaatttt tttttaagtt aaaaaaggaa caataataga cagaaaatga    420
```

-continued

```
atgaaaaatt aaatgtcata tcagaagtga agataaatta aaagtggtca aaggagaaga    480

gatctaaatg caaacttaag aaggggcaat tttttttttt tttttttttg agacgcagcc    540

tcactctgtc gc                                                         552
```

<210> SEQ ID NO 24
<211> LENGTH: 4321
<212> TYPE: DNA
<213> ORGANISM: Homo sapiens

<400> SEQUENCE: 24

```
cgagatcccg gggagccagc ttgctgggag agcgggacgg tccggagcaa gcccacaggc     60

agaggaggcg acagagggaa aaagggccga gctagccgct ccagtgctgt acaggagccg    120

aagggacgca ccacgccagc cccagcccgg ctccagcgac agccaacgcc tcttgcagcg    180

cggcggcttc gaagccgccg cccggagctg ccctttcctc ttcggtgaag tttttaaaag    240

ctgctaaaga ctcggaggaa gcaaggaaag tgcctggtag gactgacggc tgcctttgtc    300

ctcctcctct ccaccccgcc tccccccacc ctgccttccc cccctccccc gtcttctctc    360

ccgcagctgc ctcagtcggc tactctcagc caacccccct caccaccctt ctccccaccc    420

gcccccccgc ccccgtcggc ccagcgctgc cagcccgagt ttgcagagag gtaactccct    480

ttggctgcga gcgggcgagc tagctgcaca ttgcaaagaa ggctcttagg agccaggcga    540

ctggggagcg gcttcagcac tgcagccacg acccgcctgg ttagaattcc ggcggagaga    600

accctctgtt ttcccccact ctctctccac ctcctcctgc cttccccacc ccgagtgcgg    660

agcagagatc aaaagatgaa aaggcagtca ggtcttcagt agccaaaaaa caaaacaaac    720

aaaaacaaaa aagccgaaat aaaagaaaaa gataataact cagttcttat ttgcacctac    780

ttcagtggac actgaatttg gaaggtggag gattttgttt ttttctttta agatctgggc    840

atcttttgaa tctacccttc aagtattaag agacagactg tgagcctagc agggcagatc    900

ttgtccaccg tgtgtcttct tctgcacgag actttgaggc tgtcagagcg ctttttgcgt    960

ggttgctccc gcaagtttcc ttctctggag cttcccgcag gtgggcagct agctgcagcg   1020

actaccgcat catcacagcc tgttgaactc ttctgagcaa gagaagggga ggcggggtaa   1080

gggaagtagg tggaagattc agccaagctc aaggatggaa gtgcagttag ggctgggaag   1140

ggtctaccct cggccgccgt ccaagaccta ccgaggagct ttccagaatc tgttccagag   1200

cgtgcgcgaa gtgatccaga acccgggccc caggcaccca gaggccgcga gcgcagcacc   1260

tcccggcgcc agtttgctgc tgctgcagca gcagcagcag cagcagcagc agcagcagca   1320

gcagcagcag cagcagcagc agcagcaaga gactagcccc aggcagcagc agcagcagca   1380

gggtgaggat ggttctcccc aagcccatcg tagaggcccc acaggctacc tggtcctgga   1440

tgaggaacag caaccttcac agccgcagtc ggccctggag tgccaccccg agagaggttg   1500

cgtcccagag cctggagccg ccgtggccgc cagcaagggg ctgccgcagc agctgccagc   1560

acctccggac gaggatgact cagctgcccc atccacgttg tccctgctgg gccccacttt   1620

ccccggctta agcagctgct ccgctgacct taaagacatc ctgagcgagg ccagcaccat   1680

gcaactcctt cagcaacagc agcaggaagc agtatccgaa ggcagcagca gcgggagagc   1740

gagggaggcc tcgggggctc ccacttcctc caaggacaat tacttagggg gcacttcgac   1800

catttctgac aacgccaagg agttgtgtaa ggcagtgtcg gtgtccatgg gcctgggtgt   1860

ggaggcgttg gagcatctga gtccagggga acagcttcgg ggggattgca tgtacgcccc   1920

acttttggga gttccacccg ctgtgcgtcc cactccttgt gccccattgg ccgaatgcaa   1980
```

-continued

```
aggttctctg ctagacgaca gcgcaggcaa gagcactgaa gatactgctg agtattcccc   2040
tttcaaggga ggttacacca aagggctaga aggcgagagc ctaggctgct ctggcagcgc   2100
tgcagcaggg agctccggga cacttgaact gccgtctacc ctgtctctct acaagtccgg   2160
agcactggac gaggcagctg cgtaccagag tcgcgactac tacaactttc cactggctct   2220
ggccggaccg ccgccccctc cgccgcctcc ccatccccac gctcgcatca agctggagaa   2280
cccgctggac tacggcagcg cctgggcggc tgcggcggcg cagtgccgct atggggacct   2340
ggcgagcctg catggcgcgg gtgcagcggg acccggttct gggtcaccct cagccgccgc   2400
ttcctcatcc tggcacactc tcttcacagc cgaagaaggc cagttgtatg gaccgtgtgg   2460
tggtggtggg ggtggtggcg gcggcggcgg cggcggcggc ggcggcggcg gcggcggcgg   2520
cggcggcggc gaggcgggag ctgtagcccc ctacggctac actcggcccc ctcaggggct   2580
ggcgggccag gaaagcgact tcaccgcacc tgatgtgtgg taccctggcg gcatggtgag   2640
cagagtgccc tatcccagtc ccacttgtgt caaaagcgaa atgggcccct ggatggatag   2700
ctactccgga ccttacgggg acatgcgttt ggagactgcc agggaccatg ttttgcccat   2760
tgactattac tttccacccc agaagacctg cctgatctgt ggagatgaag cttctgggtg   2820
tcactatgga gctctcacat gtggaagctg caaggtcttc ttcaaaagag ccgctgaagg   2880
gaaacagaag tacctgtgcg ccagcagaaa tgattgcact attgataaat tccgaaggaa   2940
aaattgtcca tcttgtcgtc ttcggaaatg ttatgaagca gggatgactc tgggagcccg   3000
gaagctgaag aaacttggta atctgaaact acaggaggaa ggagaggctt ccagcaccac   3060
cagccccact gaggagacaa cccagaagct gacagtgtca cacattgaag gctatgaatg   3120
tcagcccatc tttctgaatg tcctggaagc cattgagcca ggtgtagtgt gtgctggaca   3180
cgacaacaac cagcccgact cctttgcagc cttgctctct agcctcaatg aactgggaga   3240
gagacagctt gtacacgtgg tcaagtgggc caaggccttg cctggcttcc gcaacttaca   3300
cgtggacgac cagatggctg tcattcagta ctcctggatg gggctcatgg tgtttgccat   3360
gggctggcga tccttcacca atgtcaactc caggatgctc tacttcgccc ctgatctggt   3420
tttcaatgag taccgcatgc acaagtcccg gatgtacagc cagtgtgtcc gaatgaggca   3480
cctctctcaa gagtttggat ggctccaaat cacccccccag gaattcctgt gcatgaaagc   3540
actgctactc ttcagcatta ttccagtgga tgggctgaaa aatcaaaaat tctttgatga   3600
acttcgaatg aactacatca aggaactcga tcgtatcatt gcatgcaaaa gaaaaaatcc   3660
cacatcctgc tcaagacgct tctaccagct caccaagctc ctggactccg tgcagcctat   3720
tgcgagagag ctgcatcagt tcacttttga cctgctaatc aagtcacaca tggtgagcgt   3780
ggactttccg gaaatgatgg cagagatcat ctctgtgcaa gtgcccaaga tcctttctgg   3840
gaaagtcaag cccatctatt tccacaccca gtgaagcatt ggaaacccta tttccccacc   3900
ccagctcatg ccccctttca gatgtcttct gcctgttata actctgcact actcctctgc   3960
agtgccttgg ggaatttcct ctattgatgt acagtctgtc atgaacatgt tcctgaattc   4020
tatttgctgg gctttttttt tctctttctc tcctttcttt ttcttcttcc ctccctatct   4080
aaccctccca tggcaccttc agactttgct tcccattgtg gctcctatct gtgttttgaa   4140
tggtgttgta tgcctttaaa tctgtgatga tcctcatatg gcccagtgtc aagttgtgct   4200
tgtttacagc actactctgt gccagccaca caaacgttta cttatcttat gccacgggaa   4260
gtttagagag ctaagattat ctggggaaat caaaacaaaa aacaagcaaa caaaaaaaaa   4320
```

-continued a 4321

<210> SEQ ID NO 25
<211> LENGTH: 919
<212> TYPE: PRT
<213> ORGANISM: Homo sapiens

<400> SEQUENCE: 25

Met Glu Val Gln Leu Gly Leu Gly Arg Val Tyr Pro Arg Pro Pro Ser
1 5 10 15

Lys Thr Tyr Arg Gly Ala Phe Gln Asn Leu Phe Gln Ser Val Arg Glu
20 25 30

Val Ile Gln Asn Pro Gly Pro Arg His Pro Glu Ala Ala Ser Ala Ala
35 40 45

Pro Pro Gly Ala Ser Leu Leu Leu Leu Gln Gln Gln Gln Gln Gln Gln
50 55 60

Gln Gln Gln Gln Gln Gln Gln Gln Gln Gln Gln Gln Gln Gln Glu Thr
65 70 75 80

Ser Pro Arg Gln Gln Gln Gln Gln Gln Gly Glu Asp Gly Ser Pro Gln
85 90 95

Ala His Arg Arg Gly Pro Thr Gly Tyr Leu Val Leu Asp Glu Glu Gln
100 105 110

Gln Pro Ser Gln Pro Gln Ser Ala Leu Glu Cys His Pro Glu Arg Gly
115 120 125

Cys Val Pro Glu Pro Gly Ala Ala Val Ala Ala Ser Lys Gly Leu Pro
130 135 140

Gln Gln Leu Pro Ala Pro Pro Asp Glu Asp Asp Ser Ala Ala Pro Ser
145 150 155 160

Thr Leu Ser Leu Leu Gly Pro Thr Phe Pro Gly Leu Ser Ser Cys Ser
165 170 175

Ala Asp Leu Lys Asp Ile Leu Ser Glu Ala Ser Thr Met Gln Leu Leu
180 185 190

Gln Gln Gln Gln Gln Glu Ala Val Ser Glu Gly Ser Ser Ser Gly Arg
195 200 205

Ala Arg Glu Ala Ser Gly Ala Pro Thr Ser Ser Lys Asp Asn Tyr Leu
210 215 220

Gly Gly Thr Ser Thr Ile Ser Asp Asn Ala Lys Glu Leu Cys Lys Ala
225 230 235 240

Val Ser Val Ser Met Gly Leu Gly Val Glu Ala Leu Glu His Leu Ser
245 250 255

Pro Gly Glu Gln Leu Arg Gly Asp Cys Met Tyr Ala Pro Leu Leu Gly
260 265 270

Val Pro Pro Ala Val Arg Pro Thr Pro Cys Ala Pro Leu Ala Glu Cys
275 280 285

Lys Gly Ser Leu Leu Asp Asp Ser Ala Gly Lys Ser Thr Glu Asp Thr
290 295 300

Ala Glu Tyr Ser Pro Phe Lys Gly Gly Tyr Thr Lys Gly Leu Glu Gly
305 310 315 320

Glu Ser Leu Gly Cys Ser Gly Ser Ala Ala Ala Gly Ser Ser Gly Thr
325 330 335

Leu Glu Leu Pro Ser Thr Leu Ser Leu Tyr Lys Ser Gly Ala Leu Asp
340 345 350

Glu Ala Ala Ala Tyr Gln Ser Arg Asp Tyr Tyr Asn Phe Pro Leu Ala
355 360 365

-continued

```
Leu Ala Gly Pro Pro Pro Pro Pro Pro Pro Pro His Pro His Ala Arg
    370                 375                 380

Ile Lys Leu Glu Asn Pro Leu Asp Tyr Gly Ser Ala Trp Ala Ala Ala
385                 390                 395                 400

Ala Ala Gln Cys Arg Tyr Gly Asp Leu Ala Ser Leu His Gly Ala Gly
                405                 410                 415

Ala Ala Gly Pro Gly Ser Gly Ser Pro Ser Ala Ala Ala Ser Ser Ser
            420                 425                 430

Trp His Thr Leu Phe Thr Ala Glu Glu Gly Gln Leu Tyr Gly Pro Cys
        435                 440                 445

Gly Gly Gly Gly Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
        515                 520                 525

Ser Tyr Ser Gly Pro Tyr Gly Asp Met Arg Leu Glu Thr Ala Arg Asp
    530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
    610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
        675                 680                 685

His Asp Asn Asn Gln Pro Asp Ser Phe Ala Ala Leu Leu Ser Ser Leu
    690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
                725                 730                 735

Ile Gln Tyr Ser Trp Met Gly Leu Met Val Phe Ala Met Gly Trp Arg
            740                 745                 750

Ser Phe Thr Asn Val Asn Ser Arg Met Leu Tyr Phe Ala Pro Asp Leu
        755                 760                 765

Val Phe Asn Glu Tyr Arg Met His Lys Ser Arg Met Tyr Ser Gln Cys
    770                 775                 780

Val Arg Met Arg His Leu Ser Gln Glu Phe Gly Trp Leu Gln Ile Thr
```

-continued

```
785                 790                 795                 800

Pro Gln Glu Phe Leu Cys Met Lys Ala Leu Leu Leu Phe Ser Ile Ile
                805                 810                 815

Pro Val Asp Gly Leu Lys Asn Gln Lys Phe Phe Asp Glu Leu Arg Met
            820                 825                 830

Asn Tyr Ile Lys Glu Leu Asp Arg Ile Ile Ala Cys Lys Arg Lys Asn
        835                 840                 845

Pro Thr Ser Cys Ser Arg Arg Phe Tyr Gln Leu Thr Lys Leu Leu Asp
    850                 855                 860

Ser Val Gln Pro Ile Ala Arg Glu Leu His Gln Phe Thr Phe Asp Leu
865                 870                 875                 880

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
            900                 905                 910

Pro Ile Tyr Phe His Thr Gln
        915
```

<210> SEQ ID NO 26
<211> LENGTH: 507
<212> TYPE: DNA
<213> ORGANISM: Homo sapiens
<220> FEATURE:
<221> NAME/KEY: modified_base
<222> LOCATION: (172)..(182)
<223> OTHER INFORMATION: a, g, c, t, unknown or other

<400> SEQUENCE: 26

```
agcattatcc atggccagtg attgatggac ttgttcaggt cctatgcaga gtgcttcata     60

tatctcatct caatcctcta aataaccatg aaagttgatg attatctcat ggtacagatg    120

ggaggctaag agtgtttaat tttccccaag ttccagtgct agtaagtgtt gnnnnnnnnn    180

nntgaacctg tgttaatggt gtttctagtc gatgctgtta tctgttgcac cacattttga    240

ataatcttgg actttcagag tatgaaggac gattaaatat aacccctttgg tataaatgtt    300

ctctctctcg ctcctctgta acaattggag aaacagagtt ctaacaatat taaaatcagc    360

catagacaga gagtagtgag aaatatactt tttttaatac agaaggttcc ctgaagtact    420

tttagtatta ttctaaatta agcaataacc aatgaacaat tttggtcata agcagtttct    480

ctccagaaaa aaaaaaaaaa agtcgac                                         507
```

<210> SEQ ID NO 27
<211> LENGTH: 444
<212> TYPE: DNA
<213> ORGANISM: Homo sapiens

<400> SEQUENCE: 27

```
aattctagaa gtccaaatca ctcattgttt gtgaaagctg agctcacagc aaaacaagcc     60

accatgaagc tgtcggtgtg tctcctgctg gtcacgctgg ccctctgctg ctaccaggcc    120

aatgccgagt tctgcccagc tcttgtttct gagctgttag acttcttctt cattagtgaa    180

cctctgttca agttaagtct tgccaaattt gatgcccctc cggaagctgt tgcagccaag    240

ttaggagtga agagatgcac ggatcagatg tcccttcaga aacgaagcct cattgcggaa    300

gtcctggtga aaatattgaa gaaatgtagt gtgtgacatg taaaaacttt catcctggtt    360

tccactgtct ttcaatgaca ccctgatctt cactgcagaa tgtaaaggtt tcaacgtctt    420

gctttaataa atcacttgct ctac                                            444
```

<210> SEQ ID NO 28
<211> LENGTH: 90
<212> TYPE: PRT
<213> ORGANISM: Homo sapiens

<400> SEQUENCE: 28

```
Met Lys Leu Ser Val Cys Leu Leu Leu Val Thr Leu Ala Leu Cys Cys
  1               5                  10                  15

Tyr Gln Ala Asn Ala Glu Phe Cys Pro Ala Leu Val Ser Glu Leu Leu
             20                  25                  30

Asp Phe Phe Phe Ile Ser Glu Pro Leu Phe Lys Leu Ser Leu Ala Lys
         35                  40                  45

Phe Asp Ala Pro Pro Glu Ala Val Ala Ala Lys Leu Gly Val Lys Arg
     50                  55                  60

Cys Thr Asp Gln Met Ser Leu Gln Lys Arg Ser Leu Ile Ala Glu Val
 65                  70                  75                  80

Leu Val Lys Ile Leu Lys Lys Cys Ser Val
                 85                  90
```

<210> SEQ ID NO 29
<211> LENGTH: 5061
<212> TYPE: DNA
<213> ORGANISM: Homo sapiens

<400> SEQUENCE: 29

```
atggctcaga tatttagcaa cagcggattt aaagaatgtc cattttcaca tccggaacca     60

acaagagcaa aagatgtgga caaagaagaa gcattacaga tggaagcaga ggctttagca    120

aaactgcaaa aggatagaca agtgactgac aatcagagag gctttgagtt gtcaagcagc    180

accagaaaaa aagcacaggt ttataacaag caggattatg atctcatggt gtttcctgaa    240

tcagattccc aaaaaagagc attagatatt gatgtagaaa agctcaccca agctgaactt    300

gagaaactat tgctggatga cagtttcgag actaaaaaaa cacctgtatt accagttact    360

cctattctga gcccttcctt ttcagcacag ctctatttta gacctactat tcagagagga    420

cagtggccac ctggattacc tgggccttcc acttatgctt taccttctat ttatccttct    480

acttacagta aacaggctgc attccaaaat ggcttcaatc caagaatgcc cacttttcca    540

tctacagaac ctatatattt aagtcttccg ggacaatctc catatttctc atatcctttg    600

acacctgcca caccctttca tccacaagga agcttaccta tctatcgtcc agtagtcagt    660

actgacatgg caaaactatt tgacaaaata gctagtacat cagaattttt aaaaaatggg    720

aaagcaagga ctgatttgga gataacagat tcaaaagtca gcaatctaca ggtatctcca    780

aagtctgagg atatcagtaa atttgactgg ttagacttgg atcctctaag taagcctaag    840

gtggataatg tggaggtatt agaccatgag gaagagaaaa atgtttcaag tttgctagca    900

aaggatcctt gggatgctgt tcttcttgaa gagagatcga cagcaaattg tcatcttgaa    960

agaaaggtga atggaaaatc cctttctgtg gcaactgtta caagaagcca gtctttaaat   1020

attcgaacaa ctcagcttgc aaaagcccag ggccatatat ctcagaaaga cccaaatggg   1080

accagtagtt tgccaactgg aagttctctt cttcaagaag ttgaagtaca gaatgaggag   1140

atggcagctt tttgtcgatc cattacaaaa ttgaagacca aatttccata taccaatcac   1200

cgcacaaacc caggctattt gttaagtcca gtcacagcgc aaagaaacat atgcggagaa   1260

aatgctagtg tgaaggtctc cattgacatt gaaggatttc agctaccagt tacttttacg   1320
```

-continued

```
tgtgatgtga gttctactgt agaaatcatt ataatgcaag ccctttgctg ggtacatgat   1380
gacttgaatc aagtagatgt tggcagctat gttctaaaag tttgtggtca agaggaagtg   1440
ctgcagaata atcattgcct tggaagtcat gagcatattc aaaactgtcg aaaatgggac   1500
acagaaatta gactacaact cttgaccttc agtgcaatgt gtcaaaatct ggcccgaaca   1560
gcagaagatg atgaaacacc cgtggattta aacaaacacc tgtatcaaat agaaaaacct   1620
tgcaaagaag ccatgacgag acaccctgtt gaagaactct tagattctta tcacaaccaa   1680
gtagaactgg ctcttcaaat tgaaaaccaa caccgagcag tagatcaagt aattaaagct   1740
gtaagaaaaa tctgtagtgc tttagatggt gtcgagactc ttgccattac agaatcagta   1800
aagaagctaa agagagcagt taatcttcca aggagtaaaa ctgctgatgt gacttctttg   1860
tttggaggag aagacactag caggagttca actaggggct cacttaatcc tgaaaatcct   1920
gttcaagtaa gcataaacca attaactgca gcaatttatg atcttctcag actccatgca   1980
aattctggta ggagtcctac agactgtgcc caaagtagca agagtgtcaa ggaagcatgg   2040
actacaacag agcagctcca gtttactatt tttgctgctc atggaatttc aagtaattgg   2100
gtatcaaatt atgaaaaata ctacttgata tgttcactgt ctcacaatgg aaaggatctt   2160
tttaaaccta ttcaatcaaa gaaggttggc acttacaaga atttcttcta tcttattaaa   2220
tgggatgaac taatcatttt tcctatccag atatcacaat tgccattaga atcagttctt   2280
caccttactc tttttggaat tttaaatcag agcagtggaa gttcccctga ttctaataag   2340
cagagaaagg gaccagaagc tttgggcaaa gtttctttac ctctttgtga ctttagacgg   2400
tttttaacat gtggaactaa acttctatat ctttggactt catcacatac aaattctgtt   2460
cctggaacag ttaccaaaaa aggatatgtc atggaaagaa tagtgctaca ggttgatttt   2520
ccttctcctg catttgatat tatttataca actcctcaag ttgacagaag cattatacag   2580
caacataact tagaaacact agagaatgat ataaaaggga aacttcttga tattcttcat   2640
aaagactcat cacttggact ttctaaagaa gataaagctt ttttatggga gaaacgttat   2700
tattgcttca aacacccaaa ttgtcttcct aaaatattag caagcgcccc aaactggaaa   2760
tggggtaatc ttgccaaaac ttactcattg cttcaccagt ggcctgcatt gtacccacta   2820
attgcattgg aacttcttga ttcaaaattt gctgatcagg aagtaagatc cctagctgtg   2880
acctggattg aggccattag tgatgatgag ctaacagatc ttcttccaca gtttgtacaa   2940
gctttgaaat atgaaattta cttgaatagt tcattagtgc aattcctttt gtccagggca   3000
ttgggaaata tccagatagc acacaattta tattggcttc tcaaagatgc cctgcatgat   3060
gtacagttta gtacccgata cgaacatgtt ttgggtgctc tcctgtcagt aggaggaaaa   3120
cgacttagag aagaacttct aaaacagacg aaacttgtac agcttttagg aggagtagca   3180
gaaaaagtaa ggcaggctag tggatcagcc agacaggttg ttctccaaag aagtatggaa   3240
cgagtacagt cctttttcca gaaaaataaa tgccgtctcc ctctcaagcc aagtctagtg   3300
gcaaaagaat taaatattaa gtcgtgttcc ttcttcagtt ctaatgctgt ccccctaaaa   3360
gtcacaatgg tgaatgctga ccctctggga gaagaaatta atgtcatgtt taaggttggt   3420
gaagatcttc ggcaagatat gttagcttta cagatgataa agattatgga taagatctgg   3480
cttaaagaag gactagatct gaggatggta attttcaaat gtctctcaac tggcagagat   3540
cgaggcatgg tggagctggt tcctgcttcc gataccctca ggaaaatcca agtggaatat   3600
ggtgtgacag gatcctttaa agataaacca cttgcagagt ggctaaggaa atacaatccc   3660
tctgaagaag aatatgaaaa ggcttcagag aactttatct attcctgtgc tggatgctgt   3720
```

-continued gtagccacct atgttttagg catctgtgat cgacacaatg acaatataat gcttcgaagc 3780
acgggacaca tgtttcacat tgactttgga aagtttttgg gacatgcaca gatgtttggc 3840
agcttcaaaa gggatcgggc tccttttgtg ctgacctctg atatggcata tgtcattaat 3900
gggggtgaaa agcccaccat tcgttttcag ttgtttgtgg acctctgctg tcaggcctac 3960
aacttgataa gaaagcagac aaaccttttt cttaacctcc tttcactgat gattccttca 4020
gggttaccag aacttacaag tattcaagat ttgaaatacg ttagagatgc acttcaaccc 4080
caaactacag acgcagaagc tacaattttc tttactaggc ttattgaatc aagtttggga 4140
agcattgcca caaagtttaa cttcttcatt cacaaccttg ctcagcttcg tttttctggt 4200
cttccttcta atgatgagcc catcctttca ttttcaccta aaacatactc ctttagacaa 4260
gatggtcgaa tcaaggaagt ctctgttttt acatatcata agaaatacaa cccagataaa 4320
cattatattt atgtagtccg aattttgtgg gaaggacaga ttgaaccatc atttgtcttc 4380
cgaacatttg tcgaatttca ggaacttcac aataagctca gtattatttt tccactttgg 4440
aagttaccag gctttcctaa taggatggtt ctaggaagaa cacacataaa agatgtagca 4500
gccaaaagga aaattgagtt aaacagttac ttacagagtt tgatgaatgc ttcaacggat 4560
gtagcagagt gtgatcttgt ttgtactttc ttccaccctt tacttcgtga tgagaaagct 4620
gaagggatag ctaggtctgc agatgcaggt tccttcagtc ctactccagg ccaaatagga 4680
ggagctgtga aattatccat ctcttaccga aatggtactc ttttcatcat ggtgatgcat 4740
atcaaagatc ttgttactga agatggagct gacccaaatc catatgtcaa aacataccta 4800
cttccagata accacaaaac atccaaacgt aaaaccaaaa tttcacgaaa aacgaggaat 4860
ccgacattca atgaaatgct tgtatacagt ggatatagca aagaaaccct aagacagcga 4920
gaacttcaac taagtgtact cagtgcagaa tctctgcggg agaatttttt cttgggtgga 4980
gtaaccctgc ctttgaaaga tttcaacttg agcaaagaga cggttaaatg gtatcagctg 5040
actgcggcaa catacttgta a 5061

<210> SEQ ID NO 30
<211> LENGTH: 1686
<212> TYPE: PRT
<213> ORGANISM: Homo sapiens

<400> SEQUENCE: 30

Met Ala Gln Ile Phe Ser Asn Ser Gly Phe Lys Glu Cys Pro Phe Ser
1               5                   10                  15

His Pro Glu Pro Thr Arg Ala Lys Asp Val Asp Lys Glu Glu Ala Leu
            20                  25                  30

Gln Met Glu Ala Glu Ala Leu Ala Lys Leu Gln Lys Asp Arg Gln Val
        35                  40                  45

Thr Asp Asn Gln Arg Gly Phe Glu Leu Ser Ser Ser Thr Arg Lys Lys
    50                  55                  60

Ala Gln Val Tyr Asn Lys Gln Asp Tyr Asp Leu Met Val Phe Pro Glu
65                  70                  75                  80

Ser Asp Ser Gln Lys Arg Ala Leu Asp Ile Asp Val Glu Lys Leu Thr
                85                  90                  95

Gln Ala Glu Leu Glu Lys Leu Leu Leu Asp Asp Ser Phe Glu Thr Lys
            100                 105                 110

Lys Thr Pro Val Leu Pro Val Thr Pro Ile Leu Ser Pro Ser Phe Ser
        115                 120                 125

-continued

```
Ala Gln Leu Tyr Phe Arg Pro Thr Ile Gln Arg Gly Gln Trp Pro Pro
    130                 135                 140

Gly Leu Pro Gly Pro Ser Thr Tyr Ala Leu Pro Ser Ile Tyr Pro Ser
145                 150                 155                 160

Thr Tyr Ser Lys Gln Ala Ala Phe Gln Asn Gly Phe Asn Pro Arg Met
                165                 170                 175

Pro Thr Phe Pro Ser Thr Glu Pro Ile Tyr Leu Ser Leu Pro Gly Gln
            180                 185                 190

Ser Pro Tyr Phe Ser Tyr Pro Leu Thr Pro Ala Thr Pro Phe His Pro
        195                 200                 205

Gln Gly Ser Leu Pro Ile Tyr Arg Pro Val Val Ser Thr Asp Met Ala
    210                 215                 220

Lys Leu Phe Asp Lys Ile Ala Ser Thr Ser Glu Phe Leu Lys Asn Gly
225                 230                 235                 240

Lys Ala Arg Thr Asp Leu Glu Ile Thr Asp Ser Lys Val Ser Asn Leu
                245                 250                 255

Gln Val Ser Pro Lys Ser Glu Asp Ile Ser Lys Phe Asp Trp Leu Asp
            260                 265                 270

Leu Asp Pro Leu Ser Lys Pro Lys Val Asp Asn Val Glu Val Leu Asp
        275                 280                 285

His Glu Glu Glu Lys Asn Val Ser Ser Leu Leu Ala Lys Asp Pro Trp
    290                 295                 300

Asp Ala Val Leu Leu Glu Glu Arg Ser Thr Ala Asn Cys His Leu Glu
305                 310                 315                 320

Arg Lys Val Asn Gly Lys Ser Leu Ser Val Ala Thr Val Thr Arg Ser
                325                 330                 335

Gln Ser Leu Asn Ile Arg Thr Thr Gln Leu Ala Lys Ala Gln Gly His
            340                 345                 350

Ile Ser Gln Lys Asp Pro Asn Gly Thr Ser Ser Leu Pro Thr Gly Ser
        355                 360                 365

Ser Leu Leu Gln Glu Val Glu Val Gln Asn Glu Glu Met Ala Ala Phe
    370                 375                 380

Cys Arg Ser Ile Thr Lys Leu Lys Thr Lys Phe Pro Tyr Thr Asn His
385                 390                 395                 400

Arg Thr Asn Pro Gly Tyr Leu Leu Ser Pro Val Thr Ala Gln Arg Asn
                405                 410                 415

Ile Cys Gly Glu Asn Ala Ser Val Lys Val Ser Ile Asp Ile Glu Gly
            420                 425                 430

Phe Gln Leu Pro Val Thr Phe Thr Cys Asp Val Ser Ser Thr Val Glu
        435                 440                 445

Ile Ile Ile Met Gln Ala Leu Cys Trp Val His Asp Asp Leu Asn Gln
    450                 455                 460

Val Asp Val Gly Ser Tyr Val Leu Lys Val Cys Gly Gln Glu Glu Val
465                 470                 475                 480

Leu Gln Asn Asn His Cys Leu Gly Ser His Glu His Ile Gln Asn Cys
                485                 490                 495

Arg Lys Trp Asp Thr Glu Ile Arg Leu Gln Leu Leu Thr Phe Ser Ala
            500                 505                 510

Met Cys Gln Asn Leu Ala Arg Thr Ala Glu Asp Asp Glu Thr Pro Val
        515                 520                 525

Asp Leu Asn Lys His Leu Tyr Gln Ile Glu Lys Pro Cys Lys Glu Ala
    530                 535                 540

Met Thr Arg His Pro Val Glu Glu Leu Leu Asp Ser Tyr His Asn Gln
```

-continued

```
545                 550                 555                 560

Val Glu Leu Ala Leu Gln Ile Glu Asn Gln His Arg Ala Val Asp Gln
                565                 570                 575

Val Ile Lys Ala Val Arg Lys Ile Cys Ser Ala Leu Asp Gly Val Glu
            580                 585                 590

Thr Leu Ala Ile Thr Glu Ser Val Lys Lys Leu Lys Arg Ala Val Asn
        595                 600                 605

Leu Pro Arg Ser Lys Thr Ala Asp Val Thr Ser Leu Phe Gly Gly Glu
    610                 615                 620

Asp Thr Ser Arg Ser Ser Thr Arg Gly Ser Leu Asn Pro Glu Asn Pro
625                 630                 635                 640

Val Gln Val Ser Ile Asn Gln Leu Thr Ala Ala Ile Tyr Asp Leu Leu
                645                 650                 655

Arg Leu His Ala Asn Ser Gly Arg Ser Pro Thr Asp Cys Ala Gln Ser
            660                 665                 670

Ser Lys Ser Val Lys Glu Ala Trp Thr Thr Thr Glu Gln Leu Gln Phe
        675                 680                 685

Thr Ile Phe Ala Ala His Gly Ile Ser Ser Asn Trp Val Ser Asn Tyr
    690                 695                 700

Glu Lys Tyr Tyr Leu Ile Cys Ser Leu Ser His Asn Gly Lys Asp Leu
705                 710                 715                 720

Phe Lys Pro Ile Gln Ser Lys Lys Val Gly Thr Tyr Lys Asn Phe Phe
                725                 730                 735

Tyr Leu Ile Lys Trp Asp Glu Leu Ile Ile Phe Pro Ile Gln Ile Ser
            740                 745                 750

Gln Leu Pro Leu Glu Ser Val Leu His Leu Thr Leu Phe Gly Ile Leu
        755                 760                 765

Asn Gln Ser Ser Gly Ser Ser Pro Asp Ser Asn Lys Gln Arg Lys Gly
    770                 775                 780

Pro Glu Ala Leu Gly Lys Val Ser Leu Pro Leu Cys Asp Phe Arg Arg
785                 790                 795                 800

Phe Leu Thr Cys Gly Thr Lys Leu Leu Tyr Leu Trp Thr Ser Ser His
                805                 810                 815

Thr Asn Ser Val Pro Gly Thr Val Thr Lys Lys Gly Tyr Val Met Glu
            820                 825                 830

Arg Ile Val Leu Gln Val Asp Phe Pro Ser Pro Ala Phe Asp Ile Ile
        835                 840                 845

Tyr Thr Thr Pro Gln Val Asp Arg Ser Ile Ile Gln Gln His Asn Leu
    850                 855                 860

Glu Thr Leu Glu Asn Asp Ile Lys Gly Lys Leu Leu Asp Ile Leu His
865                 870                 875                 880

Lys Asp Ser Ser Leu Gly Leu Ser Lys Glu Asp Lys Ala Phe Leu Trp
                885                 890                 895

Glu Lys Arg Tyr Tyr Cys Phe Lys His Pro Asn Cys Leu Pro Lys Ile
            900                 905                 910

Leu Ala Ser Ala Pro Asn Trp Lys Trp Gly Asn Leu Ala Lys Thr Tyr
        915                 920                 925

Ser Leu Leu His Gln Trp Pro Ala Leu Tyr Pro Leu Ile Ala Leu Glu
    930                 935                 940

Leu Leu Asp Ser Lys Phe Ala Asp Gln Glu Val Arg Ser Leu Ala Val
945                 950                 955                 960

Thr Trp Ile Glu Ala Ile Ser Asp Asp Glu Leu Thr Asp Leu Leu Pro
                965                 970                 975
```

-continued

```
Gln Phe Val Gln Ala Leu Lys Tyr Glu Ile Tyr Leu Asn Ser Ser Leu
            980                 985                 990

Val Gln Phe Leu Leu Ser Arg Ala Leu Gly Asn Ile Gln Ile Ala His
        995                 1000                1005

Asn Leu Tyr Trp Leu Leu Lys Asp Ala Leu His Asp Val Gln Phe Ser
   1010                1015                1020

Thr Arg Tyr Glu His Val Leu Gly Ala Leu Leu Ser Val Gly Gly Lys
1025                1030                1035                1040

Arg Leu Arg Glu Glu Leu Leu Lys Gln Thr Lys Leu Val Gln Leu Leu
                1045                1050                1055

Gly Gly Val Ala Glu Lys Val Arg Gln Ala Ser Gly Ser Ala Arg Gln
            1060                1065                1070

Val Val Leu Gln Arg Ser Met Glu Arg Val Gln Ser Phe Phe Gln Lys
        1075                1080                1085

Asn Lys Cys Arg Leu Pro Leu Lys Pro Ser Leu Val Ala Lys Glu Leu
   1090                1095                1100

Asn Ile Lys Ser Cys Ser Phe Phe Ser Ser Asn Ala Val Pro Leu Lys
1105                1110                1115                1120

Val Thr Met Val Asn Ala Asp Pro Leu Gly Glu Glu Ile Asn Val Met
                1125                1130                1135

Phe Lys Val Gly Glu Asp Leu Arg Gln Asp Met Leu Ala Leu Gln Met
            1140                1145                1150

Ile Lys Ile Met Asp Lys Ile Trp Leu Lys Glu Gly Leu Asp Leu Arg
        1155                1160                1165

Met Val Ile Phe Lys Cys Leu Ser Thr Gly Arg Asp Arg Gly Met Val
   1170                1175                1180

Glu Leu Val Pro Ala Ser Asp Thr Leu Arg Lys Ile Gln Val Glu Tyr
1185                1190                1195                1200

Gly Val Thr Gly Ser Phe Lys Asp Lys Pro Leu Ala Glu Trp Leu Arg
                1205                1210                1215

Lys Tyr Asn Pro Ser Glu Glu Glu Tyr Glu Lys Ala Ser Glu Asn Phe
            1220                1225                1230

Ile Tyr Ser Cys Ala Gly Cys Cys Val Ala Thr Tyr Val Leu Gly Ile
        1235                1240                1245

Cys Asp Arg His Asn Asp Asn Ile Met Leu Arg Ser Thr Gly His Met
   1250                1255                1260

Phe His Ile Asp Phe Gly Lys Phe Leu Gly His Ala Gln Met Phe Gly
1265                1270                1275                1280

Ser Phe Lys Arg Asp Arg Ala Pro Phe Val Leu Thr Ser Asp Met Ala
                1285                1290                1295

Tyr Val Ile Asn Gly Gly Glu Lys Pro Thr Ile Arg Phe Gln Leu Phe
            1300                1305                1310

Val Asp Leu Cys Cys Gln Ala Tyr Asn Leu Ile Arg Lys Gln Thr Asn
        1315                1320                1325

Leu Phe Leu Asn Leu Leu Ser Leu Met Ile Pro Ser Gly Leu Pro Glu
   1330                1335                1340

Leu Thr Ser Ile Gln Asp Leu Lys Tyr Val Arg Asp Ala Leu Gln Pro
1345                1350                1355                1360

Gln Thr Thr Asp Ala Glu Ala Thr Ile Phe Phe Thr Arg Leu Ile Glu
                1365                1370                1375

Ser Ser Leu Gly Ser Ile Ala Thr Lys Phe Asn Phe Phe Ile His Asn
            1380                1385                1390
```

-continued

```
Leu Ala Gln Leu Arg Phe Ser Gly Leu Pro Ser Asn Asp Glu Pro Ile
       1395                1400                1405

Leu Ser Phe Ser Pro Lys Thr Tyr Ser Phe Arg Gln Asp Gly Arg Ile
   1410                1415                1420

Lys Glu Val Ser Val Phe Thr Tyr His Lys Lys Tyr Asn Pro Asp Lys
1425                1430                1435                1440

His Tyr Ile Tyr Val Val Arg Ile Leu Trp Glu Gly Gln Ile Glu Pro
               1445                1450                1455

Ser Phe Val Phe Arg Thr Phe Val Glu Phe Gln Glu Leu His Asn Lys
           1460                1465                1470

Leu Ser Ile Ile Phe Pro Leu Trp Lys Leu Pro Gly Phe Pro Asn Arg
       1475                1480                1485

Met Val Leu Gly Arg Thr His Ile Lys Asp Val Ala Ala Lys Arg Lys
   1490                1495                1500

Ile Glu Leu Asn Ser Tyr Leu Gln Ser Leu Met Asn Ala Ser Thr Asp
1505                1510                1515                1520

Val Ala Glu Cys Asp Leu Val Cys Thr Phe Phe His Pro Leu Leu Arg
               1525                1530                1535

Asp Glu Lys Ala Glu Gly Ile Ala Arg Ser Ala Asp Ala Gly Ser Phe
           1540                1545                1550

Ser Pro Thr Pro Gly Gln Ile Gly Gly Ala Val Lys Leu Ser Ile Ser
       1555                1560                1565

Tyr Arg Asn Gly Thr Leu Phe Ile Met Val Met His Ile Lys Asp Leu
   1570                1575                1580

Val Thr Glu Asp Gly Ala Asp Pro Asn Pro Tyr Val Lys Thr Tyr Leu
1585                1590                1595                1600

Leu Pro Asp Asn His Lys Thr Ser Lys Arg Lys Thr Lys Ile Ser Arg
               1605                1610                1615

Lys Thr Arg Asn Pro Thr Phe Asn Glu Met Leu Val Tyr Ser Gly Tyr
           1620                1625                1630

Ser Lys Glu Thr Leu Arg Gln Arg Glu Leu Gln Leu Ser Val Leu Ser
       1635                1640                1645

Ala Glu Ser Leu Arg Glu Asn Phe Phe Leu Gly Gly Val Thr Leu Pro
   1650                1655                1660

Leu Lys Asp Phe Asn Leu Ser Lys Glu Thr Val Lys Trp Tyr Gln Leu
1665                1670                1675                1680

Thr Ala Ala Thr Tyr Leu
               1685


<210> SEQ ID NO 31
<211> LENGTH: 476
<212> TYPE: DNA
<213> ORGANISM: Homo sapiens

<400> SEQUENCE: 31

ttttttttag agactaaacc atagcaagga gtttgtgatc actgtatagc gctgagtgaa     60

acctcaaaat acattctgga atttgtaagg gatgctttcg tcgacttttt tttttttttt    120

ttggtatttt cactgtcaat tatgcctcgt attatttatt tatttgccaa aatacgactg    180

tatgaaaaaa agctacctca tagagctcat gacacataat aggtattcac tgagcatttg    240

gtgatttgtt aagcactcac atcaataaaa tatttcagct caacaggcac actaggggcc    300

agatgagcac tgactttccc cattgaggag tctcgattac ctcatgtctc acttcaaaca    360

atttattttt cttgtatgca tagctgggtt caagagttct ttcttgtttt gtcggatata    420
```

-continued ttctttttct tttgttttttg taggtcctat aatacagtaa agacatcaaa tagacc 476

<210> SEQ ID NO 32
<211> LENGTH: 537
<212> TYPE: DNA
<213> ORGANISM: Homo sapiens

<400> SEQUENCE: 32
cagtcagatt ttttttttgc ttaactaaga caaagtgaat aattcactgt gagccaaatt 60
ctttcttgat tcctcttttt ggagcagtcc atctttatgg gaaaaccagc ctagaatggt 120
gatttcagtt tcaggtgatt tcgatagaat tgtatttggc tcagaaatga taagactggg 180
gccaagaaaa attttaaact ttttttttg taatcatatt actagtttga tttcatatga 240
acttcctttg ttgactttct ttgccattaa tttaaaagtt ccagtatcct caatatttga 300
tgtcttatat gtacagaatc ctttccagct gtaagtcatc agcaagtaaa aaatttagta 360
tggcaatagt tttcataaga ggttttttaa aacagaaaaa tgttgacatt gccagcctct 420
gggttgcatt ttgggatatg ctacatttca aaggtatctt ttaaatctga aggcaaagac 480
tttttcaaca tctgaatatt ctgatttaca gaaattataa aaaaaaaagt cgacgcg 537

<210> SEQ ID NO 33
<211> LENGTH: 1994
<212> TYPE: DNA
<213> ORGANISM: Homo sapiens

<400> SEQUENCE: 33
ttttaagatg gagttttcgc tcttgttgcc caggctggag tgcagtggtg caatcttggc 60
tcactgcaac ctctgccccc cgggttcagg cgattctctc ctctcagtct ctcaagtaac 120
tgggattaca ggcacacacc accacggcca gctaattatt ttgtattttg agtcgagagg 180
agaattcacc atattggcct caggtaatcc gcccgcctcg gcctcccaaa gtgttgggat 240
tatgggcgtg agccagccac ggtgcccggc ccgttttatt gtttgaaaaa caagtacagg 300
ttgttattat ccaagaattg ttgatagagt atatactgta tttgaagtgt agaactgagg 360
cagaggctga ttaatataac tagtttacat ttgttagcct ttcacatctg tgaaggaata 420
aagtacagac aaaagtggaa aacaaaccag aaaaaaaaaa attgtgaagc acagagctgc 480
ttaaaagagt ggtgtcacat taaaagaaaa aagtcacaga aataagtcag tattttgttt 540
agagactaga actccaactg ctagccaact gcctagaata tagtaaatat tttctagttt 600
cttaaatgac tagtaatatt cctacattat gtgatggcat ttcccaaact gtttaattag 660
atgttagatt tgtagccaaa tatgtctagg aaatgcttaa acaatataaa acagttttaa 720
tgattggctt tttagaacgt tatatattag tgtgctttat gcatatccaa gaggtgagtg 780
aggtatttgg ggtttttcag acttacttga ttacagatct ggagtatctc aaaacagttg 840
ttttgtggaa aacactttgg caaactctga gtcttagtca ttaaaaatag tttttgggta 900
aacaacagtg taatagaaat ggaaattact gattcacatt gagccatgaa gaatttattt 960
tcagcgattt ttatagaagt tgctttatga caaagaaagc tttggttaac tggcatttgg 1020
catttcacac ccctaaattt tctacatgag gatttatttc tctggttctc tcactttctc 1080
actcagttat actgaattca tttatgatga gcgctctcaa ccattcttat tcatcaaagc 1140
tgaagttggc agagccctct ctggtacctg attagaagtc cgtcttccgt ctcataggga 1200
agtgttagag atggataatg tttctgtgta gcagaagtag tcattatgtc cccttaaatt 1260
cggtcacttt gactgcagta gagcttctta gtgagcagtc tgtgatggag tatactttcg 1320

-continued gagaagctca tggtggggga aacctggaat ttatctaaat atttcatttc tttgataaat 1380
tacattaaaa aattaataag agtatctatt tggtgaaatc attttcctcc acgtgaccaa 1440
atgagaaatt tagtgaaaga tttaaaatca tttttcagac tttttccaca ttagttggga 1500
agcaaacccc ttttttaagg caatgtcagt tattaagctt tagggaacca catgccactt 1560
taggtaacac atgattggag agattgaaga gtgaagtccc tgctttaaag tgtactcctg 1620
tggacacagt aatgcatata tttaaaatgg ttcatgttaa gagtaggtat atttctatct 1680
aaatactctg tagcttttgt gattcaggga aatgagtgga gcctcacagg cacaagaatc 1740
tagtaaattc taggtttctt gtgtggaact cagtgggcaa aatcttaact gagtgaattc 1800
ttgattattg gtatcacatt tattagtctg tatgtatctg tgtcatcgat ctccttaaga 1860
agagactcgt agatattgac tgggagaccc aagctgaatg ctaaaatctg ctccatggat 1920
ataagctgat gcagtcatca tttcacatta aaatgtacca cagctatata tgccgcaaaa 1980
aaaaaaaaaa aaaa 1994

<210> SEQ ID NO 34
<211> LENGTH: 660
<212> TYPE: DNA
<213> ORGANISM: Homo sapiens
<220> FEATURE:
<221> NAME/KEY: modified_base
<222> LOCATION: (559)
<223> OTHER INFORMATION: a, g, c, t, unknown or other
<220> FEATURE:
<221> NAME/KEY: modified_base
<222> LOCATION: (587)
<223> OTHER INFORMATION: a, g, c, t, unknown or other
<220> FEATURE:
<221> NAME/KEY: modified_base
<222> LOCATION: (597)
<223> OTHER INFORMATION: a, g, c, t, unknown or other
<220> FEATURE:
<221> NAME/KEY: modified_base
<222> LOCATION: (616)
<223> OTHER INFORMATION: a, g, c, t, unknown or other
<220> FEATURE:
<221> NAME/KEY: modified_base
<222> LOCATION: (627)
<223> OTHER INFORMATION: a, g, c, t, unknown or other
<220> FEATURE:
<221> NAME/KEY: modified_base
<222> LOCATION: (642)
<223> OTHER INFORMATION: a, g, c, t, unknown or other

<400> SEQUENCE: 34
ctactactaa attcgcggcc gcgtcgactt tttttttttt ttgtcttatg tctctaatct 60
gcactgttca gctcttttag gcactgcaaa gttgtcttga attaggaaag aggtgctaga 120
atgtgggcgt gggtgttgac ctacatctga acaatttaca tatgattcac cacaattaaa 180
caatttggtt tgaaatagct ataattaagt tattatcaga gaagtattta ctagtctaga 240
aattctaaat ttatcttcac atacacccta actgagaaaa gggccacatt ttctgcactc 300
tattaagtaa agcaaatgct gaactaaatg cctccatgtt aacatttata ttgttaagtt 360
actgacagca tattctatga atgattacgt tagtcgtttc tttaaaaatt ataggtttga 420
aatagcaaga aaaatatgaa atgatggtag acaaaaaaga gtttcagttt ctaacttcta 480
actatatata tacacacaca catgcacaca gaattgcctt cccggatgta tagaaattat 540
atacagccat gtccaggcnc gatggaaatt atgggggaat atccaantta ggatacncgt 600
gccgaatcgc cgggtntaaa taatacnggt ttataatgga cnatccacaa tcctggttta 660

-continued

<210> SEQ ID NO 35
<211> LENGTH: 5211
<212> TYPE: DNA
<213> ORGANISM: Homo sapiens

<400> SEQUENCE: 35
ccgcggctgg gagacagcga gccagagtct gggtgtttgt gcgagagcca cggcgggggc 60
tggggcgagt ggccggcatg gctgaaggct gcgctctgca accttgaaga gccgctgcat 120
tgagaggcca gggacaggga gaccggtgcg atggcagagc gcggcccccg ccgctgcgcc 180
gggccggccc ggctggcctg agccgccgga ggagcggggc tgcctctgcg cgtccatgga 240
gcagcgggaa gggcgaaact ccggagcgcc gcgtccctgc gccgctgcgg cggactgctg 300
aaggggccga gcccgcgcgg accgccgagg aagagacccc cgctccagcc cgcaggccgg 360
ctgcccgggg gcggcggggg acatcggagg gcagcggagc gagcagcgcc gcgggagagg 420
ccggcgcggg aggcggccgc agcaatgccg ggcccgctag ggctgctctg cttcctcgcc 480
ctggggctgc tcggctcggc cgggcccagc ggcgcggcgc cgcctctctg cgcggcgccc 540
tgcagctgcg acggcgaccg tcgggtggac tgctccggga aggggctgac ggccgtgccc 600
gaggggctca gcgccttcac ccaagcgctg gatatcagta tgaacaacat tactcagttg 660
ccagaagatg catttaagaa ctttcctttt ctagaagagc tacaattggc gggcaacgac 720
ctttctttta tccacccaaa ggccttgtct gggttgaaag aactcaaagt tctaacgctc 780
cagaataatc agttgaaaac agtacccagt gaagccattc gagggctgag tgctttgcag 840
tctttgcgtt tagatgccaa ccatattacc tcagtccccg aggacagttt tgaaggactt 900
gttcagttac ggcatctgtg gctggatgac aacagcttga cggaggtgcc tgtgcacccc 960
ctcagcaatc tgcccaccct acaggcgctg accctggctc tcaacaagat ctcaagcatc 1020
cctgactttg catttaccaa cctttcaagc ctggtagttc tgcatcttca taacaataaa 1080
attagaggcc tgagtcaaca ctgttttgat ggactagata acctggagac cttagacttg 1140
agttataata acttggggga atttcctcag gctattaaag cccgtcctag ccttaaagag 1200
ctaggatttc atagtaattc tatttctgtt atccctgatg gagcatttga tggtaatcca 1260
ctcttaagaa ctatacattt gtatgataat cctctgtctt ttgtggggaa ctcagcatct 1320
cacaatttat ctgatcttca ttccctagtc attcgtggtg caagcatggt gcagcagttc 1380
cccaatctta caggaactgt ccacctggaa agtctgactt tgacaggtac aaagataagc 1440
agcataccta ataatttgtg tcaagaacaa aagatgctta ggactttgga cttgtcttac 1500
aataatataa gagaccttcc aagttttaat ggttgccatg ctctggaaga aatttcttta 1560
cagcgtaatc aaatctacca aataaaggaa ggcacctttc aaggcctgat atctctaagg 1620
attctagatc tgagtagaaa cctgatacat gaaattcaca gtagagcttt tgccacactt 1680
gggccaataa ctaacctaga tgtaagtttc aatgaattaa cttcctttcc tacggaaggc 1740
ccgaatgggc taaatcaact gaaacttgtg ggcaacttca agctgaaaga agccttagca 1800
gcaaaagact ttgttaacct caggtcttta tcggtaccat atgcttatca gtgctgtgca 1860
ttttggggtt gtgactctta tgcaaattta aacacagaag ataacagcct ccaggaccac 1920
agtgtggcac aggagaaagg tactgctgat gcagcaaatg tcacaagcac tcttgaaaat 1980
gaagaacata gtcaaataat tatccattgt acaccttcaa caggtgcttt taagccctgt 2040
gaatatttac tgggaagctg gatgattcgt cttactgtgt ggttcatttt cttggttgca 2100
ttatttttca acctgcttgt tattttaaca acatttgcat cttgtacatc actgccttcg 2160

-continued

```
tccaaattgt ttataggctt gatttctgtg tctaacttat tcatgggaat ctatactggc   2220
atcctaactt ttcttgatgc tgtgtcctgg ggcagattcg ctgaatttgg catttggtgg   2280
gaaactggca gtggctgcaa agtagctggg tttcttgcag ttttctcctc agaaagtgcc   2340
atatttttat taatgctagc aactgtcgaa agaagcttat ctgcaaaaga tataatgaaa   2400
aatgggaaga gcaatcatct caaacagttc cgggttgctg ccctttcggc tttcctaggt   2460
gctacagtag caggctgttt tccccttttc catagagggg aatattctgc atcacccctt   2520
tgtttgccat ttcctacagg tgaaacgcca tcattaggat tcactgtaac gttagtgcta   2580
ttaaactcac tagcattttt attaatggcc gttatctaca ctaagctata ctgcaacttg   2640
gaaaaagagg acctctcaga aaactcacaa tctagcatga ttaagcatgt cgcttggcta   2700
atcttcacca attgcatctt tttctgccct gtggcgtttt tttcatttgc accattgatc   2760
actgcaatct ctatcagccc cgaaataatg aagtctgtta ctctgatatt ttttccattg   2820
cctgcttgcc tgaatccagt cctgtatgtt ttcttcaacc caaagtttaa agaagactgg   2880
aagttactga agcgacgtgt taccaagaaa agtggatcag tttcagtttc catcagtagc   2940
caaggtggtt gtctggaaca ggatttctac tacgactgtg gcatgtactc acatttgcag   3000
ggcaacctga ctgtttgcga ctgctgcgaa tcgtttcttt taacaaagcc agtatcatgc   3060
aaacacttga taaaatcaca cagctgtcct gcattggcag tggcttcttg ccaaagacct   3120
gagggctact ggtccgactg tggcacacag tcggcccact ctgattatgc agatgaagaa   3180
gattcctttg tctcagacag ttctgaccag gtgcaggcct gtggacgagc ctgcttctac   3240
cagagtagag gattcccttt ggtgcgctat gcttacaatc taccaagagt taaagactga   3300
actactgtgt gtgtaaccgt ttcccccgtc aaccaaaatc agtgtttata gagtgaaccc   3360
tattctcatc tttcatctgg gaagcacttc tgtaatcact gcctggtgtc acttagaaga   3420
aggagaggtg gcagtttatt tctcaaacca gtcattttca aagaacaggt gcctaaatta   3480
taaattggtg aaaaatgcaa tgtccaagca atgtatgatc tgtttgaaac aaatatatga   3540
cttgaaaagg atcttaggtg tagtagagca atataatgtt agtttttttct gatccataag   3600
aagcaaattt atacctattt gtgtattaag cacaagataa agaacagctg ttaatatttt   3660
ttaaaaatct attttaaaat gtgattttct ataactgaag aaaatatctt gctaatttta   3720
cctaatgttt catccttaat ctcaggacaa cttactgcag ggccaaaaaa gggactgtcc   3780
cagctagaac tgtgagagta tacataggca ttactttatt atgttttcac ttgccatcct   3840
tgacataaga gaactataaa ttttgtttaa gcaatttata aatctaaaac ctgaagatgt   3900
ttttaaaaca atattaacag ctgttaggtt aaaaaaatag ctggacattt gttttcagtc   3960
attatacatt gctttggtcc aatcagtaat tttttcttaa gtgttttgtg attacactac   4020
tagaaaaaaa gtaaaaggct aattgctgtg tgggtttagt cgatttggct aaactactaa   4080
ctaatgtggg ggtttaatag tatctgaggg atttggtggc ttcatgtaat gttctcatta   4140
atgaatactt cctaatatcg ttggctctac taatattttc caatttgctg ggatgtcacc   4200
tagcaatagc ttggattata tagaaagtaa actgtggtca atacttgcat ttaattagac   4260
gaaacgggga gtaattatga cacgaagtac ttatgtttat ttcttagtga gctggattat   4320
cttgaacctg tgctattaaa tggaaatttc catacatctt ccccatacta ttttttataa   4380
aagagcctat tcaatagctc agaggttgaa ctctggttaa acaagataat atgttattaa   4440
taaaaataga agaagaaaga ataaagctta gtcctgtgtc tttaaaaatt aaaaatttta   4500
```

-continued

```
cttgattccc atctatgggc tttagaccta ttactgggtg gagtcttaaa gttataattg   4560

ttcaatatgt tttttgaaca gtgtgctaaa tcaatagcaa acccactgcc atattagtta   4620

ttctgaatat actaaaaaaa tccagctaga ttgcagttta ataattaaac tgtacatact   4680

gtgcatataa tgaattttta tcttatgtaa attattttta gaacacaagt tgggaaatgt   4740

ggcttctgtt catttcgttt aattaaagct acctcctaaa ctatagtggc tgccagtagc   4800

agactgttaa attgtggttt atatactttt tgcattgtaa atagtctttg ttgtacattg   4860

tcagtgtaat aaaaacagaa tctttgtata tcaaaatcat gtagtttgta taaaatgtgg   4920

gaaggattta tttacagtgt gttgtaattt tgtaaggcca actatttaca agttttaaaa   4980

attgctatca tgtatattta cacatctgat aaatattaaa tcataacttg gtaagaaact   5040

cctaattaaa aggtttttc caaaattcag gttattgaaa atttttcatt ttattcattt   5100

aaaaactaga ataacagata tataaaagtg ttaatctttg tgctatatgg tatgaaatac   5160

aatattgtac tcagtgtttt gaattattaa agtttctaga aagcaaaaaa a            5211
```

```
<210> SEQ ID NO 36
<211> LENGTH: 951
<212> TYPE: PRT
<213> ORGANISM: Homo sapiens

<400> SEQUENCE: 36

Met Pro Gly Pro Leu Gly Leu Leu Cys Phe Leu Ala Leu Gly Leu Leu
  1               5                  10                  15

Gly Ser Ala Gly Pro Ser Gly Ala Ala Pro Pro Leu Cys Ala Ala Pro
             20                  25                  30

Cys Ser Cys Asp Gly Asp Arg Arg Val Asp Cys Ser Gly Lys Gly Leu
         35                  40                  45

Thr Ala Val Pro Glu Gly Leu Ser Ala Phe Thr Gln Ala Leu Asp Ile
     50                  55                  60

Ser Met Asn Asn Ile Thr Gln Leu Pro Glu Asp Ala Phe Lys Asn Phe
 65                  70                  75                  80

Pro Phe Leu Glu Glu Leu Gln Leu Ala Gly Asn Asp Leu Ser Phe Ile
                 85                  90                  95

His Pro Lys Ala Leu Ser Gly Leu Lys Glu Leu Lys Val Leu Thr Leu
            100                 105                 110

Gln Asn Asn Gln Leu Lys Thr Val Pro Ser Glu Ala Ile Arg Gly Leu
        115                 120                 125

Ser Ala Leu Gln Ser Leu Arg Leu Asp Ala Asn His Ile Thr Ser Val
    130                 135                 140

Pro Glu Asp Ser Phe Glu Gly Leu Val Gln Leu Arg His Leu Trp Leu
145                 150                 155                 160

Asp Asp Asn Ser Leu Thr Glu Val Pro Val His Pro Leu Ser Asn Leu
                165                 170                 175

Pro Thr Leu Gln Ala Leu Thr Leu Ala Leu Asn Lys Ile Ser Ser Ile
            180                 185                 190

Pro Asp Phe Ala Phe Thr Asn Leu Ser Ser Leu Val Val Leu His Leu
        195                 200                 205

His Asn Asn Lys Ile Arg Gly Leu Ser Gln His Cys Phe Asp Gly Leu
    210                 215                 220

Asp Asn Leu Glu Thr Leu Asp Leu Ser Tyr Asn Asn Leu Gly Glu Phe
225                 230                 235                 240

Pro Gln Ala Ile Lys Ala Arg Pro Ser Leu Lys Glu Leu Gly Phe His
                245                 250                 255
```

-continued

```
Ser Asn Ser Ile Ser Val Ile Pro Asp Gly Ala Phe Asp Gly Asn Pro
            260                 265                 270

Leu Leu Arg Thr Ile His Leu Tyr Asp Asn Pro Leu Ser Phe Val Gly
        275                 280                 285

Asn Ser Ala Ser His Asn Leu Ser Asp Leu His Ser Leu Val Ile Arg
    290                 295                 300

Gly Ala Ser Met Val Gln Gln Phe Pro Asn Leu Thr Gly Thr Val His
305                 310                 315                 320

Leu Glu Ser Leu Thr Leu Thr Gly Thr Lys Ile Ser Ser Ile Pro Asn
                325                 330                 335

Asn Leu Cys Gln Glu Gln Lys Met Leu Arg Thr Leu Asp Leu Ser Tyr
            340                 345                 350

Asn Asn Ile Arg Asp Leu Pro Ser Phe Asn Gly Cys His Ala Leu Glu
        355                 360                 365

Glu Ile Ser Leu Gln Arg Asn Gln Ile Tyr Gln Ile Lys Glu Gly Thr
    370                 375                 380

Phe Gln Gly Leu Ile Ser Leu Arg Ile Leu Asp Leu Ser Arg Asn Leu
385                 390                 395                 400

Ile His Glu Ile His Ser Arg Ala Phe Ala Thr Leu Gly Pro Ile Thr
                405                 410                 415

Asn Leu Asp Val Ser Phe Asn Glu Leu Thr Ser Phe Pro Thr Glu Gly
            420                 425                 430

Pro Asn Gly Leu Asn Gln Leu Lys Leu Val Gly Asn Phe Lys Leu Lys
        435                 440                 445

Glu Ala Leu Ala Ala Lys Asp Phe Val Asn Leu Arg Ser Leu Ser Val
    450                 455                 460

Pro Tyr Ala Tyr Gln Cys Cys Ala Phe Trp Gly Cys Asp Ser Tyr Ala
465                 470                 475                 480

Asn Leu Asn Thr Glu Asp Asn Ser Leu Gln Asp His Ser Val Ala Gln
                485                 490                 495

Glu Lys Gly Thr Ala Asp Ala Ala Asn Val Thr Ser Thr Leu Glu Asn
            500                 505                 510

Glu Glu His Ser Gln Ile Ile Ile His Cys Thr Pro Ser Thr Gly Ala
        515                 520                 525

Phe Lys Pro Cys Glu Tyr Leu Leu Gly Ser Trp Met Ile Arg Leu Thr
    530                 535                 540

Val Trp Phe Ile Phe Leu Val Ala Leu Phe Phe Asn Leu Leu Val Ile
545                 550                 555                 560

Leu Thr Thr Phe Ala Ser Cys Thr Ser Leu Pro Ser Ser Lys Leu Phe
                565                 570                 575

Ile Gly Leu Ile Ser Val Ser Asn Leu Phe Met Gly Ile Tyr Thr Gly
            580                 585                 590

Ile Leu Thr Phe Leu Asp Ala Val Ser Trp Gly Arg Phe Ala Glu Phe
        595                 600                 605

Gly Ile Trp Trp Glu Thr Gly Ser Gly Cys Lys Val Ala Gly Phe Leu
    610                 615                 620

Ala Val Phe Ser Ser Glu Ser Ala Ile Phe Leu Leu Met Leu Ala Thr
625                 630                 635                 640

Val Glu Arg Ser Leu Ser Ala Lys Asp Ile Met Lys Asn Gly Lys Ser
                645                 650                 655

Asn His Leu Lys Gln Phe Arg Val Ala Ala Leu Ser Ala Phe Leu Gly
            660                 665                 670
```

-continued

```
Ala Thr Val Ala Gly Cys Phe Pro Leu Phe His Arg Gly Glu Tyr Ser
        675                 680                 685

Ala Ser Pro Leu Cys Leu Pro Phe Pro Thr Gly Glu Thr Pro Ser Leu
    690                 695                 700

Gly Phe Thr Val Thr Leu Val Leu Leu Asn Ser Leu Ala Phe Leu Leu
705                 710                 715                 720

Met Ala Val Ile Tyr Thr Lys Leu Tyr Cys Asn Leu Glu Lys Glu Asp
                725                 730                 735

Leu Ser Glu Asn Ser Gln Ser Ser Met Ile Lys His Val Ala Trp Leu
            740                 745                 750

Ile Phe Thr Asn Cys Ile Phe Phe Cys Pro Val Ala Phe Phe Ser Phe
        755                 760                 765

Ala Pro Leu Ile Thr Ala Ile Ser Ile Ser Pro Glu Ile Met Lys Ser
    770                 775                 780

Val Thr Leu Ile Phe Phe Pro Leu Pro Ala Cys Leu Asn Pro Val Leu
785                 790                 795                 800

Tyr Val Phe Phe Asn Pro Lys Phe Lys Glu Asp Trp Lys Leu Leu Lys
                805                 810                 815

Arg Arg Val Thr Lys Lys Ser Gly Ser Val Ser Val Ser Ile Ser Ser
            820                 825                 830

Gln Gly Gly Cys Leu Glu Gln Asp Phe Tyr Tyr Asp Cys Gly Met Tyr
        835                 840                 845

Ser His Leu Gln Gly Asn Leu Thr Val Cys Asp Cys Cys Glu Ser Phe
    850                 855                 860

Leu Leu Thr Lys Pro Val Ser Cys Lys His Leu Ile Lys Ser His Ser
865                 870                 875                 880

Cys Pro Ala Leu Ala Val Ala Ser Cys Gln Arg Pro Glu Gly Tyr Trp
                885                 890                 895

Ser Asp Cys Gly Thr Gln Ser Ala His Ser Asp Tyr Ala Asp Glu Glu
            900                 905                 910

Asp Ser Phe Val Ser Asp Ser Ser Asp Gln Val Gln Ala Cys Gly Arg
        915                 920                 925

Ala Cys Phe Tyr Gln Ser Arg Gly Phe Pro Leu Val Arg Tyr Ala Tyr
    930                 935                 940

Asn Leu Pro Arg Val Lys Asp
945                 950


<210> SEQ ID NO 37
<211> LENGTH: 1884
<212> TYPE: DNA
<213> ORGANISM: Homo sapiens

<400> SEQUENCE: 37

atgctgcgag ccgcagtgat cctgctgctc atcaggacct ggctcgcgga gggcaactac      60

cccagtccca tcccgaaatt ccacttcgag ttctcctctg ctgtgcccga agtcgtcctg     120

aacctcttca actgcaaaaa ttgtgcaaat gaagctgtgg ttcaaaagat tttggacagg     180

gtgctgtcaa gatacgatgt ccgcctgaga ccgaattttg gaggtgcccc tgtgcctgtg     240

agaatatcta tttatgtcac gagcattgaa cagatctcag aaatgaatat ggactacacg     300

atcacgatgt tttttcatca gacttggaaa gattcacgct tagcatacta tgagaccacc     360

ctgaacttga ccctggacta tcggatgcat gagaagttgt gggtccctga ctgctacttt     420

ttgaacagca aggatgcttt cgtgcatgat gtgactgtgg agaatcgcgt gtttcagctt     480

cacccagatg gaacggtgcg gtacggcatc cgactcacca ctacagcagc ttgttccctg     540
```

-continued

```
gatctgcata aattccctat ggacaagcag gcctgcaacc tggtggtaga gagctatggt    600

tacacggttg aagacatcat attattctgg gatgacaatg ggaacgccat ccacatgact    660

gaggagctgc atatccctca gttcactttc ctgggaagga cgattactag caaggaggtg    720

tatttctaca caggttccta catacgcctg atactgaagt tccaggttca gagggaagtt    780

aacagctacc ttgtgcaagt ctactggcct actgtcctca ccactattac ctcttggata    840

tcgttttgga tgaactatga ttcctctgca gccagggtga caattggctt aacttcaatg    900

ctcatcctga ccaccatcga ctcacatctg cgggataagc tccccaacat ttcctgtatc    960

aaggccattg atatctatat cctcgtgtgc ttgttctttg tgttcctgtc cttgctggag   1020

tatgtctaca tcaactatct ttctacagt cgaggacctc ggcgccagcc taggcgacac   1080

aggagacccc gaagagtcat tgcccgctac cgctaccagc aagtggtggt aggaaacgtg   1140

caggatggcc tgattaacgt ggaagacgga gtcagctctc tccccatcac cccagcgcag   1200

gccccccctgg caagcccgga aagcctcggt tctttgacgt ccacctccga gcaggcccag   1260

ctggccacct cggaaagcct cagcccactc acttctctct caggccaggc ccccctggcc   1320

actggagaaa gcctgagcga tctcccctcc acctcagagc aggcccggca cagctatggt   1380

gttcgcttta atggtttcca ggctgatgac agtatttttc ctaccgaaat ccgcaaccgt   1440

gtcgaagccc atggccatgg tgttacccat gaccatgaag attccaatga gagcttgagc   1500

tcggatgagc gccatggcca tggccccagt gggaagccca tgcttcacca tggcgagaag   1560

ggtgtgcaag aagcaggctg ggaccttgat gacaacaatg acaagagcga ctgccttgcc   1620

attaaggagc aattcaagtg tgatactaac agtacctggg gccttaatga tgatgagctc   1680

atggcccatg gccaagagaa ggacagtagc tcagagtctg aggatagttg ccccccaagc   1740

cctgggtgct ccttcactga agggttctcc ttcgatctct ttaatcctga ctacgtccca   1800

aaggtcgaca agtggtcccg gttcctcttc cctctggcct ttgggttgtt caacattgtt   1860

tactgggtat accatatgta ttag                                          1884
```

<210> SEQ ID NO 38
<211> LENGTH: 627
<212> TYPE: PRT
<213> ORGANISM: Homo sapiens

<400> SEQUENCE: 38

```
Met Leu Arg Ala Ala Val Ile Leu Leu Leu Ile Arg Thr Trp Leu Ala
  1               5                  10                  15

Glu Gly Asn Tyr Pro Ser Pro Ile Pro Lys Phe His Phe Glu Phe Ser
             20                  25                  30

Ser Ala Val Pro Glu Val Val Leu Asn Leu Phe Asn Cys Lys Asn Cys
         35                  40                  45

Ala Asn Glu Ala Val Val Gln Lys Ile Leu Asp Arg Val Leu Ser Arg
     50                  55                  60

Tyr Asp Val Arg Leu Arg Pro Asn Phe Gly Gly Ala Pro Val Pro Val
 65                  70                  75                  80

Arg Ile Ser Ile Tyr Val Thr Ser Ile Glu Gln Ile Ser Glu Met Asn
                 85                  90                  95

Met Asp Tyr Thr Ile Thr Met Phe Phe His Gln Thr Trp Lys Asp Ser
            100                 105                 110

Arg Leu Ala Tyr Tyr Glu Thr Thr Leu Asn Leu Thr Leu Asp Tyr Arg
        115                 120                 125
```

-continued

```
Met His Glu Lys Leu Trp Val Pro Asp Cys Tyr Phe Leu Asn Ser Lys
    130                 135                 140

Asp Ala Phe Val His Asp Val Thr Val Glu Asn Arg Val Phe Gln Leu
145                 150                 155                 160

His Pro Asp Gly Thr Val Arg Tyr Gly Ile Arg Leu Thr Thr Thr Ala
                165                 170                 175

Ala Cys Ser Leu Asp Leu His Lys Phe Pro Met Asp Lys Gln Ala Cys
            180                 185                 190

Asn Leu Val Val Glu Ser Tyr Gly Tyr Thr Val Glu Asp Ile Ile Leu
        195                 200                 205

Phe Trp Asp Asp Asn Gly Asn Ala Ile His Met Thr Glu Glu Leu His
    210                 215                 220

Ile Pro Gln Phe Thr Phe Leu Gly Arg Thr Ile Thr Ser Lys Glu Val
225                 230                 235                 240

Tyr Phe Tyr Thr Gly Ser Tyr Ile Arg Leu Ile Leu Lys Phe Gln Val
                245                 250                 255

Gln Arg Glu Val Asn Ser Tyr Leu Val Gln Val Tyr Trp Pro Thr Val
            260                 265                 270

Leu Thr Thr Ile Thr Ser Trp Ile Ser Phe Trp Met Asn Tyr Asp Ser
        275                 280                 285

Ser Ala Ala Arg Val Thr Ile Gly Leu Thr Ser Met Leu Ile Leu Thr
    290                 295                 300

Thr Ile Asp Ser His Leu Arg Asp Lys Leu Pro Asn Ile Ser Cys Ile
305                 310                 315                 320

Lys Ala Ile Asp Ile Tyr Ile Leu Val Cys Leu Phe Phe Val Phe Leu
                325                 330                 335

Ser Leu Leu Glu Tyr Val Tyr Ile Asn Tyr Leu Phe Tyr Ser Arg Gly
            340                 345                 350

Pro Arg Arg Gln Pro Arg Arg His Arg Arg Pro Arg Arg Val Ile Ala
        355                 360                 365

Arg Tyr Arg Tyr Gln Gln Val Val Val Gly Asn Val Gln Asp Gly Leu
    370                 375                 380

Ile Asn Val Glu Asp Gly Val Ser Ser Leu Pro Ile Thr Pro Ala Gln
385                 390                 395                 400

Ala Pro Leu Ala Ser Pro Glu Ser Leu Gly Ser Leu Thr Ser Thr Ser
                405                 410                 415

Glu Gln Ala Gln Leu Ala Thr Ser Glu Ser Leu Ser Pro Leu Thr Ser
            420                 425                 430

Leu Ser Gly Gln Ala Pro Leu Ala Thr Gly Glu Ser Leu Ser Asp Leu
        435                 440                 445

Pro Ser Thr Ser Glu Gln Ala Arg His Ser Tyr Gly Val Arg Phe Asn
    450                 455                 460

Gly Phe Gln Ala Asp Asp Ser Ile Phe Pro Thr Glu Ile Arg Asn Arg
465                 470                 475                 480

Val Glu Ala His Gly His Gly Val Thr His Asp His Glu Asp Ser Asn
                485                 490                 495

Glu Ser Leu Ser Ser Asp Glu Arg His Gly His Gly Pro Ser Gly Lys
            500                 505                 510

Pro Met Leu His His Gly Glu Lys Gly Val Gln Glu Ala Gly Trp Asp
        515                 520                 525

Leu Asp Asp Asn Asn Asp Lys Ser Asp Cys Leu Ala Ile Lys Glu Gln
    530                 535                 540

Phe Lys Cys Asp Thr Asn Ser Thr Trp Gly Leu Asn Asp Asp Glu Leu
```

-continued

```
545                 550                 555                 560

Met Ala His Gly Gln Glu Lys Asp Ser Ser Ser Glu Ser Glu Asp Ser
                565                 570                 575

Cys Pro Pro Ser Pro Gly Cys Ser Phe Thr Glu Gly Phe Ser Phe Asp
            580                 585                 590

Leu Phe Asn Pro Asp Tyr Val Pro Lys Val Asp Lys Trp Ser Arg Phe
        595                 600                 605

Leu Phe Pro Leu Ala Phe Gly Leu Phe Asn Ile Val Tyr Trp Val Tyr
    610                 615                 620

His Met Tyr
625
```

<210> SEQ ID NO 39
<211> LENGTH: 331
<212> TYPE: DNA
<213> ORGANISM: Homo sapiens
<220> FEATURE:
<221> NAME/KEY: modified_base
<222> LOCATION: (89)..(91)
<223> OTHER INFORMATION: a, g, c, t, unknown or other

<400> SEQUENCE: 39

```
caaaaattgt gcaaatgaag ctgtggttca aaagattttg gacagggtgc tgtcaagata     60

cgatgtccgc ctgagaccga attttggann natgcttgct actaacagta cccggggcct    120

taatgaagat gagctcatgg cccatggcca agagaaggac agtagctcag agtctgagga    180

tagttgcccc ccaagccctg ggtgctcctt cactgaaggg ttctccttcg atctccttaa    240

tcctgactac gtcccaaagg tcgacaagtg gtcccggttc ctcttccctc tggcctttgg    300

gttgttcaac attgtagcgg ccgaacgatg c                                   331
```

<210> SEQ ID NO 40
<211> LENGTH: 110
<212> TYPE: PRT
<213> ORGANISM: Homo sapiens
<220> FEATURE:
<221> NAME/KEY: MOD_RES
<222> LOCATION: (30)
<223> OTHER INFORMATION: Any amino acid

<400> SEQUENCE: 40

```
Lys Asn Cys Ala Asn Glu Ala Val Val Gln Lys Ile Leu Asp Arg Val
  1               5                  10                  15

Leu Ser Arg Tyr Asp Val Arg Leu Arg Pro Asn Phe Gly Xaa Met Leu
             20                  25                  30

Ala Thr Asn Ser Thr Arg Gly Leu Asn Glu Asp Glu Leu Met Ala His
         35                  40                  45

Gly Gln Glu Lys Asp Ser Ser Ser Glu Ser Glu Asp Ser Cys Pro Pro
     50                  55                  60

Ser Pro Gly Cys Ser Phe Thr Glu Gly Phe Ser Phe Asp Leu Leu Asn
 65                  70                  75                  80

Pro Asp Tyr Val Pro Lys Val Asp Lys Trp Ser Arg Phe Leu Phe Pro
                 85                  90                  95

Leu Ala Phe Gly Leu Phe Asn Ile Val Ala Ala Glu Arg Cys
            100                 105                 110
```

<210> SEQ ID NO 41
<211> LENGTH: 3737
<212> TYPE: DNA
<213> ORGANISM: Homo sapiens -continued

<400> SEQUENCE: 41
ggcgtccgcg cacacctccc cgcgccgccg ccgccaccgc ccgcactccg ccgcctctgc 60
ccgcaaccgc tgagccatcc atgggggtcg cgggccgcaa ccgtcccggg gcggcctggg 120
cggtgctgct gctgctgctg ctgctgccgc cactgctgct gctggcgggg gccgtcccgc 180
cgggtcgggg ccgtgccgcg gggccgcagg aggatgtaga tgagtgtgcc caagggctag 240
atgactgcca tgccgacgcc ctgtgtcaga acacacccac ctcctacaag tgctcctgca 300
agcctggcta ccaaggggaa ggcaggcagt gtgaggacat cgatgaatgt ggaaatgagc 360
tcaatggagg ctgtgtccat gactgtttga atattccagg caattatcgt tgcacttgtt 420
ttgatggctt catgttggct catgacggtc ataattgtct tgatgtggac gagtgcctgg 480
agaacaatgg cggctgccag catacctgtg tcaacgtcat ggggagctat gagtgctgct 540
gcaaggaggg gtttttcctg agtgacaatc agcacacctg cattcaccgc tcggaagagg 600
gcctgagctg catgaataag gatcacggct gtagtcacat ctgcaaggag gccccaaggg 660
gcagcgtcgc ctgtgagtgc aggcctggtt ttgagctggc caagaaccag agagactgca 720
tcttgacctg taaccatggg aacggtgggt gccagcactc ctgtgacgat acagccgatg 780
gcccagagtg cagctgccat ccacagtaca agatgcacac agatgggagg agctgccttg 840
agcgagagga cactgtcctg gaggtgacag agagcaacac cacatcagtg gtggatgggg 900
ataaacgggt gaaacggcgg ctgctcatgg aaacgtgtgc tgtcaacaat ggaggctgtg 960
accgcacctg taaggatact tcgacaggtg tccactgcag ttgtcctgtt ggattcactc 1020
tccagttgga tgggaagaca tgtaaagata ttgatgagtg ccagacccgc aatggaggtt 1080
gtgatcattt ctgcaaaaac atcgtgggca gttttgactg cggctgcaag aaaggattta 1140
aattattaac agatgagaag tcttgccaag atgtggatga gtgctctttg gataggacct 1200
gtgaccacag ctgcatcaac caccctggca catttgcttg tgcttgcaac cgagggtaca 1260
ccctgtatgg cttcacccac tgtggagaca ccaatgagtg cagcatcaac aacggaggct 1320
gtcagcaggt ctgtgtgaac acagtgggca gctatgaatg ccagtgccac cctgggtaca 1380
agctccactg gaataaaaaa gactgtgtgg aagtgaaggg gctcctgccc acaagtgtgt 1440
caccccgtgt gtccctgcac tgcggtaaga gtggtggagg agacgggtgc ttcctcagat 1500
gtcactctgg cattcacctc tcttcagatg tcaccaccat caggacaagt gtaaccttta 1560
agctaaatga aggcaagtgt agtttgaaaa atgctgagct gtttcccgag ggtctgcgac 1620
cagcactacc agagaagcac agctcagtaa aagagagctt ccgctacgta aaccttacat 1680
gcagctctgg caagcaagtc ccaggagccc ctggccgacc aagcacccct aaggaaatgt 1740
ttatcactgt tgagtttgag cttgaaacta accaaaagga ggtgacagct tcttgtgacc 1800
tgagctgcat cgtaaagcga accgagaagc ggctccgtaa agccatccgc acgctcagaa 1860
aggccgtcca cagggagcag tttcacctcc agctctcagg catgaacctc gacgtggcta 1920
aaaagcctcc cagaacatct gaacgccagg cagagtcctg tggagtgggc cagggtcatg 1980
cagaaaacca atgtgtcagt tgcagggctg ggacctatta tgatggagca cgagaacgct 2040
gcattttatg tccaaatgga accttccaaa atgaggaagg acaaatgact tgtgaaccat 2100
gcccaagacc aggaaattct ggggccctga agaccccaga agcttggaat atgtctgaat 2160
gtggaggtct gtgtcaacct ggtgaatatt ctgcagatgg ctttgcacct tgccagctct 2220
gtgccctggg cacgttccag cctgaagctg gtcgaacttc ctgcttcccc tgtggaggag 2280

-continued

```
gccttgccac caaacatcag ggagctactt cctttcagga ctgtgaaacc agagttcaat   2340

gttcacctgg acatttctac aacaccacca ctcaccgatg tattcgttgc ccagtgggaa   2400

cataccagcc tgaatttgga aaaaataatt gtgtttcttg cccaggaaat actacgactg   2460

actttgatgg ctccacaaac ataacccagt gtaaaaacag aagatgtgga ggggagctgg   2520

gagatttcac tgggtacatt gaatccccaa actacccagg caattaccca gccaacaccg   2580

agtgtacgtg gaccatcaac ccacccccca agcgccgcat cctgatcgtg gtccctgaga   2640

tcttcctgcc catagaggac gactgtgggg actatctggt gatgcggaaa acctcttcat   2700

ccaattctgt gacaacatat gaaacctgcc agacctacga acgccccatc gccttcacct   2760

ccaggtcaaa gaagctgtgg attcagttca agtccaatga agggaacagc gctagagggt   2820

tccaggtccc atacgtgaca tatgatgagg actaccagga actcattgaa gacatagttc   2880

gagatggcag gctctatgca tctgagaacc atcaggaaat acttaaggat aagaaactta   2940

tcaaggctct gtttgatgtc ctggcccatc cccagaacta tttcaagtac acagcccagg   3000

agtcccgaga gatgtttcca agatcgttca tccgattgct acgttccaaa gtgtccaggt   3060

ttttgagacc ttacaaatga ctcagcccac gtgccactca atacaaatgt tctgctatag   3120

ggttggtggg acagagctgt cttccttctg catgtcagca cagtcgggta ttgctgcctc   3180

ccgtatcagt gactcattag agttcaattt ttatagataa tacagatatt ttggtaaatt   3240

gaacttggtt tttctttccc agcatcgtgg atgtagactg agaatggctt tgagtggcat   3300

cagcttctca ctgctgtggg cggatgtctt ggatagatca cgggctggct gagctggact   3360

ttggtcagcc taggtgagac tcacctgtcc ttctggggtc ttactcctcc tcaaggagtc   3420

tgtagtggaa aggaggccac agaataagct gcttattctg aaacttcagc ttcctctagc   3480

ccggccctct ctaagggagc cctctgcact cgtgtgcagg ctctgaccag gcagaacagg   3540

caagagggga gggaaggaga cccctgcagg ctccctccac ccaccttgag acctgggagg   3600

actcagtttc tccacagcct tctccagcct gtgtgataca agtttgatcc caggaacttg   3660

agttctaagc agtgctcgtg aaaaaaaaaa gcagaaagaa ttagaaataa ataaaaacta   3720

agcacttctg gagacat                                                  3737
```

<210> SEQ ID NO 42
<211> LENGTH: 999
<212> TYPE: PRT
<213> ORGANISM: Homo sapiens

<400> SEQUENCE: 42

```
Met Gly Val Ala Gly Arg Asn Arg Pro Gly Ala Ala Trp Ala Val Leu
  1               5                  10                  15

Leu Leu Leu Leu Leu Leu Pro Pro Leu Leu Leu Leu Ala Gly Ala Val
             20                  25                  30

Pro Pro Gly Arg Gly Arg Ala Ala Gly Pro Gln Glu Asp Val Asp Glu
         35                  40                  45

Cys Ala Gln Gly Leu Asp Asp Cys His Ala Asp Ala Leu Cys Gln Asn
     50                  55                  60

Thr Pro Thr Ser Tyr Lys Cys Ser Cys Lys Pro Gly Tyr Gln Gly Glu
 65                  70                  75                  80

Gly Arg Gln Cys Glu Asp Ile Asp Glu Cys Gly Asn Glu Leu Asn Gly
                 85                  90                  95

Gly Cys Val His Asp Cys Leu Asn Ile Pro Gly Asn Tyr Arg Cys Thr
            100                 105                 110
```

-continued

```
Cys Phe Asp Gly Phe Met Leu Ala His Asp Gly His Asn Cys Leu Asp
        115                 120                 125

Val Asp Glu Cys Leu Glu Asn Asn Gly Gly Cys Gln His Thr Cys Val
    130                 135                 140

Asn Val Met Gly Ser Tyr Glu Cys Cys Cys Lys Glu Gly Phe Phe Leu
145                 150                 155                 160

Ser Asp Asn Gln His Thr Cys Ile His Arg Ser Glu Glu Gly Leu Ser
                165                 170                 175

Cys Met Asn Lys Asp His Gly Cys Ser His Ile Cys Lys Glu Ala Pro
            180                 185                 190

Arg Gly Ser Val Ala Cys Glu Cys Arg Pro Gly Phe Glu Leu Ala Lys
        195                 200                 205

Asn Gln Arg Asp Cys Ile Leu Thr Cys Asn His Gly Asn Gly Gly Cys
    210                 215                 220

Gln His Ser Cys Asp Asp Thr Ala Asp Gly Pro Glu Cys Ser Cys His
225                 230                 235                 240

Pro Gln Tyr Lys Met His Thr Asp Gly Arg Ser Cys Leu Glu Arg Glu
                245                 250                 255

Asp Thr Val Leu Glu Val Thr Glu Ser Asn Thr Thr Ser Val Val Asp
            260                 265                 270

Gly Asp Lys Arg Val Lys Arg Arg Leu Leu Met Glu Thr Cys Ala Val
        275                 280                 285

Asn Asn Gly Gly Cys Asp Arg Thr Cys Lys Asp Thr Ser Thr Gly Val
    290                 295                 300

His Cys Ser Cys Pro Val Gly Phe Thr Leu Gln Leu Asp Gly Lys Thr
305                 310                 315                 320

Cys Lys Asp Ile Asp Glu Cys Gln Thr Arg Asn Gly Gly Cys Asp His
                325                 330                 335

Phe Cys Lys Asn Ile Val Gly Ser Phe Asp Cys Gly Cys Lys Lys Gly
            340                 345                 350

Phe Lys Leu Leu Thr Asp Glu Lys Ser Cys Gln Asp Val Asp Glu Cys
        355                 360                 365

Ser Leu Asp Arg Thr Cys Asp His Ser Cys Ile Asn His Pro Gly Thr
    370                 375                 380

Phe Ala Cys Ala Cys Asn Arg Gly Tyr Thr Leu Tyr Gly Phe Thr His
385                 390                 395                 400

Cys Gly Asp Thr Asn Glu Cys Ser Ile Asn Asn Gly Gly Cys Gln Gln
                405                 410                 415

Val Cys Val Asn Thr Val Gly Ser Tyr Glu Cys Gln Cys His Pro Gly
            420                 425                 430

Tyr Lys Leu His Trp Asn Lys Lys Asp Cys Val Glu Val Lys Gly Leu
        435                 440                 445

Leu Pro Thr Ser Val Ser Pro Arg Val Ser Leu His Cys Gly Lys Ser
    450                 455                 460

Gly Gly Gly Asp Gly Cys Phe Leu Arg Cys His Ser Gly Ile His Leu
465                 470                 475                 480

Ser Ser Asp Val Thr Thr Ile Arg Thr Ser Val Thr Phe Lys Leu Asn
                485                 490                 495

Glu Gly Lys Cys Ser Leu Lys Asn Ala Glu Leu Phe Pro Glu Gly Leu
            500                 505                 510

Arg Pro Ala Leu Pro Glu Lys His Ser Ser Val Lys Glu Ser Phe Arg
        515                 520                 525

Tyr Val Asn Leu Thr Cys Ser Ser Gly Lys Gln Val Pro Gly Ala Pro
```

-continued

```
    530                 535                 540

Gly Arg Pro Ser Thr Pro Lys Glu Met Phe Ile Thr Val Glu Phe Glu
545                 550                 555                 560

Leu Glu Thr Asn Gln Lys Glu Val Thr Ala Ser Cys Asp Leu Ser Cys
                565                 570                 575

Ile Val Lys Arg Thr Glu Lys Arg Leu Arg Lys Ala Ile Arg Thr Leu
            580                 585                 590

Arg Lys Ala Val His Arg Glu Gln Phe His Leu Gln Leu Ser Gly Met
        595                 600                 605

Asn Leu Asp Val Ala Lys Lys Pro Pro Arg Thr Ser Glu Arg Gln Ala
    610                 615                 620

Glu Ser Cys Gly Val Gly Gln Gly His Ala Glu Asn Gln Cys Val Ser
625                 630                 635                 640

Cys Arg Ala Gly Thr Tyr Tyr Asp Gly Ala Arg Glu Arg Cys Ile Leu
                645                 650                 655

Cys Pro Asn Gly Thr Phe Gln Asn Glu Glu Gly Gln Met Thr Cys Glu
            660                 665                 670

Pro Cys Pro Arg Pro Gly Asn Ser Gly Ala Leu Lys Thr Pro Glu Ala
        675                 680                 685

Trp Asn Met Ser Glu Cys Gly Gly Leu Cys Gln Pro Gly Glu Tyr Ser
    690                 695                 700

Ala Asp Gly Phe Ala Pro Cys Gln Leu Cys Ala Leu Gly Thr Phe Gln
705                 710                 715                 720

Pro Glu Ala Gly Arg Thr Ser Cys Phe Pro Cys Gly Gly Gly Leu Ala
                725                 730                 735

Thr Lys His Gln Gly Ala Thr Ser Phe Gln Asp Cys Glu Thr Arg Val
            740                 745                 750

Gln Cys Ser Pro Gly His Phe Tyr Asn Thr Thr Thr His Arg Cys Ile
        755                 760                 765

Arg Cys Pro Val Gly Thr Tyr Gln Pro Glu Phe Gly Lys Asn Asn Cys
    770                 775                 780

Val Ser Cys Pro Gly Asn Thr Thr Thr Asp Phe Asp Gly Ser Thr Asn
785                 790                 795                 800

Ile Thr Gln Cys Lys Asn Arg Arg Cys Gly Gly Glu Leu Gly Asp Phe
                805                 810                 815

Thr Gly Tyr Ile Glu Ser Pro Asn Tyr Pro Gly Asn Tyr Pro Ala Asn
            820                 825                 830

Thr Glu Cys Thr Trp Thr Ile Asn Pro Pro Pro Lys Arg Arg Ile Leu
        835                 840                 845

Ile Val Val Pro Glu Ile Phe Leu Pro Ile Glu Asp Asp Cys Gly Asp
    850                 855                 860

Tyr Leu Val Met Arg Lys Thr Ser Ser Ser Asn Ser Val Thr Thr Tyr
865                 870                 875                 880

Glu Thr Cys Gln Thr Tyr Glu Arg Pro Ile Ala Phe Thr Ser Arg Ser
                885                 890                 895

Lys Lys Leu Trp Ile Gln Phe Lys Ser Asn Glu Gly Asn Ser Ala Arg
            900                 905                 910

Gly Phe Gln Val Pro Tyr Val Thr Tyr Asp Glu Asp Tyr Gln Glu Leu
        915                 920                 925

Ile Glu Asp Ile Val Arg Asp Gly Arg Leu Tyr Ala Ser Glu Asn His
    930                 935                 940

Gln Glu Ile Leu Lys Asp Lys Lys Leu Ile Lys Ala Leu Phe Asp Val
945                 950                 955                 960
```

-continued

```
Leu Ala His Pro Gln Asn Tyr Phe Lys Tyr Thr Ala Gln Glu Ser Arg
                965                 970                 975

Glu Met Phe Pro Arg Ser Phe Ile Arg Leu Leu Arg Ser Lys Val Ser
            980                 985                 990

Arg Phe Leu Arg Pro Tyr Lys
        995
```

<210> SEQ ID NO 43
<211> LENGTH: 907
<212> TYPE: DNA
<213> ORGANISM: Homo sapiens
<220> FEATURE:
<221> NAME/KEY: modified_base
<222> LOCATION: (444)..(461)
<223> OTHER INFORMATION: a, g, c, t, unknown or other
<220> FEATURE:
<221> NAME/KEY: modified_base
<222> LOCATION: (859)
<223> OTHER INFORMATION: a, g, c, t, unknown or other
<220> FEATURE:
<221> NAME/KEY: modified_base
<222> LOCATION: (878)
<223> OTHER INFORMATION: a, g, c, t, unknown or other

<400> SEQUENCE: 43

```
tttcttcatt ttatgctttt ctccccttta tatatactgg gcggtttttc cttgagaaat     60

tttccatctc attaattctc ctgcagcaat tcataactct ttgggggcat tcctttgttt    120

tttgatatga ctactacctg actgtatata gtttcccttt tttttttttc ctcccagatt    180

ctctcctttc tactggcatc cttttccatt ttactcaatt ttcctcagtt aggttgactt    240

gcttttatac ctgtgtgatg ctccttgcca gatatctagc aaatgccccc aggatccaat    300

catttttttc ctaagaaaac tgaaaagaag catggcaaat aacagagctt ggaaaatagg    360

aaactttaaa atacaaagcc cagtgaaatc tacttggaag ccaatgctta gaggcaagag    420

acagtgattc aaataggtgt tgannnnnnn nnnnnnnnnn natgatcagc atagcaaaga    480

tcactttcca acattggaaa gttatgcata ttccaattga gctagccctt ttaaacagcc    540

ttaaaattgt ataaaagaga agaaatttaa gatattgaaa actggtagat aataaaacct    600

aaataaagct ggttttggaa gagcagtggc cactgtgatt gacaatgggg gcacttactg    660

ttaaggggat ttataacaga agtacttgaa cagaattgtg aagagaatag aattgtgcat    720

tcttttatct gcccagaacc acagctccca tgggaaatac tccacctcat tctacaacct    780

tctggctgca acaaaagcag tcaaattaaa acataaccca aagggggtac ctaacccaac    840

ttgagaaaat catagcatnc tccctttggc tataactntt tccacatgaa atacattcaa    900

atgcctt                                                              907
```

<210> SEQ ID NO 44
<211> LENGTH: 539
<212> TYPE: DNA
<213> ORGANISM: Homo sapiens

<400> SEQUENCE: 44

```
tttttttttt ttttttggga ttttagtatg ccttgcaatt ttttcccttt attctgatgc     60

atgaagtacc cactaaaagt gactgctgtt agtatagctt cagtaatgag gtgatgaggt    120

gacagggcag gtgatgctct cttagtctct ttaggctact attacaaaat acttcagact    180

gagtaattca taaacaacag agattattgt tcacagatct ggaggctgga aagtacaaga    240

ctaaagggcc agaatatttg gtgtttggtg aaggtcaaac attcagacac tctcaacgac    300
```

-continued

```
tatagcgaca gcagcagtct tcaggaatcc tatgtgaggg acaaacactc agaagccagc    360

tggagtgttc tagaatccta tgtgagggac aaacattcag accccagcag tagtgttgtg    420

gaatcctatg tgagggacaa actttcaaac ccttgtagca gtgttctgga atcctatgtg    480

agggacaaaa attcagaacc ttgtagcagt gttctggaat cctatgtgag gaacaatca     539
```

<210> SEQ ID NO 45
<211> LENGTH: 3632
<212> TYPE: DNA
<213> ORGANISM: Homo sapiens

<400> SEQUENCE: 45

```
gccaagcacg aagggttccg cgcgccttcc tcagagcctg cgcaccctgt tcgacatcct     60

gacgaccggc ggcgcggctg cgtgcacctg cgcacctcct tcttgaagcg ccgacggcgg    120

gccccccggg accccacgcg cgccccggcc cggcccgggg atcagccgcc gccgccgccg    180

caagcgcctt ggtgttcgct ccggccgacg agccgcggac ggtcctggag aggaagcccc    240

tgcccctggg cgtgcgcgcc cctctggccg gtcccagcgc cgccgcccgc agcccggagc    300

agctgtgcgc cccggctgag gcggcgccct gccccgcgga gcccgagcgg tcccagagcg    360

cggcgctgga accgagctcc agcgcggacg cagggacggg accggggagc ggctcttcgt    420

ggactccgga tcctggaggg cgcctcggcg ggtctggagg gaaagggctt catgcttgtc    480

gcggtgcagt ggcgtgcagg gccctggagc ggactcaggg gatgcccggc gggctccccg    540

tgcccgaggg gaacgtcgga ggcacaccat cgccagcggc gtggactgcg gcctgctgaa    600

gcagatgaag gagctggagc aggagaagga ggtgctgctg cagggtttgg agatgatggc    660

gcggggccgc gactggtacc agcagcagct gcaacgagtg caggagcgcc agcgccgcct    720

gggccagagc agagccagcg ccgactttgg ggctgcaggg agcccccgcc cactggggcg    780

gctactgccc aaggtacaag aggtggcccg gtgcctgggg gagctgctgg ctgcagcctg    840

tgccagccgg gccctgcccc cgtcctcctc cgggcccccc tgccctgccc tgacgtccac    900

ctcacccccg gtctggcagc agcagaccat cctcatgctg aaggagcaga accgactcct    960

cacccaggag gtgaccgaga agagtgagcg catcacgcag ctggagcagg agaagtcggc   1020

gctcattaag cagctgtttg aggcccgcgc cctgagccag caggacgggg gacctctgga   1080

ttccaccttc atctagtcct tgtgggccgc gtgggccccc agggccagcc tggcactcag   1140

cccttcgagg gtgggcgccc catcgcaccc accctctctg gctggagacc cccggcaggc   1200

ccaggcacag tcccggagtg ggcgccttcc tgccgccctt gccagatggg ctccccaggc   1260

ctgcccccgg ctggtccccg caccgagcgc ttgactccgt tttggctcct ggttgytgac   1320

atgggctggg ggctctcttg agtccgcata gtccgcagct actactggcc gctgtcagtg   1380

gacagtgggg taccccctcca tgagttagcg tccccccgtt tccagcggtg ccgccctggg   1440

tcccatcttc agggaaaggc actgcccacg ccaggctgca cttccaacaa cgggcagcag   1500

agggcgcggg gcggctccga cgcgggtcca agggcagctt cccgctcaac cagggcacca   1560

ggacgaggtg gctgtagctc ggacggacgg aagtagatgg agggggtggg gacggcctgt   1620

aagcgggggg tgcctgcctg gctggggagc cccagggata gcggtcggac ttcaggttct   1680

ggccaaggct gagggaccct ggctgcagcg gatcggcacg ccgggtgggc gagagcttgg   1740

cctgcatgtg cctcccacag accctggggt gatggccttc cccctcttgg ccgggacgtt   1800

gccccacgtt gagtcccaca caacatcctg tgagcctggc tccccaggag ggcccccaga   1860
```

-continued

```
cagctcccag gcacgtcata ggcaaagcct gtttccccg actcaggatt tccaaggcct   1920

ggggtcctgc tcaccccct ttgctctcac gcccagcctg tccccaggtt tcagctggga   1980

gaggccacct ccctcagcca aggaaaacga gaacccccag ggtacaggag gaggctgggg   2040

caggtcccct tgggtgtcac tccctcagcc cctgcccagg cccactcccg ctggtgctgg   2100

agtacgcact ggtggggggg ccctgctcag cccaacctgg agggtcccag tgtcaccaga   2160

accaggggca cggcaacagc atcgatgggt tctgcagccc agggcccccg atgcggggtc   2220

agtgtgtgtg gggcgcaggg cctccgatgc ggggtcagtg cgtggggggc gcagggcccc   2280

cgatgcgggg tcagtgcgtg gggggcgcag ggccccctcg tgtccagggc actttggtac   2340

actgtcccac aaggcacctg tctcagagga ggggccctgg caggcagcgt ggcaactcct   2400

tccggagccc agctccatgc taacctgccc acagcaaccc cacagagcca cattccctgc   2460

tgcacctggt ctgcagggtg tcccaggaca ggcccaagtc agcccagcat gcagctgccc   2520

tcctaccctg aagatgggag tggctttcc aggggacata aggatgtcag gcctggacct   2580

cctgggcagg aaagggtgca ggtcctgagg gcctgtgccc cacagcccca gcacccaggt   2640

ggactgcagc gcagtgggtg ggccagtggc agccagggag aagccccccg tcagcaggct   2700

ggggtctgcc caccagggcc tccccacgtc tgcctttgag ggtgcctgcc atgccctggg   2760

ggatcctggc atctttactg gactggaagc aggagacaga acagtgtctg tcccggggtg   2820

acttcatcag gagaccgccc acatagagct ggaccccgca gctgaagcgg aaatgtgaga   2880

caggctggca cctccggaaa aactgccttt cagccttggt gttccgtgca aggtgaaaag   2940

aaataggtcc tcccagttta cagcttgaaa tcaggctagt gagtggccct ggagaccacg   3000

aggggagaat ttaaaggccc cggctggcag ggtctaggtg gctggcagag gcacatgcag   3060

accctgcctg gagcctgccc taggacgctg ggcgggtcag tctccgtgca ggatgtgagc   3120

agcgtccctg ggctctatcc gcgaggtgcc agtagcgtgt gcaggtacat acacgtgcgt   3180

gcacactgtg atgacacccg gaaatgtctc aggatgttga aatgtgtcct tgggggcaga   3240

agtgtcccca gttgagaatc tgccccagag gaacacaccc acaccaggcc tcaggatttt   3300

gtgttgatca agttccaagg aaaaggaaca tctcagccgg gcgtggtggt tcacgcctgg   3360

aatcccagca cttgaggcca ggagttccag agcagcctgg gcaacgcagt gagagacccc   3420

atctctacaa raaaaaaaaa agaaagaaag aaaatgagag atccaggttt aaaaattcat   3480

aaacaccaca aggaaacaat acactatgag acccagcaga agcaacagat tgactctaga   3540

cccagatact agaattatca gagagaatat aaagtaacag tgttttatat atctaaagaa   3600

ataaaagaga tttctggaaa catgaaaaaa aa                                 3632
```

<210> SEQ ID NO 46
<211> LENGTH: 353
<212> TYPE: PRT
<213> ORGANISM: Homo sapiens

<400> SEQUENCE: 46

```
Met Lys Val Glu Ser Arg Gly Pro Pro Ser Cys Trp Leu Arg Ala Arg
1               5                   10                  15

Ala Ser Asn Ser Cys Leu Met Ser Ala Asp Phe Ser Cys Ser Ser Cys
            20                  25                  30

Val Met Arg Ser Leu Phe Ser Val Thr Ser Trp Val Arg Ser Arg Phe
        35                  40                  45

Cys Ser Phe Ser Met Arg Met Val Cys Cys Cys Gln Thr Gly Gly Glu
    50                  55                  60
```

-continued

```
Val Asp Val Arg Ala Gly Gln Gly Gly Pro Glu Glu Asp Gly Gly Arg
 65                  70                  75                  80

Ala Arg Leu Ala Gln Ala Ala Ala Ser Ser Ser Pro Arg His Arg Ala
                 85                  90                  95

Thr Ser Cys Thr Leu Gly Ser Ser Arg Pro Ser Gly Arg Gly Leu Pro
            100                 105                 110

Ala Ala Pro Lys Ser Ala Leu Ala Leu Leu Trp Pro Arg Arg Arg Trp
        115                 120                 125

Arg Ser Cys Thr Arg Cys Ser Cys Cys Trp Tyr Gln Ser Arg Pro Arg
    130                 135                 140

Ala Ile Ile Ser Lys Pro Cys Ser Ser Thr Ser Phe Ser Cys Ser Ser
145                 150                 155                 160

Ser Phe Ile Cys Phe Ser Arg Pro Gln Ser Thr Pro Leu Ala Met Val
                165                 170                 175

Cys Leu Arg Arg Ser Pro Arg Ala Arg Gly Ala Arg Arg Ala Ser Pro
            180                 185                 190

Glu Ser Ala Pro Gly Pro Cys Thr Pro Leu His Arg Asp Lys His Glu
        195                 200                 205

Ala Leu Ser Leu Gln Thr Arg Arg Gly Ala Leu Gln Asp Pro Glu Ser
    210                 215                 220

Thr Lys Ser Arg Ser Pro Val Pro Ser Leu Arg Pro Arg Trp Ser Ser
225                 230                 235                 240

Val Pro Ala Pro Arg Ser Gly Thr Ala Arg Ala Pro Arg Gly Arg Ala
                245                 250                 255

Pro Pro Gln Pro Gly Arg Thr Ala Ala Pro Gly Cys Gly Arg Arg Arg
            260                 265                 270

Trp Asp Arg Pro Glu Gly Arg Ala Arg Pro Gly Ala Gly Ala Ser Ser
        275                 280                 285

Pro Gly Pro Ser Ala Ala Arg Arg Pro Glu Arg Thr Pro Arg Arg Leu
    290                 295                 300

Arg Arg Arg Arg Arg Leu Ile Pro Gly Pro Gly Arg Gly Ala Arg Gly
305                 310                 315                 320

Val Pro Gly Gly Pro Pro Ser Ala Leu Gln Glu Gly Gly Ala Gln Val
                325                 330                 335

His Ala Ala Ala Pro Pro Val Val Arg Met Ser Asn Arg Val Arg Arg
            340                 345                 350

Leu
```

<210> SEQ ID NO 47
<211> LENGTH: 4827
<212> TYPE: DNA
<213> ORGANISM: Homo sapiens

<400> SEQUENCE: 47

```
caaagctcta agtatgctgg gacagatact acaaatgaac tttatgatga gcgaattaac     60

ctgatttata gtcctgtact ttctctacgt gccatatcca ttattaaaga aatgagtcta    120

agtaggaagt agagttaacc tatagtttca tttcttgaat ttcttattct ctttcttcag    180

tctttttcag ttaacctaca cacacacaca cacacacaca cacacacaca cacatatgtt    240

tataagtggg atgggagaac gggtacggtg ataattaaaa gaggtaaggt ttctcttgag    300

atgaaaatgt tctaaaattg tgatggcgga tgcacacctc tgaatatatt aaaagccatt    360

gaaatgaaaa aagggtgggg ggaatccaaa agtgtagcag acccaacctt gagatttgct    420
```

-continued

```
tgtttgggaa tgaattttcc aataacttga aagttgtaaa aactcacact tctcagggtt    480
aggtgtcaga aagaaaagga agtaatttat tctttaataa agcaattgtt aaatactctt    540
tagaactacc actgattgca attttgcagt gtctactcat agtgtctata taggtaccat    600
gaaaaagatg tacttgtgaa actgttctca tgttacttca gaaaaatttt gcttctaagt    660
gtgtattcta tgtctggtta aatgttcatt gaattttatt taatcattaa tctcaacagc    720
attaaacagt caataacata aatgacagtc ttctctttgt actcctccct gtacaacatc    780
acagagctcc atctgtatac acgaaagtca catgaaaata gaactcagtg ttttgtatta    840
catagtctat tcagtacatt tagaagtatt ttgcctccaa tattcaacca cagtaaaaga    900
ctcagtgaga acgcgtggtg gcgctgcagg ttaagatgac ggaaaataca actgcctacg    960
cagctccagg atccagcaaa ccgtttccca aagcctggaa gcaaaagaat agctgagcca   1020
gagcgaacgt gagtgtgaaa cctctttaag acaccgttgg gctgcttggt tctgacattc   1080
tggactgcaa aacagttcta ctaggatcct ggggatacat gaagcttctg tgaaccaact   1140
tttcaagaaa aagcaatgga gattggatgg atgcacaatc ggagacaaag gcaagtcctt   1200
gttttctttg ttttgctgag cttgtctggg gcgggcgccg agttggggtc ctattccgta   1260
gtggaagaaa cggagagagg ctcttttgtg gcaaatctag gaaaagacct ggggttgggg   1320
ttgacagaga tgtccacccg caaggccagg atcatttccc aggggaacaa acagcatttg   1380
cagctcaagg ctcaaactgg ggatttgctc ataaatgaga agctagatcg agaggagcta   1440
tgcggtccca ctgagccttg catactacat ttccaagtgt taatggaaaa ccctttagaa   1500
atatttcagg ctgaactgag ggtgatagat ataaatgacc attctcccat gttcactgaa   1560
aaggaaatga ttctaaaaat accggaaaac agtcctctag gaactgagtt ccctctgaat   1620
catgctttgg acttggacgt aggaagcaat aatgttcaaa actataaaat cagcccaagc   1680
tctcatttcc gggttctaat ccatgaattc agagatggca ggaaataccc tgagctagtg   1740
ttggataaag agctggatcg ggaggaggag cctcaactaa gattaaccct gacagcgctg   1800
gatggtggct ctccaccgcg atctggaact gctcaggtcc gtattgaagt ggtggacatc   1860
aatgataacg ctcctgagtt tgagcagccc atctacaaag tgcagattcc agagaacagt   1920
cctcttggct ccctggttgc caccgtctcc gccagggatt tagacggcgg agccaatgga   1980
aaaatatcat acacactctt tcagccttcg gaggatatta gtaaaacttt ggaggtaaat   2040
cctatgacag ggaagttcg  actgagaaag caagtagatt tcgaaatggt tacgtcttat   2100
gaagtgcgca tcaaagccac agatgggga  ggtctttcag gaaagtgcac tcttctcctg   2160
caggtggtgg acgtgaatga caatcccca  caggtgacca tgtctgcact caccagcccc   2220
atcccagaga actcgcctga gatagtagtt gctgttttca gcgtttcaga tcctgactcc   2280
ggaaacaatg ggaagacgat ttcctccatc caggaagacc ttccctttct tctaaaacct   2340
tcagtcaaga acttttacac cttggtaacg gagagagcac tcgacagaga agcaagagct   2400
gaatataata tcaccctcac cgtcacagat atggggactc caaggctgaa aacggagcac   2460
aacataacag tgcagatatc agatgtcaat gataacgccc ccactttcac ccaaacctcc   2520
tacaccctgt tcgtccgcga gaacaacagc cccgccctgc acatcggcag cgtcagcgcc   2580
acagacagag actcaggcac caacgcccag gtcacctact cgctgctgcc gccccaggac   2640
ccgcacctgc ccctcgcctc cctggtctcc atcaacgcag acaacggcca cctgttcgcc   2700
ctcaggtcgc tggactacga ggccctgcgg gagttcgagt tccgcgtgag cgccacagac   2760
cgcggctccc cggctttgag cagcgaggcg ctggtgcgcg tgctggtgct ggacgccaac   2820
```

-continued

```
gacaactcgc ccttcgtgct gtacccgctg cagaacggct ccgcgccctg cactgagctg   2880
gtgccccggg cggccgagcc gggctacctg gtgaccaagg tggtggcggt ggacggcgac   2940
tcgggccaga atgcctggct gtcgtaccag ctgctcaagg ccacggagcc cgggctgttc   3000
ggtgtgtggg cgcacaatgg cgaggtgcgc accgccaggc tgctgagcga gcgcgacgca   3060
gccaagcaga ggctggtggt gctggtcaag gacaatggcg agcctccgcg ctcggccacc   3120
gccacgctgc acgtgctcct ggtggacggc ttctcccagc ccttcctgcc gctcccagag   3180
gcggcccccg gccagaccca ggccaactcg ctcactgtct acctggtggt ggcgttggcc   3240
tcggtgtcgt cgctcttcct cttttcggtg ctcctgttcg tggcggtgcg gctgtgcagg   3300
aggagcaggg cggcctcggt gggccgctgc tcgatgcctg agggcccctt tccagggcgt   3360
ctggtggacg taagcggcac cgggaccctg tcccagagct accaatacga ggtgtgtctg   3420
acaggaggct cagaaacaag tgagttcaag ttcctgaagc cgattatccc caacttctct   3480
ccttagggca ctaggaaaga aatagattaa aattccaccc ttcacaatag ctttggattt   3540
aattattgat aggaacccat ttgataaatt ccttaacttc ttatgattgt cttgttgatt   3600
aaattgttca tgctcaccac caccaataag gtatttttct ctgattgtta gttcaaatta   3660
tattgttaat tccagtttcc cttttcctca tatttacccc gaagaggtgt tgcatataga   3720
atcccaatta acaaaatata ctttatcttc aaagttgatg tcatttaaaa tttttccgtc   3780
tttatatttt atttacttcc tattcatttt ttgctccatt tttcatgtta cttctcagtt   3840
tcctagaact tcaagtatta aaataacctg ttgcatgtat taggcatatt tcctatgtta   3900
catttctttt gtctattttc ctttcaaaat tggtattttt gttgggctca attttcatta   3960
taatactttt cttaaagttt ctttctttct tttcttttct ttcttttttt tttttccctt   4020
tttgagacag ggtcttactc ttgtcaccca ggctggagtg cagtggcaca atcttggctc   4080
actgcaacct ctgcctcctg ggctcaacgg atccttccac ctcagcctcc caagtagctt   4140
ggactatagg tgcatgccac catgcctggc taatcttttg cagcgatgag attttgccaa   4200
gttgcccagg ctgatcttga actcctgggc tcaagccatc ctccctcctc agcctcccaa   4260
aattctggga ttacaggcat aagccaatgt gcccatccaa agttttattt atttattttt   4320
ttgagatgga gtctcgtaaa gttaccttta aaaaaaaagt tctattttcc ctgtattggt   4380
atctccttaa ataaaataaa atattcctat tgtaagtgat atgagaaatc tttaaccagc   4440
cttatctaaa aataaaaaga gaagccattg taagacattc agtatgtgta aatgtgtttg   4500
tgtttgtaga caaaaggcaa aggtattatg taaaaatatt taataattta ttctttctat   4560
tactgaatta aaaaatcaga ggtccctgtt atatttttaa tggctaacaa ctcaatctca   4620
ttaagttgga aaaaaaactt atcaaagaga catttacatg gtttggcttt tatattcatc   4680
atagtataca ttggcggtat ctagcccttt ctctgtaaaa tatccctatg tttaatctgt   4740
atttcttgct tattatatgt aaagttgagc ttctttctag atattaggcc tttgaataaa   4800
attctatgtg agtcagaaaa aaaaaaa                                       4827
```

<210> SEQ ID NO 48
<211> LENGTH: 776
<212> TYPE: PRT
<213> ORGANISM: Homo sapiens

<400> SEQUENCE: 48

```
Met Glu Ile Gly Trp Met His Asn Arg Arg Gln Arg Gln Val Leu Val
  1               5                  10                  15
```

-continued

```
Phe Phe Val Leu Leu Ser Leu Ser Gly Ala Gly Ala Glu Leu Gly Ser
            20                  25                  30

Tyr Ser Val Val Glu Glu Thr Glu Arg Gly Ser Phe Val Ala Asn Leu
        35                  40                  45

Gly Lys Asp Leu Gly Leu Gly Leu Thr Glu Met Ser Thr Arg Lys Ala
    50                  55                  60

Arg Ile Ile Ser Gln Gly Asn Lys Gln His Leu Gln Leu Lys Ala Gln
65                  70                  75                  80

Thr Gly Asp Leu Leu Ile Asn Glu Lys Leu Asp Arg Glu Glu Leu Cys
                85                  90                  95

Gly Pro Thr Glu Pro Cys Ile Leu His Phe Gln Val Leu Met Glu Asn
            100                 105                 110

Pro Leu Glu Ile Phe Gln Ala Glu Leu Arg Val Ile Asp Ile Asn Asp
        115                 120                 125

His Ser Pro Met Phe Thr Glu Lys Glu Met Ile Leu Lys Ile Pro Glu
    130                 135                 140

Asn Ser Pro Leu Gly Thr Glu Phe Pro Leu Asn His Ala Leu Asp Leu
145                 150                 155                 160

Asp Val Gly Ser Asn Asn Val Gln Asn Tyr Lys Ile Ser Pro Ser Ser
                165                 170                 175

His Phe Arg Val Leu Ile His Glu Phe Arg Asp Gly Arg Lys Tyr Pro
            180                 185                 190

Glu Leu Val Leu Asp Lys Glu Leu Asp Arg Glu Glu Glu Pro Gln Leu
        195                 200                 205

Arg Leu Thr Leu Thr Ala Leu Asp Gly Gly Ser Pro Pro Arg Ser Gly
    210                 215                 220

Thr Ala Gln Val Arg Ile Glu Val Val Asp Ile Asn Asp Asn Ala Pro
225                 230                 235                 240

Glu Phe Glu Gln Pro Ile Tyr Lys Val Gln Ile Pro Glu Asn Ser Pro
                245                 250                 255

Leu Gly Ser Leu Val Ala Thr Val Ser Ala Arg Asp Leu Asp Gly Gly
            260                 265                 270

Ala Asn Gly Lys Ile Ser Tyr Thr Leu Phe Gln Pro Ser Glu Asp Ile
        275                 280                 285

Ser Lys Thr Leu Glu Val Asn Pro Met Thr Gly Glu Val Arg Leu Arg
    290                 295                 300

Lys Gln Val Asp Phe Glu Met Val Thr Ser Tyr Glu Val Arg Ile Lys
305                 310                 315                 320

Ala Thr Asp Gly Gly Gly Leu Ser Gly Lys Cys Thr Leu Leu Leu Gln
                325                 330                 335

Val Val Asp Val Asn Asp Asn Pro Pro Gln Val Thr Met Ser Ala Leu
            340                 345                 350

Thr Ser Pro Ile Pro Glu Asn Ser Pro Glu Ile Val Val Ala Val Phe
        355                 360                 365

Ser Val Ser Asp Pro Asp Ser Gly Asn Asn Gly Lys Thr Ile Ser Ser
    370                 375                 380

Ile Gln Glu Asp Leu Pro Phe Leu Leu Lys Pro Ser Val Lys Asn Phe
385                 390                 395                 400

Tyr Thr Leu Val Thr Glu Arg Ala Leu Asp Arg Glu Ala Arg Ala Glu
                405                 410                 415

Tyr Asn Ile Thr Leu Thr Val Thr Asp Met Gly Thr Pro Arg Leu Lys
            420                 425                 430
```

-continued

```
Thr Glu His Asn Ile Thr Val Gln Ile Ser Asp Val Asn Asp Asn Ala
        435                 440                 445

Pro Thr Phe Thr Gln Thr Ser Tyr Thr Leu Phe Val Arg Glu Asn Asn
    450                 455                 460

Ser Pro Ala Leu His Ile Gly Ser Val Ser Ala Thr Asp Arg Asp Ser
465                 470                 475                 480

Gly Thr Asn Ala Gln Val Thr Tyr Ser Leu Leu Pro Pro Gln Asp Pro
                485                 490                 495

His Leu Pro Leu Ala Ser Leu Val Ser Ile Asn Ala Asp Asn Gly His
            500                 505                 510

Leu Phe Ala Leu Arg Ser Leu Asp Tyr Glu Ala Leu Arg Glu Phe Glu
        515                 520                 525

Phe Arg Val Ser Ala Thr Asp Arg Gly Ser Pro Ala Leu Ser Ser Glu
    530                 535                 540

Ala Leu Val Arg Val Leu Val Leu Asp Ala Asn Asp Asn Ser Pro Phe
545                 550                 555                 560

Val Leu Tyr Pro Leu Gln Asn Gly Ser Ala Pro Cys Thr Glu Leu Val
                565                 570                 575

Pro Arg Ala Ala Glu Pro Gly Tyr Leu Val Thr Lys Val Val Ala Val
            580                 585                 590

Asp Gly Asp Ser Gly Gln Asn Ala Trp Leu Ser Tyr Gln Leu Leu Lys
        595                 600                 605

Ala Thr Glu Pro Gly Leu Phe Gly Val Trp Ala His Asn Gly Glu Val
    610                 615                 620

Arg Thr Ala Arg Leu Leu Ser Glu Arg Asp Ala Ala Lys Gln Arg Leu
625                 630                 635                 640

Val Val Leu Val Lys Asp Asn Gly Glu Pro Pro Arg Ser Ala Thr Ala
                645                 650                 655

Thr Leu His Val Leu Leu Val Asp Gly Phe Ser Gln Pro Phe Leu Pro
            660                 665                 670

Leu Pro Glu Ala Ala Pro Gly Gln Thr Gln Ala Asn Ser Leu Thr Val
        675                 680                 685

Tyr Leu Val Val Ala Leu Ala Ser Val Ser Ser Leu Phe Leu Phe Ser
    690                 695                 700

Val Leu Leu Phe Val Ala Val Arg Leu Cys Arg Arg Ser Arg Ala Ala
705                 710                 715                 720

Ser Val Gly Arg Cys Ser Met Pro Glu Gly Pro Phe Pro Gly Arg Leu
                725                 730                 735

Val Asp Val Ser Gly Thr Gly Thr Leu Ser Gln Ser Tyr Gln Tyr Glu
            740                 745                 750

Val Cys Leu Thr Gly Gly Ser Glu Thr Ser Glu Phe Lys Phe Leu Lys
        755                 760                 765

Pro Ile Ile Pro Asn Phe Ser Pro
    770                 775


<210> SEQ ID NO 49
<211> LENGTH: 473
<212> TYPE: DNA
<213> ORGANISM: Homo sapiens

<400> SEQUENCE: 49

ttttttttg ataatacaca gactttaatt aaaattgtac taaaattaaa tgtctaaata     60

aattagaatg gtacatggta catctaaatg tatgtttata tattttattt gtgcatttta    120

ttcctagggt tgcttttgct ttagtttgta aaacgttctt atttttatga taatgtagta    180
```

-continued

```
tatactaaat aaagaaaaat caggaaatag aaaatgaaga agaaaacatt agctattgtc    240

aaccaaataa aaattgtgca atctctaagc acatgaacta tgtattattt gtacagcatg    300

tacaatgttt atgcttcaca gggtgaggta gagactgcaa aacattgaac ctgggacaaa    360

taagaaagta aggaaatttt cacaacatat taatattata gaaaatgttg aacttaacag    420

ttaagataca agtagtgaaa aatgatagta tttaaggaga tctagaaaat tta           473


<210> SEQ ID NO 50
<211> LENGTH: 4060
<212> TYPE: DNA
<213> ORGANISM: Homo sapiens

<400> SEQUENCE: 50

gattccggga ggcaagtgag gagagaagat gctgtagcgt cctcaccggc tgccagcagg     60

gaaatggtcc aggagtgctg ggtgtgagcc tcccttctcc tcaagccgga gactgcggtt    120

gtcattgatc aattgaagaa gcaaggaccc gaaatcacag acattagcaa tgatgtgtga    180

agtgatgccc acgattaatg aggacacccc aatgagccaa agggggtccc aaagcagtgg    240

ctcggactca gactcccatt ttgagcagct gatggtgaat atgctagatg aaagggatcg    300

tcttctagac acccttcggg agacccagga aagcctctca cttgcccagc aaagacttca    360

ggatgtcatc tatgaccgag actcactcca gagacagctc aattcagccc tgccacagga    420

tatcgaatcc ctaacaggag ggctggctgg ttctaagggg gctgatccac cggaatttgc    480

tgcactgaca aaagaattaa atgcctgcag ggaacaactt ctagaaaagg aagaagaaat    540

ctctgaactt aaagctgaaa gaaacaacac aagactatta ctggagcatt tggagtgcct    600

tgtgtcacga catgaaagat cactaagaat gacggtggta aaacggcaag cccagtctcc    660

ctcaggagta tccagtgaag ttgaagttct caaggcactg aaatctttgt ttgagcacca    720

caaggccttg gatgaaaagg taagggagcg actgagggtt tctttagaaa gagtctctgc    780

actggaagaa gaactagctg ctgctaatca ggagattgtt gccttgcgtg aacaaaatgt    840

tcatatacaa agaaaaatgg catcaagcga gggatccaca gagtcagaac atcttgaagg    900

gatggaacct ggacagaaag tccatgagaa gcgtttgtcc aatggttcta tagactcaac    960

cgatgaaact agtcaaatag ttgaactaca agaattgctt gaaaagcaaa actatgaaat   1020

ggcccagatg aaagaacgtt tagcagccct ttcttcccga gtgggagagg tggaacagga   1080

agcagagaca gcaagaaagg atctcattaa aacagaagaa atgaacacca agtatcaaag   1140

ggacattagg gaggccatgg cacaaaagga agatatggaa gaaagaatta caacccttga   1200

aaagcgttac ctcagtgctc agagagaatc tacctccata catgacatga atgataaact   1260

agaaaatgag ttagcaaata aagaagctat cctacggcag atggaagaga aaaacagaca   1320

gttacaagaa cgtcttgagc tagctgaaga aaagttgcag cagaccatga gaaaggctga   1380

aaccttgcct gaagtagagg ctgaactggc tcagagaatt gcagccctaa ccaaggctga   1440

agagacacat ggaaatattg aagaacgtat gagacattta gagggtcaac ttgaagagaa   1500

gaatcaagaa cttcaaagag ctaggcaaag agagaaaatg aatgaggagc ataacaagag   1560

attatcggat acggttgata gacttctgac tgaatccaat gaacgcctac aactacactt   1620

aaaggaaaga atggctgctc tagaagaaaa gaatgtttta attcaagaat cagaaacttt   1680

cagaaagaat cttgaagaat ctttacatga taaggaaagc ttagcagaag aaattgaaaa   1740

gctgagatct gaacttgacc aattgaaaat gagaactggc tctttaattg aacccacaat   1800
```

-continued

```
accaagaact catctagaca cctcagctga gttgcggtac tcagtgggat ccctagtgga   1860

cagccagtct gattacagaa caactaaagt aataagaaga ccaaggagag gccgcatggg   1920

tgtgcgaaga gatgagccaa aggtgaaatc tcttggggat cacgagtgga atagaactca   1980

acagattgga gtactaagca gccacccttt tgaaagtgac actgaaatgt ctgatattga   2040

tgatgatgac agagaaacaa tttttagctc aatggatctt ctctctccaa gtggtcattc   2100

cgatgcccag acgctagcca tgatgcttca ggaacaattg gatgccatca acaaagaaat   2160

caggctaatt caggaagaaa aagaatctac agagttgcgt gctgaagaaa ttgaaaatag   2220

agtggctagt gtgagcctcg aaggcctgaa tttggcaatg gtccacccag gtacctccat   2280

tactgcctct gttacagctt catcgctggc cagttcatct ccccccagtg gacactcaac   2340

tccaaagctc accccctcgaa gccctgccag ggaaatggat cggatgggag tcatgacact   2400

gccaagtgat ctgaggaaac atcggagaaa gattgcagtt gtggaagaag atggtcgaga   2460

ggacaaagca acaattaaat gtgaaacttc tcctcctcct acccctagag ccctcagaat   2520

gactcacact ctcccttctt cctaccacaa tgatgctcga agtagtttat ctgtctctct   2580

tgagccagaa agcctcgggc ttggtagtgc caacagcagc caagactctc ttcacaaagc   2640

ccccaagaag aaaggaatca agtcttcaat aggacgtttg tttggtaaaa aagaaaaagc   2700

tcgacttggg cagctccgag gctttatgga gactgaagct gcagctcagg agtccctggg   2760

gttaggcaaa ctcggaactc aagctgagaa ggatcgaaga ctaaagaaaa agcatgaact   2820

tcttgaagaa gctcggagaa agggattacc ttttgcccag tgggatgggc caactgtggt   2880

cgcatggcta gagctttggt tgggaatgcc tgcgtggtac gtggcagcct gccgagccaa   2940

cgtgaagagt ggtgccatca tgtctgcttt atctgacact gagatccaga gagaaattgg   3000

aatcagcaat ccactgcatc gcttaaaact tcgattagca atccaggaga tggtttccct   3060

aacaagtcct tcagctcctc caacatctcg aactccttca ggcaacgttt gggtgactca   3120

tgaagaaatg gaaaatcttg cagctccagc aaaaacgaaa gaatctgagg aaggaagctg   3180

ggcccagtgt ccggtttttc tacagaccct ggcttatgga gatatgaatc atgagtggat   3240

tggaaatgaa tggcttccca gcttggggtt acctcagtac agaagttact ttatggaatg   3300

cttggtagat gcaagaatgt tagatcacct aacaaaaaaa gatctccgtg tccatttaaa   3360

aatggtggat agtttccatc gaacaagttt acaatatgga attatgtgct taaagaggtt   3420

gaattatgac agaaaagaac tagaaagaag acgggaagca agccaacatg aaataaaaga   3480

cgtgttggtg tggagcaatg accgagttat tcgctggata caagcaattg gacttcgaga   3540

atatgcaaat aatatacttg agagcggtgt gcatggctca cttatagccc tggatgaaaa   3600

ctttgactac agcagcttag ctttattatt acagattcca acacagaaca cccaggcaag   3660

gcagattctt gaaagagaat acaataacct cttggccctg ggaactgaaa ggcgactgga   3720

tgaaagtgat gacaagaact tcagacgtgg atcaacctgg agaaggcagt ttcctcctcg   3780

tgaagtacat ggaatcagca tgatgcctgg gtcctcagaa acattaccag ctggatttag   3840

gttaaccaca acctctgggc agtcaagaaa aatgacaaca gatgttgctt catcaagact   3900

gcagaggtta gacaactcca ctgttcgcac atactcatgt tgaccagcca ctcaaaggag   3960

gcagcactga cctgctatgg cgtcttttca gtctactcta cctaaagtgc actaccatct   4020

aagaagacga gcagtgaaaa cctttgtgaa aactgaattc                         4060
```

<210> SEQ ID NO 51
<211> LENGTH: 1257

-continued

<212> TYPE: PRT
<213> ORGANISM: Homo sapiens

<400> SEQUENCE: 51

Met Met Cys Glu Val Met Pro Thr Ile Asn Glu Asp Thr Pro Met Ser
1 5 10 15

Gln Arg Gly Ser Gln Ser Ser Gly Ser Asp Ser Asp Ser His Phe Glu
20 25 30

Gln Leu Met Val Asn Met Leu Asp Glu Arg Asp Arg Leu Leu Asp Thr
35 40 45

Leu Arg Glu Thr Gln Glu Ser Leu Ser Leu Ala Gln Gln Arg Leu Gln
50 55 60

Asp Val Ile Tyr Asp Arg Asp Ser Leu Gln Arg Gln Leu Asn Ser Ala
65 70 75 80

Leu Pro Gln Asp Ile Glu Ser Leu Thr Gly Gly Leu Ala Gly Ser Lys
85 90 95

Gly Ala Asp Pro Pro Glu Phe Ala Ala Leu Thr Lys Glu Leu Asn Ala
100 105 110

Cys Arg Glu Gln Leu Leu Glu Lys Glu Glu Glu Ile Ser Glu Leu Lys
115 120 125

Ala Glu Arg Asn Asn Thr Arg Leu Leu Leu Glu His Leu Glu Cys Leu
130 135 140

Val Ser Arg His Glu Arg Ser Leu Arg Met Thr Val Val Lys Arg Gln
145 150 155 160

Ala Gln Ser Pro Ser Gly Val Ser Ser Glu Val Glu Val Leu Lys Ala
165 170 175

Leu Lys Ser Leu Phe Glu His His Lys Ala Leu Asp Glu Lys Val Arg
180 185 190

Glu Arg Leu Arg Val Ser Leu Glu Arg Val Ser Ala Leu Glu Glu Glu
195 200 205

Leu Ala Ala Ala Asn Gln Glu Ile Val Ala Leu Arg Glu Gln Asn Val
210 215 220

His Ile Gln Arg Lys Met Ala Ser Ser Glu Gly Ser Thr Glu Ser Glu
225 230 235 240

His Leu Glu Gly Met Glu Pro Gly Gln Lys Val His Glu Lys Arg Leu
245 250 255

Ser Asn Gly Ser Ile Asp Ser Thr Asp Glu Thr Ser Gln Ile Val Glu
260 265 270

Leu Gln Glu Leu Leu Glu Lys Gln Asn Tyr Glu Met Ala Gln Met Lys
275 280 285

Glu Arg Leu Ala Ala Leu Ser Ser Arg Val Gly Glu Val Glu Gln Glu
290 295 300

Ala Glu Thr Ala Arg Lys Asp Leu Ile Lys Thr Glu Glu Met Asn Thr
305 310 315 320

Lys Tyr Gln Arg Asp Ile Arg Glu Ala Met Ala Gln Lys Glu Asp Met
325 330 335

Glu Glu Arg Ile Thr Thr Leu Glu Lys Arg Tyr Leu Ser Ala Gln Arg
340 345 350

Glu Ser Thr Ser Ile His Asp Met Asn Asp Lys Leu Glu Asn Glu Leu
355 360 365

Ala Asn Lys Glu Ala Ile Leu Arg Gln Met Glu Glu Lys Asn Arg Gln
370 375 380

Leu Gln Glu Arg Leu Glu Leu Ala Glu Glu Lys Leu Gln Gln Thr Met
385 390 395 400

-continued

```
Arg Lys Ala Glu Thr Leu Pro Glu Val Glu Ala Glu Leu Ala Gln Arg
                405                 410                 415

Ile Ala Ala Leu Thr Lys Ala Glu Glu Thr His Gly Asn Ile Glu Glu
            420                 425                 430

Arg Met Arg His Leu Glu Gly Gln Leu Glu Glu Lys Asn Gln Glu Leu
        435                 440                 445

Gln Arg Ala Arg Gln Arg Glu Lys Met Asn Glu Glu His Asn Lys Arg
    450                 455                 460

Leu Ser Asp Thr Val Asp Arg Leu Leu Thr Glu Ser Asn Glu Arg Leu
465                 470                 475                 480

Gln Leu His Leu Lys Glu Arg Met Ala Ala Leu Glu Glu Lys Asn Val
                485                 490                 495

Leu Ile Gln Glu Ser Glu Thr Phe Arg Lys Asn Leu Glu Glu Ser Leu
            500                 505                 510

His Asp Lys Glu Ser Leu Ala Glu Glu Ile Glu Lys Leu Arg Ser Glu
        515                 520                 525

Leu Asp Gln Leu Lys Met Arg Thr Gly Ser Leu Ile Glu Pro Thr Ile
    530                 535                 540

Pro Arg Thr His Leu Asp Thr Ser Ala Glu Leu Arg Tyr Ser Val Gly
545                 550                 555                 560

Ser Leu Val Asp Ser Gln Ser Asp Tyr Arg Thr Thr Lys Val Ile Arg
                565                 570                 575

Arg Pro Arg Arg Gly Arg Met Gly Val Arg Arg Asp Glu Pro Lys Val
            580                 585                 590

Lys Ser Leu Gly Asp His Glu Trp Asn Arg Thr Gln Gln Ile Gly Val
        595                 600                 605

Leu Ser Ser His Pro Phe Glu Ser Asp Thr Glu Met Ser Asp Ile Asp
    610                 615                 620

Asp Asp Asp Arg Glu Thr Ile Phe Ser Ser Met Asp Leu Leu Ser Pro
625                 630                 635                 640

Ser Gly His Ser Asp Ala Gln Thr Leu Ala Met Met Leu Gln Glu Gln
                645                 650                 655

Leu Asp Ala Ile Asn Lys Glu Ile Arg Leu Ile Gln Glu Glu Lys Glu
            660                 665                 670

Ser Thr Glu Leu Arg Ala Glu Glu Ile Glu Asn Arg Val Ala Ser Val
        675                 680                 685

Ser Leu Glu Gly Leu Asn Leu Ala Met Val His Pro Gly Thr Ser Ile
    690                 695                 700

Thr Ala Ser Val Thr Ala Ser Ser Leu Ala Ser Ser Ser Pro Pro Ser
705                 710                 715                 720

Gly His Ser Thr Pro Lys Leu Thr Pro Arg Ser Pro Ala Arg Glu Met
                725                 730                 735

Asp Arg Met Gly Val Met Thr Leu Pro Ser Asp Leu Arg Lys His Arg
            740                 745                 750

Arg Lys Ile Ala Val Val Glu Glu Asp Gly Arg Glu Asp Lys Ala Thr
        755                 760                 765

Ile Lys Cys Glu Thr Ser Pro Pro Pro Thr Pro Arg Ala Leu Arg Met
    770                 775                 780

Thr His Thr Leu Pro Ser Ser Tyr His Asn Asp Ala Arg Ser Ser Leu
785                 790                 795                 800

Ser Val Ser Leu Glu Pro Glu Ser Leu Gly Leu Gly Ser Ala Asn Ser
                805                 810                 815
```

-continued

```
Ser Gln Asp Ser Leu His Lys Ala Pro Lys Lys Lys Gly Ile Lys Ser
            820                 825                 830

Ser Ile Gly Arg Leu Phe Gly Lys Lys Glu Lys Ala Arg Leu Gly Gln
        835                 840                 845

Leu Arg Gly Phe Met Glu Thr Glu Ala Ala Ala Gln Glu Ser Leu Gly
    850                 855                 860

Leu Gly Lys Leu Gly Thr Gln Ala Glu Lys Asp Arg Arg Leu Lys Lys
865                 870                 875                 880

Lys His Glu Leu Leu Glu Glu Ala Arg Arg Lys Gly Leu Pro Phe Ala
                885                 890                 895

Gln Trp Asp Gly Pro Thr Val Val Ala Trp Leu Glu Leu Trp Leu Gly
            900                 905                 910

Met Pro Ala Trp Tyr Val Ala Ala Cys Arg Ala Asn Val Lys Ser Gly
        915                 920                 925

Ala Ile Met Ser Ala Leu Ser Asp Thr Glu Ile Gln Arg Glu Ile Gly
    930                 935                 940

Ile Ser Asn Pro Leu His Arg Leu Lys Leu Arg Leu Ala Ile Gln Glu
945                 950                 955                 960

Met Val Ser Leu Thr Ser Pro Ser Ala Pro Pro Thr Ser Arg Thr Pro
                965                 970                 975

Ser Gly Asn Val Trp Val Thr His Glu Glu Met Glu Asn Leu Ala Ala
            980                 985                 990

Pro Ala Lys Thr Lys Glu Ser Glu Glu Gly Ser Trp Ala Gln Cys Pro
        995                 1000                1005

Val Phe Leu Gln Thr Leu Ala Tyr Gly Asp Met Asn His Glu Trp Ile
   1010                 1015                1020

Gly Asn Glu Trp Leu Pro Ser Leu Gly Leu Pro Gln Tyr Arg Ser Tyr
1025                1030                1035                1040

Phe Met Glu Cys Leu Val Asp Ala Arg Met Leu Asp His Leu Thr Lys
               1045                1050                1055

Lys Asp Leu Arg Val His Leu Lys Met Val Asp Ser Phe His Arg Thr
           1060                1065                1070

Ser Leu Gln Tyr Gly Ile Met Cys Leu Lys Arg Leu Asn Tyr Asp Arg
       1075                1080                1085

Lys Glu Leu Glu Arg Arg Arg Glu Ala Ser Gln His Glu Ile Lys Asp
   1090                1095                1100

Val Leu Val Trp Ser Asn Asp Arg Val Ile Arg Trp Ile Gln Ala Ile
1105                1110                1115                1120

Gly Leu Arg Glu Tyr Ala Asn Asn Ile Leu Glu Ser Gly Val His Gly
               1125                1130                1135

Ser Leu Ile Ala Leu Asp Glu Asn Phe Asp Tyr Ser Ser Leu Ala Leu
           1140                1145                1150

Leu Leu Gln Ile Pro Thr Gln Asn Thr Gln Ala Arg Gln Ile Leu Glu
       1155                1160                1165

Arg Glu Tyr Asn Asn Leu Leu Ala Leu Gly Thr Glu Arg Arg Leu Asp
   1170                1175                1180

Glu Ser Asp Asp Lys Asn Phe Arg Arg Gly Ser Thr Trp Arg Arg Gln
1185                1190                1195                1200

Phe Pro Pro Arg Glu Val His Gly Ile Ser Met Met Pro Gly Ser Ser
               1205                1210                1215

Glu Thr Leu Pro Ala Gly Phe Arg Leu Thr Thr Thr Ser Gly Gln Ser
           1220                1225                1230

Arg Lys Met Thr Thr Asp Val Ala Ser Ser Arg Leu Gln Arg Leu Asp
```

-continued

```
      1235                1240                1245

Asn Ser Thr Val Arg Thr Tyr Ser Cys
   1250                1255


<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 52

His His His His His His
  1               5


<210> SEQ ID NO 53
<211> LENGTH: 266
<212> TYPE: DNA
<213> ORGANISM: Homo sapiens

<400> SEQUENCE: 53

gggattctct tttcttttat tcttgtctgt tctgcctcac tcccgagctc tactgactcc     60

caacagagcg cccaagaaga aaatggccat aagtggagtc cctgtgctag gatttttcat    120

catagctgtg ctgatgagcg ctcaggaatc atgggctatc aaagaagaac atgtgatcat    180

ccaggccgag ttctatctga atcctgacca atcaggcgag tttatgtttg actttgatgg    240

tgatgagatt ttccatgtgg atatgg                                         266


<210> SEQ ID NO 54
<211> LENGTH: 355
<212> TYPE: DNA
<213> ORGANISM: Homo sapiens
<220> FEATURE:
<221> NAME/KEY: modified_base
<222> LOCATION: (2)
<223> OTHER INFORMATION: a, g, c, t, unknown or other
<220> FEATURE:
<221> NAME/KEY: modified_base
<222> LOCATION: (15)
<223> OTHER INFORMATION: a, g, c, t, unknown or other
<220> FEATURE:
<221> NAME/KEY: modified_base
<222> LOCATION: (29)
<223> OTHER INFORMATION: a, g, c, t, unknown or other
<220> FEATURE:
<221> NAME/KEY: modified_base
<222> LOCATION: (86)
<223> OTHER INFORMATION: a, g, c, t, unknown or other
<220> FEATURE:
<221> NAME/KEY: modified_base
<222> LOCATION: (301)
<223> OTHER INFORMATION: a, g, c, t, unknown or other

<400> SEQUENCE: 54

anttcggcac agcgngggga tacaactcng gagtcctctg agagagccac caaggaggag     60

caggggagcg acggccgggg cagaanttga gaccacccag cagaggagct aggccagtcc    120

atctgcattt gtcacccaag aactcttacc atgaagaccc tcctactgtt ggcagtgatc    180

atgatctttg gcctactgca ggcccatggg aatttggtga atttccacag aatgatcaag    240

ttgacgacag gaaaggaagc cgcactcagt tatggcttct atggctgcca ctgtggcgtg    300

ngtggcagag gatcccccaa ggatgcaacg gatcgctgct gtgtcactca tgact         355


<210> SEQ ID NO 55
```

-continued

<211> LENGTH: 5189
<212> TYPE: DNA
<213> ORGANISM: Homo sapiens

<400> SEQUENCE: 55
ggactgcgaa aggagcaggg ttgcggagct agggctccag cctgcggccg cgcattcttg 60
cgtctggcca gccgcgagct ctaagggtcg gccccgcccg gtccgccccc gcggctccct 120
gccaggctct cgcgggcgcg ctcggggtgg ggcctcgcgg ctggcggaga tgcggccggg 180
gctgcgcggt ggtgatgcga gcctgctggg cggcgcgccg gggcagccgg agccgcgcgc 240
cgcggcgctg taatcggaca ccaagagcgc tcgcccccgg cctccggcca ctttccattc 300
actccgaggt gcttgattga gcgacgcgga gaagagctcc gggtgccgcg gcactgcagc 360
gctgagattc ctttacaaag aaactcagag gaccgggaag aaagaatttc acctttgcga 420
cgtgctagaa aataaggtcg tctgggaaaa ggactggaga cacaagcgca tccaaccccg 480
gtagcaaact gatgactttt ccgtgctgat ttctttcaac ctcggtattt tcccttggat 540
attaacttgc atatctgaag aaatggcatt ccggacaatt tgcgtgttgg ttggagtatt 600
tatttgttct atctgtgtga aaggatcttc ccagccccaa gcaagagttt atttaacatt 660
tgatgaactt cgagaaacca agacctctga atacttcagc ctttcccacc atcctttaga 720
ctacaggatt ttattaatgg atgaagatca ggaccggata tatgtgggaa gcaaagatca 780
cattctttcc ctgaatatta acaatataag tcaagaagct ttgagtgttt tctggccagc 840
atctacaatc aaagttgaag aatgcaaaat ggctggcaaa gatcccacac acggctgtgg 900
gaactttgtc cgtgtaattc agactttcaa tcgcacacat ttgtatgtct gtgggagtgg 960
cgctttcagt cctgtctgta cttacttgaa cagagggagg agatcagagg accaagtttt 1020
catgattgac tccaagtgtg aatctggaaa aggacgctgc tctttcaacc ccaacgtgaa 1080
cacggtgtct gttatgatca atgaggagct tttctctgga atgtatatag atttcatggg 1140
gacagatgct gctatttttc gaagtttaac caagaggaat gcggtcagaa ctgatcaaca 1200
taattccaaa tggctaagtg aacctatgtt tgtagatgca catgtcatcc cagatggtac 1260
tgatccaaat gatgctaagg tgtacttctt cttcaaagaa aaactgactg acaataacag 1320
gagcacgaaa cagattcatt ccatgattgc tcgaatatgt cctaatgaca ctggtggact 1380
gcgtagcctt gtcaacaagt ggaccacttt cttaaaggcg aggctggtgt gctcggtaac 1440
agatgaagac ggcccagaaa cacactttga tgaattagag gatgtgtttc tgctggaaac 1500
tgataacccg aggacaacac tagtgtatgg catttttaca acatcaagct cagttttcaa 1560
aggatcagcc gtgtgtgtgt atcatttatc tgatatacag actgtgttta atgggccttt 1620
tgcccacaaa gaagggccca atcatcagct gatttcctat cagggcagaa ttccatatcc 1680
tcgccctgga acttgtccag gaggagcatt tacacccaat atgcgaacca ccaaggagtt 1740
cccagatgat gttgtcactt ttattcggaa ccatcctctc atgtacaatt ccatctaccc 1800
aatccacaaa aggcctttga ttgttcgtat tggcactgac tacaagtata caaagatagc 1860
tgtggatcga gtgaacgctg ctgatgggag ataccatgtc ctgtttctcg gaacagatcg 1920
gggtactgtg caaaaagtgg ttgttcttcc tactaacaac tctgtcagtg gcgagctcat 1980
tctggaggag ctggaagtct ttaagaatca tgctcctata acaacaatga aaatttcatc 2040
taaaaagcaa cagttgtatg tgagttccaa tgaaggggtt tcccaggtat ctctgcaccg 2100
ctgccacatc tatggtacag cctgtgctga ctgctgcctg gcgcgggacc cttattgcgc 2160
ctgggatggc cattcctgtt ccagattcta cccaactggg aaacggagga gccgaagaca 2220

-continued

```
agatgtgaga catggaaacc cactgactca atgcagagga tttaatctaa aagcatacag   2280
aaatgcagct gaaattgtgc agtatggagt aaaaaataac accacttttc tggagtgtgc   2340
ccccaagtct ccgcaggcat ctatcaagtg gctgttacag aaagacaaag acaggaggaa   2400
agaggttaag ctgaatgaac gaataatagc cacttcacag ggactcctga tccgctctgt   2460
tcagggttct gaccaaggac tttatcactg cattgctaca gaaaatagtt tcaagcagac   2520
catagccaag atcaacttca aagttttaga ttcagaaatg gtggctgttg tgacggacaa   2580
atggtcccca tggacctggg ccagctctgt gagggcttta cccttccacc cgaaggacat   2640
catgggggca ttcagccact cagaaatgca gatgattaac caatattgca aagacactcg   2700
gcagcaacat cagcagggag atgaatcaca gaaaatgaga ggggactatg gcaagttaaa   2760
ggccctcatc aatagtcgga aaagtagaaa caggaggaat cagttgccag agtcataata   2820
ttttcttatg tgggtcttat gcttccatta acaaatgctc tgtcttcaat gatcaaattt   2880
tgagcaaaga aacttgtgct ttaccaaggg gaattactga aaaaggtgat tactcctgaa   2940
gtgagtttta cacgaactga aatgagcatg cattttcttg tatgatagtg actagcacta   3000
gacatgtcat ggtcctcatg gtgcatataa atatatttaa cttaacccag attttattta   3060
tatctttatt cacctttttct tcaaaatcga tatggtggct gcaaaactag aattgttgca   3120
tccctcaatt gaatgagggc catatccctg tggtattcct ttcctgcttt ggggctttag   3180
aattctaatt gtcagtgatt ttgtatatga aaacaagttc caaatccaca gcttttacgt   3240
agtaaaagtc ataaatgcat atgacagaat ggctatcaaa agaaatagaa aaggaagacg   3300
gcatttaaag ttgtataaaa acacgagtta ttcataaaga gaaaatgatg agtttttatg   3360
gttccaatga aatatgttgg ggtttttttta agattgtaaa aataatcagt tactggtatc   3420
tgtcactgac ctttgtttcc ttattcagga agataaaaat cagtaaccta ccccatgaag   3480
atatttggtg ggagttatat cagtgaagca gtttggttta tattcttatg ttatcacctt   3540
ccaaacaaaa gcacttactt tttttggaag ttatttattt tagactcaaa gaatataatc   3600
ttgcactact cagttattac tgtttgttct cttattccct agtctgtgtg gcaaattaaa   3660
caatataaga aggaaaaatt tgaagtatta gacttctaaa taaggggtga aatcatcaga   3720
aagaaaaatc aaagtagaaa ctactaattt tttaagagga atttataaca aatatggcta   3780
gttttcaact tcagtactca aattcaatga ttcttccttt tattaaaacc agtctcagat   3840
atcatactga tttttaagtc aacactatat attttatgat cttttcagtg tgatggcaag   3900
gtgcttgtta tgtctagaaa gtaagaaaac aatatgagga gacattctgt ctttcaaaag   3960
gtaatggtac atacgttcac tggtctctaa gtgtaaaagt agtaaatttt gtgatgaata   4020
aaataattat ctcctaattg tatgttagaa taattttatt agaataattt catactgaaa   4080
ttattttctc caaataaaaa ttagatggaa aaatgtgaaa aaaattattc atgctctcat   4140
atatatttta aaaacactac ttttgctttt ttatttacct tttaagacat tttcatgctt   4200
ccaggtaaaa acagatattg taccatgtac ctaatccaaa tatcatataa acattttatt   4260
tatagttaat aatctatgat gaaggtaatt aaagtagatt atggcctttt taagtattgc   4320
agtctaaaac ttcaaaaact aaaatcattg tcaaaattaa tatgattatt aatcagaata   4380
tcagaatatg attcactatt taaactatga taaattatga taatatatga ggaggcctcg   4440
ctatagcaaa aatagttaaa atgctgacat aacaccaaac ttcatttttt aaaaaatctg   4500
ttgttccaaa tgtgtataat tttaaagtaa tttctaaagc agtttattat aatggtttgc   4560
```

-continued

```
ctgcttaaaa ggtataatta aacttctttt ctcttctaca ttgacacaca gaaatgtgtc   4620

aatgtaaagc caaaaccatc ttctgtgttt atggccaatc tattctcaaa gttaaaagta   4680

aaattgtttc agagtcacag ttccctttat ttcacataag cccaaactga tagacagtaa   4740

cggtgtttag ttttatacta tatttgtgct atttaattct ttctattttc acaattatta   4800

aattgtgtac actttcatta cttttaaaaa tgtagaaatt cttcatgaac ataactctgc   4860

tgaatgtaaa agaaaatttt ttttcaaaaa tgctgttaat gtatactact ggtggttgat   4920

tggttttatt ttatgtagct tgacaattca gtgacttaat atctattcca tttgtattgt   4980

acataaaatt ttctagaaat acactttttt ccaaagtgta agtttgtgaa tagattttag   5040

catgatgaaa ctgtcataat ggtgaatgtt caatctgtgt aagaaaacaa actaaatgta   5100

gttgtcacac taaaatttaa ttggatattg atgaaatcat tggcctggca aaataaaaca   5160

tgttgaattc cccaaaaaaa aaaaaaaaa                                       5189
```

<210> SEQ ID NO 56
<211> LENGTH: 651
<212> TYPE: DNA
<213> ORGANISM: Homo sapiens

<400> SEQUENCE: 56

```
gagccaaggc attccctgtg gcgcaggtgt cagccccggt ggtggtggtc ggtgagctat     60

gcactgtgct acctccctgg gccccgcagc tcttgggctc tgtgagtgct tgtccttctt    120

ccctgacctc ttcttcagtg ctttgtctcc aaagaagtgg ctgacagatg aagtcctcaa    180

agtcatctac ttcatcatca tcacctgtct gttgcacagc cacctcctcc aagctgtcct    240

ccaggtcatc cacaaaatcc cggaagcgga ggcggtcatg acggaagatg ccatcctcac    300

caaagaaagc aggtgagagg ggtagctcct tggtcagctg cccagcccag ggcagccgtg    360

ccaagtatgt tcttagcaga gaggccagct cctgttgccg cactggggct agctctgtgc    420

caaagaaagt caggccctcc tgccgggcac actcgtccac acctgagcag ccctggggtg    480

cccggtactt gggcctcaac agctctgccc aggatggcag ggggtcatgg ctgtccttag    540

tcccttccct ccaacgaggt tgcttctgct tttctccaga ggagtgggag ctacactttc    600

cttgggggtc ttcgggcctg tgttgcctct tttgtcccga tctcacctgg c             651
```

<210> SEQ ID NO 57
<211> LENGTH: 697
<212> TYPE: DNA
<213> ORGANISM: Homo sapiens

<400> SEQUENCE: 57

```
agagcacagg ctttgaccga tagtaacctc tgcgctcggt gcagccgaat ctataaaagg     60

aactagtccc ggcaaaaacc ccgtaattgc gagcgagagt gagtggggcc gggacccgca    120

gagccgagcc gacccttctc tcccgggctg cggcagggca gggcggggag ctccgcgcac    180

caacagagcc ggttctcagg gcgctttgct ccttgttttt tccccggttc tgttttctcc    240

ccttctccgg aaggcttgtc aaggggtagg agaaagagac gcaaacacaa aagtggaaaa    300

cagttaatga ccagccacgg cgtccctgct gtgagctctg gccgctgcct tccagggctc    360

ccgagccaca cgctgggsgt gctggctgag ggaacatggc ttgttggcct cagctgaggt    420

tgctgctgtg gaagaacctc actttcagaa gaagacaaac atgtcagctg ctgctggaag    480

tggcctggcc tctatttatc ttcctgatcc tgatctctgt tcggctgagc tacccaccct    540

atgaacaaca tgaatgccat tttccaaata aagccatgcc ctctgcagga acacttcctt    600
```

```
gggttcaggg gattatctgt aatgccaaca acccctgttt ccgttacccg actcctgggg    660

aggctcccgg agttgttgga aactttaaca aatccat                             697


<210> SEQ ID NO 58
<211> LENGTH: 2001
<212> TYPE: DNA
<213> ORGANISM: Homo sapiens

<400> SEQUENCE: 58

ggtgactggc ccagccgcac cgcgtctccc gccttctccg cagccccgca ggccccgggc     60

cctgtcattc ccagcgctgc cctgtcttgc gttccagtgt tccagcttct gcgagatgac    120

cctcaaggcg agcgagggcg agagtggggg cagcatgcac acggcgctct ccgacctcta    180

cctggagcat ttgctgcaga agcgtagtcg gccagaggct gtatcgcatc cattgaatac    240

tgtgaccgag gacatgtaca ccaacgggtc tcctgcccca ggtagccctg cccaggtcaa    300

gggacaggag gtgcggaaag tgcgactcat acagtttgag aaggtcacag aagagcccat    360

gggaatcacg ctgaagctga atgaaaaaca gtcctgtacg gtggccagaa ttcttcatgg    420

tggcatgatc catagacaag gctcccttca cgtgggggat gagatcctag aaatcaatgg    480

cacaaatgtg acaaatcatt cagtggatca gctgcagaag gcgatgaaag aaaccaaagg    540

aatgatctca ttaaaagtaa ttcccaacca gcaaagccgt cttcctgcac tacagatgtt    600

catgagagcg cagtttgact atgatcccaa aaaggacaat ctgatccctt gcaaggaggc    660

gggactgaag tttgctactg ggacattat ccagattatc aacaaggatg acagcaattg    720

gtggcaggga cgggtggaag gctcctccaa ggagtcagca ggattgatcc cttcccctga    780

gctgcaggaa tggcgagtgg caagtatggc tcagtcagct cctagcgaag ccccgagctg    840

cagtcccttt gggaagaaga agaagtacaa agacaaatat ctggccaagc acagctcgat    900

ttttgatcag ttggatgttg tttcctacga ggaagtcgtt cggctccctg cattcaagag    960

gaagaccctg gtgctgatcg gagccagtgg ggtgggtcgc agccacatta agaatgccct   1020

gctcagccag aatccggaga agtttgtgta ccctgtccca tatacaacac ggccgccaag   1080

gaagagtgag gaagatggga aggagtacca ctttatctca acggaggaga tgacgaggaa   1140

catctctgcc aatgagttct tggagtttgg cagctaccaa ggcaacatgt ttggcaccaa   1200

atttgaaaca gtgcaccaga tccataagca gaacaagatt gccatccttg acattgagcc   1260

ccagaccctg aaaattgttc ggacagcaga actttcgcct ttcattgtgt tcattgcacc   1320

tactgaccag ggcactcaga cagaagccct gcagcagctg cagaaggact ctgaggccat   1380

ccgcagccag tacgctcact actttgacct ctcactggtc aataatggtg ttgatgaaac   1440

ccttaagaaa ttacaagaag ccttcgacca agcgtgcagt tctccacagt gggtgcctgt   1500

ctcctgggtt tactaagctt gtagaatggg ggaacccact gtatgcccct ctccagcatt   1560

tggaattcca cccgccttgc tttaagacaa acagggctgc tccaactagt tttgtgtcag   1620

cttccagctc tctgcagcta tcctaattca gccagtaagg ttcagtcttc ttgctcaggc   1680

tcctgaaggg ttgattctcc tgatagatgg ggccccactg atctggattt gaaaaggatt   1740

tctagaaatt gggggtaaga agtactacca aaatgtaact gctaatcaag ggtgatgcac   1800
```

-continued

```
agcaaaagca atggacccca tccctctaaa gcctgccctc ctttgccttc aactgtatat   1860

gctgggtatt tcatttgtct ttttattttg gagaaagcgt ttttaactgc aactttctat   1920

aatgccaaaa tgacacatct gtgcaataga atgatgtctg ctctagggaa accttcaaaa   1980

gcaataaaaa tgctgtgttg g                                             2001
```